US011752248B2

(12) United States Patent
Beavers et al.

(10) Patent No.: US 11,752,248 B2
(45) Date of Patent: *Sep. 12, 2023

(54) MEDICAL TREATMENT SYSTEM AND METHODS USING A PLURALITY OF FLUID LINES

(71) Applicant: DEKA Products Limited Partnership, Manchester, NH (US)

(72) Inventors: David A. Beavers, Manchester, NH (US); Michael G. Norris, Manchester, NH (US); John M. Kerwin, Manchester, NH (US); Andrew S. Coll, Goffstown, NH (US); Paul G. Girouard, Allenstown, NH (US); Robert J. Bryant, Jr., Manchester, NH (US); Geoffrey P. Spencer, Manchester, NH (US); Joseph P. Rushlow, Goffstown, NH (US); Jacob W. Scarpaci, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 1132 days.

This patent is subject to a terminal disclaimer.

(21) Appl. No.: 16/247,204

(22) Filed: Jan. 14, 2019

(65) Prior Publication Data

US 2019/0321535 A1 Oct. 24, 2019

Related U.S. Application Data

(60) Division of application No. 14/732,564, filed on Jun. 5, 2015, now Pat. No. 10,201,647, which is a
(Continued)

(51) Int. Cl.
*A61M 1/28* (2006.01)
*A61M 1/00* (2006.01)
(Continued)

(52) U.S. Cl.
CPC .............. *A61M 1/282* (2014.02); *A61M 1/71* (2021.05); *A61M 1/80* (2021.05); *A61M 1/166* (2014.02);
(Continued)

(58) Field of Classification Search
CPC ........ A61M 1/0023; A61M 1/14; A61M 1/16; A61M 1/1601; A61M 1/1615;
(Continued)

(56) References Cited

U.S. PATENT DOCUMENTS 2,339,876 A 1/1944 Phillips
3,083,943 A 4/1963 Stewart et al.
(Continued)

FOREIGN PATENT DOCUMENTS

CA 1119971 A 3/1982
CA 1323312 C 10/1993
(Continued)

OTHER PUBLICATIONS

U.S. Appl. No. 16/658,877, filed Oct. 21, 2019, Wilt et al.
(Continued)

*Primary Examiner* — Shefali D Patel
(74) *Attorney, Agent, or Firm* — Wolf, Greenfield & Sacks, P.C.

(57) ABSTRACT

Improvements in fluid volume measurement systems are disclosed for a pneumatically actuated diaphragm pump in general, and a peritoneal dialysis cycler using a pump cassette in particular. Pump fluid volume measurements are based on pressure measurements in a pump control chamber and a reference chamber in a two-chamber model, with different sections being modeled using a combination of adiabatic, isothermal and polytropic processes. Real time or instantaneous fluid flow measurements in a pump chamber of the diaphragm pump are also disclosed, in this case using
(Continued)

a one-chamber ideal gas model and using a high speed processor to obtain and process pump control chamber pressures during fluid flow into or out of the pump chamber. Improved heater control circuitry is also disclosed, to provide added or redundant safety measures, or to reduce current leakage from a heater element during pulse width modulation control of the heater element. Improvements are also disclosed in an application of negative pressure during a drain phase in peritoneal dialysis therapy, and to control an amount of intraperitoneal fluid accumulation during the therapy. Improvements in efficiency are also disclosed in movement of fluid into and out of a two-pump cassette and a heater bag of the peritoneal dialysis cycler, and in synchronization of operation of two or more pumps in the peritoneal dialysis cycler or other fluid handling devices using a multi-pump arrangement.

17 Claims, 200 Drawing Sheets

Related U.S. Application Data continuation-in-part of application No. 13/667,696, filed on Nov. 2, 2012, now Pat. No. 9,078,971.

(60) Provisional application No. 62/159,737, filed on May 11, 2015, provisional application No. 62/155,937, filed on May 1, 2015, provisional application No. 62/008,342, filed on Jun. 5, 2014, provisional application No. 61/555,926, filed on Nov. 4, 2011.

(51) Int. Cl.
    *G01V 8/20* (2006.01)
    *A61M 1/16* (2006.01)
    *A61M 1/36* (2006.01)

(52) U.S. Cl.
    CPC .............. *A61M 1/28* (2013.01); *A61M 1/288* (2014.02); *A61M 1/3656* (2014.02); *A61M 2205/12* (2013.01); *A61M 2205/13* (2013.01); *A61M 2205/14* (2013.01); *A61M 2205/33* (2013.01); *A61M 2205/3306* (2013.01); *A61M 2205/3327* (2013.01); *A61M 2205/3331* (2013.01); *A61M 2205/3334* (2013.01); *A61M 2205/3379* (2013.01); *A61M 2205/502* (2013.01); *G01V 8/20* (2013.01)

(58) Field of Classification Search
    CPC .... A61M 1/1621; A61M 1/1647; A61M 1/71; A61M 1/73; A61M 1/732; A61M 1/734; A61M 1/80; A61M 1/90; A61M 1/91; A61M 1/915; A61M 1/95; A61M 27/00; A61M 2205/3327; A61M 2205/3331; A61M 2205/3334; A61M 2205/3379; A61M 2205/3396; A61M 2205/50; A61M 2205/502; A61M 1/0058; A61M 1/166; A61M 1/28; A61M 1/282; A61M 1/288; A61M 1/3656; A61M 1/77; A61M 1/84; A61M 1/85; A61M 1/92; A61M 2205/12; A61M 2205/13; A61M 2205/14; A61M 2205/33; A61M 2205/3306; G01V 8/20
    See application file for complete search history.

(56) References Cited

U.S. PATENT DOCUMENTS

| | | |
|---|---|---|
| 3,111,125 A | 11/1963 | Schulte et al. |
| 3,568,214 A | 3/1971 | Goldschmied et al. |
| 3,711,770 A | 1/1973 | Wilson |
| 3,882,861 A | 5/1975 | Kettering et al. |
| 3,946,731 A | 3/1976 | Lichtenstein |
| 3,989,044 A | 11/1976 | Meierhoefer |
| 4,096,859 A | 6/1978 | Agarwal et al. |
| 4,133,312 A | 1/1979 | Burd |
| 4,137,168 A | 1/1979 | Perrot |
| 4,155,852 A | 5/1979 | Fischel et al. |
| 4,222,127 A | 9/1980 | Donachy et al. |
| 4,266,814 A | 5/1981 | Gallagher |
| 4,267,040 A | 5/1981 | Schal |
| 4,346,703 A | 8/1982 | Dennehey et al. |
| 4,381,545 A | 4/1983 | Biddle, III et al. |
| 4,441,357 A | 4/1984 | Kahn et al. |
| 4,479,762 A | 10/1984 | Bilstad et al. |
| 4,517,081 A | 5/1985 | Amiot et al. |
| 4,594,058 A | 6/1986 | Fischell |
| 4,624,664 A | 11/1986 | Peluso et al. |
| 4,628,186 A | 12/1986 | Bergemann et al. |
| 4,661,246 A | 4/1987 | Ash |
| 4,666,598 A | 5/1987 | Heath et al. |
| 4,668,400 A | 5/1987 | Veech |
| 4,695,385 A | 9/1987 | Boag |
| 4,718,022 A | 1/1988 | Cochran |
| 4,752,292 A | 6/1988 | Lopez et al. |
| 4,767,526 A | 8/1988 | Vantard |
| 4,778,447 A | 10/1988 | Velde et al. |
| 4,778,451 A | 10/1988 | Kamen |
| 4,781,535 A | 11/1988 | Frawley et al. |
| 4,797,655 A | 1/1989 | Orndal et al. |
| 4,808,161 A | 2/1989 | Kamen |
| 4,826,482 A | 5/1989 | Kamen |
| 4,828,543 A | 5/1989 | Weiss et al. |
| 4,828,693 A | 5/1989 | Lindsay et al. |
| 4,844,072 A | 7/1989 | French et al. |
| 4,927,411 A | 5/1990 | Pastrone et al. |
| 4,950,235 A | 8/1990 | Slate et al. |
| 4,969,363 A | 11/1990 | Mochizuki |
| 4,971,700 A | 11/1990 | Tsuji et al. |
| 4,976,162 A | 12/1990 | Kamen |
| 4,997,570 A | 3/1991 | Polaschegg |
| 5,002,471 A | 3/1991 | Perlov |
| 5,024,756 A | 6/1991 | Sternby |
| 5,033,513 A | 7/1991 | Bartholomew |
| 5,098,262 A | 3/1992 | Wecker et al. |
| 5,100,554 A | 3/1992 | Polaschegg |
| 5,135,489 A | 8/1992 | Jepson et al. |
| 5,178,182 A | 1/1993 | Kamen |
| 5,247,434 A | 9/1993 | Peterson et al. |
| 5,257,978 A | 11/1993 | Haber et al. |
| 5,275,724 A | 1/1994 | Bucchianeri et al. |
| 5,281,206 A | 1/1994 | Lopez |
| 5,293,028 A | 3/1994 | Payne |
| 5,318,414 A | 6/1994 | Lundback |
| 5,324,422 A | 6/1994 | Colleran et al. |
| 5,350,357 A | 9/1994 | Kamen et al. |
| 5,351,686 A | 10/1994 | Steuer et al. |
| 5,378,231 A | 1/1995 | Johnson et al. |
| 5,401,256 A | 3/1995 | Stone et al. |
| 5,415,528 A | 5/1995 | Ogden et al. |
| 5,421,823 A | 6/1995 | Kamen et al. |
| 5,423,738 A | 6/1995 | Robinson et al. |
| 5,427,509 A | 6/1995 | Chapman et al. |
| 5,431,626 A | 7/1995 | Bryant et al. |
| 5,431,627 A | 7/1995 | Pastrone et al. |
| 5,431,811 A | 7/1995 | Tusini et al. |
| 5,438,510 A | 8/1995 | Bryant et al. |
| 5,458,468 A | 10/1995 | Ye et al. |
| 5,472,325 A | 12/1995 | Svendsen |
| 5,472,614 A | 12/1995 | Rossi |
| 5,474,683 A | 12/1995 | Bryant et al. |
| 5,486,286 A | 1/1996 | Peterson et al. |
| 5,487,827 A | 1/1996 | Peterson et al. |
| 5,496,273 A | 3/1996 | Pastrone et al. |
| 5,536,258 A | 7/1996 | Folden |
| 5,575,310 A | 11/1996 | Kamen et al. |
| 5,580,460 A | 12/1996 | Polaschegg |
| 5,586,438 A | 12/1996 | Fahy |
| 5,591,344 A | 1/1997 | Kenley et al. |

(56) References Cited

U.S. PATENT DOCUMENTS

| | | |
|---|---|---|
| 5,609,572 A | 3/1997 | Lang |
| 5,616,248 A | 4/1997 | Schal |
| 5,628,908 A | 5/1997 | Kamen et al. |
| 5,645,531 A | 7/1997 | Thompson et al. |
| 5,676,644 A | 10/1997 | Toavs et al. |
| 5,676,645 A | 10/1997 | Van Waeg et al. |
| 5,690,831 A | 11/1997 | Kenley et al. |
| 5,702,597 A | 12/1997 | Chevallet et al. |
| 5,714,060 A | 2/1998 | Kenley et al. |
| 5,744,027 A | 4/1998 | Connell et al. |
| 5,769,811 A | 6/1998 | Stacey et al. |
| 5,776,091 A | 7/1998 | Brugger et al. |
| 5,782,508 A | 7/1998 | Bartholomew |
| 5,788,851 A | 8/1998 | Kenley et al. |
| 5,795,317 A | 8/1998 | Brierton et al. |
| 5,808,181 A | 9/1998 | Wamsiedler et al. |
| 5,827,223 A | 10/1998 | Butterfield |
| 5,846,419 A | 12/1998 | Nederlof |
| 5,863,421 A | 1/1999 | Peter, Jr. et al. |
| 5,882,047 A | 3/1999 | Ostrander et al. |
| 5,906,978 A | 5/1999 | Ash |
| 5,925,011 A | 7/1999 | Faict et al. |
| 5,948,251 A | 9/1999 | Brugger |
| 6,039,877 A | 3/2000 | Chevallet et al. |
| 6,041,801 A | 3/2000 | Gray et al. |
| 6,044,691 A | 4/2000 | Kenley et al. |
| 6,070,761 A | 6/2000 | Bloom et al. |
| 6,077,055 A | 6/2000 | Vilks |
| 6,122,538 A | 9/2000 | Sliwa, Jr. et al. |
| 6,146,523 A | 11/2000 | Kenley et al. |
| 6,165,149 A | 12/2000 | Utterberg et al. |
| 6,213,996 B1 | 4/2001 | Jepson et al. |
| 6,223,130 B1 | 4/2001 | Gray et al. |
| 6,228,047 B1 | 5/2001 | Dadson |
| 6,234,989 B1 | 5/2001 | Brierton et al. |
| 6,261,065 B1 | 7/2001 | Nayak et al. |
| 6,270,673 B1 | 8/2001 | Belt et al. |
| 6,277,272 B1 | 8/2001 | Nikaido et al. |
| 6,284,131 B1 | 9/2001 | Hogard et al. |
| 6,295,918 B1 | 10/2001 | Simmons et al. |
| 6,302,653 B1 * | 10/2001 | Bryant .................. F04B 51/00 417/63 |
| 6,321,597 B1 | 11/2001 | Demers et al. |
| 6,327,895 B1 | 12/2001 | Jeppsson et al. |
| 6,382,923 B1 | 5/2002 | Gray |
| 6,394,983 B1 | 5/2002 | Mayoral et al. |
| 6,406,426 B1 | 6/2002 | Reuss et al. |
| 6,416,293 B1 | 7/2002 | Bouchard et al. |
| 6,423,053 B1 | 7/2002 | Lee |
| 6,468,241 B1 | 10/2002 | Gelfand et al. |
| 6,481,980 B1 | 11/2002 | Vandlik et al. |
| 6,485,263 B1 | 11/2002 | Bryant et al. |
| 6,497,676 B1 | 12/2002 | Childers et al. |
| 6,503,062 B1 | 1/2003 | Gray et al. |
| 6,505,691 B2 | 1/2003 | Judge et al. |
| 6,520,747 B2 | 2/2003 | Gray et al. |
| 6,522,844 B2 | 2/2003 | Yamane et al. |
| 6,543,814 B2 | 4/2003 | Bartholomew |
| 6,579,253 B1 | 6/2003 | Burbank et al. |
| 6,602,424 B1 | 8/2003 | Kramer et al. |
| 6,614,008 B2 | 9/2003 | Tidrick |
| 6,638,478 B1 | 10/2003 | Treu et al. |
| 6,649,063 B2 | 11/2003 | Brugger et al. |
| 6,663,353 B2 | 12/2003 | Lipscomb et al. |
| 6,673,314 B1 | 1/2004 | Burbank et al. |
| 6,692,457 B2 | 2/2004 | Flaherty |
| 6,723,062 B1 | 4/2004 | Westberg et al. |
| 6,743,201 B1 | 6/2004 | Donig et al. |
| 6,750,468 B2 | 6/2004 | Malmstrom et al. |
| 6,758,975 B2 | 7/2004 | Peabody et al. |
| 6,811,707 B2 | 11/2004 | Rovatti et al. |
| 6,814,547 B2 | 11/2004 | Childers et al. |
| 6,814,718 B2 | 11/2004 | McGuckin, Jr. et al. |
| 6,821,441 B2 | 11/2004 | Pedrini et al. |
| 6,852,090 B2 | 2/2005 | Burbank et al. |
| 6,860,846 B2 | 3/2005 | Odak et al. |
| 6,868,309 B1 | 3/2005 | Begelman |
| 6,877,419 B2 | 4/2005 | Ohrle et al. |
| 6,905,314 B2 | 6/2005 | Danby |
| 6,905,479 B1 | 6/2005 | Bouchard et al. |
| 6,929,751 B2 | 8/2005 | Bowman, Jr. et al. |
| 6,939,471 B2 | 9/2005 | Gross et al. |
| 6,949,079 B1 | 9/2005 | Westberg et al. |
| 6,953,323 B2 | 10/2005 | Childers et al. |
| 7,029,245 B2 | 4/2006 | Maianti et al. |
| 7,041,076 B1 | 5/2006 | Westberg et al. |
| 7,083,719 B2 | 8/2006 | Bowman, Jr. et al. |
| 7,147,616 B2 | 12/2006 | Pedrazzi et al. |
| 7,153,286 B2 | 12/2006 | Busby et al. |
| 7,175,606 B2 | 2/2007 | Bowman, Jr. et al. |
| 7,238,164 B2 | 7/2007 | Childers et al. |
| 7,273,465 B2 | 9/2007 | Ash |
| 7,300,413 B2 | 11/2007 | Burbank et al. |
| 7,303,540 B2 | 12/2007 | O'Mahony et al. |
| 7,318,292 B2 | 1/2008 | Helbling et al. |
| 7,327,273 B2 | 2/2008 | Hung et al. |
| 7,364,563 B2 | 4/2008 | Lucke et al. |
| 7,461,968 B2 | 12/2008 | Demers et al. |
| 7,465,285 B2 | 12/2008 | Hutchinson et al. |
| 7,473,238 B2 | 1/2009 | Brugger et al. |
| 7,500,962 B2 | 3/2009 | Childers et al. |
| 7,524,417 B2 | 4/2009 | Sunohara et al. |
| 7,544,179 B2 | 6/2009 | Distler et al. |
| 7,544,301 B2 | 6/2009 | Shah et al. |
| 7,559,524 B2 | 7/2009 | Gray et al. |
| 7,560,686 B2 | 7/2009 | Bisch et al. |
| 7,563,240 B2 | 7/2009 | Gross et al. |
| 7,575,564 B2 | 8/2009 | Childers |
| 7,615,028 B2 | 11/2009 | O'Mahony |
| 7,632,078 B2 | 12/2009 | Demers et al. |
| 7,648,627 B2 | 1/2010 | Beden et al. |
| 7,699,806 B2 | 4/2010 | Ware et al. |
| 7,708,714 B2 | 5/2010 | Connell et al. |
| 7,736,328 B2 | 6/2010 | Childers et al. |
| 7,744,553 B2 | 6/2010 | Kelly et al. |
| 7,758,532 B2 | 7/2010 | Mori et al. |
| 7,776,006 B2 | 8/2010 | Childers et al. |
| 7,780,619 B2 | 8/2010 | Brugger et al. |
| 7,794,141 B2 | 9/2010 | Perry et al. |
| 7,909,795 B2 | 3/2011 | Childers et al. |
| 7,922,899 B2 | 4/2011 | Vasta et al. |
| 7,935,074 B2 | 5/2011 | Plahey et al. |
| 8,002,726 B2 | 8/2011 | Karoor et al. |
| 8,029,454 B2 | 10/2011 | Kelly et al. |
| 8,105,265 B2 | 1/2012 | Demers et al. |
| 8,113,244 B2 | 2/2012 | Kamen et al. |
| 8,180,443 B1 | 5/2012 | Kleinekofort et al. |
| 8,197,439 B2 | 6/2012 | Wang et al. |
| 8,219,196 B2 | 7/2012 | Torgerson |
| 8,246,826 B2 | 8/2012 | Wilt et al. |
| 8,266,967 B2 | 9/2012 | Kitani et al. |
| 8,287,480 B2 | 10/2012 | Sasaki et al. |
| 8,292,594 B2 | 10/2012 | Tracey et al. |
| 8,298,152 B2 | 10/2012 | Konig et al. |
| 8,330,579 B2 | 12/2012 | Kneip et al. |
| 8,350,195 B2 | 1/2013 | Hedmann et al. |
| 8,357,298 B2 | 1/2013 | Demers et al. |
| 8,366,316 B2 | 2/2013 | Kamen et al. |
| 8,366,655 B2 | 2/2013 | Kamen et al. |
| 8,393,690 B2 | 3/2013 | Grant et al. |
| 8,409,441 B2 | 4/2013 | Wilt |
| 8,469,331 B2 | 6/2013 | Burbank et al. |
| 8,512,553 B2 | 8/2013 | Cicchello et al. |
| 8,556,225 B2 | 10/2013 | Gray |
| 8,597,229 B2 | 12/2013 | Pan |
| 8,597,505 B2 | 12/2013 | Fulkerson et al. |
| 8,612,055 B2 | 12/2013 | Ali et al. |
| 8,673,139 B2 | 3/2014 | Hedmann et al. |
| 8,708,950 B2 | 4/2014 | Scarpaci et al. |
| 8,721,879 B2 | 5/2014 | van der Merwe et al. |
| 8,721,884 B2 | 5/2014 | Wilt et al. |
| 8,764,702 B2 | 7/2014 | Childers et al. |
| 8,821,475 B2 | 9/2014 | Distler et al. |
| 8,840,581 B2 | 9/2014 | McGill et al. |

(56) References Cited

U.S. PATENT DOCUMENTS

| | | |
|---|---|---|
| 8,858,787 B2 | 10/2014 | Muller et al. |
| 8,870,549 B2 | 10/2014 | Tracey et al. |
| 8,870,812 B2 | 10/2014 | Alberti et al. |
| 8,881,600 B2 | 11/2014 | Puppini et al. |
| 8,882,700 B2 | 11/2014 | Chapman et al. |
| 8,906,240 B2 | 12/2014 | Crnkovich et al. |
| 8,968,232 B2 | 3/2015 | Kamen et al. |
| 8,986,252 B2 | 3/2015 | Cummings et al. |
| 9,022,969 B2 | 5/2015 | Helmore et al. |
| 9,028,440 B2 | 5/2015 | Helmore et al. |
| 9,039,395 B2 | 5/2015 | Gray et al. |
| 9,066,668 B2 | 6/2015 | McGrath et al. |
| 9,072,831 B2 | 7/2015 | Kelly et al. |
| 9,078,971 B2 | 7/2015 | Scarpaci et al. |
| 9,084,566 B2 | 7/2015 | Zdeblick |
| 9,089,653 B2 | 7/2015 | O'Mahony |
| 9,121,403 B2 | 9/2015 | Lanigan et al. |
| 9,248,225 B2 | 2/2016 | Demers et al. |
| 9,302,039 B2 | 4/2016 | Kelly et al. |
| 9,358,332 B2 | 6/2016 | McGill et al. |
| 9,366,781 B2 | 6/2016 | Scarpaci et al. |
| 9,488,167 B2 | 11/2016 | Gray et al. |
| 9,494,150 B2 | 11/2016 | Gray et al. |
| 9,494,151 B2 | 11/2016 | Gray et al. |
| 9,514,283 B2 | 12/2016 | Childers et al. |
| 9,517,295 B2 | 12/2016 | Wilt et al. |
| 9,555,179 B2 | 1/2017 | Wilt et al. |
| 9,561,317 B2 | 2/2017 | Distler et al. |
| 9,561,318 B2 | 2/2017 | Distler et al. |
| 9,593,678 B2 | 3/2017 | Gray et al. |
| 9,603,985 B2 | 3/2017 | Wilt et al. |
| 9,713,667 B2 | 7/2017 | Distler et al. |
| 9,719,964 B2 | 8/2017 | Blumberg, Jr. |
| 9,724,012 B2 | 8/2017 | Chetham |
| 9,724,458 B2 | 8/2017 | Grant et al. |
| 9,750,865 B2 | 9/2017 | Vasta et al. |
| 9,770,546 B2 | 9/2017 | Vasta |
| 9,839,775 B2 | 12/2017 | McGill et al. |
| 9,839,776 B2 | 12/2017 | Helmore et al. |
| 9,861,732 B2 | 1/2018 | Scarpaci et al. |
| 9,907,897 B2 | 3/2018 | Burbank et al. |
| 9,907,972 B2 | 3/2018 | Kameli |
| 9,981,079 B2 | 5/2018 | Scarpaci et al. |
| 9,987,410 B2 | 6/2018 | Helmore et al. |
| 10,058,694 B2 | 8/2018 | Norris et al. |
| 10,098,996 B2 | 10/2018 | Scarpaci et al. |
| 10,172,988 B2 | 1/2019 | McGill et al. |
| 10,195,330 B2 | 2/2019 | Coll et al. |
| 10,201,647 B2 | 2/2019 | Norris et al. |
| 10,265,451 B2 | 4/2019 | McGill et al. |
| 10,449,280 B2 | 10/2019 | Wilt et al. |
| 10,463,774 B2 | 11/2019 | Ballantyne et al. |
| 10,485,914 B2 | 11/2019 | Scarpaci et al. |
| 10,537,671 B2 | 1/2020 | Wilt et al. |
| 10,576,194 B2 | 3/2020 | Distler et al. |
| 10,682,450 B2 | 6/2020 | Wilt et al. |
| 10,871,157 B2 | 12/2020 | Tracey et al. |
| 10,881,778 B2 | 1/2021 | Scarpaci et al. |
| 11,007,311 B2 | 5/2021 | Scarpaci et al. |
| 11,033,670 B2 | 6/2021 | Scarpaci et al. |
| 11,033,671 B2 | 6/2021 | van der Merwe et al. |
| 11,154,646 B2 | 10/2021 | Wilt et al. |
| 11,247,036 B2 | 2/2022 | Helmore et al. |
| 11,253,636 B2 | 2/2022 | McGill et al. |
| 11,364,329 B2 | 6/2022 | Demers et al. |
| 11,400,272 B2 | 8/2022 | Norris et al. |
| 11,478,577 B2 | 10/2022 | McGill et al. |
| 11,511,024 B2 | 11/2022 | McGill et al. |
| 11,529,444 B2 | 12/2022 | Wilt et al. |
| 11,568,043 B2 | 1/2023 | Ballantyne et al. |
| 2002/0022809 A1 | 2/2002 | Sudo et al. |
| 2002/0103453 A1 | 8/2002 | Burbank et al. |
| 2002/0165503 A1 | 11/2002 | Morris et al. |
| 2002/0182090 A1 | 12/2002 | Gray |
| 2003/0004492 A1 | 1/2003 | Munis et al. |
| 2003/0100858 A1 | 5/2003 | Utterberg et al. |
| 2003/0138334 A1 | 7/2003 | Vandlik et al. |
| 2003/0220607 A1 | 11/2003 | Busby et al. |
| 2003/0220627 A1 | 11/2003 | Distler et al. |
| 2004/0087895 A1 | 5/2004 | Cho et al. |
| 2004/0194210 A1 | 10/2004 | Foster et al. |
| 2004/0243049 A1 | 12/2004 | Brugger et al. |
| 2004/0254513 A1 | 12/2004 | Shang et al. |
| 2005/0045540 A1 | 3/2005 | Connell et al. |
| 2005/0095141 A1 | 5/2005 | Lanigan et al. |
| 2005/0145010 A1 | 7/2005 | Vanderveen et al. |
| 2005/0209563 A1 | 9/2005 | Hopping et al. |
| 2005/0234385 A1 | 10/2005 | Vandlik et al. |
| 2005/0242034 A1 | 11/2005 | Connell et al. |
| 2006/0002823 A1 | 1/2006 | Feldstein |
| 2006/0084906 A1 | 4/2006 | Burbank et al. |
| 2006/0129110 A1 | 6/2006 | Smith et al. |
| 2006/0144396 A1 | 7/2006 | DeVries et al. |
| 2006/0195064 A1 | 8/2006 | Plahey et al. |
| 2007/0023334 A1 | 2/2007 | Hallstadius et al. |
| 2007/0112297 A1 | 5/2007 | Plahey et al. |
| 2007/0135758 A1 | 6/2007 | Childers et al. |
| 2007/0265559 A1 | 11/2007 | Kunishige et al. |
| 2008/0021377 A1 | 1/2008 | Kienman et al. |
| 2008/0033346 A1 | 2/2008 | Childers et al. |
| 2008/0058697 A1 | 3/2008 | Kamen et al. |
| 2008/0065006 A1 | 3/2008 | Roger et al. |
| 2008/0097283 A1 | 4/2008 | Plahey |
| 2008/0114330 A1 | 5/2008 | Distler et al. |
| 2008/0125693 A1 | 5/2008 | Gavin et al. |
| 2008/0132828 A1 | 6/2008 | Howard |
| 2008/0138223 A1 | 6/2008 | Lanigan et al. |
| 2008/0161751 A1 | 7/2008 | Plahey et al. |
| 2008/0175719 A1 | 7/2008 | Tracey et al. |
| 2008/0203023 A1 | 8/2008 | Burbank et al. |
| 2008/0240929 A1 | 10/2008 | Kamen et al. |
| 2009/0007642 A1 | 1/2009 | Busby et al. |
| 2009/0009290 A1 | 1/2009 | Kneip et al. |
| 2009/0024070 A1 | 1/2009 | Gelfand et al. |
| 2009/0076433 A1 | 3/2009 | Folden et al. |
| 2009/0076434 A1 | 3/2009 | Mischelevich et al. |
| 2009/0088675 A1 | 4/2009 | Kelly et al. |
| 2009/0113335 A1 | 4/2009 | Sandoe et al. |
| 2009/0124963 A1 | 5/2009 | Hogard et al. |
| 2009/0182263 A1 | 7/2009 | Burbank et al. |
| 2009/0202367 A1 | 8/2009 | Gray et al. |
| 2009/0222119 A1 | 9/2009 | Plahey et al. |
| 2009/0294359 A1 | 12/2009 | Hopping et al. |
| 2009/0306573 A1 | 12/2009 | Gagner et al. |
| 2010/0040481 A1 | 2/2010 | Wolff |
| 2010/0076516 A1 | 3/2010 | Padiy et al. |
| 2010/0114027 A1 | 5/2010 | Jacobson et al. |
| 2010/0191180 A1 | 7/2010 | Childers et al. |
| 2010/0191181 A1 | 7/2010 | Childers et al. |
| 2010/0192686 A1 | 8/2010 | Kamen et al. |
| 2010/0268161 A1 | 10/2010 | Traversaz |
| 2010/0280486 A1 | 11/2010 | Khair et al. |
| 2010/0296953 A1 | 11/2010 | Gray |
| 2010/0312162 A1 | 12/2010 | Masaoka et al. |
| 2011/0005992 A1 | 1/2011 | Kelly et al. |
| 2011/0009797 A1 | 1/2011 | Kelly et al. |
| 2011/0060204 A1* | 3/2011 | Weston .................. A61M 1/90 604/319 |
| 2011/0071465 A1 | 3/2011 | Wang et al. |
| 2011/0218600 A1 | 9/2011 | Kamen et al. |
| 2011/0303588 A1 | 12/2011 | Kelly et al. |
| 2012/0238991 A1 | 9/2012 | Zhang et al. |
| 2013/0104120 A1 | 4/2013 | Arrizza et al. |
| 2013/0193041 A1 | 8/2013 | Rohde |
| 2013/0204174 A1 | 8/2013 | Oide et al. |
| 2013/0304020 A1 | 11/2013 | Wilt et al. |
| 2013/0343936 A1 | 12/2013 | Gray |
| 2014/0100526 A1 | 4/2014 | Ueda et al. |
| 2014/0112828 A1 | 4/2014 | Grant et al. |
| 2014/0231319 A1 | 8/2014 | Olde et al. |
| 2014/0260551 A1 | 9/2014 | Gray et al. |
| 2014/0260556 A1 | 9/2014 | Gray et al. |
| 2014/0276428 A1 | 9/2014 | Gray et al. |
| 2014/0286794 A1 | 9/2014 | Gray et al. |

(56) References Cited

U.S. PATENT DOCUMENTS

| | | |
|---|---|---|
| 2014/0288488 A1 | 9/2014 | Distler et al. |
| 2014/0288489 A1 | 9/2014 | Distler et al. |
| 2014/0288490 A1 | 9/2014 | Distler et al. |
| 2014/0309611 A1 | 10/2014 | Wilt et al. |
| 2014/0319041 A1 | 10/2014 | Wilt et al. |
| 2015/0151047 A1 | 6/2015 | Anderson et al. |
| 2015/0196699 A9 | 7/2015 | Wilt et al. |
| 2016/0030657 A1 | 2/2016 | Kelly et al. |
| 2016/0030658 A1 | 2/2016 | van der Merwe et al. |
| 2016/0058933 A1 | 3/2016 | Ballantyne et al. |
| 2016/0082173 A1 | 3/2016 | Coll et al. |
| 2016/0101227 A1 | 4/2016 | Norris et al. |
| 2016/0101278 A1 | 4/2016 | Norris et al. |
| 2016/0144093 A1 | 5/2016 | Demers et al. |
| 2016/0175506 A1 | 6/2016 | Wilt et al. |
| 2018/0256803 A1 | 9/2018 | Helmore et al. |
| 2018/0296746 A1 | 10/2018 | van der Merwe et al. |
| 2019/0060629 A1 | 2/2019 | Norris et al. |
| 2019/0099534 A1 | 4/2019 | McGill et al. |
| 2019/0167883 A1 | 6/2019 | Girouard et al. |
| 2019/0314565 A1 | 10/2019 | McGill et al. |
| 2019/0321535 A1 | 10/2019 | Beavers et al. |
| 2019/0344002 A1 | 11/2019 | McGill et al. |
| 2020/0086030 A1 | 3/2020 | Scarpaci et al. |
| 2020/0086035 A1 | 3/2020 | Wilt et al. |
| 2020/0139031 A1 | 5/2020 | Wilt et al. |
| 2020/0171226 A1 | 6/2020 | Wilt et al. |
| 2020/0215252 A1 | 7/2020 | Distler et al. |
| 2020/0222609 A1 | 7/2020 | Ballantyne et al. |
| 2020/0376185 A1 | 12/2020 | Wilt et al. |
| 2020/0376186 A1 | 12/2020 | Wilt et al. |
| 2020/0400595 A1 | 12/2020 | Kamen et al. |
| 2021/0060231 A1 | 3/2021 | Grant et al. |
| 2021/0228793 A1 | 7/2021 | Scarpaci et al. |
| 2021/0275735 A1 | 9/2021 | Scarpaci et al. |
| 2021/0316058 A1 | 10/2021 | van der Merwe et al. |
| 2021/0361841 A1 | 11/2021 | van der Merwe et al. |
| 2022/0133968 A1 | 5/2022 | Wilt et al. |
| 2022/0152286 A1 | 5/2022 | Wilt et al. |
| 2022/0233754 A1 | 7/2022 | McGill et al. |
| 2022/0249755 A1 | 8/2022 | Helmore et al. |
| 2022/0280706 A1 | 9/2022 | Demers et al. |
| 2022/0412907 A1 | 12/2022 | Khosravi et al. |

FOREIGN PATENT DOCUMENTS

| | | |
|---|---|---|
| CA | 2336478 A1 | 2/2000 |
| CA | 2341993 A1 | 3/2000 |
| CA | 2704411 A1 | 5/2009 |
| DE | 19704564 A1 | 8/1998 |
| EP | 0 406 562 A2 | 1/1991 |
| EP | 1195171 A2 | 4/2002 |
| EP | 1356836 A2 | 10/2003 |
| EP | 1666078 A2 | 6/2006 |
| GB | 2181311 A | 4/1987 |
| JP | S58-169462 A | 10/1983 |
| JP | S59-115049 A | 7/1984 |
| JP | H04-358779 A | 12/1992 |
| JP | H06-77745 | 3/1994 |
| JP | H06-154314 A | 6/1994 |
| JP | H06-207845 A | 7/1994 |
| JP | H06-75504 U | 10/1994 |
| JP | H06-312014 A | 11/1994 |
| JP | H07-24062 A | 1/1995 |
| JP | H11-128343 A | 5/1999 |
| JP | H11-285144 A | 10/1999 |
| JP | 2001-112863 A | 4/2001 |
| JP | 2003-180825 A | 7/2003 |
| JP | 2003-246246 A | 9/2003 |
| JP | 2003-265599 A | 9/2003 |
| JP | 2004-147721 A | 5/2004 |
| JP | 2005-013502 A | 1/2005 |
| JP | 2005-034671 A | 2/2005 |
| JP | 2005-261558 A | 9/2005 |
| JP | 2005-283342 A | 10/2005 |
| JP | 2006-198141 A | 8/2006 |
| JP | 2006-343254 A | 12/2006 |
| JP | 2007-020961 A | 2/2007 |
| JP | 2007-035582 A | 2/2007 |
| JP | 2008-104737 A | 5/2008 |
| JP | 2008-136673 A | 6/2008 |
| WO | WO 84/02473 A1 | 7/1984 |
| WO | WO 94/11093 A1 | 5/1994 |
| WO | WO 94/20157 A1 | 9/1994 |
| WO | WO 96/25214 A1 | 8/1996 |
| WO | WO 96/40320 A1 | 12/1996 |
| WO | WO 97/10013 A1 | 3/1997 |
| WO | WO 97/11771 A1 | 4/1997 |
| WO | WO 2000/057935 A1 | 10/2000 |
| WO | WO 01/18396 A1 | 3/2001 |
| WO | WO 01/019430 A1 | 3/2001 |
| WO | WO 01/37895 A2 | 5/2001 |
| WO | WO 02/30267 A2 | 4/2002 |
| WO | WO 03/099353 A2 | 12/2003 |
| WO | WO 2004/041081 A1 | 5/2004 |
| WO | WO 2005/044435 A2 | 5/2005 |
| WO | WO 2006/088419 A2 | 8/2006 |
| WO | WO 2006/120415 A1 | 11/2006 |
| WO | WO 2007/014470 A2 | 2/2007 |
| WO | WO 2007/062197 A1 | 5/2007 |
| WO | WO 2007/113936 A1 | 10/2007 |
| WO | WO 2007/120812 A2 | 10/2007 |
| WO | WO 2009/051669 A1 | 4/2009 |
| WO | WO 2015/183976 A2 | 12/2015 |
| WO | WO 2015/183981 A2 | 12/2015 |

OTHER PUBLICATIONS

U.S. Appl. No. 16/916,039, filed Jun. 29, 2020, Kamen et al.
U.S. Appl. No. 16/901,926, filed Jun. 15, 2020, Wilt et al.
U.S. Appl. No. 16/507,302, filed Jul. 10, 2019, McGill et al.
U.S. Appl. No. 15/012,764, filed Feb. 1, 2016, Demers et al.
U.S. Appl. No. 16/207,349, filed Dec. 3, 2018, McGill et al.
U.S. Appl. No. 17/317,626, filed May 11, 2021, Scarpaci et al.
U.S. Appl. No. 17/026,804, filed Sep. 21, 2020, Grant et al.
U.S. Appl. No. 17/141,091, filed Jan. 4, 2021, Scarpaci et al.
U.S. Appl. No. 16/266,804, filed Feb. 4, 2019, Girouard et al.
U.S. Appl. No. 16/723,053, filed Dec. 20, 2019, Wilt et al.
U.S. Appl. No. 16/723,408, filed Dec. 20, 2019, Wilt et al.
U.S. Appl. No. 16/808,134, filed Mar. 3, 2020, Distler et al.
U.S. Appl. No. 16/112,287, filed Aug. 24, 2018, Norris et al.
U.S. Appl. No. 16/011,294, filed Jun. 18, 2018, van der Merwe et al.
U.S. Appl. No. 16/671,855, filed Nov. 1, 2019, Ballantyne et al.
EP 15731438.6, Dec. 4, 2018, Examination Report.
EP 20168965.0, Jul. 8, 2020, Extended European Search Report.
JP 2016-571234, Apr. 2, 2019, Office Action.
SG 11201610049U, Dec. 14, 2017, †††Search Report and Written Opinion.
PCT/US2015/034570, Nov. 4, 2015, †††International Search Report and Written Opinion.
PCT/US2015/034570, Dec. 15, 2016, †††International Preliminary Report on Patentablility.
Examination Report for EP Application No. 15731438.6 filed Jun. 5, 2015, which Examination Report dated Dec. 4, 2018, and claims as pending for EP Application No. 15731438.6 as of Jul. 31, 2017.
Extended European Search Report for EP Application No. 20168965.0 dated Jul. 8, 2020 and claims pending as of Jul. 8, 2020.
Office Action for JP Application No. 2016-571234 filed Jun. 5, 2015, which Office Action dated Apr. 2, 2019 and claims as pending for JP 2016-571234 as of Jun. 5, 2018.
Search Report and Written Opinion for SG Application No. 11201610049U filed Nov. 30, 2016, which Search Report and Written Opinion dated Dec. 14, 2017, and claims as pending for SG Application No. 11201610049U as of Dec. 14, 2017.
Office Action for U.S. Appl. No. 14/732,564, published as US 2016-0101227 on Apr. 14, 2016, which Office Action dated Mar. 20, 2018, and claims as pending for U.S. Appl. No. 14/732,564 as of Mar. 20, 2018.

(56) References Cited

OTHER PUBLICATIONS

International Search Report and Written Opinion for Application No. PCT/US2015/034570 dated Nov. 4, 2015.
International Preliminary Report on Patentability for Application No. PCT/US2015/034570 dated Dec. 15, 2016.
[No Author Listed] Homechoice Patient At-Home Guide, Jun. 1998. 84 pages.
No Author Listed, Patient At-Home Guide, HomeChoice Automated PD System. Version 2.0 (published May 1997); Baxter Healthcare Corporation. Copyright 1994. 61 pages.
2008K2 Hemodialysis Machine Operator's Manual. Fresenius Medical Care. https://laz2qm2bxvodlae4oellp3es-wpengine.netdna-ssl.com/wp-content/uploads/2018/09/490136_Rev_K.pdf.
Bengtsson et al., Haemo dialysis software architecture design experiences. Proceeedings of the 1999 International Conferene on Software Engineering. IEEE Cat. No. 99CB37002. New York, NY. 1999:516-25.
Choppy et al., Architectural patterns for problem frames—relating software requirements and architectures. IEEE Proceedings: Software, IEE. Stevenage, GB. Aug. 5, 2005;52(4):198-208.
Gentilini et al., Automatic controllers capable of regulating mutliple patient outputs for higher-quality anesthesia treatment. IEEE Engineering in Medicine and Biology Magazine. IEEE Service Centers. Piscataway, NJ. Jan. 1, 2001;20(1):39-53.
Harel et al., Statecharts: A visual formalism for complex systems. Retrieved from the Internet: http://www.wisdom.weizmann.ac.il/~harel/Statecharts87.pdf> Retrieved on Jul. 2, 2002.
Krasner et al., A cookbook for using the model-view-controller user interface paradigm in smalltalk-80. JOOP. Aug. 1, 1988;1(3):26-49.
Mineshima et al., Efficacy of internal filtration enhanced hemodialysis. Artifical Organs. 1999;28(1):127-33.
Office Action for JP Application No. 2020-112801 dated Nov. 2, 2021 and claims pending as of Nov. 2, 2021.
U.S. Appl. No. 17/466,806, filed Sep. 3, 2021, Grant et al.
U.S. Appl. No. 16/901,897, filed Jun. 15, 2020, Wilt et al.
U.S. Appl. No. 17/974,364, filed Oct. 26, 2022, Wilt et al.
U.S. Appl. No. 17/975,495, filed Oct. 27, 2022, McGill et al.
U.S. Appl. No. 17/346,959, filed Jun. 14, 2021, van der Merwe et al.
U.S. Appl. No. 18/103,458, filed Jan. 30, 2023, Ballantyne et al.

\* cited by examiner

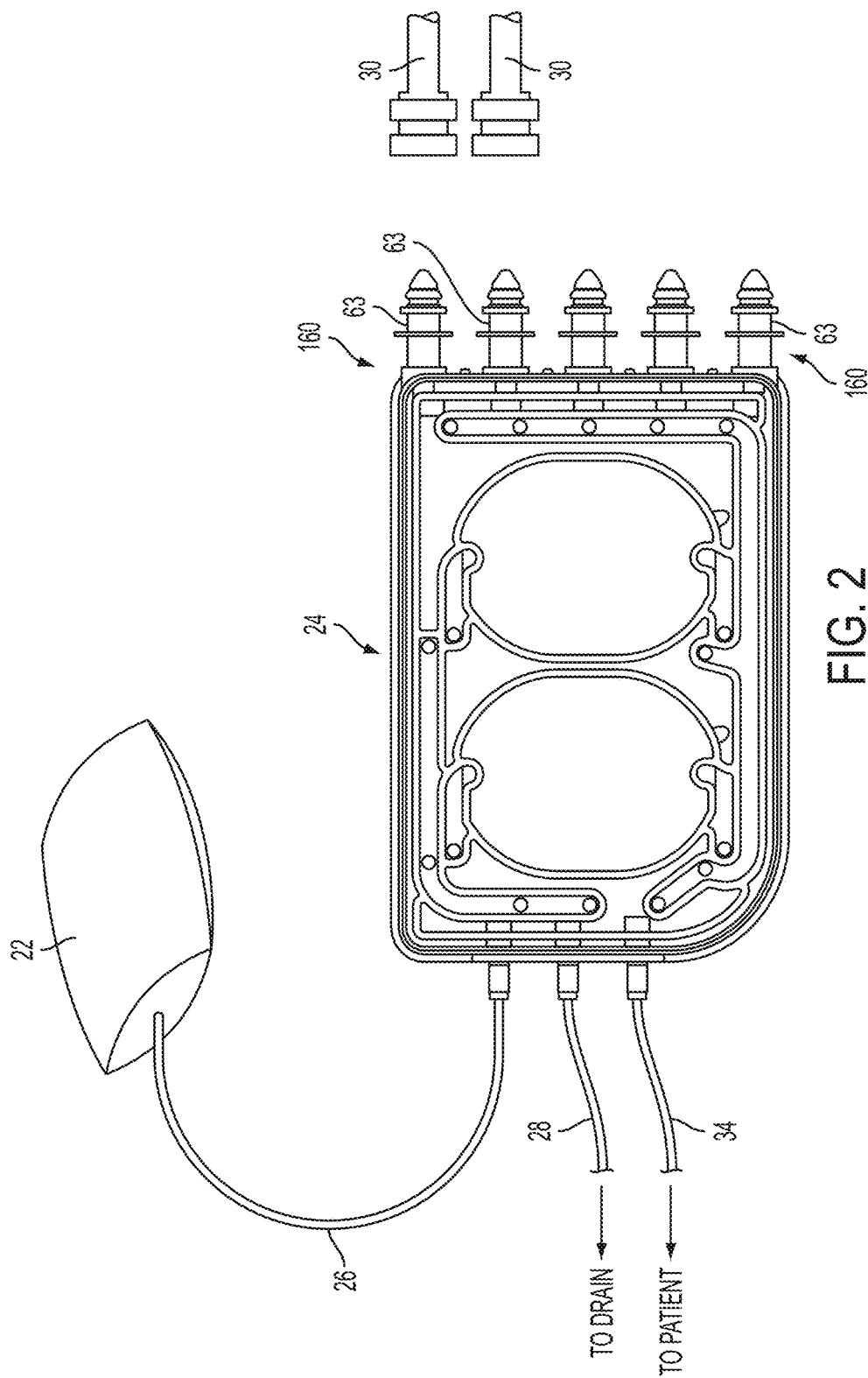

SOLUTION BAG RESULTS 01/01/2012 12:00 PM

HELP

VERIFY THE PROGRAMMED SOLUTION BAGS ARE INSERTED WITH LINE CAPS ATTACHED

| CAP | ☑ | ☑ DIALYSATE TYPE 1, CONCENTRATION, BAG VOLUME | 5632 |
| CAP | ☑ | ☑ DIALYSATE TYPE 2, CONCENTRATION, BAG VOLUME | 5632 |
| CAP | ☒ | ☒ DIALYSATE TYPE 3, CONCENTRATION, BAG VOLUME | 5632 |
| CAP | ☒ | ☒ DIALYSATE TYPE 4, CONCENTRATION, BAG VOLUME | 5632 |
| CAP | ☒ | ☒ NONE | 5632 |

BACK

RETRY — 5634

FIG. 45

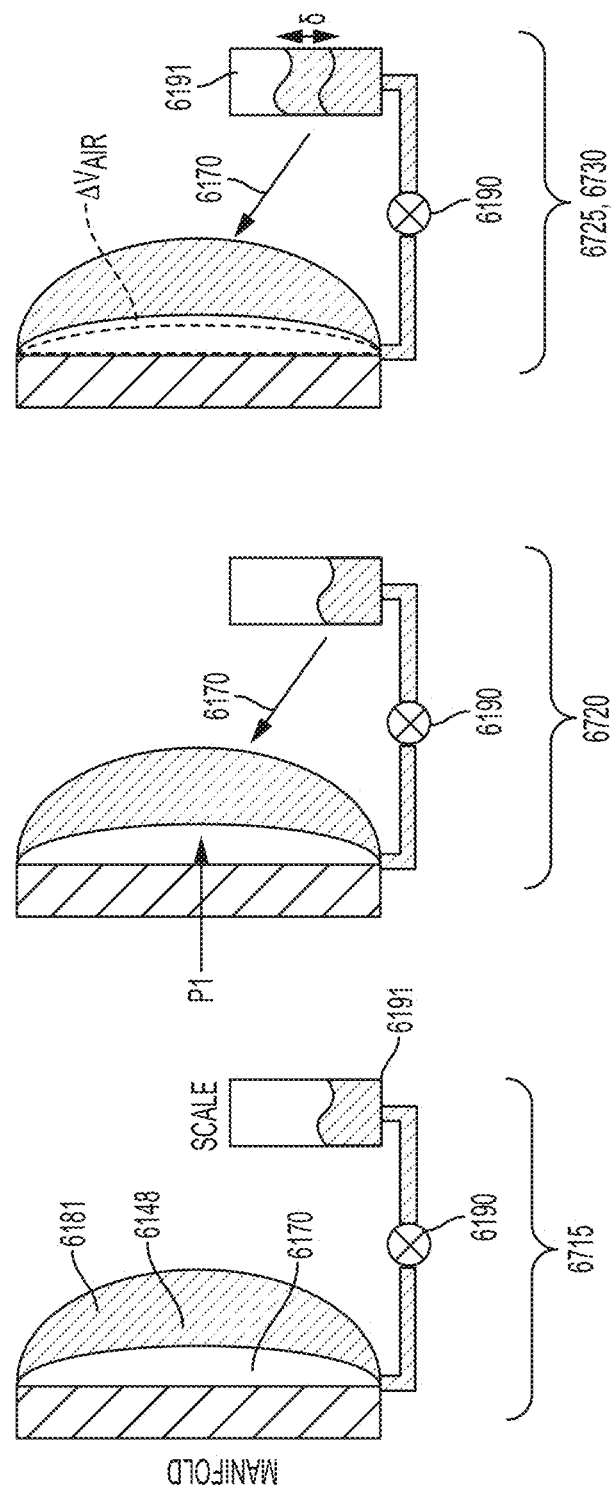

MEDICAL TREATMENT SYSTEM AND METHODS USING A PLURALITY OF FLUID LINES

CROSS REFERENCE TO RELATED APPLICATIONS

This application is a division of U.S. patent application Ser. No. 14/732,564 filed Jun. 5, 2015, now U.S. Pat. No. 10,201,647, which claims the benefit of the following:

U.S. Provisional Application No. 62/008,342 filed Jun. 5, 2014;

U.S. Provisional Application No. 62/155,937 filed May 1, 2015; and

U.S. Provisional Application No. 62/159,737 filed May 11, 2015.

U.S. patent application Ser. No. 14/732,564 is also a continuation-in-part of U.S. patent application Ser. No. 13/667,696 filed Nov. 2, 2012, now U.S. Pat. No. 9,078,971, which claims the benefit of U.S. Provisional Application No. 61/555,926 filed Nov. 4, 2011. All of the above applications are hereby incorporated by reference in their entirety.

BACKGROUND

Peritoneal Dialysis (PD) involves the periodic infusion of sterile aqueous solution (called peritoneal dialysis solution, or dialysate) into the peritoneal cavity of a patient. Diffusion and osmosis exchanges take place between the solution and the bloodstream across the natural body membranes. These exchanges transfer waste products to the dialysate that the kidneys normally excrete. The waste products typically consist of solutes like sodium and chloride ions, and other compounds normally excreted through the kidneys like urea, creatinine, and water. The diffusion of water across the peritoneal membrane during dialysis is called ultrafiltration.

Conventional peritoneal dialysis solutions include dextrose in concentrations sufficient to generate the necessary osmotic pressure to remove water from the patient through ultrafiltration.

Continuous Ambulatory Peritoneal Dialysis (CAPD) is a popular form of PD. A patient performs CAPD manually about four times a day. During a drain/fill procedure for CAPD, the patient initially drains spent peritoneal dialysis solution from his/her peritoneal cavity, and then infuses fresh peritoneal dialysis solution into his/her peritoneal cavity. This drain and fill procedure usually takes about 1 hour.

Automated Peritoneal Dialysis (APD) is another popular form of PD. APD uses a machine, called a cycler, to automatically infuse, dwell, and drain peritoneal dialysis solution to and from the patient's peritoneal cavity. APD is particularly attractive to a PD patient, because it can be performed at night while the patient is asleep. This frees the patient from the day-to-day demands of CAPD during his/her waking and working hours.

The APD sequence typically lasts for several hours. It often begins with an initial drain phase to empty the peritoneal cavity of spent dialysate. The APD sequence then proceeds through a succession of fill, dwell, and drain phases that follow one after the other. Each fill/dwell/drain sequence is called a cycle.

During the fill phase, the cycler transfers a predetermined volume of fresh, warmed dialysate into the peritoneal cavity of the patient. The dialysate remains (or "dwells") within the peritoneal cavity for a period of time. This is called the dwell phase. During the drain phase, the cycler removes the spent dialysate from the peritoneal cavity.

The number of fill/dwell/drain cycles that are required during a given APD session depends upon the total volume of dialysate prescribed for the patient's APD regimen, and is either entered as part of the treatment prescription or calculated by the cycler.

APD can be and is practiced in different ways.

Continuous Cycling Peritoneal Dialysis (CCPD) is one commonly used APD modality. During each fill/dwell/drain phase of CCPD, the cycler infuses a prescribed volume of dialysate. After a prescribed dwell period, the cycler completely drains this liquid volume from the patient, leaving the peritoneal cavity empty, or "dry." Typically, CCPD employs 4-8 fill/dwell/drain cycles to achieve a prescribed therapy volume.

After the last prescribed fill/dwell/drain cycle in CCPD, the cycler infuses a final fill volume. The final fill volume dwells in the patient for an extended period of time. It is drained either at the onset of the next CCPD session in the evening, or during a mid-day exchange. The final fill volume can contain a different concentration of dextrose than the fill volume of the successive CCPD fill/dwell/drain fill cycles the cycler provides.

Intermittent Peritoneal Dialysis (IPD) is another APD modality. IPD is typically used in acute situations, when a patient suddenly enters dialysis therapy. IPD can also be used when a patient requires PD, but cannot undertake the responsibilities of CAPD or otherwise do it at home.

Like CCPD, IPD involves a series of fill/dwell/drain cycles. Unlike CCPD, IPD does not include a final fill phase. In IPD, the patient's peritoneal cavity is left free of dialysate (or "dry") in between APD therapy sessions.

Tidal Peritoneal Dialysis (TPD) is another APD modality. Like CCPD, TPD includes a series of fill/dwell/drain cycles. Unlike CCPD, TPD does not completely drain dialysate from the peritoneal cavity during each drain phase. Instead, TPD establishes a base volume during the first fill phase and drains only a portion of this volume during the first drain phase. Subsequent fill/dwell/drain cycles infuse and then drain a replacement volume on top of the base volume. The last drain phase removes all dialysate from the peritoneal cavity.

There is a variation of TPD that includes cycles during which the patient is completely drained and infused with a new full base volume of dialysis.

TPD can include a final fill cycle, like CCPD. Alternatively, TPD can avoid the final fill cycle, like IPD.

APD offers flexibility and quality of life enhancements to a person requiring dialysis. APD can free the patient from the fatigue and inconvenience that the day to day practice of CAPD represents to some individuals. APD can give back to the patient his or her waking and working hours free of the need to conduct dialysis exchanges.

Still, the complexity and size of past machines and associated disposables for various APD modalities have dampened widespread patient acceptance of APD as an alternative to manual peritoneal dialysis methods.

SUMMARY OF INVENTION

In one aspect, a system is disclosed for measuring an amount of liquid in a pumping chamber of a pneumatically actuated diaphragm pump. The system comprises a fluid inlet and fluid outlet valve connected to the pumping chamber; a diaphragm separating a pneumatically actuated control chamber from the pumping chamber, the control chamber fluidly connected to a reference chamber of known volume via a conduit that includes a reference chamber valve; the control chamber fluidly connected via one or more actuation valves to a source of positive or negative pneumatic pressure; and a controller configured to control the fluid inlet and outlet valves, the reference chamber valve, and the one or more actuation valves, and to receive pressure data from a first pressure sensor connected to the actuation chamber and a second pressure sensor connected to the reference chamber. The controller is configured to isolate the pumping chamber by closing the fluid inlet and outlet valves, charge the control chamber with a first pneumatic pressure; vent the reference chamber or fix a pneumatic pressure in the reference chamber that is different from the control chamber pneumatic pressure; measure a first control chamber pressure and a first reference chamber pressure, connect the control chamber to the reference chamber by opening the reference chamber valve, measure a third equalized pneumatic pressure in the control and reference chambers, and compute a control chamber volume based on an ideal gas model that assumes an adiabatic pressure equalization process in the reference chamber and a polytropic pressure equalization process in the control chamber.

The model optionally can further assume an isothermal process in the conduit as a gas moves from the control chamber to the reference chamber during the equalization process. The model applied to the control chamber can also use a polytropic coefficient in the ideal gas model, wherein the controller is programmed to vary the polytropic coefficient as a pre-defined function of the control chamber volume. The controller can also be programmed to compute a polytropic coefficient based on an estimated volume of the control chamber using a model that assumes an adiabatic pressure equalization process in the control chamber.

In another aspect, a system is disclosed for measuring an amount of liquid in a pumping chamber of a pneumatically actuated diaphragm pump. The system comprises a fluid inlet and fluid outlet valve connected to the pumping chamber; a diaphragm separating a pneumatically actuated control chamber from the pumping chamber, the control chamber fluidly connected to a reference chamber of known volume via a conduit that includes a reference chamber valve; the control chamber fluidly connected via one or more actuation valves to a source of positive or negative pneumatic pressure; and a controller configured to control the fluid inlet and outlet valves, the reference chamber valve, and the one or more actuation valves, and to receive pressure data from a first pressure sensor connected to the actuation chamber and a second pressure sensor connected to the reference chamber.

The controller is configured to isolate the pumping chamber by closing the fluid inlet and outlet valves, charge the control chamber with a first pneumatic pressure; vent the reference chamber or fix a pneumatic pressure in the reference chamber that is different from the control chamber pneumatic pressure; measure a first control chamber pressure and a first reference chamber pressure, connect the control chamber to the reference chamber by opening the reference chamber valve and equalizing pressures between the control chamber and the reference chamber, measure a third equalized pneumatic pressure in the control and reference chambers. The controller is configured to compute a control chamber volume based on an ideal gas model that assumes the presence of three closed mass systems of a gas comprising: a first mass system that occupies the control chamber at the end of pressure equalization; a second mass system that occupies the reference chamber before pressure equalization; and a third mass system that occupies the conduit, a part of the control chamber and a part of the reference chamber after equalization of pressure begins between the control and reference chambers.

The model can optionally assume an expansion of the first mass system after pressure equalization begins, the expansion being modeled as a polytropic process. The model can also assume a compression of the second mass system after pressure equalization begins, the compression being modeled as an adiabatic process. The third mass system can be modeled to be subdivided into component volumes, a first component volume occupying part of the control chamber and being modeled polytropically, a second component volume occupying part of the reference chamber and being modeled adiabatically, and a third component volume occupying the conduit and being modeled isothermally.

In another aspect, a system is disclosed for measuring an amount of liquid in a pumping chamber of a pneumatically actuated diaphragm pump. The system comprises a fluid inlet and fluid outlet valve connected to the pumping chamber; a diaphragm separating a pneumatically actuated control chamber from the pumping chamber, the control chamber fluidly connected to a reference chamber of known volume via a conduit that includes a reference chamber valve; the control chamber fluidly connected via one or more actuation valves to a source of positive or negative pneumatic pressure; and a controller configured to control the fluid inlet and outlet valves, the reference chamber valve, and the one or more actuation valves, and to receive pressure data from a first pressure sensor connected to the actuation chamber and a second pressure sensor connected to the reference chamber.

The controller is configured to isolate the pumping chamber by closing the fluid inlet and outlet valves, charge the control chamber with a first pneumatic pressure; vent the reference chamber or fix a pneumatic pressure in the reference chamber that is different from the control chamber pneumatic pressure; measure a first control chamber pressure and a first reference chamber pressure, connect the control chamber to the reference chamber by opening the reference chamber valve and equalizing pressures between the control chamber and the reference chamber, measure a third equalized pneumatic pressure in the control and reference chambers. The controller is configured to compute the control chamber volume based on an ideal gas model that assumes the presence of three closed mass systems of a gas comprising: a first mass system that occupies the control chamber before pressure equalization; a second mass system that occupies the reference chamber at the end of pressure equalization; and a third mass system that occupies the conduit, a part of the control chamber and a part of the reference chamber after equalization of pressure begins between the control and reference chambers.

The model can optionally assume a compression of the first mass system after pressure equalization begins, the compression being modeled as a polytropic process. The model can also assume an expansion of the second mass system after pressure equalization begins, the expansion being modeled as an adiabatic process. The third mass system can be modeled to be subdivided into component volumes, a first component volume occupying part of the control chamber being modeled polytropically, a second component volume occupying part of the reference chamber being modeled adiabatically, and a third component volume occupying the conduit being modeled isothermally.

In another aspect, a system is disclosed for measuring an amount of liquid in a pumping chamber of a pneumatically actuated diaphragm pump. The system comprises a fluid inlet and fluid outlet valve connected to the pumping chamber; a diaphragm separating a pneumatically actuated control chamber from the pumping chamber, the control chamber fluidly connected to a reference chamber of known volume via a conduit that includes a reference chamber valve; the control chamber fluidly connected via one or more actuation valves to a source of positive or negative pneumatic pressure; and a controller configured to control the fluid inlet and outlet valves, the reference chamber valve, and the one or more actuation valves, and to receive pressure data from a first pressure sensor connected to the actuation chamber and a second pressure sensor connected to the reference chamber.

The controller is configured to isolate the pumping chamber by closing the fluid inlet and outlet valves, charge the control chamber with a first pneumatic pressure; vent the reference chamber or fix a pneumatic pressure in the reference chamber that is different from the control chamber pneumatic pressure; measure a first control chamber pressure and a first reference chamber pressure, connect the control chamber to the reference chamber by opening the reference chamber valve and equalizing pressures between the control chamber and the reference chamber, measure a third equalized pneumatic pressure in the control and reference chambers. The controller is configured to compute a control chamber volume based on an ideal gas model under a polytropic process, and is configured to select a polytropic coefficient for the model using a pre-determined function in which the value of the polytropic coefficient depends on and varies with the control chamber volume.

The pre-determined function can be determined by fixing the control chamber volume at a known volume, and calculating a polytropic coefficient corresponding to the known volumes of the control and reference chambers, and the measured first, second and third pressures before and after equalization of pressures. The calculation is repeated a plurality of times, each time corresponding to fixing the control chamber volume at a different known volume. The function can correspond to a stored look-up table from which the controller selects a polytropic coefficient corresponding to the volume of the control chamber being computed. Or the function can correspond to an equation that has been fitted to a plurality of calculated polytropic coefficients corresponding to a series of known control chamber volumes.

In another aspect, A method for the measuring a volume comprises: providing a chamber defined by one or more rigid impermeable boundaries and one movable impermeable boundary, wherein the volume of the chamber varies; fixing the movable boundary; charging the chamber with a gas to a pre-charge pressure value above ambient pressure and allowing the gas to come to thermal equilibrium with the boundaries of the chamber; recording the pressure in the chamber as the first pressure; releasing the movable boundary and allowing the gas in the chamber to displace the movable boundary, which displaces a volume of fluid equivalent to the volume swept by the movable boundary; allowing the gas in the chamber to again come to thermal equilibrium with the boundaries of the chamber; recording the volume of displaced fluid; recording the pressure in the chamber as the second pressure; and determining the volume of the chamber before displacement based on the first pressure, the second pressure, the volume of displaced fluid, and an ideal gas model of the chamber gas between the recording of the first pressure and the recording of the second pressure.

The ideal gas model can assume an isothermal process between the recording of the first pressure and the recording of the second pressure. The method can further comprise determining the volume of the chamber after displacement based on the first pressure, the second pressure, the volume of displaced fluid and an ideal gas model of the chamber gas between the recording of the first pressure and the recording of the second pressure.

In another aspect, a method is disclosed for calibrating a known volume-measurement-procedure comprising: providing a liquid pump apparatus having a pump chamber separated from a pump control chamber by a movable membrane, and a reference chamber that is fluidly connectable to the pump control chamber, wherein the pump chamber is selectively connected to a liquid volume measurement device; filling the liquid side of the pump chamber so it occupies most of the pump control chamber; making a first provisional measurement of the pump control chamber volume using a known volume measurement procedure; charging the pump control chamber with a gas to a pre-charge pressure value and allowing the gas to come to thermal equilibrium with the boundaries of the pump control chamber; firstly recording the pressure in the pump control chamber as the first pressure; connecting the pump to the volume measurement device, so that the charge pressure displaces the membrane, which displaces liquid; allowing the gas in the pump control chamber to come to thermal equilibrium with boundaries of the pump control chamber; recording the volume of displaced fluid measured by the volume measurement device; secondly recording the pressure in the pump control chamber as the second pressure; determining the volume of the pump control chamber before displacement based on the first pressure, the second pressure, the volume of displaced fluid and an ideal gas model of the gas in the control chamber between the recording of the first pressure and the recording of the second pressure; and calculating a first calibration coefficient based on the volume of the pump control chamber and the first provisional volume measurement.

The method can further comprise: repeating the steps of making, charging, firstly recording the pressure, connecting, allowing, recording the volume, secondly recording the pressure, and determining until substantially all the liquid in pump chamber has been expelled; storing the calibration coefficient and the provisional volume measurements as a related pairs; and fitting a calibration equation to the stored values of calibration coefficient as a function of the related provisional volume measurements. The accuracy of the determined volumes of the pump control chamber can be improved by averaging 1) a given determined volume, 2) the preceding determined volume plus the preceding displaced water volume, and 3) the following determined volume minus the following displaced water volume. The accuracy of the first determined volume of the pump control chamber can also be improved by averaging 1) the first determined volume, and 2) the following determined volume minus the following displaced water volume. The accuracy of the last determined volume of the pump control chamber can also be improved by averaging 1) the last determined volume, and 2) the preceding determined volume plus the preceding displaced water volume.

Determining the volume of the pump control chamber can be based on the ideal gas model assumes a polytropic process with an expansion coefficient near 1. The method can further: execute a plurality of pumping strokes with the liquid pump apparatus, wherein the known volume-measurement-procedure occurs after each fill and deliver stroke and the volume of liquid displaced by the liquid pump apparatus is recorded for each stroke; correcting the volumetric results of the known volume-measurement-procedure with the calibration equation; calculating a volume measurement error based on the corrected volumetric results and the recorded volume of displaced liquid; re-determining the volumes of the pump control chamber before displacement based an ideal gas model, where the polytropic coefficient is adjusted based on the volume measurement error; re-calculating the calibration coefficients; re-correcting the volumetric results of the known volume-measurement-procedure with the re-calculated calibration equation; and re-calculating the volume measurement error based on the re-corrected volumetric results and the recorded volume of displaced liquid.

In another aspect, a system is disclosed for measuring an amount of liquid in a pumping chamber of a pneumatically actuated diaphragm pump comprising: a fluid inlet and fluid outlet valve connected to the pumping chamber; a diaphragm separating a pneumatically actuated control chamber from the pumping chamber, the control chamber fluidly connected to a reference chamber of known volume via a conduit that includes a reference chamber valve; the control chamber fluidly connected via one or more actuation valves to a source of positive or negative pneumatic pressure; a controller configured to control the fluid inlet and outlet valves, the reference chamber valve, and the one or more actuation valves, and to receive pressure data from a first pressure sensor connected to the actuation chamber and a second pressure sensor connected to the reference chamber; wherein the controller is configured to isolate the pumping chamber by closing the fluid inlet and outlet valves, charge the control chamber with a first pneumatic pressure; vent the reference chamber or fix a pneumatic pressure in the reference chamber that is different from the control chamber pneumatic pressure; measure a first control chamber pressure and a first reference chamber pressure, connect the control chamber to the reference chamber by opening the reference chamber valve and equalizing pressures between the control chamber and the reference chamber, measure a third equalized pneumatic pressure in the control and reference chambers, and compute a control chamber volume based on an ideal gas model under a polytropic process, wherein the controller is configured to select a polytropic coefficient for the model using a pre-determined function in which the value of the polytropic coefficient depends on and varies with an estimate of the control chamber volume that is calculated from the first control chamber pressure, the first reference chamber pressure and the third equalized pressure based on an ideal gas model.

The pre-determined function optionally can be determined by fixing the control chamber volume at a known volume, and calculating the estimate of the control chamber volume and a polytropic coefficient corresponding to the known volumes of the control and reference chambers, and the measured first, second and third pressures before and after equalization of pressures; wherein said calculation is repeated a plurality of times, each said time corresponding to fixing the control chamber volume at a different known volume. The function can correspond to a stored look-up table from which the controller selects a polytropic coefficient corresponding to the estimate of control chamber volume being computed. The function can also correspond to an equation that has been fitted to a plurality of calculated polytropic coefficients corresponding to a series of estimated control chamber volumes.

In another aspect, a system is disclosed for measuring an amount of liquid in a pumping chamber of a pneumatically actuated diaphragm pump comprising: a fluid inlet and fluid outlet valve connected to the pumping chamber; a diaphragm separating a pneumatically actuated control chamber from the pumping chamber, the control chamber fluidly connected to a reference chamber of known volume via a conduit that includes a reference chamber valve; the control chamber fluidly connected via one or more actuation valves to a source of positive or negative pneumatic pressure; a controller configured to control the fluid inlet and outlet valves, the reference chamber valve, and the one or more actuation valves, and to receive pressure data from a first pressure sensor connected to the actuation chamber and a second pressure sensor connected to the reference chamber; wherein the controller is configured to isolate the pumping chamber by closing the fluid inlet and outlet valves, charge the control chamber with a first pneumatic pressure; vent the reference chamber or fix a pneumatic pressure in the reference chamber that is different from the control chamber pneumatic pressure; measure a first control chamber pressure and a first reference chamber pressure, connect the control chamber to the reference chamber by opening the reference chamber valve and equalizing pressures between the control chamber and the reference chamber, measure a third equalized pneumatic pressure in the control and reference chambers, and compute a control chamber volume based on an ideal gas model under a polytropic process, wherein the controller is configured to select a polytropic coefficient for the model using a pre-determined function in which the value of the polytropic coefficient depends on and varies with the control chamber volume.

The pre-determined function optionally can be determined by fixing the control chamber volume at a known volume, and calculating a polytropic coefficient corresponding to the known volumes of the control and reference chambers, and the measured first, second and third pressures before and after equalization of pressures; wherein said calculation is repeated a plurality of times, each said time corresponding to fixing the control chamber volume at a different known volume. The function can correspond to a stored look-up table from which the controller selects a polytropic coefficient corresponding to the volume of the control chamber being computed. The function can also correspond to an equation that has been fitted to a plurality of calculated polytropic coefficients corresponding to a series of known control chamber volumes.

In another aspect, a method is disclosed for calibrating a known volume measurement procedure of claim 2a, wherein the accuracy of the determined volumes of the pump control chamber are improved by averaging 1) a given determined volume, 2) the preceding determined volume plus the preceding displaced water volume, and 3) the following determined volume minus the following displaced water volume.

In another aspect, a system is disclosed for calculating a change in fluid volume in a pumping chamber of a pneumatically actuated diaphragm pump using a gas having a heat capacity ratio of n. The system comprises a control chamber separated from the pumping chamber by a flexible diaphragm; a fluid inlet or outlet of the pumping chamber; a valve connecting the control chamber to a pressurized source of the gas; a pressure sensor fluidly connected to the control chamber; and a controller that receives pressure data from the pressure sensor, that controls the valve, and that is configured to regulate pressure in the control chamber by opening or closing the valve. The controller is configured to compute a change in volume of the control chamber as fluid enters or leaves the pumping chamber by monitoring a pressure change in the control chamber when the valve is closed. This computation assigns a first chamber volume to a first measured pressure, and calculates a second chamber volume based on a second later measured pressure using an equation in which a ratio of the second measured pressure to the first measured pressure is assumed to be equal to a ratio of the first chamber volume to the second chamber volume, raised to a power between 1 and n.

The assigned first chamber volume can be derived from an initial condition in which the control chamber is pressurized with air, the pumping chamber and control chamber are isolated, a measurement of control chamber pressure is taken, the control chamber is connected to a reference chamber having a known volume and measured pressure, and the controller derives an initial volume of the control chamber using a model based on an ideal gas equation. The controller can calculate a third chamber volume as fluid continues to enter or leave the pumping chamber by assigning the second chamber volume to the second measured pressure and calculating a third chamber volume based on a third measured pressure using an equation in which a ratio of the third measured pressure to the second measured pressure is assumed to be equal to a ratio of the second chamber volume to the third chamber volume, raised to a power between 1 and n. The controller can calculate a fluid flow into or out of the pumping chamber based on a difference between the first, second and third chamber volumes. The controller can repeat the calculations periodically during a time period in which fluid continues to enter or leave the pumping chamber, and can suspend the calculations during a time period in which the valve is opened to connect the control chamber with the pressurized source of the gas. The pressurized source of the gas can be a positively pressurized source or a negatively pressurized source. The gas can be air. The value of n can be approximately 1.4. The value of n can be adjusted by the controller by comparing a cumulative calculated volume of fluid moved into or out of the pumping chamber during a pump stroke to a volume change in the pumping chamber calculated from an initial volume determination at a beginning of the pump stroke and a final volume determination at an end of the pump stroke.

In another aspect, a method is disclosed for determining an amount of fluid delivered by a diaphragm pump having a pumping chamber separated from a pneumatically actuated control chamber by a diaphragm, and having pneumatically actuated inlet and outlet valves. The method is implemented by a controller that closes the outlet valve, opens the inlet valve, and connects the control chamber to a negative pressure source to apply negative pneumatic pressure to the diaphragm pump to draw fluid into the pumping chamber. The controller closes the inlet valve, connects the control chamber to the positive pressure source, isolates the control chamber, measures a first control chamber pressure, measures a first reference chamber pressure in a reference chamber having a known volume, connects the control chamber to the reference chamber, and calculates a first volume of the control chamber. It then opens the outlet valve, and connects the control chamber to a positive pressure source to apply a positive pneumatic pressure to the diaphragm pump to expel fluid from the pumping chamber. It then closes the outlet valve; vents the control chamber to reduce pressure in the control chamber toward atmospheric pressure; connects the control chamber to the positive pressure source, isolates the control chamber, measures a second control chamber pressure, measures a second reference chamber pressure, connects the control chamber to the reference chamber, and calculates a second volume of the control chamber; and then determines the amount of fluid delivered by the diaphragm pump based on the first and second volumes of the control chamber.

In another aspect, a method is disclosed for determining an amount of fluid delivered by a pumping cassette comprising a first and a second diaphragm pump each said diaphragm pump having a pumping chamber separated from a pneumatically actuated control chamber by a diaphragm, and each having pneumatically actuated inlet and outlet valves, the method comprising having a controller perform for each of diaphragm pumps the steps of: closing the outlet valve, opening the inlet valve, and connecting the control chamber to a negative pressure source to apply negative pneumatic pressure to the diaphragm pump to draw fluid into the pumping chamber; closing the inlet valve, connecting the control chamber to the positive pressure source, isolating the control chamber, measuring a first control chamber pressure, measuring a first reference chamber pressure in a reference chamber having a known volume, connecting the control chamber to the reference chamber, and calculating a first volume of the control chamber; opening the outlet valve, and connecting the control chamber to a positive pressure source to apply a positive pneumatic pressure to the diaphragm pump to expel fluid from the pumping chamber; closing the outlet valve; venting the control chamber to reduce pressure in the control chamber toward atmospheric pressure; connecting the control chamber to the positive pressure source, isolating the control chamber, measuring a second control chamber pressure, measuring a second reference chamber pressure, connecting the control chamber to the reference chamber, and calculating a second volume of the control chamber; and determining the amount of fluid delivered by the diaphragm pump based on the first and second volumes of the control chamber. Expelling fluid from the pumping chamber of the second diaphragm pump is performed after the control chamber of the first diaphragm pump is vented, and expelling fluid from the pumping chamber of the first diaphragm pump is performed after the control chamber of the second diaphragm pump is vented.

In another aspect, a system is disclosed for measuring a volume of liquid in a pumping chamber of a peritoneal dialysis pump cassette comprising: a base unit in which the pump cassette can be installed, the base unit including a control block having a control chamber depression configured to mate with the pumping chamber of the pumping cassette, and to move a flexible diaphragm between the pumping chamber and the control chamber under positive or negative pneumatic pressure. The control chamber depression is in communication via one or more pump actuation valves in the base unit with a source of positive or negative pressure, and in communication via a vent valve in the base unit with a vent connected to atmospheric pressure. A controller is configured to control the one or more pump actuation valves to operate the pumping cassette to fill the pumping chamber with liquid and to deliver liquid from the pumping chamber. The controller is configured to control one or more pneumatically actuated membrane inlet and outlet valves in the pump cassette via one or more inlet and outlet actuation valves in the base unit connected to the source of positive or negative pneumatic pressure. The controller is also configured to measure pneumatic pressure in the control chamber via a pressure sensor, and to calculate a volume of liquid in the pumping chamber, the calculation involving pneumatically pressurizing the control chamber before taking a pressure measurement. The controller is also configured to connect the control chamber with the vent after commanding a liquid delivery stroke of the pump cassette and before pneumatically pressurizing the control chamber to perform a pumping chamber liquid volume calculation.

In another aspect, a system is disclosed for adjusting negative pressure used to withdraw fluid from a cavity of a patient, the system comprising: a pump configured to provide negative pressure to a fluid line connected to the cavity; a controller configured to measure and control the negative pressure provided by the pump. The controller is also configured to measure a rate of flow of fluid from the fluid line to the pump. The controller is arranged to control the pump by providing a first negative pressure to the fluid line, measuring the rate of fluid flow, and control the pump by providing a second negative pressure to the fluid line that is greater in magnitude than the first negative pressure if the measured rate of fluid flow exceeds a pre-determined value.

A system is also disclosed for adjusting negative pressure used to withdraw fluid from a cavity of a patient. The system comprises: a pump configured to provide negative or positive pressure to a fluid line connected to the cavity; a controller configured to measure and control the pressure provided by the pump. The controller is also configured to measure a rate of flow of fluid from the fluid line to the pump, so that the controller is arranged to control the pump by providing negative pressure to the fluid line, measuring the rate of fluid flow, and control the pump by providing a positive pressure to the fluid line if the measured rate of fluid flow is less than a pre-determined value, and wherein the controller is arranged to re-apply negative pressure to the fluid line if a measured fluid flow upon application of the positive pressure is greater than a pre-determined amount.

A system is also disclosed for adjusting negative pressure used to withdraw fluid from a cavity of a patient, the system comprising: a pump configured to provide negative pressure to a fluid line connected to the cavity; a controller configured to measure and control the pressure provided by the pump. The controller is also configured to measure a flow rate of fluid from the fluid line to the pump. The controller is then arranged to control the pump by providing negative pressure in an amount that varies continuously as a function of the measured flow rate of the fluid, such that the variation in negative pressure applied by the pump is limited to within a pre-determined range of negative pressures.

A system is also disclosed for adjusting negative pressure used to withdraw fluid from a cavity of a patient, the system comprising: a pump configured to provide negative pressure to a fluid line connected to the cavity; a controller configured to measure and control the pressure provided by the pump; the controller also being configured to measure a flow rate of fluid from the fluid line to the pump. A user interface is configured to provide a user a measure of the negative pressure applied by the pump, and configured to receive input from the user to adjust the amount of negative pressure applied by the pump, such that the controller is arranged to receive via the user interface a command from the user to adjust the negative pressure applied by the pump, and to effectuate the adjustment.

A system is also disclosed for adjusting negative pressure used to withdraw fluid from a cavity of a patient, the system comprising: a pump configured to provide negative pressure to a fluid line connected to the cavity; a controller configured to measure and control the pressure provided by the pump; the controller also configured to measure a flow rate of fluid from the fluid line to the pump, and to compute a pumping duration based on the measured flow rate. A user interface is configured to provide a user a measure of the negative pressure applied by the pump, and configured to receive input from the user to adjust the amount of negative pressure applied by the pump, such that the controller is arranged to receive via the user interface a command from the user to adjust the negative pressure applied by the pump, to compute a change in the pumping duration resulting from the adjustment, to display information about the change in pumping duration on the user interface, and to receive from the user a command to proceed or not proceed with the adjustment.

In another aspect, a system is disclosed for performing automated peritoneal dialysis comprising; a cycler comprising a fluid pump and controller, the controller configured to measure and control an amount of fluid pumped to a peritoneal cavity and to track a remaining volume of the fluid in a solution bag. The controller is configured to: control a dialysis therapy by administering a pre-determined number of therapy cycles, each therapy cycle comprising a fill phase, dwell phase and drain phase; and maintain a pre-determined minimum volume of intra-peritoneal fluid during the dwell phase. It is also configured to cancel a final therapy cycle if a calculated final volume of fluid remaining in the solution bag for the final therapy cycle is less than a volume required to maintain the minimum intra-peritoneal fluid volume for the final therapy cycle dwell phase; divide the remaining final volume of fluid in the solution bag among a remaining number of therapy cycle fill volumes; and divide a duration of the final therapy cycle dwell phase among a remaining number of therapy cycle dwell phases. The controller is also configured to further adjust the fill volumes of the remaining number of therapy cycles, or the duration of the dwell phases of the remaining number of therapy cycles to prevent an accumulation of intra-peritoneal fluid during the remaining therapy cycles from exceeding a pre-determined maximum intra-peritoneal volume of fluid.

In another aspect, a system in an automated peritoneal dialysis apparatus is disclosed for replenishing a heater bag with fluid during a dialysis therapy comprising a fluid fill phase, a fluid dwell phase, and a fluid drain phase. The system comprises a controller configured to: track a remaining volume of fluid remaining in the heater bag; compute a replenish volume of fluid to be infused into the heater bag comprising subtracting the remaining volume from a fill volume of fluid to be infused into a patient in a subsequent fill phase of the dialysis therapy; compute a replenish volume transfer time required to transfer the replenish volume from a fluid source to the heater bag; compute a replenish volume heating time required to heat the replenish volume to within a pre-determined range of a pre-determined temperature set point; and compute a remaining dwell time required to complete the fluid dwell phase. The controller is also configured to control a fluid heater of the peritoneal dialysis apparatus to heat the replenish fluid as it enters the heater bag, and to control a fluid pump of the peritoneal dialysis apparatus to initiate pumping of the replenish volume to the heater bag when the remaining dwell time is equal to or greater than the greater of the replenish volume transfer time or the replenish volume heating time.

In another aspect, a system for replenishing a fluid heater bag of a medical fluid delivery apparatus is disclosed, the system comprising: a processor configured to receive temperature data associated with a fluid in the heater bag, to control a heater to heat the fluid in the heater bag, to control a fluid pump to pump the fluid in a replenish operation into the heater bag from a fluid source, to pump the fluid in a fill phase out of the heater bag to a patient, to control a dwell phase during which the fluid remains in the patient, and to pump the fluid in a drain phase out of the patient to a destination. The controller is further configured to determine a replenish volume to be transferred to the heater bag during the replenish operation, the replenish volume determination made by subtracting the volume of fluid in the bag at the beginning of the replenish operation from a volume of fluid to be pumped to the patient in the next fill phase; compute a replenish volume transfer time required to transfer the replenish volume from the fluid source to the heater bag; compute a replenish volume heating time required to heat the fluid to within a pre-determined range of a pre-determined temperature set point; compute a drain time required to complete the drain phase; and control the fluid pump to initiate pumping of the fluid in the replenish operation at a remaining dwell time during the dwell phase that is approximately equal to the greater of (1) the drain time plus the replenish volume heating time or (2) the drain time plus the replenish volume transfer time.

In another aspect, a solution expiration timing system is disclosed for an automated dialysis apparatus connected to a first fluid reservoir and a fluid heating reservoir. The system comprises a controller configured to begin a first solution expiration timer when a fluid is pumped from the first fluid reservoir to the fluid heating reservoir; begin a second solution expiration timer when the fluid in the fluid heating reservoir achieves a pre-determined temperature; wherein the controller is configured to declare a first expiration time when a first pre-determined time interval has elapsed, and to declare a second expiration time when a second pre-determined time interval has elapsed; and wherein the controller stops fluid transfer from the first fluid reservoir to the fluid heating reservoir at the first expiration time, and stops fluid transfer from the fluid heating reservoir to a user at the second expiration time.

In another aspect, a solution expiration timing system is disclosed for an automated dialysis apparatus connected to a first fluid reservoir containing a first fluid and a second fluid reservoir containing a second fluid. The system comprises a controller configured to: begin a first solution expiration timer when the first fluid is pumped from the first fluid reservoir to a fluid heating reservoir; begin a second solution expiration timer when the second fluid is pumped from the second fluid reservoir to the fluid heating reservoir; wherein the controller is configured to declare a first expiration time when a first pre-determined time interval has elapsed, and to declare a second expiration time when a second pre-determined time interval has elapsed; and wherein the controller stops fluid transfer from the first fluid reservoir to the fluid heating reservoir at the first expiration time, and stops fluid transfer from the second fluid reservoir to the fluid heating reservoir at the second expiration time.

In another aspect, a system is disclosed for detecting that a fluid line is primed with liquid. The system comprises a fluid pump having a pumping chamber configured to pump a liquid from a proximal portion to a distal portion of the fluid line at a pre-determined pressure; a sensor configured to measure the flow of liquid in the fluid line or to measure pressure in the pumping chamber to determine the flow of liquid in the fluid line; and a controller configured to receive data from the sensor and to compare the flow of liquid or a change in the flow of liquid in the fluid line with a pre-determined value. The distal portion of the fluid line comprises a flow restrictor that measurably reduces the flow of liquid in the fluid line when air in the distal portion of the fluid line is replaced by the liquid being pumped by the pump; and the controller declares the fluid line to be primed when the reduction in measured liquid flow reaches the predetermined value.

In another aspect, an automated peritoneal dialysis cycler is equipped with an autoconnect apparatus for spiking solution lines for dialysis therapy. A cap detection system is disclosed for detecting the presence of a solution line or spike cap on a cap stripper, the cap detection system comprising: a position sensor for the cap stripper configured to detect a position of the cap stripper relative to a plane in which a plurality of cassette spikes or a plurality of solution lines reside when placed in the cycler; a controller configured to command movement of the cap stripper toward or away from the plane, or laterally in a direction parallel with the plane, and to receive information from the position sensor to compare the position of the cap stripper relative to a first or second pre-determined fully deployed position of the cap stripper toward the plane. The controller is configured to: command the cap stripper to move toward the plane when one or more solution lines are installed in the cycler, and to issue an alert if a cap on the cap stripper prevents a final position of the cap stripper from reaching the first pre-determined fully deployed position; or command the cap stripper to move laterally a pre-determined distance and then toward the plane when no solution lines are installed in the cycler, and to issue an alert if a cap on the cap stripper prevents a final position of the cap stripper from reaching the second pre-determined fully deployed position.

In another aspect, an identification system is disclosed for a fluid line connected to a fluid container for medical use. The system comprises an image sensor configured to read an image generated by fluorescent light, the image comprising a pattern of coded information characterizing the fluid in the container; a fluid line mount configured to hold the fluid line in a fixed position within a field of view of the image sensor; an identification tag attached to a portion of the fluid line on or near the mount; the identification tag having an identifying marking arranged to emit fluorescent light in the pattern of the image in response to absorption of light having a non-visible wavelength; an emitter configured to emit light in the non-visible wavelength onto the identification tag; and a controller configured to receive an electronic signal from the image sensor and to decode the information in the image pattern emitted by the identifying marking of the identification tag.

In another aspect, a brace is disclosed for a distal portion of a fluid line, the fluid line configured to receive a hollow spike in a fluid handling apparatus, the brace comprising: a rigid clamping member configured to encircle the distal portion of the fluid line after being mounted on the distal portion of the fluid line, having one or more features on an inside surface of the clamping member configured to cooperate with one or more complementary features on an outside surface of the distal portion of the fluid line. The brace is arranged to be mountable on the distal portion of the fluid line to constrain it from bending out of alignment with a longitudinal axis of the hollow spike before or after an initiation of a spiking of the distal portion of the fluid line.

In another aspect, an electronic circuit is disclosed for reducing touch or leakage current from a heating element of an automated peritoneal dialysis apparatus. The circuit comprises: a first relay connecting a first pole of an AC mains source to a first end of the heating element; a second relay connecting a second pole of the AC mains source to a second end of the heating element; and a controller configured to control current delivery to the heating element by transmitting an on signal to both the first and second relays or an off signal to both the first and second relays, the on signal causing AC mains current to flow through the heating element, and the off signal preventing AC mains current from flowing through the heating element. The heating element is isolated from AC mains voltage when the controller transmits an off signal.

In another aspect, an electronic circuit is disclosed for delivering electric power to an automated peritoneal dialysis apparatus from a power source having a first voltage or a higher second voltage, the electronic circuit comprising: a heater comprising a first heater element connected to a second heater element by a heater select relay, the heater select relay configured to connect the first heater element either in series or in parallel with the second heater element; a current sense element configured to measure a current flow through the heater; a controller configured to set a default configuration of the heater select relay on powering up so that the first heater element is in series with the second heater element; wherein the controller is programmed to receive information on current flow from the current sense element, and is programmed to command the heater select relay to set the first heater element in parallel with the second heater element if a measured current is less than a pre-determined target current for the heater.

In another aspect, a control system is disclosed for a heater of an automated peritoneal dialysis apparatus comprising: a resistive heating element; a solid state relay connecting an electrical power source to the heating element; a first processor configured to generate and send a pulse width modulated signal to a gating circuit; a second processor configured to generate and send a safety signal to the gating circuit; wherein the gating circuit is configured to reproduce or transmit the pulse width modulated signal to operate the solid state relay if the safety signal is in a first mode, and is configured to prevent the operation of the solid state relay if the safety signal is in a second mode.

The gating circuit optionally can operate the solid state relay through optical transmission. The optical transmission can be performed using a light emitting diode of an opto-isolator. The solid state relay can comprise a triac or a pair of silicon control rectifiers. The solid state relay connects a first pole of an AC mains voltage source to the heating element, and a second solid state relay connects a second pole of the AC mains voltage source to the heating element, such that the pulse width modulated signal reproduced or transmitted by the gating circuit operates both the solid state relay and the second solid state relay. The solid state relay can also connect a first pole of an AC mains voltage source to the heating element, and a second solid state relay connects a second pole of the AC mains voltage source to the heating element, such that a second gating circuit is configured to receive the pulse width modulated signal from the first processor and the safety signal from the second processor, and such that the second gating circuit is configured to reproduce or transmit the pulse width modulated signal to operate the second solid state relay if the safety signal is in the first mode, and is configured to prevent the operation of the second solid state relay if the safety signal is in the second mode.

In another aspect, a housing is disclosed for an automated peritoneal dialysis apparatus comprising: a dual pressure reservoir integrally formed in the housing, the dual pressure reservoir having a first section separated from a second section by a dividing wall; the first section configured for positive air pressurization by a pump via a first port; the second section configured for negative air pressurization by the pump via a second port; and a cover plate for enclosing the first and second sections, said cover plate forming a seal against a perimeter wall of the first section, a perimeter wall of the second section, and the dividing wall between the first and second sections.

A housing is also disclosed for an automated peritoneal dialysis apparatus that comprises: a dual pressure reservoir integrally formed in the housing, the dual pressure reservoir having a first section separated from a second section by a dividing wall; the first section configured for positive air pressurization by a pump via a first port, and comprising a first perimeter wall joining with the dividing wall and a first set of one or more stiffening members extending from a portion of the first perimeter wall to the dividing wall; the second section configured for negative air pressurization by the pump via a second port, and comprising a second perimeter wall joining with the dividing wall and a second set of one or more stiffening members extending from a portion of the second perimeter wall to the dividing wall; and a cover plate for enclosing the first and second sections, said cover plate forming a seal against the first and second perimeter walls and the dividing wall between the first and second sections.

A housing is also for an automated peritoneal dialysis apparatus comprising: a dual pressure reservoir integrally formed in the housing, the dual pressure reservoir having a first section separated from a second section by a dividing wall; the first section configured for positive air pressurization by a pump via a first port, and comprising a first perimeter wall joining with the dividing wall; the second section configured for negative air pressurization by the pump via a second port, and comprising a second perimeter wall joining with the dividing; and a cover plate for enclosing the first and second sections, said cover plate forming a seal against the first and second perimeter walls and the dividing wall between the first and second sections; such that a plurality of stiffening members are attached to an inside surface of the cover plate, so that when the cover plate is attached to the dual pressure reservoir, a first set of said stiffening members extends in the first section from a portion of the first perimeter wall to the dividing wall, and a second set of said stiffening members extends in the second section from a portion of the second perimeter wall to the dividing wall.

A housing is also disclosed for a dual pressure air reservoir comprising: a first reservoir surrounding a second reservoir, the first and second reservoirs separated by a dividing wall, and the first reservoir having an outer perimeter wall; the first reservoir configured for negative air pressurization by a pump via a first port; the second reservoir configured for positive air pressurization by the pump via a second port; a cover plate for enclosing the first and second reservoirs, said cover plate forming a seal against the outer perimeter wall of the first reservoir and the dividing wall between the first and second reservoirs; such that a surface area of the cover plate defined by outer perimeter wall and the dividing wall is greater than a surface area of the cover plate defined by an area within the dividing wall; and such that a depth of the second reservoir is greater than a depth of the first reservoir so that a volume of the first reservoir is approximately equal to a volume of the second reservoir.

BRIEF DESCRIPTION OF THE DRAWINGS

Aspects of the invention are described below with reference to illustrative embodiments that are shown, at least in part, in the following figures, in which like numerals reference like elements, and wherein:

FIG. 2 is a schematic view of an illustrative set for use with the APD system of FIG. 1;

FIG. 45 shows an example screen depicting a result of an identification tag analysis generated for display on a user interface;

FIG. 113B is a flow chart for calibrating partial stroke volumes for the FMS calibration method;

FIG. 113C is a depiction of process used for calibrating partial stroke volumes in the diaphragm pump;

FIG. 113D is a depiction of correction of volume measurements during partial stroke calibration when the pump diaphragm approaches the chamber wall;

FIG. 114 shows a pressure tracing from a control or actuation chamber of a pumping cassette during a liquid delivery stroke;

FIG. 115 shows a graph plotting pressure in a control or actuation chamber during a liquid deliver stroke and a cumulative volume estimation plot during the liquid delivery stroke;

FIG. 116 shows a flowchart outlining a number of steps which may be used to estimate control chamber volume changes over time;

FIG. 117 shows a flowchart outlining a number of steps to adjust an equation used to estimate control chamber volume changes over time during a pump stroke;

FIG. 118 shows a flowchart outlining a number of steps to detect end of stroke based on flow rate during a stroke;

FIG. 119 shows a flowchart outlining a number of steps to determine end of stroke by predicting time necessary to complete a stroke;

FIG. 120 shows a flowchart outlining a number of steps to detect a reduced flow condition while a pump stroke is in progress;

FIG. 121 shows a flowchart outlining a number of steps to determine a target volume of fluid has been moved;

FIG. 122 shows a flowchart outlining steps to detect that fluid line has been primed by estimating flow rate and stroke displacement;

Figure 10:
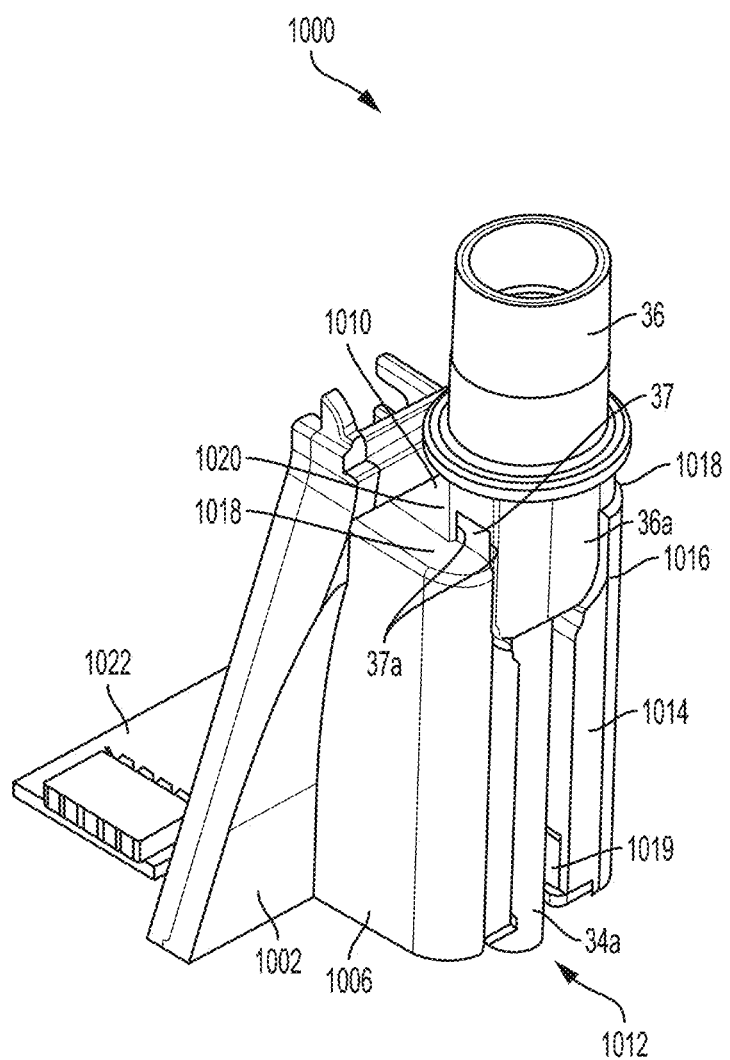
FIG. 10 is a front perspective view of an exemplary configuration of a fluid line state detector or liquid level detector.
Figure 123:
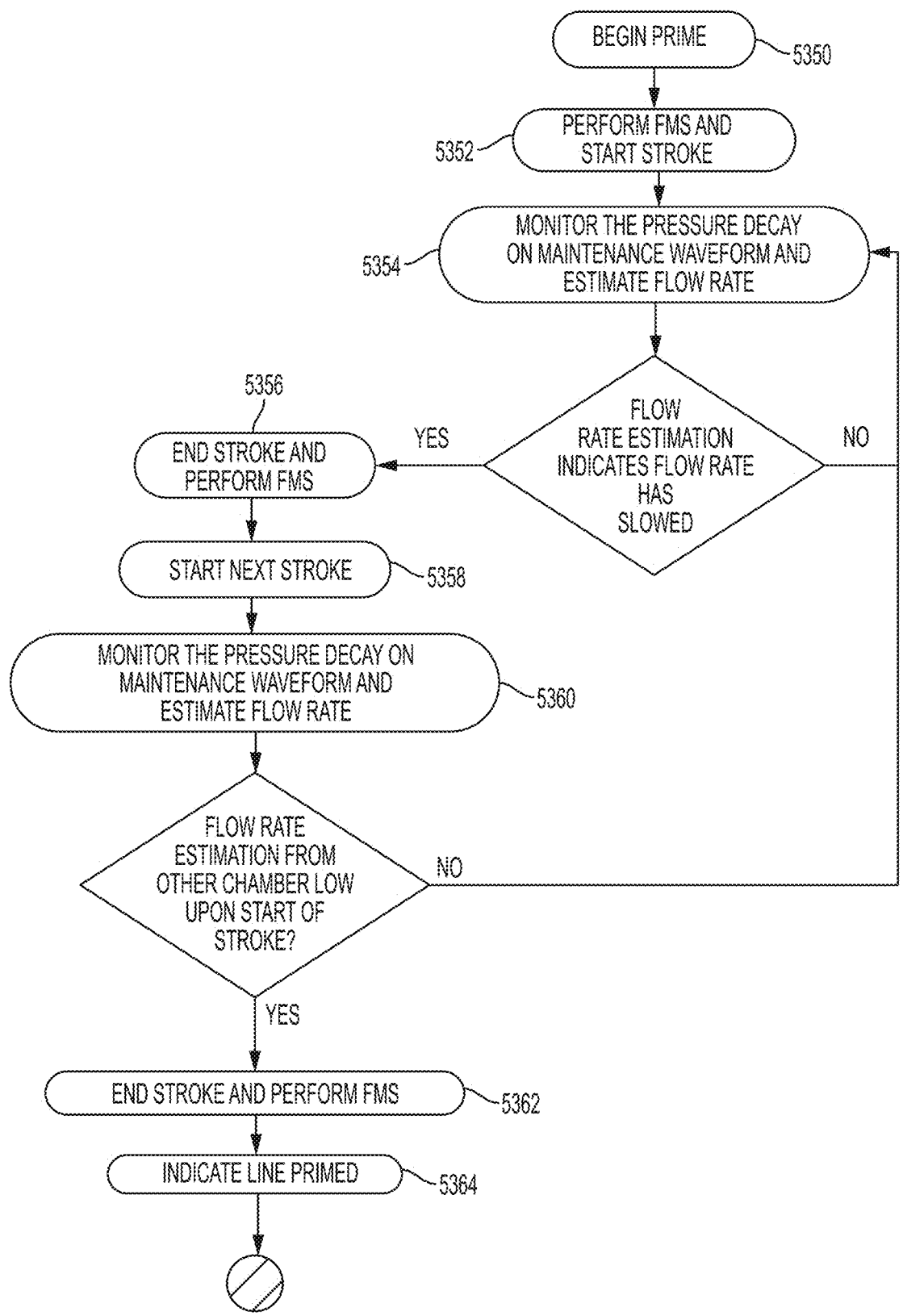
Figure 124:
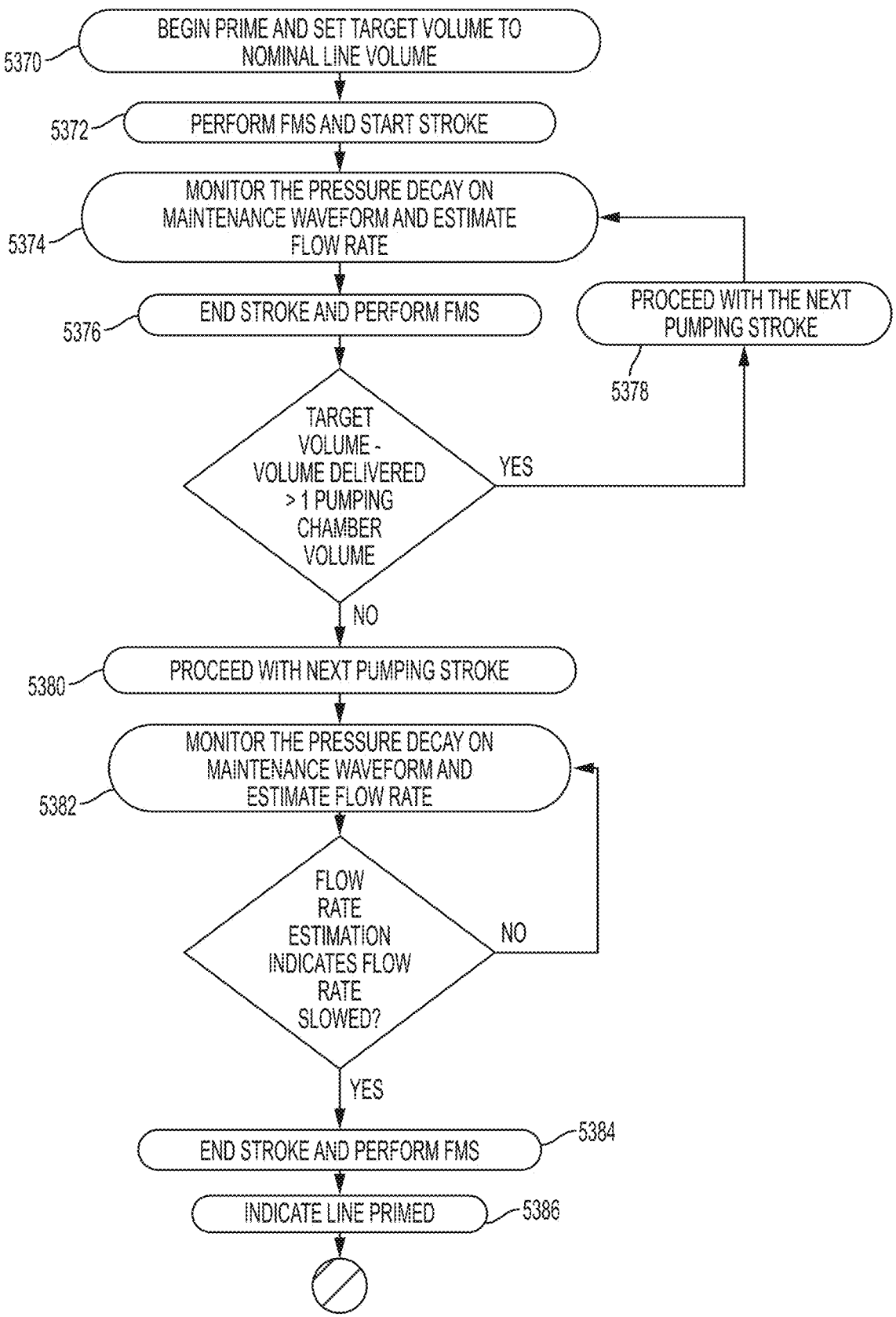
Figure 125:
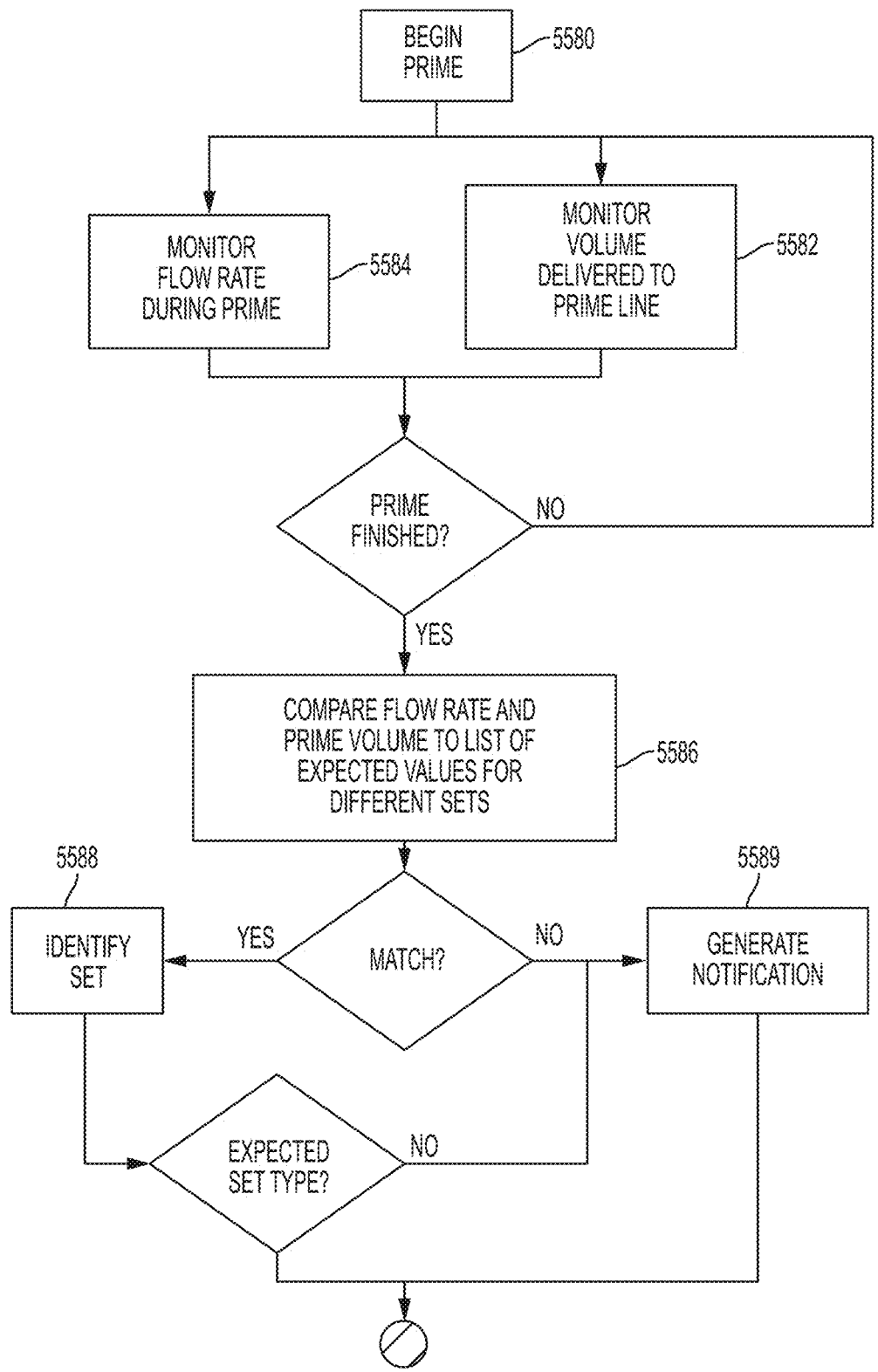
Figure 126:
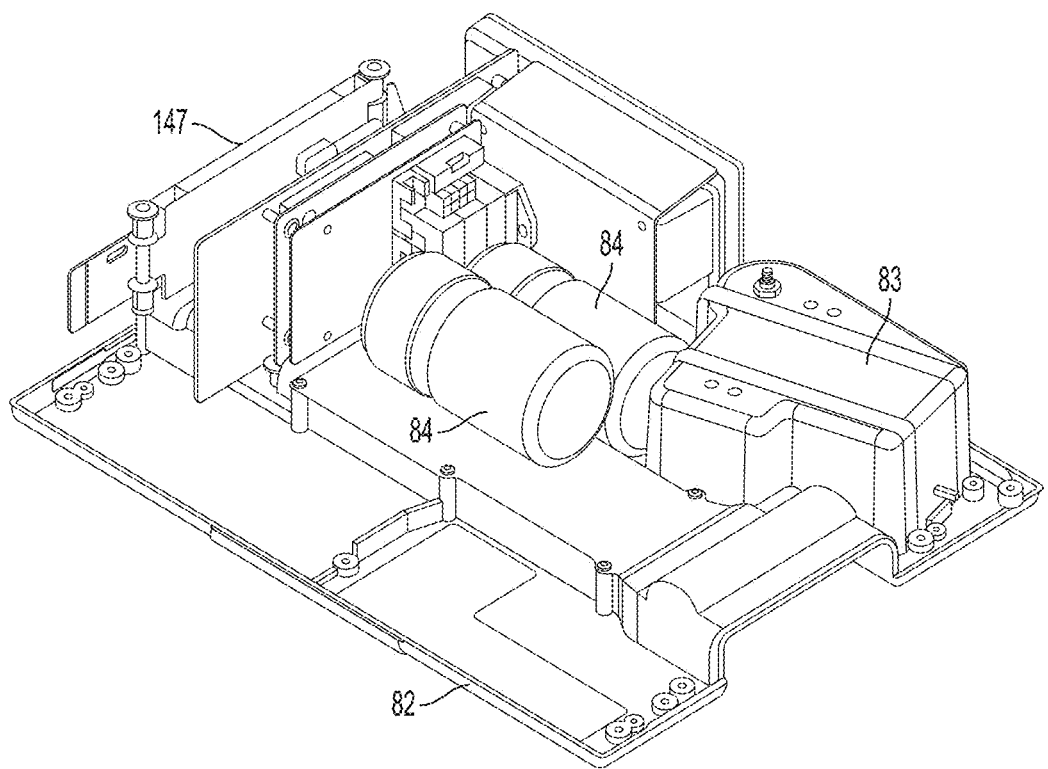
Figure 127:
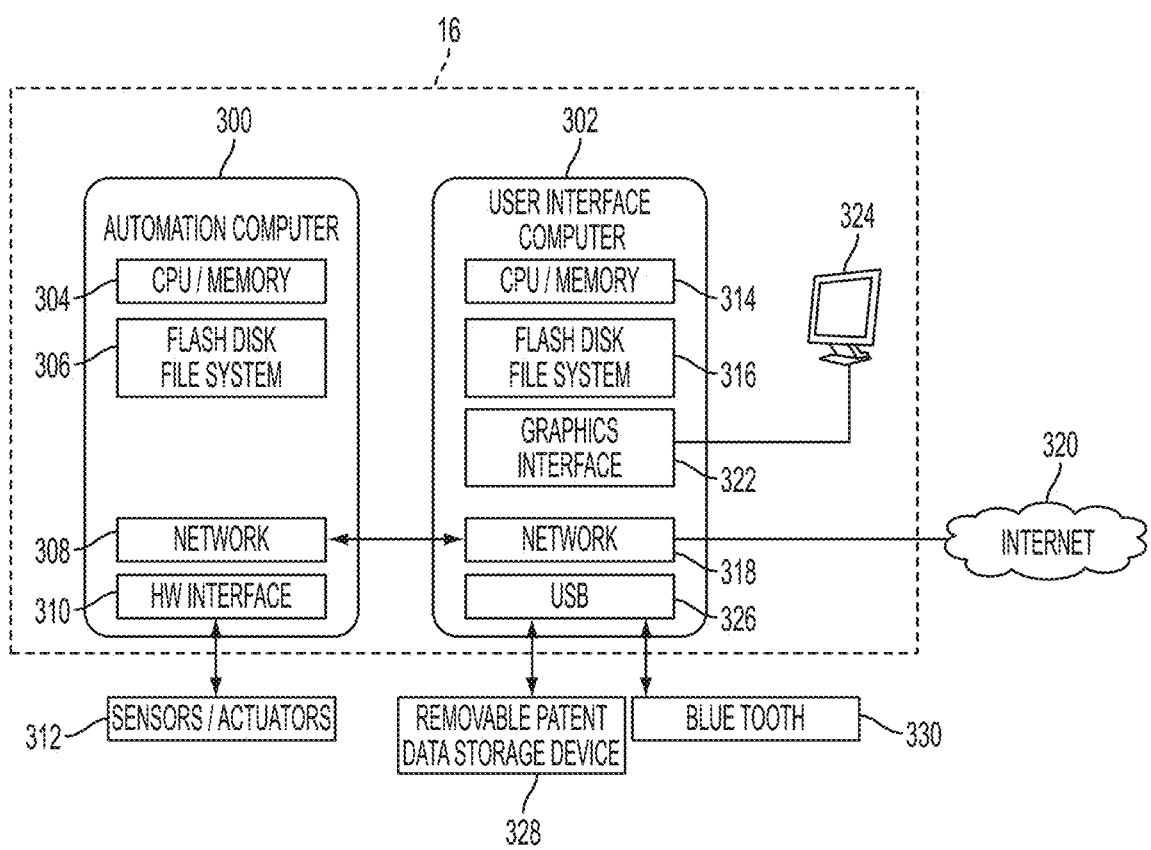
Figure 128:
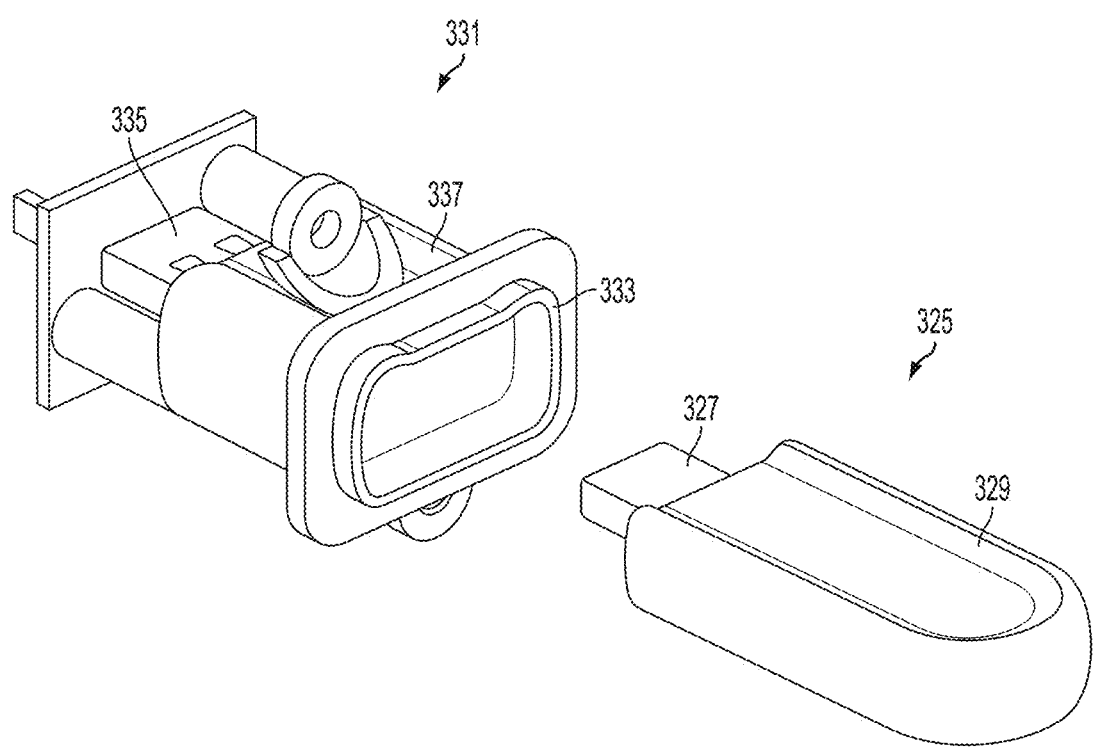
Figure 129:
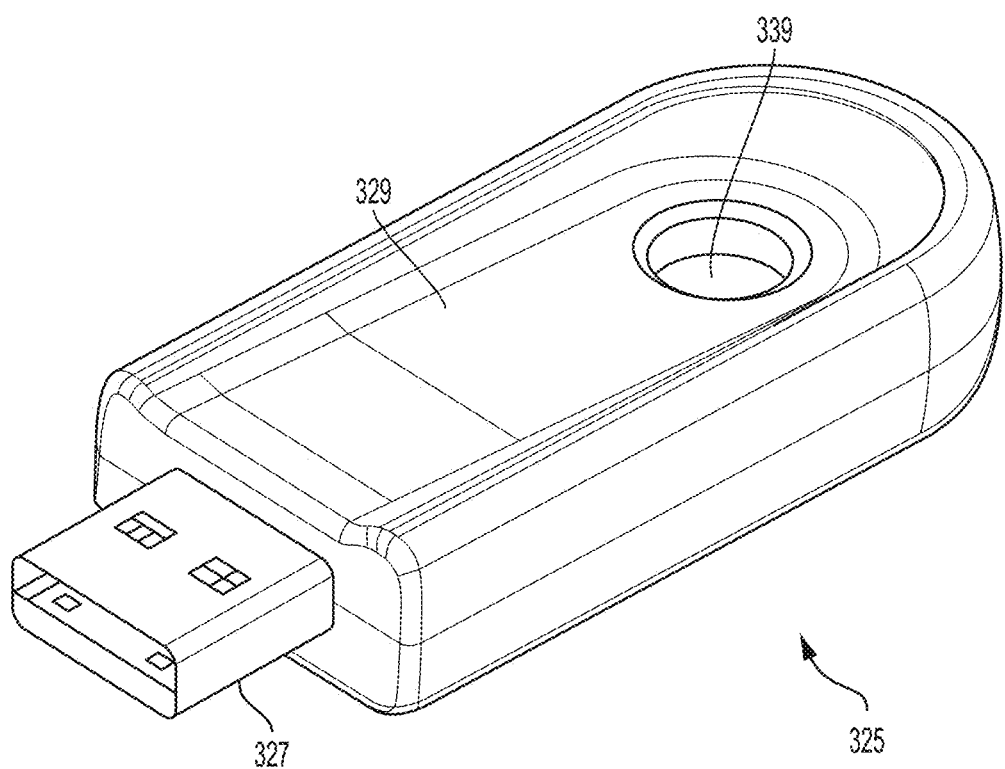
Figure 130:
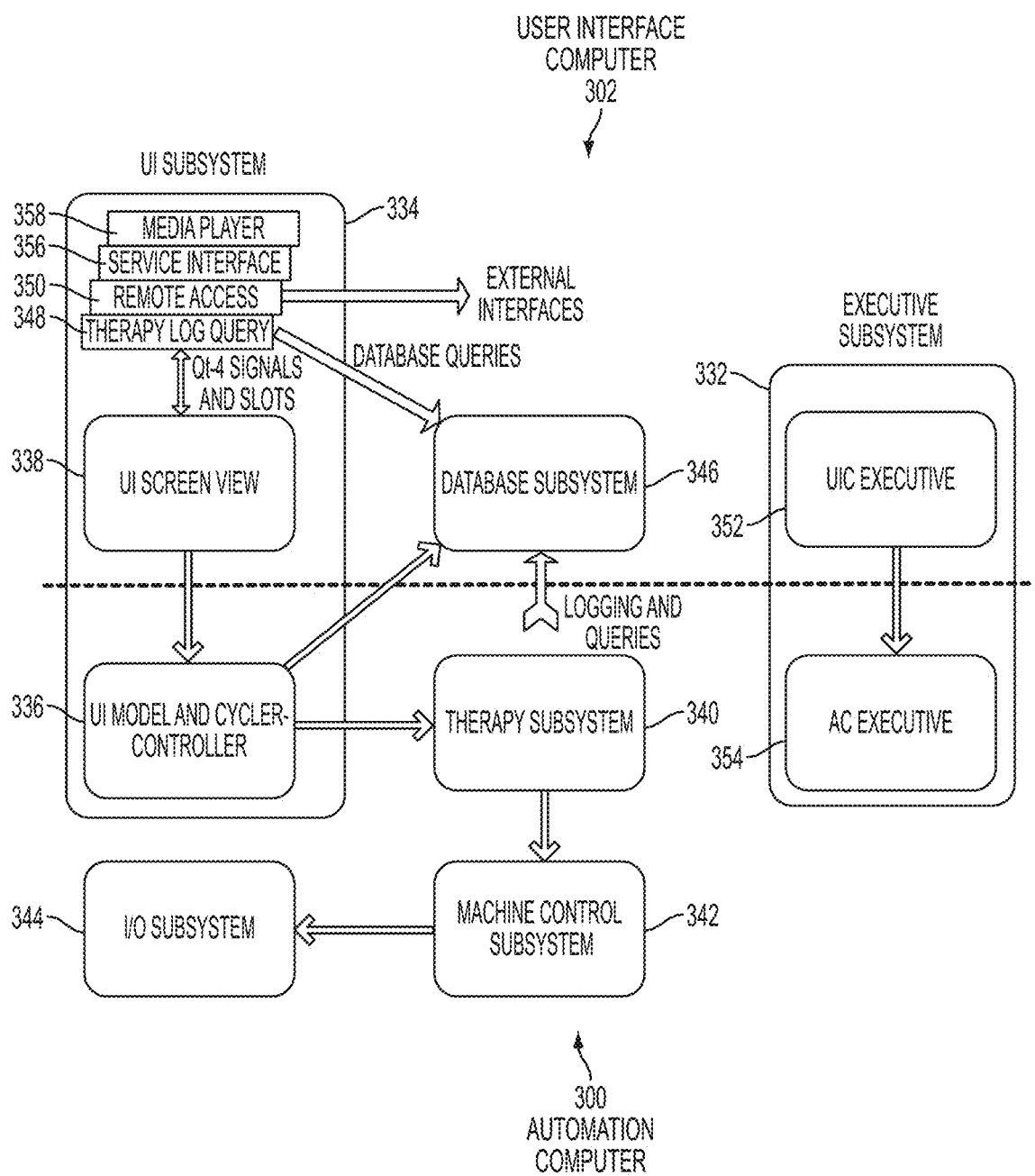
Figure 131:
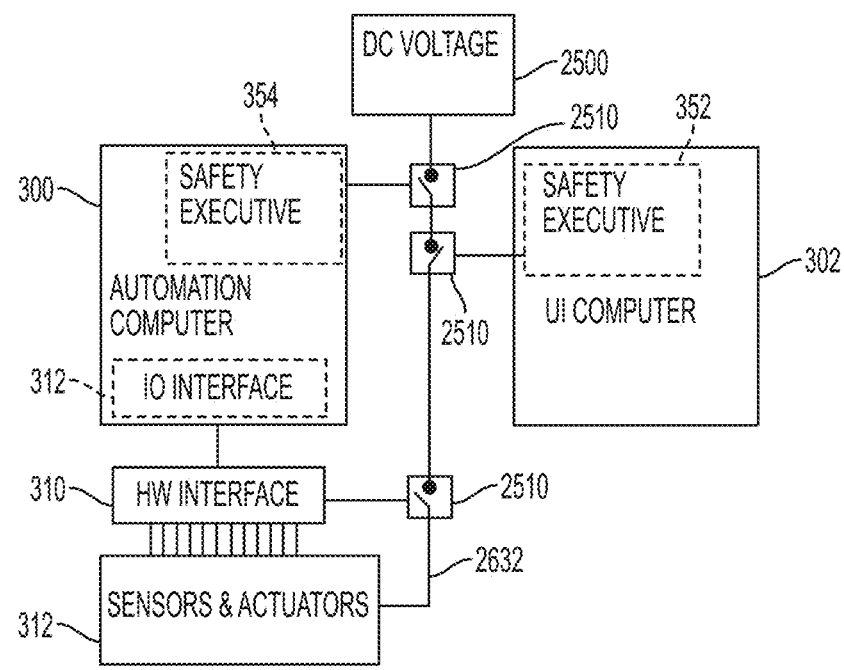
Figure 132:
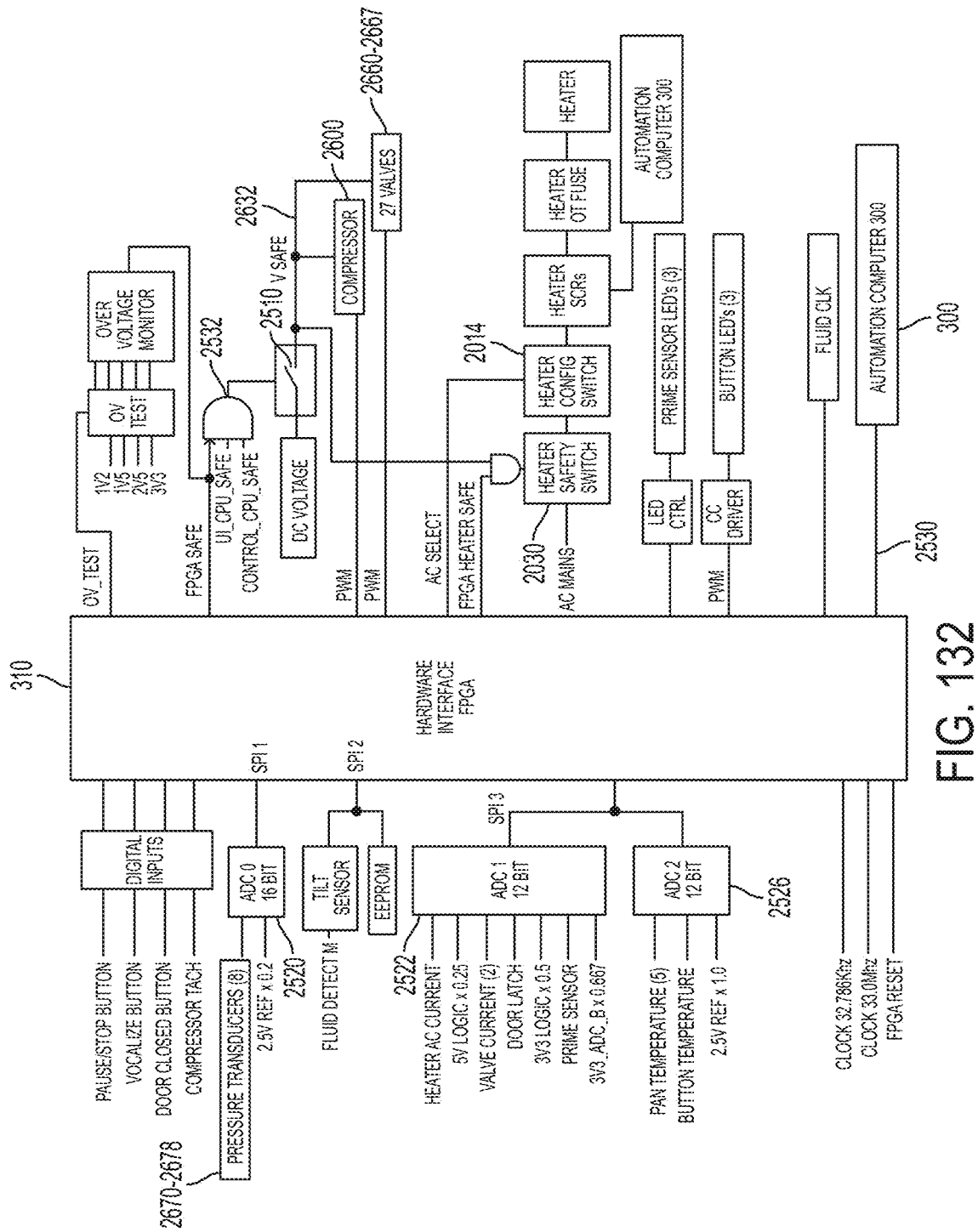
Figure 133:
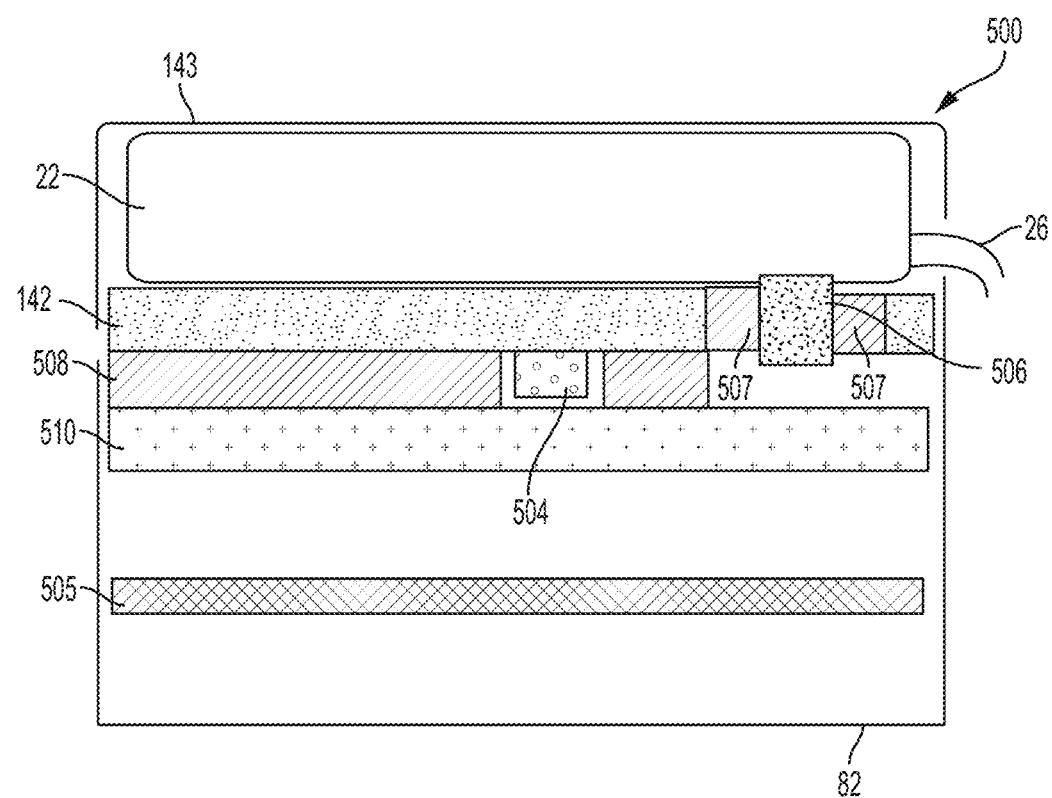
Figure 134:
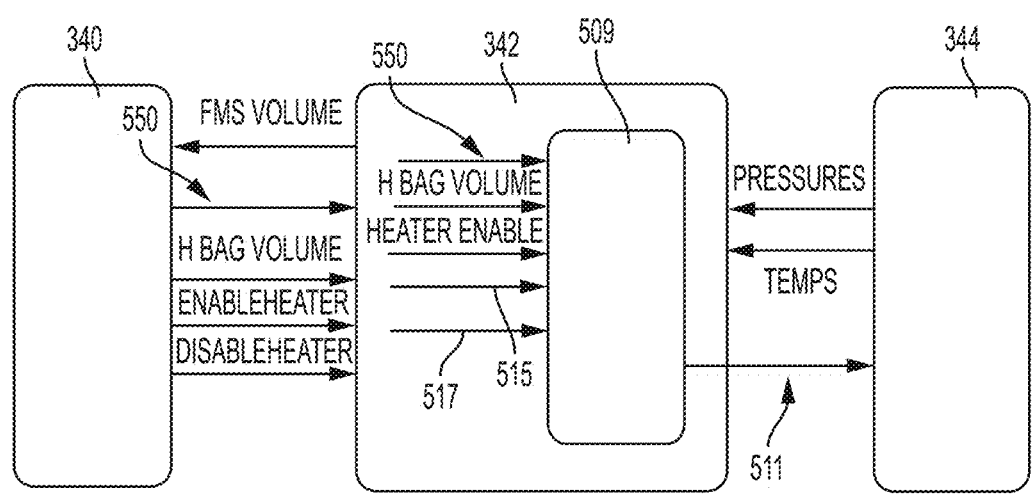
Figure 135:
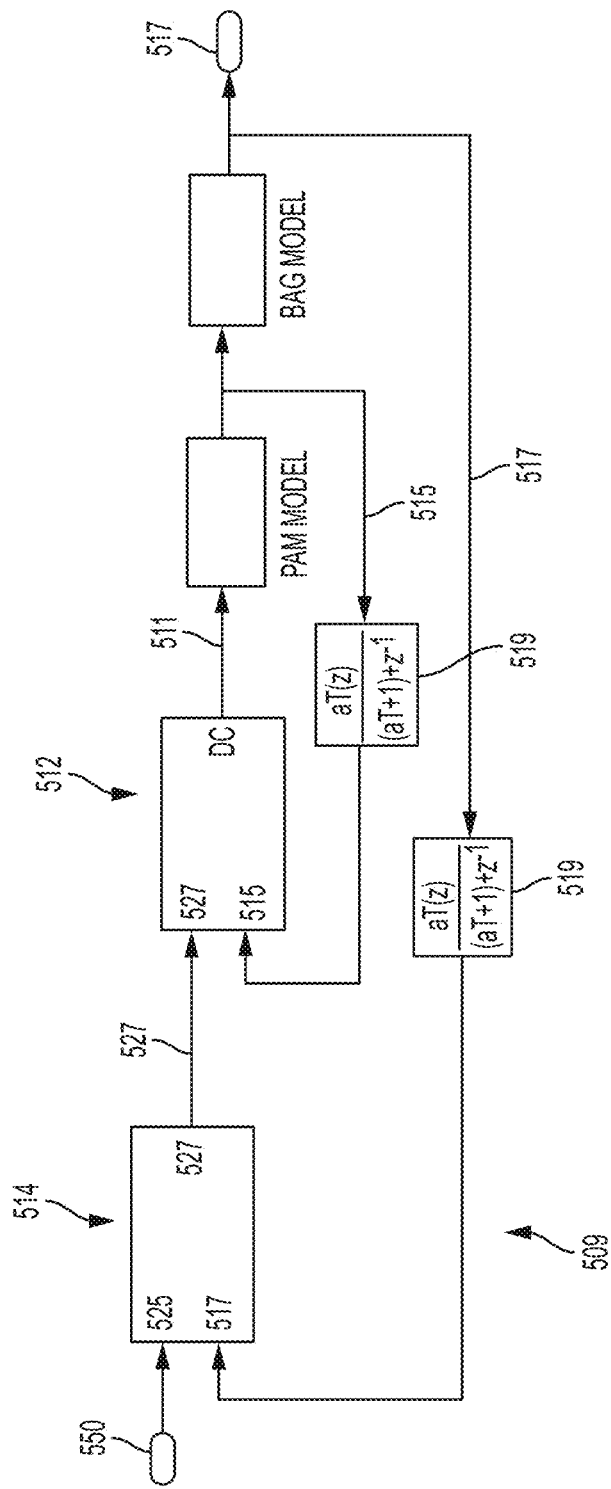
Figure 136:
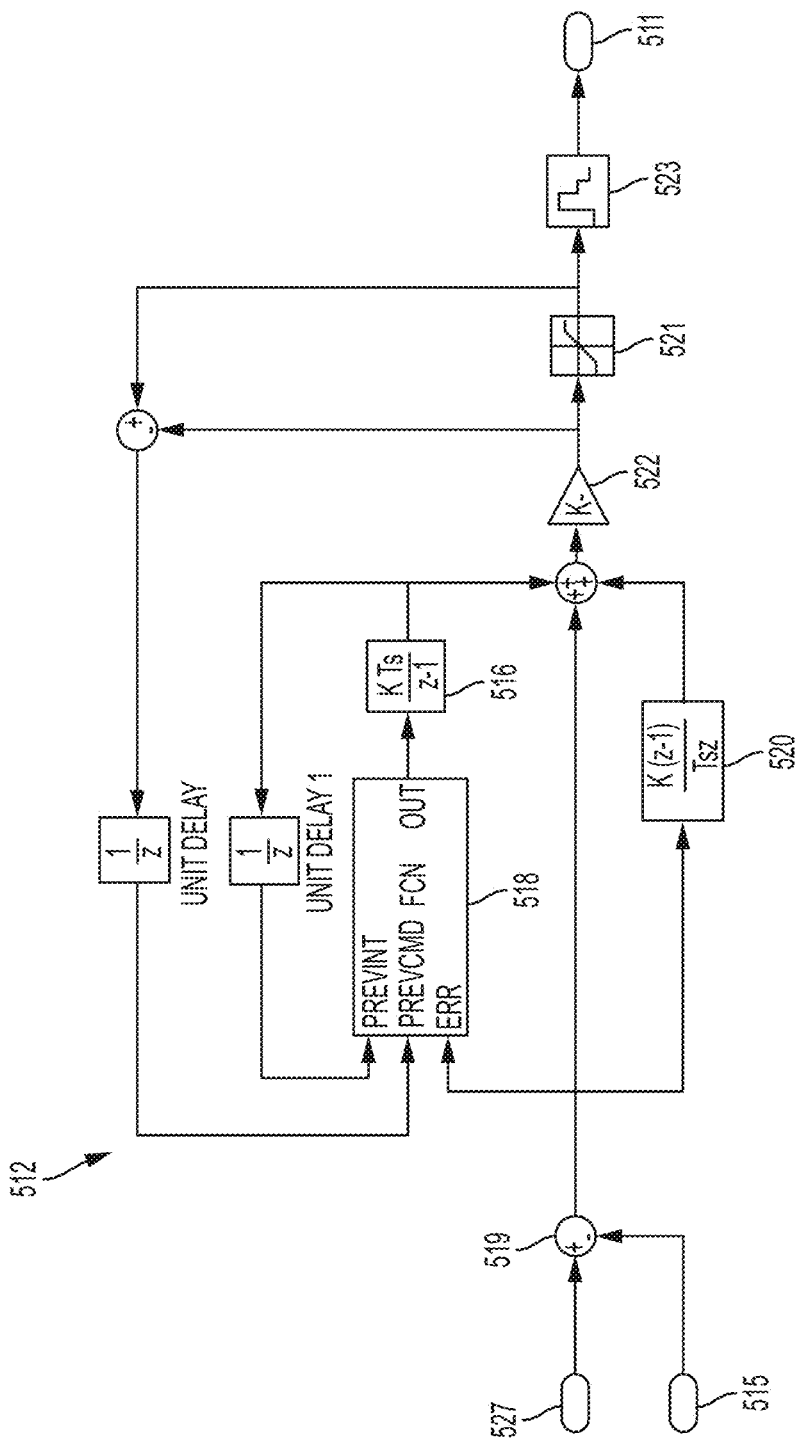
Figure 137:
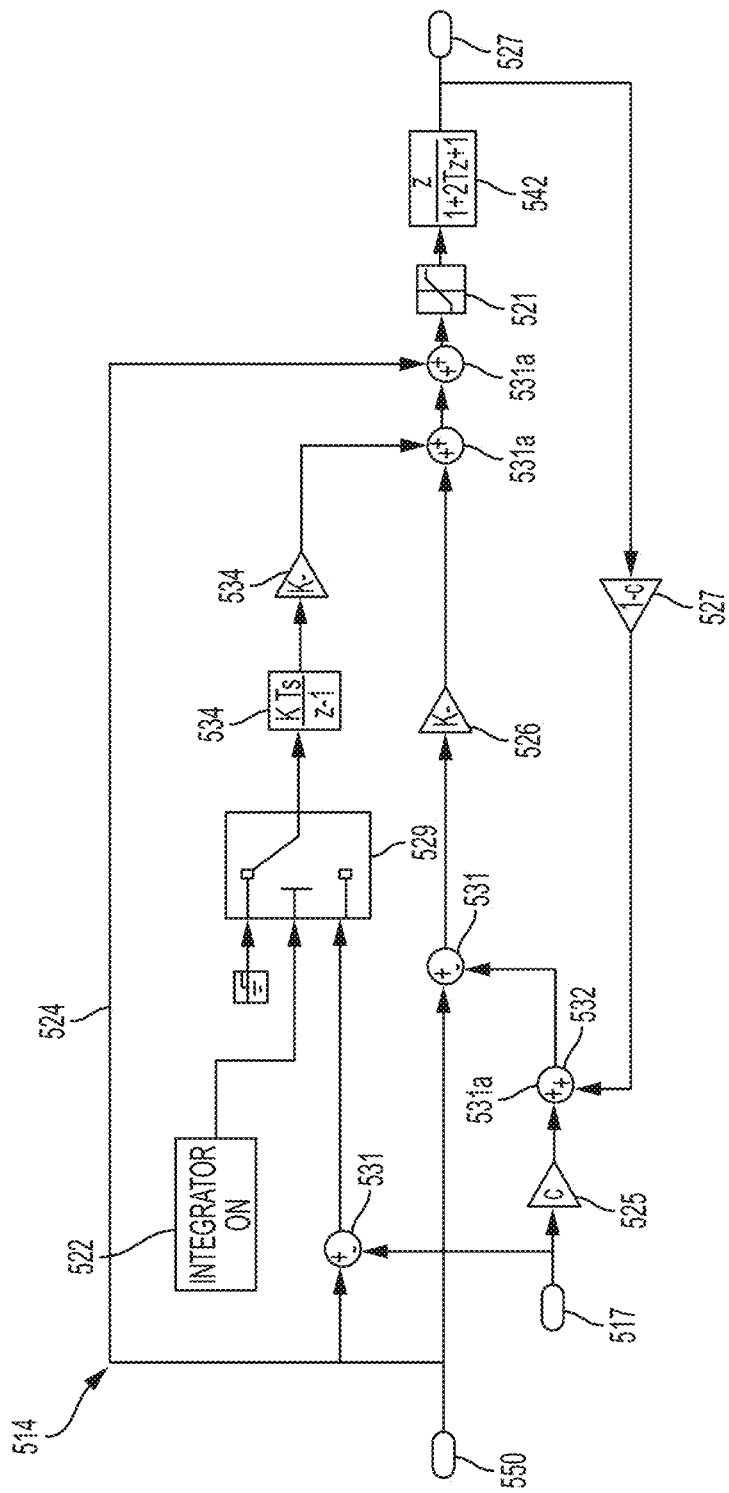
Figure 138:
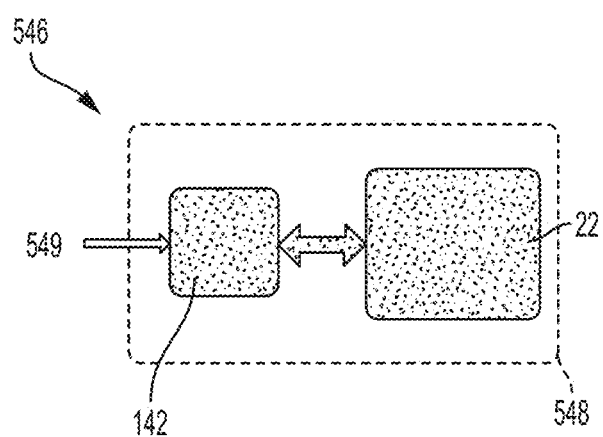
Figure 139:
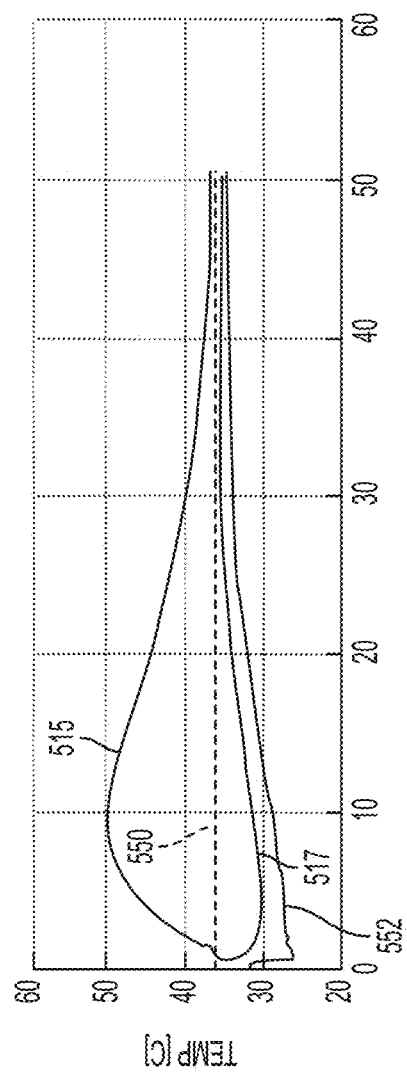
Figure 140:
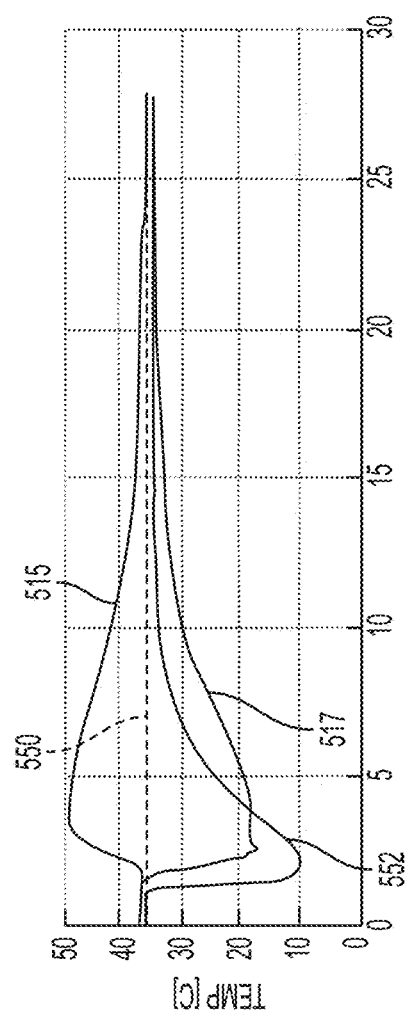
Figure 141:
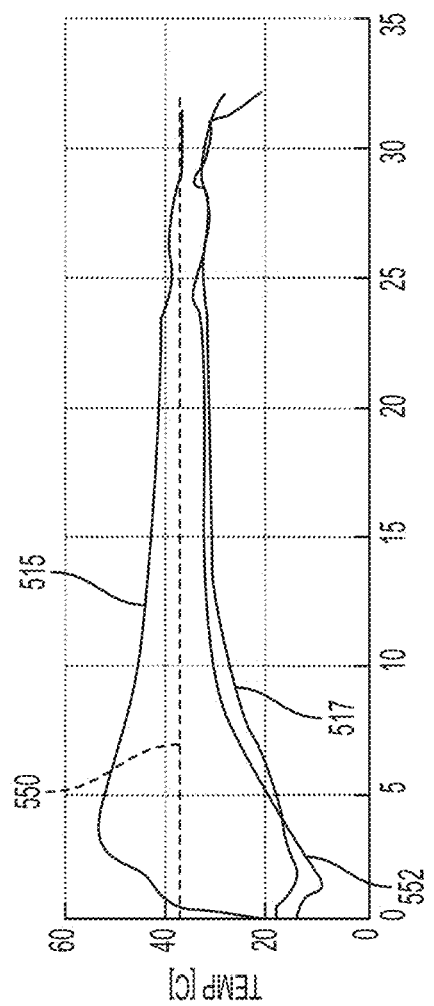
Figure 142:
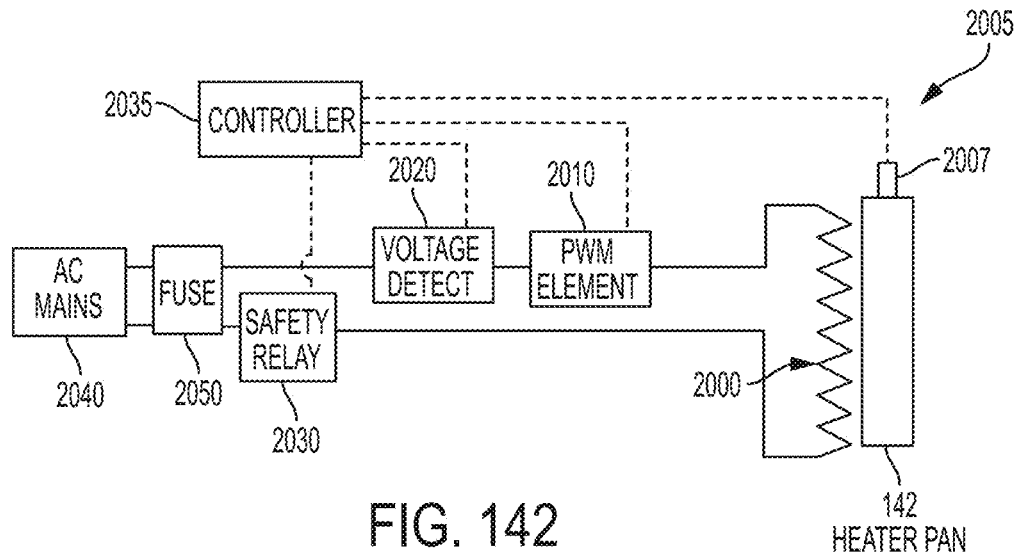
Figure 143:
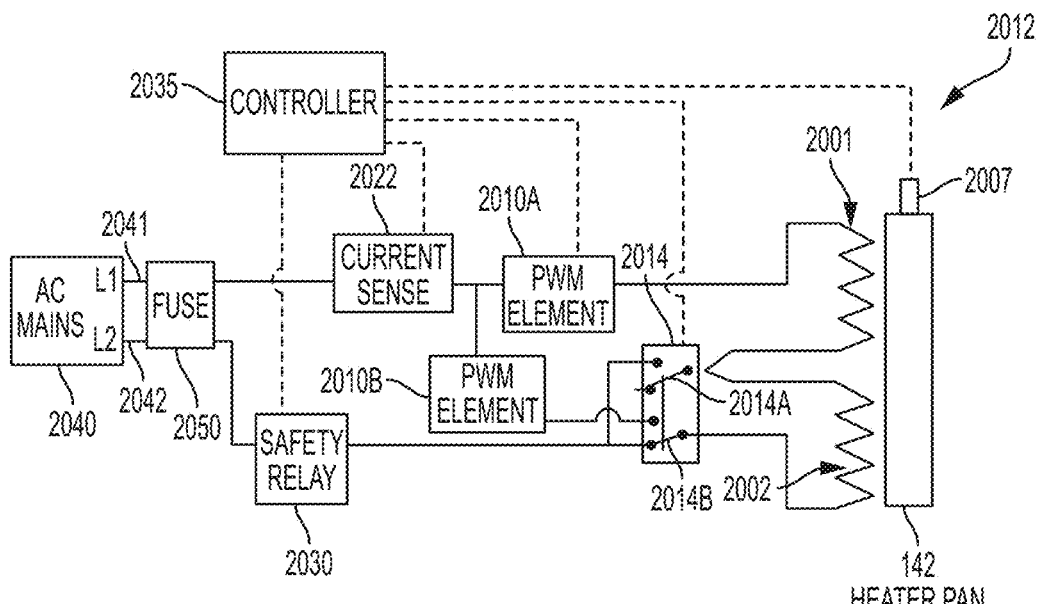
Figure 144:
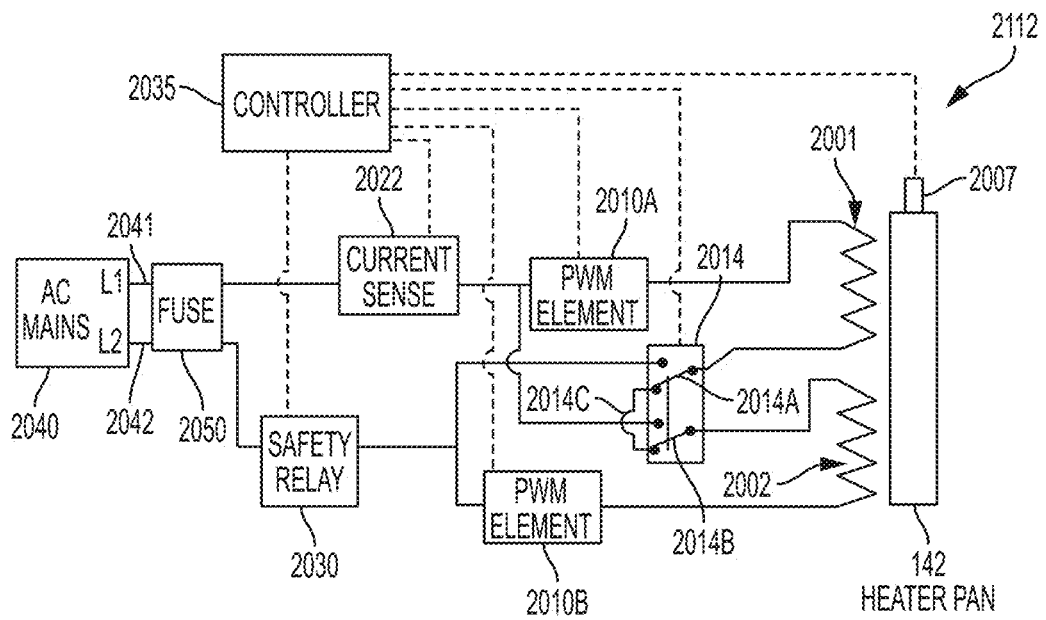
Figure 145:
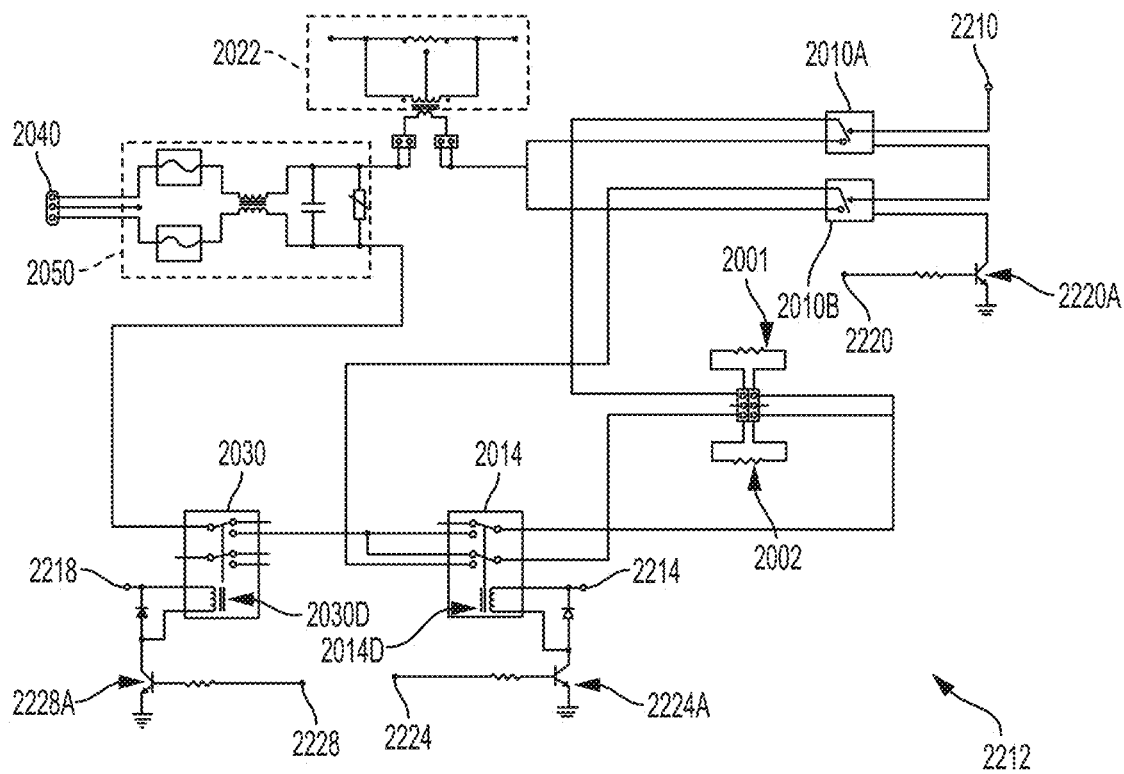
Figure 146:
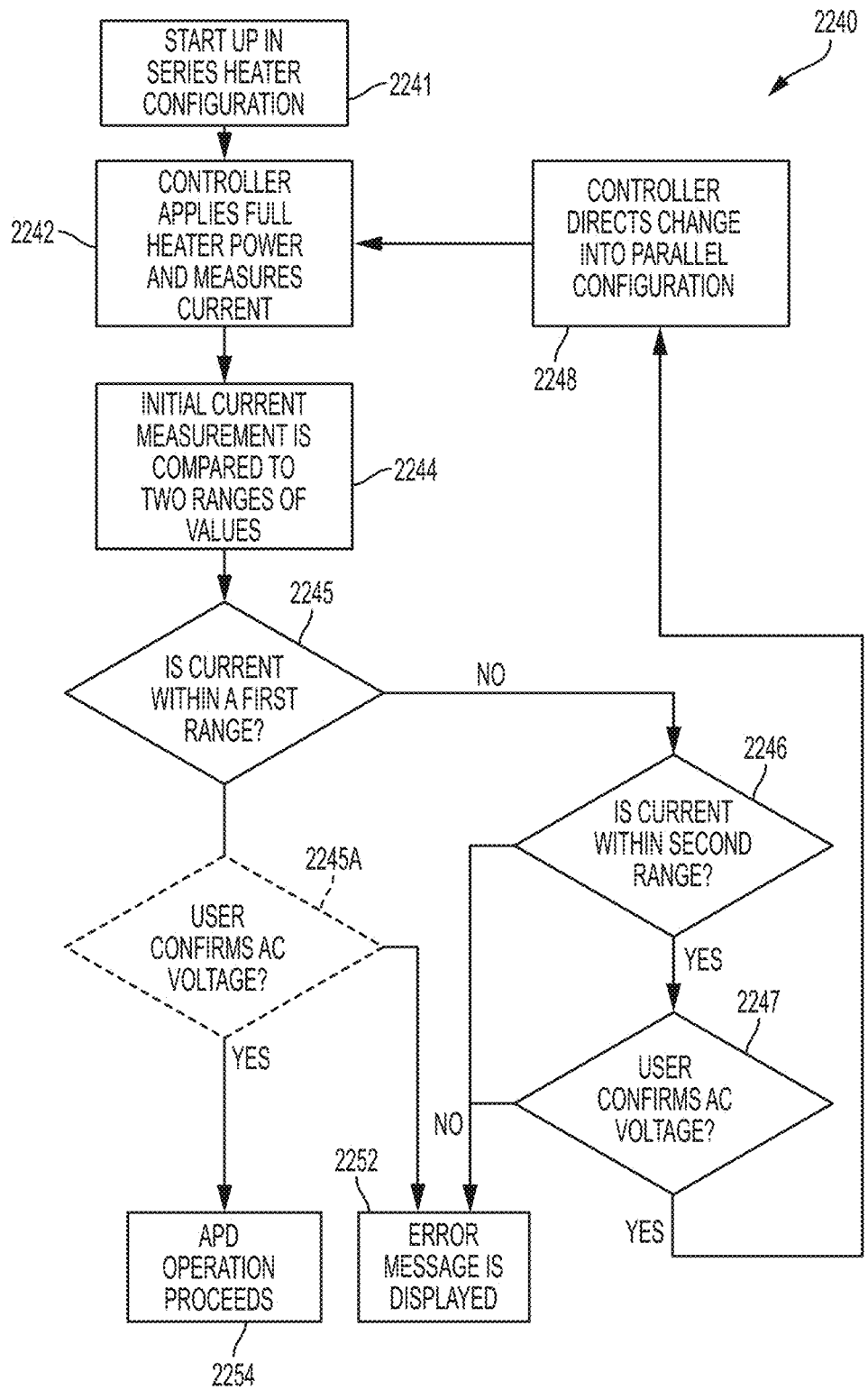
Figure 147:
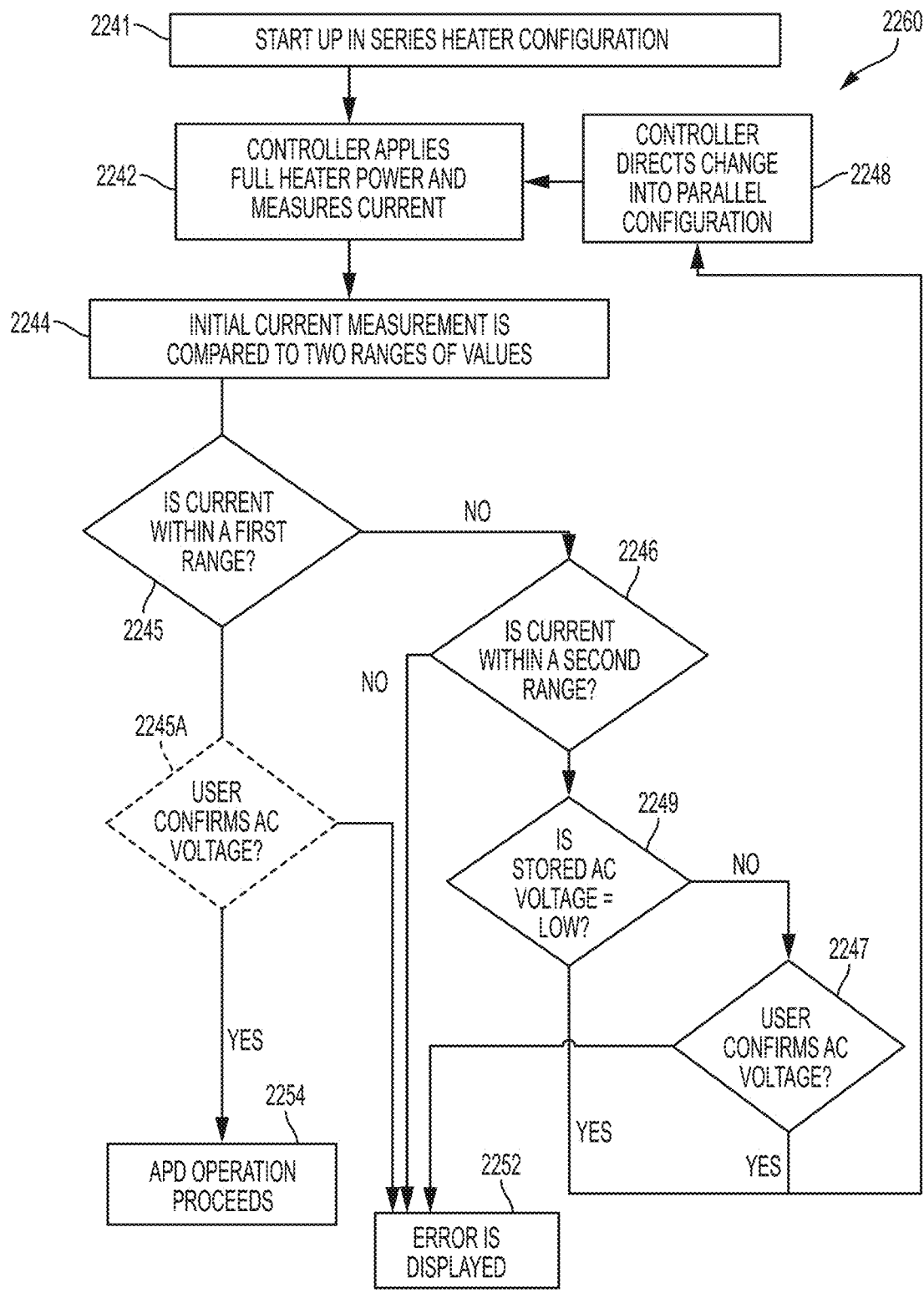
Figure 148:
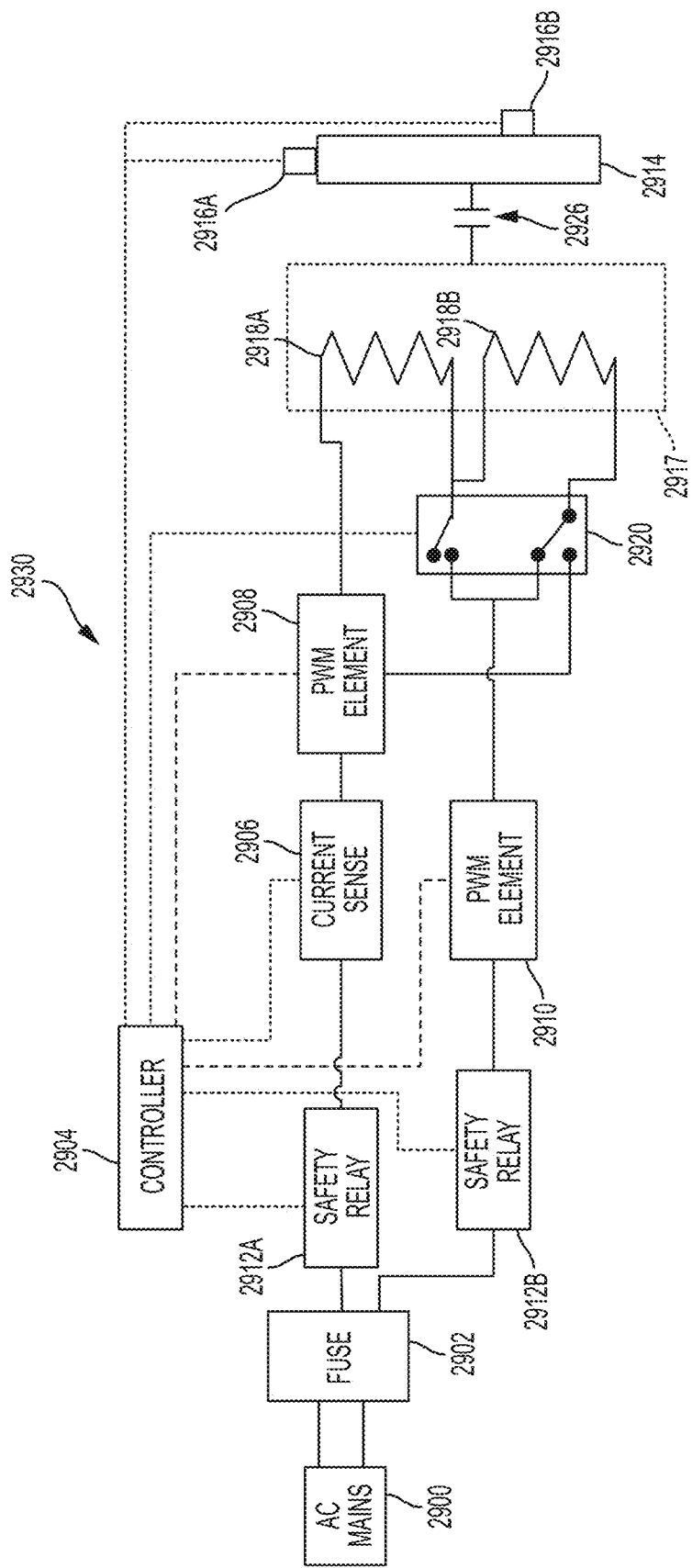
Figure 149:
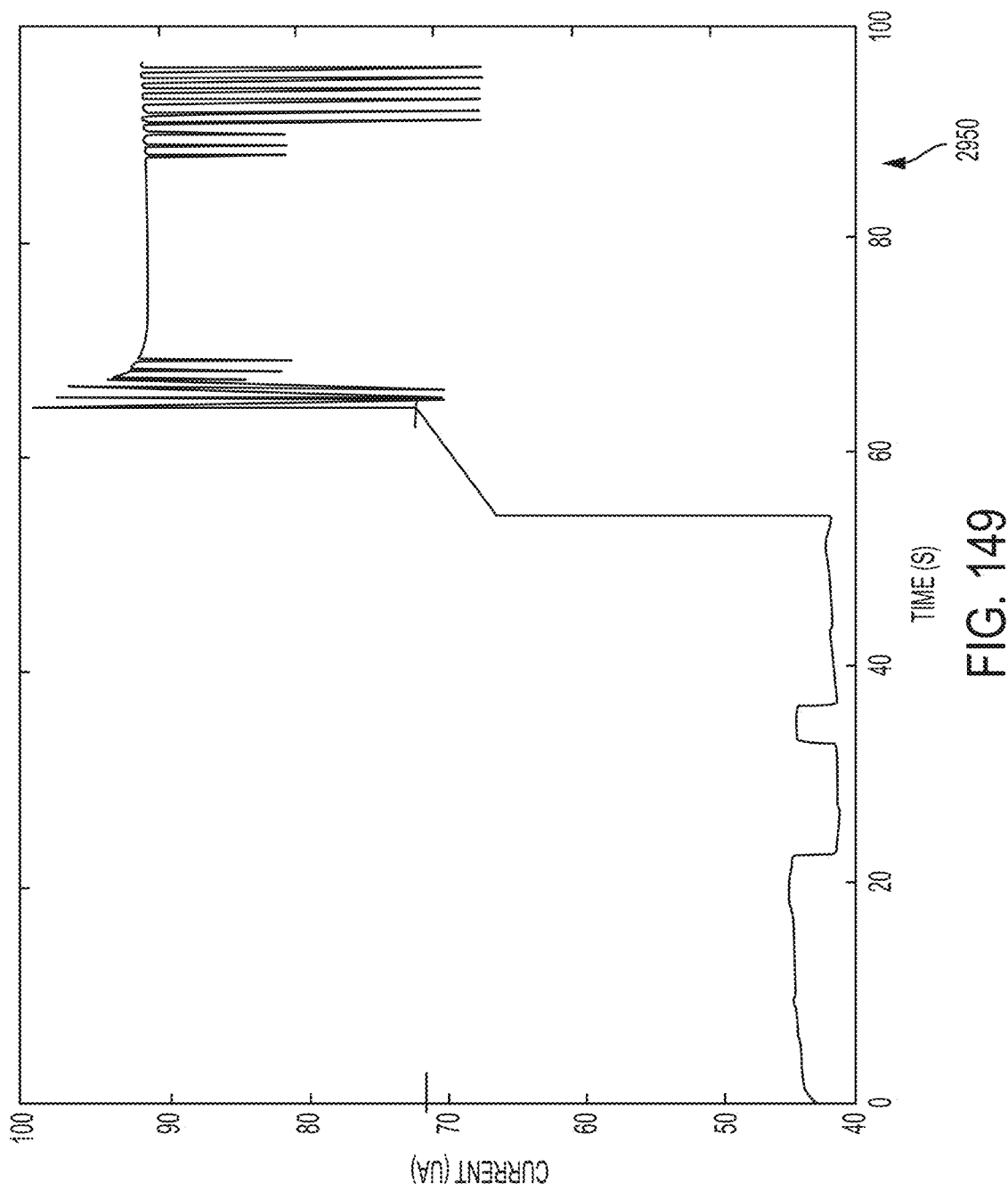
Figure 150:
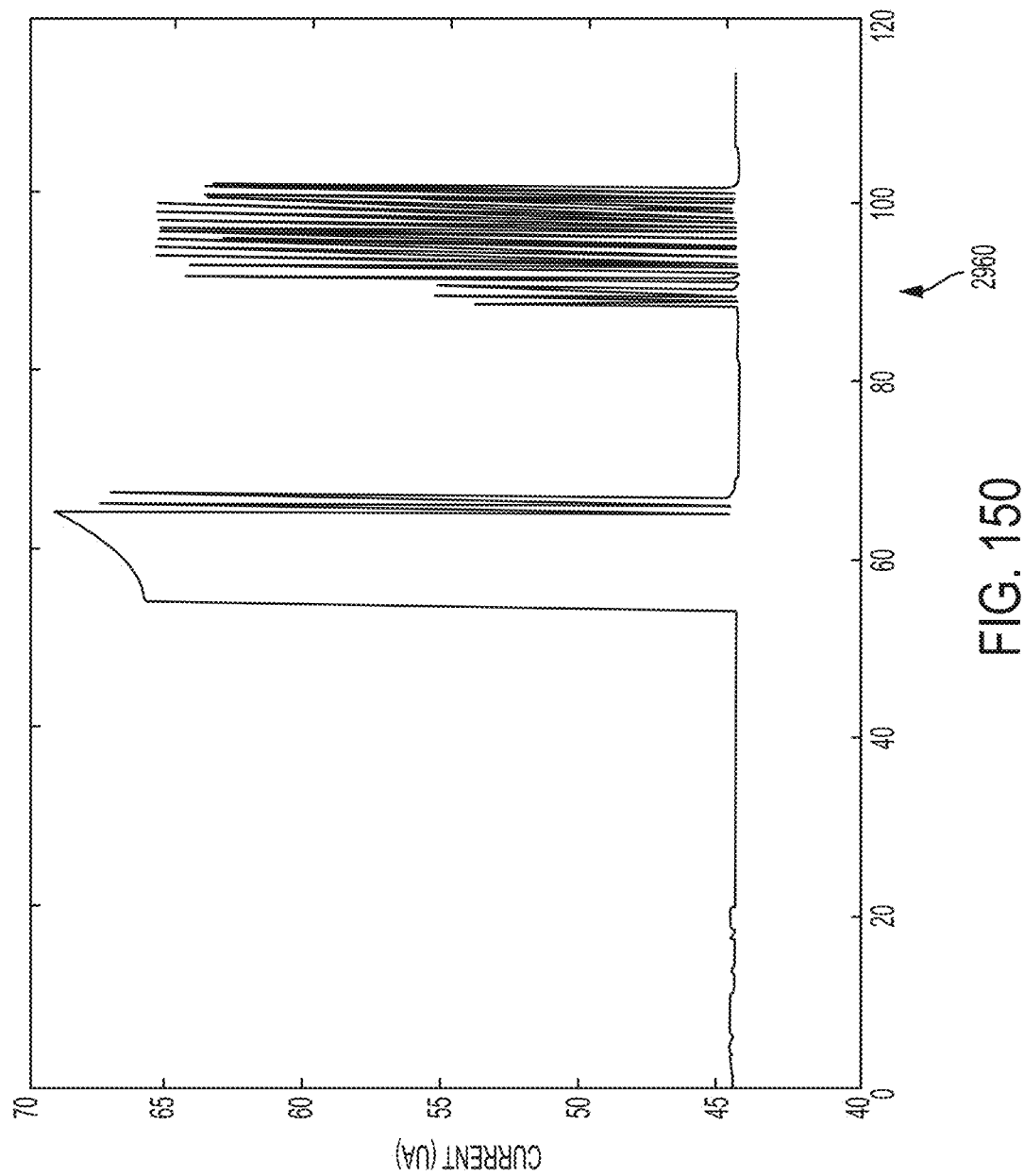
Figure 151:
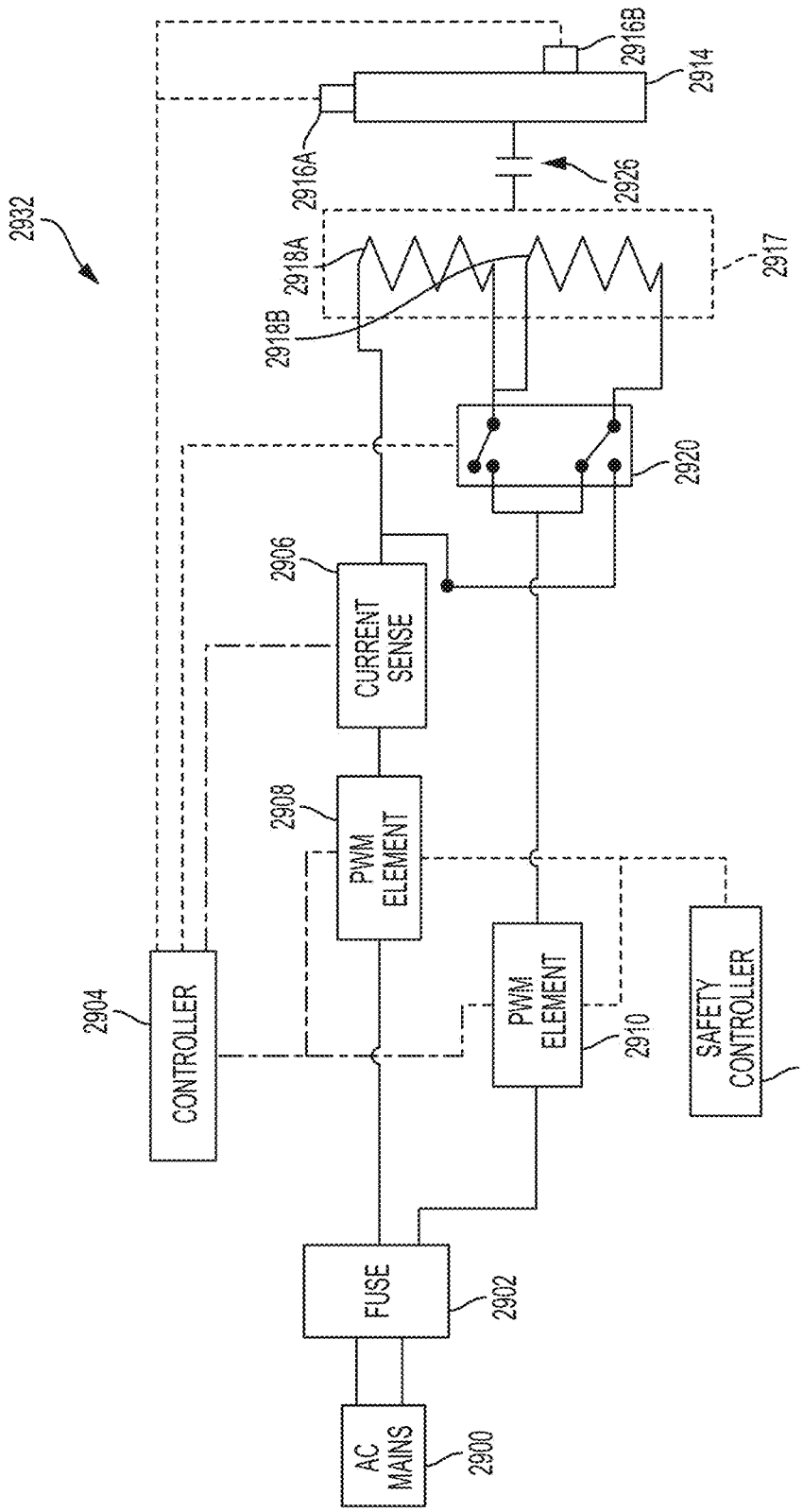
Figure 151A:
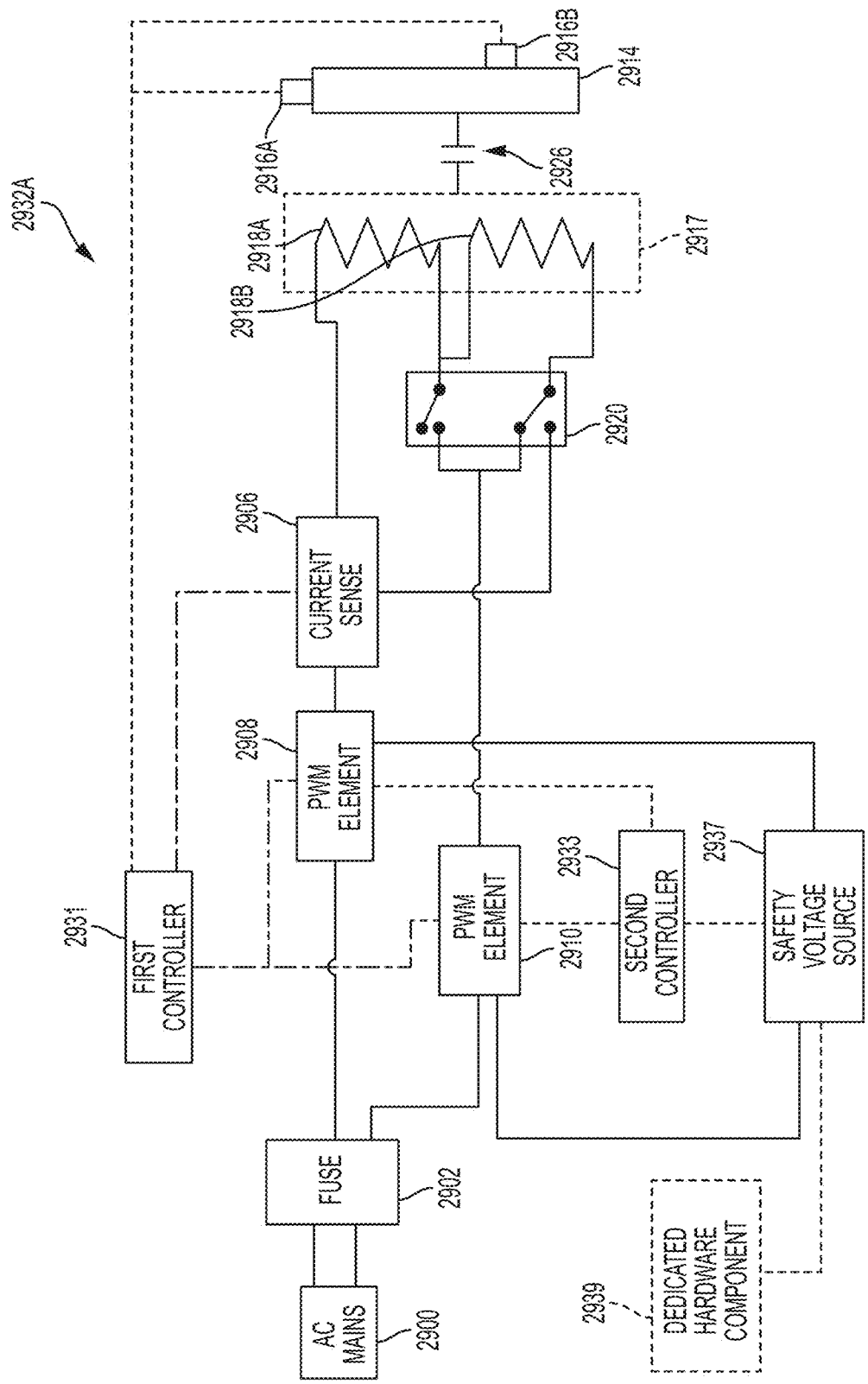
Figure 152:
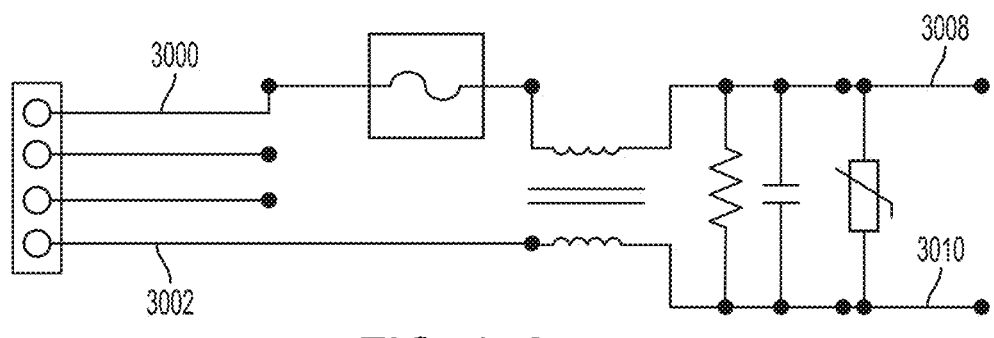
Figure 153:
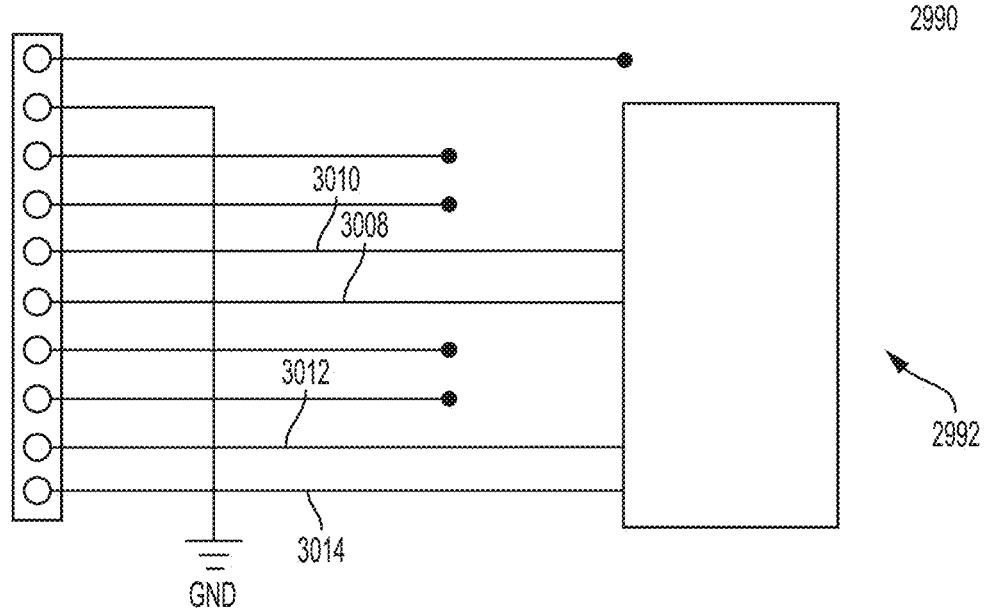
Figure 154:
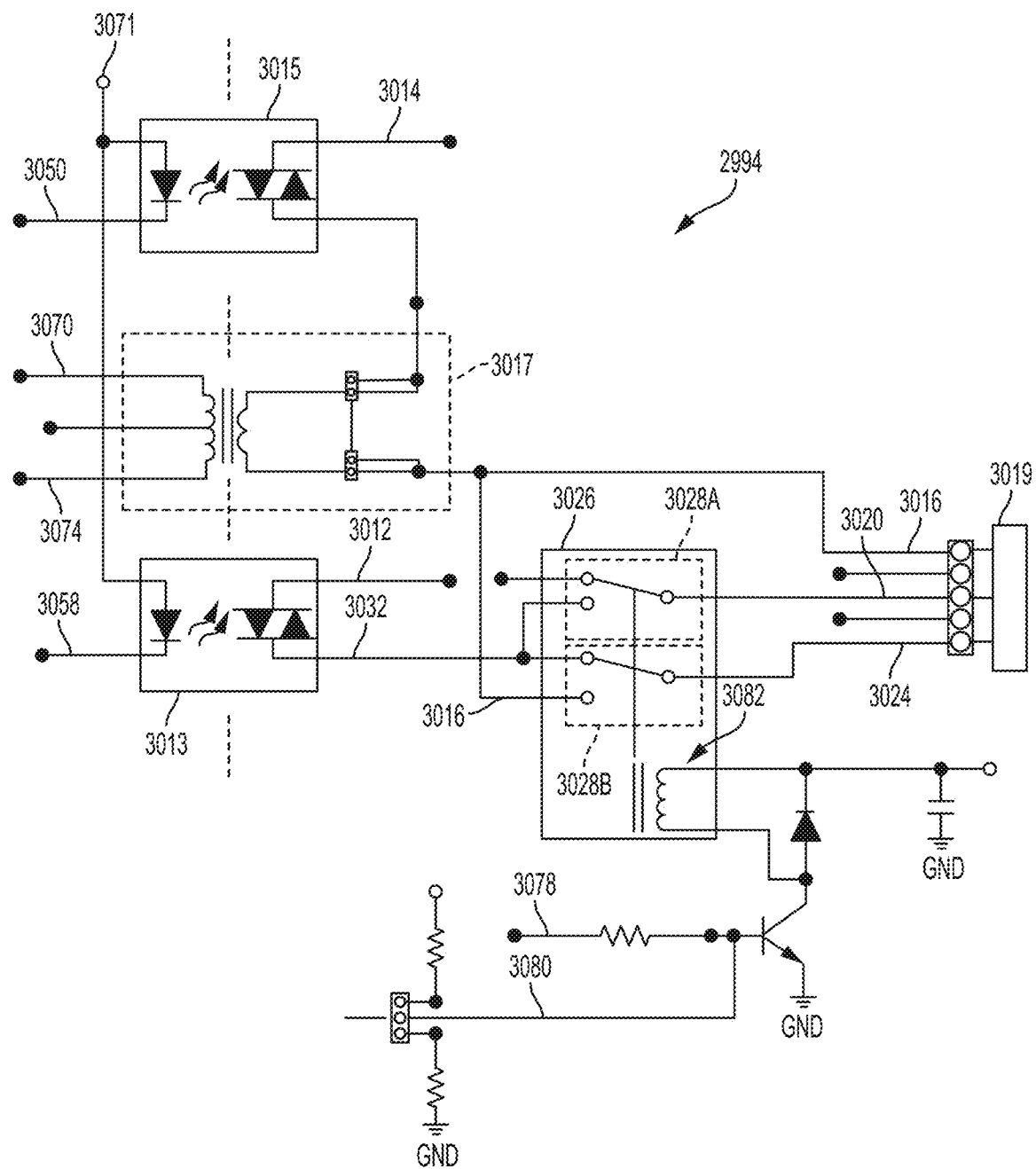
Figure 155:
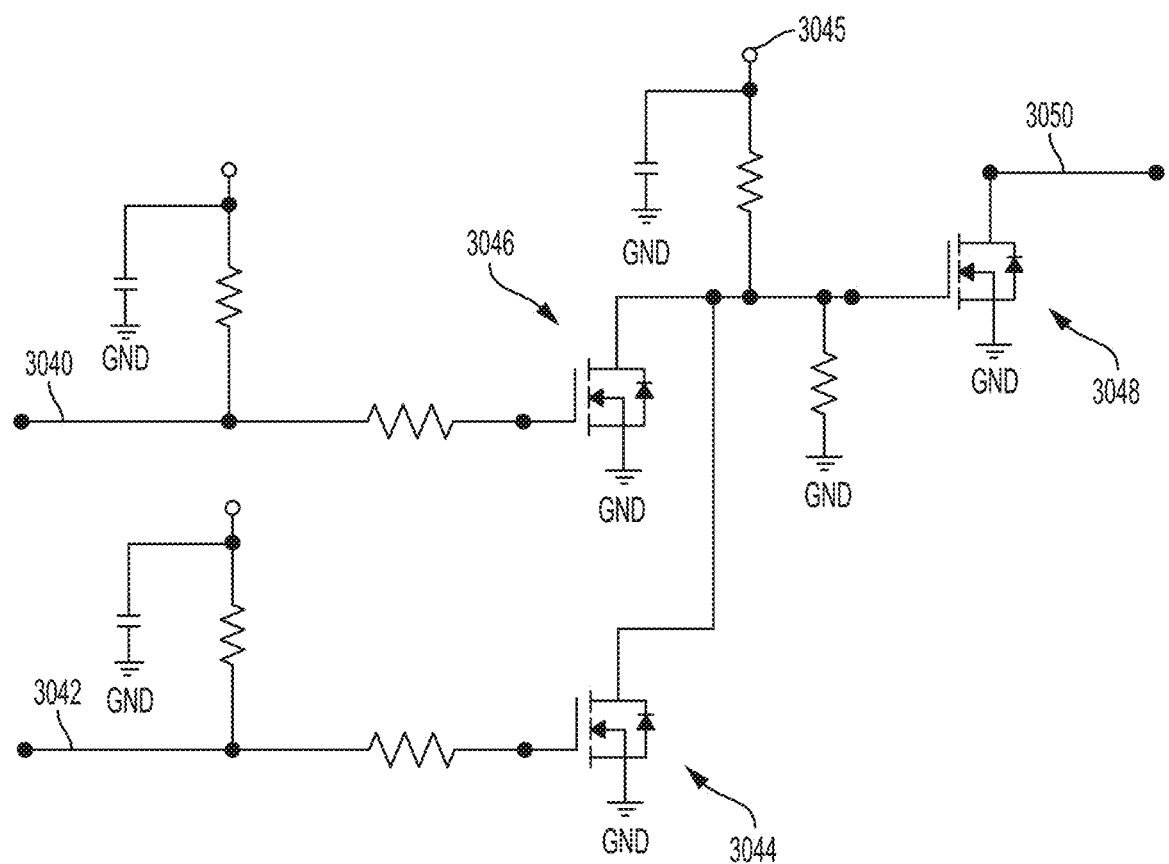
Figure 156:
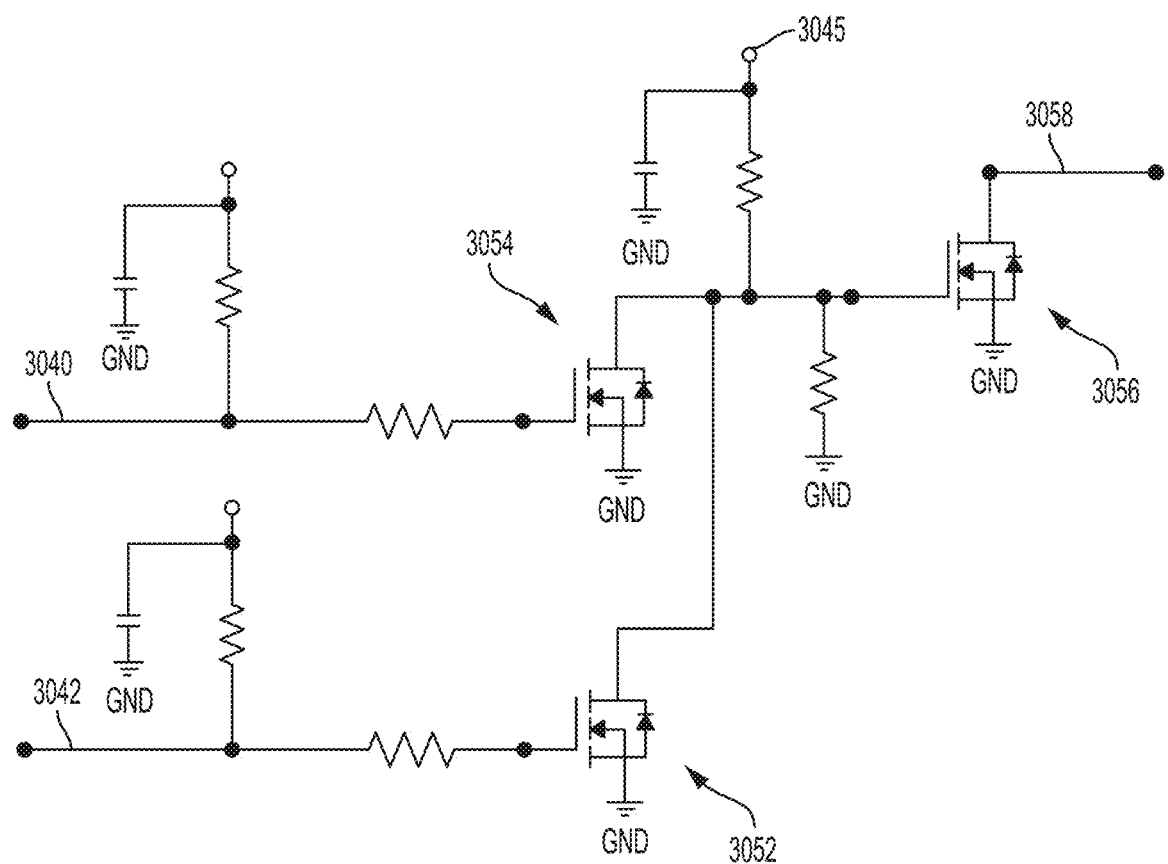
Figure 157:
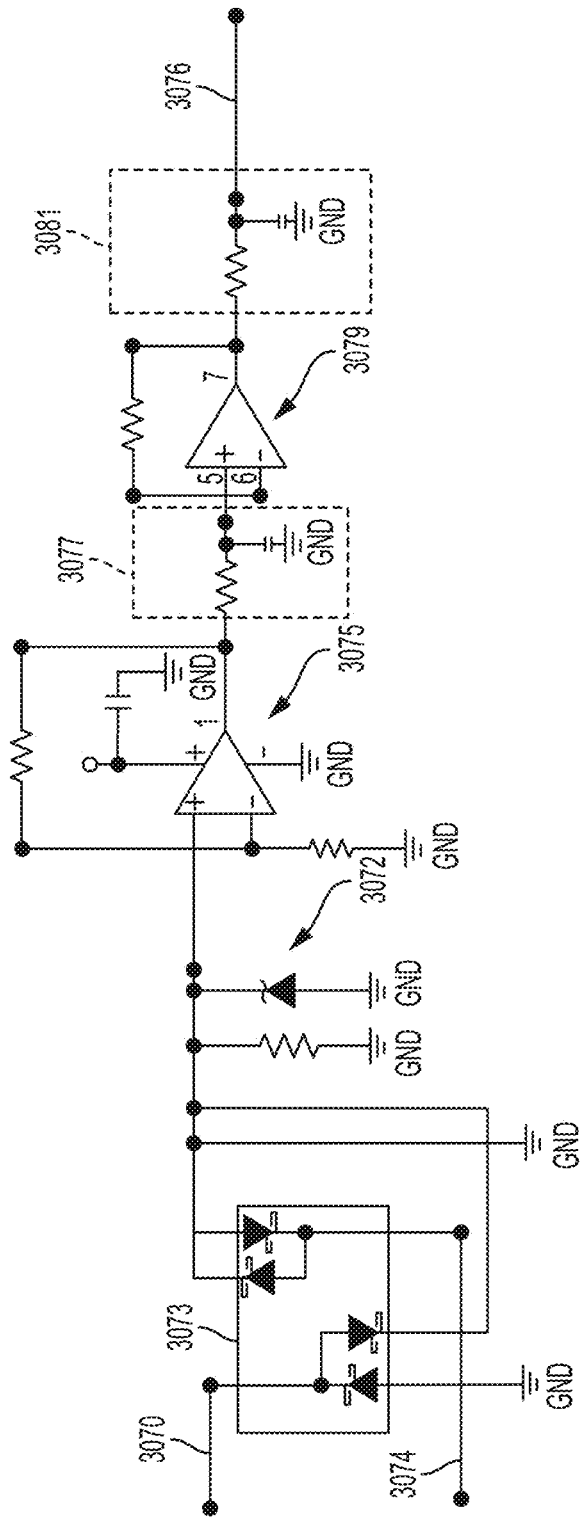
Figure 158:
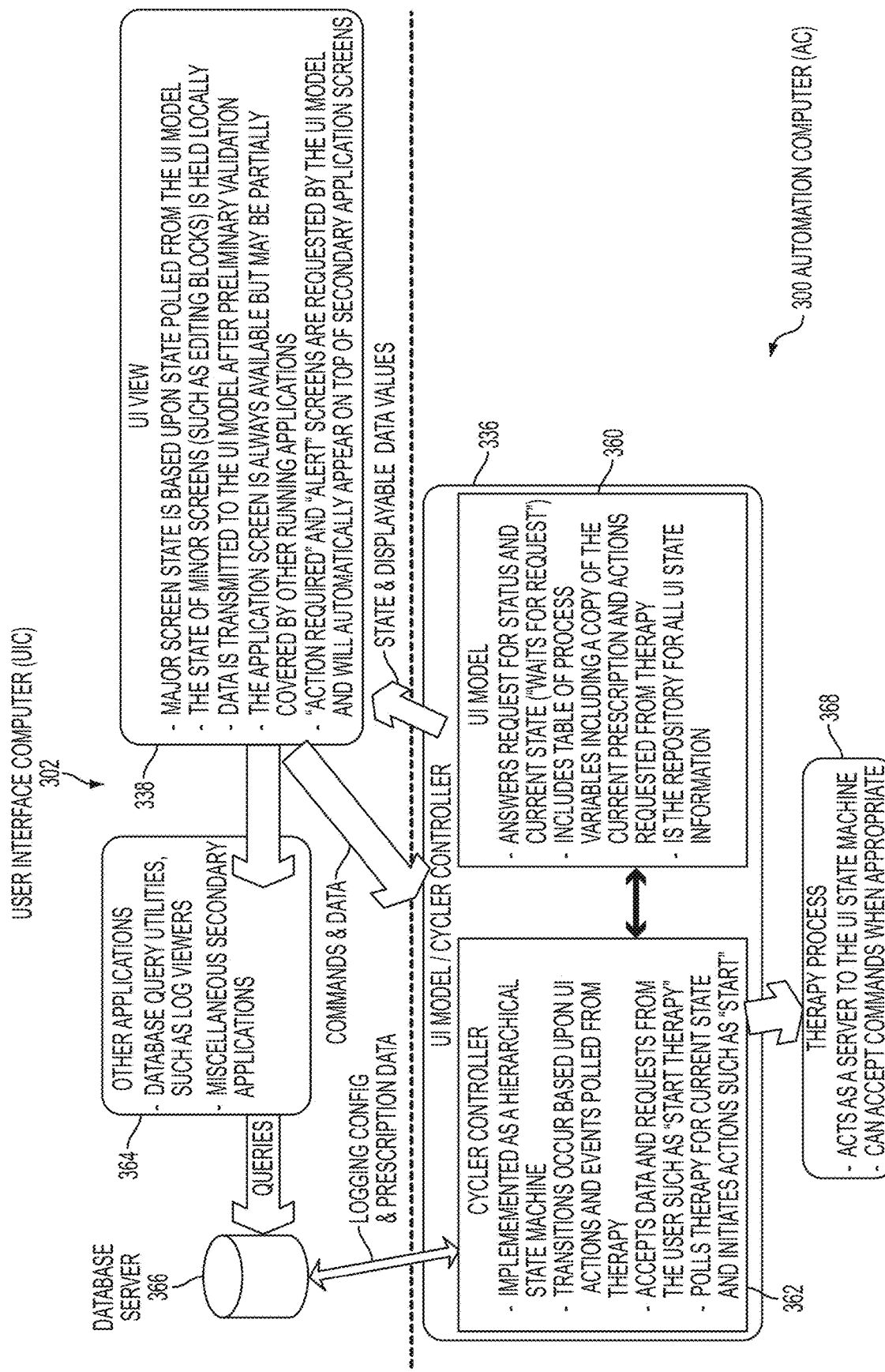
Figure 159:
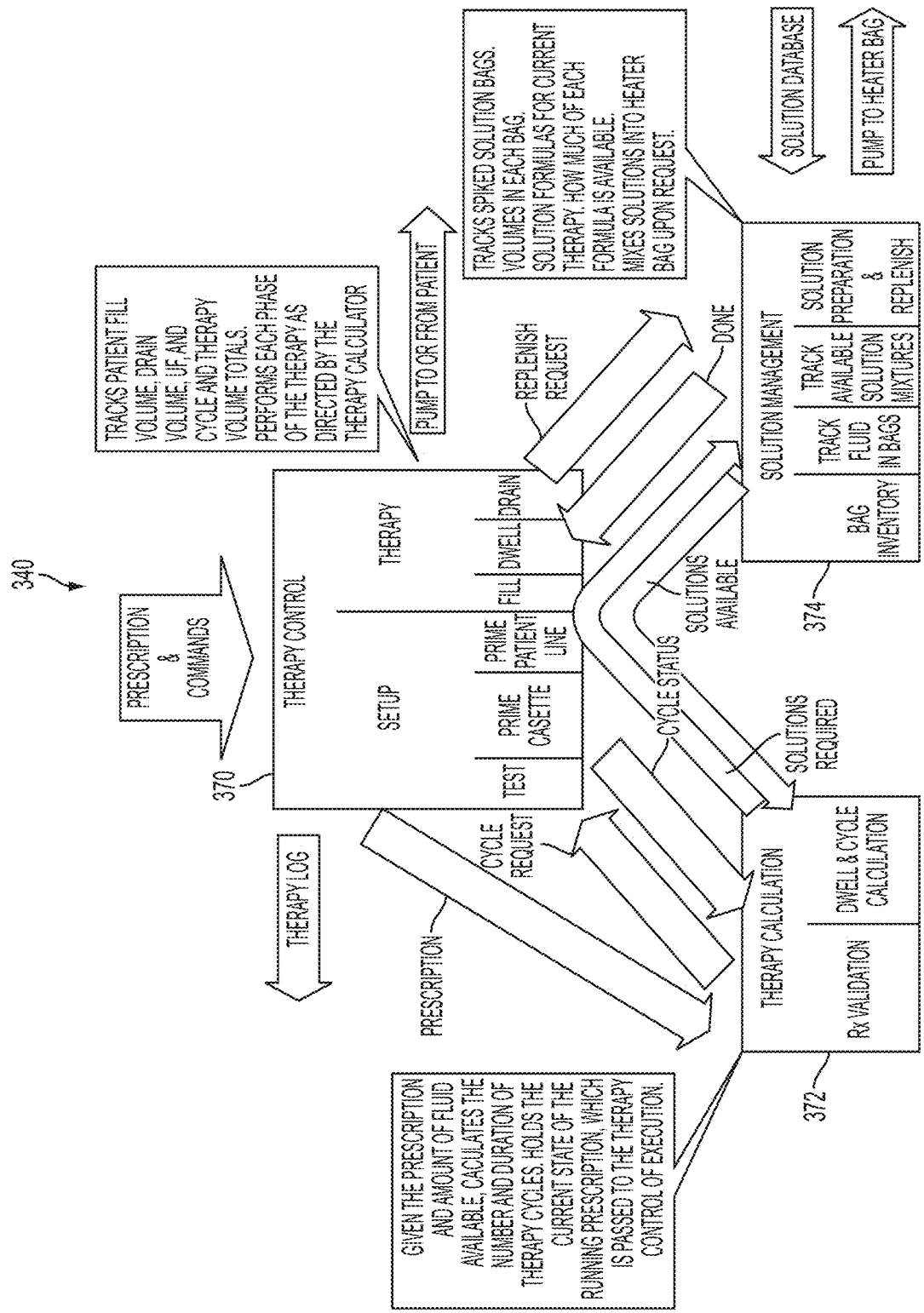
Figure 160:
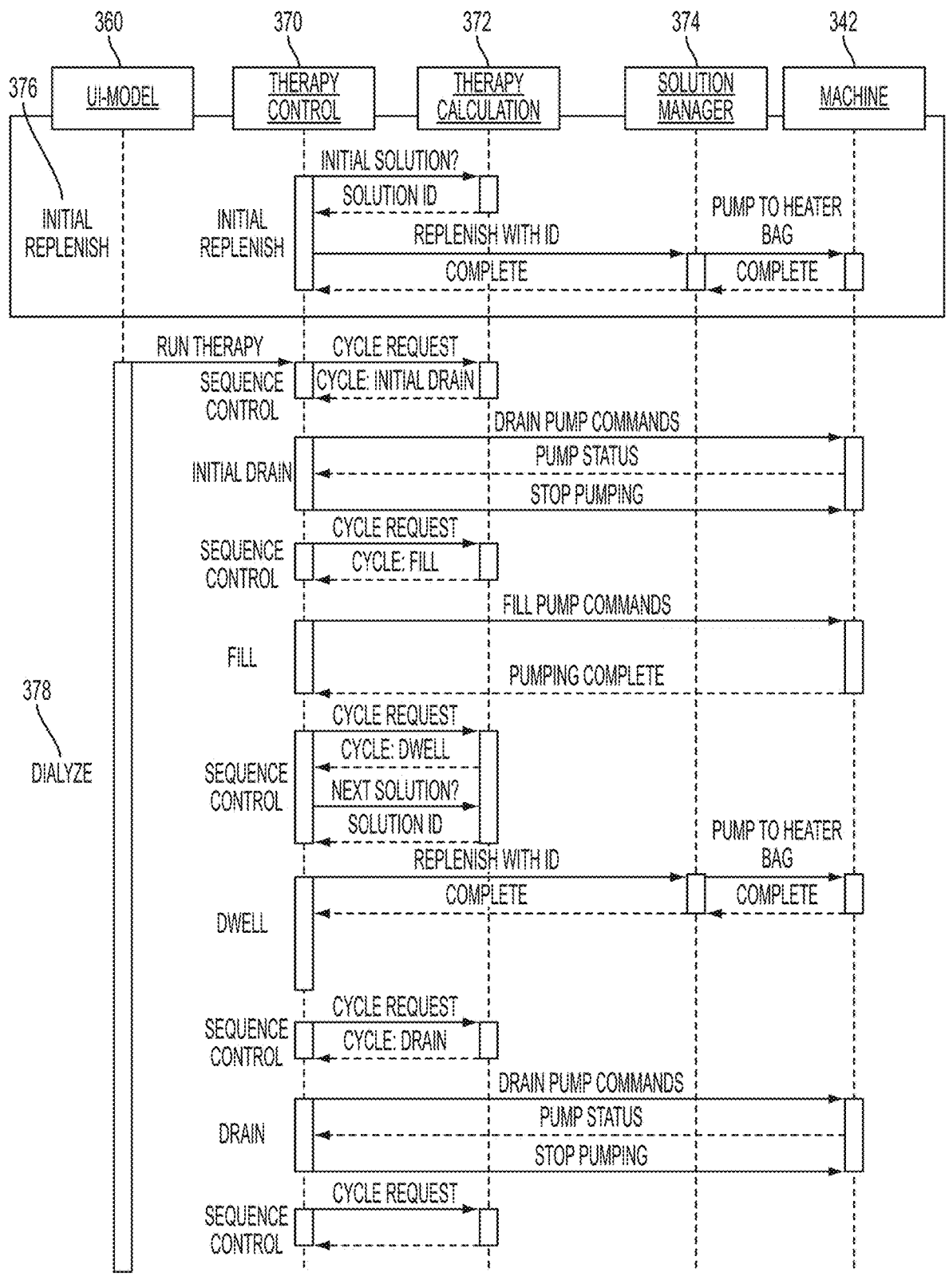
Figure 167:
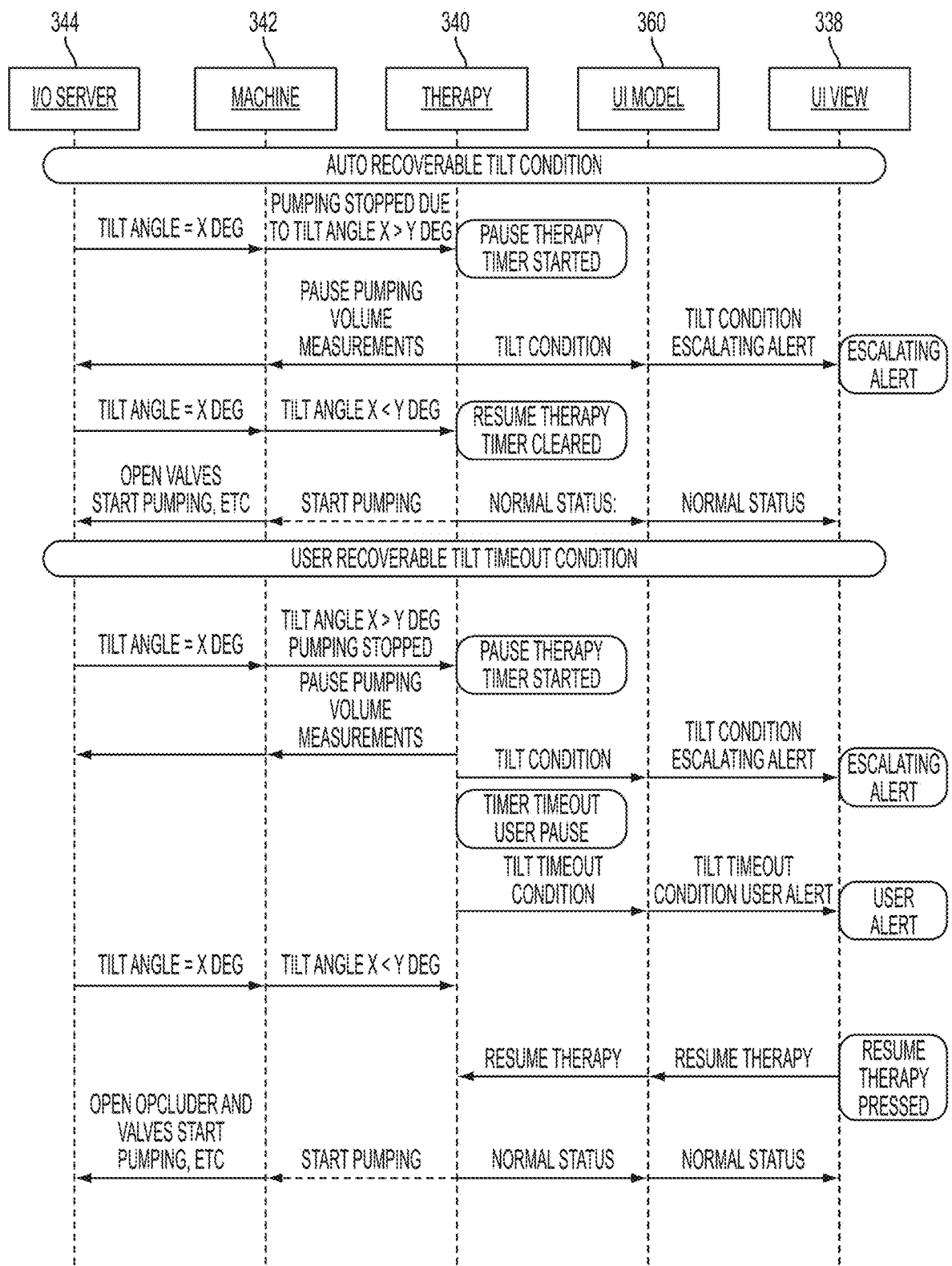
Figure 168:
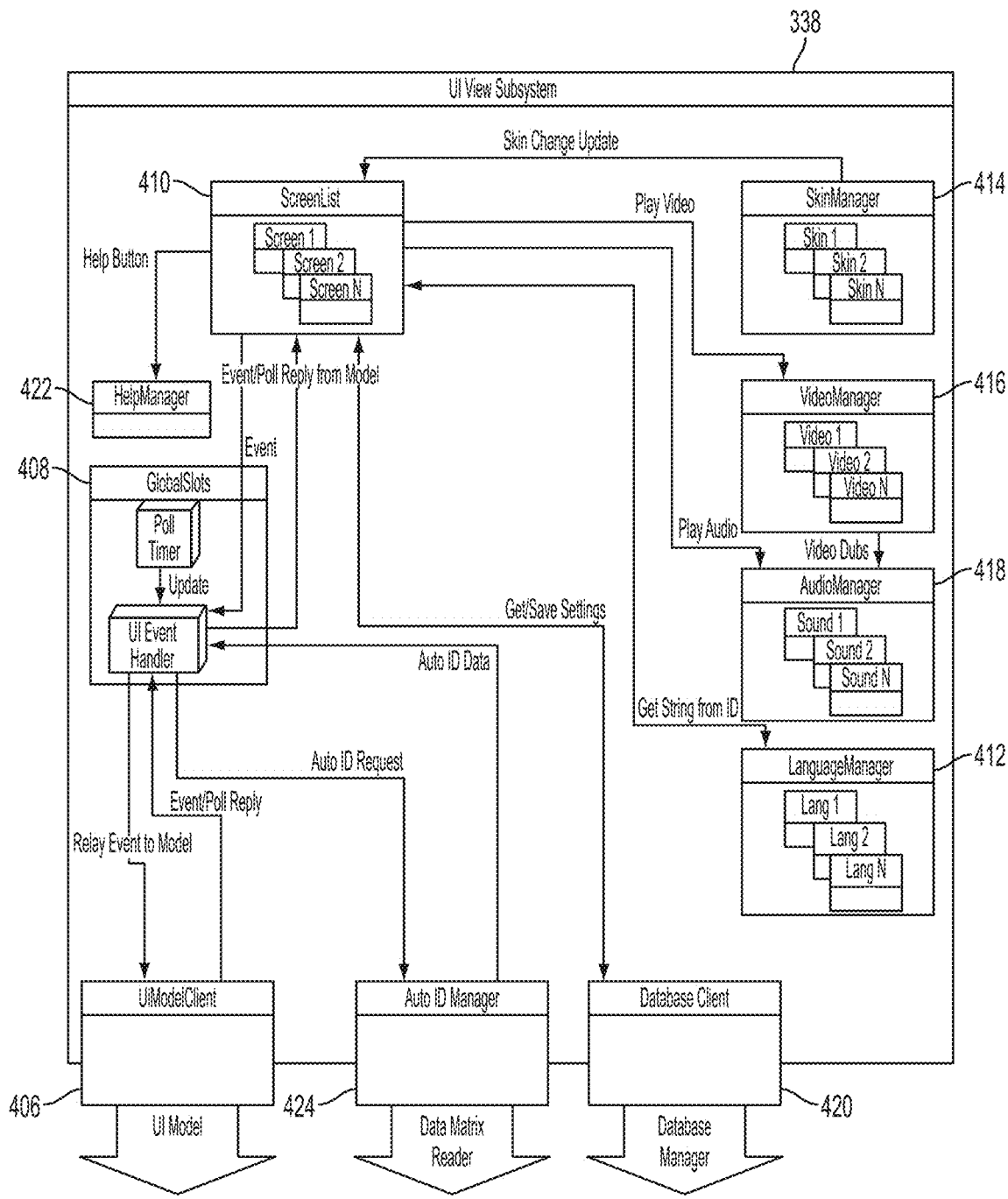
Figure 169:
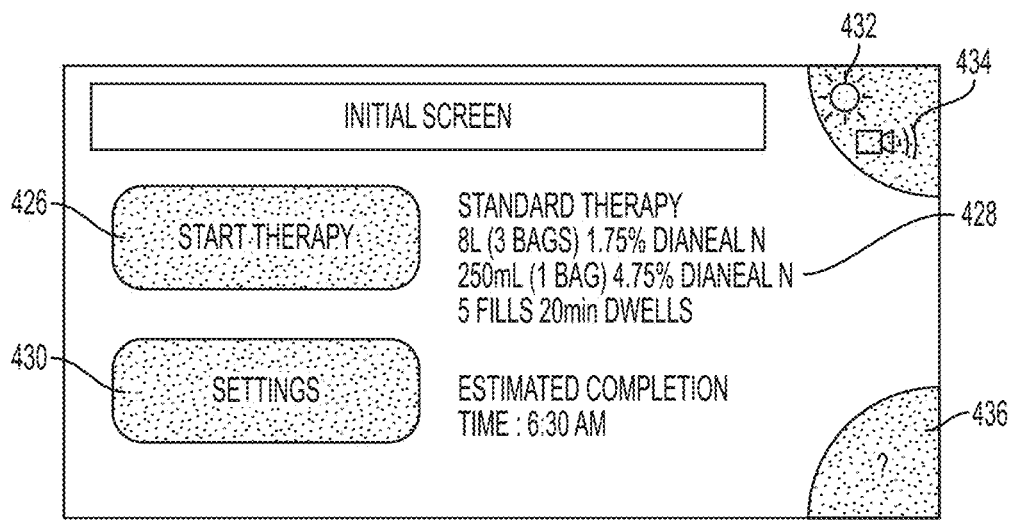
Figure 170:
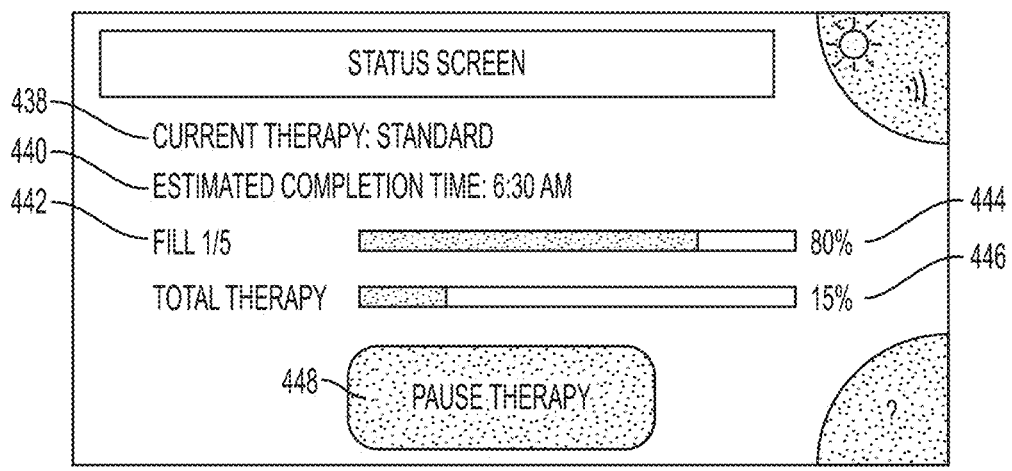
Figure 171:
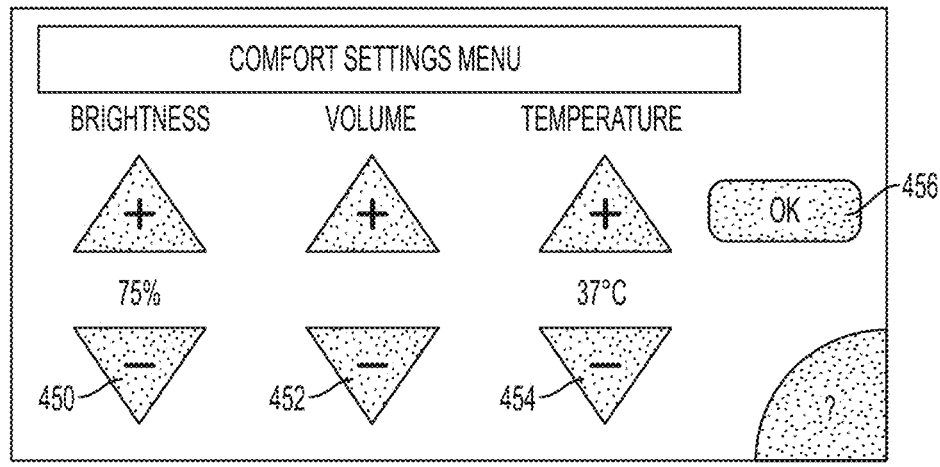
Figure 172:
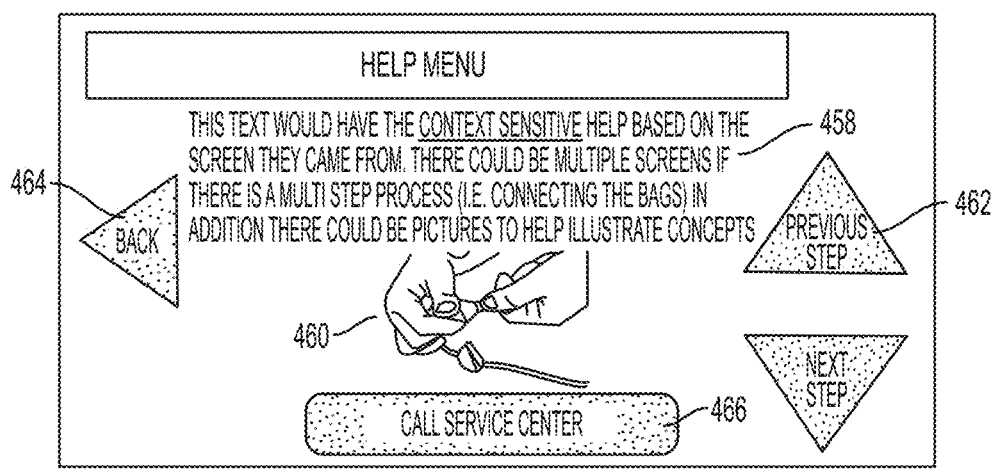
Figure 173:
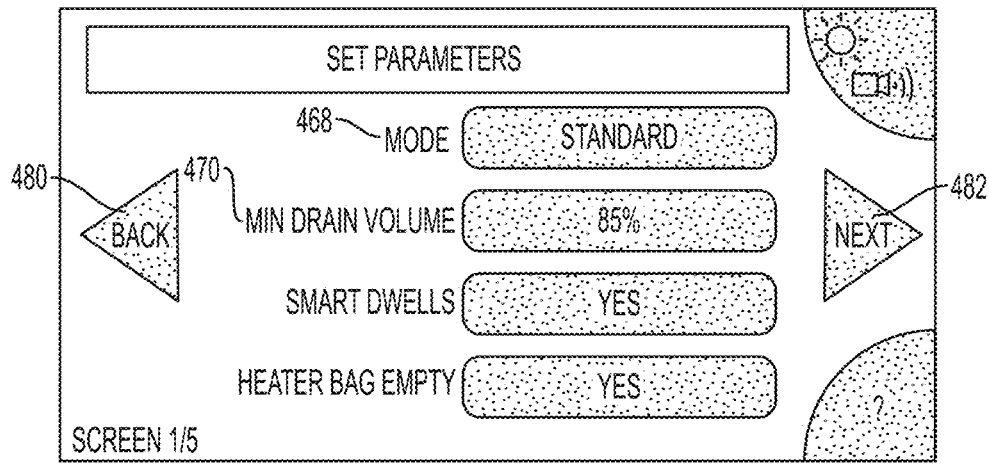
Figure 174:
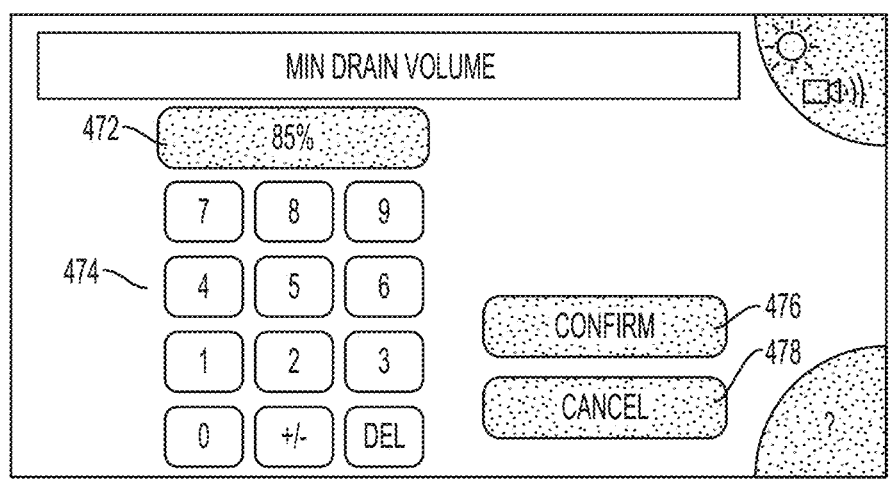
Figure 175:
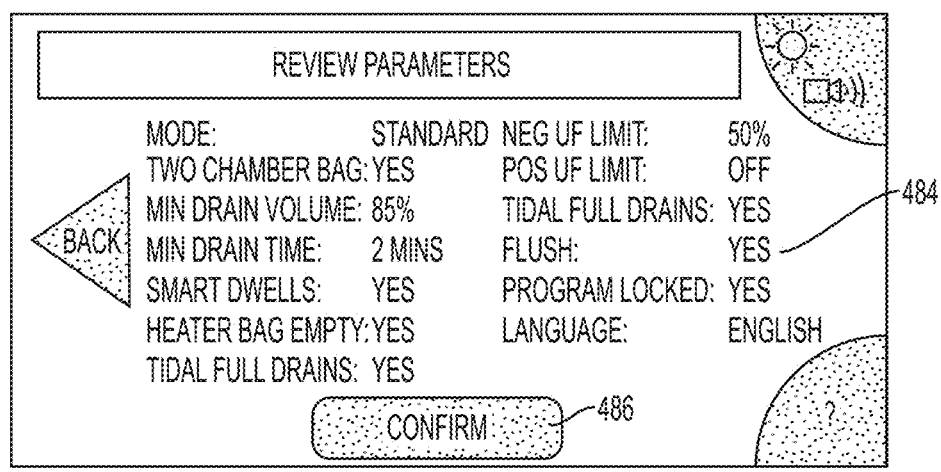
Figure 176:
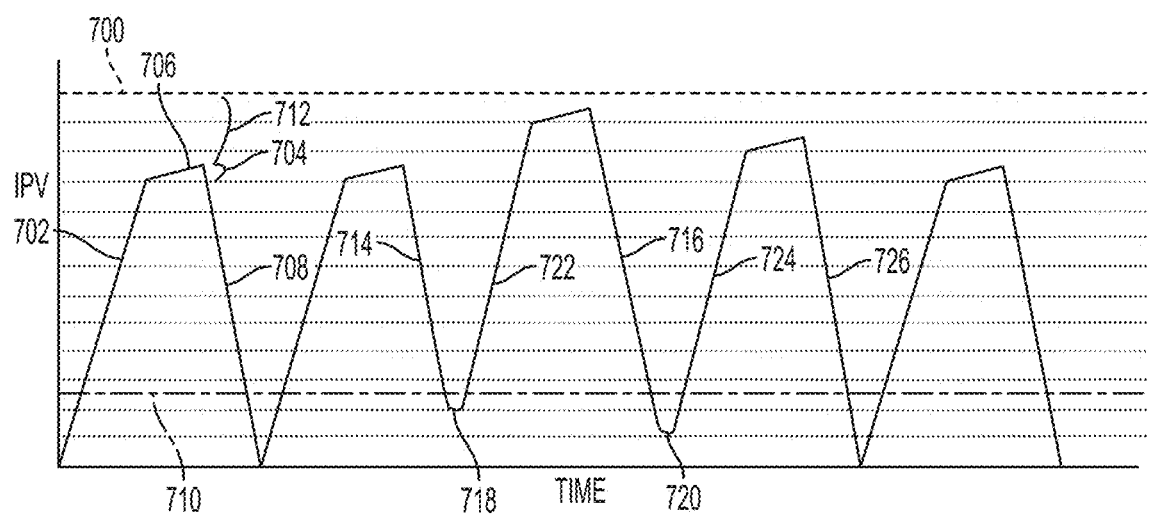
Figure 177:
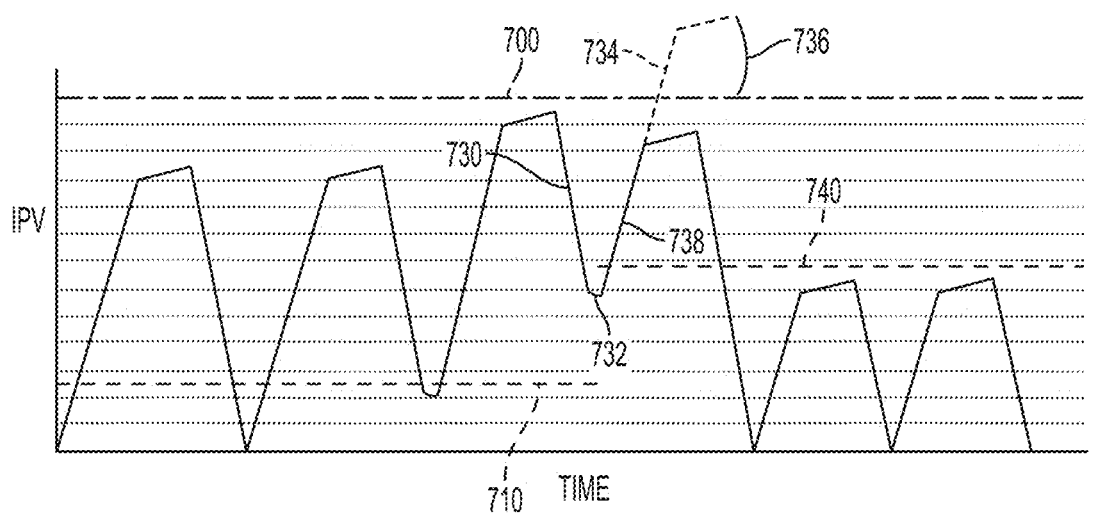
Figure 178:
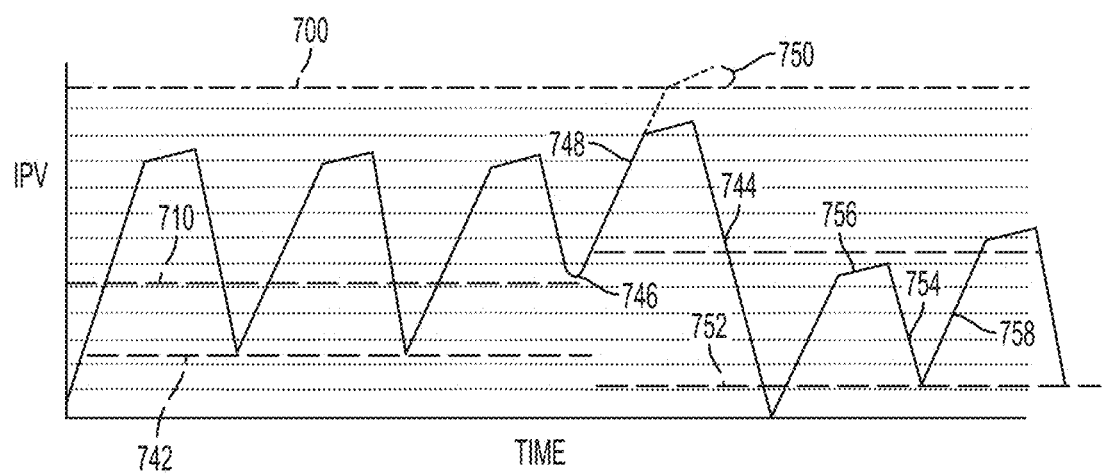
Figure 179:
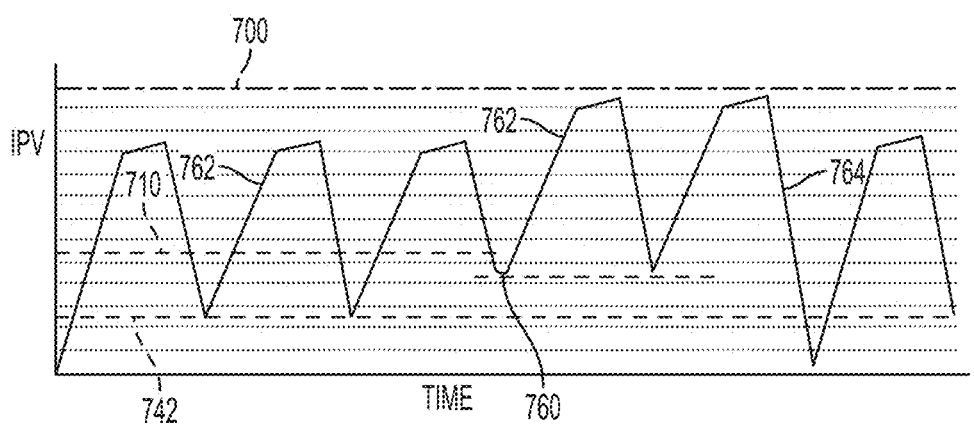
Figure 180:
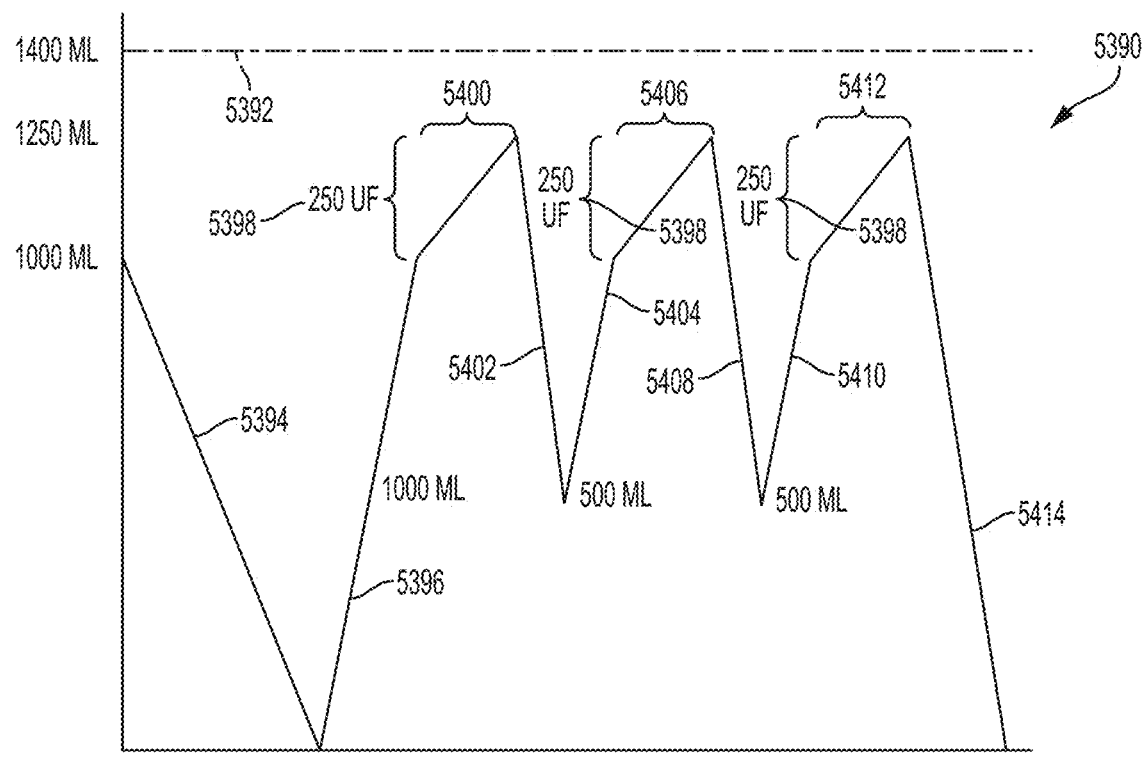
Figure 181:
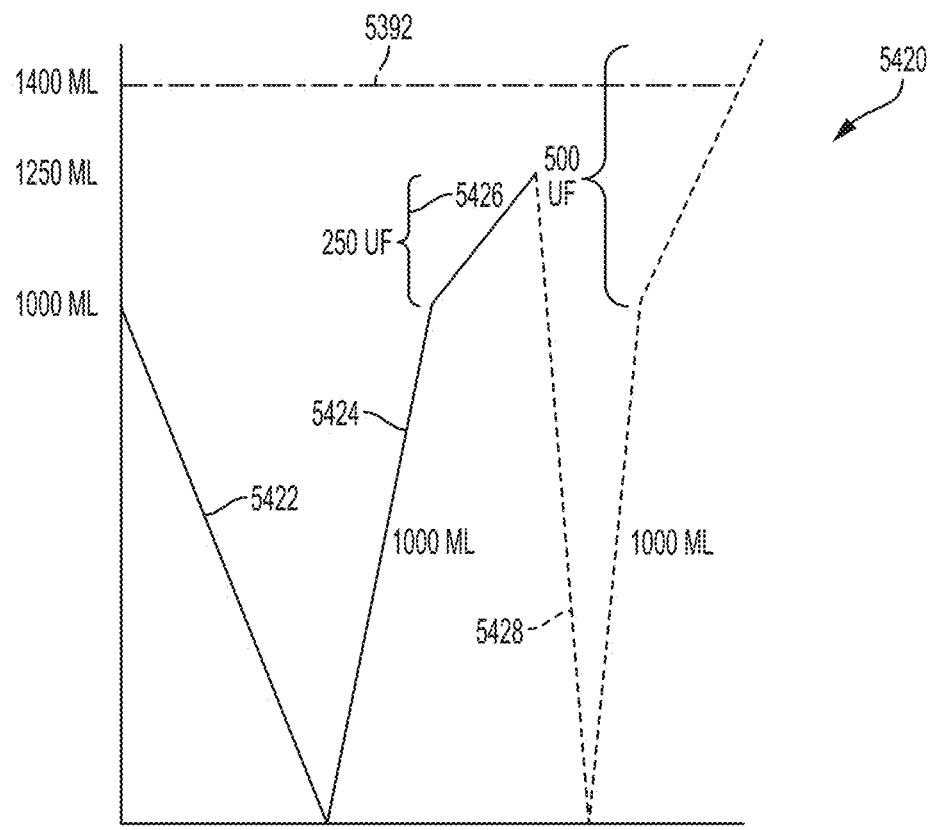
Figure 182:
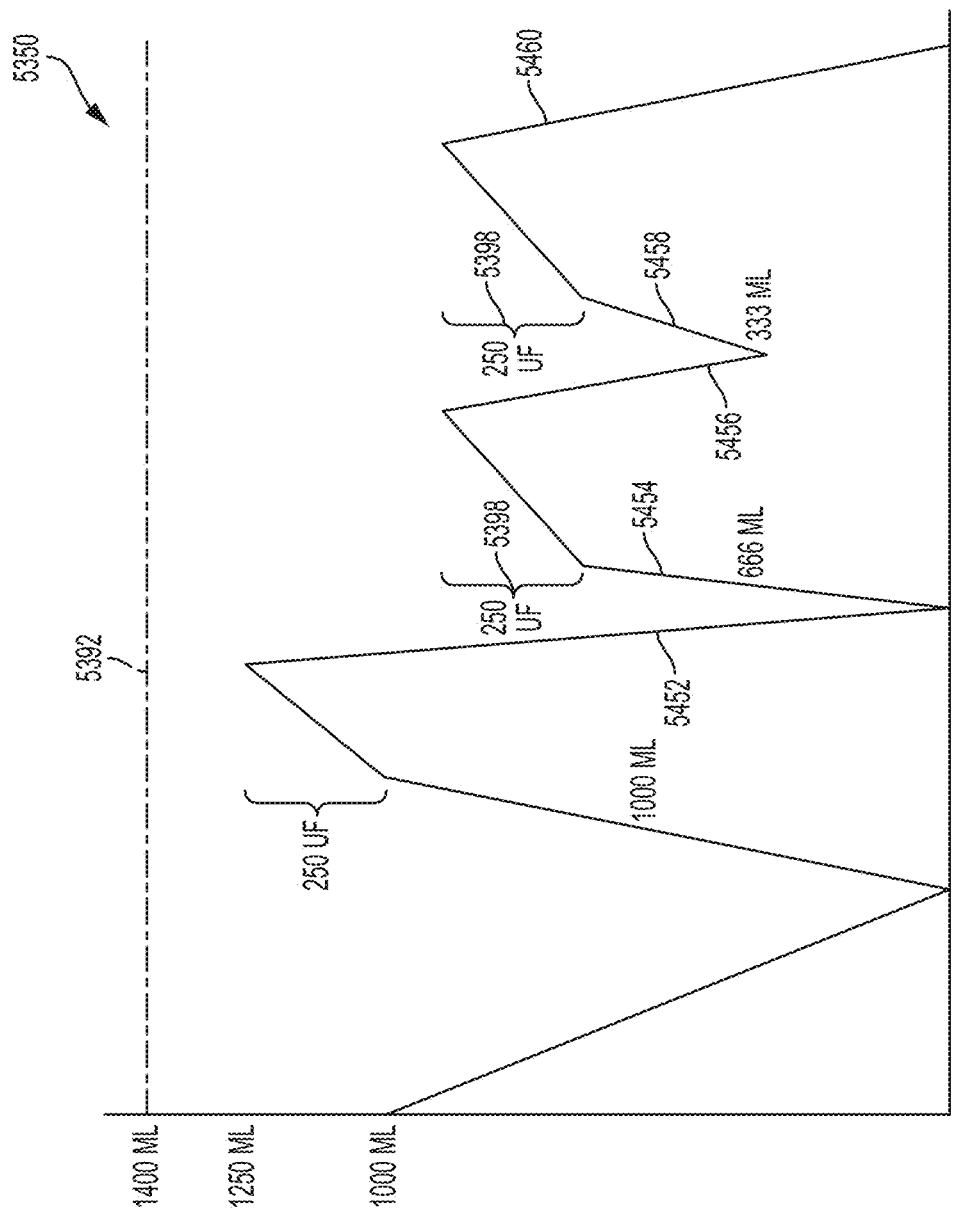
Figure 183:
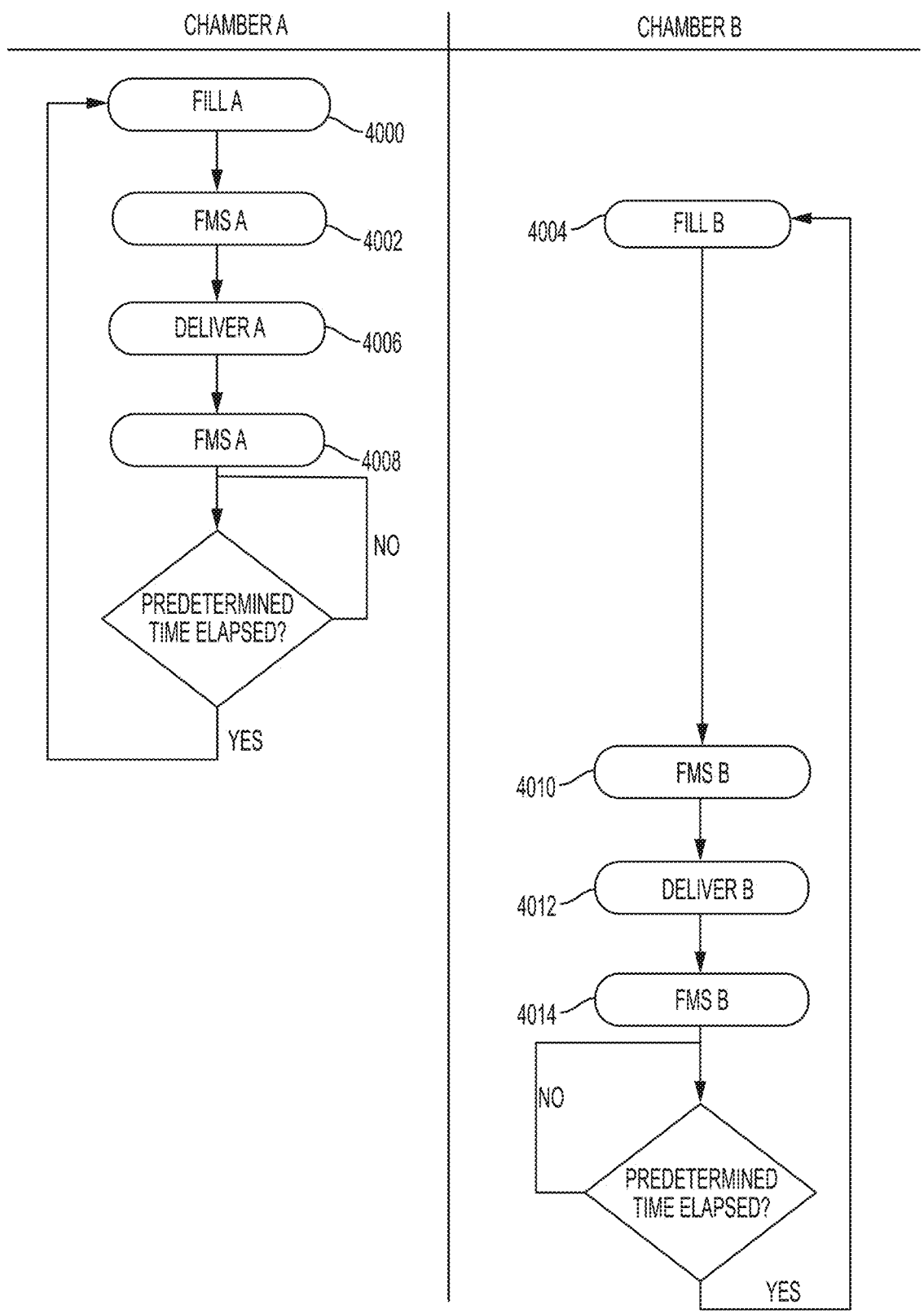
Figure 184:
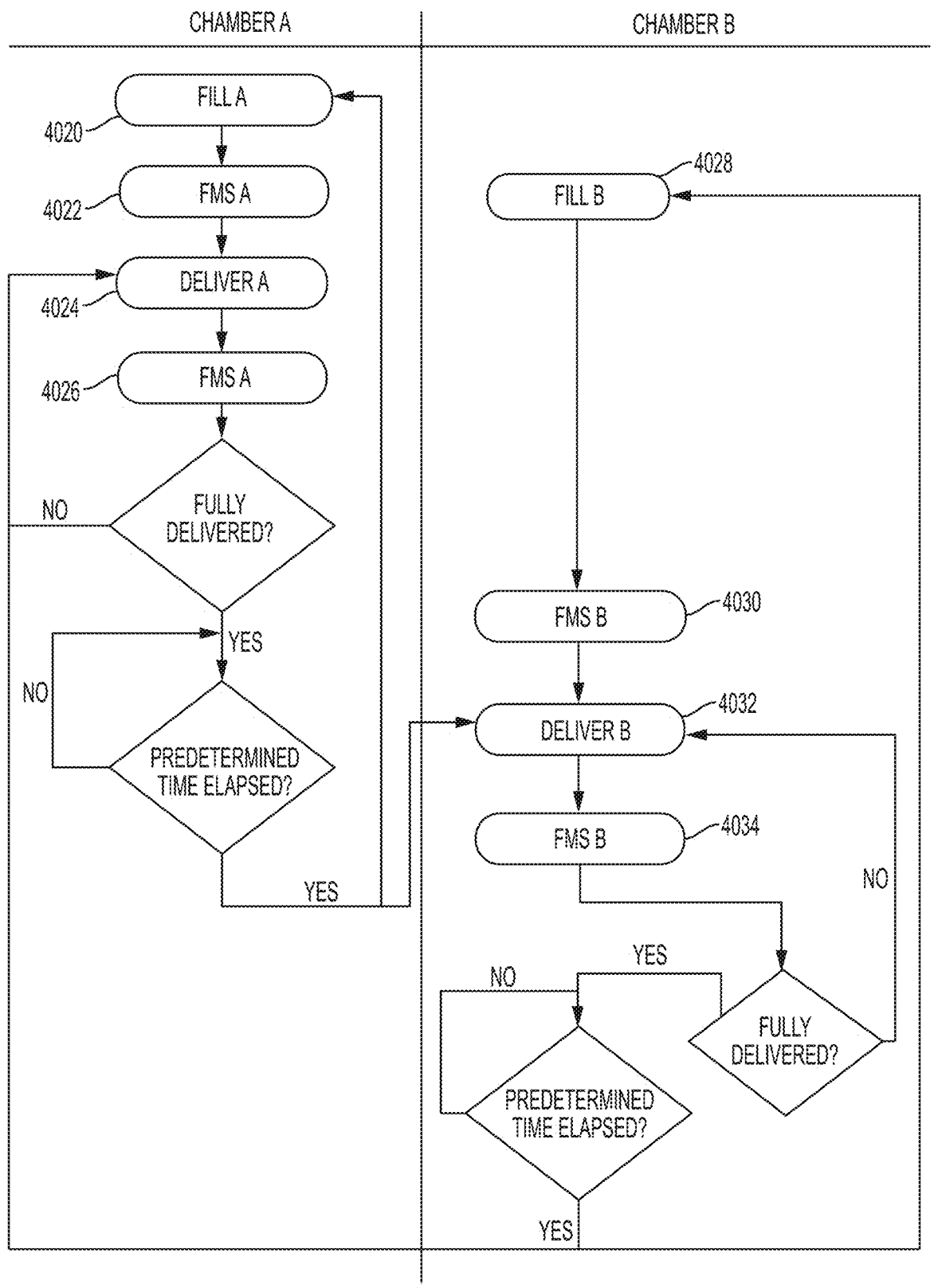
Figure 185:
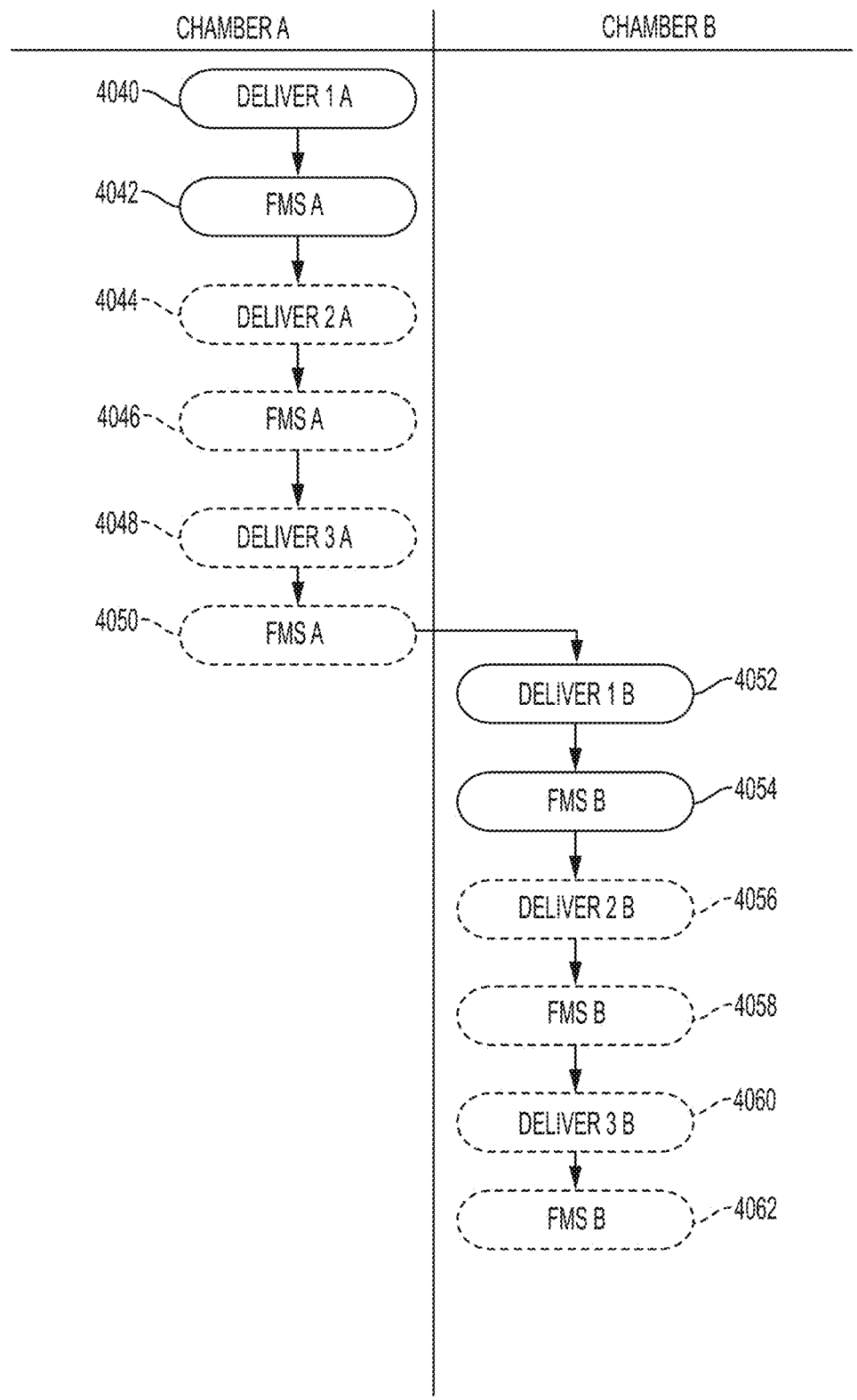
Figure 186:
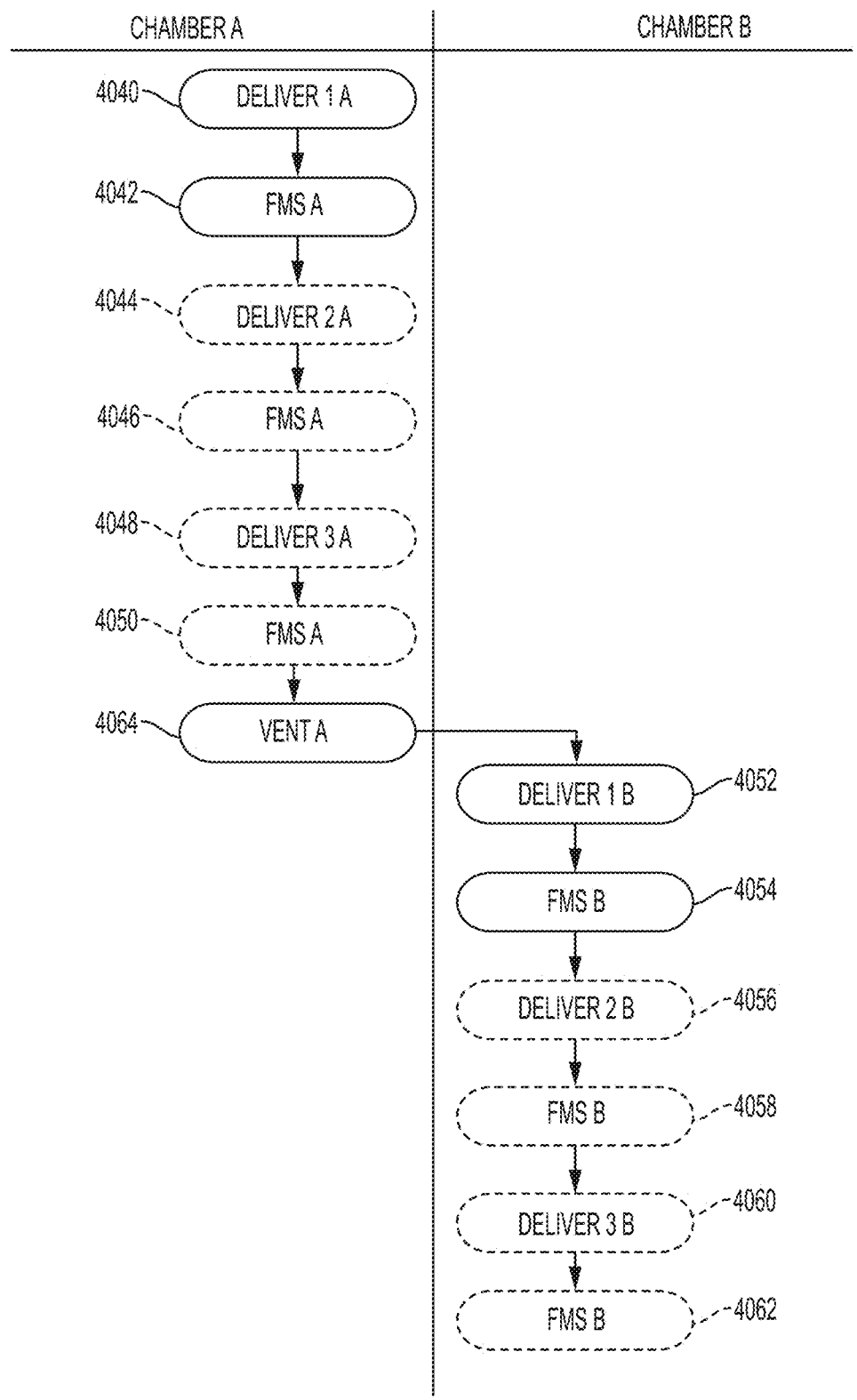
Figure 187A:
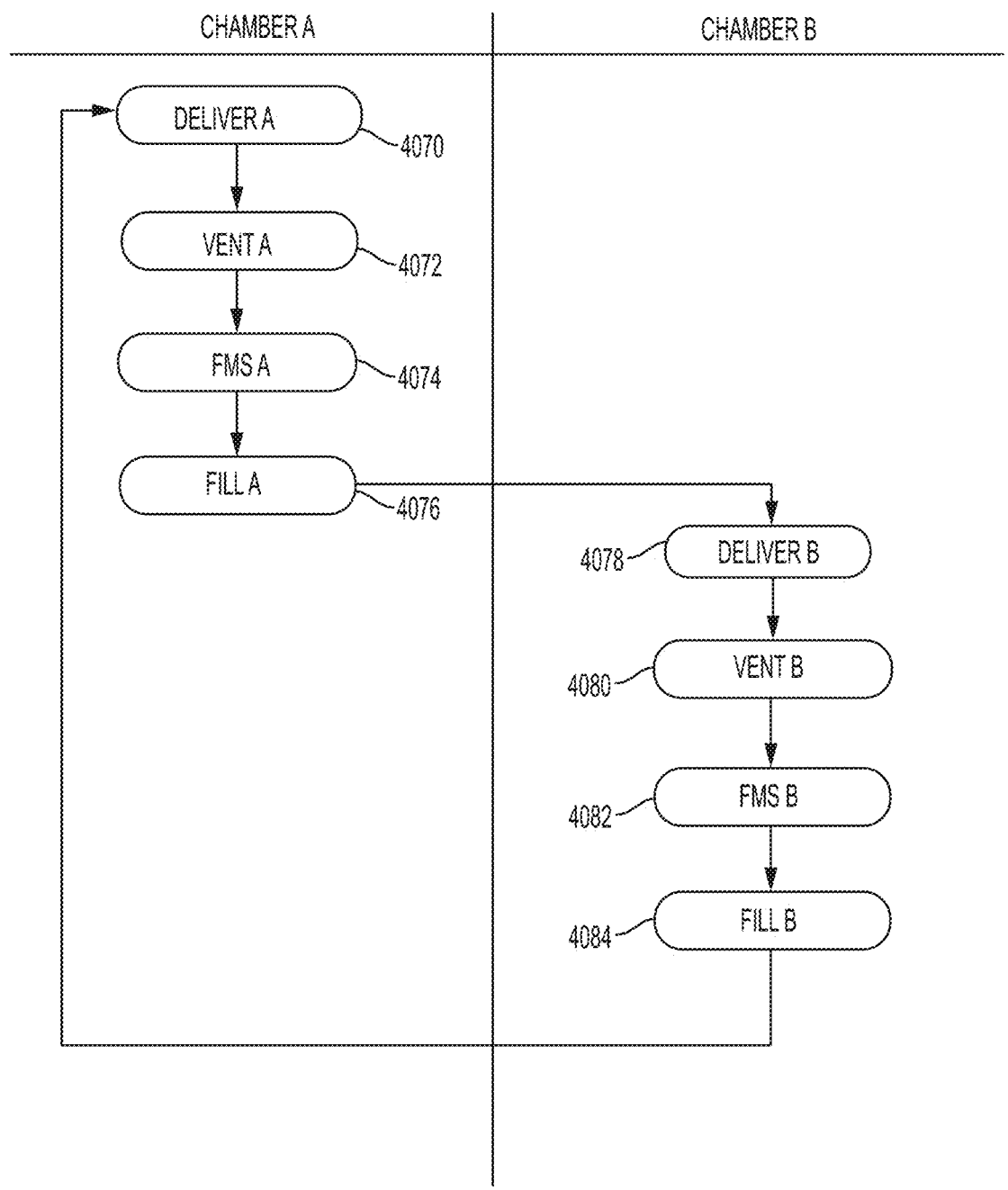
Figure 187B:
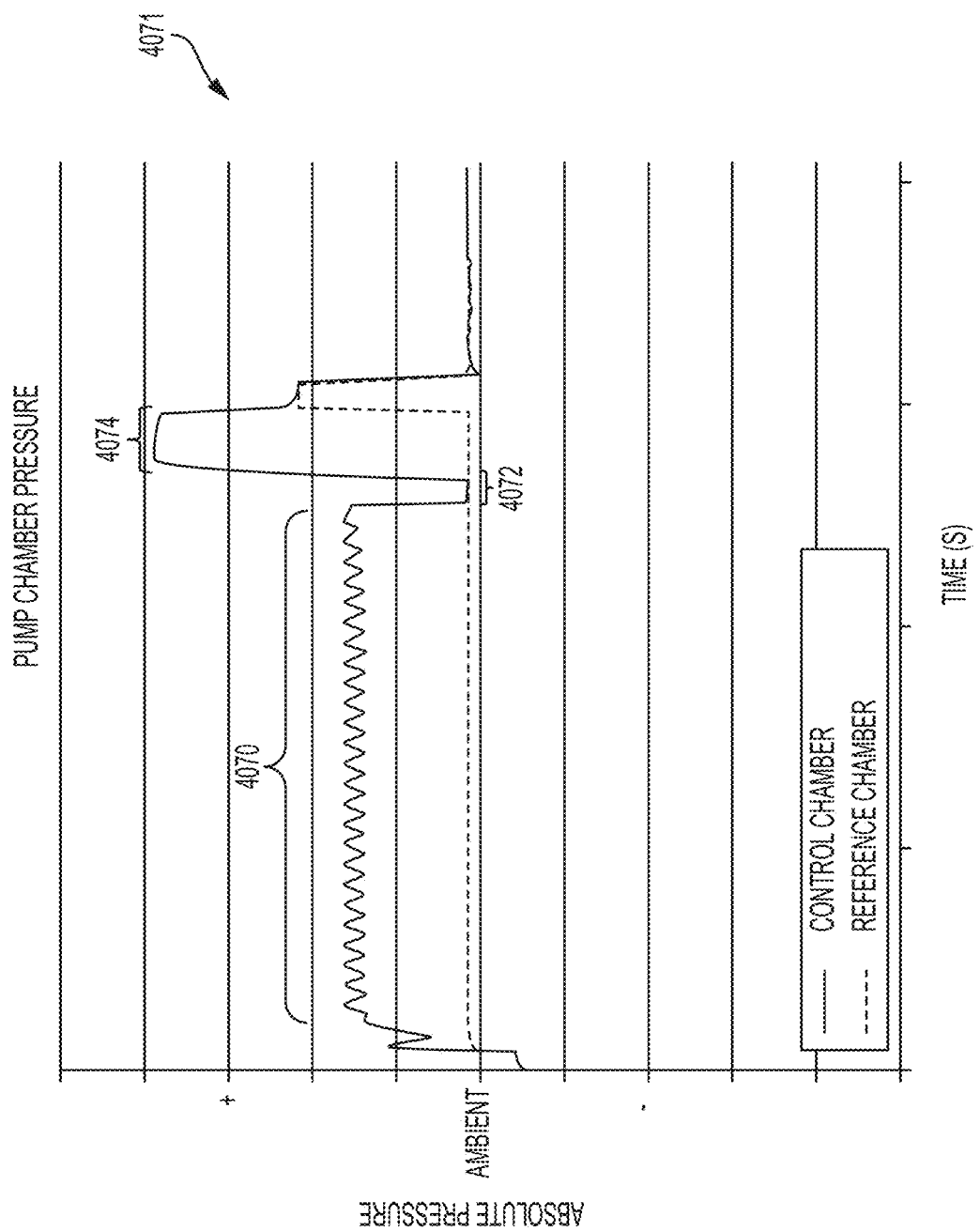
Figure 188:
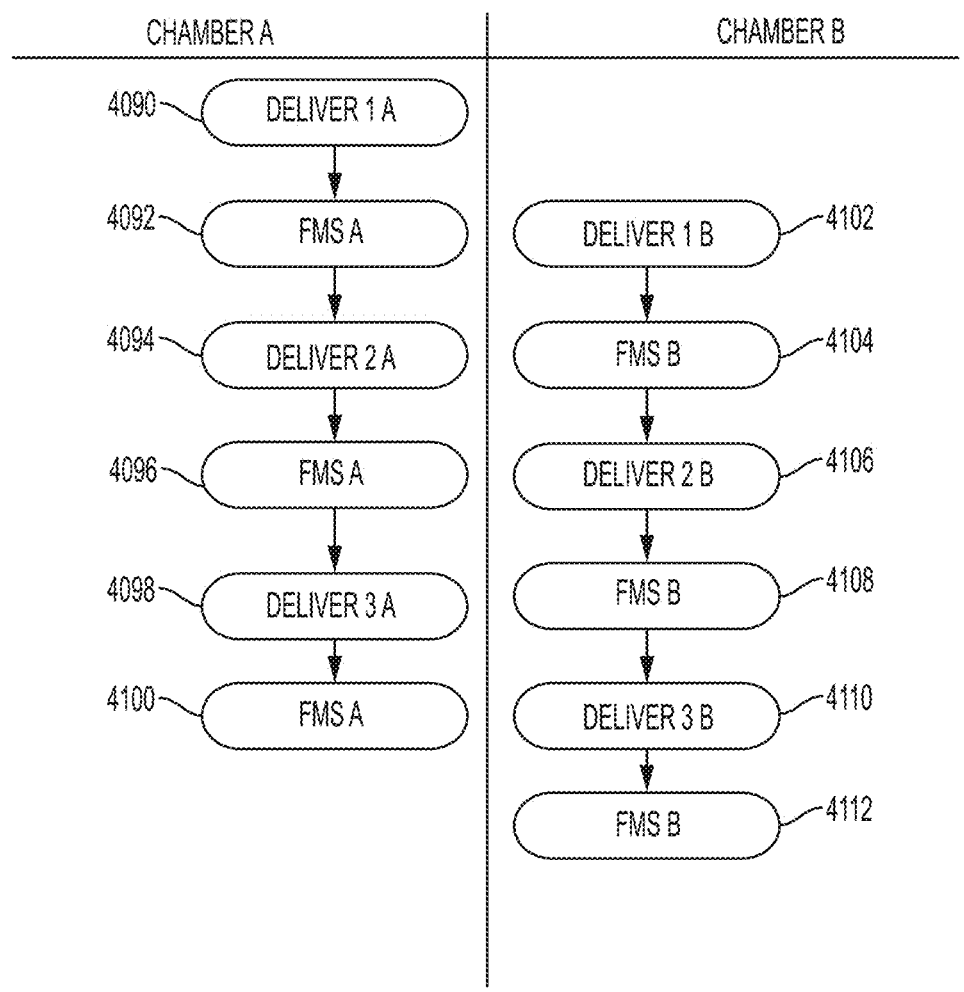
Figure 189:
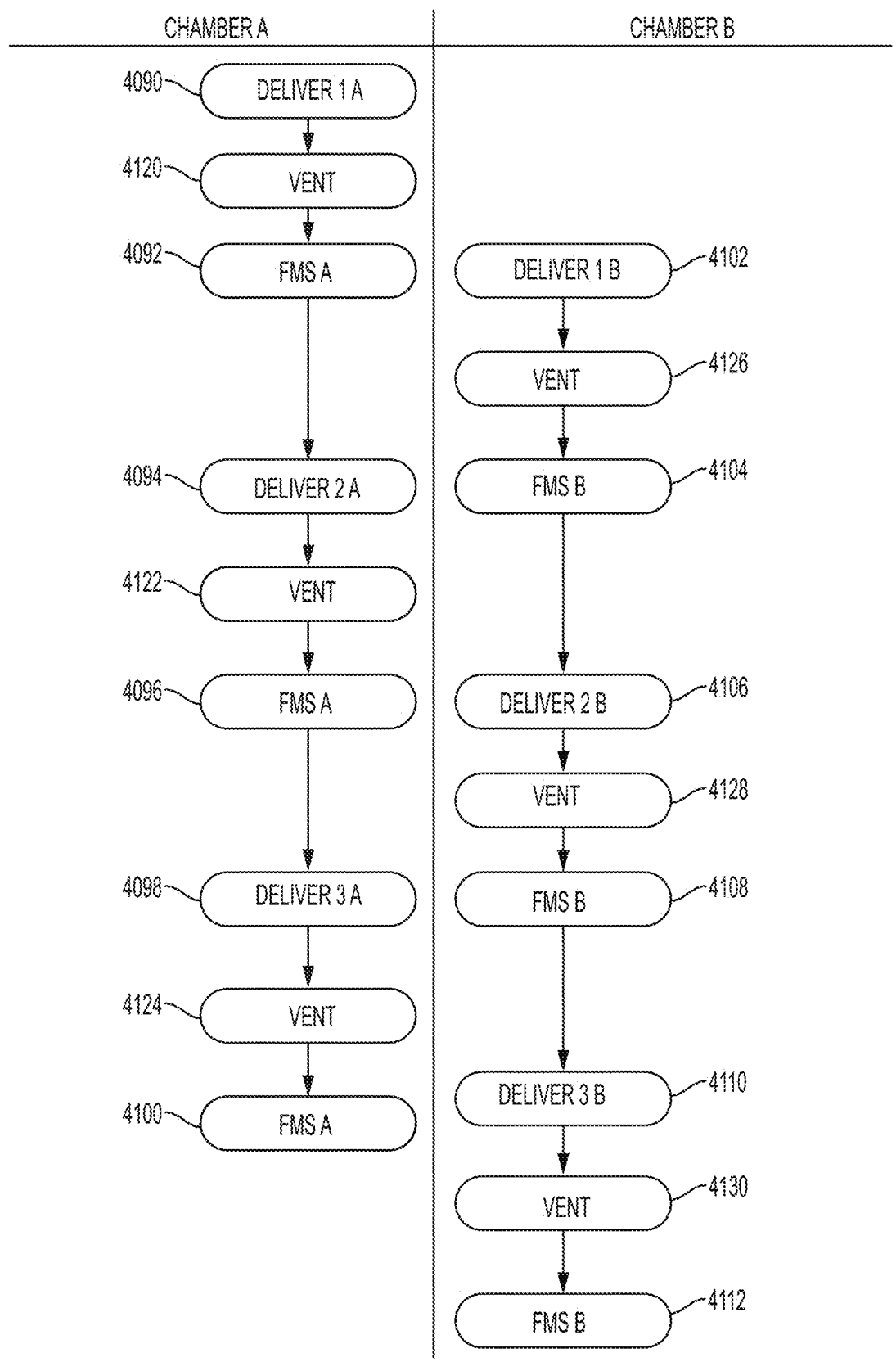
Figure 190:
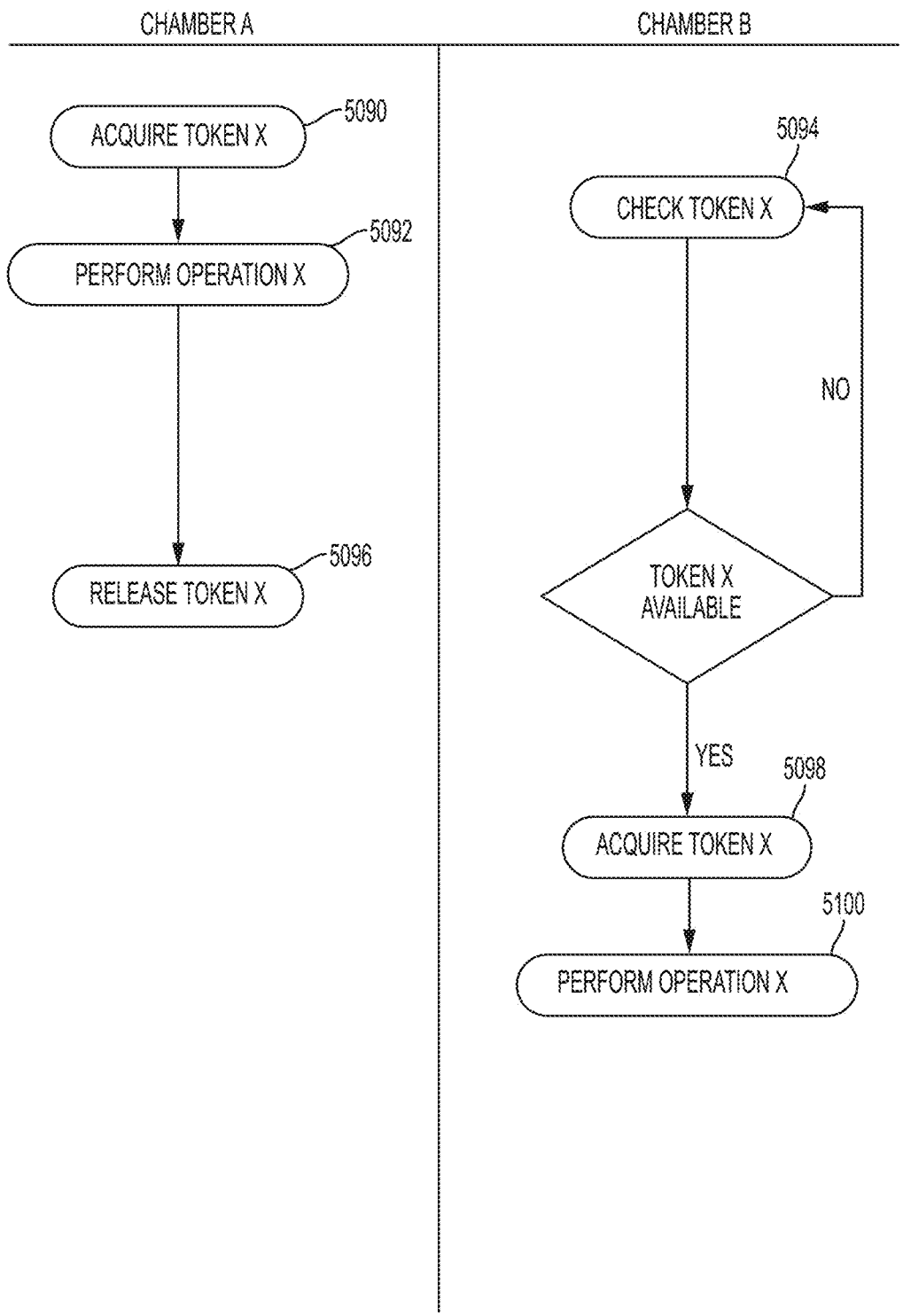
Figure 191:
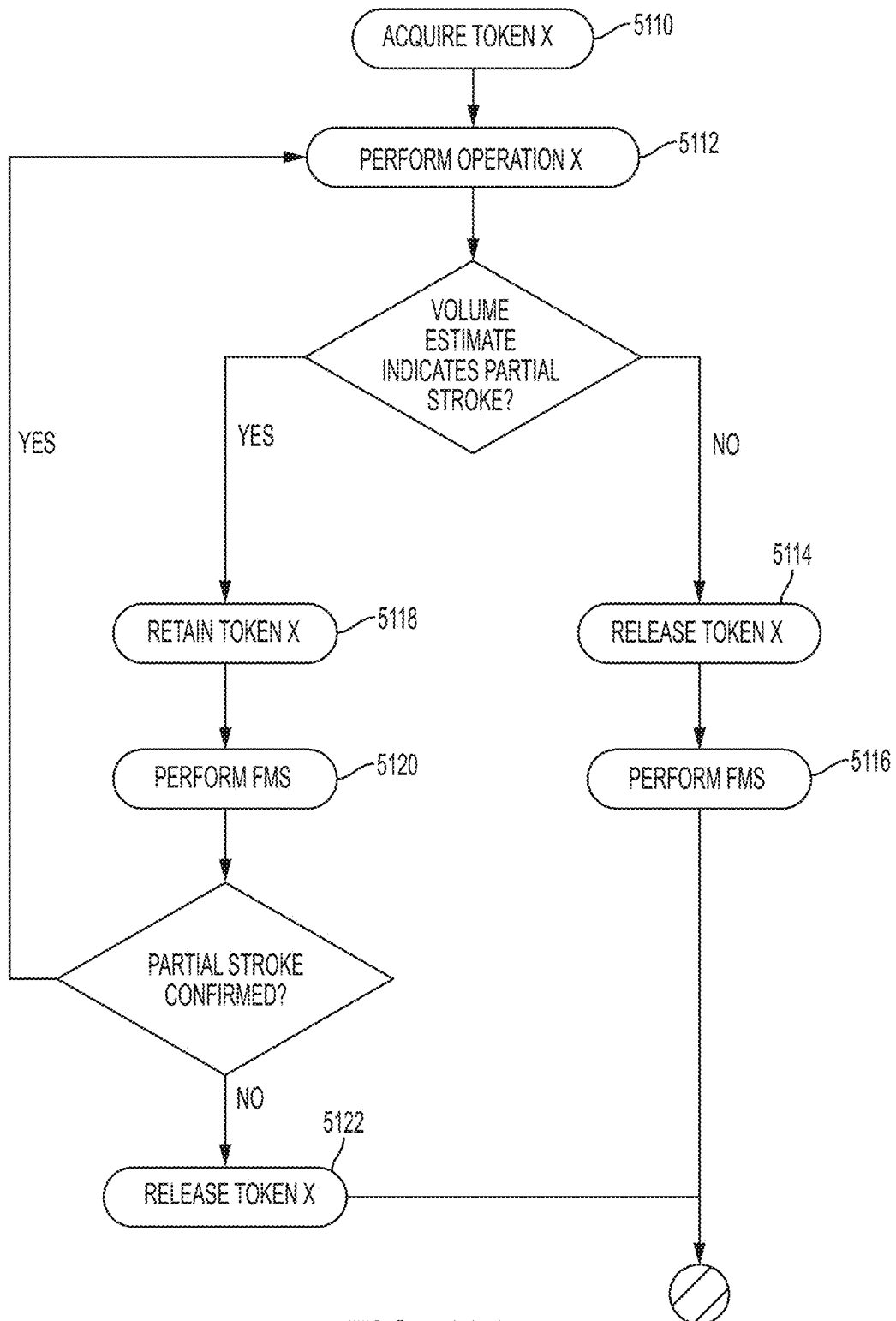
Figure 192:
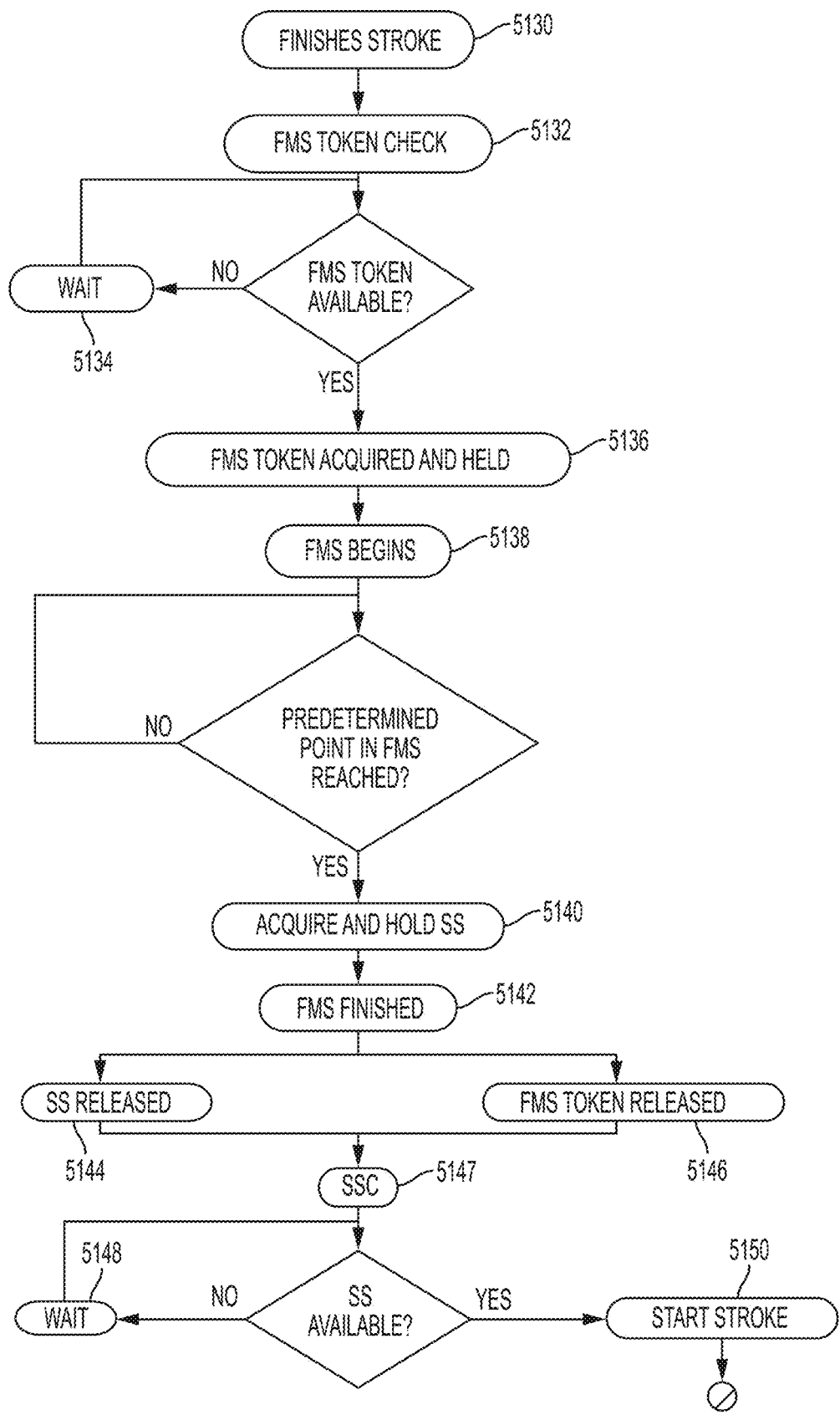
Figure 193:
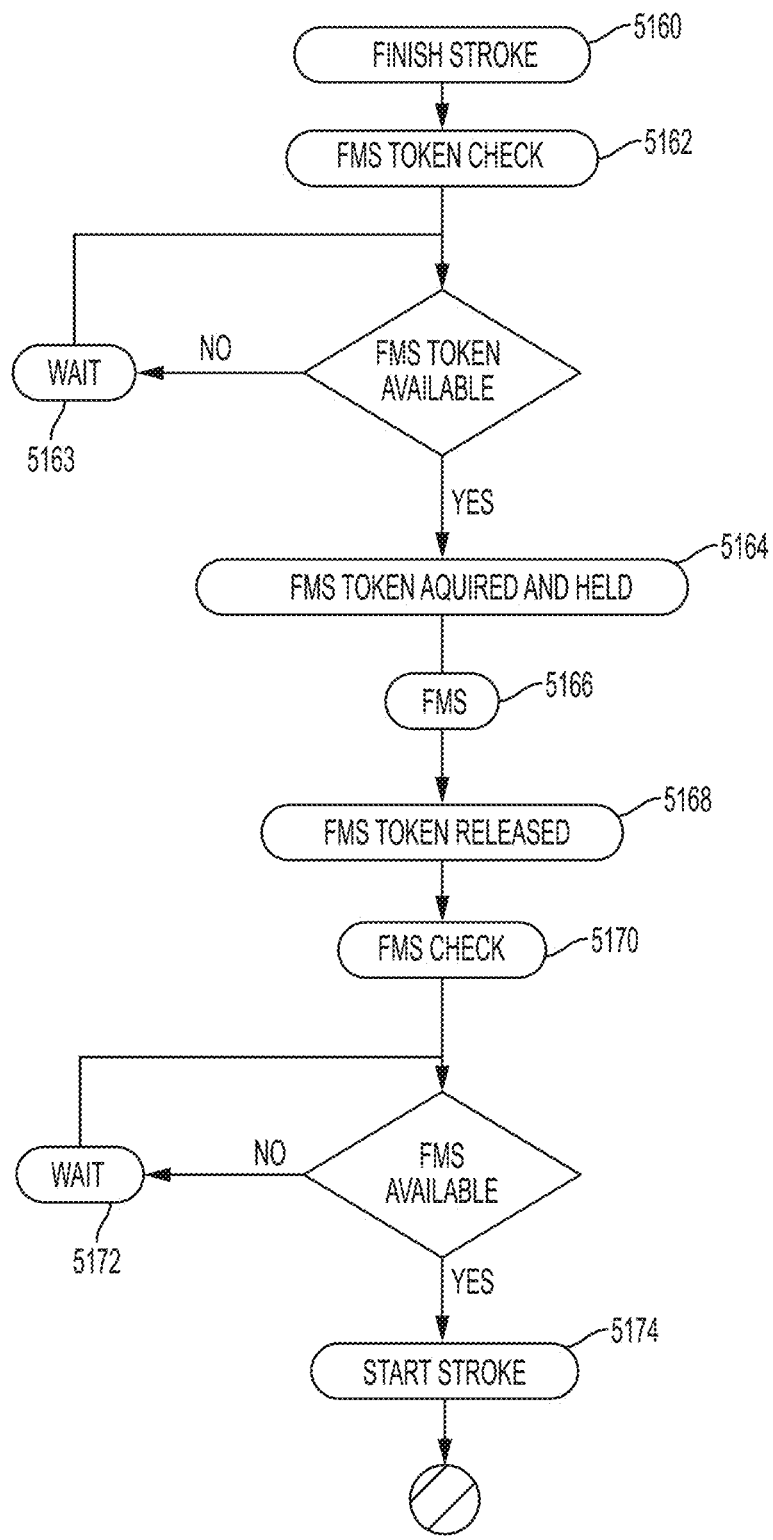
Figure 194:
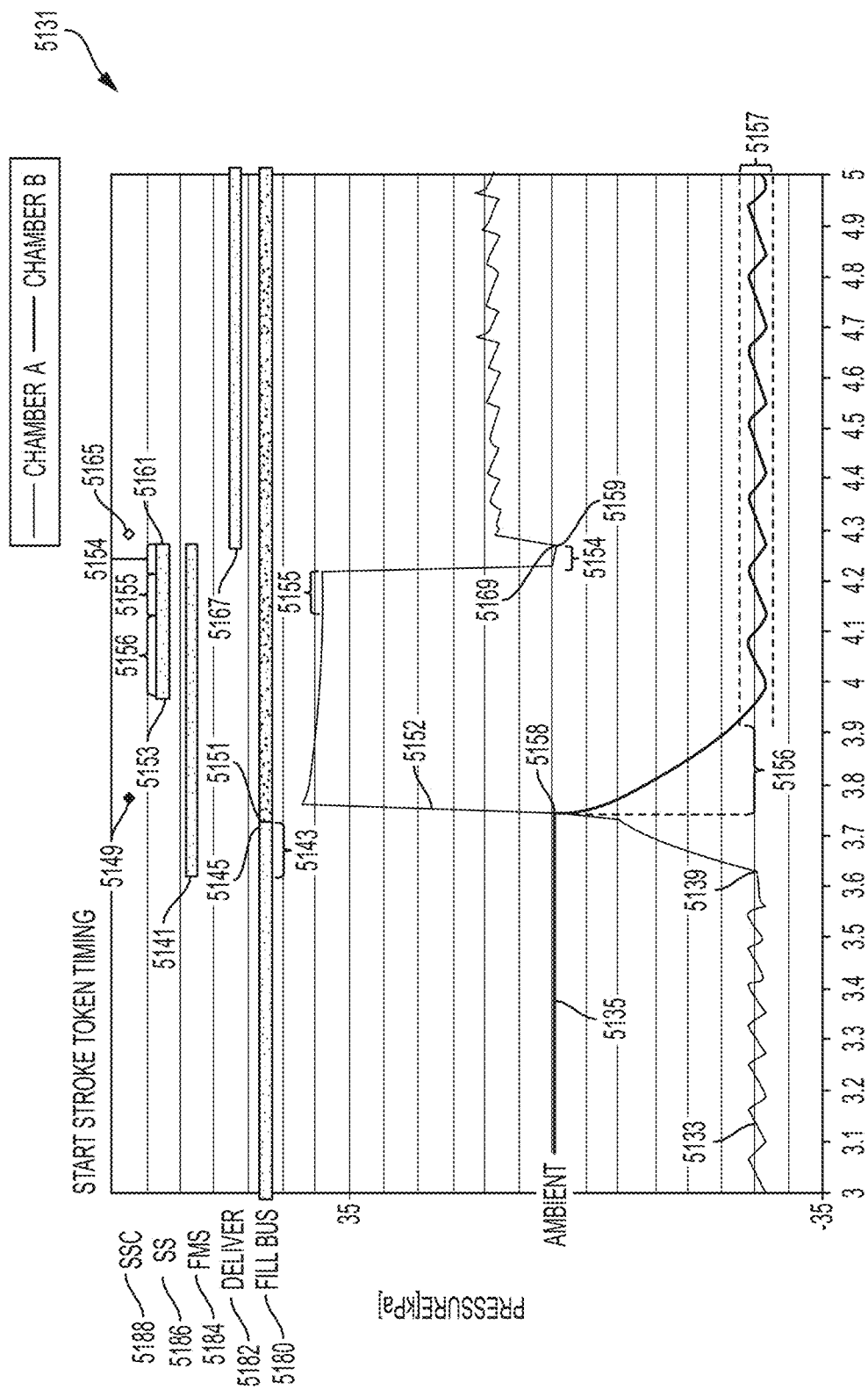
Figure 195:
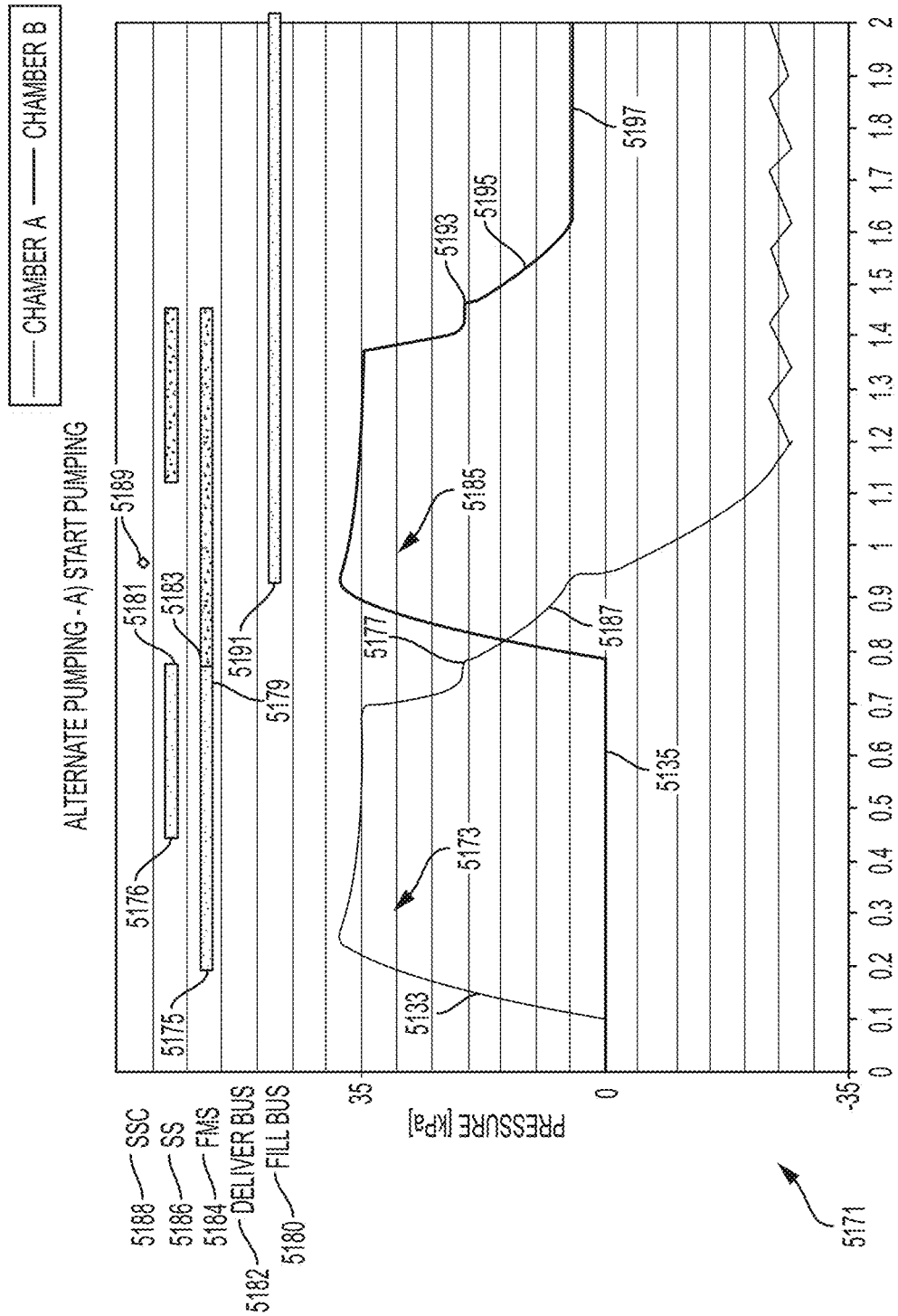
Figure 196:
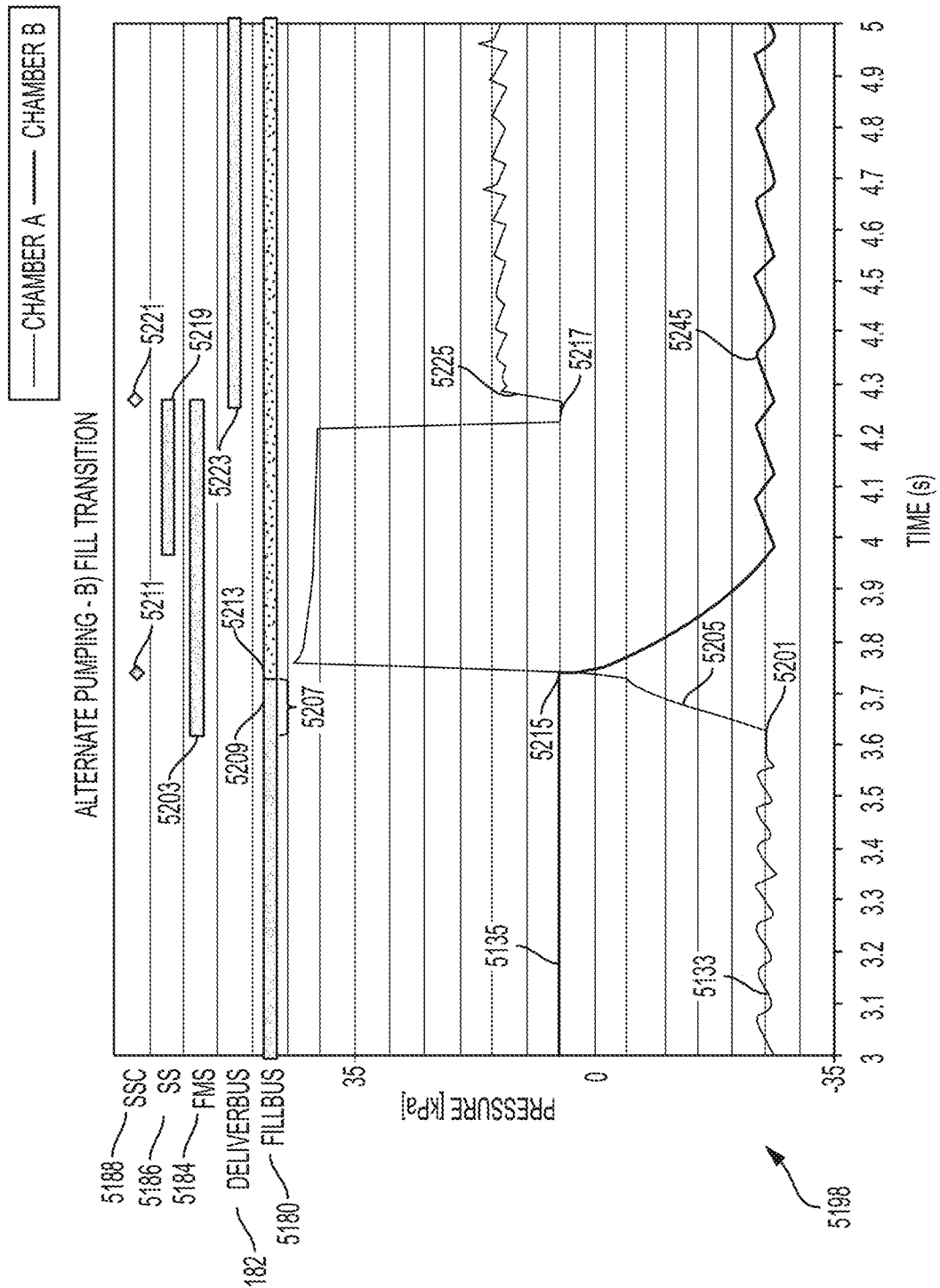
Figure 197:
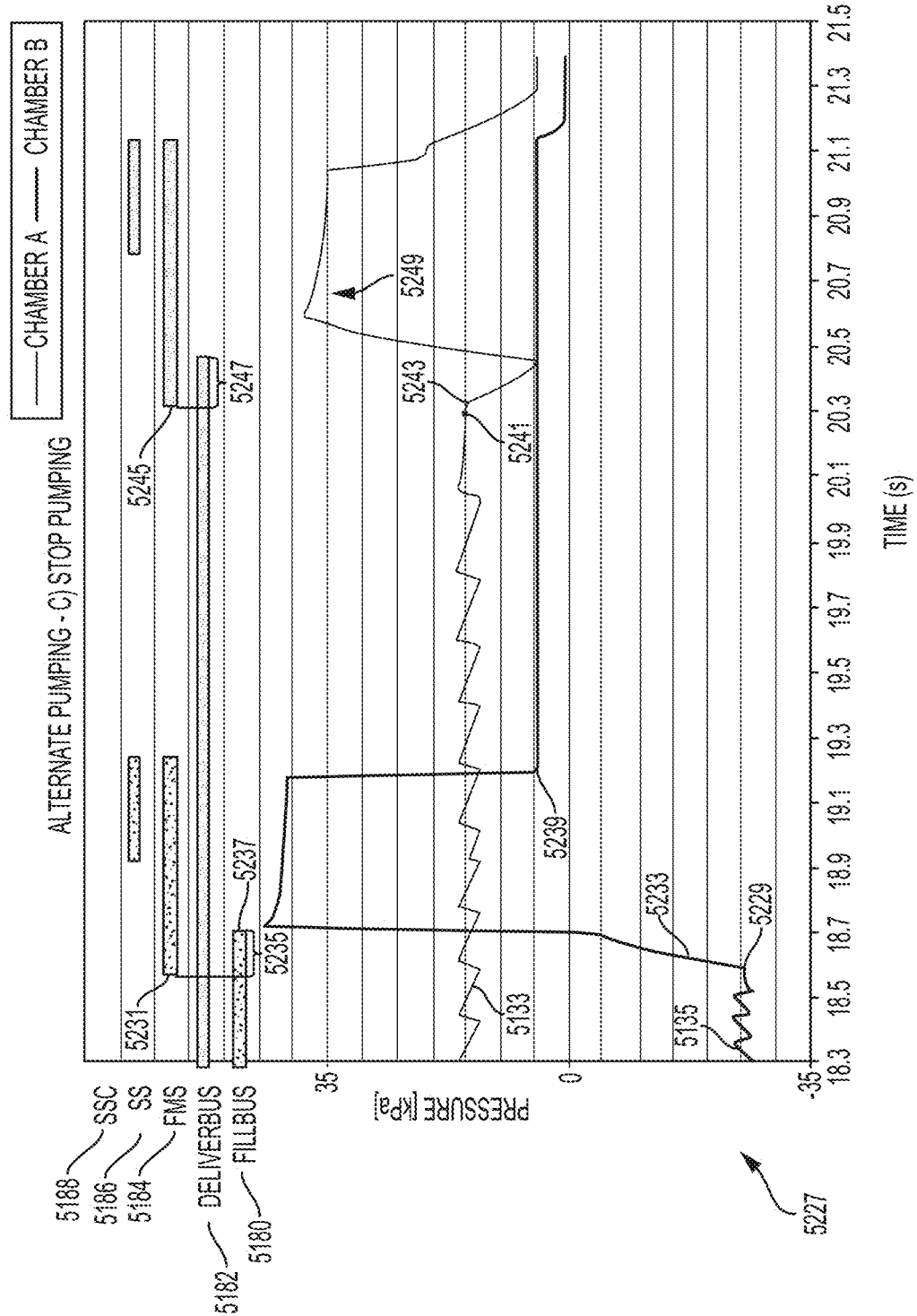
Figure 198:
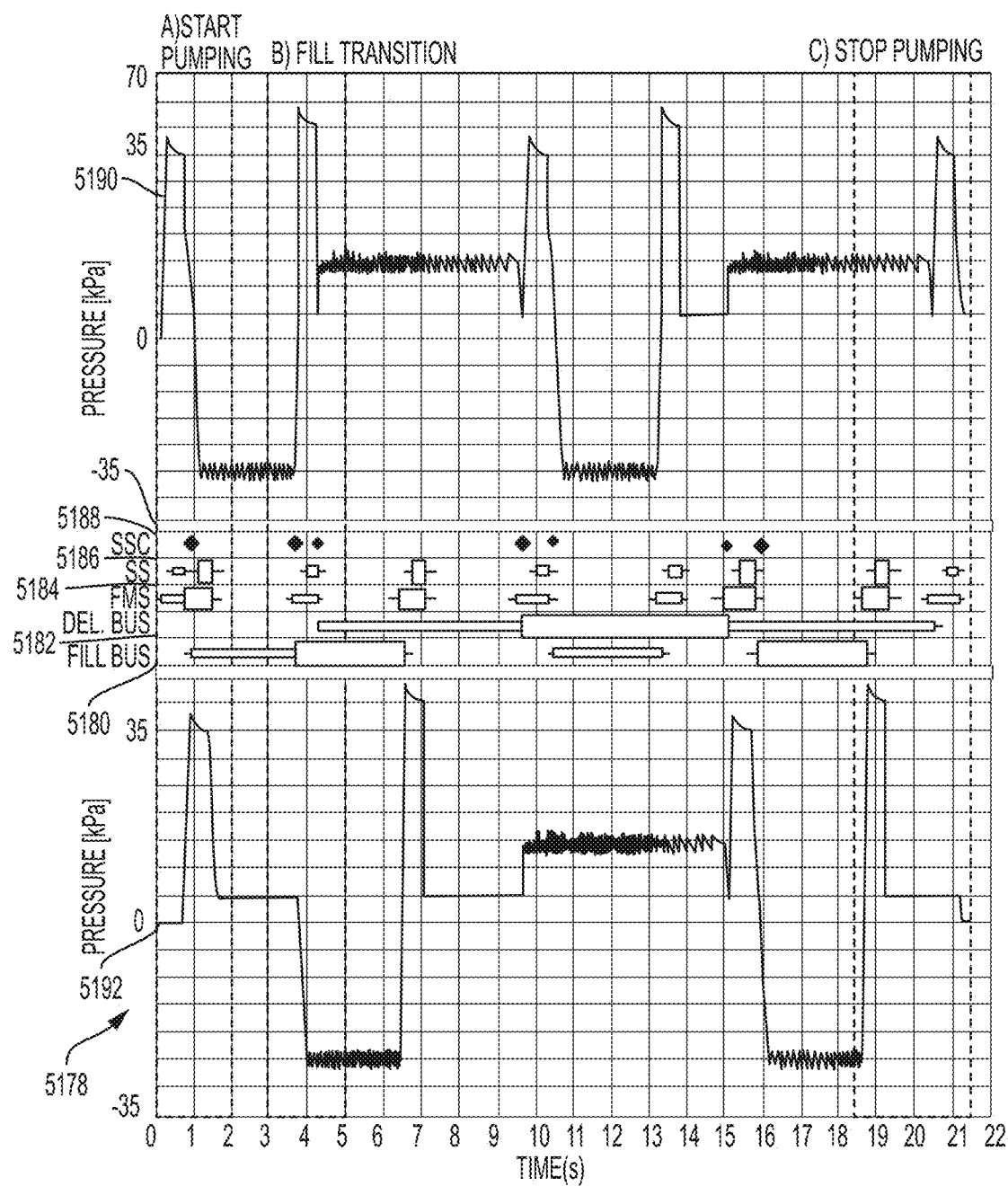
Figure 199:
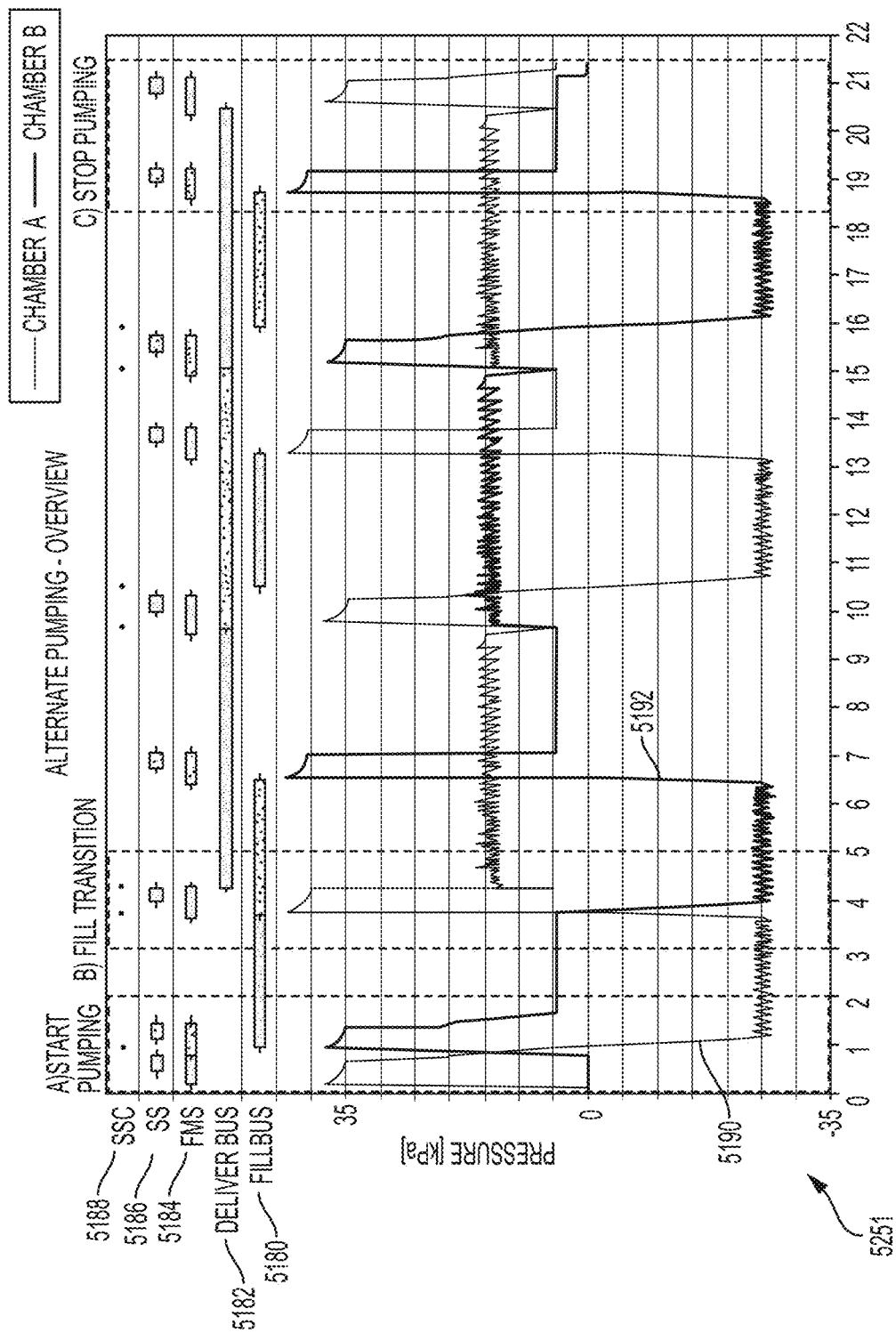
Figure 200:
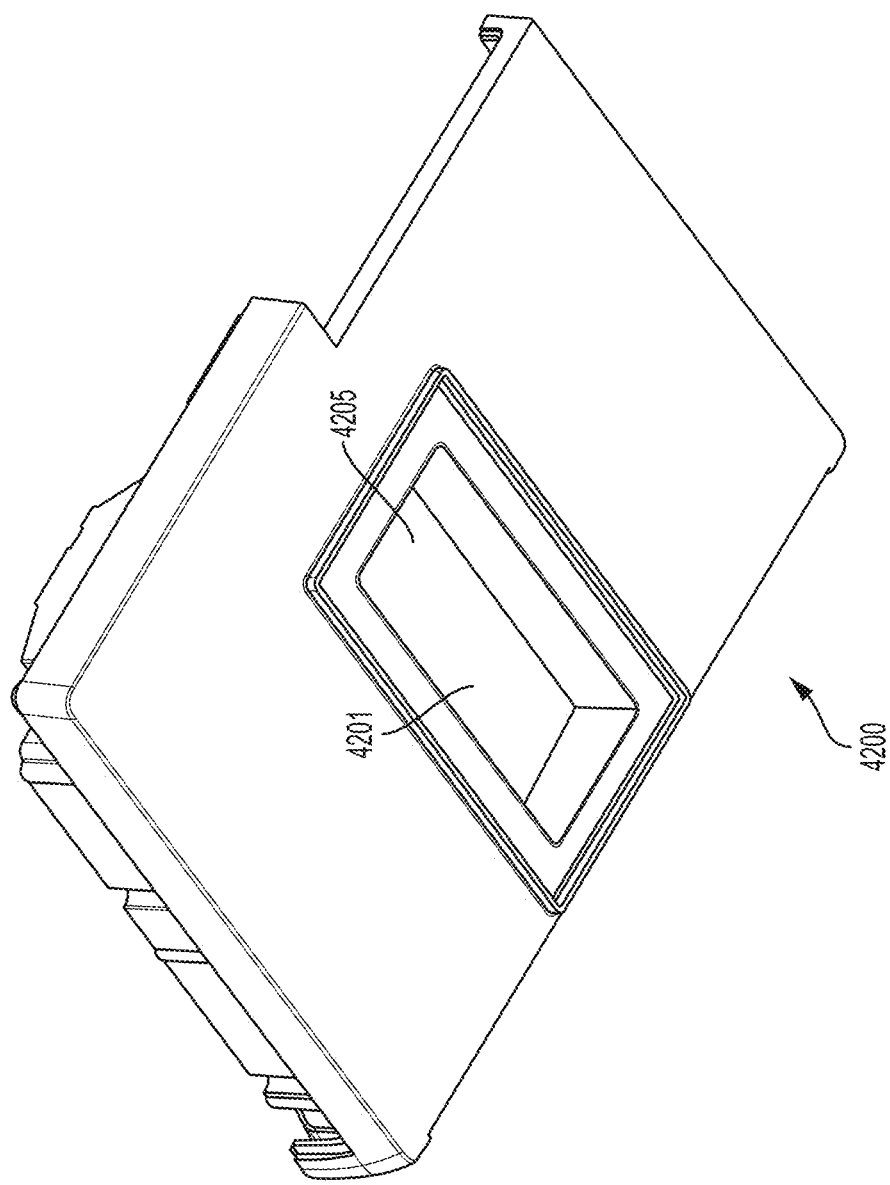
Figure 201:
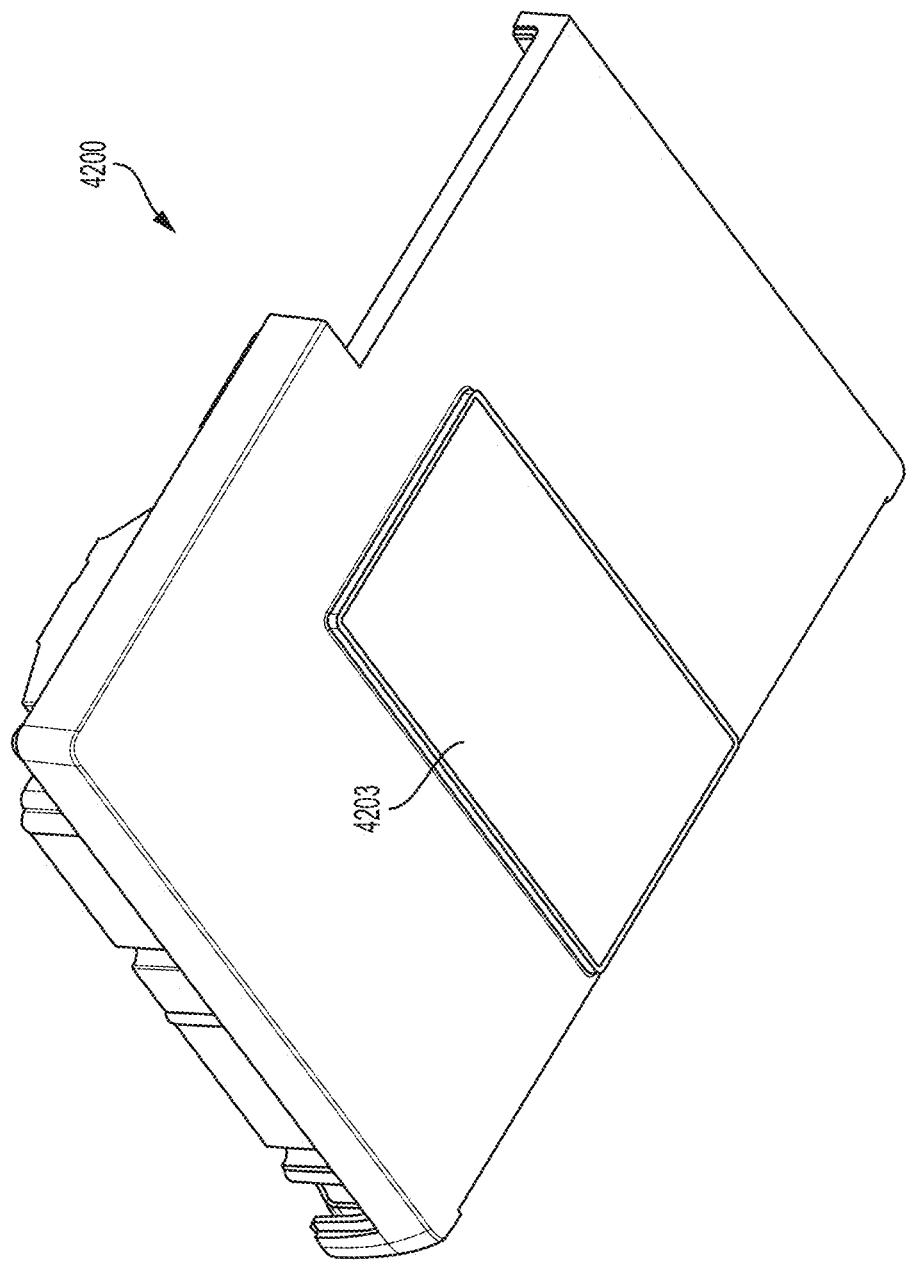
Figure 202:
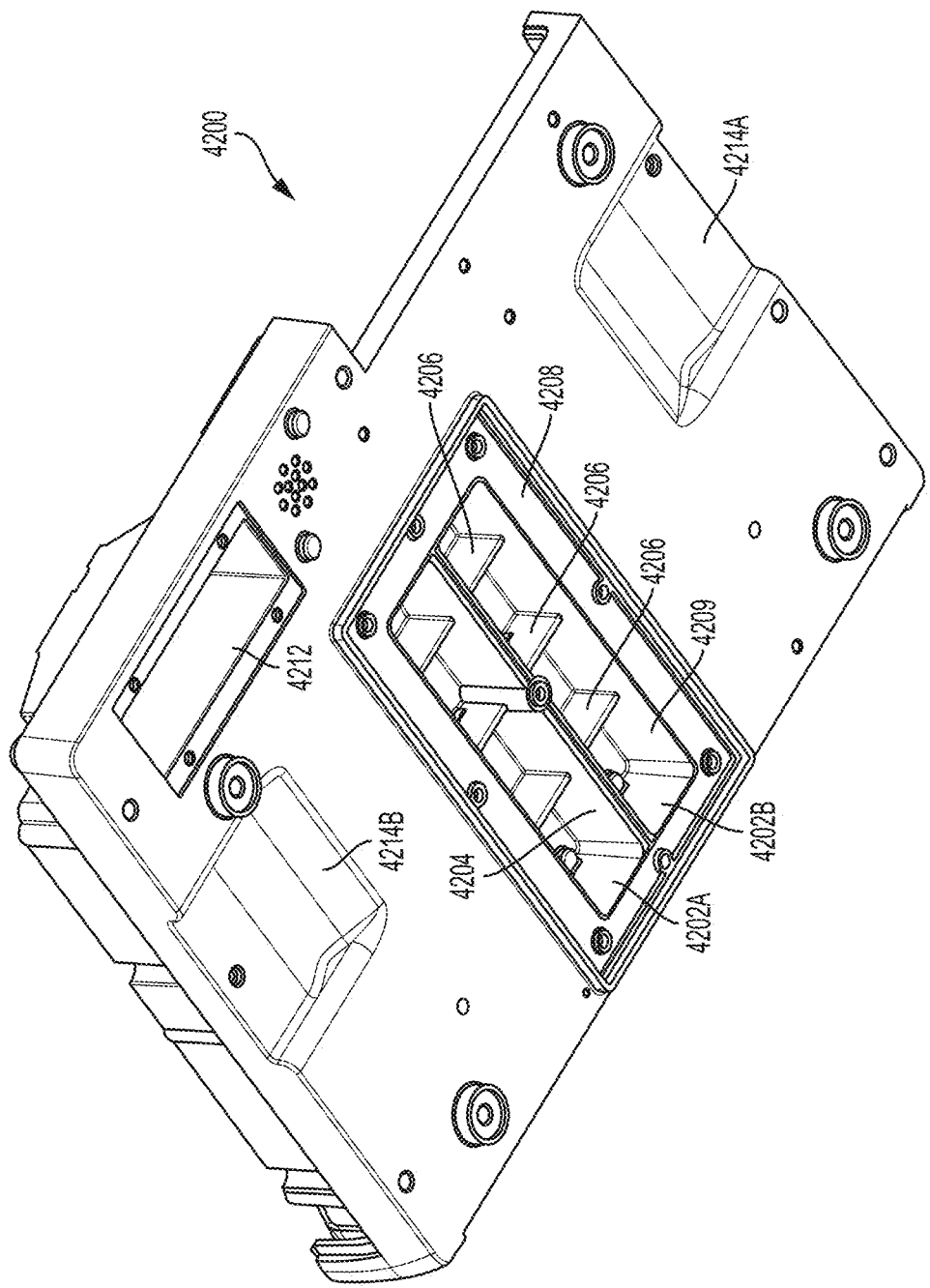
Figure 203:
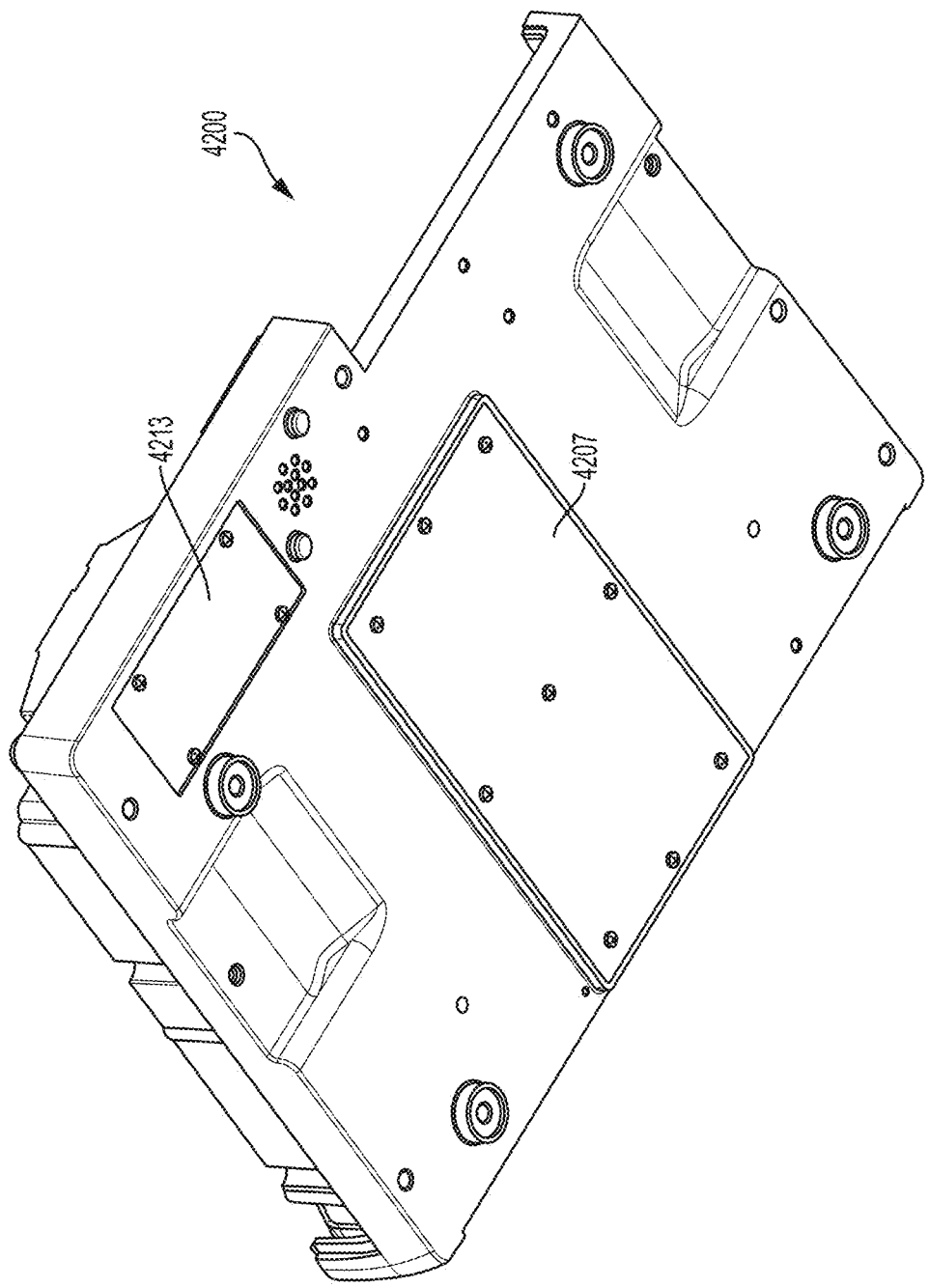
Figure 204:
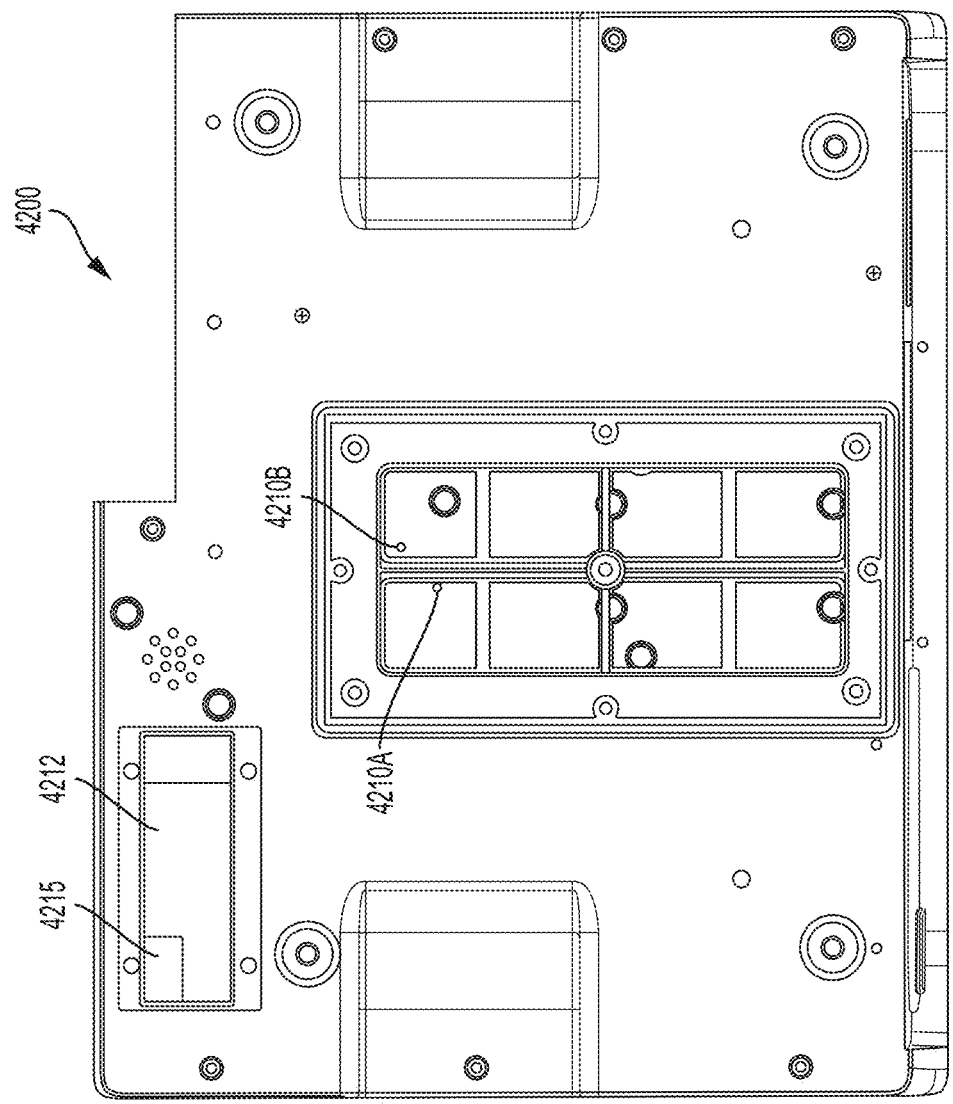
Figure 205:
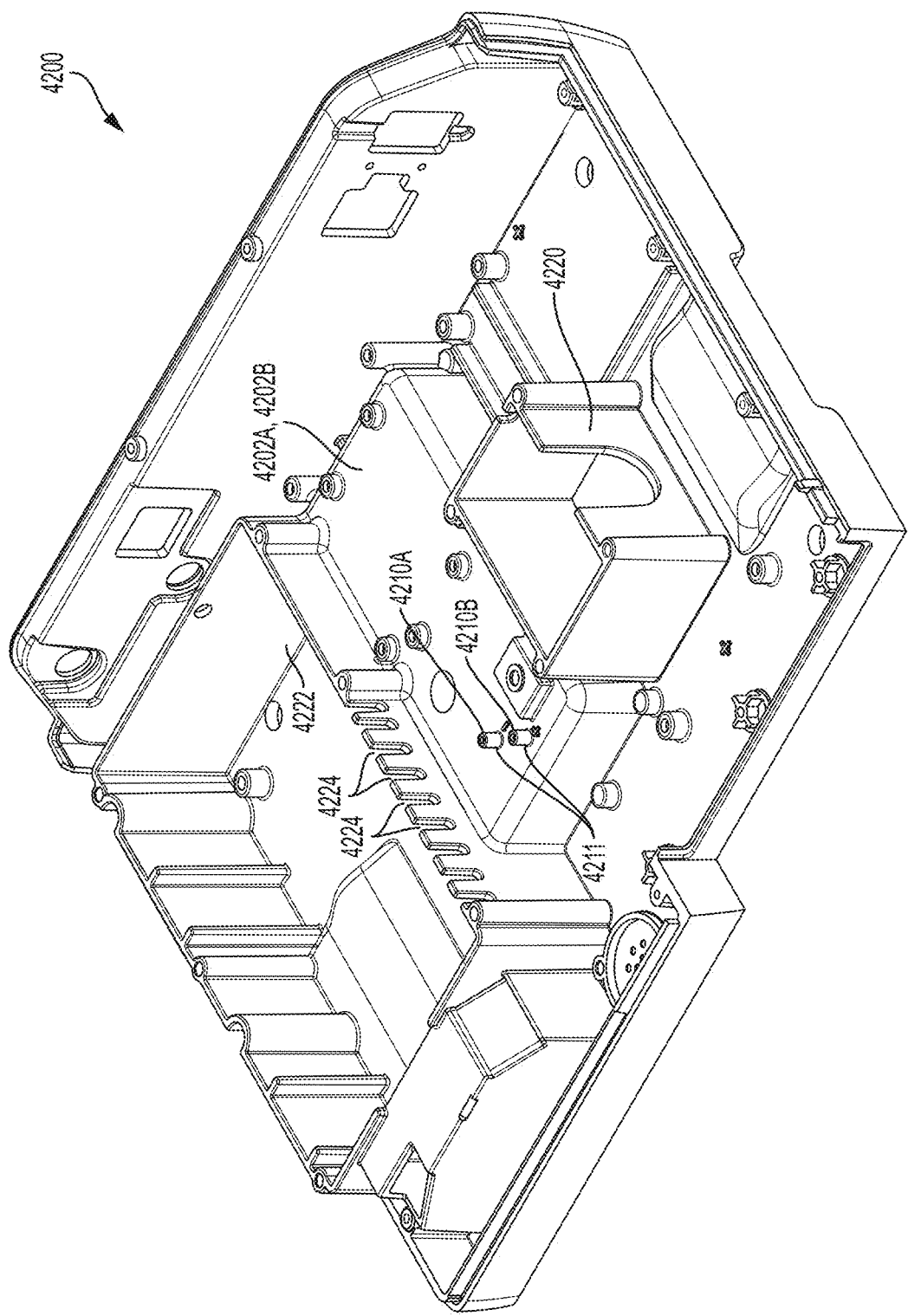
Figure 206:
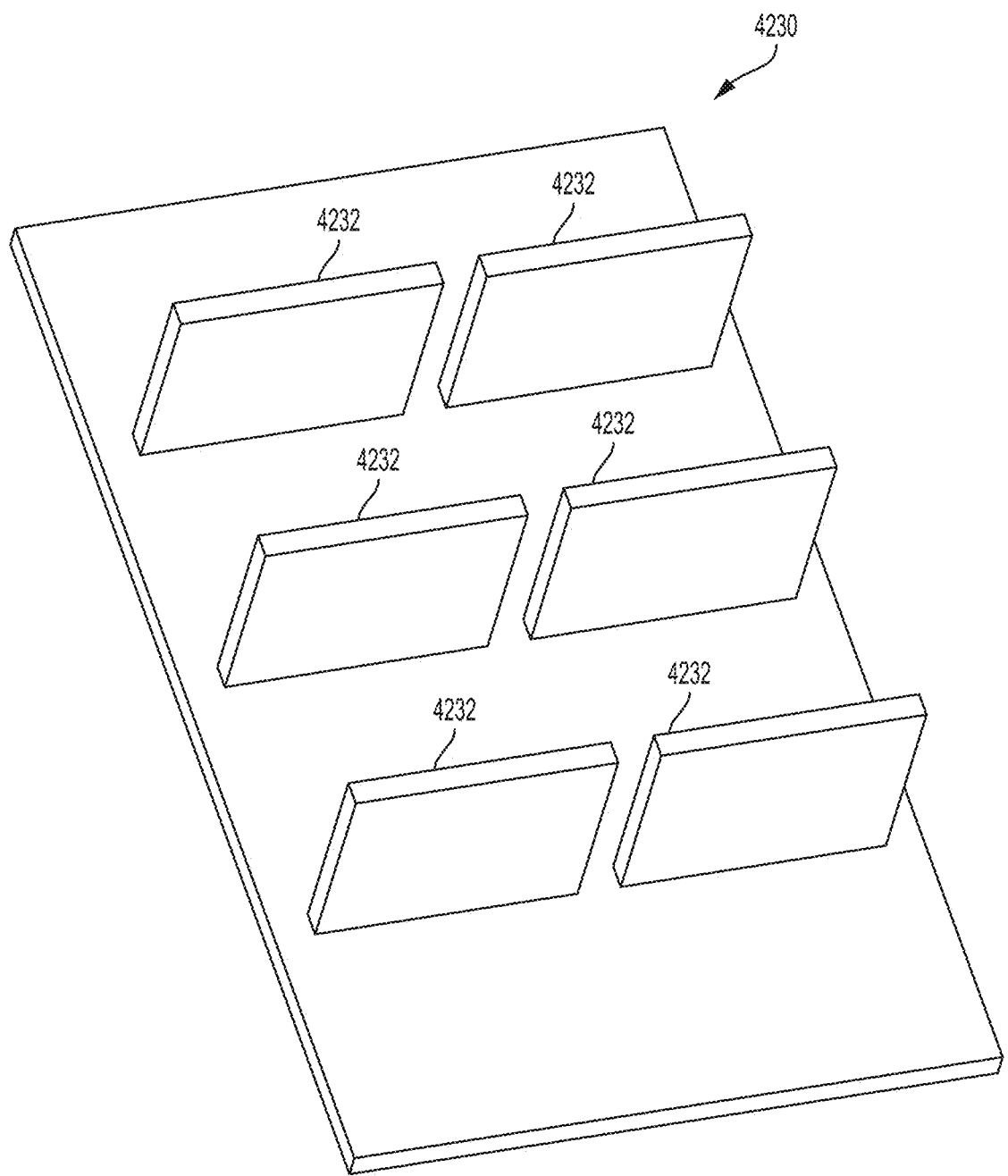
Figure 207:
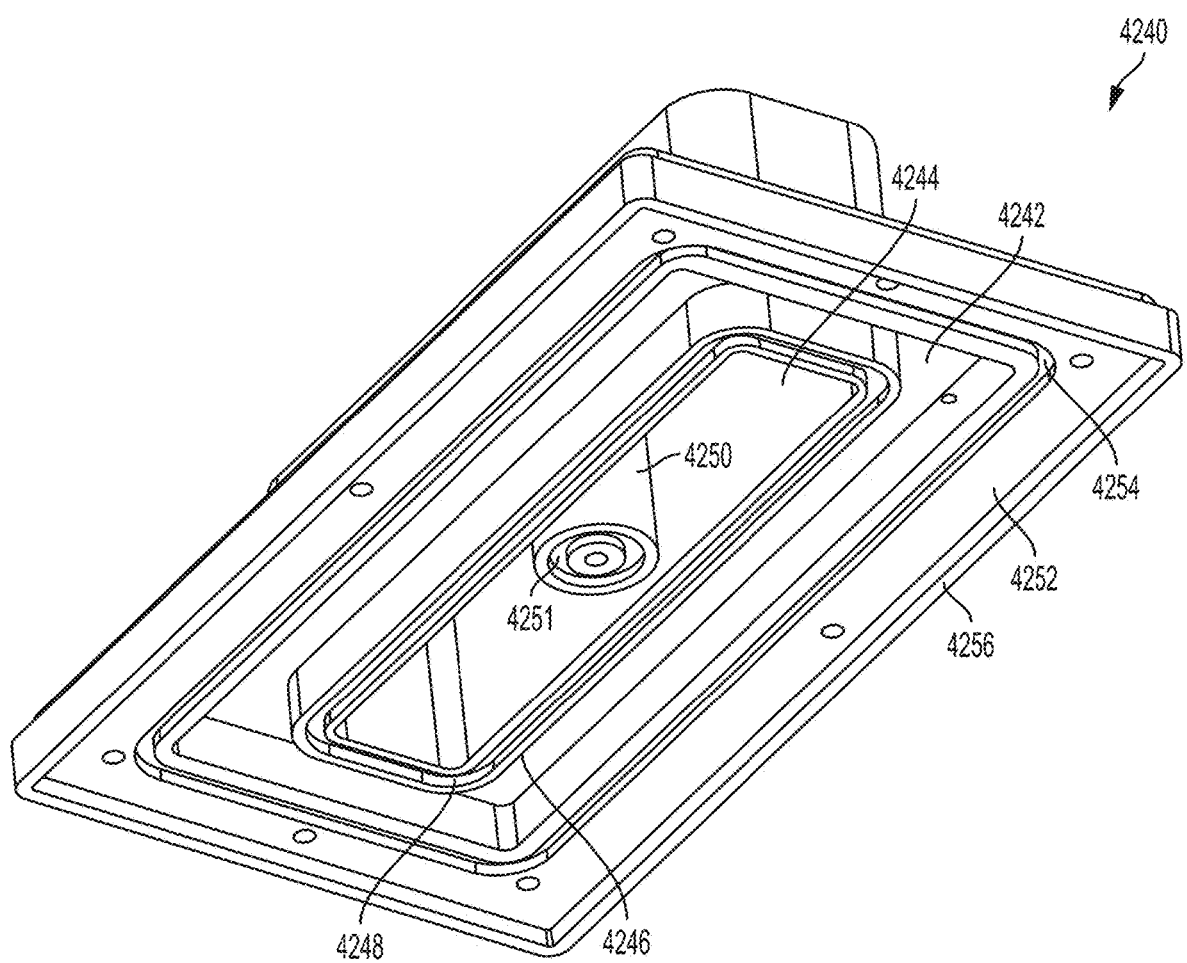
Figure 208:
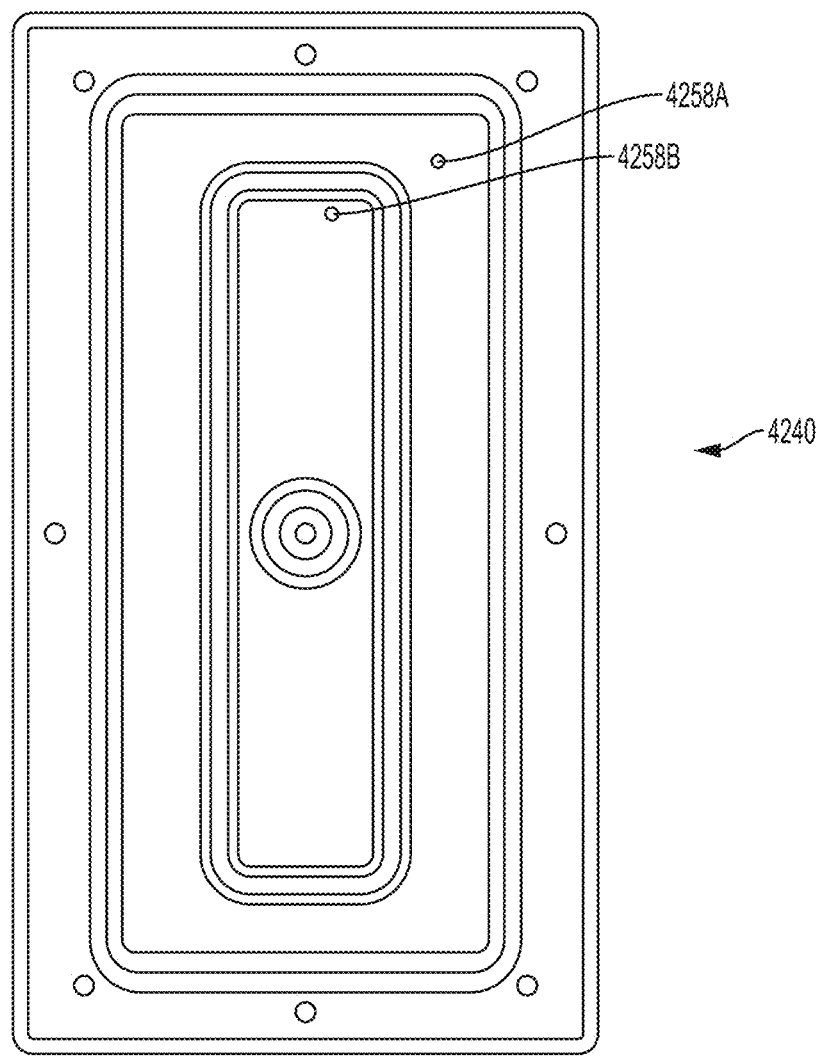
Figure 209:
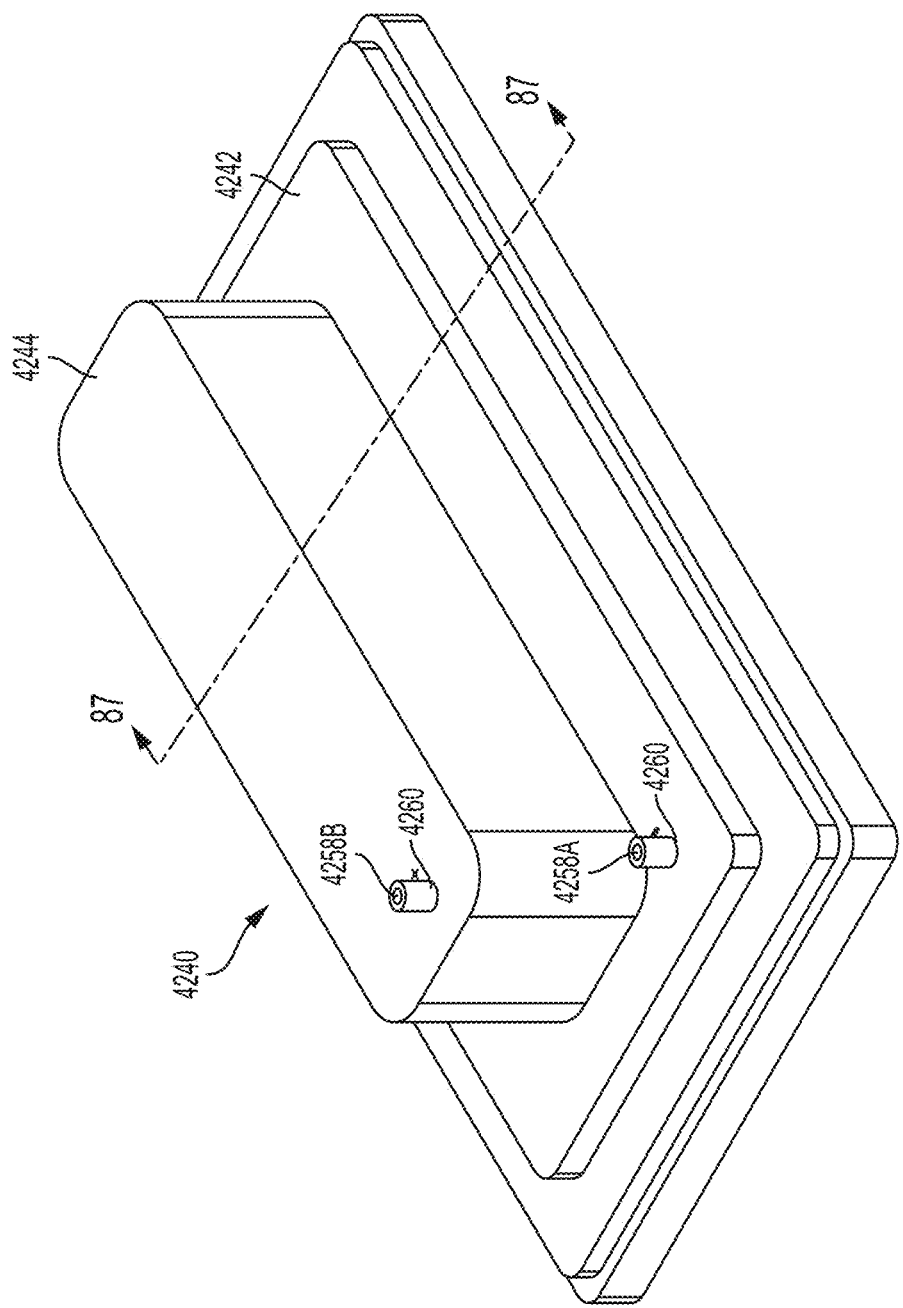
Figure 210:
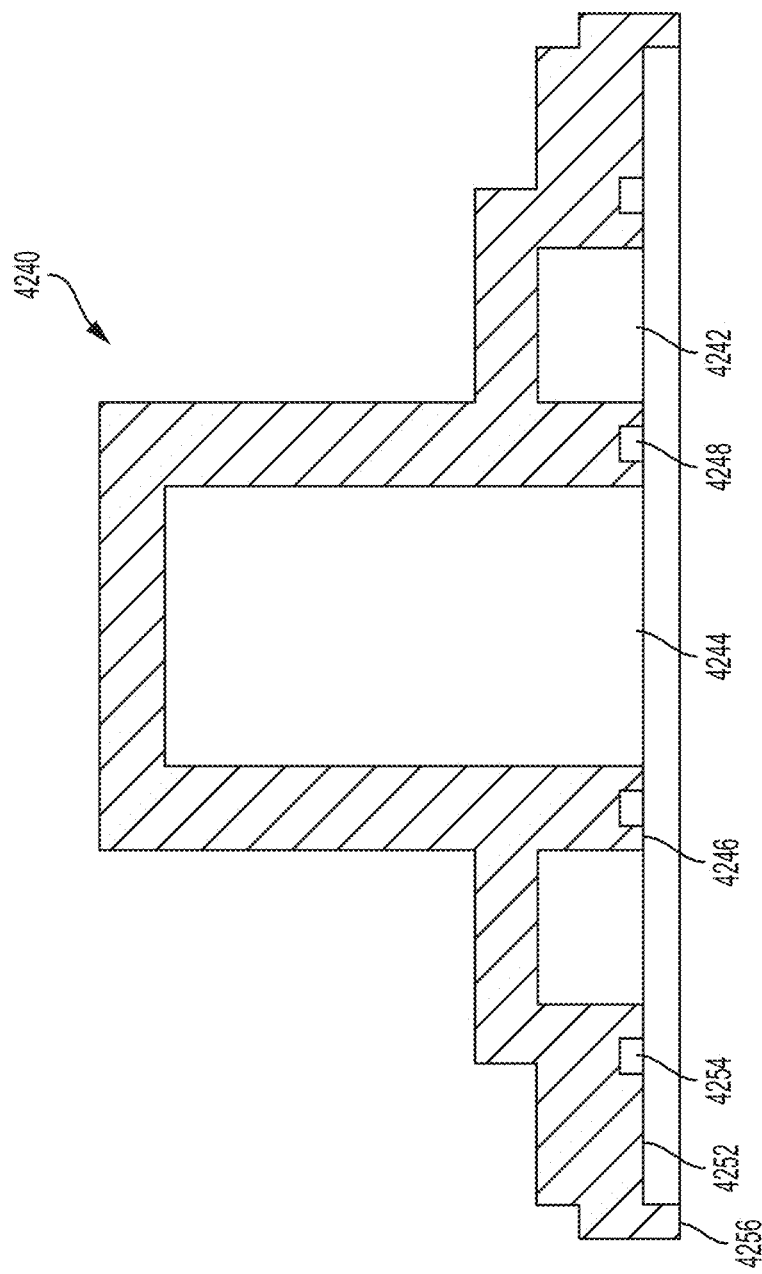
Figure 211:
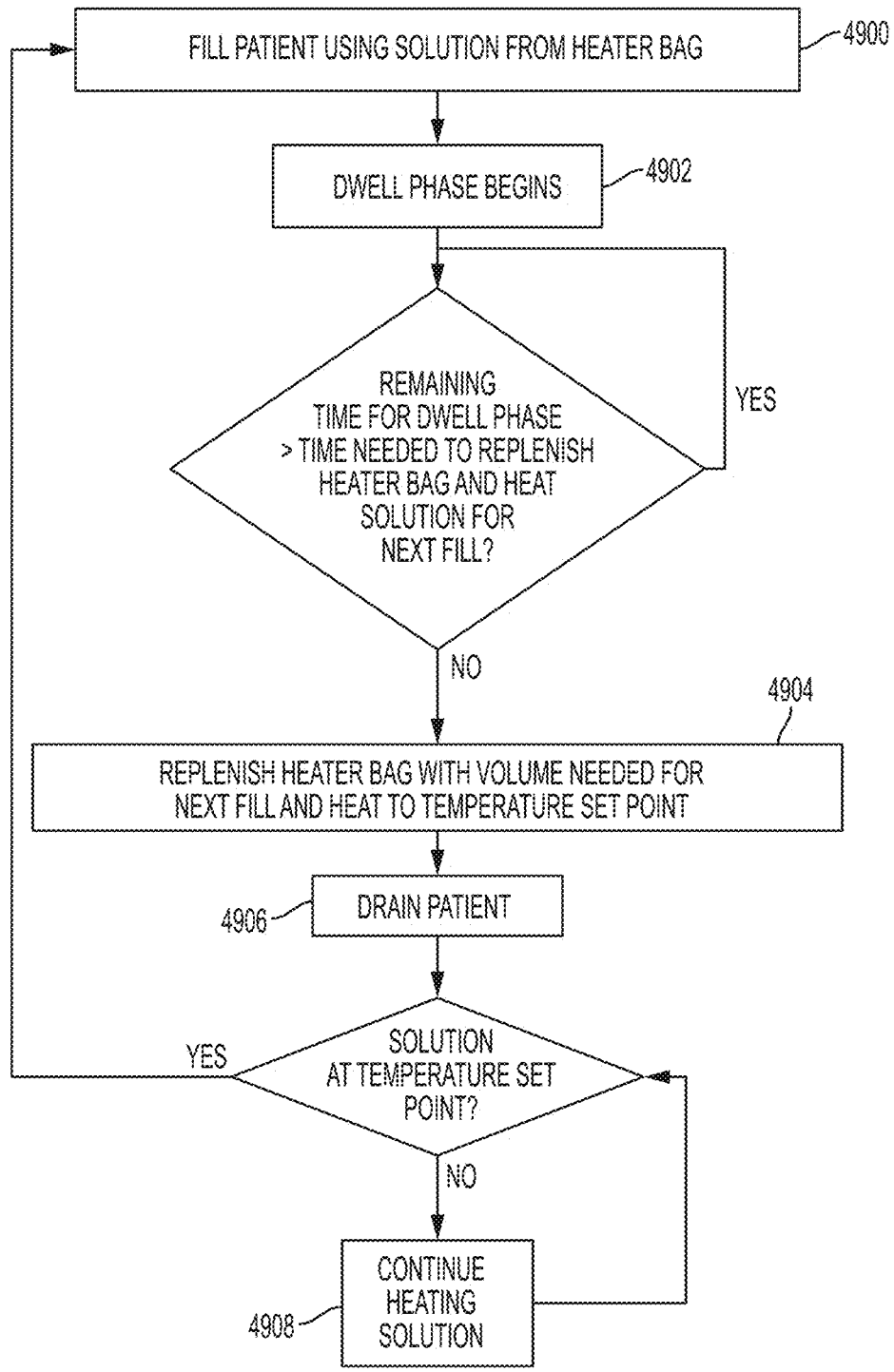
Figure 212:
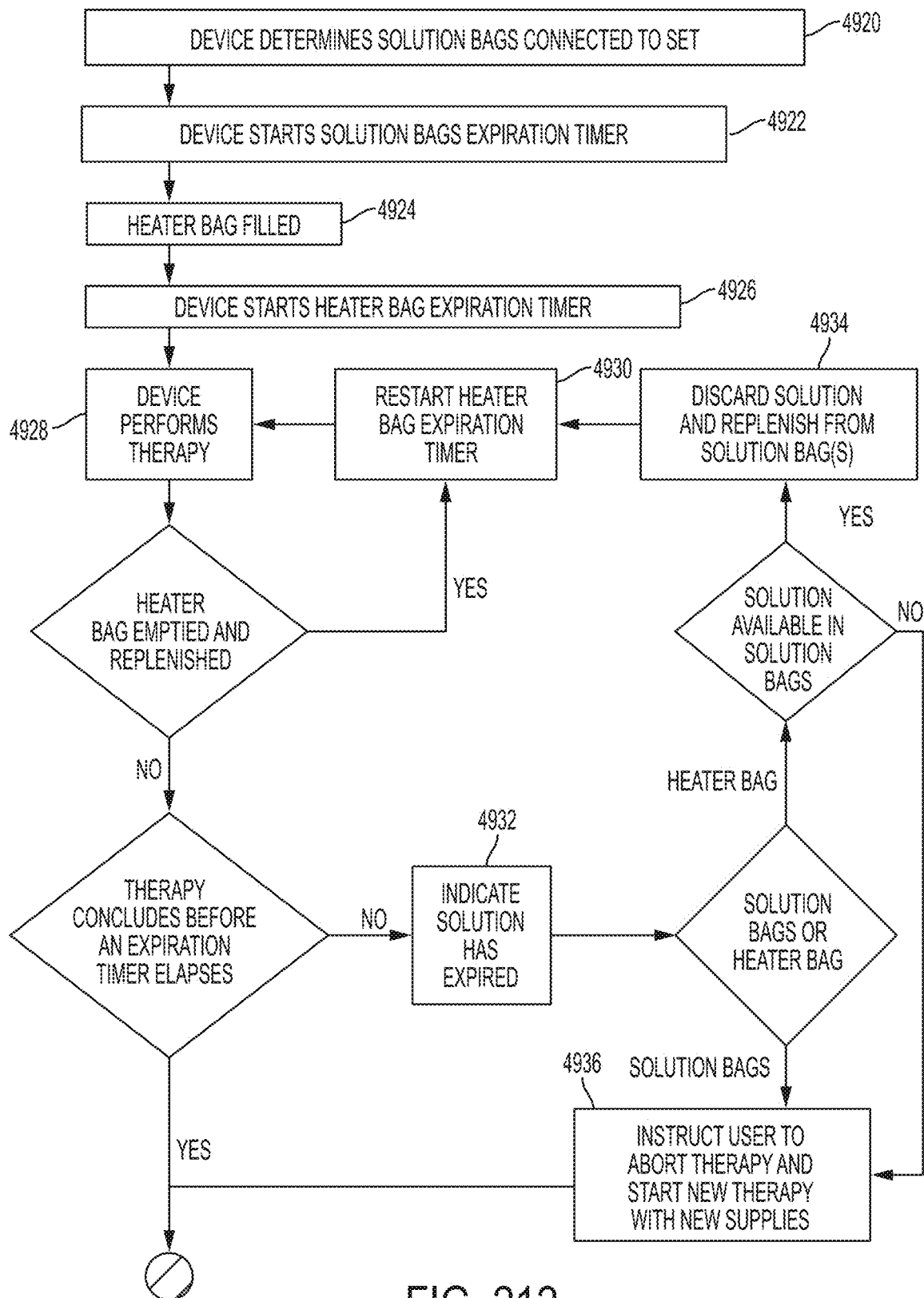
Figure 213:
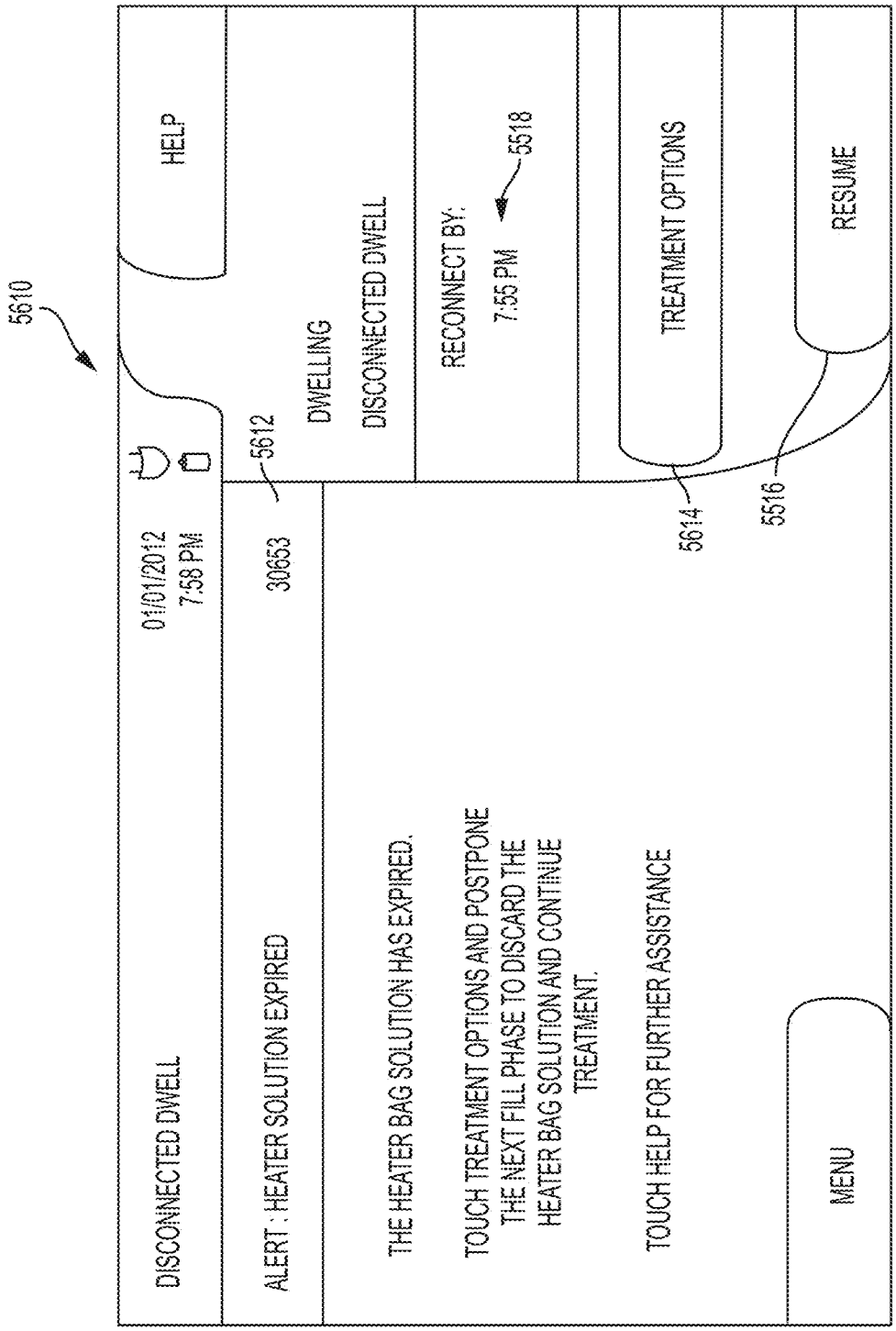
Figure 214A:
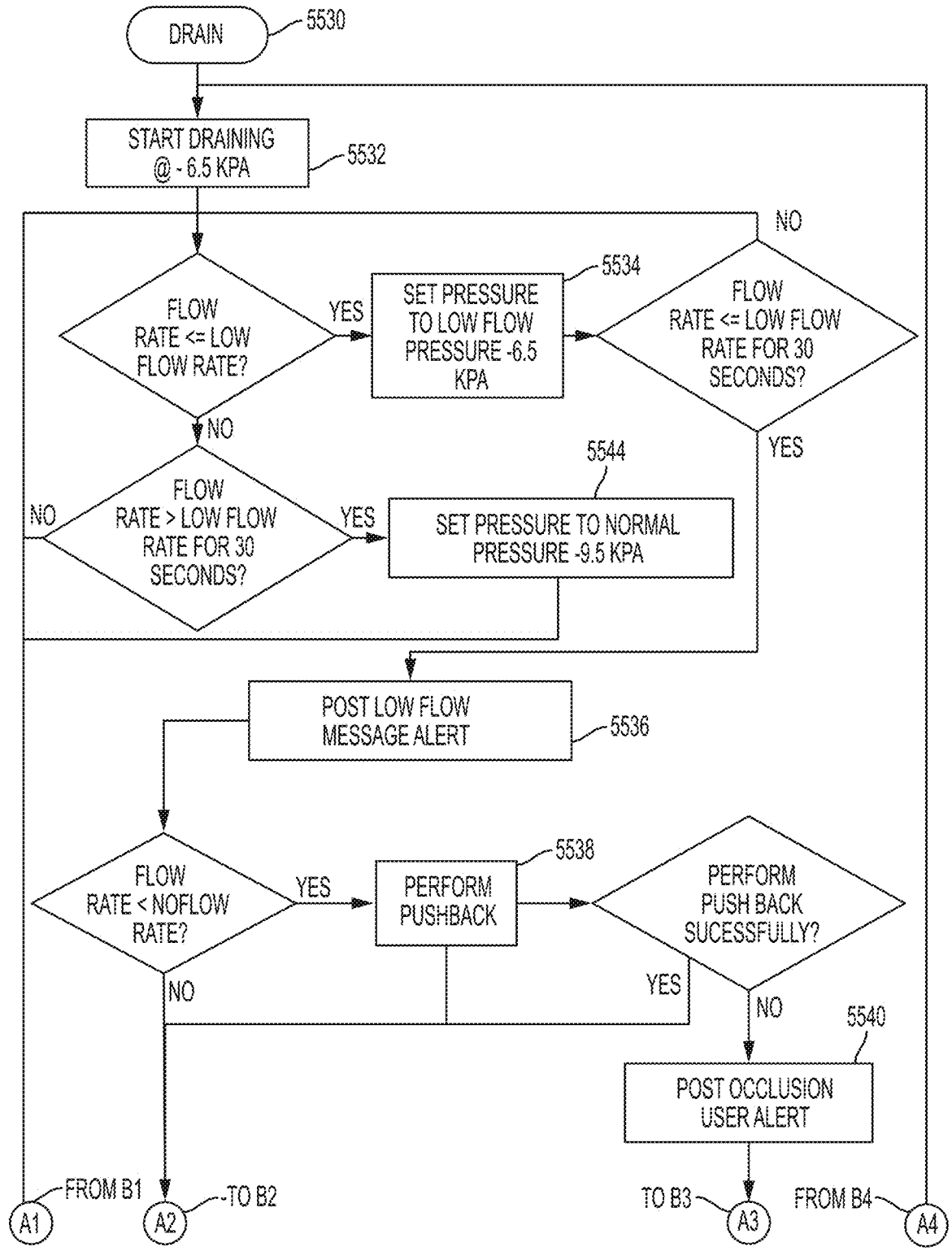
Figure 214B:
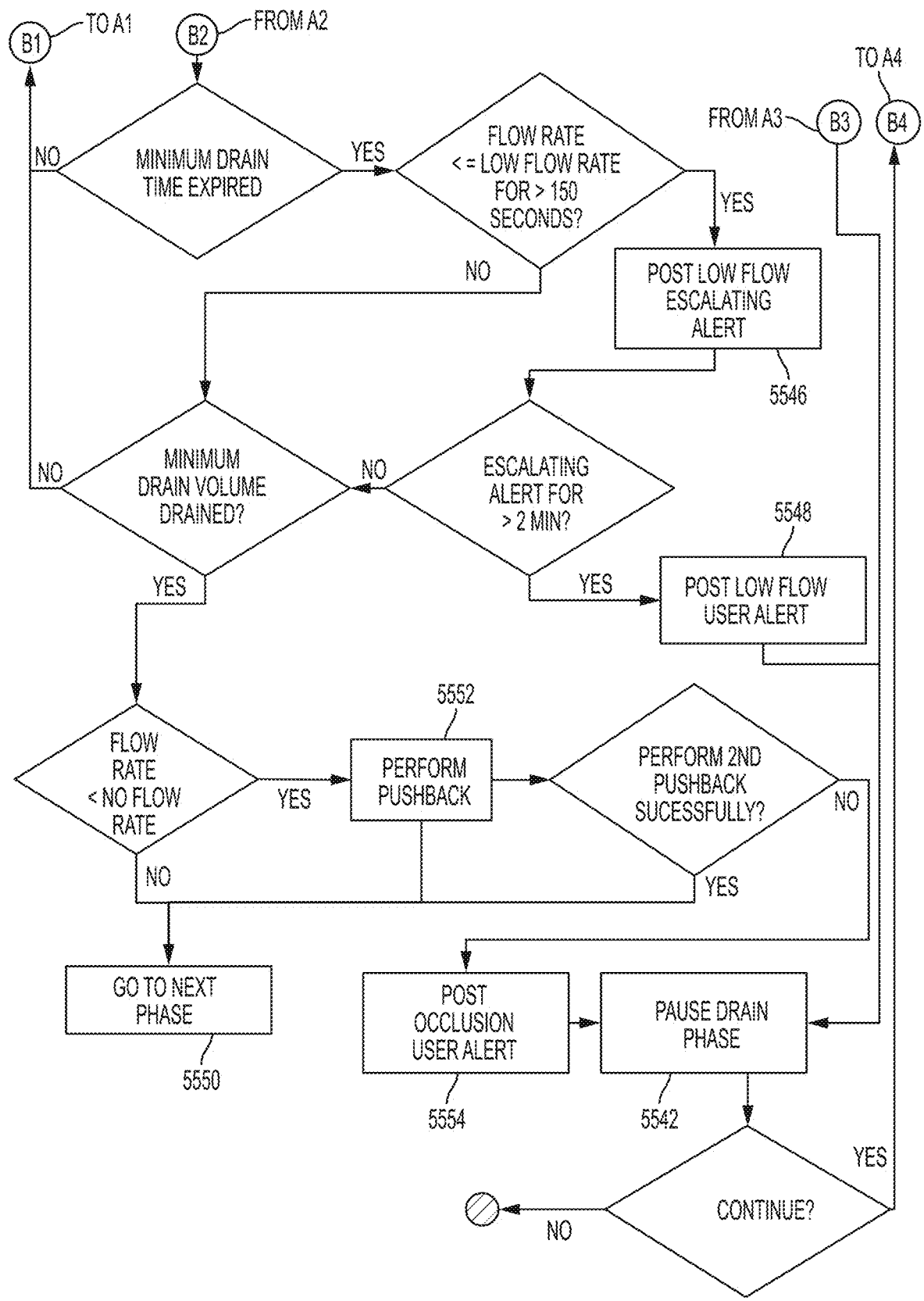
Figure 215:
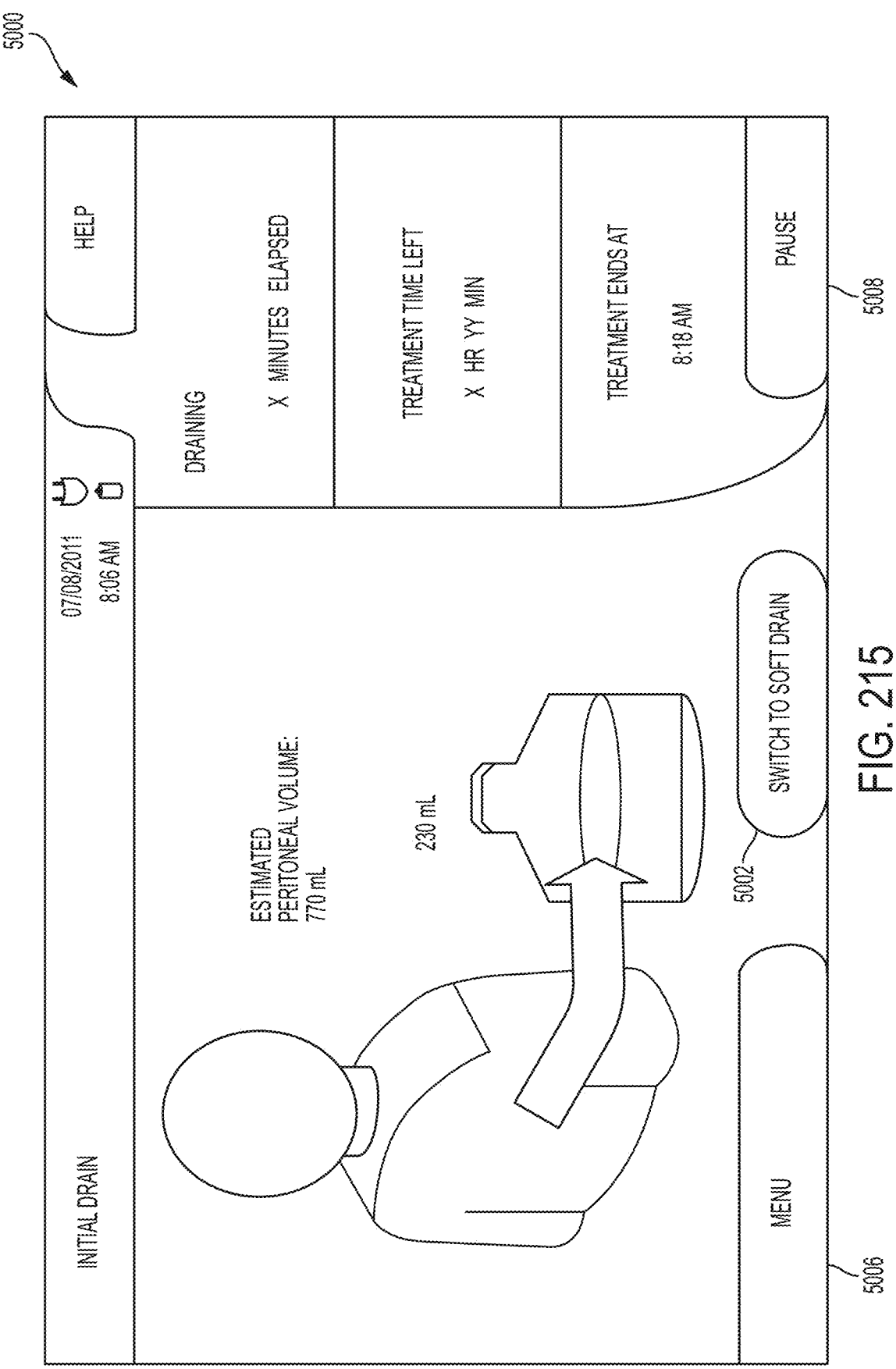
Figure 216:
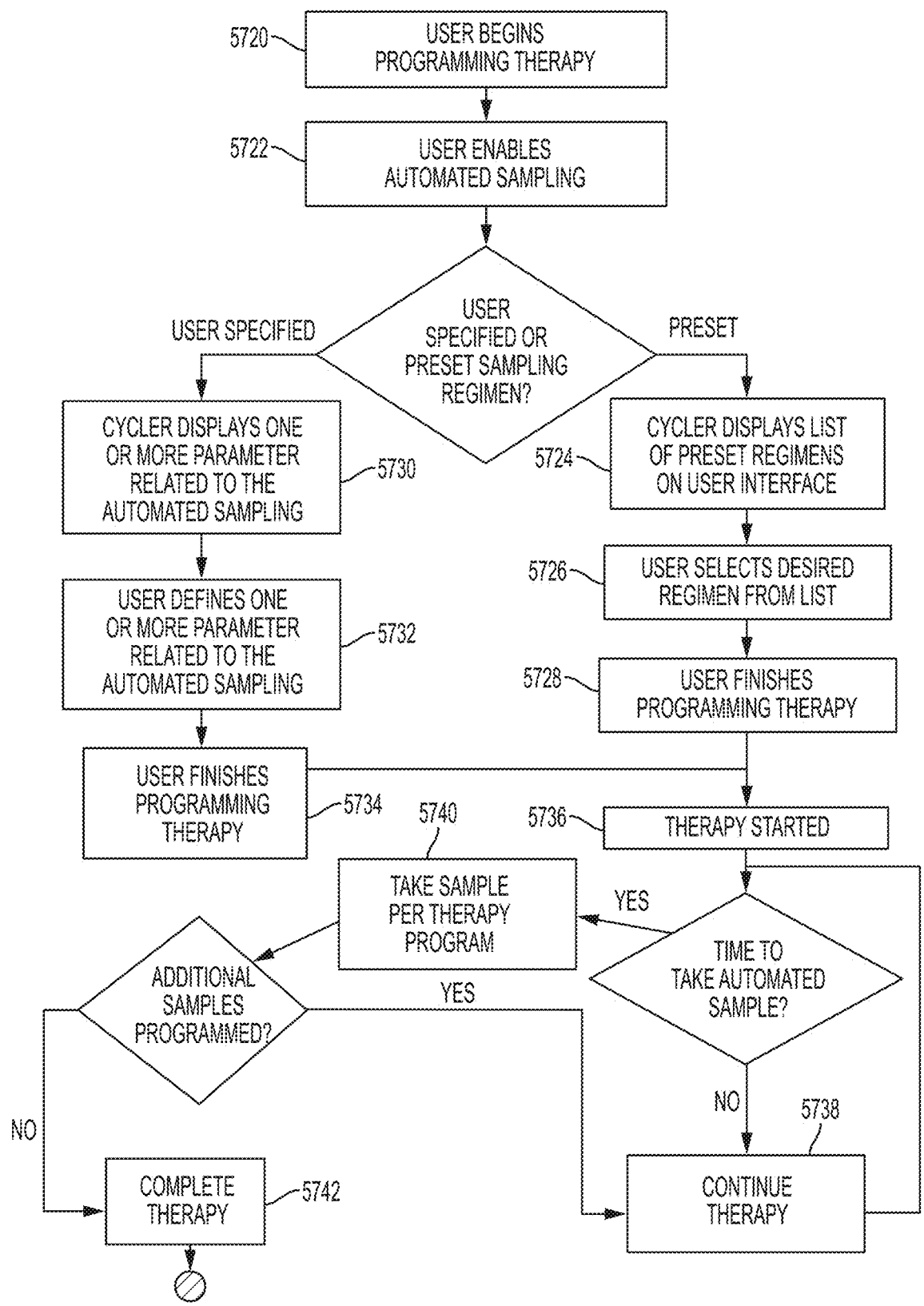
Figure 217:
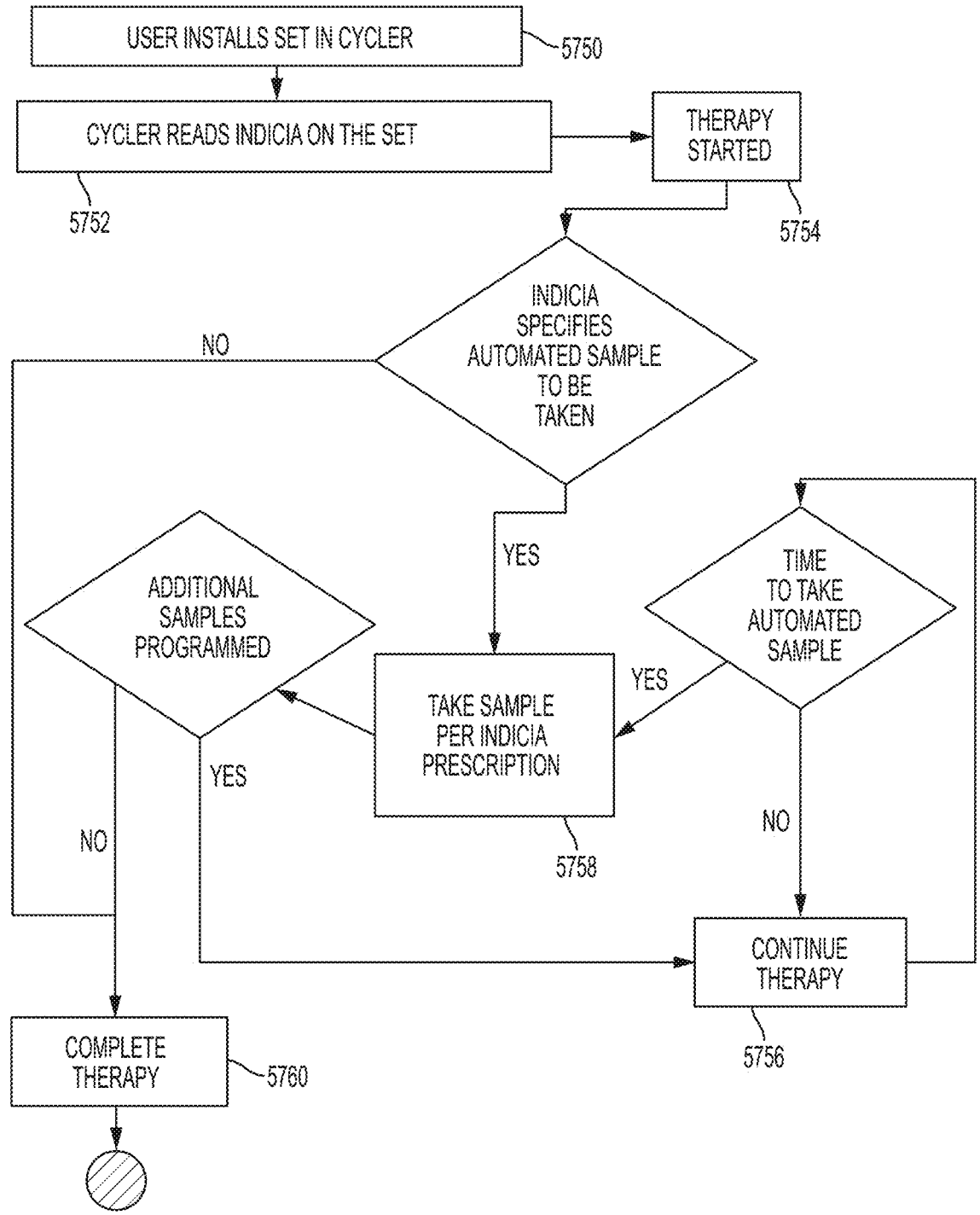

FIG. 123 shows a flowchart outlining steps to detect that a fluid line has been primed by estimating flow rate during pumping strokes;

FIG. 124 shows a flowchart outlining steps to detect that a fluid line has been primed by estimating flow rate during pumping strokes;

FIG. 125 shows a flowchart outlining steps which may be used by a cycler to differentiate which set of one or more different sets has been installed in a medical device;

FIG. 126 is a perspective view of an interior section of the cycler of FIG. 10 with the upper portion of the housing removed;

FIG. 127 is a schematic block diagram illustrating an exemplary implementation of control system for an APD system;

FIG. 128 shows an exemplary patient data key and associated port for transferring patient data to and from the APD system;

FIG. 129 shows a patient data key with an alternative housing configuration;

FIG. 130 shows a block diagram of software subsystems of a user interface computer and an automation computer;

FIG. 131 is a schematic block diagram illustrating an exemplary arrangement of the multiple processors controlling the cycler and the safe line;

FIG. 132 is a schematic block diagram illustrating exemplary connections between the hardware interface processor and the sensors, the actuators and the automation computer;

FIG. 133 shows a schematic cross section of the cycler illustrating the components of the heater system for the heater bag;

FIG. 134 shows software processes interacting with a heater controller process;

FIG. 135 shows a block diagram of a nested feedback loop to control the heater bag temperature;

FIG. 136 shows a block diagram of an alternative nested feedback loop to control the heater bag temperature;

FIG. 137 shows a block diagram of another alternative nested feedback loop to control the heater bag temperature;

FIG. 138 shows a block diagram of the thermal model of the heater bag and heater tray;

FIG. 139 shows a temperature response of the heater bag and heater tray for nominal conditions;

FIG. 140 shows a temperature response of the heater bag and heater tray for warm conditions;

FIG. 141 shows a temperature response of the heater bag and heater tray for cold conditions;

FIG. 142 is a schematic block diagram of one embodiment of a heater control system;

FIG. 143 is a schematic block diagram illustrating a heater circuit configured with a pair of heating elements;

FIG. 144 is a schematic block diagram illustrating a heater circuit configured with a pair of heating elements with reduced potential for current leakage;

FIG. 145 is a circuit diagram of a heater circuit configured with a pair of heating elements;

FIG. 146 shows a flow chart outlining a method to select the heater configuration in an APD cycler;

FIG. 147 shows a flow chart outlining a method to select the heater configuration in an APD cycler where a stored value of the AC mains voltage is queried during selection of the heater configuration;

FIG. 148 shows an example heater circuit which may be included in an automated dialysis machine;

FIG. 149 is a graph depicting leakage current to a heater pan from a heater element over time;

FIG. 150 is another graph depicting leakage current to a heater pan from a heater element over time;

FIG. 151 is a schematic of a heater circuit which may be included in an automated dialysis machine;

FIG. 151A is a schematic of a heater circuit with a safety voltage source;

FIG. 152 depicts an AC mains input for the example circuit of FIG. 148;

FIG. 153 depicts AC mains input connected to the AC switch of the circuit of FIG. 148;

FIG. 154 shows first and second lines of AC mains switch outs connected to pulse width modulated elements;

FIG. 155 depicts a modulation or gating circuit that may be used in the circuit of FIGS. 148-154;

FIG. 156 depicts a modulation or gating circuit similar to that of FIG. 155;

FIG. 157 depicts example circuitry that may be included in a heater circuit that includes a current sense element;

FIG. 158 shows a flow of information between various subsystems and processes of the APD system;

FIG. 159 illustrates an operation of the therapy subsystem of FIG. 157;

FIG. 160 is a sequence diagram depicting interactions of therapy module processes during initial replenish and dialyze portions of the therapy;

FIGS. 161-166 show screen views relating to alerts and alarms that may be displayed on a touch screen user interface for the APD system;

FIG. 167 illustrates component states and operations for error condition detection and recovery;

FIG. 168 shows exemplary modules of a UI view subsystem for the APD system;

FIG. 169 shows an illustrative user interface initial screen that provides the user the option of selecting in between start therapy or settings;

FIG. 170 shows an illustrative user interface status screen that provides information on the status of the therapy;

FIG. 171 shows an illustrative user interface menu screen with various comfort settings;

FIG. 172 shows an illustrative user interface help menu screen;

FIG. 173 shows an illustrative user interface screen that allows a user to set a set of parameters;

FIG. 174 shows an illustrative user interface screen that allows a user to adjust the minimum drain volume;

FIG. 175 shows an illustrative user interface screen that allows a user to review and confirm the settings;

FIG. 176 is an illustration of an adaptive tidal therapy mode during CCPD;

FIG. 177 is an illustration of the implementation of a revised-cycle mode during CCPD;

FIG. 178 is an illustration of the implementation of a revised-cycle mode during a tidal therapy;

FIG. 179 is an illustration of the implementation of an adaptive tidal mode during a tidal therapy;

FIG. 180 is an illustration showing peritoneal volume over time for a tidal therapy;

FIG. 181 is another illustration showing peritoneal volume over time for a tidal therapy;

FIG. 182 is an illustration of peritoneal volume over time for a tidal therapy which includes an adapted fill;

FIG. 183 shows a flow chart depicting an embodiment of synchronization of operations between two pumping chambers of a pump cassette;

FIG. 184 shows a flow chart depicting another embodiment of synchronization of operations between two pumping chambers of a pump cassette;

FIG. 185 shows a flow chart depicting another embodiment of synchronization of operations between two pumping chambers of a pump cassette;

FIG. 186 shows a flow chart depicting another embodiment of synchronization of operations between two pumping chambers of a pump cassette, including venting;

FIG. 187A shows a flow chart depicting another embodiment of synchronization of operations between two pumping chambers of a pump cassette, including venting;

FIG. 187B depicts an example graph that plots pressure in a control chamber over a deliver stroke, back pressure relief step, and volume measurement step;

FIG. 188 shows a flow chart depicting another embodiment of synchronization of operations between two pumping chambers of a pump cassette, including venting;

FIG. 189 shows a flow chart depicting another embodiment of synchronization of operations between two pumping chambers of a pump cassette, including venting;

FIG. 190 shows a flowchart depicting a synchronization scheme in which pump chambers are treated as independent state machines which acquire exclusive access tokens;

FIG. 191 shows a flowchart in which the amount of fluid moved during a pumping stroke is checked before that chamber releases possession of a token;

FIG. 192 shows a flowchart outlining steps which may be used when a pump chamber is performing an FMS measurement;

FIG. 193 shows a flowchart outlining steps which may be used when a pump chamber is performing an FMS measurement synchronized using an FMS token;

FIG. 194 shows a relationship between pressure tracings of a two-pump apparatus and resource tokens assigned to the pumps at various times during pumping operations;

FIG. 195 shows a relationship between pressure tracings of a two-pump apparatus and resource tokens assigned to the pumps during initiation of a pumping operation;

FIG. 196 shows a relationship between pressure tracings of a two-pump apparatus and resource tokens assigned to the pumps during a pump chamber fill transition between the two pumps;

FIG. 197 shows a relationship between pressure tracings of a two-pump apparatus and resource tokens assigned to the pumps when the pumps are stopped;

FIG. 198 depicts is a graph showing pressures of a pair of pump chambers and assignment of resource tokens during a number of pump strokes and chamber volume measurements;

FIG. 199 is a graph showing pressures (in kPa) of pumping chambers as well as the ownership status of a number of resources and tokens over a number of pump strokes;

FIG. 200 shows a device housing portion with a molded-in pressure reservoir;

FIG. 201 shows the device housing portion of FIG. 200, with a sealing member covering the pressure reservoir;

FIG. 202 shows a device housing portion with another embodiment of a molded-in pressure reservoir having two compartments;

FIG. 203 shows the device housing portion of FIG. 202, with a sealing member covering the pressure reservoir;

FIG. 204 is a bottom plan view of the housing portion of FIG. 202;

FIG. 205 is a perspective view of internal features of a device housing portion;

FIG. 206 shows a sealing member with reinforcing ribs;

FIG. 207 shows another embodiment of a two-compartment pressure reservoir assembly suitable for co-molding with or attachment to a device housing portion;

FIG. 208 is a bottom plan view of the assembly of FIG. 207;

FIG. 209 is a view of the assembly of FIG. 207 as seen from within a housing portion into which the assembly is included;

FIG. 210 is a cross-sectional view of the assembly of FIG. 207 at a location indicated by FIG. 209;

FIG. 211 shows a flowchart outlining steps which may be used to replenish a heater bag with dialysate solution;

FIG. 212 shows a flowchart outlining steps which may be employed by a cycler which uses solution expiration timers;

FIG. 213 shows an example screen which may be generated by a processor for display on a user interface of a cycler indicating a solution expiration timer;

FIG. 214A and FIG. 214B are flowcharts of a cycler performing an initial drain that starts with a flow check;

FIG. 215 shows a screen shot which may be generated for display on a user interface of a cycler during a drain that includes a soft drain option;

FIG. 216 shows a flowchart outlining steps which may be used to program and collected an automated effluent sample using a cycler; and FIG. 217 shows a flowchart outlining steps which may be used to program and collected an automated effluent sample using a cycler.

DETAILED DESCRIPTION

Although aspects of the invention are described in relation to a peritoneal dialysis system, certain aspects of the invention can be used in other medical applications, including infusion systems such as intravenous infusion systems or extracorporeal blood flow systems, and irrigation and/or fluid exchange systems for the stomach, intestinal tract, urinary bladder, pleural space or other body or organ cavity. Thus, aspects of the invention are not limited to use in peritoneal dialysis in particular, or dialysis in general.

APD System

Figure 1:
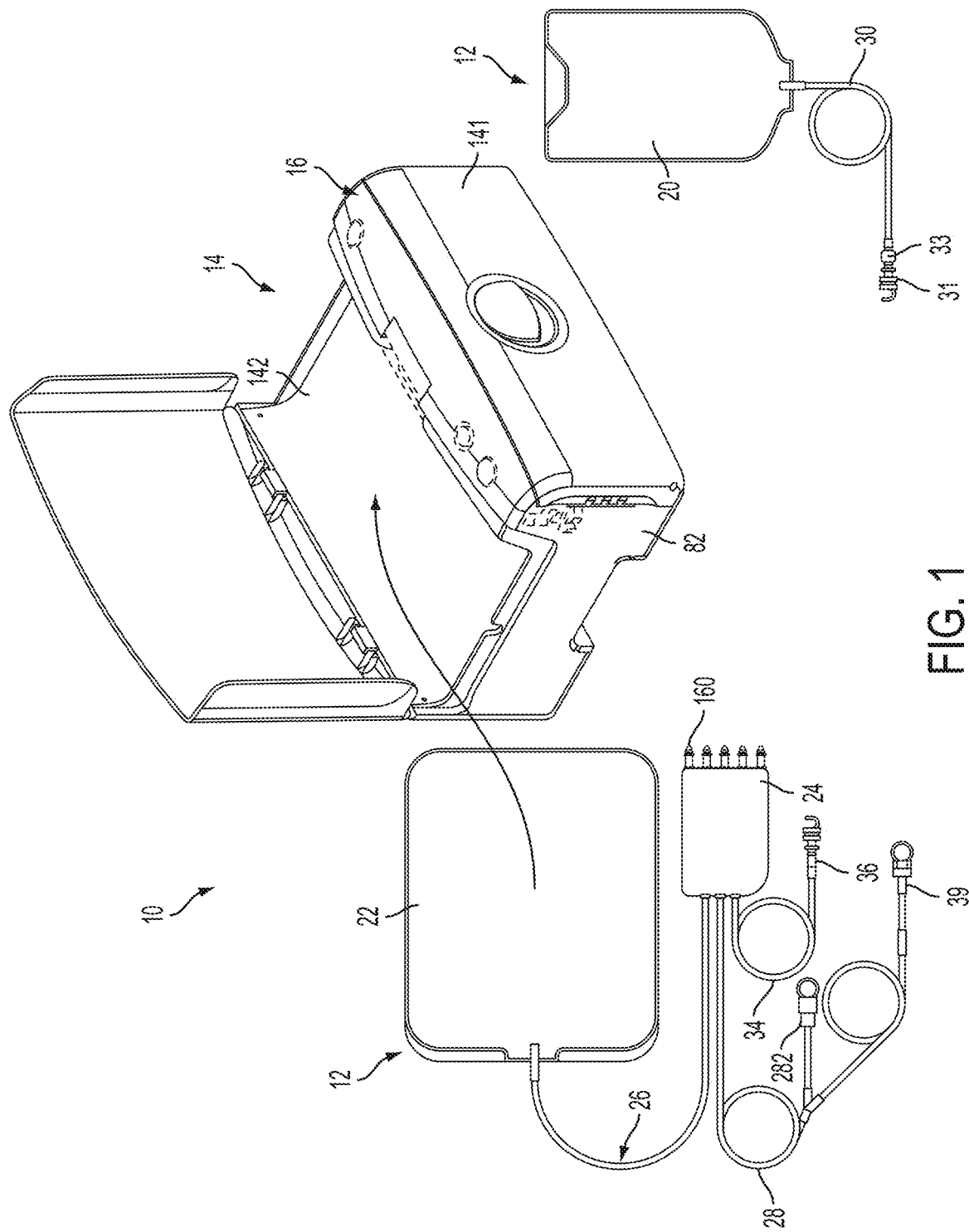
FIG. 1 shows a schematic view of an automated peritoneal dialysis (APD) system that incorporates one or more aspects of the invention.

FIG. 1 shows an automated peritoneal dialysis (APD) system 10 that may incorporate one or more aspects of the invention. As shown in FIG. 1, for example, the system 10 in this illustrative embodiment includes a dialysate delivery set 12 (which, in certain embodiments, can be a disposable set), a cycler 14 that interacts with the delivery set 12 to pump liquid provided by a solution container 20 (e.g., a bag), and a control system 16 (e.g., including a programmed computer or other data processor, computer memory, an interface to provide information to and receive input from a user or other device, one or more sensors, actuators, relays, pneumatic pumps, tanks, a power supply, and/or other suitable components—only a few buttons for receiving user control input are shown in FIG. 1, but further details regarding the control system components are provided below) that governs the process to perform an APD procedure. In this illustrative embodiment, the cycler 14 and the control system 16 are associated with a common housing 82, but may be associated with two or more housings and/or may be separate from each other. The cycler 14 may have a compact footprint, suited for operation upon a table top or other relatively small surface normally found in the home. The cycler 14 may be lightweight and portable, e.g., carried by hand via handles at opposite sides of the housing 82.

The set 12 in this embodiment is intended to be a single use, disposable item, but instead may have one or more reusable components, or may be reusable in its entirety. The user associates the set 12 with the cycler 14 before beginning each APD therapy session, e.g., by mounting a cassette 24 within a front door 141 of the cycler 14, which interacts with the cassette 24 to pump and control fluid flow in the various lines of the set 12. For example, dialysate may be pumped both to and from the patient to effect APD. Post therapy, the user may remove all or part of the components of the set 12 from the cycler 14.

As is known in the art, prior to use, the user may connect a patient line 34 of the set 12 to his/her indwelling peritoneal catheter (not shown) at a connection 36. In one embodiment, the cycler 14 may be configured to operate with one or more different types of cassettes 24, such as those having differently sized patient lines 34. For example, the cycler 14 may be arranged to operate with a first type of cassette with a patient line 34 sized for use with an adult patient, and a second type of cassette with a patient line 34 sized for an infant or pediatric use. The pediatric patient line 34 may be shorter and have a smaller inner diameter than the adult line so as to minimize the volume of the line, allowing for more controlled delivery of dialysate and helping to avoid returning a relatively large volume of used dialysate to the pediatric patient when the set 12 is used for consecutive drain and fill cycles. A heater bag 22, which is connected to the cassette 24 by a line 26, may be placed on a heater container receiving portion (in this case, a tray) 142 of the cycler 14. The cycler 14 may pump fresh dialysate (via the cassette 24) into the heater bag 22 so that the dialysate may be heated by the heater tray 142, e.g., by electric resistance heating elements associated with the tray 142 to a temperature of about 37 degrees C. Heated dialysate may be provided from the heater bag 22 to the patient via the cassette 24 and the patient line 34. In an alternative embodiment, the dialysate can be heated on its way to the patient as it enters, or after it exits, the cassette 24 by passing the dialysate through tubing in contact with the heater tray 142, or through an in-line fluid heater (which may be provided in the cassette 24). Used dialysate may be pumped from the patient via the patient line 34 to the cassette 24 and into a drain line 28, which may include one or more clamps to control flow through one or more branches of the drain line 28. In this illustrative embodiment, the drain line 28 may include a connector 39 for connecting the drain line 28 to a dedicated drain receptacle, and an effluent sample port 282 for taking a sample of used dialysate for testing or other analysis. The user may also mount the lines 30 of one or more containers 20 within the door 141. The lines 30 may also be connected to a continuous or real-time dialysate preparation system. (The lines 26, 28, 30, 34 may include a flexible tubing and/or suitable connectors and other components (such as pinch valves, etc.) as desired.) The containers 20 may contain sterile peritoneal dialysis solution for infusion, or other materials (e.g., materials used by the cycler 14 to formulate dialysate by mixing with water, or admixing different types of dialysate solutions). The lines 30 may be connected to spikes 160 of the cassette 24, which are shown in FIG. 1 covered by removable caps. In one aspect of the invention described in more detail below, the cycler 14 may automatically remove caps from one or more spikes 160 of the cassette 24 and connect lines 30 of solution containers 20 to respective spikes 160. This feature may help reduce the possibility of infection or contamination by reducing the chance of contact of non-sterile items with the spikes 160.

Figure 1A:
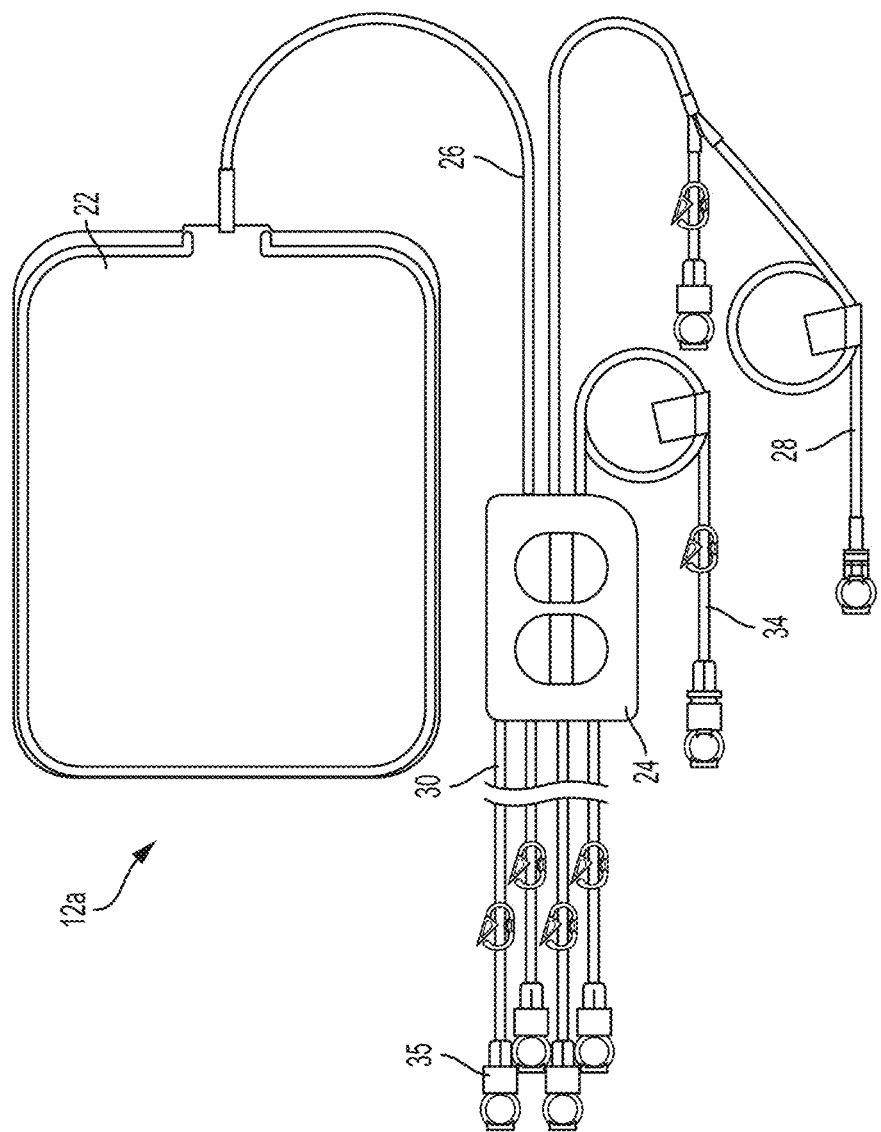
FIG. 1A shows an alternative arrangement for a dialysate delivery set shown in FIG. 1.

In another aspect, a dialysate delivery set 12a may not have cassette spikes 160. Instead, one or more solution lines 30 may be permanently affixed to the inlet ports of cassette 24, as shown in FIG. 1A. In this case, each solution line 30 may have a (capped) spike connector 35 for manual connection to a solution container or dialysate bag 20.

With various connections made, the control system 16 may pace the cycler 14 through a series of fill, dwell, and/or drain cycles typical of an APD procedure. For example, during a fill phase, the cycler 14 may pump dialysate (by way of the cassette 24) from one or more containers 20 (or other source of dialysate supply) into the heater bag 22 for heating. Thereafter, the cycler 14 may infuse heated dialysate from the heater bag 22 through the cassette 24 and into the patient's peritoneal cavity via the patient line 34. Following a dwell phase, the cycler 14 may institute a drain phase, during which the cycler 14 pumps used dialysate from the patient via the line 34 (again by way of the cassette 24), and discharges spent dialysis solution into a nearby drain (not shown) via the drain line 28.

The cycler 14 does not necessarily require the solution containers 20 and/or the heater bag 22 to be positioned at a prescribed head height above the cycler 14, e.g., because the cycler 14 is not necessarily a gravity flow system. Instead, the cycler 14 may emulate gravity flow, or otherwise suitably control flow of dialysate solution, even with the source solution containers 20 above, below or at a same height as the cycler 14, with the patient above or below the cycler, etc. For example, the cycler 14 can emulate a fixed head height during a given procedure, or the cycler 14 can change the effective head height to either increase or decrease pressure applied to the dialysate during a procedure. The cycler 14 may also adjust the rate of flow of dialysate. In one aspect of the invention, the cycler 14 may adjust the pressure and/or flow rate of dialysate when provided to the patient or drawn from the patient so as to reduce the patient's sensation of the fill or drain operation. Such adjustment may occur during a single fill and/or drain cycle, or may be adjusted across different fill and/or drain cycles. In one embodiment, the cycler 14 may taper the pressure used to draw used dialysate from the patient near the end of a drain operation. Because the cycler 14 may establish an artificial head height, it may have the flexibility to interact with and adapt to the particular physiology or changes in the relative elevation of the patient.

Cassette

In one aspect of the invention, a cassette 24 may include patient and drain lines that are separately occludable with respect to solution supply lines. That is, safety critical flow to and from patient line may be controlled, e.g., by pinching the lines to stop flow, without the need to occlude flow through one or more solution supply lines. This feature may allow for a simplified occluder device since occlusion may be performed with respect to only two lines as opposed to occluding other lines that have little or no effect on patient safety. For example, in a circumstance where a patient or drain connection becomes disconnected, the patient and drain lines may be occluded. However, the solution supply and/or heater bag lines may remain open for flow, allowing the cycler 14 to prepare for a next dialysis cycle; e.g., separate occlusion of patient and drain lines may help ensure patient safety while permitting the cycler 14 to continue to pump dialysate from one or more containers 20 to the heater bag 22 or to other solution containers 20.

In another aspect of the invention, the cassette may have patient, drain and heater bag lines at one side or portion of the cassette and one or more solution supply lines at another side or portion of the cassette, e.g., an opposite side of the cassette. Such an arrangement may allow for separate occlusion of patient, drain or heater bag lines with respect to solution lines as discussed above. Physically separating the lines attached to the cassette by type or function allows for more efficient control of interaction with lines of a certain type or function. For example, such an arrangement may allow for a simplified occluder design because less force is required to occlude one, two or three of these lines than all lines leading to or away from the cassette. Alternately, this arrangement may allow for more effective automated connection of solution supply lines to the cassette, as discussed in more detail below. That is, with solution supply lines and their respective connections located apart from patient, drain and/or heater bag lines, an automated de-capping and connection device may remove caps from spikes on the cassette as well as caps on solution supply lines, and connect the lines to respective spikes without interference by the patient, drain or heater bag lines.

FIG. 2 shows an illustrative embodiment of a cassette 24 that incorporates aspects of the invention described above. In this embodiment, the cassette 24 has a generally planar body and the heater bag line 26, the drain line 28 and the patient line 34 are connected at respective ports on the left end of the cassette body, while the right end of the cassette body may include five spikes 160 to which solution supply lines 30 may be connected. In the arrangement shown in FIG. 2, each of the spikes 160 is covered by a spike cap 63, which may be removed, exposing the respective spike and allowing connection to a respective line 30. As described above, the lines 30 may be attached to one or more solution containers or other sources of material, e.g., for use in dialysis and/or the formulation of dialysate, or connected to one or more collection bags for sampling purposes or for peritoneal equilibration testing (PET test).

Figure 3:
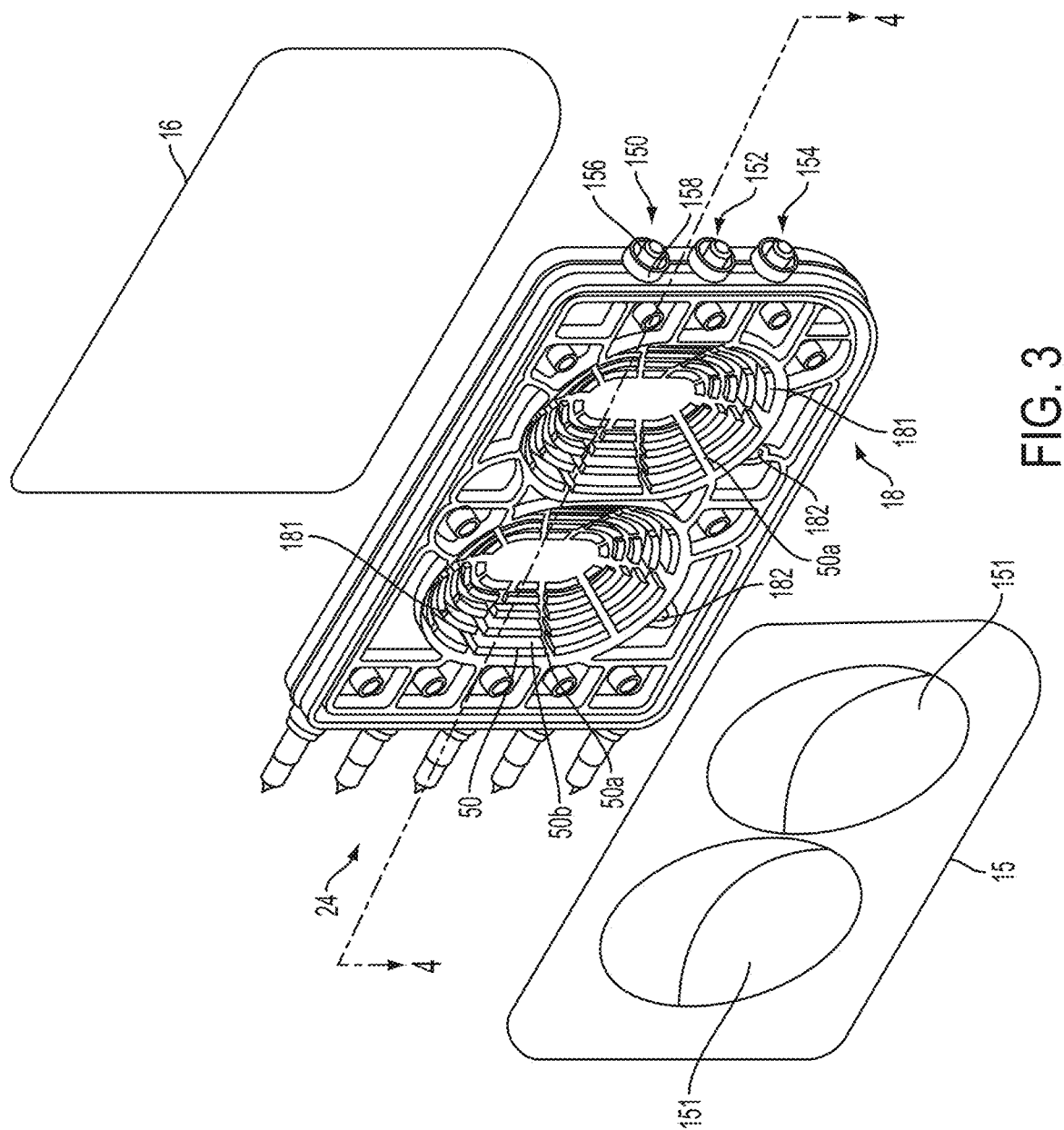
FIG. 3 is an exploded perspective view of a cassette in a first embodiment.
Figure 4:
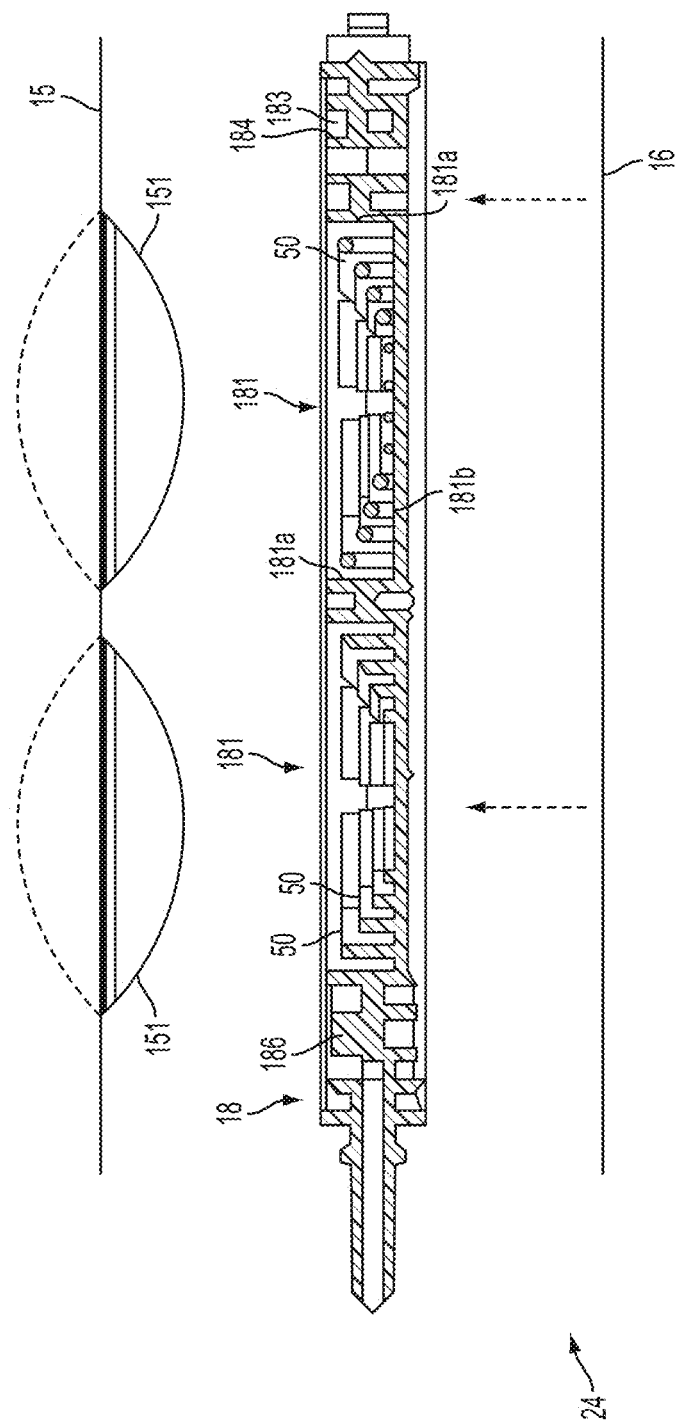
FIG. 4 is a cross sectional view of the cassette along the line 4-4 in FIG. 3.

FIGS. 3 and 4 show exploded views (perspective and top views, respectively) of the cassette 24 in this illustrative embodiment. The cassette 24 is formed as a relatively thin and flat member having a generally planar shape, e.g., may include components that are molded, extruded or otherwise formed from a suitable plastic. In this embodiment, the cassette 24 includes a base member 18 that functions as a frame or structural member for the cassette 24 as well as forming, at least in part, various flow channels, ports, valve portions, etc. The base member 18 may be molded or otherwise formed from a suitable plastic or other material, such as a polymethyl methacrylate (PMMA) acrylic, or a cyclic olefin copolymer/ultra low density polyethylene (COC/ULDPE), and may be relatively rigid. In an embodiment, the ratio of COC to ULDPE can be approximately 85%/15%. FIG. 3 also shows the ports for the heater bag (port 150), drain (port 152) and the patient (port 154) that are formed in the base member 18. Each of these ports may be arranged in any suitable way, such as, for example, a central tube 156 extending from an outer ring or skirt 158, or a central tube alone. Flexible tubing for each of the heater bag, drain and patient lines 26, 28, 34 may be connected to the central tube 156 and engaged by the outer ring 158, if present.

Both sides of the base member 18 may be covered, at least in part, by a membrane 15 and 16, e.g., a flexible polymer film made from, for example, polyvinyl chloride (PVC), that is cast, extruded or otherwise formed. Alternatively, the sheet may be formed as a laminate of two or more layers of poly-cyclohexylene dimethylene cyclohexanedicarboxylate (PCCE) and/or ULDPE, held together, for example, by a coextrudable adhesive (CXA). In some embodiments, the membrane thickness may be in the range of approximately 0.002 to 0.020 inches thick. In a preferred embodiment, the thickness of a PVC-based membrane may be in the range of approximately 0.012 to 0.016 inches thick, and more preferably approximately 0.014 inches thick. In another preferred embodiment, such as, for example, for laminate sheets, the thickness of the laminate may be in the range of approximately 0.006 to 0.010 inches thick, and more preferably approximately 0.008 inches thick.

Both membranes 15 and 16 may function not only to close or otherwise form a part of flowpaths of the cassette 24, but also may be moved or otherwise manipulated to open/close valve ports and/or to function as part of a pump diaphragm, septum or wall that moves fluid in the cassette 24. For example, the membranes 15 and 16 may be positioned on the base member 18 and sealed (e.g., by heat, adhesive, ultrasonic welding or other means) to a rim around the periphery of the base member 18 to prevent fluid from leaking from the cassette 24. The membrane 15 may also be bonded to other, inner walls of the base member 18, e.g., those that form various channels, or may be pressed into sealing contact with the walls and other features of the base member 18 when the cassette 24 suitably mounted in the cycler 14. Thus, both of the membranes 15 and 16 may be sealed to a peripheral rim of the base member 18, e.g., to help prevent leaking of fluid from the cassette 24 upon its removal from the cycler 14 after use, yet be arranged to lie, unattached, over other portions of the base member 18. Once placed in the cycler 14, the cassette 24 may be squeezed between opposed gaskets or other members so that the membranes 15 and 16 are pressed into sealing contact with the base member 18 at regions inside of the periphery, thereby suitably sealing channels, valve ports, etc., from each other.

Other arrangements for the membranes 15 and 16 are possible. For example, the membrane 16 may be formed by a rigid sheet of material that is bonded or otherwise made integral with the body 18. Thus, the membrane 16 need not necessarily be, or include, a flexible member. Similarly, the membrane 15 need not be flexible over its entire surface, but instead may include one or more flexible portions to permit pump and/or valve operation, and one or more rigid portions, e.g., to close flowpaths of the cassette 24. It is also possible that the cassette 24 may not include the membrane 16 or the membrane 15, e.g., where the cycler 14 includes a suitable member to seal pathways of the cassette, control valve and pump function, etc.

Figure 5:
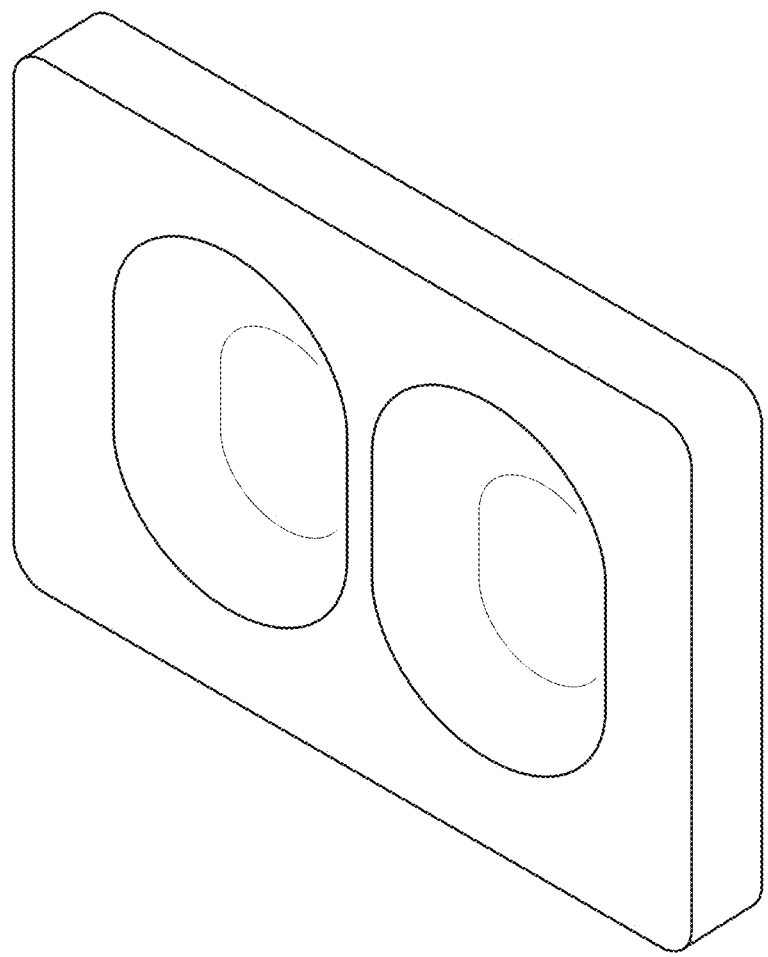
FIG. 5 is a perspective view of a vacuum mold that may be used to form a membrane having pre-formed pump chamber portions in an illustrative embodiment.

In accordance with another aspect of the invention, the membrane 15 may include a pump chamber portion 151 ("pump membrane") that is formed to have a shape that closely conforms to the shape of a corresponding pump chamber 181 depression in the base 18. For example, the membrane 15 may be generally formed as a flat member with thermoformed (or otherwise formed) dome-like shapes 151 that conform to the pump chamber depressions of the base member 18. The dome-like shape of the pre-formed pump chamber portions 151 may be constructed, for example, by heating and forming the membrane over a vacuum form mold of the type shown in FIG. 5. As shown in FIG. 5, the vacuum may be applied through a collection of holes along the wall of the mold. Alternatively, the wall of the mold can be constructed of a porous gas-permeable material, which may result in a more uniformly smooth surface of the molded membrane. In one example, the molded membrane sheet 15 is trimmed while attached to the vacuum form mold. The vacuum form mold then presses the trimmed membrane sheet 15 against the cassette body 18 and bonds them together. In one embodiment the membrane sheets 15,16 are heat-welded to the cassette body 18. In this way, the membrane 15 may move relative to the pump chambers 181 to effect pumping action without requiring stretching of the membrane 15 (or at least minimal stretching of the membrane 15), both when the membrane 15 is moved maximally into the pump chambers 181 and (potentially) into contact with spacer elements 50 (e.g., as shown in solid line in FIG. 4 while pumping fluid out of the pump chamber 181), and when the membrane 15 is maximally withdrawn from the pump chamber 181 (e.g., as shown in dashed line in FIG. 4 when drawing fluid into the pump chamber 181). Avoiding stretching of the membrane 15 may help prevent pressure surges or other changes in fluid delivery pressure due to sheet stretch and/or help simplify control of the pump when seeking to minimize pressure variation during pump operation. Other benefits may be found, including reduced likelihood of membrane 15 failure (e.g., due to tears in the membrane 15 resulting from stresses place on the membrane 15 during stretching), and/or improved accuracy in pump delivery volume measurement, as described in more detail below. In one embodiment, the pump chamber portions 151 may be formed to have a size (e.g., a define a volume) that is about 85-110% of the pump chamber 181, e.g., if the pump chamber portions 151 define a volume that is about 100% of the pump chamber volume, the pump chamber portion 151 may lie in the pump chamber 181 and in contact with the spacers 50 while at rest and without being stressed.

Providing greater control of the pressure used to generate a fill and delivery stroke of liquid into and out of a pump chamber may have several advantages. For example, it may be desirable to apply the minimum negative pressure possible when the pump chamber draws fluid from the patient's peritoneal cavity during a drain cycle. A patient may experience discomfort during the drain cycle of a treatment in part because of the negative pressure being applied by the pumps during a fill stroke. The added control that a pre-formed membrane can provide to the negative pressure being applied during a fill stroke may help to reduce the patient's discomfort.

A number of other benefits may be realized by using pump membranes pre-formed to the contour of the cassette pump chamber. For example, the flow rate of liquid through the pump chamber can be made more uniform, because a constant pressure or vacuum can be applied throughout the pump stroke, which in turn may simplify the process of regulating the heating of the liquid. Moreover, temperature changes in the cassette pump may have a smaller effect on the dynamics of displacing the membrane, as well as the accuracy of measuring pressures within the pump chambers. In addition, pressure spikes within the fluid lines can be minimized. Also, correlating the pressures measured by pressure transducers on the control (e.g. pneumatic) side of the membrane with the actual pressure of the liquid on the pump chamber side of the membrane may be simpler. This in turn may permit more accurate head height measurements of the patient and fluid source bags prior to therapy, improve the sensitivity of detecting air in the pump chamber, and improve the accuracy of volumetric measurements. Furthermore, eliminating the need to stretch the membrane may allow for the construction and use of pump chambers having greater volumes.

In this embodiment, the cassette 24 includes a pair of pump chambers 181 that are formed in the base member 18, although one pump chamber or more than two pump chambers are possible. In accordance with an aspect of the invention, the inner wall of pump chambers 181 includes spacer elements 50 that are spaced from each other and extend from the inner wall of pump chamber 18 to help prevent portions of the membrane 15 from contacting the inner wall of pump chamber 181. (As shown on the right-side pump chamber 181 in FIG. 4, the inner wall is defined by side portions 181a and a bottom portion 181b. The spacers 50 extend upwardly from the bottom portion 181b in this embodiment, but could extend from the side portions 181a or be formed in other ways.) By preventing contact of the membrane 15 with the pump chamber inner wall, the spacer elements 50 may provide a dead space (or trap volume) which may help trap air or other gas in the pump chamber 181 and inhibit the gas from being pumped out of the pump chamber 181 in some circumstances. In other cases, the spacers 50 may help the gas move to an outlet of the pump chamber 181 so that the gas may be removed from the pump chamber 181, e.g., during priming. Also, the spacers 50 may help prevent the membrane 15 from sticking to the pump chamber inner wall and/or allow flow to continue through the pump chamber 181, even if the membrane 15 is pressed into contact with the spacer elements 50. In addition, the spacers 50 help to prevent premature closure of the outlet port of the pump chamber (openings 187 and/or 191) if the sheet happens to contact the pump chamber inner wall in a non-uniform manner. Further details regarding the arrangement and/or function of spacers 50 are provided in U.S. Pat. Nos. 6,302,653 and 6,382,923, both of which are incorporated herein by reference.

In this embodiment, the spacer elements 50 are arranged in a kind of "stadium seating" arrangement such that the spacer elements 50 are arranged in a concentric elliptical pattern with ends of the spacer elements 50 increasing in height from the bottom portion 181b of the inner wall with distance away from the center of the pump chamber 181 to form a semi-elliptical domed shaped region (shown by dotted line in FIG. 4). Positioning spacer elements 50 such that the ends of the spacer elements 50 form a semi-elliptical region that defines the domed region intended to be swept by the pump chamber portion 151 of the membrane 15 may allow for a desired volume of dead space that minimizes any reduction to the intended stroke capacity of pump chambers 181. As can be seen in FIG. 3 (and FIG. 6), the "stadium seating" arrangement in which spacer elements 50 are arranged may include "aisles" or breaks 50a in the elliptical pattern. Breaks (or aisles) 50a help to maintain an equal gas level throughout the rows (voids or dead space) 50b between spacer elements 50 as fluid is delivered from the pump chamber 181. For example, if the spacer elements 50 were arranged in the stadium seating arrangement shown in FIG. 6 without breaks (or aisles) 50a or other means of allowing liquid and air to flow between spacer elements 50, the membrane 15 might bottom out on the spacer element 50 located at the outermost periphery of the pump chamber 181, trapping whatever gas or liquid is present in the void between this outermost spacer element 50 and the side portions 181a of the pump chamber wall. Similarly, if the membrane 15 bottomed out on any two adjacent spacer elements 50, any gas and liquid in the void between the elements 50 may become trapped. In such an arrangement, at the end of the pump stroke, air or other gas at the center of pump chamber 181 could be delivered while liquid remains in the outer rows. Supplying breaks (or aisles) 50a or other means of fluidic communication between the voids between spacer elements 50 helps to maintain an equal gas level throughout the voids during the pump stroke, such that air or other gas may be inhibited from leaving the pump chamber 181 unless the liquid volume has been substantially delivered.

In certain embodiments, spacer elements 50 and/or the membrane 15 may be arranged so that the membrane 15 generally does not wrap or otherwise deform around individual spacers 50 when pressed into contact with them, or otherwise extend significantly into the voids between spacers 50. Such an arrangement may lessen any stretching or damage to membrane 15 caused by wrapping or otherwise deforming around one or more individual spacer elements 50. For example, it has also been found to be advantageous in this embodiment to make the size of the voids between spacers 50 approximately equal in width to the width of the spacers 50. This feature has shown to help prevent deformation of the membrane 15, e.g., sagging of the membrane into the voids between spacers 50, when the membrane 15 is forced into contact with the spacers 50 during a pumping operation.

In accordance with another aspect of the invention, the inner wall of pump chambers 181 may define a depression that is larger than the space, for example a semi-elliptical or domed space, intended to be swept by the pump chamber portion 151 of the membrane 15. In such instances, one or more spacer elements 50 may be positioned below the domed region intended to be swept by the membrane portion 151 rather than extending into that domed region. In certain instances, the ends of spacer elements 50 may define the periphery of the domed region intended to be swept by the membrane 15. Positioning spacer elements 50 outside of, or adjacent to, the periphery of the domed region intended to be swept by the membrane portion 151 may have a number of advantages. For example, positioning one or more spacer elements 50 such that the spacer elements are outside of, or adjacent to, the domed region intended to be swept by the flexible membrane provides a dead space between the spacers and the membrane, such as described above, while minimizing any reduction to the intended stroke capacity of pump chambers 181.

Figure 6:
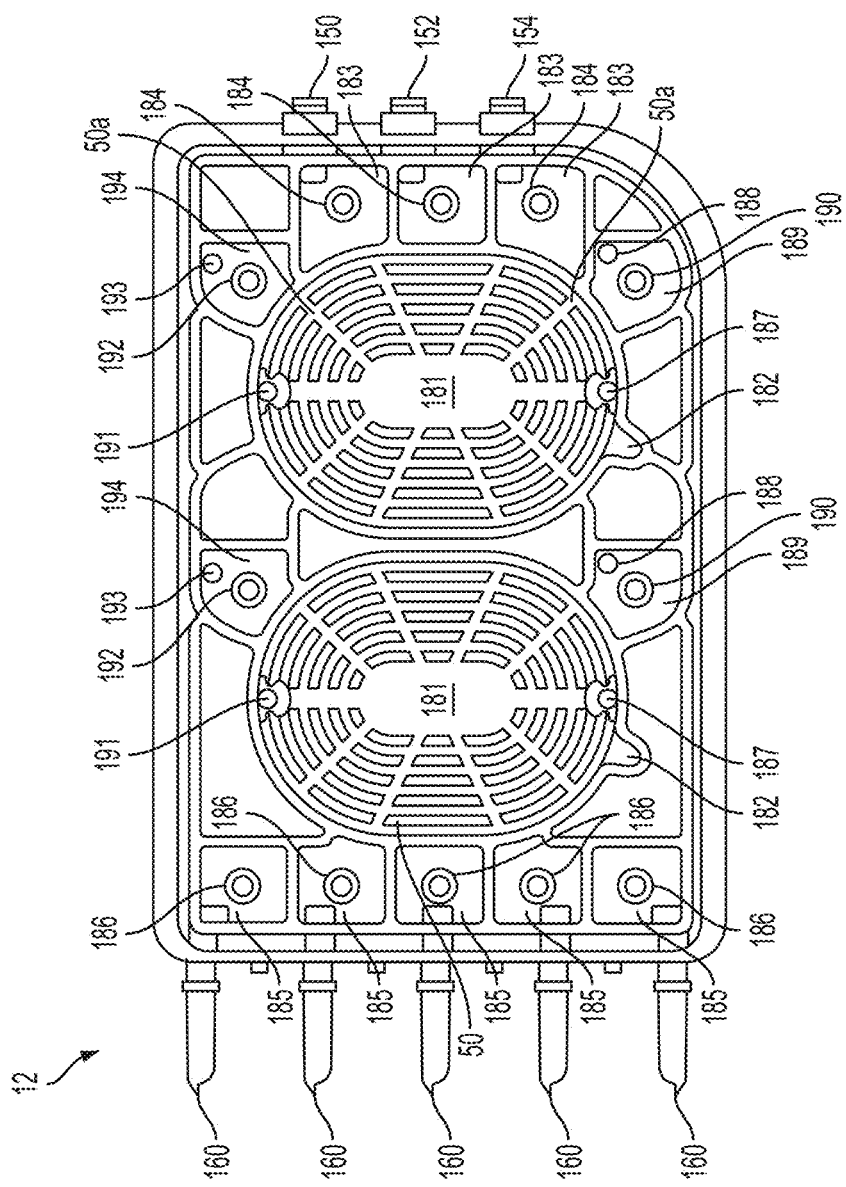
FIG. 6 shows a front view of the cassette body of FIG. 3.
Figure 7:
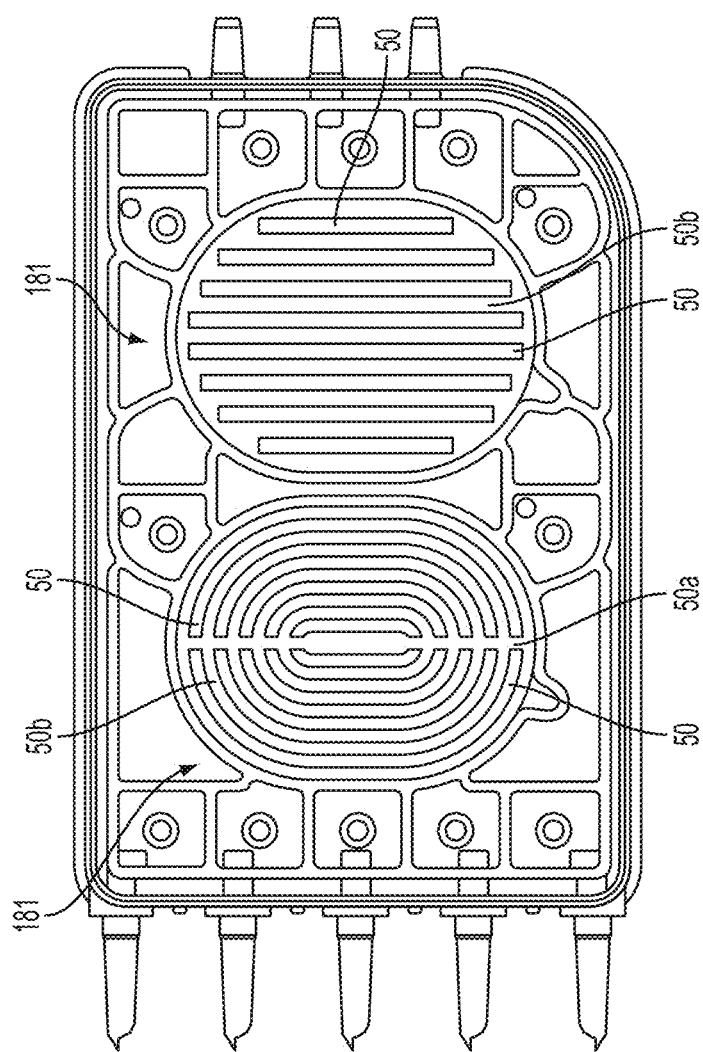
FIG. 7 is a front view of a cassette body including two different spacer arrangements in an illustrative embodiment.

It should be understood that the spacer elements 50, if present, in a pump chamber may be arranged in any other suitable way, such as for example, shown in FIG. 7. The left side pump chamber 181 in FIG. 7 includes spacers 50 arranged similarly to that in FIG. 6, but there is only one break or aisle 50a that runs vertically through the approximate center of the pump chamber 181. The spacers 50 may be arranged to define a concave shape similar to that in FIG. 6 (i.e., the tops of the spacers 50 may form the semi-elliptical shape shown in FIGS. 3 and 4), or may be arranged in other suitable ways, such as to form a spherical shape, a box-like shape, and so on. The right-side pump chamber 181 in FIG. 7 shows an embodiment in which the spacers 50 are arranged vertically with voids 50b between spacers 50 also arranged vertically. As with the left-side pump chamber, the spacers 50 in the right-side pump chamber 181 may define a semi-elliptical, spherical, box-like or any other suitably shaped depression. It should be understood, however, that the spacer elements 50 may have a fixed height, a different spatial pattern than those shown, and so on.

Also, the membrane 15 may itself have spacer elements or other features, such as ribs, bumps, tabs, grooves, channels, etc., in addition to, or in place of the spacer elements 50. Such features on the membrane 15 may help prevent sticking of the membrane 15, etc., and/or provide other features, such as helping to control how the sheet folds or otherwise deforms when moving during pumping action. For example, bumps or other features on the membrane 15 may help the sheet to deform consistently and avoid folding at the same area(s) during repeated cycles. Folding of a same area of the membrane 15 at repeated cycles may cause the membrane 15 to prematurely fail at the fold area, and thus features on the membrane 15 may help control the way in which folds occur and where.

Figure 8:
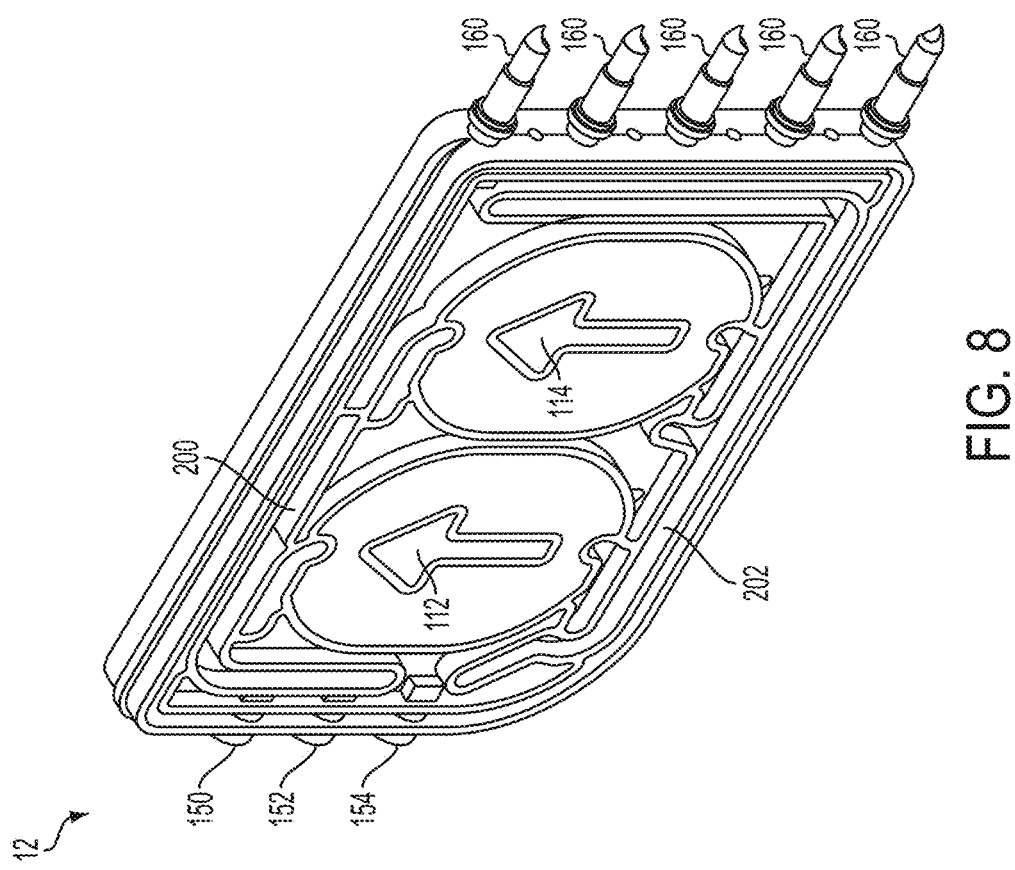
FIG. 8 is a rear perspective view of the cassette body of FIG. 3.
Figure 9:
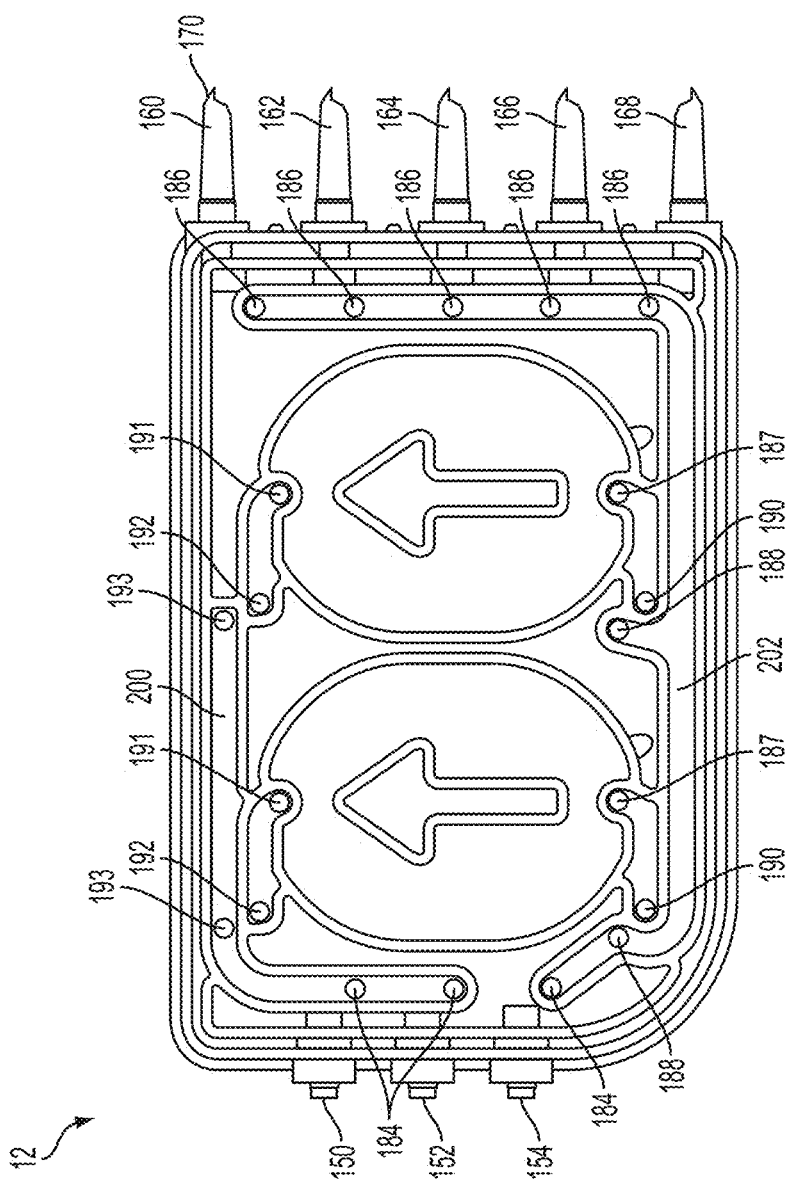
FIG. 9 is a rear view of the cassette body of FIG. 3.

In this illustrative embodiment, the base member 18 of the cassette 24 defines a plurality of controllable valve features, fluid pathways and other structures to guide the movement of fluid in the cassette 24. FIG. 6 shows a plan view of the pump chamber side of the base member 18, which is also seen in perspective view in FIG. 3. FIG. 8 shows a perspective view of a back side of the base member 18, and FIG. 9 shows a plan view of the back side of the base member 18. The tube 156 for each of the ports 150, 152 and 154 fluidly communicates with a respective valve well 183 that is formed in the base member 18. The valve wells 183 are fluidly isolated from each other by walls surrounding each valve well 183 and by sealing engagement of the membrane 15 with the walls around the wells 183. As mentioned above, the membrane 15 may sealingly engage the walls around each valve well 183 (and other walls of the base member 18) by being pressed into contact with the walls, e.g., when loaded into the cycler 14. Fluid in the valve wells 183 may flow into a respective valve port 184, if the membrane 15 is not pressed into sealing engagement with the valve port 184. Thus, each valve port 184 defines a valve (e.g., a "volcano valve") that can be opened and closed by selectively moving a portion of the membrane 15 associated with the valve port 184. As will be described in more detail below, the cycler 14 may selectively control the position of portions of the membrane 15 so that valve ports (such as ports 184) may be opened or closed so as to control flow through the various fluid channels and other pathways in the cassette 24. Flow through the valve ports 184 leads to the back side of the base member 18. For the valve ports 184 associated with the heater bag and the drain (ports 150 and 152), the valve ports 184 lead to a common channel 200 formed at the back side of the base member 18. As with the valve wells 183, the channel 200 is isolated from other channels and pathways of the cassette 24 by the sheet 16 making sealing contact with the walls of the base member 18 that form the channel 200. For the valve port 184 associated with the patient line port 154, flow through the port 184 leads to a common channel 202 on the back side of the base member 18. Common channel 200 may also be referred to herein as an upper fluidic bus and common channel 202 may also be referred to herein as a lower fluidic bus.

Returning to FIG. 6, each of the spikes 160 (shown uncapped in FIG. 6) fluidly communicates with a respective valve well 185, which are isolated from each other by walls and sealing engagement of the membrane 15 with the walls that form the wells 185. Fluid in the valve wells 185 may flow into a respective valve port 186, if the membrane 15 is not in sealing engagement with the port 186. (Again, the position of portions of the membrane 15 over each valve port 186 can be controlled by the cycler 14 to open and close the valve ports 186.) Flow through the valve ports 186 leads to the back side of the base member 18 and into the common channel 202. Thus, in accordance with one aspect of the invention, a cassette may have a plurality of solution supply lines (or other lines that provide materials for providing dialysate) that are connected to a common manifold or channel of the cassette, and each line may have a corresponding valve to control flow from/to the line with respect to the common manifold or channel. Fluid in the channel 202 may flow into lower openings 187 of the pump chambers 181 by way of openings 188 that lead to lower pump valve wells 189 (see FIG. 6). Flow from the lower pump valve wells 189 may pass through a respective lower pump valve port 190 if a respective portion of the membrane 15 is not pressed in sealing engagement with the port 190. As can be seen in FIG. 9, the lower pump valve ports 190 lead to a channel that communicates with the lower openings 187 of the pump chambers 181. Flow out of the pump chambers 181 may pass through the upper openings 191 and into a channel that communicates with an upper valve port 192. Flow from the upper valve port 192 (if the membrane 15 is not in sealing engagement with the port 192) may pass into a respective upper valve well 194 and into an opening 193 that communicates with the common channel 200 on the back side of the base member 18.

As will be appreciated, the cassette 24 may be controlled so that the pump chambers 181 can pump fluid from and/or into any of the ports 150, 152 and 154 and/or any of the spikes 160. For example, fresh dialysate provided by one of the containers 20 that is connected by a line 30 to one of the spikes 160 may be drawn into the common channel 202 by opening the appropriate valve port 186 for the proper spike 160 (and possibly closing other valve ports 186 for other spikes). Also, the lower pump valve ports 190 may be opened and the upper pump valve ports 192 may be closed. Thereafter, the portion of the membrane 15 associated with the pump chambers 181 (i.e., pump membranes 151) may be moved (e.g., away from the base member 18 and the pump chamber inner wall) so as to lower the pressure in the pump chambers 181, thereby drawing fluid in through the selected spike 160 through the corresponding valve port 186, into the common channel 202, through the openings 188 and into the lower pump valve wells 189, through the (open) lower pump valve ports 190 and into the pump chambers 181 through the lower openings 187. The valve ports 186 are independently operable, allowing for the option to draw fluid through any one or a combination of spikes 160 and associated source containers 20, in any desired sequence, or simultaneously. (Of course, only one pump chamber 181 need be operable to draw fluid into itself. The other pump chamber may be left inoperable and closed off to flow by closing the appropriate lower pump valve port 190.)

With fluid in the pump chambers 181, the lower pump valve ports 190 may be closed, and the upper pump valve ports 192 opened. When the membrane 15 is moved toward the base member 18, the pressure in the pump chambers 181 may rise, causing fluid in the pump chambers 181 to pass through the upper openings 191, through the (open) upper pump valve ports 192 and into the upper pump valve wells 194, through the openings 193 and into the common channel 200. Fluid in the channel 200 may be routed to the heater bag port 150 and/or the drain port 152 (and into the corresponding heater bag line or drain line) by opening the appropriate valve port 184. In this way, for example, fluid in one or more of the containers 20 may be drawn into the cassette 24, and pumped out to the heater bag 22 and/or the drain.

Fluid in the heater bag 22 (e.g., after having been suitably heated on the heater tray for introduction into the patient) may be drawn into the cassette 24 by opening the valve port 184 for the heater bag port 150, closing the lower pump valve ports 190, and opening the upper pump valve ports 192. By moving the portions of the membrane 15 associated with the pump chambers 181 away from the base member 18, the pressure in the pump chambers 181 may be lowered, causing fluid flow from the heater bag 22 and into the pump chambers 181. With the pump chambers 181 filled with heated fluid from the heater bag 22, the upper pump valve ports 192 may be closed and the lower pump valve ports 190 opened. To route the heated dialysate to the patient, the valve port 184 for the patient port 154 may be opened and valve ports 186 for the spikes 160 closed. Movement of the membrane 15 in the pump chambers 181 toward the base member 18 may raise the pressure in the pump chambers 181 causing fluid to flow through the lower pump valve ports 190, through the openings 188 and into the common channel 202 to, and through, the (open) valve port 184 for the patient port 154. This operation may be repeated a suitable number of times to transfer a desired volume of heated dialysate to the patient.

When draining the patient, the valve port 184 for the patient port 154 may be opened, the upper pump valve ports 192 closed, and the lower pump valve ports 190 opened (with the spike valve ports 186 closed). The membrane 15 may be moved to draw fluid from the patient port 154 and into the pump chambers 181. Thereafter, the lower pump valve ports 190 may be closed, the upper valve ports 192 opened, and the valve port 184 for the drain port 152 opened. Fluid from the pump chambers 181 may then be pumped into the drain line for disposal or for sampling into a drain or collection container. (Alternatively, fluid may also be routed to one or more spikes 160/lines 30 for sampling or drain purposes). This operation may be repeated until sufficient dialysate is removed from the patient and pumped to the drain.

The heater bag 22 may also serve as a mixing container. Depending on the specific treatment requirements for an individual patient, dialysate or other solutions having different compositions can be connected to the cassette 24 via suitable solution lines 30 and spikes 160. Measured quantities of each solution can be added to heater bag 22 using cassette 24, and admixed according to one or more predetermined formulae stored in microprocessor memory and accessible by control system 16. Alternatively, specific treatment parameters can be entered by the user via user interface 144. The control system 16 can be programmed to compute the proper admixture requirements based on the type of dialysate or solution containers connected to spikes 160, and can then control the admixture and delivery of the prescribed mixture to the patient.

In accordance with an aspect of the invention, the pressure applied by the pumps to dialysate that is infused into the patient or removed from the patient may be controlled so that patient sensations of "tugging" or "pulling" resulting from pressure variations during drain and fill operations may be minimized. For example, when draining dialysate, the suction pressure (or vacuum/negative pressure) may be reduced near the end of the drain process, thereby minimizing patient sensation of dialysate removal. A similar approach may be used when nearing the end of a fill operation, i.e., the delivery pressure (or positive pressure) may be reduced near the end of fill. Different pressure profiles may be used for different fill and/or drain cycles in case the patient is found to be more or less sensitive to fluid movement during different cycles of the therapy. For example, a relatively higher (or lower) pressure may be used during fill and/or drain cycles when a patient is asleep, as compared to when the patient is awake. The cycler 14 may detect the patient's sleep/awake state, e.g., using an infrared motion detector and inferring sleep if patient motion is reduced, or using a detected change in blood pressure, brain waves, or other parameter that is indicative of sleep, and so on. Alternately, the cycler 14 may simply "ask" the patient—"are you asleep?" and control system operation based on the patient's response (or lack of response).

Patient Line State Detection Apparatus

In one aspect, a fluid line state detector detects when a fluid line to a patient, such as patient line 34, is adequately primed with fluid before it is connected to the patient. (It should be understood that although a fluid line state detector is described in connection with a patient line, aspects of the invention include the detection of the presence any suitable tubing segment or other conduit and/or a fill state of the tubing segment or other conduit. Thus, aspects of the invention are not limited to use with a patient line, as a tubing state detector may be used with any suitable conduit.) In some embodiments, a fluid line state detector can be used to detect adequate priming of a tubing segment of the patient-connecting end of a fluid line. The patient line 34 may be connected to an indwelling catheter in a patient's blood vessel, in a body cavity, subcutaneously, or in another organ. In one embodiment, the patient line 34 may be a component of a peritoneal dialysis system 10, delivering dialysate to and receiving fluid from a patient's peritoneal cavity. A tubing segment near the distal end of the line may be placed in an upright position in a cradle within which the sensor elements of the detector are located. FIG. 10 shows a front perspective view of an exemplary configuration of a fluid line state detector 1000, which may be mounted on, or otherwise exposed at, the left side exterior of the housing 82, e.g., to the left of the front door 141. The fluid line state detector will be described as a patient line state detector 1000, for purposes of example. The patient line 34 should preferably be primed prior to being connected to the patient, because air could otherwise be delivered into the patient, raising the risk of complications. It may be permissible in some settings to allow up to 1 mL of air to be present in the patient line 34 prior to being connected to a patient's peritoneal dialysis catheter. The exemplary configurations of the patient line state detector 1000 described below will generally meet or exceed this standard, as they are capable of detecting a liquid level in a properly positioned tubing segment of line 34 so that at most about 0.2 mL of air remains in the distal end of line 34 after priming.

In one aspect, a first configuration patient line state detector 1000 may include a base member 1002. There may also be a patient line state detector housing 1006 affixed to (or commonly molded with) the base member 1002, such that the detector housing 1006 may extend outwardly from the base member 1002. The detector housing 1006 defines a tube or connector holding channel 1012 within which a tubing segment 34a near the distal end of a patient line 34, or its associated connector 36 may be positioned. The portion of the detector housing 1006 facing the base member 1002 may be substantially hollow, and as a result an open cavity 1008 (shown in FIG. 11 and FIG. 13) may be created behind the detector housing 1006. The open cavity 1008 may accommodate the placement and positioning of sensor elements (1026, 1028, 1030 and 1032 shown in FIG. 13) next to the channel 1012 within which tubing segment 34a may be positioned. In an alternative embodiment, there may also optionally be a stabilizing tab 1010 extending outwardly from the base member 1002. The stabilizing tab 1010 may have a concave outer shape, so that it may substantially conform to the curvature of the patient line connector 36 when the patient line 34 is placed in the patient line state detector housing 1006. The stabilizing tab 1010 may help to prevent the connector 36 from moving during priming of the patient line 34, increasing the accuracy and efficiency of the priming process. The detector housing 1006 may have a shape that generally helps to define the tube or connector holding channel 1012, which in turn may have dimensions that vary to accommodate the transition from tubing segment 34a to tube connector 36.

In this illustrative embodiment, the channel 1012 may substantially conform to the shape of the patient line connector 36. As a result the channel 1012 may be "U-shaped" so as to encompass a portion of the connector 36 when it is placed into the channel 1012. The channel 1012 may be made up of two distinct features; a tube portion 1014 and a cradle 1016. In another aspect, the tube portion 1014 may be positioned below the cradle 1016. Additionally, the cradle 1016 may be formed by a pair of side walls 1018 and a back wall 1020. Both of the side walls 1018 may be slightly convex in shape, while the back wall 1020 may be generally flat or otherwise may have a contour generally matching the shape of the adjacent portion of connector 36. A generally convex shape of the side walls 1018 helps to lock the patient line connector 36 into place when positioned in the cradle 1016.

In an illustrative embodiment for a first configuration of patient line state detector 1000, a region 36a of the patient line connector 36 may have a generally planar surface that can rest securely against the opposing back wall 1020 of channel 1012. Additionally, this region 36a of the connector 36 may have recesses 37 on opposing sides, which can be positioned adjacent to the opposing side walls 1018 of channel 1012 when the connector 36 is positioned within the detector housing 1006. The recesses 37 can be defined by flanking raised elements 37a of connector 36. One of these recesses 37 is partially visible in FIG. 10. The two side walls 1018 may have a generally mating shape (such as, e.g. a convex shape) to engage recesses 37 and to help lock connector 36 into place within cradle 1016. This helps to prevent the connector 36 and tubing segment 34a from being inadvertently removed from the detector housing 1006 during priming of the patient line 34. If the raised elements 37a of connector 36 are made of sufficiently flexible material (such as, e.g., polypropylene, polyethylene, or other similar polymer-based material) a threshold pulling force against connector 36 will be capable of disengaging connector 36 and tubing segment 34a from the detector housing 1006.

In another aspect, the tube portion 1014 of the cavity 1012 may surround a majority of tubing segment 34a at a point just before tubing segment 34a attaches to the connector 36. The tube portion 1014 may contain a majority of tubing segment 34a using three structures: the two side walls 1018 and the back wall 1020. In an embodiment, the two side walls 1018 and back wall 1020 may be transparent or sufficiently translucent (constructed from, e.g. plexiglass) so as to allow the light from a plurality of LED's (such as, e.g., LED's 1028, 1030, and 1032 in FIG. 13) to be directed through the walls without being significantly blocked or diffused. An optical sensor 1026 (shown in FIG. 12), may also be positioned along one of the walls 1018, and can detect the light being emitted by the LED's. In the illustrated embodiment, a transparent or translucent plastic insert 1019 may be constructed to snap into the main detector housing 1006 in the region where the LED's have been positioned in the housing.

Figure 12:
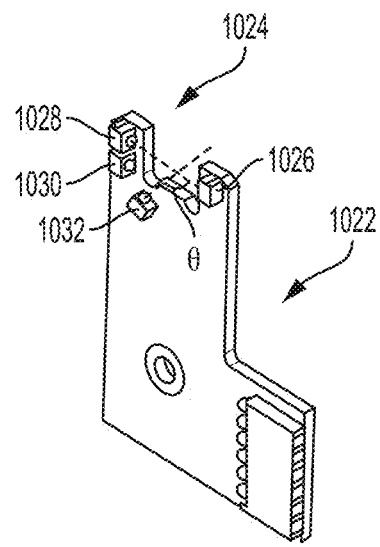
FIG. 12 is a perspective layout view of three LEDs and an optical detector surface-mounted on a printed circuit board.
Figure 13:
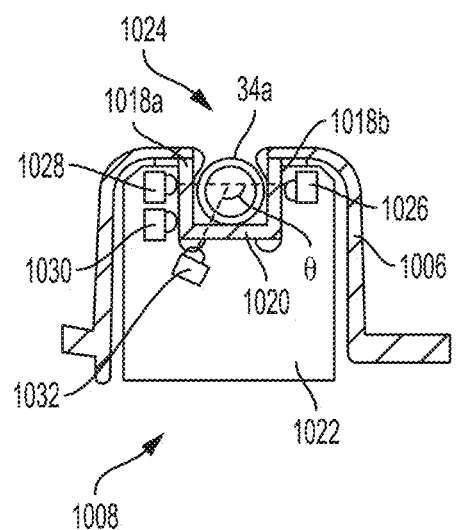
FIG. 13 is a plan view of three LEDs and an optical detector mounted on a detector circuit board.
Figure 14:
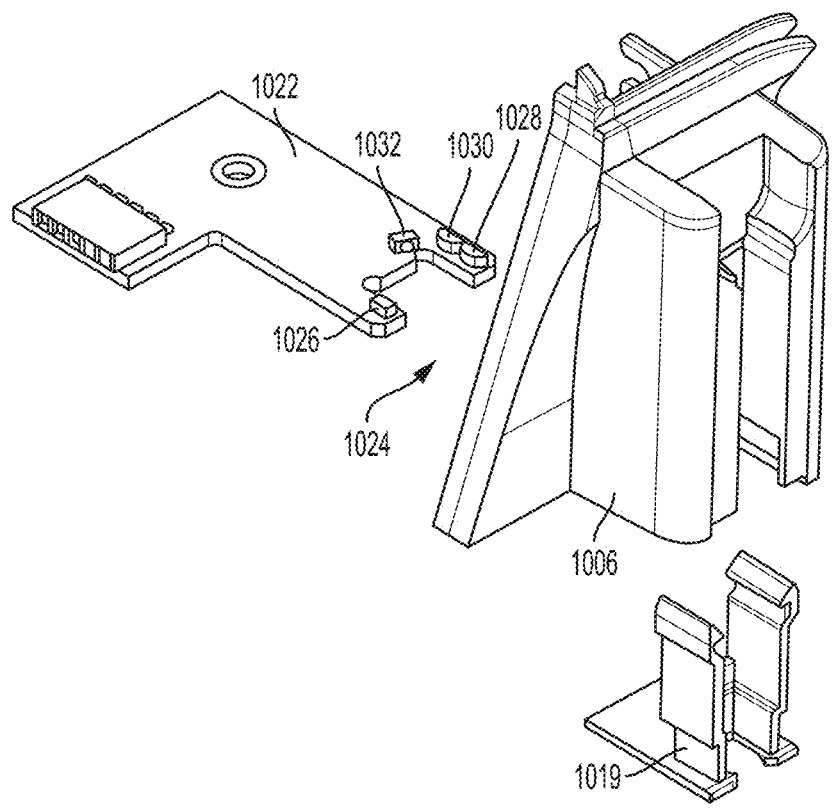
FIG. 14 is an exploded perspective view of the detector of FIG. 10 showing the printed circuit board and transparent or translucent plastic insert.

FIG. 12 shows a perspective layout view with LED's 1028, 1030, and 1032 and optical sensor 1026 surface-mounted on a patient line state detector printed circuit board 1022. FIG. 13 shows a plan view of LED's 1028, 1030, and 1032 and optical sensor 1026 mounted on detector circuit board 1022, where the detector circuit board 1022 can be positioned adjacent the back wall 1020 and side walls 1018 of detector housing 1006. FIG. 14 is an exploded perspective view of detection assembly 1000 showing the relative positions of the printed circuit board 1022 and the translucent or transparent plastic insert 1019 with respect to the housing 1006.

Figure 11:
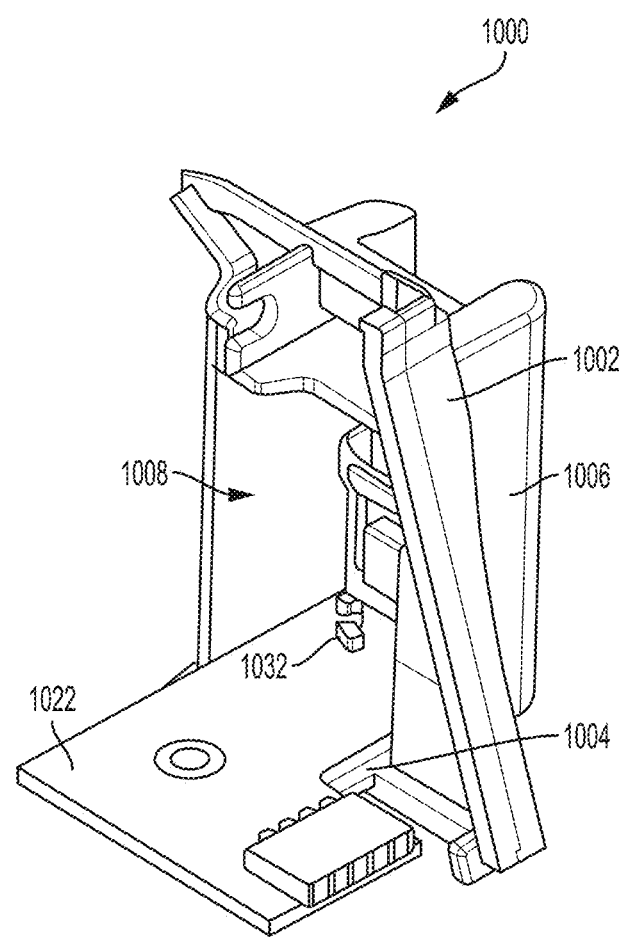
FIG. 11 is a rear perspective view of a fluid line state detector or liquid level detector.

Referring also to the illustrative embodiment of FIG. 11, the detector circuit board 1022 may be positioned on a support structure 1004 and inside open cavity 1008, which was formed from detector housing 1006 extending outwardly from base member 1002. The base member 1002 and support structure 1004 may be affixed to one another, or may be commonly molded, so that the base member 1002 is generally perpendicular to the support structure 1004. This orientation generally permits the plane of the detector circuit board 1022 to be generally perpendicular to the long axis of tubing segment 34a when secured within channel 1012. The detector circuit board 1022 may conform generally to the cross-sectional shape of open cavity 1008, and it may also include a cutout 1024 (FIG. 12, 13) generally matching the cross-sectional shape of channel 1012 formed by back wall 1020 and side walls 1018 (FIG. 10). The detector circuit board 1022 may then be positioned within open cavity 1008 with cutout 1024 nearly adjacent to side walls 1018 and back wall 1020 of detector housing 1006 in order to ensure proper alignment of the detector circuit board 1022 with tubing segment 34a or connector 36.

The detector circuit board 1022 may include a plurality of LED's and at least one optical sensor, which may be attached to circuit board 1022, and in one embodiment, the LED's and optical sensor may be surface-mounted to circuit board 1022. In one aspect, the detector circuit board 1022 may include a first LED 1028, a second LED 1030, a third LED 1032, and an optical sensor 1026. A first LED 1028 and a second LED 1030 may be positioned so as to direct light through the same side wall 1018a of channel 1012. The light emitted by the first LED 1028 and the second LED 1030 may be directed in a generally parallel direction, generally perpendicular to the side wall 1018a to which they are nearest. An optical sensor 1026 may be positioned along the opposite side wall 1018b of channel 1012. Furthermore, a third LED 1032 may be positioned along the back wall 1020 of channel 1012. In this illustrative embodiment, such a configuration of the LED's and the optical sensor 1026 allows the patient line state detector 1000 to detect three different states during the course of priming the patient line 34; a tubing segment 34a or connector 36 nearly completely filled with fluid (primed state), an incompletely filled tubing segment 34a or connector 36 (non-primed state), or the absence of a tubing segment 34a and/or connector 36 from channel 1012 (line-absent state).

When used in a peritoneal dialysis system such as, for example peritoneal dialysis system 10, configuring the detector circuit board 1022 in this fashion allows the appropriate control signal to be sent to the PD cycler controller system 16. Controller system 16 may then inform the user, via user interface 144, to position the distal end of line 34 in the patient line state detector 1000 prior to making a connection to the peritoneal dialysis catheter. The controller may then monitor for placement of tubing segment 34a within patient line state detector 1000. The controller may then proceed to direct the priming of line 34, to direct termination of priming once line 34 is primed, and then to instruct the user to disengage the distal end of line 34 from the patient line state detector 1000 and connect it to the user's peritoneal dialysis catheter.

Surface mounting the LED's 1028, 1030, and 1032 and the optical sensor 1026 to the circuit board 1022 can simplify manufacturing processes for the device, can allow the patient line state detector 1000 and circuit board 1022 to occupy a relatively small amount of space, and can help eliminate errors that may arise from movement of the LED's or the optical sensor relative to each other or to the channel 1012. Were it not for surface mounting of the sensor components, misalignment of the components could occur either during assembly of the device, or during its use.

In one aspect, the optical axis (or central optical axis) of LED 1032 may form an oblique angle with the optical axis of optical sensor 1026. In the illustrated embodiment, the optical axis of a first LED 1028, a second LED 1030, and an optical sensor 1026 are each generally parallel to each other and to back wall 1020 of channel 1012. Thus, the amount of light directed toward optical sensor 1026 from the LED's may vary depending on the presence or absence of (a) a translucent or transparent conduit within channel 1012 and/or (b) the presence of liquid within the conduit (which, for example, may be tubing segment 34a). Preferably, LED 1032 may be positioned near the side wall (e.g., 1018a) that is farthest from optical sensor 1026 in order for some of the light emitted by LED 1032 to be refracted by the presence of a translucent or transparent tubing segment 34a within channel 1012. The degree of refraction away from or toward optical sensor 1026 may depend on the presence or absence of fluid in tubing segment 34a.

In various embodiments, the oblique angle of LED 1032 with respect to optical sensor 1026 creates a more robust system for determining the presence or absence of liquid with a translucent or transparent conduit in channel 1012. LED 1032 may be positioned so that its optical axis can form any angle between 91° and 179° with respect to the optical axis of optical sensor 1026. Preferably the angle may be set within the range of about 95° to about 135° with respect to the optical sensor's optical axis. More preferably, LED 1032 may be set to have an optical axis of about 115°+/−5° with respect to the optical axis of optical sensor 1026. In an illustrative embodiment shown in FIG. 13, the angle θ of the optical axis of LED 1032 with respect to the optical axis of optical sensor 1026 was set to approximately 115°, +/−5°.

(The optical axis of optical sensor 1026 in this particular embodiment is roughly parallel to back wall 1020, and roughly perpendicular to side wall 1018b). The advantage of angling LED 1032 with respect to the optical axis of optical sensor 1026 was confirmed in a series of tests comparing the performance of the optical sensor 1026 in distinguishing a fluid filled tube segment (wet tube) from an air filled tube segment (dry tube) using an LED 1032 oriented at about a 115° angle vs. an LED whose optical axis was directed either perpendicularly or parallel to the optical axis of optical sensor 1026. The results showed that an angled LED-based system was more robust in distinguishing the presence or absence of liquid in tubing segment 34a. Using an angled LED 1032, it was possible to select an optical sensor signal strength threshold above which an empty tubing segment 34a could reliably be detected. It was also possible to select an optical sensor signal strength threshold below which a liquid-filled tubing segment 34a could reliably be detected.

Figure 15:
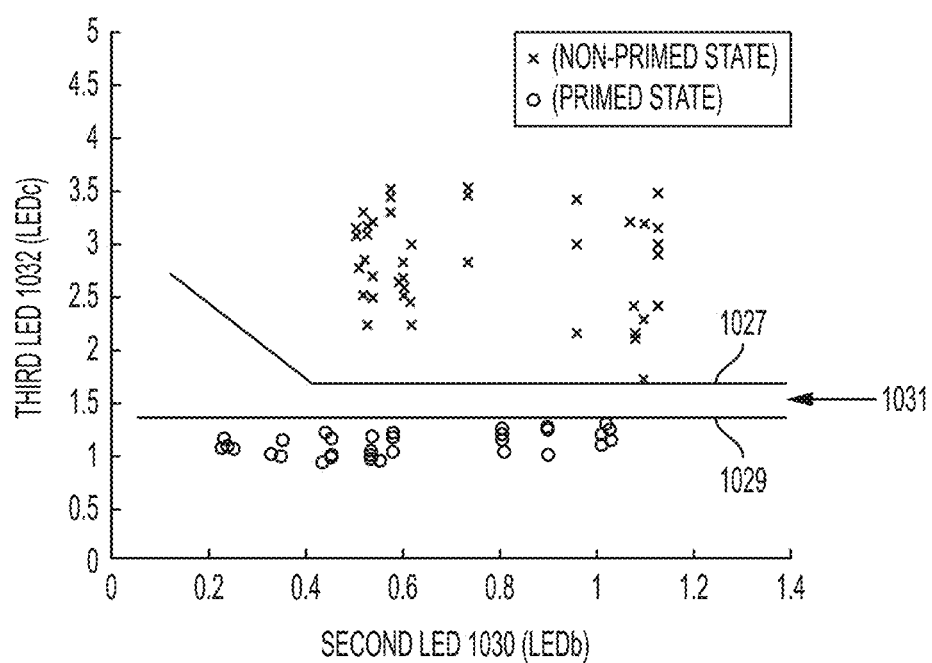
FIG. 15 is a graph showing the ability of the liquid level detector of FIG. 10 to distinguish between a primed and a non-primed fluid line.

FIG. 15 shows a graph of test results demonstrating the ability of patient line state detector 1000 to distinguish between a liquid-filled tubing segment 34a (primed state) and an empty tubing segment 34a (non-primed state). The results were recorded with LED 1032 (third LED) oriented at an angle of about 115° with respect to the optical axis of optical sensor 1026, and LED 1030 (second LED) oriented roughly parallel to the optical axis of optical sensor 1026. The results plotted in FIG. 15 demonstrate that patient line state detector 1000 can reliably discriminate between a primed state and a non-primed state. When the relative signal strength associated with light received from LED 1030 was approximately 0.4 or above, it was possible to resolve an upper signal detection threshold 1027 and a lower signal detection threshold 1029 for a non-primed vs. primed state using only the light signal received from LED 1032. The upper threshold 1027 can be used to identify the non-primed state, and the lower threshold 1029 can be used to identify the primed state. The data points located above the upper-threshold 1027 are associated with an empty tubing segment 34a (non-primed state), and the data points located below the lower-threshold 1029 are associated with a liquid-filled tubing segment 34a (primed state). A relatively narrow region 1031 between these two threshold values defines a band of relative signal strength associated with light received from LED 1032 in which an assessment of the priming state of tubing segment 34a may be indeterminate. A controller (such as, e.g., control system 16) may be programmed to send the user an appropriate message whenever a signal strength associated with light received from LED 1032 falls within this indeterminate range. For example, the user may be instructed to assess whether tubing segment 34a and/or connector 36 are properly mounted in patient line state detector 1000. In the context of a peritoneal dialysis system, if optical sensor 1026 generates a signal corresponding with an empty tubing segment 34a, the controller can direct the cycler to continue to prime patient line 34 with dialysate. A signal corresponding to a liquid-filled tubing segment 34a can be used by the controller to stop further priming and instruct the user that the fluid line 34 is ready to be connected to a dialysis catheter.

In an embodiment, the cycler controller may continuously monitor the received signal from one of the LED's at the initiation of the priming procedure. Upon detection of a change in the received signal, the controller may halt further fluid pumping to carry out a full measurement using all of the LED's. If the received signals are well within the range indicating a wet tube, then further priming may be halted. However, if the received signals are within the indeterminate region 1031 or within the 'dry' region, then the cycler may command a series of small incremental pulses of fluid into the patient line by the pumping cassette, with a repeat reading of the LED signal strengths after each pulse of fluid. The priming can then be halted as soon as a reading is achieved that indicates a fluid-filled line at the level of the sensor. Incremental pulses of fluid may be accomplished by commanding brief pulses of the valve connecting the pressure reservoir to the pump actuation or control chamber. Alternatively, the controller may command the application of continuous pressure to the pump actuation or control chamber, and command the pump's outlet valve to open briefly and close to generate the series of fluid pulses.

Figure 16:
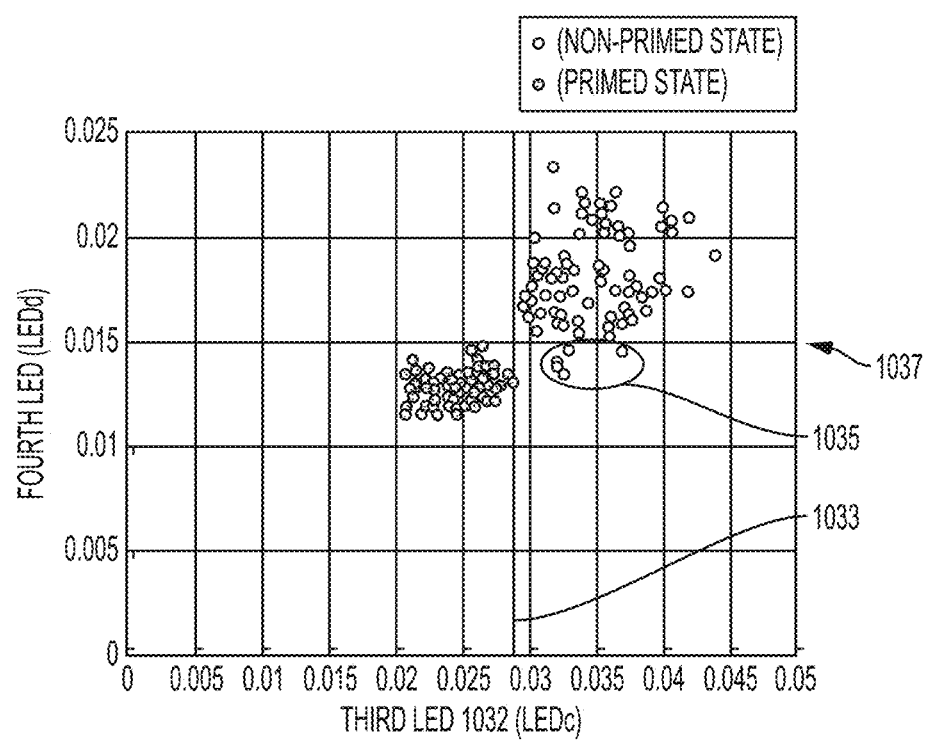
FIG. 16 is a graph showing measurements collected by an optical sensor comparing liquid detection using an orthogonally oriented LED vs. an angled LED.

FIG. 16 shows a graph of test results demonstrating the superiority of an angled LED 1032 (LEDc) when compared with an LED (LEDd) whose optical axis is roughly perpendicular to the optical axis of optical sensor 1026. In this case, the relative signal strength generated by optical sensor 1026 in response to light from LEDc was plotted against the signal strength associated with light from LEDd. Although some separation between a liquid-filled ('primed') and empty ('non-primed') tubing segment 34a was apparent at an LEDd relative signal strength of about 0.015, there remained a substantial number of 'non-primed' data points 1035 that cannot be distinguished from 'primed' data points based on this threshold value. On the other hand, a relative signal strength 1033 associated with light from LEDc of 0.028-0.03 can effectively discriminate between 'primed' tubing segment 34a (primed state) and 'non-primed' tubing segment 34a (non-primed state). Thus an angled LED (1032) can generate more reliable data than an orthogonally oriented LED.

In another embodiment, a patient line state detector 1000 can also determine whether a tubing segment 34a is present in channel 1012. In one aspect, a first LED 1028 and a second LED 1030 may be positioned next to one another. One LED (e.g., LED 1028) may be positioned so that its optical axis passes through approximately the center of a properly positioned translucent or transparent conduit or tubing segment 34a in channel 1012. The second LED (e.g. LED 1030) may be positioned so that its optical axis is shifted slightly off center with respect to conduit or tubing segment 34a in channel 1012. Such an on-center/off-center pairing of LED's on one side of channel 1012, with an optical sensor 1026 on the opposing side of channel 1012, has been shown to increase the reliability of determining whether a liquid conduit or tubing segment 34a is present or absent within channel 1012. In a series of tests in which a tubing segment 34a was alternately absent, present but improperly positioned, or present and properly positioned within channel 1012, signal measurements were taken by the optical sensor 1026 from the first LED and the second LED 1030. The signals received from each LED were plotted against each other, and the results are shown in FIG. 17.

Figure 17:
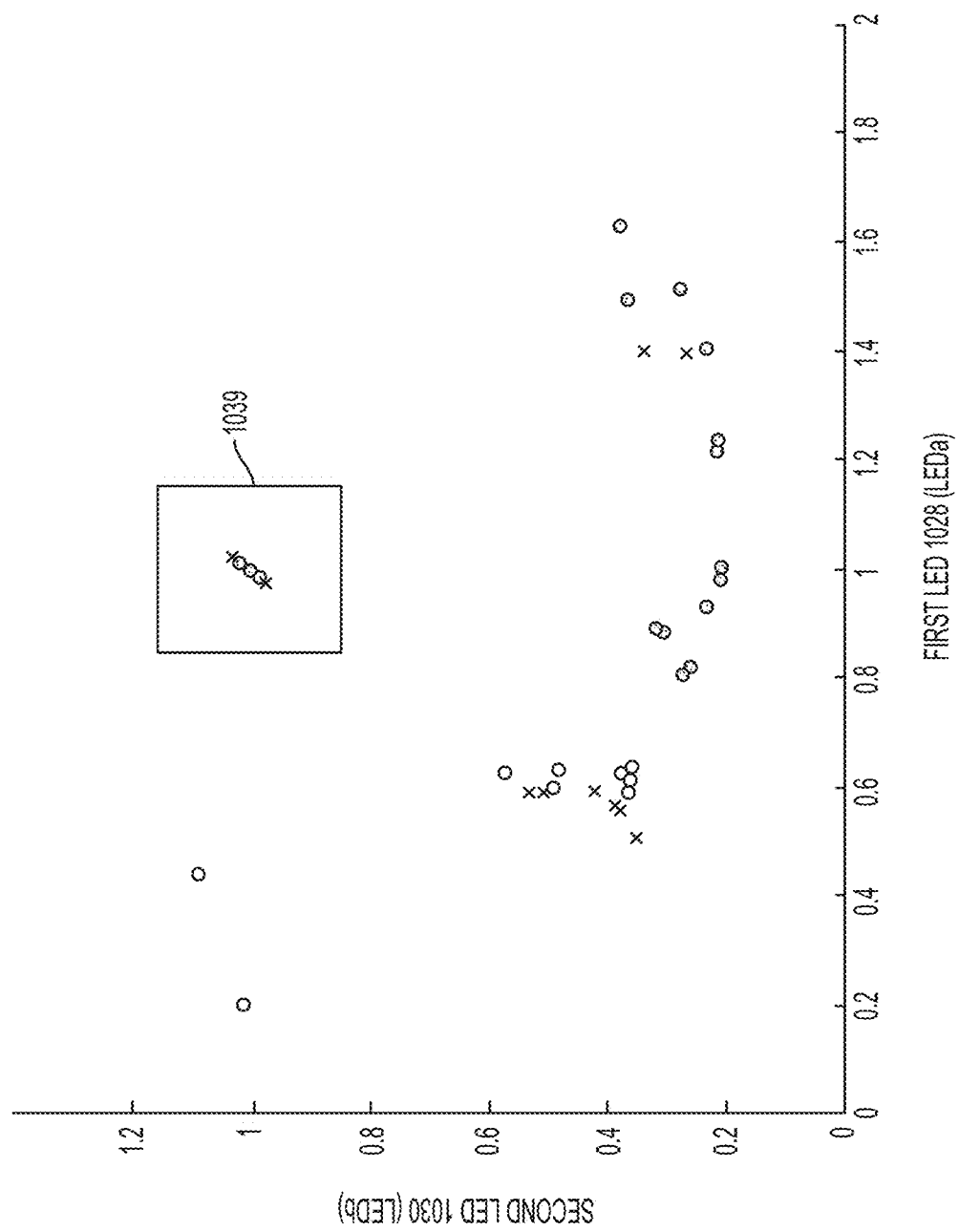
FIG. 17 is a graph showing the ability of the liquid level detector of FIG. 10 to distinguish between the presence and absence of a tubing segment within the detector.

As shown in FIG. 17, in the majority of cases in which tubing segment 34a was absent from channel 1012 (region 1039), the signal strength received by optical sensor 1026 attributable to LEDa (LEDa reception strength) was found not to be significantly different from the signal strength received from LEDa during a calibration step in which LEDa was illuminated in a known absence of any tubing in channel 1012. Similarly, the signal strength associated with LEDb (LEDb reception strength), was found not to be significantly different from LEDb during a calibration step in which LEDb was illuminated in a known absence of any tubing in channel 1012. Patient line state detector 1000 can reliably determine that no tube is present within channel

1012 if the ratio of LEDa to its calibration value, and the ratio of LEDb to its calibration value are each approximately 1±20%. In a preferred embodiment, the threshold ratio can be set at 1±15%. In an embodiment in which patient line state detector 1000 is used in conjunction with a peritoneal dialysis cycler, LEDa and LEDb values within region 1039 of FIG. 17, for example, can be used to indicate the absence of tube segment 34*a* from channel 1012. The cycler controller can be programmed to pause further pumping actions and inform the user via user interface 144 of the need to properly position the distal end of patient line 34 within patient line state detector 1000.

The configuration and alignment of the three LED's and the optical sensor 1026 described above is capable of generating the required data using translucent or transparent fluid conduits (e.g. tubing segment 34*a*) having a wide range of translucence. In additional testing, patient line state detector 1000 was found to be capable of providing reliable data to distinguish liquid from air in a fluid conduit, or the presence or absence of a fluid conduit, using samples of tubing having significantly different degrees of translucence. It was also capable of providing reliable data regardless of whether the PVC tubing being used was unsterilized, or sterilized (e.g., EtOx-sterilized).

The measurements taken by the optical sensor 1026 from the LED's can be used as inputs to a patient line state detector algorithm in order to detect the state of tubing segment 34*a*. Besides detecting a full, empty, or absent tubing segment 34*a*, the result of the algorithm may be indeterminate, possibly indicating movement or improper positioning of the tubing segment 34*a* within the patient line state detector 1000, or possibly the presence of a foreign object in channel 1012 of patient line state detector 1000. Manufacturing variations may cause the output from the LED's and the sensitivity of optical sensor 1026 to vary among different assemblies. Therefore, it may be advantageous to perform an initial calibration of the patient line state detector 1000. For example, the following procedure may be used to obtain calibration values of the LED's and sensor:
  (1) Ensure that no tubing segment 34*a* is loaded in the patient line state detector 1000.
  (2) Poll the optical sensor 1026 in four different states:
    (a) no LED illuminated
    (b) first LED 1028 (LEDa) illuminated
    (c) second LED 1030 (LEDb) illuminated
    (d) third LED 1032 (LEDc) illuminated
  (3) Subtract the 'no LED illuminated' signal value from each of the other signal values to determine their ambient corrected values, and store these three readings as 'no-tube' calibration values.

Once calibration values for the LED's and sensor are obtained, the state of tubing segment 34*a* may then be detected. In this illustrative embodiment, the patient line state detector algorithm performs a state detection in a test as follows:
  (1) Poll the optical sensor 1026 in four different states:
    (a) no LED illuminated
    (b) first LED 1028 (LEDa) illuminated
    (c) second LED 1030 (LEDb) illuminated
    (d) third LED 1032 (LEDc) illuminated
  (2) Subtract the 'no LED illuminated' value from each of the other values to determine their ambient corrected values.
  (3) Calculate the relative LED values by dividing the test values associated with each LED by their corresponding calibration ('no-tube') values.

Results:
  If the ambient corrected LEDa value is less than 0.10, then there may be a foreign object in the detector, or an indeterminate result can be reported to the user.
  If the ambient corrected LEDa and LEDb values fall within ±15% of their respective stored calibration (no-tube) values, then report to the user that no tubing segment is present in the detector.
  If the ambient corrected LEDb value is equal to or greater than about 40% of its stored calibration ('no-tube') value,
    (a) check the signal associated with LEDc
      (i) if the ambient corrected signal associated with LEDc is equal or greater than about 150% of its calibration ('no-tube') value, then report to the user that the tubing segment is empty.
      (ii) If the ambient corrected signal associated with LEDc is equal to or less than about 125% of its calibration ('no-tube') value, then report to the user that the tubing segment is filled with liquid.
      (iii) Otherwise, the result is indeterminate, and either repeat the measurement (e.g., the tubing segment may be moving, may be indented, or otherwise obscured), or report to the user that the tubing segment should be checked to ensure that it is properly inserted in the detector.
  If the ambient corrected LEDb value is less than about 40% of its stored calibration ('no-tube') value, then the LEDc threshold for determining the presence of a dry tube may be greater. In an embodiment, for example, the LEDc empty tube threshold was found empirically to follow the relationship: [LEDc empty tube threshold]=−3.75×[LEDb value]+3.

Once it is determined that the tubing segment 34*a* has been loaded in the patient line state detector 1000, the patient line state detector algorithm can perform the following:
  a) Poll the optical sensor 1026 with no LED illuminated and store this as the no LED value.
  b) Illuminate LEDc
  c) Poll the optical sensor 1026, subtract the no LED value from the LEDc value, and store this as the initial value.
  d) Begin pumping
  e) Poll the optical sensor 1026 and subtract the no LED value from the subsequent LEDc value.
  f) If this value is less than 75% of the initial value, then conclude that tubing segment 34*a* is filled with liquid, stop pumping, confirm the detector state using the above procedure, and when indicated, report to the user that priming is complete. Otherwise, keep repeating the poll, calculation, and comparison. In an embodiment, the system controller can be programmed to perform the polling protocol as frequently as desired, such as, for example, every 0.005 to 0.01 seconds. In an embodiment, the entire polling cycle can conveniently be performed every 0.5 seconds.

Figure 18:
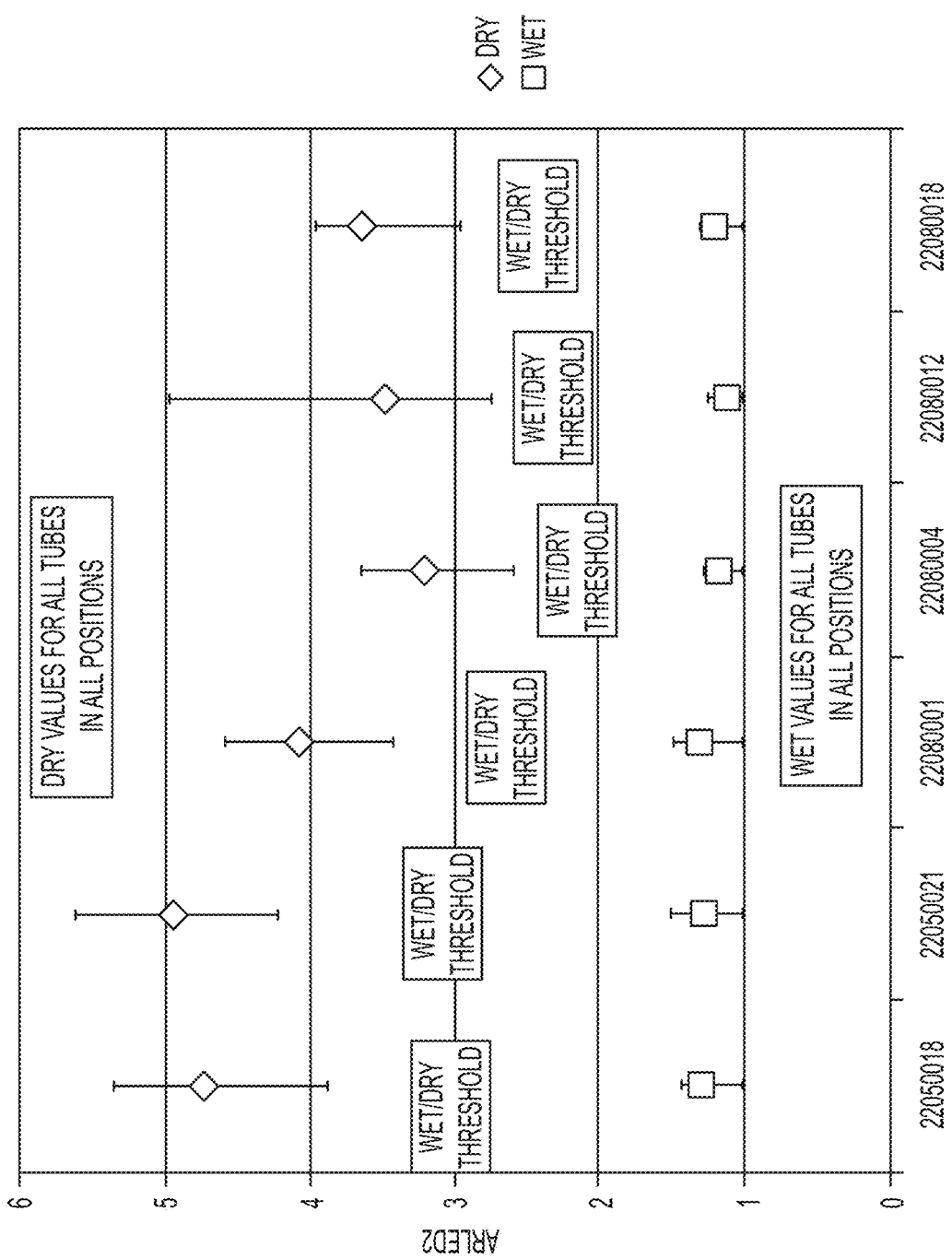
FIG. 18 is a graph showing the range of signals corresponding to a primed and a non-primed fluid line for different cyclers using the liquid detector of FIG. 10.

FIG. 18 shows the results of sample calibration procedures for six cyclers. The signal strength range that distinguishes a dry tube from a wet tube ('wet/dry threshold' ranges) is noted to vary among the different cyclers. (The variations in these ranges may be due to minor variations in manufacturing, assembly and positioning of the various components). Thus at calibration, each cycler may be assigned a wet/dry threshold signal strength range that optimally separates the data points generated with a dry tube from the data points generated with a wet tube.

Figure 19:
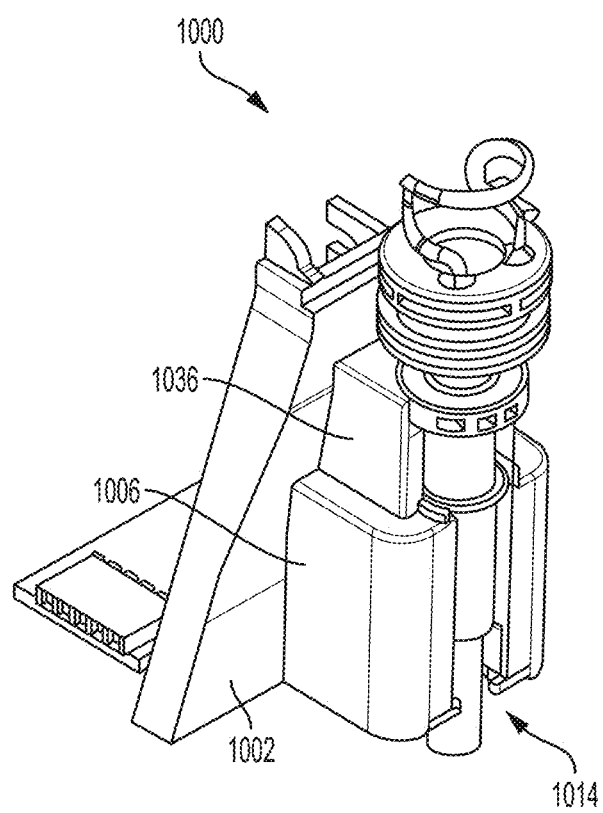
FIG. 19 is a perspective view of an alternative configuration of a liquid level detector.

FIG. 19 shows a perspective view of a second configuration of a patient line state detector 1000. Two or more different patient line state detector configurations may be necessary to accommodate varying types of patient connectors. In this illustrative embodiment, the second configuration patient line state detector 1000 may include most of the same components as in the first configuration patient line state detector 1000. However, in order to accommodate a different type of connector, the second configuration may include a raised element 1036 above housing 1006, rather than the stabilizing tab 1010 found in the first configuration patient line state detector 1000. The raised element 1036 may generally conform to the shape of a standard patient line connector cap or connector flange.

In accordance with an aspect of the disclosure, detector housing 1006 may not include a tube portion 1014. Therefore, open cavity 1008 may be arranged to allow placement of detector circuit board 1022 so that the LED's and optical sensor may be positioned next to a translucent or transparent patient line connector 36 rather than a section of tubing. Channel 1012 consequently may be shaped differently to accommodate the transmission of LED light through connector 36.

In some embodiments, the fluid line detector 1000, rather than being used to detect the prime state of a segment of tubing, may use one or more LED's simply to detect the presence of the line segment in the fluid line detector 1000. The presence and proper seating of the line segment may be determined using fewer LED's than the embodiments described above.

In other embodiments, another type of sensor may be used to detect one or more condition of interest related to a fluid line such as a fluid line 30 or patient line 34. For example, a fluid line detector 1000 may include an electrical or magnetic contact switch or physically actuated switch such as a microswitch. The fluid line detector 1000 may detect the presence of a fluid line connector 36 or tubing segment 34a with actuation of such a switch. In some embodiments, two or more such switches may be used in a fluid line detector 1000. This may provide some redundancy or may be used to detect that multiple line segments of interest are properly seated. In an embodiment, a microswitch may, for example, be disposed in the channel 1012 so as to be actuated when the tubing segment 34a is seated in the channel 1012. Alternatively or additionally, a microswitch may be disposed, for example in a cradle 1016, to be actuated when a fluid line connector 36 is positioned in the fluid line detector 1000. In such embodiments, a cycler controller (e.g. control system 16) may not allow priming of the tubing until all of the one or more switches indicate that the line and/or connector are properly seated in the fluid line detector 1000.

In another embodiment, the fluid line detector 1000 may sense the presence and state of a tube segment using a split ring resonator-based sensor. Such a detector is shown and described, for example, in U.S. patent application Ser. No. 14/341,207, filed Jul. 25, 2014, and entitled System, Method and Apparatus for Bubble Detection in a Fluid Line Using a Split-Ring Resonator, the contents of which are hereby incorporated by reference.

In some embodiments, the sensor(s) in the fluid line detector 1000 may be configured to detect the type of fluid line 34 installed in the fluid line detector 1000 (e.g., adult vs. pediatric size, opaque vs. translucent, etc.). The fluid line connector 36 and/or tubing segment 34a may, for example, have different differentiating features (e.g. different geometries) depending on the type of line being used. The sensor(s) in the fluid line detector 1000 may be configured to discern which type of line is present based upon sensing the presence or absence of such differentiating features.

For example, if a fluid line detector 1000 is configured to use microswitches, the switches may be configured to detect the presence of a particular type of fluid line connector 36. The fluid line connectors 36 on each type of line may include different features (e.g. different projections or voids, or differently disposed projections or voids). When installed in the fluid line detector 1000, the fluid line connector 36 may trip a specific switch or group of switches to detect the presence of the particular type of fluid line connector 36. If an invalid or unexpected combination of switches are actuated, or if a combination of switches is actuated that does not correspond to a fluid line geometry intended for use with the cycler or medical device, the controller may be programmed to notify the user of the incompatible or improper line. This arrangement of switches may also be used to detect improperly seated lines or connectors.

In other embodiments, the completion of priming of a fluid line 34 with a liquid can be inferred by detecting when liquid flow has replaced air flow in the lumen of the distal end of the line 34 or in a connector 36 at the distal end of the line 34. The difference in resistance to flow between air and liquid in a lumen of a given caliber can be detected by monitoring the flow rate of the liquid when under a predetermined force (by gravity or by active pumping). The caliber of the lumen may be chosen to optimize the differentiation between air flow and liquid flow. In most cases, this will involve introducing a flow restriction near or at the end of the fluid line 34 or a distal connector. A properly chosen flow restriction at the distal end of the line 34 or connector 36 will permit relatively unrestricted air flow out of the line 34, while impeding liquid flow enough to slow the advance of a liquid column through the line 34. This increased liquid flow resistance or change in pressure drop across the restriction zone can be detected by the use of a flow meter in the liquid flow path, or by measurement of the change in volume of liquid in an upstream pumping chamber over a predetermined time interval. In an embodiment in which a membrane-based positive displacement pump is used, the rate of change of liquid volume in a pumping chamber can be calculated by monitoring the pressure in an actuation chamber of the pump (through the application of Boyle's Law or other pressure-volume relationships of an ideal gas in a closed space, for example), the pressure in the actuation chamber providing an indication of the pressure in the pumping chamber of the pump. A controller receiving liquid flow data from the fluid line, or computing liquid flow out of the pumping chamber through measurement of pressure changes in the pumping chamber, can compare the liquid flow to a pre-determined value. Alternatively, the controller can calculate a drop in liquid flow rate, and compare the change in flow rate to an expected value to declare that the fluid line has been primed with liquid.

The flow-impeded zone may comprise a constriction, obstruction, partial blockage, or restriction (e.g. orifice) which allows for the easy passage of air, but impedes the passage of a liquid such as dialysate solution. The feature may comprise a short segment of distal tubing or fluid connector 36 that includes a region having a smaller cross-sectional area than that of the fluid conduit in the upstream or proximal section of the fluid line. The term 'restriction' as used herein is meant to encompass any feature that increases resistance to flow differentially between air and liquid in a fluid conduit.

In an embodiment, the restriction may be removable from the distal end of the fluid line or an associated connector. For instance, the restriction may be included in a plug or cap which remains in place on the fluid line 34 during priming of the fluid line 34. The restriction may, for example, be molded as part of the plug or cap during manufacture. This restriction may be a recess, void, channel or other flow path in the plugging portion of the cap. The plugging portion of the cap may be inserted into the fluid conduit directly, or into the lumen of an attached connector 36. Alternatively, the plug or plugging portion of the cap may be sized to have a diameter which is smaller than the diameter of the fluid conduit or its associated connector lumen. When the cap is installed the plug portion may obstruct part of the fluid conduit, creating a small gap between the outer surface of the plug and the inner wall of the conduit, and thereby generate the restriction.

When pumping fluid to prime a fluid line 34, fluid will move at a relatively high flow rate as air is freely displaced out of the fluid line 34 through the restriction. The increase in impedance when liquid reaches the restriction will slow the flow rate. Flow rate may be monitored by a controller receiving input from one or more sensors as priming occurs. When the flow rate drops, it may be inferred that the air has been pushed out of the line beyond the restriction, and that a given applied force is now attempting to push liquid through the restriction. In some embodiments, the controller may employ additional logic to discern between a number of possible causes for reduced liquid flow rates in the fluid line.

In embodiments in which the restriction is an orifice (positioned either at the distal end of the fluid line or within an attached connector), the cross-sectional area of the orifice opening may be selected so as to generate a desired amount of impedance to liquid flow. Additionally, the pumping pressure chosen may be selected such that the flow rates when pumping air and when pumping liquid are detectably different.

It may be desirable to place the restriction slightly upstream of the point at which a fluid line 34 would be fully primed. This would allow for some liquid to flow through the restriction during a determination or recognition period over which a controller is determining whether the impedance to liquid flow has changed. Having a line volume downstream from the restriction provides a fluid buffer to accumulate additional liquid while the controller makes a determination of priming and stops the fluid pump, thus helping to prevent overflow of liquid out of the distal end of the fluid line. Preferably, the delay characteristics of the pumping system in responding to a change in liquid flow impedance are determined empirically for the system once the system parameters have been selected. These parameters may include, for example, the force or pressure applied by the pump, the frequency of pumping volume determinations or flow rate measurements, the caliber and length of the tubing, the properties of the flow restriction, and the response times of the controller and pump. Once the system characteristics are determined, the post-restriction tubing or connector buffer volume needed to prevent overflow can be determined empirically. For illustrative purposes, if the flow rate through a restriction is 30 mL/min, and it takes about 5 seconds for the controller and pump to recognize and respond to the impedance change, a hysteretic fluid volume of about 2.5 mL would be moved while the system responds to the impedance change. In such an embodiment, the downstream volume beyond the restriction may be set to approximately 2.5 mL or slightly more than 2.5 mL. This may serve to help minimize the amount of air left in the fluid line 34 during priming without over-priming the line and causing fluid to overflow the line and spill out.

Alternatively, the restriction may extend along the line axis for a distance that allows the restriction flow pathway volume to approximately the flow volume anticipated while the impedance change is being detected. This embodiment may be desirable when the restriction is included in a fluid line cap.

In some embodiments, an air permeable, but substantially liquid impermeable material may be used to restrict liquid flow. Such a material may allow for relatively unrestricted passage of air, but restrict or prevent passage of liquid. This material may be placed at the end of the fluid line 34 and may allow for air to be pumped out of the line 34, but prevent overflowing and spilling when the line 34 reaches primed state. The material may then, for example, be removed along with a fluid line cap when a user uncaps the line. In some specific embodiments, the material used may be Goretex or another similar material (e.g., breathable materials that may be either microporous or macroporous). As above, a drop in flow rate when the liquid reaches the material would signal that the fluid line 34 has reached a primed state.

Figure 20:
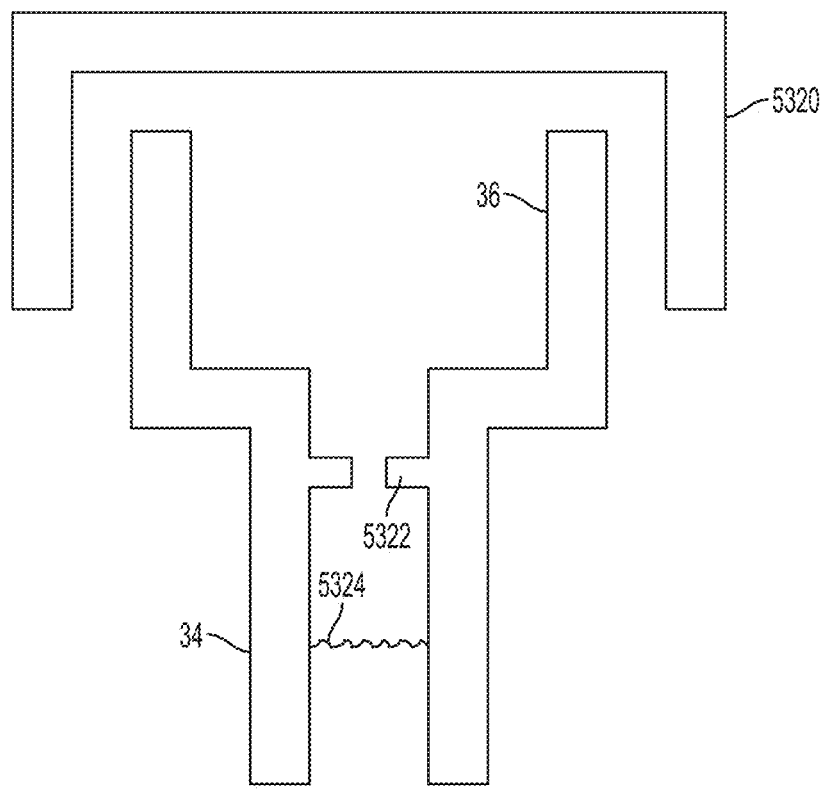
FIG. 20 and FIG. 21 show an embodiment of a fluid line cap, fluid line, and a fluid line connector.
Figure 21:
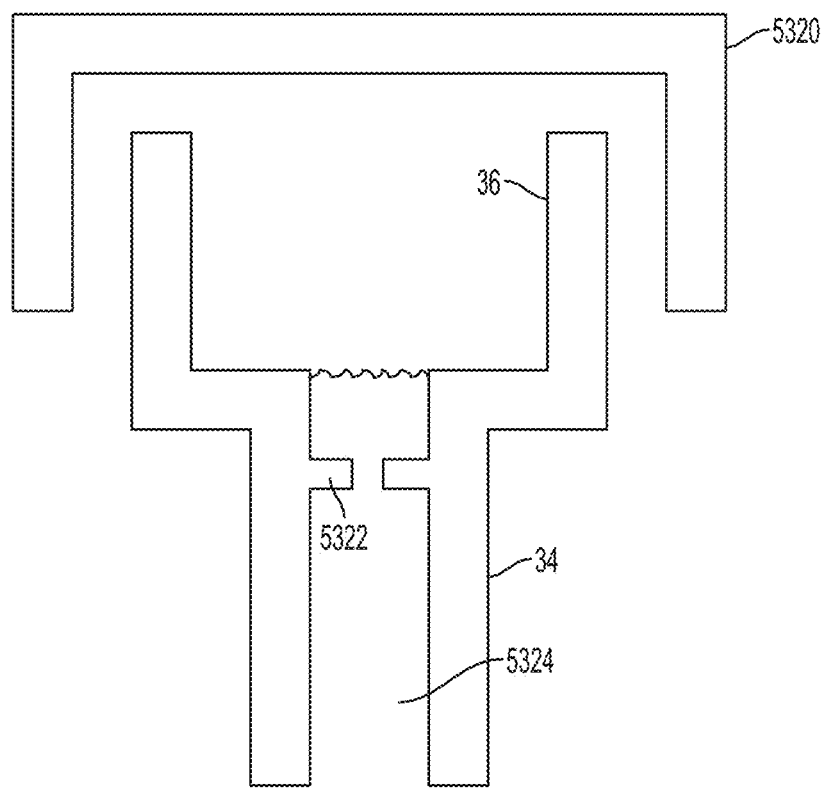

FIG. 20 and FIG. 21 depict an example representative embodiment of a fluid line cap 5320, fluid line 34 and a fluid line connector 36. As shown, a restriction 5322 is included in the fluid line 34. In other examples, the cap 5320 may have inside surface features that incorporate restriction similar to the restriction 5322 shown. In this example, the restriction 5322 is optionally positioned such that there is some fluid line 34 volume downstream of the restriction 5322. The restriction 5322 in the example embodiment is a section in the fluid path with a reduced cross sectional area. In other examples, the restriction 5322 may be an orifice or a membrane which is slit, perforated, or otherwise has one or more pores to increase the resistance to the passage of liquid.

As illustrated in FIG. 20 the liquid 5324 in the fluid line 34 has not yet reached the restriction 5322. At this point, the flow rate of fluid through the fluid line 34 (e.g. a stratified column of air and liquid) may be relatively high. Once the air column has been evacuated, liquid 5324 in the fluid line 34 will have reached the restriction 5322. At this point, the flow rate will drop due to an impedance change. Some liquid 5324 will continue to flow as the cycler determines that the impedance has changed. Once detected, the cycler may be programmed to stop the flow of liquid through the line. At this point, and as shown in FIG. 21, the liquid 5324 will have substantially primed the entire line 34 including the line 34 volume downstream of the restriction 5322. The controller may be programmed to notify a user that the line 34 has been primed and is ready for connection to a catheter or other device in preparation for treatment.

Figure 22:
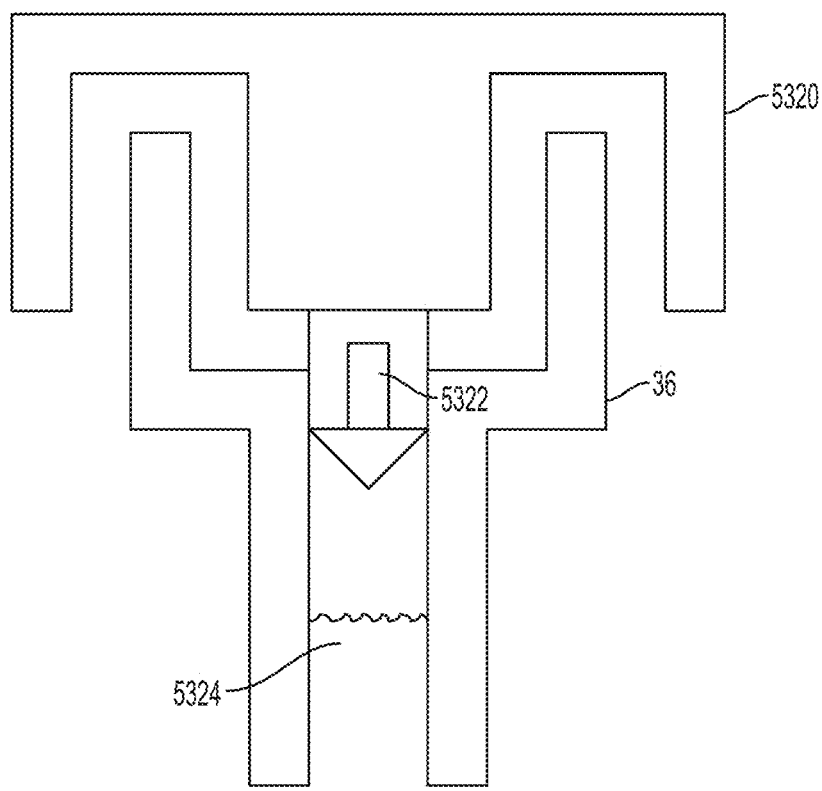
FIG. 22 and FIG. 23 show another embodiment of a fluid line cap, fluid line, and a fluid line connector.
Figure 23:
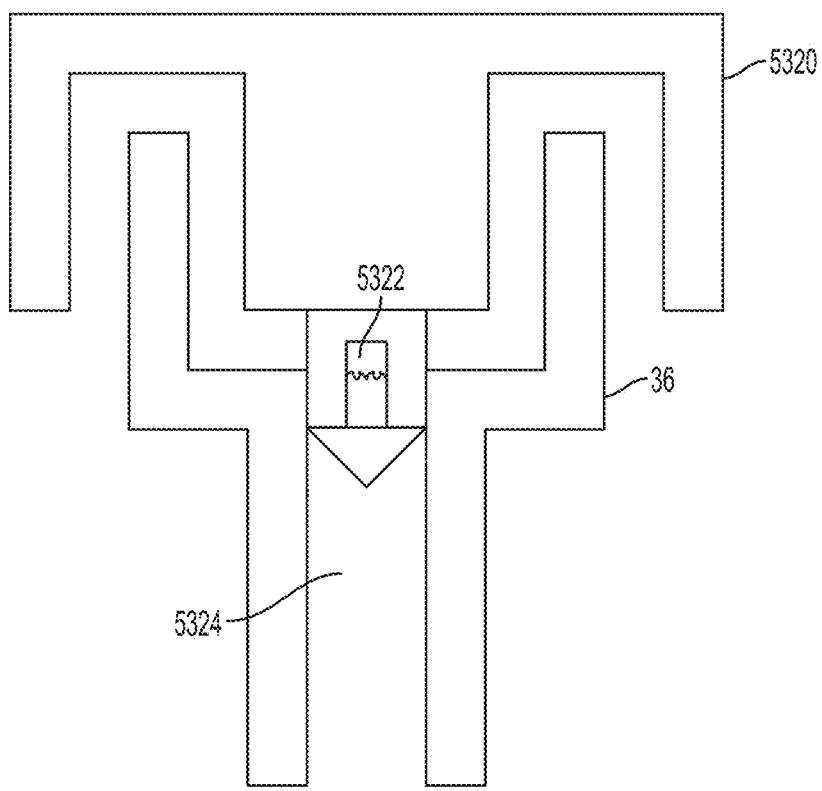

FIG. 22 and FIG. 23 depict another example embodiment of a fluid line 34, fluid line connector 36, and a fluid line cap 5320. As shown, there is no restriction in the fluid line 34 or fluid line connector 36. The fluid line cap 5320 acts as plug for the fluid line 34 and includes a restriction 5322. In the example embodiment, the restriction 5322 may comprise a notch, groove, or channel recessed into the circumference of the plugging portion of the fluid line cap 5320. The restriction 5322 may be sized to allow air to be pumped out of the line at relatively little resistance during priming, but impede the flow of liquid when the air column has been fully expelled. When the controller determines that the line 34 is primed, the controller may then instruct a user to remove line cap 5320 and attach the fluid line connector 36 to an indwelling catheter or other similar device.

As illustrated in FIG. 22 the liquid 5324 in the fluid line 34 has not yet reached the restriction 5322. At this point, the flow rate of fluid (gas plus liquid) through the fluid line 34 may be relatively high. Once the liquid 5324 in the fluid line 34 reaches the restriction 5322, the flow rate will drop due to an impedance change between gas flow and liquid flow through the restriction 5322. Some liquid 5324 will continue to flow as the controller determines that the impedance has changed. Once detected, the controller will stop the flow of liquid 5324 through the line. At this point, and as shown in FIG. 23, the liquid 5324 will have substantially primed the entire line 34. The controller may then notify a user that the line 34 has been primed and that the line cap 5320 may be removed. With the cap 5320 removed, any excess liquid 5324 pumped may fill the volume of the fluid line 34 which was previously occupied by the plugging portion of the fluid line cap 5320. Alternatively, the controller may be programmed to receive a signal from the user that the cap 5320 has been removed, and the controller may be programmed to cause the cycler or pump to advance a small quantity of liquid down the fluid line 34 to top off the distal end of the line 34 or connector 36 prior to its use.

Figure 24:
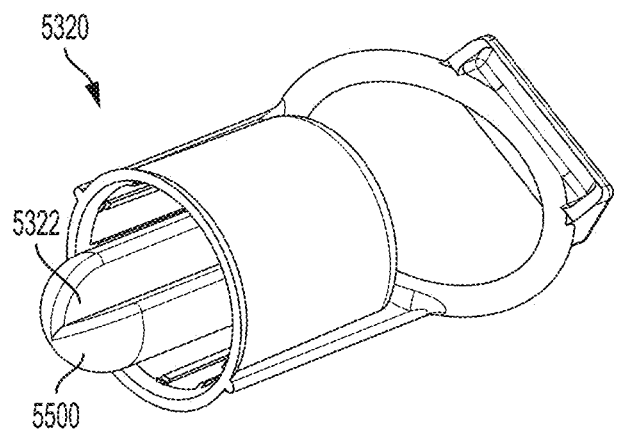
FIG. 24 shows an example of a fluid line cap including a notch.

FIG. 24 depicts a representative example of a fluid line cap 5320 with a plug or plug portion 5500. As shown, the fluid line cap 5320 includes a plug portion 5500 which may be sized to project into and snuggly fit in the fluid conduit of the fluid line 34. A notch is recessed into the plug portion 5500 of the fluid line cap 5320 and serves to create a restriction 5322 when the fluid line cap 5320 is installed on the end of the fluid line 34 or a line connector 36. In the illustration, the notch is substantially triangular in cross-section. In other embodiments, any suitable cross sectional geometry may be used. Other arrangements may be used; such as, for example, a narrow lumen through the length of an otherwise solid plug 5500. Also as shown in FIG. 24, the end of the plug portion 5500 which extends into the fluid flow path may optionally be rounded (or tapered). This may facilitate placing a fluid line cap 5320 onto a fluid line 34.

Figure 25:
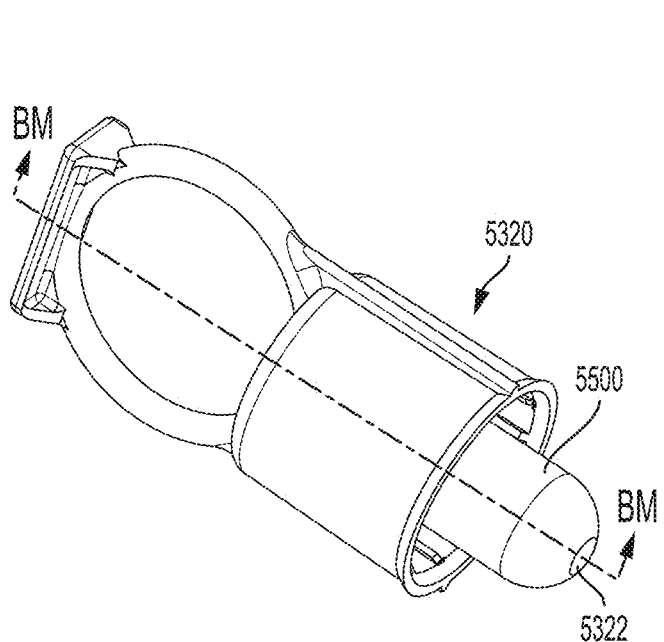
FIG. 25 shows an example of a fluid line cap including a restriction.
Figure 26:
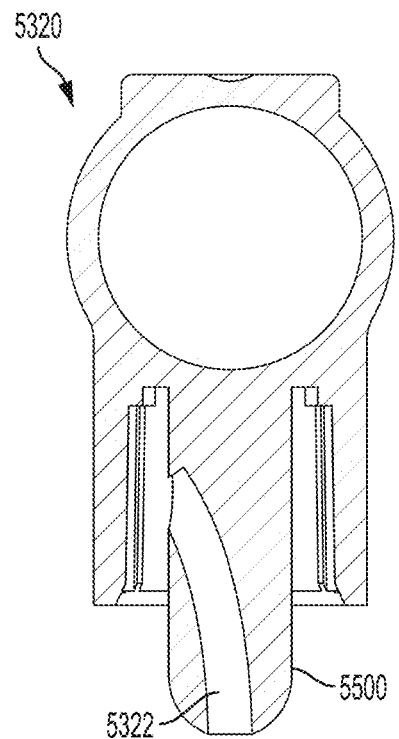
FIG. 26 shows a cross section of a fluid line cap taken at line 26-26 of FIG. 25.

FIG. 25 depicts another embodiment of a fluid line cap 5320. Similar to FIG. 24, the fluid line cap 5320 includes a plug portion 5500 which may be sized to project into and snuggly fit in the fluid conduit of the fluid line 34. The restriction 5322 in FIG. 25 is a flow path which allows for fluid to flow from the fluid conduit of the fluid line 34, through the interior of the plug portion 5500 and into an inner volume of a fluid line connector 36. A cross-sectional view taken on a longitudinal plane of the example fluid line cap 5320 is shown in FIG. 26. The cross-sectional area of the flow path is less than that of the fluid line 34 fluid conduit.

Figure 27:
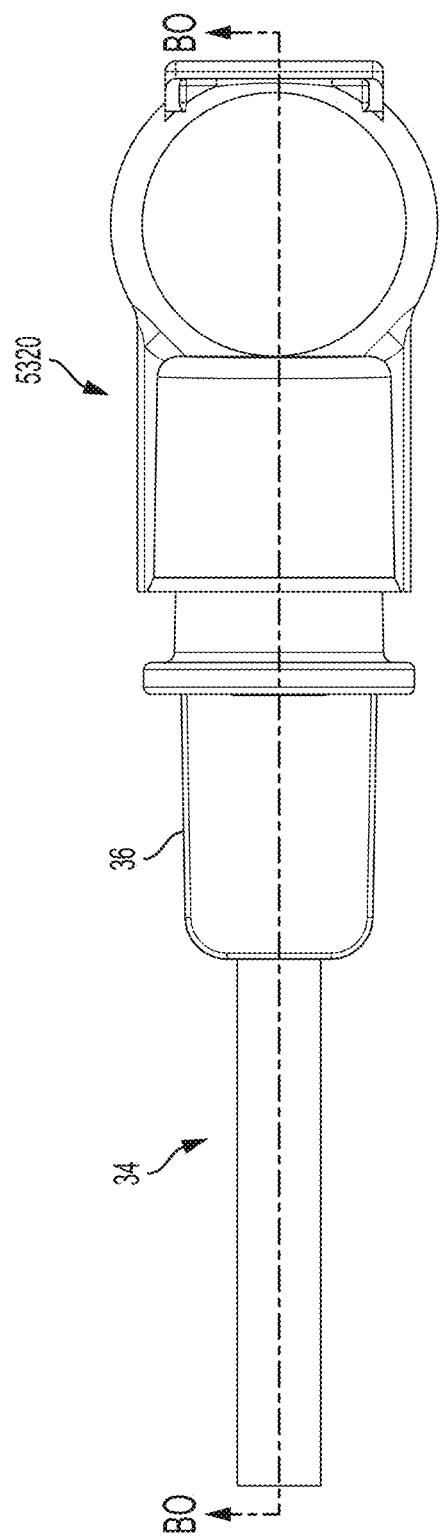
FIG. 27 shows an example of a fluid line cap installed on a fluid line connector of a fluid line.
Figure 28:
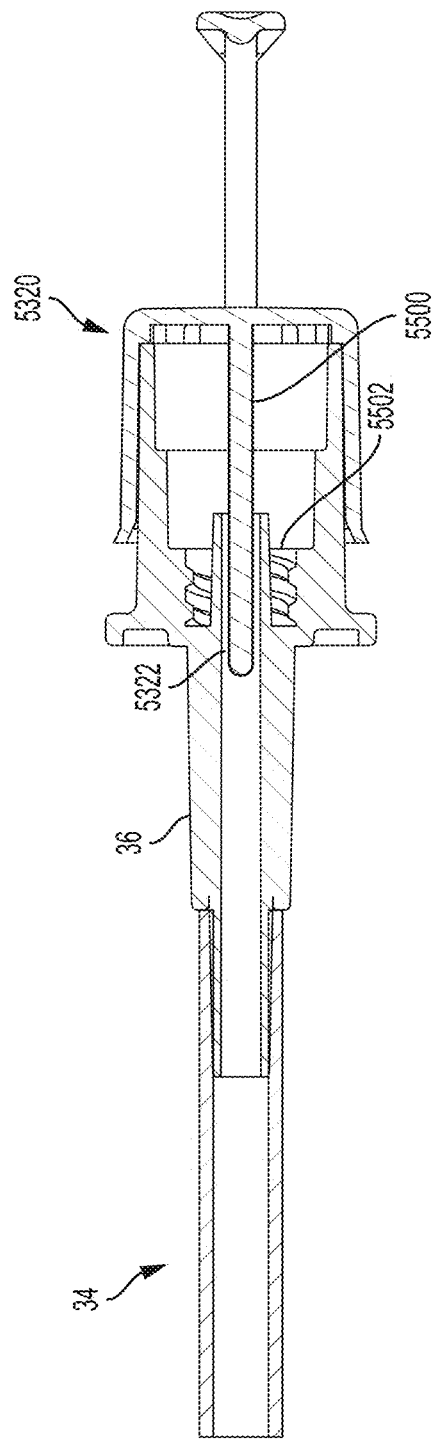
FIG. 28 shows a cross section of the fluid line cap, fluid line, and fluid line connector of FIG. 27 taken at line 28-28 of FIG. 27.

FIG. 27 shows another embodiment of a fluid line cap 5320 installed on the fluid line connector 36 of a fluid line 34. As shown in FIG. 28 a cross-section taken at line 28-28 of FIG. 27, the fluid line connector 36 includes a segment which extends into the fluid conduit of the fluid line 34. The tube of the fluid line 34 may be fixed (e.g. glued, bonded, welded, etc.) to the fluid line connector 36. The fluid line connector 36 includes a flow path which leads from the fluid conduit of the fluid line 34 to a connector fitting 5502 included as part of the fluid line connector 36. The connector fitting 5502 may mate with a cooperating feature on a complementary connector (e.g., of a patient's indwelling catheter) to allow for fluid to be delivered and/or withdrawn from a site (e.g., peritoneal cavity or another body cavity). In the example embodiment, a Luer lock is shown; however, any of a number of other suitable connectors or fittings may be used.

The cap in the example embodiment includes a plug portion 5500. The plug portion 5500 is sized so as to extend into the fluid pathway of the fluid line connector 36. In the example embodiment, the diameter of the plug portion 5500 is smaller than the diameter of the flow path in the fluid line connector 36. When the plug portion 5500 of the fluid line cap 5320 is installed into the flow path of the fluid line connector 36, a small gap remains between the outer surface of the plug portion 5500 and the inner wall of the flow path. Thus, the plug portion 5500 serves to reduce the cross-sectional area of the flow path and creates a restriction 5322.

As described above, in some embodiments, a small gap between the outer surface of the plug portion 5500 and the inner wall of the flow path need not be present. Instead, the plug portion 5500 may fit snuggly in the flow path. A notch may be recessed into the outer surface of the plug portion 5500 to reduce the cross sectional area of the flow path and create the restriction, or an otherwise solid plug inserted in the connector lumen may include a narrow flow path to create a restricted flow path.

In one aspect, the change in fluid flow impedance may be determined based on a flow rate estimation during the progression of a pumping stroke from a pumping cassette. Additionally, a stroke displacement estimation may be used to discriminate between a change in flow rate due to an empty pumping chamber and a change in flow rate due to liquid 5324 reaching the restriction 5322 in the fluid line 34. Estimation of flow rate and stroke displacement during the progression of a pumping stroke will be further described below.

In some embodiments, a controller algorithm to estimate stroke displacement may be used to stop a stroke prior to the full chamber being delivered to a fluid line. That is, a controller may be programmed to instruct a pump to perform partial delivery strokes during priming so as to avoid having the pump diaphragm reach an end-of-stroke position. This may help to ensure that any drop in flow rate is not attributable to a pump diaphragm having reached the rigid pumping chamber wall at the end of a pump stroke. When the controller determines that the volume of fluid pumped per unit of time has decreased beyond a predetermined threshold value, the liquid 5324 in the fluid line 34 may be assumed to have reached the restriction 5322, and the line may be deemed to have been primed.

In other embodiments, a controller may direct the pump to pump fluid until a flow rate discontinuity is detected. At this point, the controller may direct the pumping apparatus (e.g., cycler) to attempt to deliver a small volume of fluid from another pump chamber of a dual pump cassette. In the event that the flow discontinuity was due to the pump diaphragm reaching end-of-stroke, flow from the other chamber should be greater than the ending flow rate from the first chamber. If the discontinuity is due to a primed line condition, flow rate from the other chamber will be similar to that of the ending flow rate from the first chamber. Thus the device controller may determine that the line has been primed.

In some embodiments, a nominal interior tubing volume for a fluid line 34 may be determined. A controller may then direct a pump to move fluid down the line 34 until the volume of the fluid primed down the line 34 is within one chamber volume of the nominal tubing volume. Once the remaining volume of the line 34 is determined to be less than the volume of a full pump stroke, the controller may register the next flow rate discontinuity as indicative of a primed condition.

The nominal interior volume of the line 34 may be determined based on the type of set being used. For example, a pediatric set may have a smaller interior tubing volume than an adult set. In some embodiments, a device controller may determine this information via an optical sensor. In some embodiments the set may include a bar code or data matrix that can be read by a camera on the pumping device or cycler, the encoded information allowing the controller to determine the type of set installed. A controller receiving input from a camera may also be capable of detecting different features or geometries of a portion of a set. For example, the fluid line connector 36 may have unique, detectable geometries detectable by a fluid line detector 1000 as described above. Alternatively, a user may manually enter information on a user interface of the pumping device about the type of tubing or pump cassette in use.

Line Priming

To reduce the time needed to prime a line, it may be preferable to have the pumping device actively prime the line rather than allowing gravity-based flow to accomplish the task. In Gravity-based priming, which is a standard procedure, fluid flow through the line depends on the head height of the reservoir in which the priming fluid is stored. The flow rate of the fluid through the line during prime will increase with an increase in head height of the prime fluid reservoir. Actively priming the line through the use of one or more pumps may allow a pumping device or cycler to simulate various head heights for a reservoir while the reservoir remains in a fixed position. If the fluid pump includes pumping chamber(s) which are actuated pneumatically, the amount of pneumatic pressure applied to the pumping chamber(s) via a diaphragm can control the flow rate to a desired value without relocating the priming reservoir. Avoiding having to relocate a fluid reservoir helps to keep the pumping or dialysis system compact, reduces the setup burden on a user, and allows for relative fast priming of fluid lines.

In some embodiments in which flow paths and chambers of a pump cassette are to be primed with fluid, priming may be performed in two or more phases. In the first phase, the line may be primed with a lower effective head height (e.g., lower pump pressure or by passive gravity flow) than in a second or subsequent phase. Turbulence of a higher flow rate may lead to introduction or trapping of air bubbles or pockets in various locations or recesses of a pump cassette. This problem can be mitigated by allowing the pump cassette to be primed slowly, and subsequently proceeding to a more rapid priming process once the fluid reaches a fluid line downstream of the cassette. The length of the first phase may be predetermined empirically through testing, or by measurement of the amount of fluid volume moved from the priming reservoir to the cassette or attached fluid line.

Reducing air bubble formation or trapping is desirable for a number of reasons, including that a line priming sensor may detect the air bubbles and lead the controller to stop the process and issue a user alert.

The duration of the first priming phase may depend on the type of cassette being used (number of pumps and valves, and complexity of flow paths), and the volume of its interior fluid paths and pump chambers. Preferably, the priming is performed to allow fluid to displace air from the cassette from bottom to top, and at a sufficiently slow rate to ensure that most or all of the enclosed air is forced into the attached fluid line and then expelled into the environment.

Figure 29:
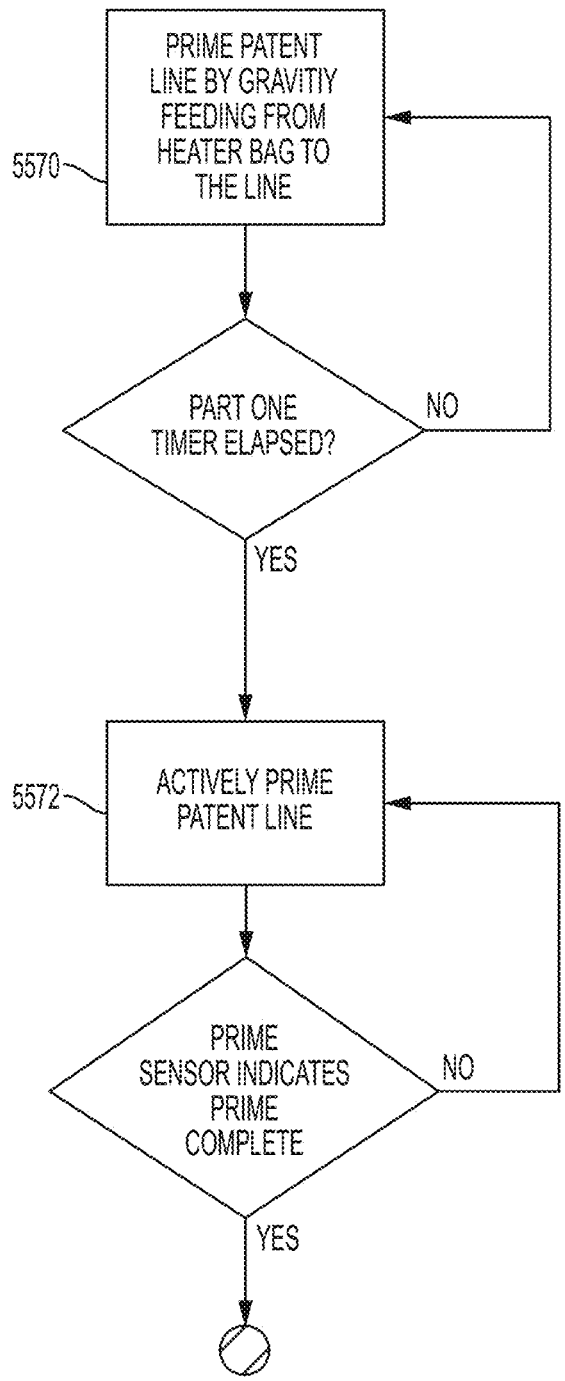
FIG. 29 shows a flowchart outlining a number of steps which may be used by a cycler to prime a line with a two part prime.

FIG. 29 depicts a flowchart detailing a number of steps a controller may use to control the priming of a cassette and attached line using two phases. In the example, the line primed is a patient line extending from a pump cassette to a patient. The steps shown may readily be generalized for priming of other fluid lines. As shown, in step 5570, the cycler begins priming the patient line by gravity feeding fluid into the line through the cassette. In the example embodiment, the priming reservoir is a heater bag. Free flow may be accomplished by controlling valves of the cassette so that an open flow path between the patient line and the heater bag is created.

When the priming operation begins in step 5570, the controller may initiate a timer for the first priming phase. The duration of the first priming phase can be determined empirically through testing so that it is sufficient to ensure that any air in the cassette has been flushed out of the cassette and into the patient line. Using the example of the cassette depicted in FIG. 3, this duration may range from 1-3 seconds. In one embodiment, the timer may be set to about 1.6 seconds. In control system embodiments that do not use a timer, but rather transition out of the first priming phase when a pre-determined volume of fluid has been transferred out of the priming reservoir, the pre-determined volume may amount to approximately 1-3 ml, given the example cassette shown in FIG. 3.

When the timer has elapsed (or the pre-determined volume has been transferred), the pumping apparatus or cycler may proceed to step 5572 and begin actively priming the line. Preferably step 5572 primes the line at a faster flow rate than step 5570. The cycler may continue to actively prime the patient line until a prime sensor indicates that the line has reached a fully primed state. In some embodiments, the controller may then signal a user on a user interface that the priming has completed and the primed line is ready to be connected.

Solution Line Organizer

Figure 30:
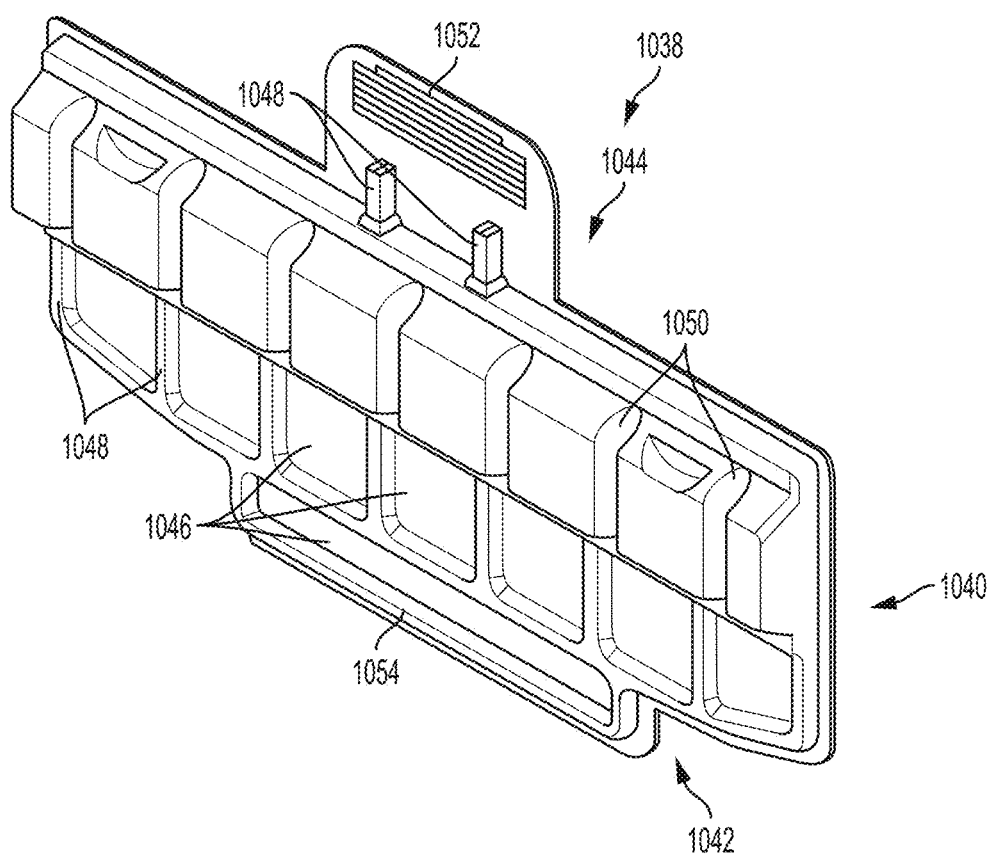
FIG. 30 is a perspective view of the front of an unloaded organizer (absent any solution lines)
Figure 31:
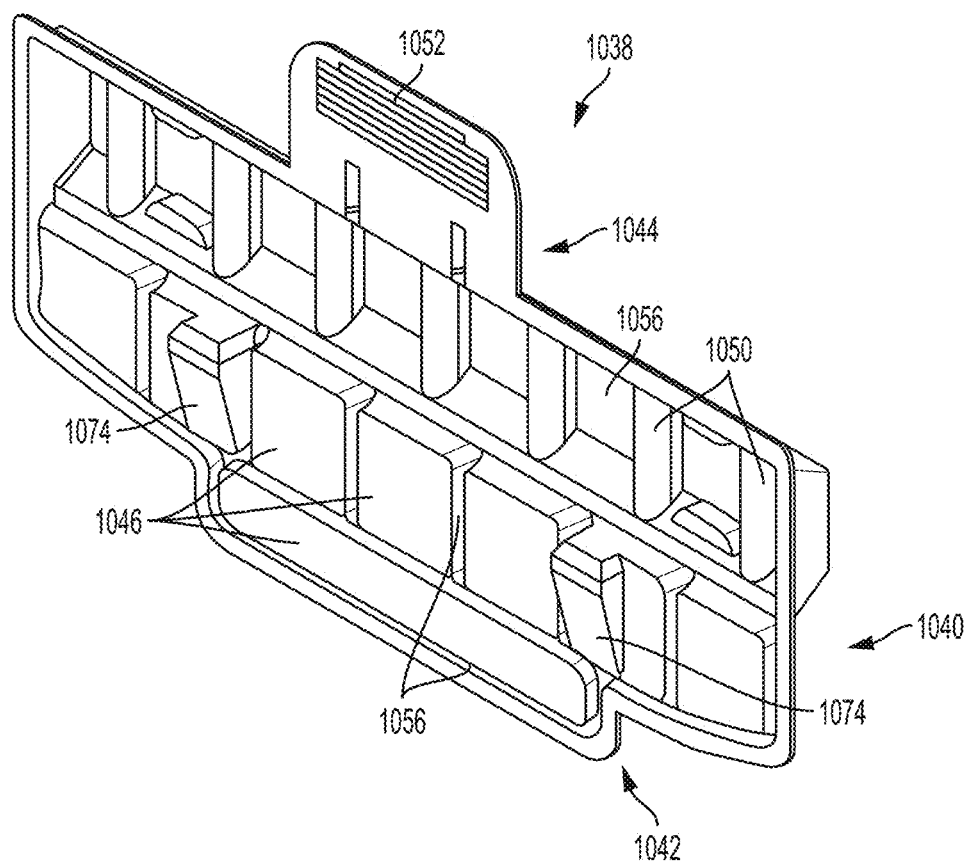
FIG. 31 is a back view of the organizer of FIG. 30.
Figure 32:
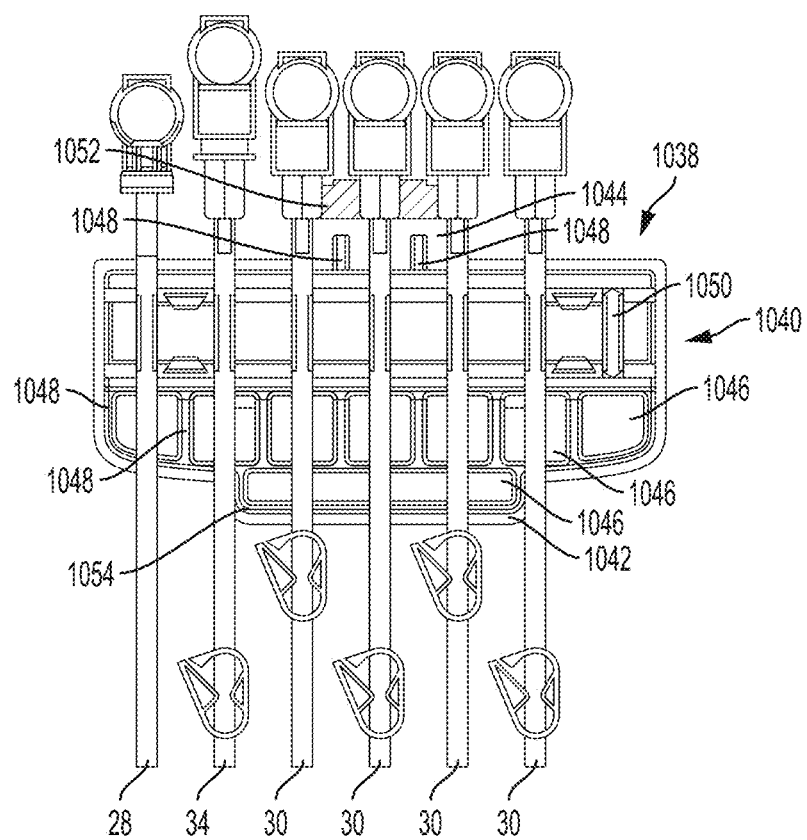
FIG. 32 is a perspective view of an organizer including a plurality of solution lines, a fluid line, and a drain line.

FIG. 30, FIG. 31, and FIG. 32, show a perspective view of the front of an unloaded organizer 1038, a perspective view of the back of an unloaded organizer 1038, and a perspective view of a loaded organizer 1038 respectively. In this embodiment, the organizer 1038 may be substantially formed from a moderately flexible material (such as, e.g., PAXON AL55-003 HDPE resin). Forming the organizer 1038 from this or another relatively flexible polymer material increases the organizer's 1038 durability when attaching and removing solution lines or solution line connectors.

The organizer 1038 may conveniently be mounted or attached to an outer wall of the cycler housing 82. The organizer 1038 may include a tube holder section 1040, a base 1042, and a tab 1044. The tube holder section 1040, the base 1042, and the tab 1044 may all be flexibly connected, and may be substantially formed from the same HDPE-based material. The tube holder section 1040 may have a generally rectangular shape, and may include a generally flat top edge and a bottom edge that may be slightly curved in an outwardly direction. The tube holder section 1040 may include a series of recessed segments 1046 that extend horizontally along the bottom edge of the tube holder section 1040. Each of the recessed segments 1046 may be separated by a series of support columns 1048, which may also define the shape and size of the segments 1046. The tube holder section 1040 may also include a raised area that extends horizontally along the top edge of the tube holder section 1040. The raised area may include a plurality of slots 1050. The slots 1050 may be defined in a vertical orientation, and may extend from the top edge of the tube holder section 1040 to the top of the recessed segments 1046. The slots 1050 may have a generally cylindrical shape so as to conform to the shape of a drain line 28, solution line 30, or patient line 34. The depth of the slots 1050 may be such that the opening of the slot 1050 is narrower then the inner region of the slot 1050. Therefore, once a line is placed into the slot 1050 it becomes locked or snap-fit into place. The line may then require a pre-determined minimum amount of force to be removed from the slot 1050. This ensures that the lines are not unintentionally removed from the organizer 1050.

In one aspect, the tab 1044 may be flexibly connected to the top edge of the tube holder section 1040. The tab 1044 may have a generally rectangular shape. In another embodiment, the tab 1044 may also include two slightly larger radius corners. The tab 1044 may also include two vertically extending support columns 1048. The support columns 1048 may be connected to the top edge of the tube holder section 1040, and may extend in an upward direction into the tab 1044. In alternative embodiment, the length and number of the support columns 1048 may vary depending on the desired degree of flexibility of the tab 1044. In another aspect, the tab 1044 may include a ribbed area 1052. The purpose of the tab 1044 and the ribbed area 1052 is to allow the organizer 1038 to be easily grasped by a user so that the user can easily install, transport, or remove the solution lines 30 from the organizer 1038. Also, the tab 1044 provides an additional area of support when removing and loading the lines into the organizer 1038.

In another aspect, the base 1042 may be flexibly connected to the bottom edge of the tube holder section 1040. The base 1042 may have a generally rectangular shape. In another embodiment, the base 1042 may also include two slightly larger radius corners. The base 1042 may include an elongated recessed segment 1046, which may be defined by a support ring 1054 that surrounds the recessed segment 1046. The support columns 1050, the support ring 1054, and the raised area may all create a series of voids 1056 along the back of the organizer 1038 (shown, e.g., in FIG. 31).

Figure 33:
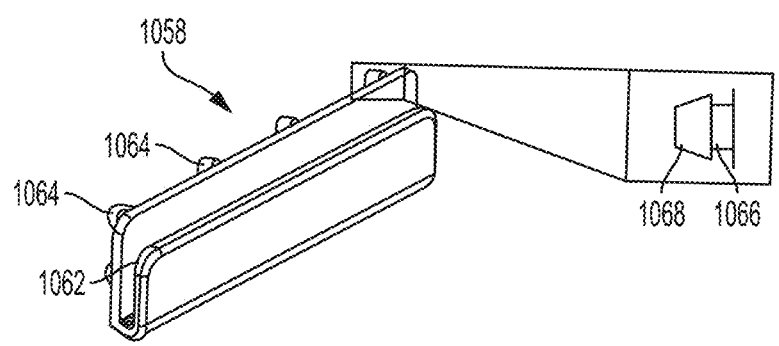
FIG. 33 is a perspective view of an organizer clip.
Figure 34:
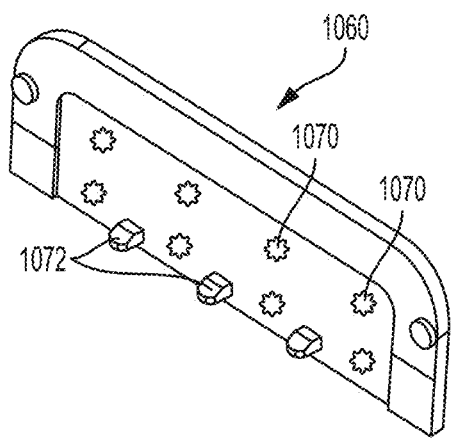
FIG. 34 is a perspective view of an organizer clip receiver.

FIG. 33 and FIG. 34 show a perspective view of an organizer clip 1058, and a perspective view of an organizer clip receiver 1060 respectively. In these illustrative embodiments, the clip 1058 may be made from a relatively high durometer polyurethane elastomer, such as, for example, 80 Shore A durometer urethane. In an alternative embodiment, the clip 1058 may be made from any type of flexible and durable material that would allow the organizer 1038 to flex and pivot along the base 1042 when positioned in the clip 1058. The clip 1058 may be "U-shaped", and may include a back portion that extends slightly higher than a front portion. Additionally, there may be a lip 1062 that extends along the top edge of the front portion of the clip 1058. The lip 1062 extends slightly into the cavity of the clip 1058. The back portion of the clip 1058 may also include a plurality of elastomeric pegs 1064 connected to (or formed from) and extending away from the back portion of the clip 1058. The pegs 1064 may include both a cylindrical section 1066 and a cone 1068. The cylindrical section 1066 may connect to the back portion of the clip 1058, and the cone 1068 may be attached to an open end of the cylindrical section 1066. The pegs 1064 allow the clip 1058 to be permanently connected to the organizer clip receiver 1060, by engaging the pegs 1064 within a plurality of holes 1070 in the organizer clip receiver 1060.

The organizer clip receiver 1060 may include a plurality of chamfered tabs 1072. The chamfered tabs 1072 may mate with corresponding slots on the back portion of the clip 1058 when the pegs 1064 are engaged with the organizer clip receiver 1060. Once the chamfered tabs 1072 engage the slots, they can extend through the back portion of the clip 1058, and act as locking mechanisms to hold the organizer 1038 in place when positioned into the clip 1058. When the organizer 1038 is positioned within the clip 1058, the chamfers 1072 fit into the void 1056 on the back of the base 1042, which was created by the raised support ring 1054. Referring again to FIG. 31, and in accordance with another aspect of the present disclosure, there may be a plurality of ramps 1074 extending outwardly from the back of the organizer 1038. The ramps 1074 may be generally shaped as inclined planes. This allows the organizer 1038 to angle away from the cycler 14 when placed into the clip 1058, which provides numerous advantages over previous designs. For example, in this illustrative embodiment, the angle of the organizer 1038 ensures that neither the tab 1044, nor any of the lines (or line caps) connected to the organizer 1038 are allowed to interfere with the heater lid 143 when the lid 143 is being opened and closed. Additionally, the angle of the organizer 1038 in relation to the cycler 14, coupled with the flexibility of the organizer 1038, both encourage the user to remove the solution lines 30 from the bottom instead of from the connector end 30a of the solution lines. Preferably, the user should not remove the solution lines 30 by grasping the connector ends 30a, because in doing so the user could inadvertently remove one or more caps 31, which could cause contamination and spills. Another advantage of the organizer 1038 is that it aids the user in connecting color coded solution lines 30 to the correct containers 20 by helping to separate the color coded lines 30.

Door Latch Sensor

Figure 35:
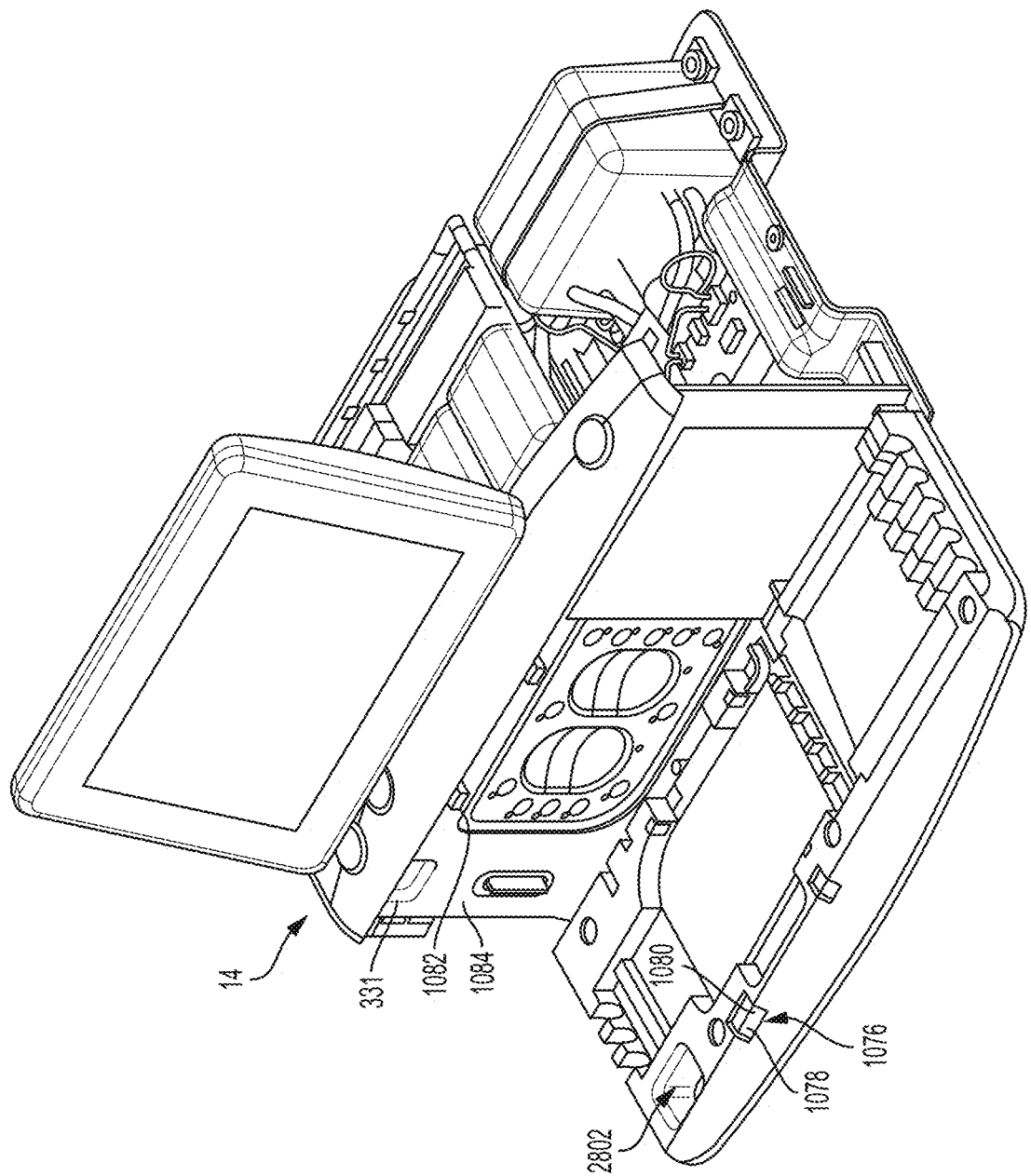
FIG. 35 is a perspective view of a door latch sensor assembly associated with a cycler.
Figure 36:
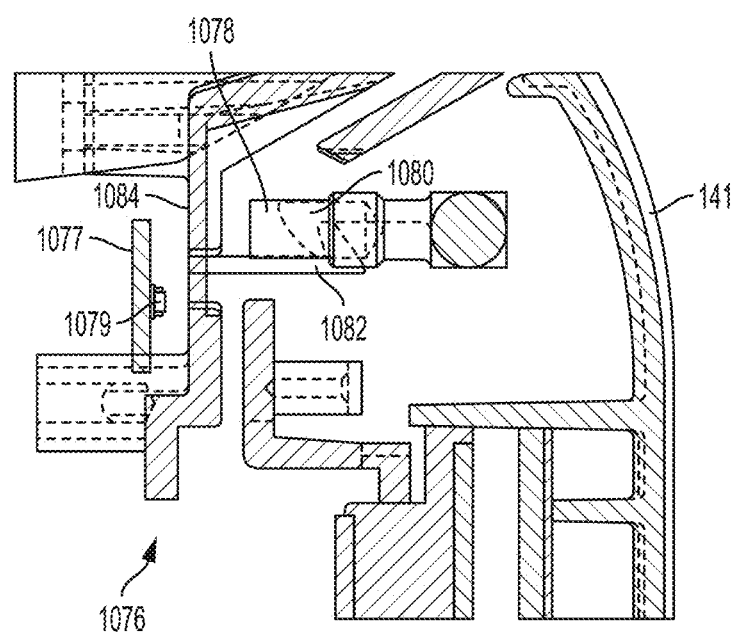
FIG. 36 is a cross-sectional view of the door latch sensor assembly of FIG. 35.

FIG. 35, shows a perspective view of a door latch sensor assembly 1076. In this illustrative embodiment, the door latch sensor assembly 1076 may include a magnet 1078 that is attached or connected to door latch 1080, and can pivot with door latch 1080 as it pivots into and our of a latching position with its mating base unit catch 1082. A sensor (not shown in FIG. 35) may be positioned behind the front panel 1084 of cycler 14, near base unit catch 1082, to detect the presence of magnet 1078 as door latch 1080 engages with base unit catch 1082. In one embodiment, the sensor may be an analog Hall effect sensor. The purpose of the door latch sensor assembly 1076 is to confirm both that the door 141 is closed and that the door latch 1080 is sufficiently engaged with catch 1082 to ensure a structurally sound connection. FIG. 36 shows a cross-sectional view of the door latch sensor assembly 1076. Sensor 1079 is positioned on a circuit board 1077 behind front panel 1084. Sensor 1079 is preferably oriented off-axis from the line of motion of magnet 1078, because in this orientation, sensor 1079 is better able to resolve a variety of positions of magnet 1078 as it approaches front panel 1084 as door 141 is closed.

In one example, the door 141 may be considered to be sufficiently engaged when the door latch 1080 has at least a 50% engagement with the catch 1082. In one embodiment, the door latch 1080 may engage to a degree of approximately 0.120 inch nominally. Additionally, the sensor 1079 may only sense a closed door 141 when the door latch 1080 is sufficiently engaged with the catch 1082. Therefore, the sensor 1082 may only sense a closed door 141 when the door latch 1080 is engaged to a degree of approximately 0.060 inch. These engagement thresholds for the door latch 1080 may be set approximately at the middle range for acceptable engagement between the door latch 1080 and the catch 1082. This can help to ensure a robust design by accounting for sensor drift due to time, temperature, and other variations. Testing was conducted to determine the robustness of the sensor 1082 by collecting numerous measurements both at room temperature (approximately 24° C.) and at an abnormally cold temperature (approximately −2° C. to 9° C.). The room temperature readings were repeatedly higher than the cold readings, but only by a small percentage of the 0 inch to 0.060 inch range.

In one aspect, the output of the sensor 1079 may be ratiometric to the voltage supplied. Therefore, both the supply voltage and the output of the sensor 1079 may be measured (see formulas below, where the supply voltage and the output of the sensor 1079 are represented by Door_Latch and Monitor_5V0 respectively). Both the output of the sensor 1079 as well as the voltage supplied may then pass through ¼ resistor dividers. Dividing the output of the sensor 1079 and the voltage supplied may allow for a stable output to be produced. This procedure may ensure that the output remains stable even if the supply voltage fluctuates.

In another aspect, the sensor 1079 may respond to both positive and negative magnetic fields. Consequently, if there is no magnetic field, the sensor 1079 may output half the supply voltage. Additionally, a positive magnetic field may cause the output of the sensor 1079 to increase, while a negative magnetic field may result in a decrease of the output of the sensor 1079. In order to obtain an accurate measurement of the output from the sensor 1079, the magnet polarity can be ignored, and the supply voltage can simultaneously be compensated for. The following formula may be used to calculate the latch sensor ratio:

$$\text{Latch Sensor Ratio} = \text{absolute value} ((V\text{Door\_Latch}/V\text{Monitor\_5V0}) - \text{noFieldRatio}) \quad (1)$$

Where the noFieldRatio is calculated by (VDoor_Latch/VMonitor_5V0) with the door 141 fully open.

Using this formula:
Ratio=0.0 indicates no magnetic field
Ratio>0.0 indicates some magnetic field; direction indeterminate.

Shims of various thicknesses may be used between the inside of door 141 and front panel 1084 to vary the degree of engagement between latch 1080 and catch 1082, in order to calibrate the strength of the magnetic field detected by sensor 1079 with various positions of engagement of the door latch assembly 1076. In one embodiment, this data can be used to develop field strength ratios with and without a shim, or in other embodiments with several shims of varying thicknesses. In one example, the door latch sensor assembly 1076 may complete the procedure for determining if the door latch 1080 is sufficiently engaged with the catch 1082 by performing the following:

Calculate the nearRatio and the farRatio:

$$\text{nearRatio} = \text{noShimRatio} - (0.025/0.060) \times (\text{noShimRatio} - \text{withShimRatio}) \quad (2)$$

$$\text{farRatio} = \text{noShimRatio} - (0.035/0.060) \times (\text{noShimRatio} - \text{withShimRatio}) \quad (3)$$

In an embodiment, the door latch sensor assembly 1076 may save the noFieldRatio, nearRatio, and farRatio to a calibration file. The door latch sensor assembly 1076 may then load the noFieldRatio, nearRatio, and farRatio from the calibration file, and the sensor assembly 1076 may then use the nearRatio and farRatio as the hysteresis limits for the sensor 1079. The door latch sensor assembly 1076 may then begin with the initial condition that the door 141 is open, and then repeatedly calculate the Latch Sensor Ratio. If the Latch Sensor Ratio is greater than the nearRatio, the door latch sensor assembly 1076 will change the latch state to closed, and if the Latch Sensor Ratio is less than the farRatio, the door latch sensor assembly 1076 will change the latch state to open. In an alternative embodiment for the door latch sensor assembly 1076, a middleRatio can be calculated from the calibration data by averaging the noShimRatio and the withShimRatio. In this case, measurements greater than the middleRatio indicate that the door latch 1080 is engaged, and measurements less than the middleRatio indicate that the door latch 1080 is not engaged.

Set Loading and Operation

Figure 37:
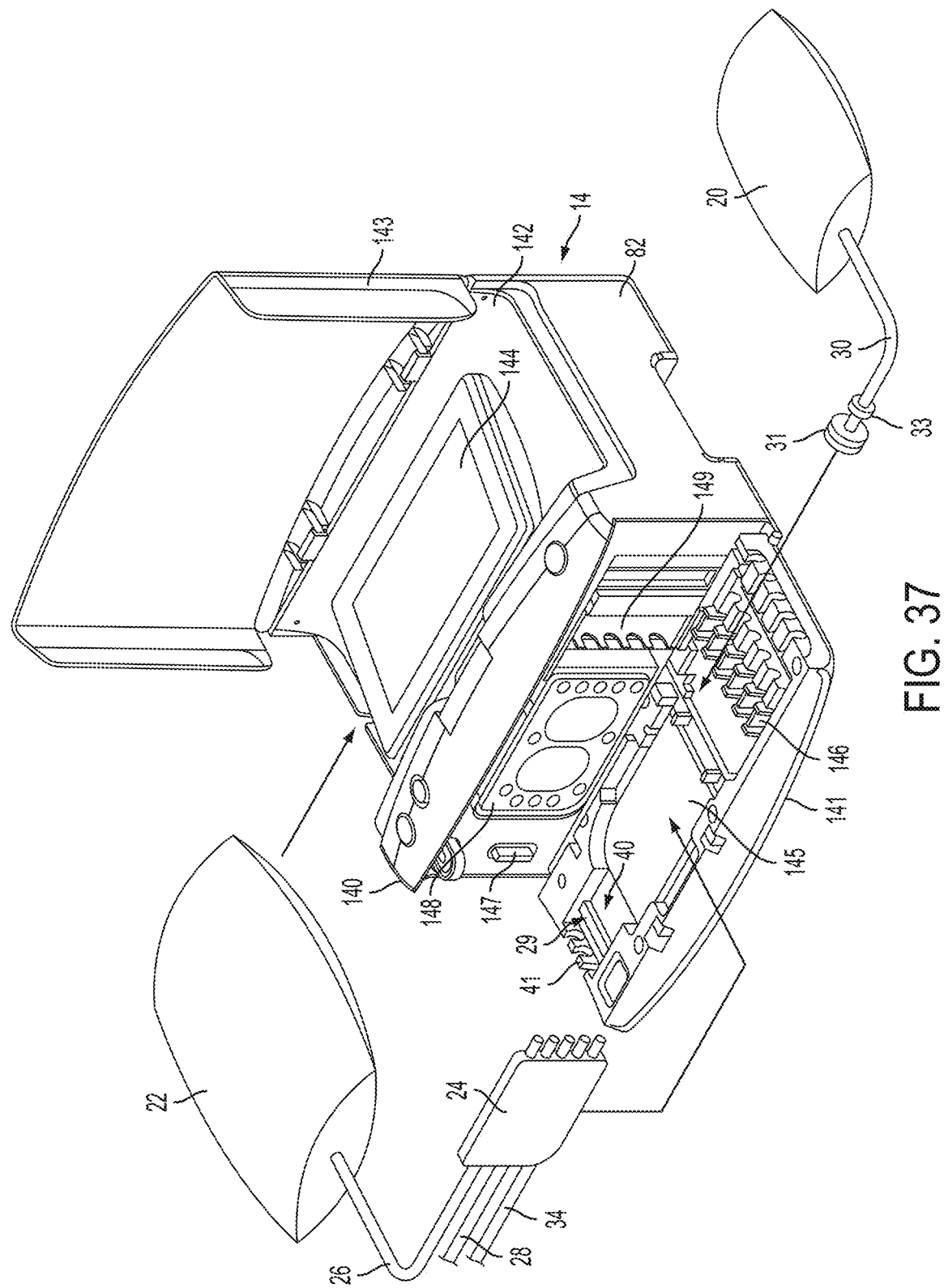
FIG. 37 is a perspective view of the APD system of FIG. 1 with the door of the cycler in an open position.

FIG. 37 shows a perspective view of the APD system 10 of FIG. 1 with the door 141 of the cycler 14 lowered into an open position, exposing a mounting location 145 for the cassette 24 and a carriage 146 for the solution lines 30. (In this embodiment, the door 141 is mounted by a hinge at a lower part of the door 141 to the cycler housing 82.) When loading the set 12, the cassette 24 is placed in the mounting location 145 with the membrane 15 and the pump chamber side of the cassette 24 facing upwardly, allowing the portions of the membrane 15 associated with the pump chambers and the valve ports to interact with a control surface 148 of the cycler 14 when the door 141 is closed. The mounting location 145 may be shaped so as to match the shape of the base member 18, thereby ensuring proper orientation of the cassette 24 in the mounting location 145. In this illustrative embodiment, the cassette 24 and mounting location 145 have a generally rectangular shape with a single larger radius corner which requires the user to place the cassette 24 in a proper orientation into the mounting location 145 or the door 141 will not close. It should be understood, however, that other shapes or orientation features for the cassette 24 and/or the mounting location 145 are possible.

In accordance with an aspect of the invention, when the cassette 24 is placed in the mounting location 145, the patient, drain and heater bag lines 34, 28 and 26 are routed through a channel 40 in the door 141 to the left as shown in FIG. 37. The channel 40, which may include guides 41 or other features, may hold the patient, drain and heater bag lines 34, 28 and 26 so that an occluder 147 may selectively close/open the lines for flow. Upon closing of door 141, occluder 147 can compress one or more of patient, drain and heater bag lines 34, 28 and 26 against occluder stop 29. Generally, the occluder 147 may allow flow through the lines 34, 28 and 26 when the cycler 14 is operating (and operating properly), yet occlude the lines when the cycler 14 is powered down (and/or not operating properly). Occlusion of the lines may be performed by pressing on the lines, or otherwise pinching the lines to close off the flow path in the lines. Preferably, the occluder 147 may selectively occlude at least the patient and drain lines 34 and 28.

When the cassette 24 is mounted and the door 141 is closed, the pump chamber side of the cassette 24 and the membrane 15 may be pressed into contact with the control surface 148, e.g., by an air bladder, spring or other suitable arrangement in the door 141 behind the mounting location 145 that squeezes the cassette 24 between the mounting location 145 and the control surface 148. This containment of the cassette 24 may press the membranes 15 and 16 into contact with walls and other features of the base member 18, thereby isolating channels and other flow paths of the cassette 24 as desired. The control surface 148 may include a flexible gasket or membrane, e.g., a sheet of silicone rubber or other material that is associated with the membrane 15 and can selectively move portions of the membrane 15 to cause pumping action in the pump chambers 181 and opening/closing of valve ports of the cassette 24. The control surface 148 may be associated with the various portions of the membrane 15, e.g., placed into intimate contact with each other, so that portions of the membrane 15 move in response to movement of corresponding portions of the control surface 148. For example, the membrane 15 and control surface 148 may be positioned close together, and a suitable vacuum (or pressure that is lower relative to ambient) may be introduced through vacuum ports suitably located in the control surface 148, and maintained, between the membrane 15 and the control surface 148 so that the membrane 15 and the control surface 148 are essentially stuck together, at least in regions of the membrane 15 that require movement to open/close valve ports and/or to cause pumping action. In another embodiment, the membrane 15 and control surface 148 may be adhered together, or otherwise suitably associated.

In some embodiments, the surface of the control surface 148 or gasket facing the corresponding cassette membrane overlying the pump chambers and/or valves is textured or roughened. The texturing creates a plurality of small passages horizontally or tangentially along the surface of the gasket when the gasket is pulled against the surface of the corresponding cassette membrane. This may improve evacuation of air between the gasket surface and the cassette membrane surface in the textured locations. It may also improve the accuracy of pump chamber volume determinations using pressure-volume relationships (such as, for example, in the FMS procedures described elsewhere), by minimizing trapped pockets of air between the gasket and the membrane. It may also improve the detection of any liquid that may leak into the potential space between the gasket and the cassette membrane. In an embodiment, the texturing may be accomplished by masking the portions of the gasket mold that do not form the portions of the gasket corresponding to the pump membrane and valve membrane locations. A chemical engraving process such as the Mold-Tech® texturing and chemical engraving process may then be applied to the unmasked portions of the gasket mold. Texturing may also be accomplished by any of a number of other processes, such as, for example, sand blasting, laser etching, or utilizing a mold manufacturing process using electrical discharge machining.

Before closing the door 141 with the cassette 24 loaded, one or more solution lines 30 may be loaded into the carriage 146. The end of each solution line 30 may include a cap 31 and a region 33 for labeling or attaching an indicator or identifier. The indicator, for example, can be an identification tag that snaps onto the tubing at indicator region 33. In accordance with an aspect of the invention and as will be discussed in more detail below, the carriage 146 and other components of the cycler 14 may be operated to remove the cap(s) 31 from lines 30, recognize the indicator for each line 30 (which may provide an indication as to the type of solution associated with the line, an amount of solution, etc.) and fluidly engage the lines 30 with a respective spike 160 of the cassette 24. This process may be done in an automated way, e.g., after the door 141 is closed and the caps 31 and spikes 160 are enclosed in a space protected from human touch, potentially reducing the risk of contamination of the lines 30 and/or the spikes 160 when connecting the two together. For example, upon closing of the door 141, the indicator regions 33 may be assessed (e.g., visually by a suitable imaging device and software-based image recognition, by RFID techniques, etc.) to identify what solutions are associated with which lines 30. The aspect of the invention regarding the ability to detect features of a line 30 by way of an indicator at indicator region 33 may provide benefits such as allowing a user to position lines 30 in any location of the carriage 146 without having an affect on system operation. That is, since the cycler 14 can automatically detect solution line features, there is no need to ensure that specific lines are positioned in particular locations on the carriage 146 for the system to function properly. Instead, the cycler 14 may identify which lines 30 are where, and control the cassette 24 and other system features appropriately. For example, one line 30 and connected container may be intended to receive used dialysate, e.g., for later testing.

Since the cycler 14 can identify the presence of the sample supply line 30, the cycler 14 can route used dialysate to the appropriate spike 160 and line 30. As discussed above, since the spikes 160 of the cassette 24 all feed into a common channel, the input from any particular spike 160 can be routed in the cassette 24 in any desired way by controlling valves and other cassette features.

With lines 30 mounted, the carriage 146 may be moved to the left as shown in FIG. 37 (again, while the door 141 is closed), positioning the caps 31 over a respective spike cap 63 on a spike 160 of the cassette 24 and adjacent a cap stripper 149. The cap stripper 149 may extend outwardly (toward the door 141 from within a recess in the cycler 14 housing) to engage the caps 31. For example, the cap stripper 149 may include five fork-shaped elements that engage with a corresponding groove in the caps 31, allowing the cap stripper 149 to resist left/right movement of the cap 31 relative to the cap stripper 149. By engaging the caps 31 with the cap stripper 149, the caps 31 may also grip the corresponding spike cap 63. Thereafter, with the caps 31 engaged with corresponding spike caps 63, the carriage 146 and cap stripper 149 may move to the right, removing the spike caps 63 from the spikes 160 that are engaged with a corresponding cap 31. One possible advantage of this arrangement is that spike caps 63 are not removed in locations where no solution line 30 is loaded because engagement of the cap 31 from a solution line 30 is required to remove a spike cap 63. Thus, if a solution line 30 will not be connected to a spike 160, the cap on the spike 160 is left in place. The cap stripper 149 may then stop rightward movement (e.g., by contacting a stop), while the carriage 146 continues movement to the right. As a result, the carriage 146 may pull the terminal ends of the lines 30 from the caps 31, which remain attached to the cap stripper 149. With the caps 31 removed from the lines 30 (and the spike caps 63 still attached to the caps 31), the cap stripper 149 may again retract with the caps 31 into the recess in the cycler 14 housing, clearing a path for movement of the carriage 146 and the uncapped ends of the lines 30 toward the spikes 160. The carriage 146 then moves left again, attaching the terminal ends of the lines 30 with a respective spike 160 of the cassette 24. This connection may be made by the spikes 160 piercing an otherwise closed end of the lines 30 (e.g., the spikes 160 may pierce a closed septum or wall in the terminal end), permitting fluid flow from the respective containers 20 to the cassette 24. In an embodiment, the wall or septum may be constructed of a flexible and/or self-sealing material such as, for example, PVC, polypropylene, or silicone rubber.

In accordance with an aspect of the invention, the heater bag 22 may be placed in the heater bag receiving section (e.g., a tray) 142, which is exposed by lifting a lid 143. In this embodiment, the cycler 14 includes a user or operator interface 144 that is pivotally mounted to the housing 82, as discussed below. To allow the heater bag 22 to be placed into the tray 142, the interface 144 may be pivoted upwardly out of the tray 142. As is known in the art, the heater tray 142 may heat the dialysate in the heater bag 22 to a suitable temperature, e.g., a temperature appropriate for introduction into the patient. In accordance with an aspect of the invention, the lid 143 may be closed after placement of the heater bag 22 in the tray 142, e.g., to help trap heat to speed the heating process, and/or help prevent touching or other contact with a relatively warm portion of the heater tray 142, such as its heating surfaces. In one embodiment, the lid 143 may be locked in a closed position to prevent touching of heated portions of the tray 142, e.g., in the circumstance that portions of the tray 142 are heated to temperatures that may cause burning of the skin. Opening of the lid 143 may be prevented, e.g., by a lock, until temperatures under the lid 143 are suitably low.

In accordance with another aspect of the invention, the cycler 14 includes a user or operator interface 144 that is pivotally mounted to the cycler 14 housing and may be folded down into the heater tray 142. With the interface 144 folded down, the lid 143 may be closed to conceal the interface 144 and/or prevent contact with the interface 144. The interface 144 may be arranged to display information, e.g., in graphical form, to a user, and receive input from the user, e.g., by using a touch screen and graphical user interface. The interface 144 may include other input devices, such as buttons, dials, knobs, pointing devices, etc. With the set 12 connected, and containers 20 appropriately placed, the user may interact with the interface 144 and cause the cycler 14 to start a treatment and/or perform other functions.

However, prior to initiating a dialysis treatment cycle, the cycler 14 must at least prime the cassette 24, the patient line 34, heater bag 22, etc., unless the set 12 is provided in a pre-primed condition (e.g., at the manufacturing facility or otherwise before being put into use with the cycler 14). Priming may be performed in a variety of ways, such as controlling the cassette 24 (namely the pumps and valves) to draw liquid from one or more solution containers 20 via a line 30 and pump the liquid through the various pathways of the cassette 24 so as to remove air from the cassette 24. Dialysate may be pumped into the heater bag 22, e.g., for heating prior to delivery to the patient. Once the cassette 24 and heater bag line 26 are primed, the cycler 14 may next prime the patient line 34. In one embodiment, the patient line 34 may be primed by connecting the line 34 (e.g., by the connector 36) to a suitable port or other connection point on the cycler 14 and causing the cassette 24 to pump liquid into the patient line 34. The port or connection point on the cycler 14 may be arranged to detect the arrival of liquid at the end of the patient line (e.g., optically, by conductive sensor, or other), thus detecting that the patient line is primed. As discussed above, different types of sets 12 may have differently sized patient lines 34, e.g., adult or pediatric size. In accordance with an aspect of the invention, the cycler 14 may detect the type of cassette 24 (or at least the type of patient line 34) and control the cycler 14 and cassette 24 accordingly. For example, the cycler 14 may determine a volume of liquid delivered by a pump in the cassette needed to prime the patient line 34, and based on the volume, determine the size of the patient line 34. Other techniques may be used, such as recognizing a barcode or other indicator on the cassette 24, patient line 34 or other component that indicates the patient line type.

Figure 38:
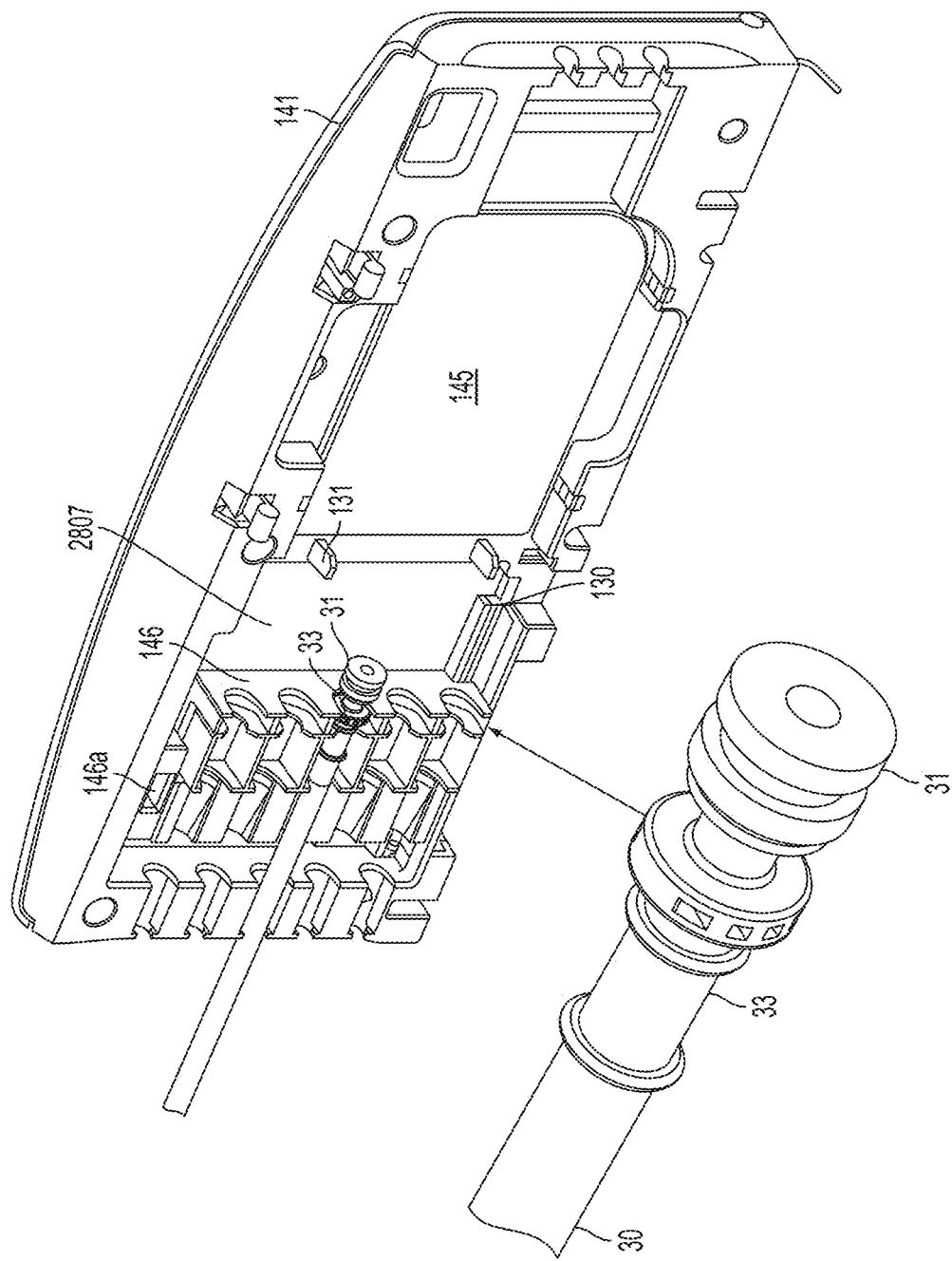
FIG. 38 is a perspective view of the inner side of the door of the cycler show in FIG. 37.

FIG. 38 shows a perspective view of the inner side of the door 141 disconnected from the housing 82 of the cycler 14. This view more clearly shows how the lines 30 are received in corresponding grooves in the door 141 and the carriage 146 such that the indicator region 33 is captured in a specific slot of the carriage 146. With the indicator at indicator region 33 positioned appropriately when the tubing is mounted to the carriage 146, a reader or other device can identify indicia of the indicator, e.g., representing a type of solution in the container 20 connected to the line 30, an amount of solution, a date of manufacture, an identity of the manufacturer, and so on. The carriage 146 is mounted on a pair of guides 130 at top and bottom ends of the carriage 146 (only the lower guide 130 is shown in FIG. 38). Thus, the carriage 146 can move left to right on the door 141 along the guides 130. When moving toward the cassette mounting location 145 (to the right in FIG. 38), the carriage 146 can move until it contacts stops 131.

Figure 39:
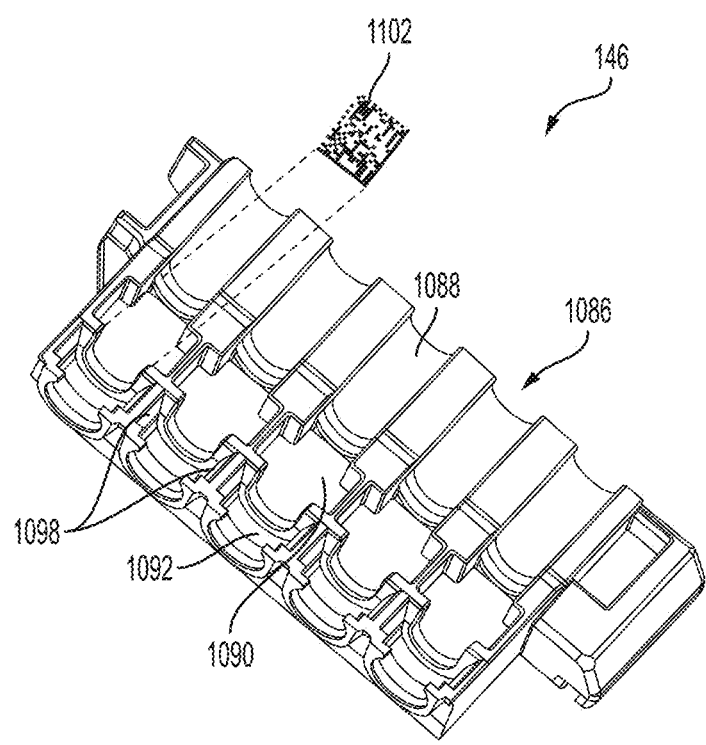
FIG. 39 is a perspective view of a carriage in a first embodiment.
Figure 40:
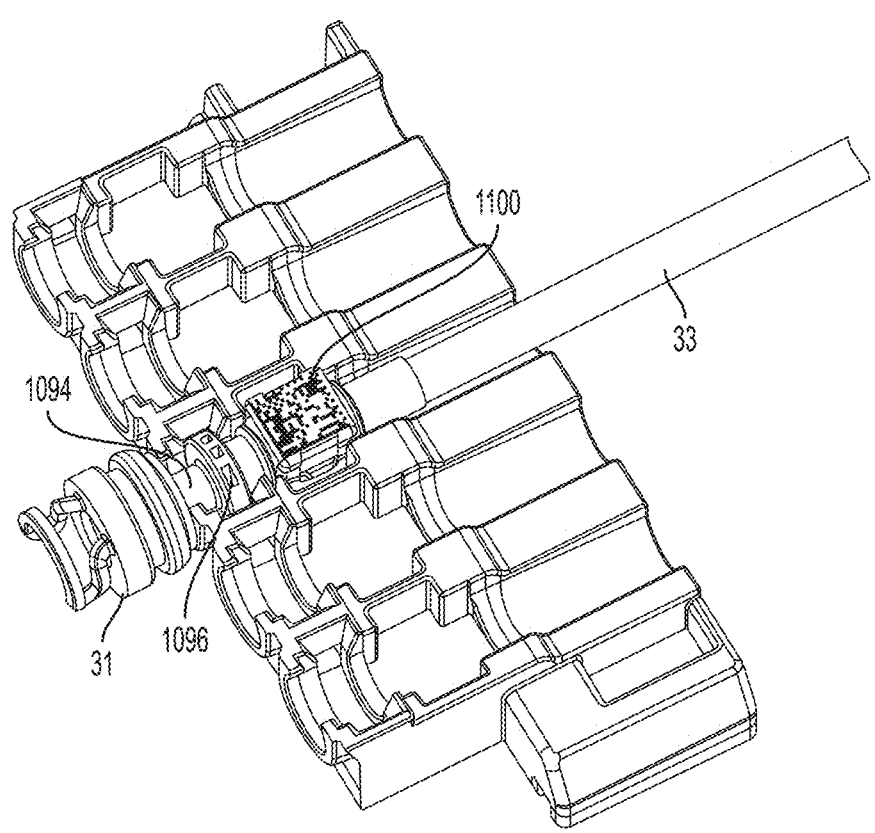
FIG. 40 is an enlarged perspective view of a solution line loaded into the carriage of FIG. 39.

FIG. 39 and FIG. 40 show a perspective view of a carriage 146, and an enlarged perspective view of a solution line 30 loaded into the carriage 146. In these illustrative embodiments, the carriage 146 may have the ability to move on the door 141 along the guide 130. The carriage 146 may include five slots 1086, and therefore may have the ability to support up to five solution lines 30. Each slot 1086 may include three different sections; a solution line section 1088, an ID section 1090, and a clip 1092. The solution line section 1088 may have a generally cylindrical shaped cavity that allows the solution lines 30 to remain organized and untangled when loaded into the carriage 146. The clip 1092 may be located at the opposite end of each of the slots 1086, relative to the solution line section 1088. The purpose of the clip 1092 is to provide a secure housing for a membrane port 1094 located at the connector end 30a of the solution line 30, and to prevent the solution line 30 from moving during treatment.

In one embodiment of the present disclosure, the clip 1092 may have a semicircular shape, and may include a middle region that extends slightly deeper than the two surrounding edge regions. The purpose of including the deeper middle region is to accommodate a membrane port flange 1096. The flange 1096 may have a substantially greater radius than the rest of the membrane port. Therefore, the deeper middle region is designed to fit the wider flange 1096, while the two edge regions provide support so that the membrane port 1094 is immobilized. Additionally, the deep middle region may have two cutouts 1098 positioned on opposite sides of the semicircle. The cutouts 1098 may have a generally rectangular shape so as to allow a small portion of the flange 1096 to extend into each of the cutouts 1098 when positioned in the clip 1092. The cutouts 1098 may be formed so that the distance between the top edges of each cutout 1098 is slightly less than the radius of the flange 1096. Therefore, a sufficient amount of force is required to snap the flange 1096 into the clip 1092. Also, allowing for the distance between the top edges of the two cutouts 1098 to be less than the radius of the flange 1096 helps to keep the solution line 30 from inadvertently becoming dislodged during treatment.

In this illustrative embodiment, the carriage 146 may provide superior performance over previous designs because of its ability to counteract any deformation of the membrane ports 1094. The carriage 146 is designed to stretch the membrane ports 1094 between the front of the flange 1096 and the back of the sleeve. If the membrane port 1094 is further stretched at any point during treatment, a wall in the carriage 146 may support the flange 1096.

In accordance with another aspect of the present disclosure, the ID section 1090 may be positioned between the solution line section 1088 and the clip 1092. The ID section 1090 may have a generally rectangular shape, thus having the ability to house an identification tag 1100 that may snap onto the solution line 30 at the indicator region 33. The indicator region 33 may have an annular shape that is sized and configured to fit within the ID section 1090 when mounted in the carriage 146. The identification tag 1100 may provide an indication as to the type of solution associated with each line 30, the amount of solution, a date of manufacture, and an identity of the manufacturer. As shown in FIG. 39, the ID section 1090 may include a two dimensional (2-D) barcode 1102, which may be imprinted on the bottom of the ID section 1090. The barcode 1102 may be a Data Matrix symbol with 10 blocks per side, and may include an "empty" Data Matrix code. The barcode 1102 may be positioned on the carriage 146 underneath the identification tag 1100, when the solution lines 30 are loaded into the carriage 146. However, in an alternative embodiment, the barcode 1102 may be added to the ID section 1090 of the carriage 146 by way of a sticker or laser engraving. Also, in another embodiment, the barcode 1102 may include a Data Matrix that consists of varying dimensions of length and width, as well as varying numbers of blocks per side.

In this illustrative embodiment, however, the specific number of blocks per side, and the specific length and width of each barcode 1102 was specifically chosen in order to provide the most robust design under a variety of conditions. Using only 10 blocks per side may result in the barcode 1102 having larger blocks, which therefore ensures that the barcode 1102 is easily readable, even under the dark conditions that exist inside of the cycler housing 82.

Figure 41:
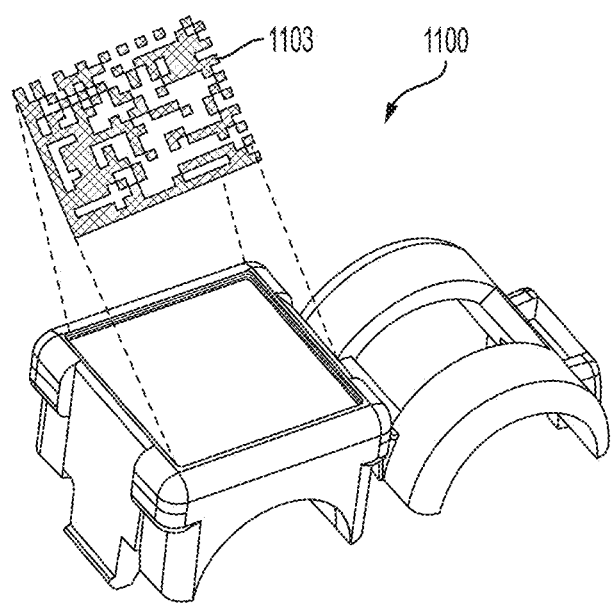
FIG. 41 is a perspective view of an open identification tag.
Figure 42:
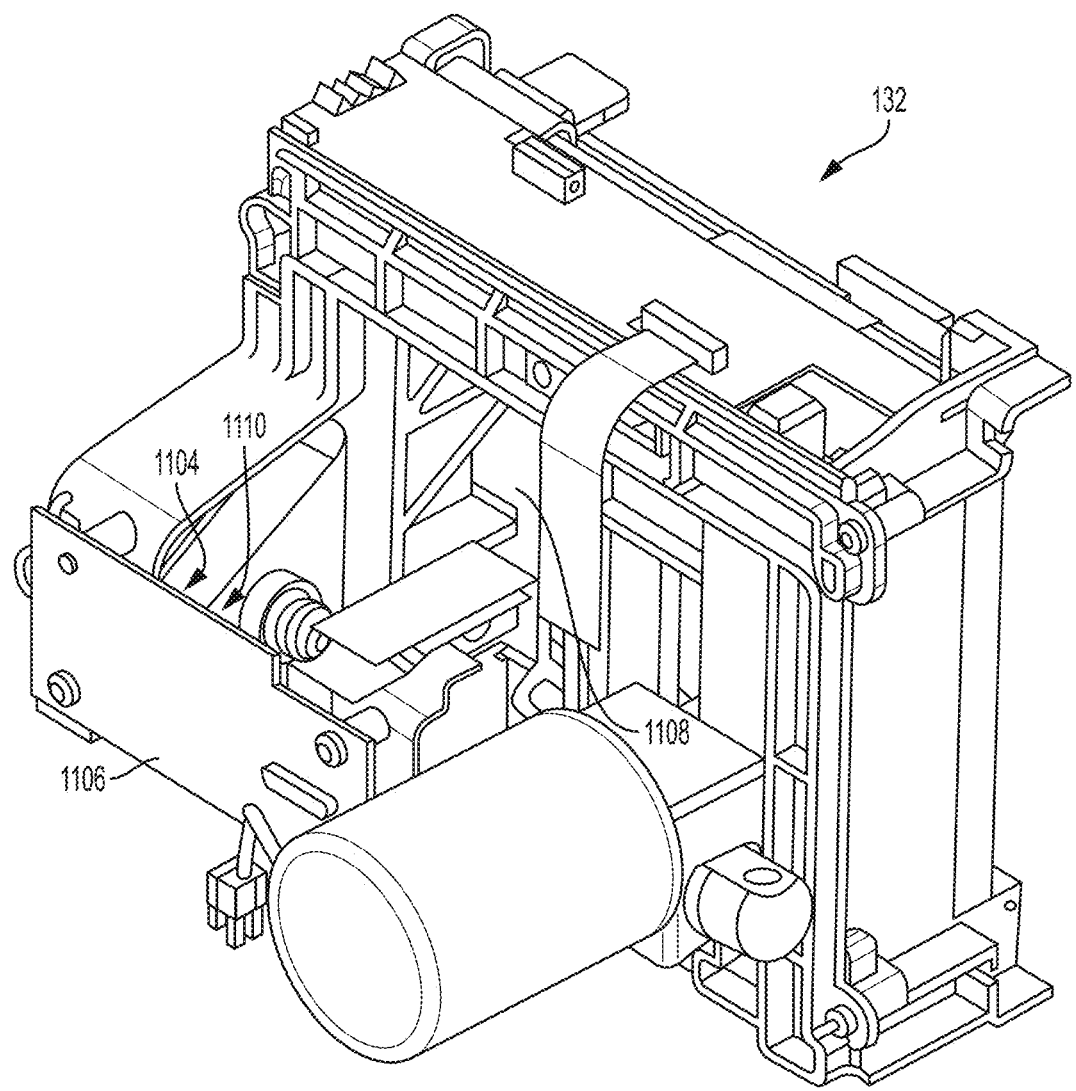
FIG. 42 is a perspective view of a carriage drive assembly including an AutoID camera mounted to an AutoID camera board.

FIG. 41 and FIG. 42 show a perspective view of a foldable identification tag 1100, and a perspective view of a carriage drive assembly 132 including an AutoID camera 1104 mounted to an AutoID camera board 1106 respectively. In accordance with an aspect of the present disclosure, the identification tag 1100 may be formed from an injection mold, and it may then fold to snap around the indicator region 33. The identification tag 1100 may include edges that are rounded, which may prevent damage to the solution containers 20 during shipping. The identification tag 1100 may also include an 8×8 mm two dimensional (2-D) Data Matrix symbol 1103 with 18 blocks per side plus a quiet zone, which may be added by way of a sticker. The information contained in these Data Matrix symbols 1103 may be provided from the camera 1104 to the control system 16, which may then obtain indicia, through various processes such as by way of image analysis. Therefore, the AutoID camera 1104 will have the ability to detect slots 1086 that contain a solution line 30 that is correctly installed, a line 30 that is incorrectly installed, or the absence of a line 30. A solution line 30 that is correctly installed will allow the camera 1104 to detect the Data Matrix symbol 1103 located on the identification tag 1100, the absence of a solution line 30 will allow the camera 1104 to detect an "empty" Data Matrix barcode 1102 located on the carriage 146 underneath the membrane port 1094, and a solution line 30 that is incorrectly loaded will occlude the "empty" Data Matrix barcode 1102, resulting in no Data Matrix being decoded by the camera 1104 for that slot. Thus, the camera 1104 should always decode a Data Matrix in every slot 1086 on the carriage 146, baring an incorrectly loaded solution line 30.

In this illustrative embodiment, ability to detect features of a solution line 30 by way of an identification tag 1100 located at indicator region 33 may provide benefits such as allowing a user to position lines 30 in any location of the carriage 146 without having an effect on system operation. Additionally, since the cycler 14 can automatically detect solution line features, there is no need to ensure that specific lines 30 are positioned in particular locations on the carriage 146 for the system to function properly. Instead, the cycler 14 may identify which lines 30 are where, and control the cassette 24 and other system features appropriately.

In accordance with another aspect of the disclosure, the identification tag 1100 must face into the carriage drive assembly 132 in order to be decoded by the camera 1104. To ensure this, the solution line receiving structures on the holder for the solution lines and the identification tag 1100 may have complementary alignment features. With reference to the example embodiments of the carriage 146 described herein, the carriage 146 and identification tag 1100 may have complementary alignment features. Additionally, the solution lines 30 with identification tags 1100 should also fit within the Cleanflash machine, thus, the solution line 30 with identification tag 1100 may be constructed to fit within a 0.53 inch diameter cylinder. In an embodiment, the alignment feature may be a simple flat bottomed bill on the identification tag 1100 and matching rib in the carriage 146. In one embodiment of the present disclosure, the bill and rib may slightly interfere, forcing the back of the identification tag 1100 in an upward direction. While this configuration may create a small amount of misalignment, it reduces misalignment in the other axis. Finally, to ensure that the identification tag 1100 is properly seated, the front of the carriage drive assembly 132 can be designed with only about 0.02 inch of clearance over the present carriage 146 and identification tag 1100 alignment.

In accordance with another aspect of the disclosure, the AutoID camera board 1106 may be mounted to the back of the carriage drive assembly 132. Additionally, the AutoID camera 1104 may be mounted to the camera board 1106. The camera board 1106 may be placed approximately 4.19 inches from the identification tag 1100. However, in an alternative embodiment, the camera board 1106 may be moved backward without any serious consequences. A plastic window 1108 may also be attached to the front of the carriage drive assembly 132, which may allow the identification tags 1100 to be imaged while also preventing fluid and finger ingress. The AutoID camera 1104 may include a camera lens, which may be any type of lens, such as those used for security applications, or lenses intended for camera phones with the IR filter removed. In accordance with an aspect of the present disclosure, the camera lens may consist of a small size, light weight, low cost, and high image quality.

Additionally, a single SMD IR LED 1110 may be attached to the camera board 1106. The LED 1110 may then illuminate the identification tags 1100 so that the camera 1104 may easily decode the Data Matrices 1103. It is important that the identification tags 1100 be illuminated because the environment inside of the cycler housing 82 is mostly absent of light. Therefore, without the LED 1110 to illuminate the identification tags 1100 the camera 1104 would be unable to decode the Data Matrices 1103. Furthermore, to avoid creating glare in front of the identification tags 1100, the LED 1110 may be mounted 0.75 inch away from the camera 1104. An FPGA may also be mounted to the camera board 1106, and may act as an intermediary between the OV3640 image sensor and a cycler's UI processor. In addition to making the processor's job easier, this architecture may allow for a different image sensor to be used without a change to any other cycler hardware or software. Finally, image decoding is handled by the open source package libdmtx, which is addressable from a number of programming languages and can run from a command line for testing.

In some embodiments, a processor associated with the camera 1104 may be capable of decoding barcodes, data matrices, or the like outside of an indicator region 33 of a solution line installed in a carriage 146. For example, a processor associated with camera 1104 may be capable of decoding an identifying marking on the packaging or overpack of a set or on the set itself before the set is installed in the cycler. For example, during setup, the user interface of a cycler may instruct a user to hold the set packaging in front of or a certain distance away from a window such as window 1108, such that an identifying marking on the packing is facing the window. In this position, the identifying marking will be in the field of the view of the image sensor of the camera 1104. The camera 1104 may then image the packing and the identifying marking may be decoded by a processor associated with the camera 1104. In some embodiments, after the identifying marking has been decoded, the user interface may prompt the user to confirm various information about the set.

The information encoded in the identifying marking on the set or set packaging may be the same as or different from that included on the indicator for each solution line. For example, the information on the set packing may be stored for logging purposes (e.g. lot number identification etc.). In some embodiments, the information decoded from the set packing may be compared to the information included on the solution lines to ensure that the information matches or corresponds. This may provide for some redundancy allowing the device to double check that the lines have been identified correctly and that the correct set was installed.

Figure 43:
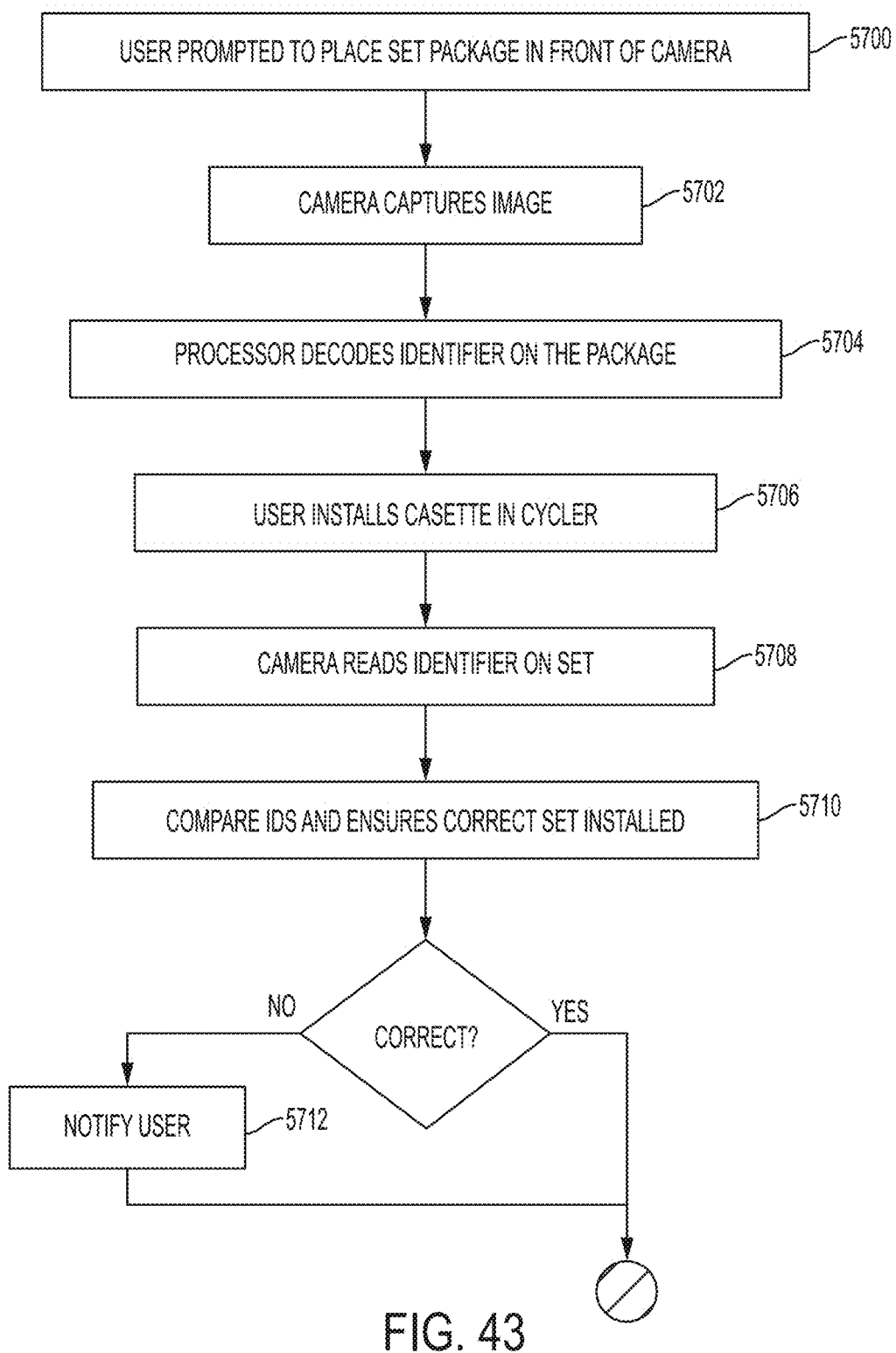
FIG. 43 shows a flowchart outlining a number of steps which may be used to determine information about a set to be installed in a cycler.

FIG. 43 depicts a flowchart detailing a number of example steps which may be used to determine information about a set to be installed in a cycler by reading an identification marking on the packaging for the set. As shown, in step 5700, a user may be instructed to place a set package in front of a camera in the cycler. This may be accomplished via a prompt generated by a processor of the cycler for display on a user interface of the cycler. The cycler may then capture an image of the identification marking on the set packaging or overpack in step 5702. In some embodiments, the user may be required to interact with the user interface of the cycler to notify the cycler processor that the set packaging has been properly positioned. This interaction may generate a signal which is recognized by a processor that then commands the image to be captured.

In step 5704, a processor of the cycler may decode the identifier on the packaging. The user may then install the cassette in the cycler in step 5706. In some embodiments, before the user installs the cassette, the user interface of the cycler may display a notification which asks a user to confirm that the set was correctly identified in step 5704. In one aspect, the cycler may display a message if the packaging is identified to be for a cassette that would be incompatible with a selected or programmed therapy.

Once the set is installed a camera in the cycler may read one or more identifying markings on the set in step 5708. In some embodiments, the identifying marking read in step 5708 may be an identification tag 1100 on each solution line of the set. A processor of the cycler may compare the information about the set gathered in step 5702 and 5708 to ensure that the correct set was installed in step 5710. In the event that the information does not match, the user may be notified in step 5712.

In some embodiments, to avoid deleterious effects of glare from visible light, the data matrices 1103 of the identification tags 1100 may include a fluorescent ink or dye which emits light of a first wavelength or spectrum in response to absorption of light of a second wavelength or spectrum shone upon it. Such an identification system can be used in any fluid handling medical device in which fluid containers or bags may have fluids of different compositions, expiration dates, or in which manufacturing lot numbers need to be recorded by the device. In an example embodiment, the system can be used in an automated peritoneal dialysis apparatus. The system comprises an image sensor or camera 1104 configured to read an image generated by fluorescent light, the image comprising a pattern of coded information characterizing the fluid in the container, the age of the container, its lot number, etc. The fluid line 33 to which the container is attached can be mounted in a mount, cradle or carriage 1088 to fix its location relative to the image sensor. The fluid line can have an attached identification tag 1100 on or near the mount, onto which a fluorescent identifying marking 1103 has been applied. The marking fluoresces a pattern of light that contains the coded information upon absorption of light having a non-visible wavelength emitted by an emitter nearby. The image sensor can be connected to a controller adapted to receive electronic signals from the image sensor board 1106 representing the image pattern containing the coded information.

For example, the data matrices 1103 may include an ink or dye which fluoresces in the visible spectrum when it absorbs light in the ultraviolet spectrum. The data matrices 1103 may be printed with such an ink or dye and applied to the identification tags 1100 as a sticker, for example. Any other suitable means of attaching a data matrix 1103 to an identification tag 1100 may also be used. In addition to an image sensor, the camera 1104 may include a camera lens which includes a filter that filters out light of the second wavelength or spectrum (e.g. a UV filter). One or more lighting elements, such as LED 1110 (e.g. an SMD LED) that generates light at the second wavelength or spectrum (e.g. UV light) may be attached or connected to the camera board 1106. The LED 1110 may then illuminate the data matrices 1103 on the identification tags 1100. In such embodiments, the data matrices 1103 will emit light in the first wavelength or spectrum (e.g. in the visible spectrum) in response to illumination by light of the second wavelength or spectrum. The camera 1104 may then receive the emitted light of the first wavelength for decoding of the data matrices 1103. The decoding of the data matrices 1103 may be accomplished as described above. The effects of glare from reflected light from the LED may be reduced in this fashion, since the camera 1104 can be configured to filter out light at the LED's emitting wavelength/spectrum.

Figure 44:
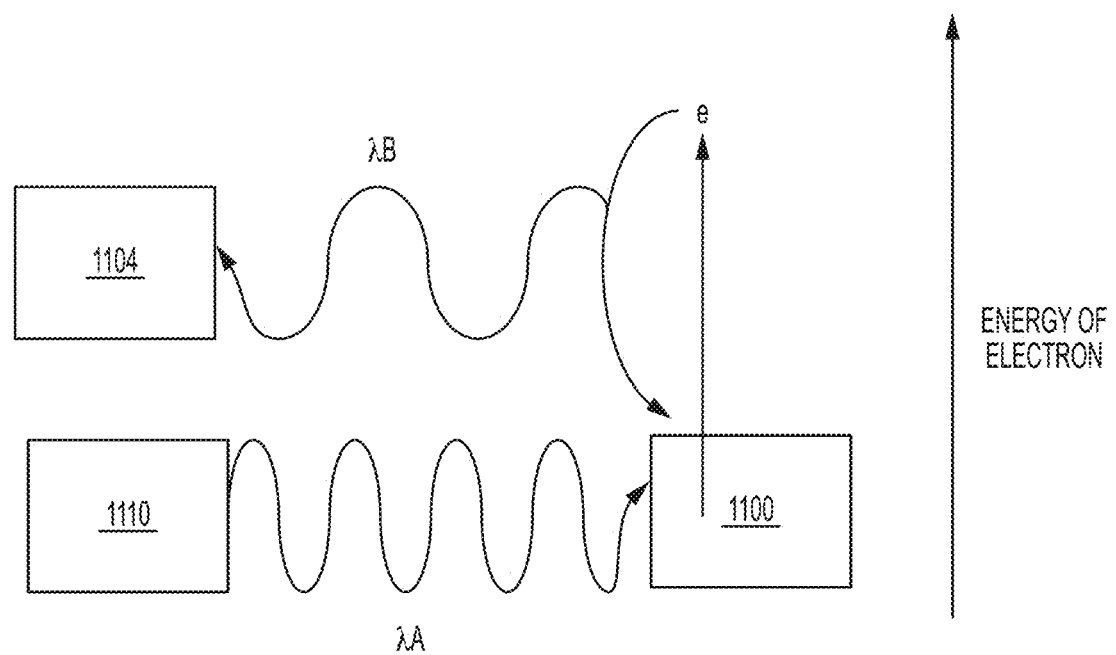
FIG. 44 shows a system including an identification tag having a code printed in a fluorescent material.

FIG. 44 depicts an illustration of a system in which the identification tag 1100 has a code printed in a fluorescent material. As shown, one or more LED's 1110 may illuminate the identification tag 1100 using light at a wavelength A. The light generated by fluorescence at wavelength B is received by the camera 1104. As mentioned above, the fluorescence may be in the visible spectrum and the wavelength emitted by the LED may be a wavelength outside of the visible spectrum such as ultraviolet light. The camera 1104 may optionally include a filter which filters out the wavelength emitted by the LED Once the identification tags 1100 of each line have been imaged by the camera 1104 and analyzed, a processor of the cycler may generate a screen for display on a user interface which displays the results. The display may indicate various characteristics about the solution identified. In other embodiments, the display may disclose characteristics of the solutions programmed for use during the therapy, and indicate whether these solutions have been detected by the camera. In an embodiment in which the controller is programmed to perform image recognition, and in which the solution line caps are in the field of view of the image sensor or camera 1104, a results screen may display whether the lines were detected in a capped or uncapped state. In the event that the programmed solutions are not all present or that a line is uncapped, the controller may be programmed to prevent the user from proceeding with therapy and to display on a screen the needed corrective actions. The screen may also optionally display information about the type of set (e.g. pediatric, adult, extended patient line, etc.) installed in the cycler if such information is collected. Preferably, this action is performed and the screen display is shown prior to the connection of the solution lines to a cassette so as not to waste any solution.

FIG. 45 depicts an example of a screen shot 5630 which may be generated for display on the user interface of a cycler. The example screen 5630 shows the results of identification tag 1100 analysis. In the example screen 5630, the characteristics of the solutions programmed for use in the therapy are shown. These characteristics may include (but are not limited to): dialysate type or name, concentration of dialysate, volume of dialysate bag, osmotic agent of the dialysate, other composition information (e.g. buffer information, ionic content information), bag type, etc. The characteristics shown may differ if the cycler is set up for at-home use or for use in a dialysis clinic. If there are fewer solution bags programmed for use in the therapy than the maximum allowed for the cycler, unused solution line or solution line cap locations may be labeled "none", "no solution", or the like.

A number of indicators 5362 may also be included on the example screen 5630. These indicators 5632 indicate to a user whether the solution has been identified as installed in the cycler. For example, a checkmark may appear in an indicator 5632 next to a listed solution type if present. An 'X' may appear if the listed item is not detected.

The example screen 5630 shown in FIG. 45 also includes an indicator 5632 associated with each solution that indicates whether a cap has been detected on the installed line. As above, any suitable method may be used to display whether a capped or uncapped line is detected.

In some embodiments, it may be desirable to include a brace, brace member or stiffener for placement on the distal end of a solution line. It may be configured to surround a portion of the line and/or an attached connector. In any fluid handling apparatus that is configured to spike the distal end of a fluid line, the distal end preferably should be constrained so as not to bend out of alignment with the longitudinal axis of a hollow spike. In some cases, the distal end of the fluid line will have been deformed during manufacture or sterilization. In other cases, the flexibility of the fluid line may render it prone to bending as the spiking procedure occurs. A brace may be rigid and constructed to be mountable over a distal portion of the fluid line, encircling the fluid line at or near the location at which the spike penetrates a septum or other barrier in the fluid line. In an embodiment, the brace comprises two rigid half-members arranged to couple together to encircle the distal end of the fluid line. The brace can be arranged to form a clamp around the fluid line at this location, the inside features of the clamp configured to mate with complementary features on the outside surface of the fluid line. Preferably, the brace can be applied to the fluid line to correct any pre-existing bend in the fluid line, or to prevent the fluid line from bending during operation of the spiking apparatus. Preferably, the outside surface of the brace when enclosing the fluid line has a shape, orientation and features that allow the brace and its enclosed fluid line to be mounted to a fluid line mount, cradle or carriage of the fluid handling apparatus. A peritoneal dialysis cycler having a fluid line autoconnect apparatus can be used as an example of such a fluid handling apparatus.

Optionally, an identification tag 1100 may be configured to function as a brace for a solution line. A brace member may serve to surround, constrain or support a portion of the terminal/distal end of the solution line (or connector) where a solution line septum is located. The brace helps to prevent the surrounded section of the line from bending or deforming out of an orientation dictated by the brace. A brace may also aid in ensuring a distal end of the line is positioned reliably in its track or cradle on the cycler.

If a solution line is bent or deformed during manufacture, for example, a brace may help to correct this by bending the line back into the proper orientation or geometry. It may, for example, be used to ensure the end of the solution line remains generally aligned along an axis. This may help to ensure that the end of the line is in a predictable orientation (e.g. coaxial with the longitudinal axis of a corresponding spike on a cassette) and is restricted from bending or deforming when a cycler is spiking or otherwise manipulating the line. A brace may also help to prevent a solution line from bending or deforming during heating with may occur during sterilization of the line or enclosed solution.

The cycler carriage may be configured to receive and support a brace member on a solution line. The carriage, in cooperation with a brace member may then provide further aid in ensuring that the solution line is in a particular or prescribed orientation and stays in this orientation as the solution line is spiked or manipulated.

A brace may, for example, be manufactured from any suitable plastic (injection molded or otherwise) of a rigidity sufficient to prevent deformation or bending of the enclosed line or connector. Preferably it is made of a material more heat resistant than the material used to make the solution line. The edges of a brace are preferably contoured (e.g. blunted or rounded) so as to limit potential for damage of the set during shipment and handling.

A brace may be constructed in two separate halves that can be joined together around a section of tubing or connector. More conveniently, the two portions of a brace can be connected by a living hinge on one side, allowing for greater ease of installation on a solution line or connector. In embodiments in which the solution line includes a solution line membrane or septum flange 1096 (see, for example, FIG. 40), the interior surface of the brace may include a recessed region sized to accept the flange. The recessed region may be molded to be flanked on each side by surfaces sized to closely surround the smaller diameter solution line.

Figure 46:
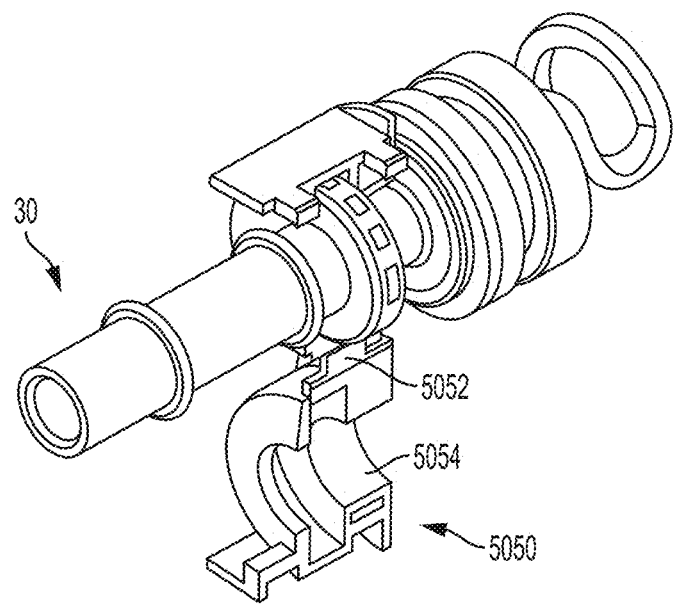
FIG. 46 shows an example brace for a solution line in an unassembled position on the solution line.

As shown in FIG. 46, a solution line 30 is depicted with an example brace 5050 being positioned around a segment of the solution line 30 in which an interior septum (not shown in FIG. 46) is disposed. In the example shown, brace 5050 may comprise two halves and include a living hinge 5052 or thin bridge of material which allows the brace 5050 to be folded into place around the solution line 30. The living hinge 5052 may be molded as an integral part of the brace 5050. Also as shown in FIG. 46, a brace 5050 may include an interior face 5054 which cooperates with features of the outer surface of the solution line 30 so that the brace 5050 may fit snuggly around and encompass the solution line 30 and its external features. Thus, when in place around the solution line 30, the brace 5050 may act to substantially constrain and/or support the portion of the solution line 30 against undesired movement or displacement.

Figure 47:
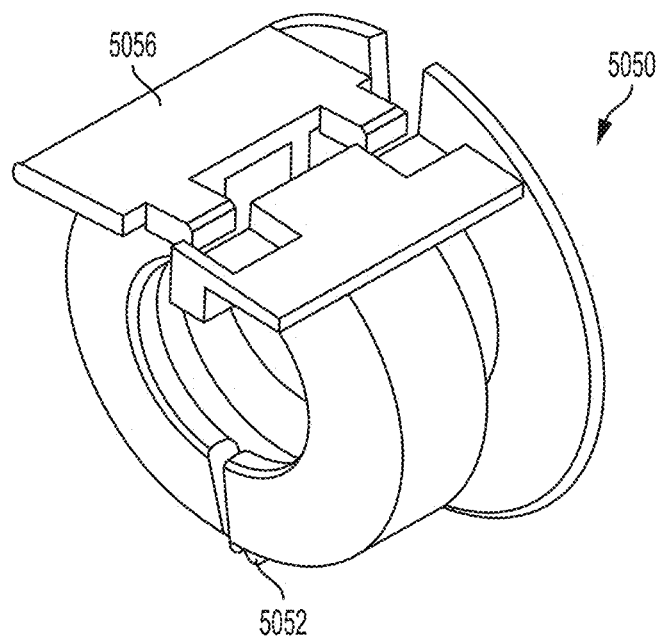
FIG. 47 is a perspective view of an example brace for a solution line.

Referring now to FIG. 47, an enlarged view of the example brace 5050 depicted in FIG. 46 is shown. As shown in FIG. 47, the brace 5050 has been closed about its living hinge 5052 such that it is nearly in an assembled, ring-like configuration. The brace 5050 may be secured together with one or more coupling features. For example, the brace 5050 may be snapped together with cooperating snap fit or interference fit features. Alternatively, the coupled portions of a brace 5050 may be coupled together with cooperating friction fit features. In some embodiments, glue or adhesive may be used to join the two halves, or a cable tie-like fastening arrangement around the outside surface of the brace may be used as well. In an example, one side of a brace 5050 may include a toothed projection that engages with a pawl in a receiving structure on the opposite side of the brace 5050. Thus when the two halves are coupled together, the coupling features act as a ratchet to prevent a user from removing the brace 5050 from an enclosed line. Thus, any identifying tag present on the brace may not easily be separated from its intended line (and associated solution bag). Any other suitable coupling arrangement which makes it difficult to separate a brace 5050 from its respective line may also be used to accomplish this goal.

In some cases, it may be desirable to allow a user to remove a brace 5050 (or an associated identification tag 1100), in which case permanent or semi-permanent coupling features are not included in the construction of the brace 5050. For example, an appliqué or sticker bearing the identification marking for the solution line 30 may be used to hold the two halves of the brace 5050 around the solution line 30. This may allow a user to easily remove the brace 5050 (or other identification tag 1100) from the solution line 30 by tearing or peeling off the identification marking.

As is shown in FIGS. 46 and 47, the brace 5050 includes a display surface 5056 that in some aspects may be substantially flat to accommodate an identification marking or code when the two halves of brace 5050 are coupled together in its assembled configuration. This display surface 5056 may serve as a surface to which an identification marking may be added (e.g. with a sticker or the like). The identification marking may also be molded/etched into or painted onto the display surface 5056. Thus, the brace 5050 may also act as an identification tag 1100. A non-flat (e.g., curved) display surface 5056 bearing an identification marking may also be used.

As shown, the display surface 5056 in FIGS. 46 and 47 would include a seam since the coupled portions of the brace 5050 couple in the center region of the display surface 5056. In alternative embodiments, a brace 5050 may be configured such that any seam produced when coupling the brace 5050 around the solution line 30 would not potentially cause an interruption of the display surface 5056. This may be desirable as it may help to ensure that an identification marking added to the display surface is not affected by the seam.

In some embodiments, the way in which the two parts of a brace are joined may provide identifying characteristics, obviating the need for an identification marking. The seam at which the two parts of the brace are joined may have pre-determined geometric patterns or projections that can be detected by an imager in a cycler. Portions of the coupled edges of a brace 5050 may be made to project a greater or lesser amount and/or may have different shapes. Braces having different seam patterns may be assigned to specific types of solution bags. Each solution bag may have a unique seam pattern.

Figure 48:
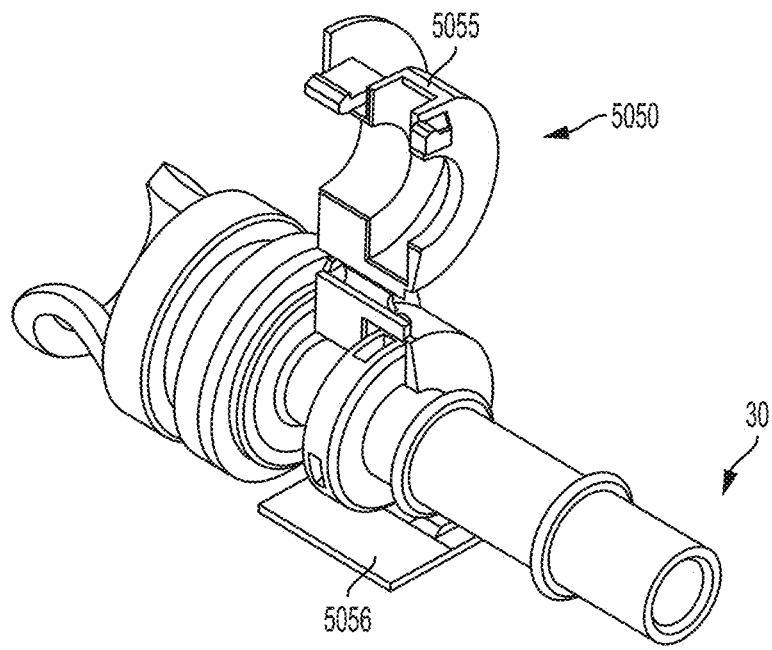
FIG. 48 shows another example brace for a solution line in an unassembled position on the solution line.
Figure 49:
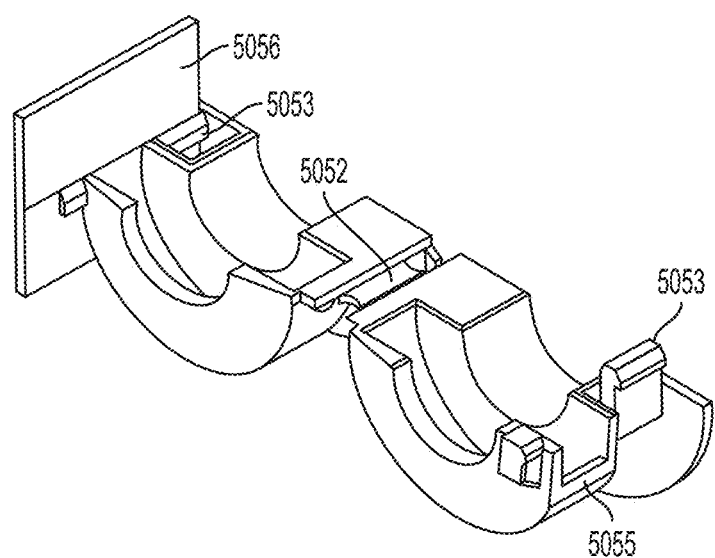
FIG. 49 is a perspective view of an example brace for a solution line.

If desired, the display surface 5056 of brace 5050 can be made to be seamless, as shown in FIGS. 48 and 49. As shown, the brace 5050 is constructed similarly to that shown in FIGS. 46 and 47 and includes a living hinge 5052 which allows the brace 5050 to be folded about the outer surface of a solution line 30. The brace 5050 may then be secured in place about the solution line 30 via the interaction of one or more coupling feature(s) 5053 on the brace 5050. In this case, the display surface 5056, intended to bear an identification marking or code, remains a single piece, so that opening the brace does not disrupt the continuity of the code or marking. As is best shown in FIG. 49, the example embodiment includes coupling features 5053 which are cooperating snap fit features. One mating face of the brace 5050 includes a projection with one or more (in this example, two) locking features. The locking features may be ramped to aid in guiding the projecting into the receiving coupling feature 5053 on the opposing mating face of the brace 5050. In the example embodiment, the locking features are optionally non-releasing. That is, there is a substantially vertical catch at the end of the projection. When snapped into the receiving coupling feature, this vertical catch will abut against an interior wall of the receiving feature making disassociation of the coupling features 5053 difficult. In alternative embodiments, the catch may be angled away from the abutting wall of the receiving element, allowing for disassociation of the two components by applying a suitable distracting force on the two components.

The body of the brace 5050 may optionally include additional mating features that are complementary with features on a solution line 30, so that it can be installed in only one orientation on the solution line 30. This may ensure that the display surfaces 5056 of a number of braces 5050 on a number of solution lines 30 are oriented substantially along the same plane. Including cooperating coupling features on the solution line 30 and the brace 5050 may help to further retain the brace 5050 in a supporting or bracing position around the solution line 30 as well.

In the example embodiment, and as best shown in FIG. 49, the display surface 5056 is formed as a flange-like protrusion or projection that extends from one half of the ring-like brace 5050 body. The display surface 5056, when the brace 5050 is assembled, overhangs a portion of the opposite half of the brace 5050 such that the coupling or mating elements of the brace 5050 are joined under the display surface 5056.

As shown, a support surface 5055 for the overhanging portion of the display surface 5056 may be included on the opposite half of the brace 5050. This support surface 5055 may help to prevent the flat feature 5056 from being bent. The support surface 5055 may be configured to include a flat surface or plateau which is in a plane substantially parallel to the display surface 5056. A number of standoffs may alternatively be used. When the brace 5050 is assembled, the support surface 5055 is disposed underneath the overhanging portion of the display surface 5056.

Figure 50:
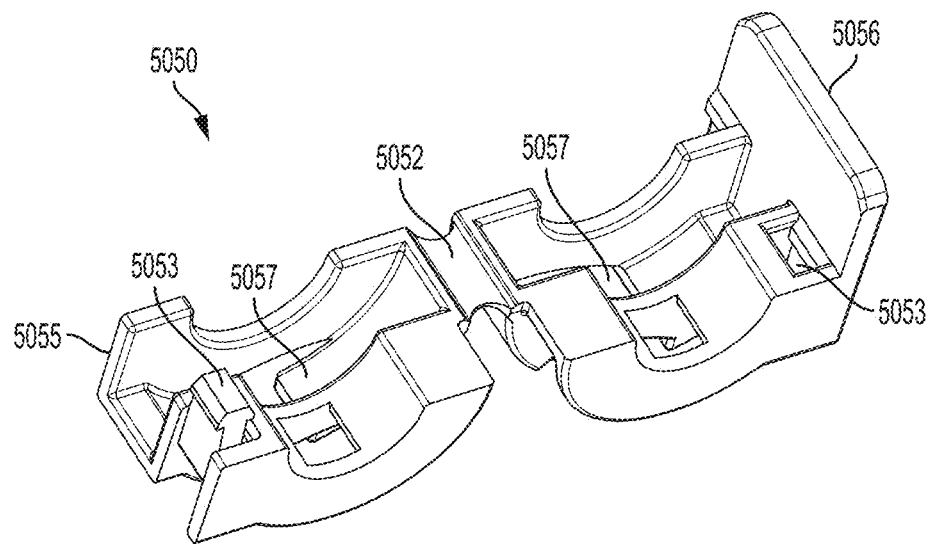
FIG. 50 is a perspective view of an example brace for a solution line.
Figure 51:
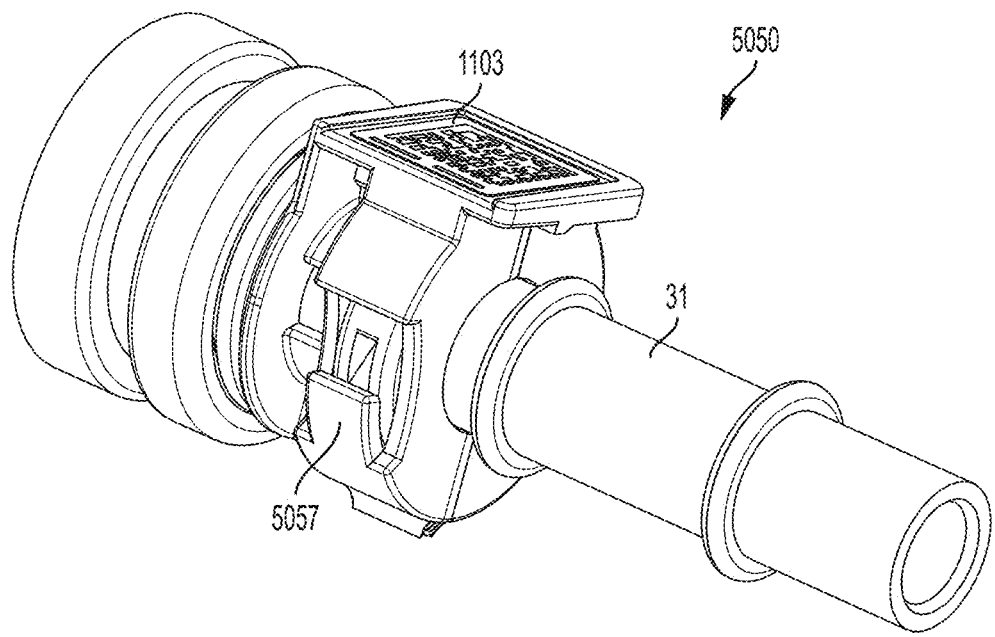
FIG. 51 shows an example brace for a solution line coupled in place on the solution line.

Another example of a seamless display surface 5056 of a brace 5050 is depicted in FIGS. 50 and 51. As shown, the brace 5050 includes a living hinge 5052 which allows the brace 5050 to be folded about the outer surface of a solution line 30. The brace 5050 may then be secured in place about the solution line 30 via the interaction of one or more coupling feature 5053 on the brace 5050. In the example embodiment in FIGS. 50 and 51, the coupling features 5053 are snap fit features. The brace 5050 also includes a support surface 5055 which is disposed underneath the overhanging portion of the display surface 5056 when the brace 5050 is assembled. In some embodiments, a display surface 5056 of a brace 5050 may include a raised surface or rim extending along at least a portion of its perimeter. This may help in positioning of a data matrix 1103, bar code, QR code, or other identifying marking on the brace 5050 for situations in which the identifying marking is an appliqué or sticker applied to the brace 5050.

As is best shown in FIG. 51, a brace 5050 may also include one or more aligning or retaining features which allow the brace to properly seat in a holder or cradle on a cycler. For example, a brace 5050 may include one or more brace-to-carriage coupling features 5057 which cooperate with complimentary coupling feature(s) in a carriage. Such features may help to retain the brace 5050 and associated solution line 30 in a carriage. Additionally, such features 5057 may help to ensure that the brace 5050 and solution line 30 are fully seated and properly installed into the carriage in the proper orientation. In some embodiments, the brace-to-carriage coupling feature or features 5057 may couple into the carriage in a snap fit engagement. An audible or tactile click during seating may signal to the user that the brace 5050 is properly positioned in the carriage. In the example embodiment, the brace-to-carriage coupling features 5057 are depicted as cantilevered projections, although other suitable coupling arrangements may be used. For example, the brace-to-carriage coupling features 5057 may be friction fit or interference fit features. Preferably, the coupling arrangement provides for releasable coupling of the brace 5050 to the carriage to allow a user to remove solution lines 30 from a carriage easily.

In some alternative embodiments, one or more fasteners such as a screw may be used to secure the portions of a brace 5050 around the solution line 30. In an alternative arrangement, a single piece brace 5050 may also be used during the manufacturing of the tubing set.

Figure 52:
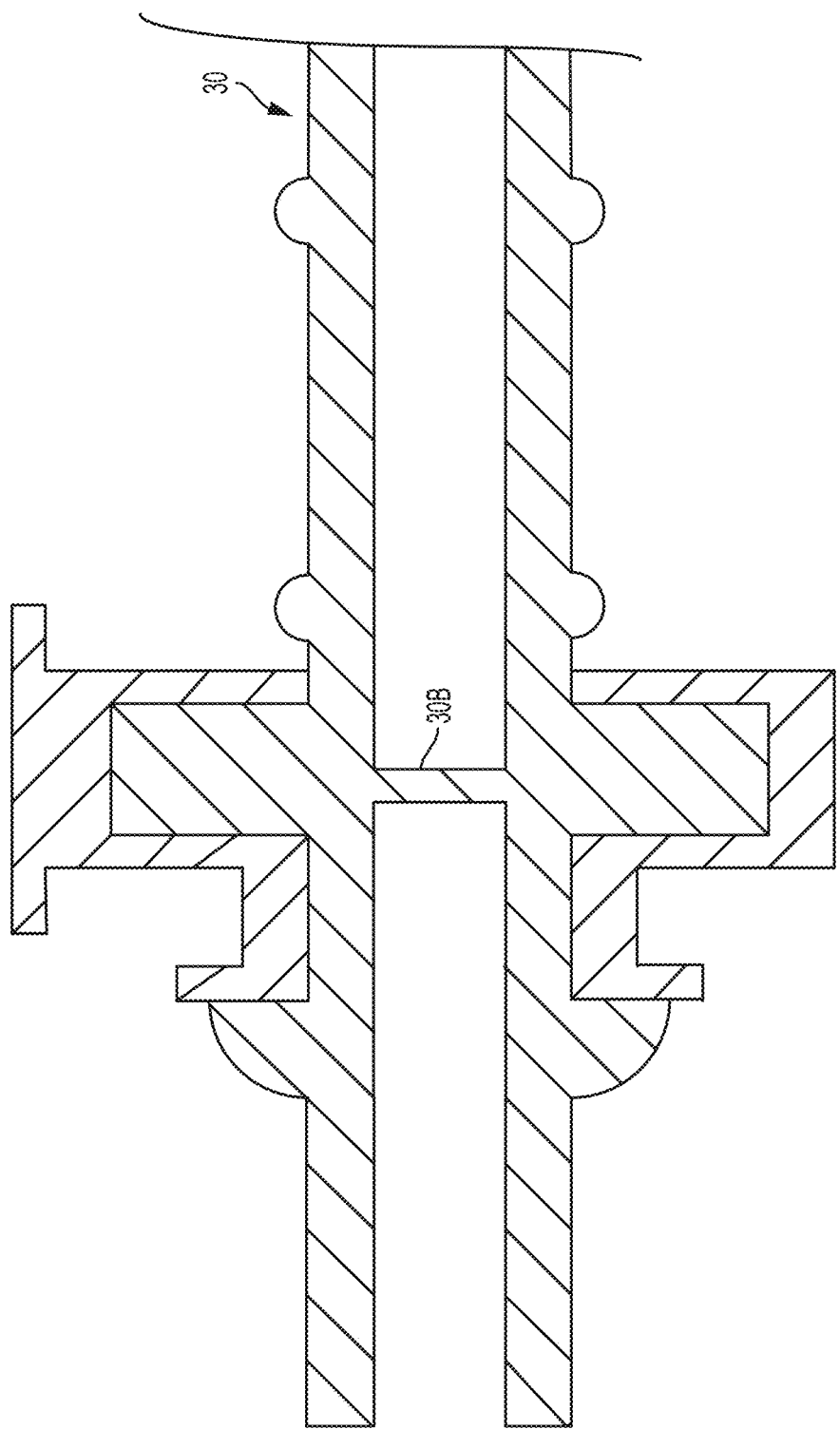
FIG. 52 is a cross-sectional view taken at the medial plane of a solution line which shows a brace in place around the solution line.
Figure 53:
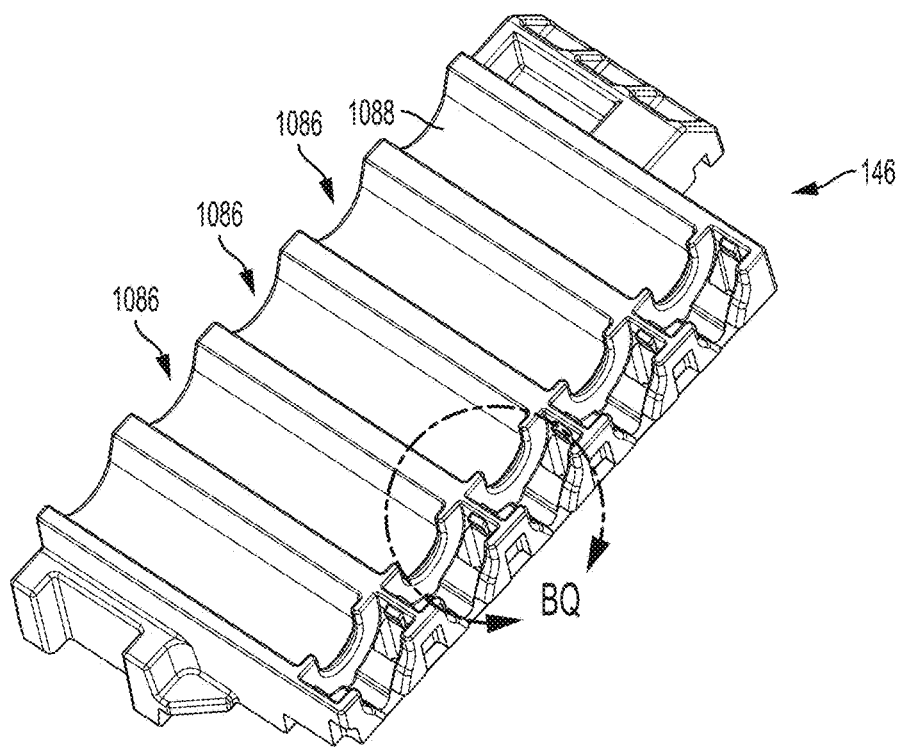
FIG. 53 shows an embodiment of a carriage which includes clip sections configured to accept a solution line about which a brace is installed.

FIG. 52 depicts a representative longitudinal cross-sectional view of the solution line 30, showing a brace 5050 in place around the solution line 30. Specifically, the brace 5050 is in place around the section of the solution line 30 where the septum 30b is located. Positioning a brace 5050 around this region of the solution line 30 helps to prevent distortions of the solution line 30 during manufacture or sterilization that would otherwise cause a misalignment of the septum 30b with a cassette spike when a connection between a cassette and the solution line 30 is attempted. Additionally, the brace 5050 may prevent significant bending or deformation of the solution line 30 when being subjected to the force from a spike. Thus, including a brace 5050 may increase ease of spiking through a septum 30b when the carriage 146 of a cycler drives the solution lines 30 onto the spikes of a cassette 24. FIG. 53 depicts an example embodiment of a carriage 146 that includes retaining features 1092 configured to accept a solution line about which a brace is installed. As shown, the cradles or slots 1086 of the carriage 146 shown in FIG. 53 do not include an ID section 1090 as shown in FIGS. 39 and 40. In this case, the identifying marking (e.g. a data matrix 1103) for the set components may be included on each brace.

Figure 54:
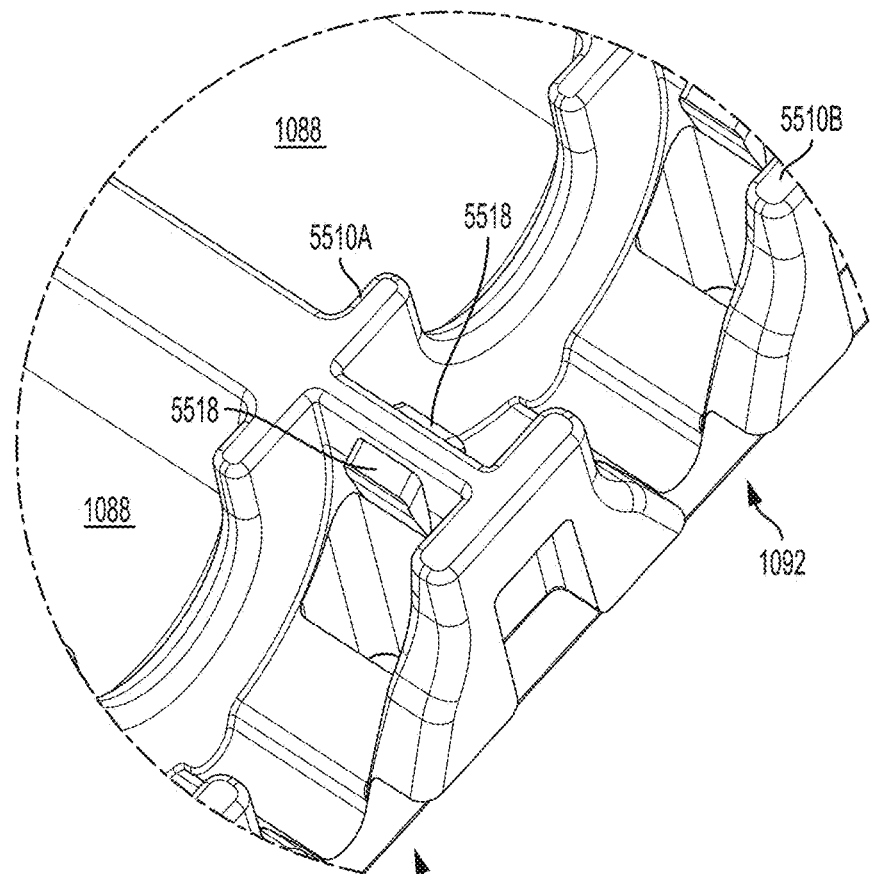
FIG. 54 shows a detailed view of region BQ of FIG. 53.

Referring now also to FIG. 54, a detailed view of region BQ of FIG. 53 is shown. The detailed view shown in FIG. 54 depicts an enlarged view of two example retaining features 1092 of the carriage 146. As shown, the retaining features 1092 may be sized so as to accept a brace when a solution line is installed in a slot 1086 of the carriage 146. The retaining features 1092 of the carriage 146 include support features which serve to support a brace during spiking of an installed solution line. Thus, the retaining features 1092 may ensure that the solution line is in a desired or prescribed alignment during spiking of the solution line. The retaining features may comprise clips or clip sections that provide a snap fit between the brace and the cradle or recess within which it is positioned.

In specific embodiments, the retaining features 1092 include may include at least one support wall or shoulder which serves as a support feature or member. In the example embodiment shown in FIGS. 53 and 54 a first support wall 5510a and second support wall 5510b are included for each retaining feature 1092. These support walls 5510a, b are depicted as flanges that can interact with a portion of a brace so as to provide support for the brace during a spiking operation. For example, each support wall 5510a, b may abut at least one face of a brace during spiking. The support walls or shoulders 5510a, b may also help to properly locate the solution line in a slot 1086 during installation of the line in carriage 146. In some embodiments, a brace may include a recess or groove which is sized to accept a support wall 5510a, b of the carriage 146.

Using the example brace 5050 embodiment shown in FIG. 51, an upstream face 5512 of the brace 5500 may be supported by the first support wall or shoulder 5510a when installed in the carriage 146 shown in FIGS. 53 and 54. The example brace 5050 in FIG. 51 includes a recessed portion 5514. The recessed portion 5514 of the brace 5050 may be sized so that when the brace 5500 is installed in the retaining member or clip 1092, the second support wall 5510b of the carriage 146 is captured within the recess. A downstream face 5516 of the brace 5050 may then be supported by a second support wall or shoulder 5510b. During spiking of solution lines installed in the carriage 146, force will be transmitted from the brace 5050 to the carriage 146 through the support walls 5510a, b. Interaction of the brace 5050 and the support walls 5510a, b of the carriage 146 may thus help to constrain the solution line in a desired alignment throughout the spiking of the line.

Also shown in FIG. 54 are a number of optional carriage-to-brace coupling features 5518. Such features may be included on a carriage 146 designed to accept a solution line with a brace 5050. These features 5518 may cooperate with one or more features included on a brace 5050 such that the brace 5050 is coupled into place and retained in a retaining or clip section 1092 of a slot or cradle 1086. This may help to keep a solution line from inadvertently becoming dislodged from the carriage 146. Preferably, an audible or tactile effect is produced when the brace couples into carriage-to-brace coupling features 5518. This may alert a user that the brace has been fully seated in the retaining or clip section 1092 of a cradle or slot 1086.

In an embodiment, the carriage-to-brace coupling features 5518 are projections that project into the cradle or slot 1086 such that the width of the retaining or clip section 1092 at the location of the features 5518 is reduced to slightly less than that of the brace 5050, requiring some inward deflection of the brace-to-carriage coupling features 5057 before the brace 5050 may snap into the clip section 1092.

In the example embodiment depicted in FIG. 54, the carriage-to-brace coupling features 5518 can be ramped or stepped. A ramped configuration may facilitate removal of a brace from the retaining or clip section 1092 after a therapy. The height and slope of the ramp is selected to present a desired degree of resistance when the user is removing a brace from a retaining or clip section 1092.

Figure 55:
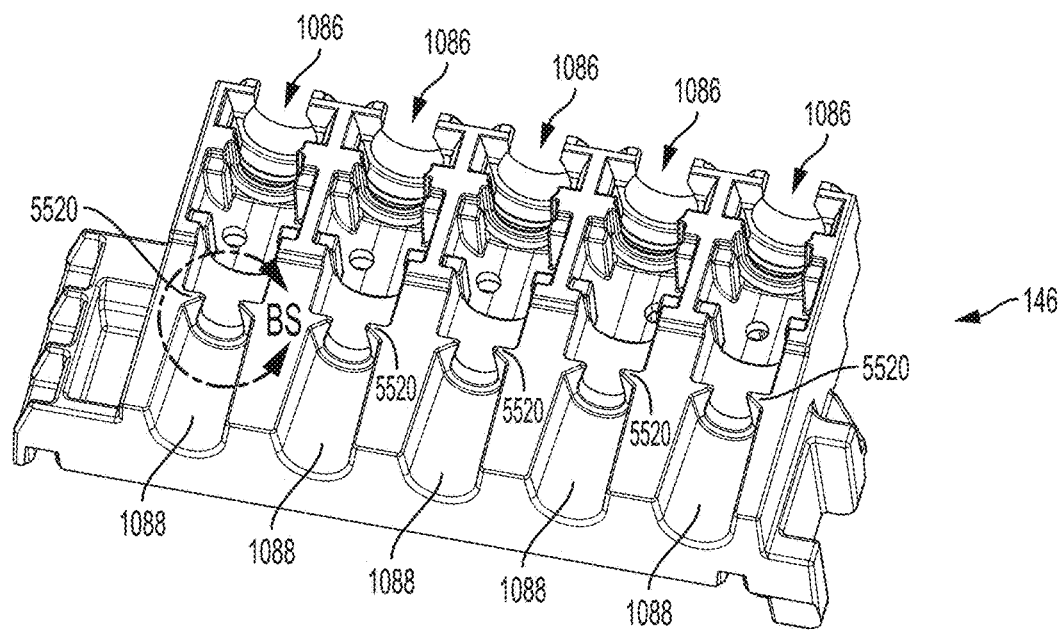
FIG. 55 is a perspective view of a carriage including a number of solution line clips or retaining elements.

Another example embodiment of a carriage 146 is depicted in FIG. 55. As shown, the example carriage 146 depicted in FIG. 55 includes a number of solution line clips or retaining elements 5520. As shown, a solution line retaining element 5520 is included in the solution line section 1088 of each slot 1086 of the carriage 146. The solution line retaining elements 5520 may act as a receiving structure into which a solution line may be placed. The solution line retaining elements 5520 help to hold a solution line in place in a slot 1086 on the carriage 146. Additionally, the solution line retaining elements 5520 are configured to help prevent a solution line from inadvertently becoming dislodged from the carriage 146 or the solution line section 1088 of a slot 1086. The solution line retaining elements 5520 are shown as an integral, continuous part of each solution line section 1088, but in alternate embodiments may be assembled into the carriage 146 as individual components.

In some embodiments, a solution line retaining element 5520 may be configured to provide an asymmetrical resistance to dislodgment of a captured solution line in a track or carriage slot 1086, so that the force required to dislodge the solution line when pulled from a first end (e.g., an upstream location) is less than a force required to dislodge the solution line if pulled from a second end (e.g. a downstream location) This may help to ensure that a solution line does not become accidentally or inadvertently dislodged from the carriage 146 or from a track during spiking or during a therapy. Additionally, this arrangement may allow a user to relatively easily remove a solution line from the carriage 146 after a therapy has completed by pulling on a first (e.g. an upstream) segment of the line. The direction of pull would generally be at an acute angle with respect to the axis of the slot 1086. Generally, a retaining member 5520 for a flexible tube segment situated in a track or slot 1086 can comprise a clip having a bottom well or channel in which the tube segment may be placed, and a top opening through which the tube segment can be inserted or removed. Inwardly directed projections of the retaining member 5520 near the top of the well help to retain the tube segment and prevent it from slipping out of the top of the retaining member 5520. The captured portion of the tube segment either must be compressed, or the projections distracted apart slightly (e.g., laterally), to allow the tube segment to be removed using a predetermined force from the retaining member. Rather than having a perpendicular orientation to the tube segment, a first face of the retaining member 5520 can be inclined away from a first portion of the tube segment as it enters the retaining member 5520. This may have the effect of reducing the force required to remove the tubing segment from the retaining member 5520 when pulling on the first portion. Thus a user may readily remove the tube segment from the retaining member 5520 by grasping the first portion of the tube segment, whereas a greater force is needed to remove the tube segment if the force is directed to the second portion of the tube segment on the other side of the retaining member 5520. Preferably, in a peritoneal dialysis cycler with an autoconnect apparatus, the second portion of the tube segment receives the cassette spikes, whereas the first portion of the tube segment leads to the solution bags (ie, is upstream of the retaining member 5520).

Figure 56:
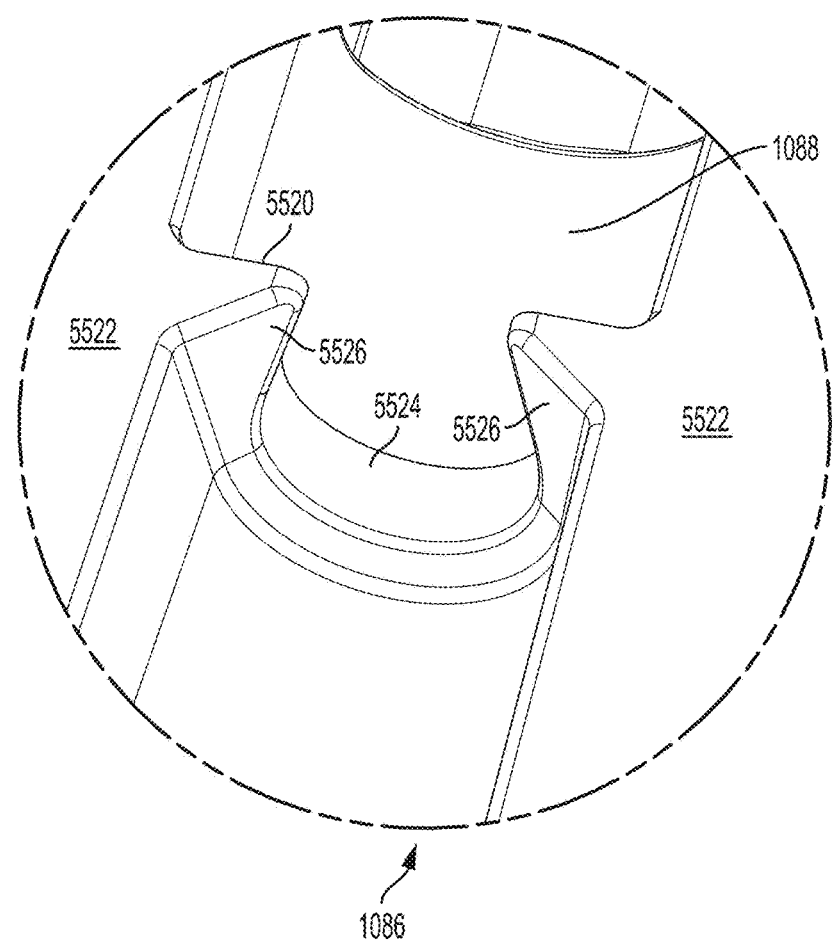
FIG. 56 shows a detailed view of region BS of FIG. 55.

Referring now also to FIG. 56, a detailed view of region BS of FIG. 55 is shown. The detailed view shown in FIG. 56 depicts an enlarged view of an example solution line retaining element 5520 included in the carriage 146. As shown, the solution line retaining element 5520 projects from the walls of the solution line section 1088 inwardly into the slot 1086. In this example, the solution line retaining element 5520 has a "U"-like shape. When a solution line is clipped into and retained by the solution line retaining element 5520, the solution line rests on a cradle portion 5524 of the element 5520.

As shown, the distance between the sidewalls 5526 of the solution line retaining element 5520 tapers as the sidewalls 5526 extend toward top face 5522 of the carriage 146. The distance between the sidewalls 5526 may be less than the diameter of a solution line at or near the top face 5522 of the carriage 146. Alternatively, the sidewalls 5526 may include a step that accomplishes a similar effect.

When a solution line is coupled into a solution line retaining element 5520, the user may be required to apply a force sufficient to deform a solution line for it to fit between the sidewalls 5526 at the top of the solution line retaining element 5520. The degree to which the sidewalls 5526 overhang the line determines the amount of force required to dislodge the line from the retaining element 5520.

As shown in FIG. 56, a guiding feature, contour or ramp may be included on either the downstream or upstream face of a solution line retaining element 5520. In the example embodiment, a guiding feature is shown on the upstream face of the solution line retaining element 5520. A guiding feature may serve to allow the solution line to be easily removed. Such a guiding feature may also facilitate installation of a solution line into a solution line clip or retaining feature 5520.

In the example embodiment shown in FIG. 56, the guiding feature is shown as a chamfer or ramp on each sidewall 5526. In other embodiments, a guiding feature may, for example, be a fillet, rounded edge, funneling feature, or other contour which is included on each sidewall 5526. In some embodiments, a physical interference element on the cycler may make contact with a solution line 30, its connector, its cap, or an associated brace if it is not properly seated in the carriage 146 when the door 141 is closed. Once contacted, this physical interference element may block the travel path of the solution line 30 as the door 141 continues to be closed by the user. This physical interference element may, for example, be disposed on or project out of a portion of the cycler against which the door is closed. In an embodiment, the interference element may be positioned so that improperly seated solution lines 30 may be pressed into a properly seated position as a user continues to pivot the door 141 toward the closed position. The physical interference element may, for example allow for only a small amount of clearance between itself and properly seated solution lines 30 or the carriage 146 when the door 141 is closed. In some embodiments, when the door 141 is in the closed position, the physical interference element may contact and/or compress a portion of a solution line 30, its connector, its cap, or an attached brace even if the solution line 30 is properly seated in the carriage 146. This may provide extra assurance that the solution line is properly seated in the carriage 146. It will also prevent a user from being able to fully close the door 141 of the cycler if a solution line 30 is unable to be pressed into a seated position on the carriage 146.

Figure 57:
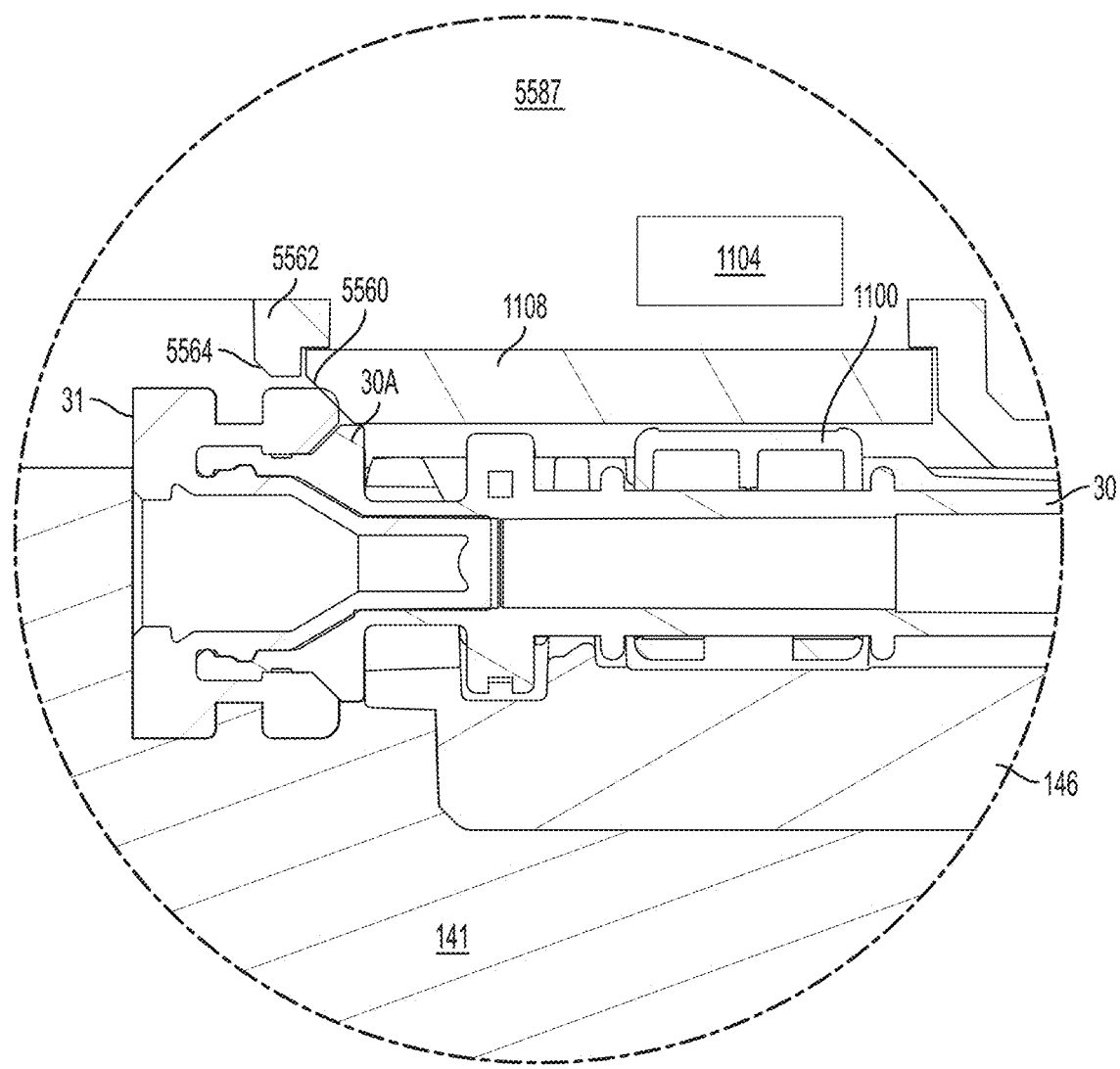
FIG. 57 is a close up cross-section view of a portion of a cycler which includes a carriage and other components.

FIG. 57 depicts a close up cross-sectional illustration of a portion of a cycler which includes a carriage 146 and other components which may be operated to remove cap(s) 31 from solution lines 30, recognize an indicator for each line 30 and fluidly engage the lines 30 with a respective spike on an installed cassette. The door 141 of the cycler is shown in the closed position. As shown, a solution line 30 is in place in the carriage 146 in FIG. 57. The solution line 30 in the example embodiment includes a solution line cap 31 which is installed over the connector end 30*a* of the solution line 30. An identification tag 1100 is shown in place around a portion of the solution line 30 and a camera 1104 is positioned to image the identification tag 1100.

In this example, the solution line cap 31 is in contact with (and optionally compressed by) a portion of the window 1108 which in FIG. 57 serves as the physical interference element. In an embodiment, the solution line cap 31 is made of an elastomeric material (such as silicone) that is compressible and soft enough to avoid damaging the interference element (in this case a portion of the window 1108). With such an arrangement, the act of closing the door 141 of the cycler may ensure that a solution line 30 is pressed into a properly seated position in the carriage 146. To avoid damaging the interference element, the solution line cap 31 is preferably the first portion of the solution line 30 to contact or the principle point of contact for the physical interference element.

If the window 1108 is to provide the physical interference when closing the door 141, the first or principle point of contact between the window 1108 and the solution line 30 is preferably toward the edge of the window 1108 or otherwise in the peripheries or out of the field of view of the camera 1104 behind the window. This may minimize any potential for wear or scuffing of the window 1108 in an area which would obscure the camera's 1104 view of an identification tag 1100.

To further minimize any potential for damage to window 1108, the point of interference contact may optionally be chamfered 5560. This chamfered feature 5560 may help to prevent damage to the window when an improperly seated solution line 30 is forced into a properly seated position as the door 141 is closed. The chamfered feature 5560 may also help to prevent a solution line 30 from snagging or catching on the window 1108 and causing the window 1108 to be damaged. As shown, the frame 5562 of the window 1108 may also optionally include a chamfer 5564 whose face is oriented substantially parallel to that of the chamfered feature 5560 on the window 1108. The chamfer 5564 may similarly help to prevent snagging or catching of a solution line 30 and may also help to prevent damage to the window 1108. In alternative embodiments, the chamfered feature 5560 and/or the chamfer 5564 may be replaced with a rounded feature.

Figure 58:
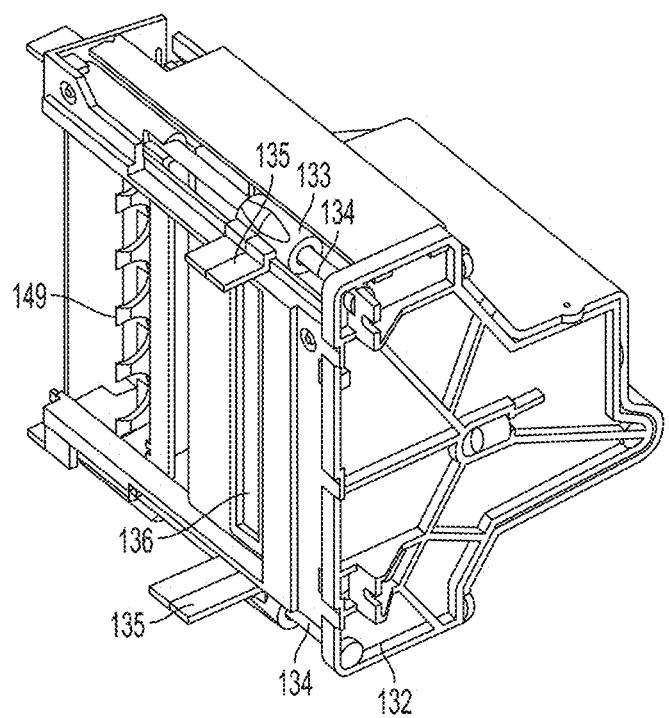
FIG. 58 is a right front perspective view of a carriage drive assembly and cap stripper in a first embodiment.

FIG. 58 shows a perspective view of a carriage drive assembly 132 in a first embodiment that functions to move the carriage 146 to remove the caps from spikes 160 on the cassette, remove caps 31 on the solution lines 30 and connect lines 30 to the spikes 160. A drive element 133 is arranged to move left to right along rods 134. In this illustrative embodiment, an air bladder powers the movement of the drive element 133 along the rods 134, but any suitable drive mechanism may be used, including motors, hydraulic systems, etc. The drive element 133 has forwardly extending tabs 135 that engage with corresponding slots 146*a* on the carriage 146 (see FIG. 38, which shows a top slot 146*a* on the carriage 146). Engagement of the tabs 135 with the slots 146*a* allows the drive element 133 to move the carriage 146 along the guides 130. The drive element 133 also includes a window 136, through which an imaging device, such as a CCD or CMOS imager, may capture image information of the indicators at indicator regions 33 on the lines 30 mounted to the carriage 146. Image information regarding the indicators at indicator regions 33 may be provided from the imaging device to the control system 16, which may obtain indicia, e.g., by image analysis. The drive element 133 can selectively move the cap stripper 149 both to the left and right along the rods 134. The cap stripper 149 extends forward and back using a separate drive mechanism, such as a pneumatic bladder.

Figure 59:
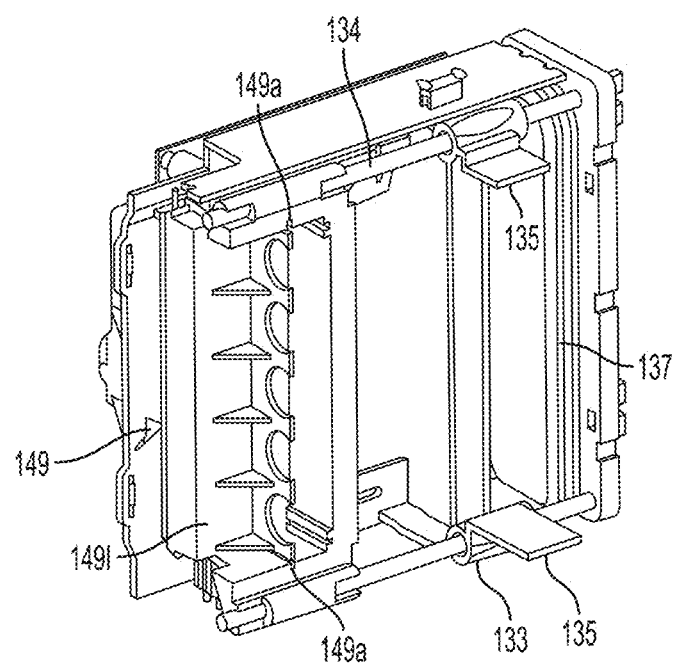
FIG. 59 is a left front perspective view of the carriage drive assembly and cap stripper of FIG. 58.
Figure 60:
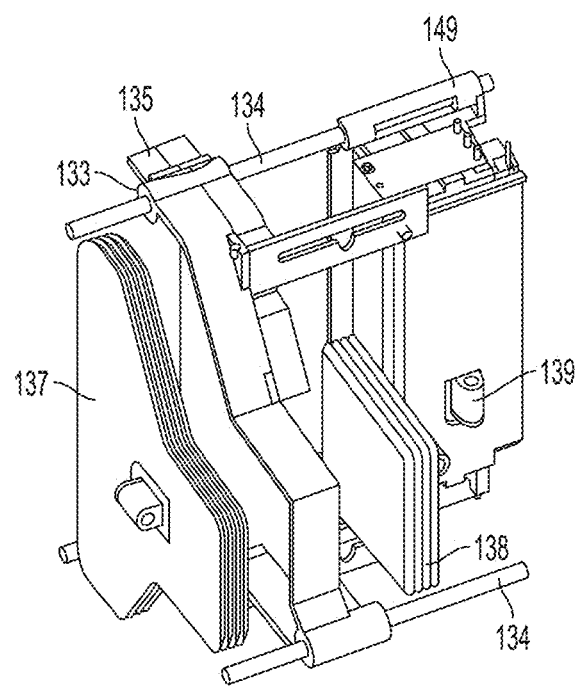
FIG. 60 is a rear perspective view of the carriage drive assembly.
Figure 61:
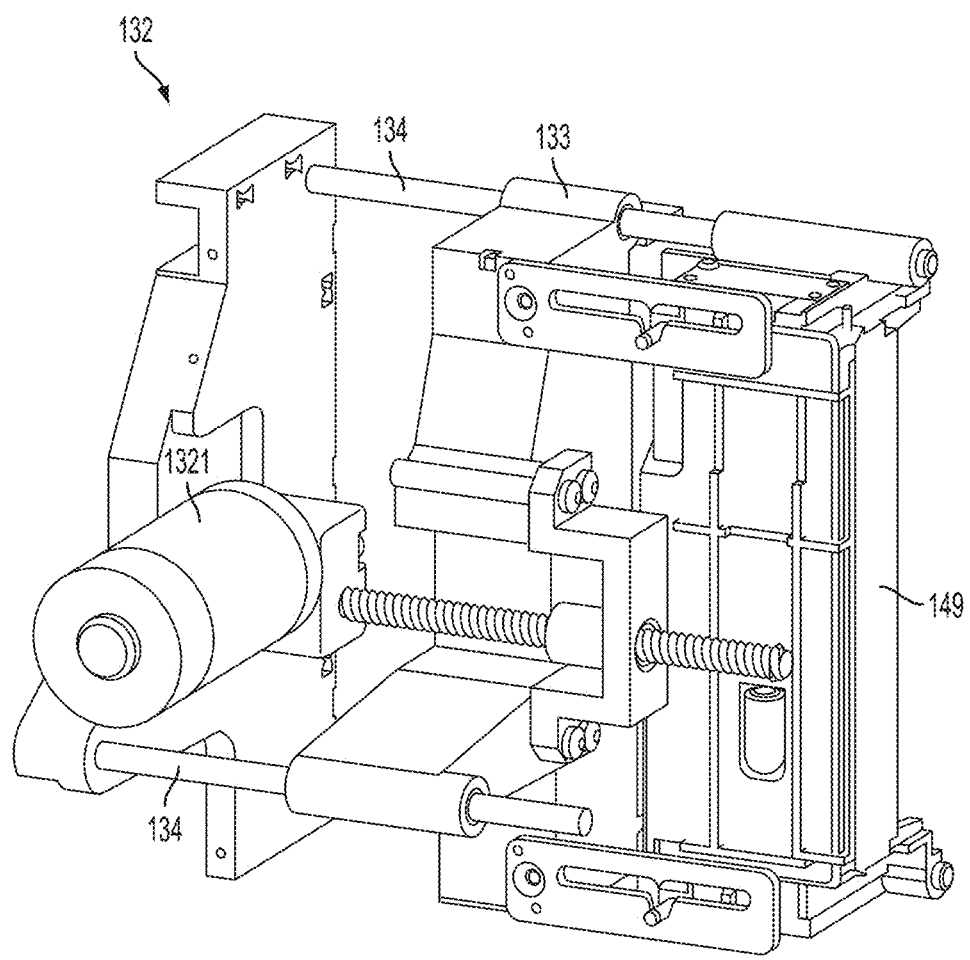
FIG. 61 is a left rear perspective view of a carriage drive assembly and cap stripper in a second illustrative embodiment.
Figure 62:
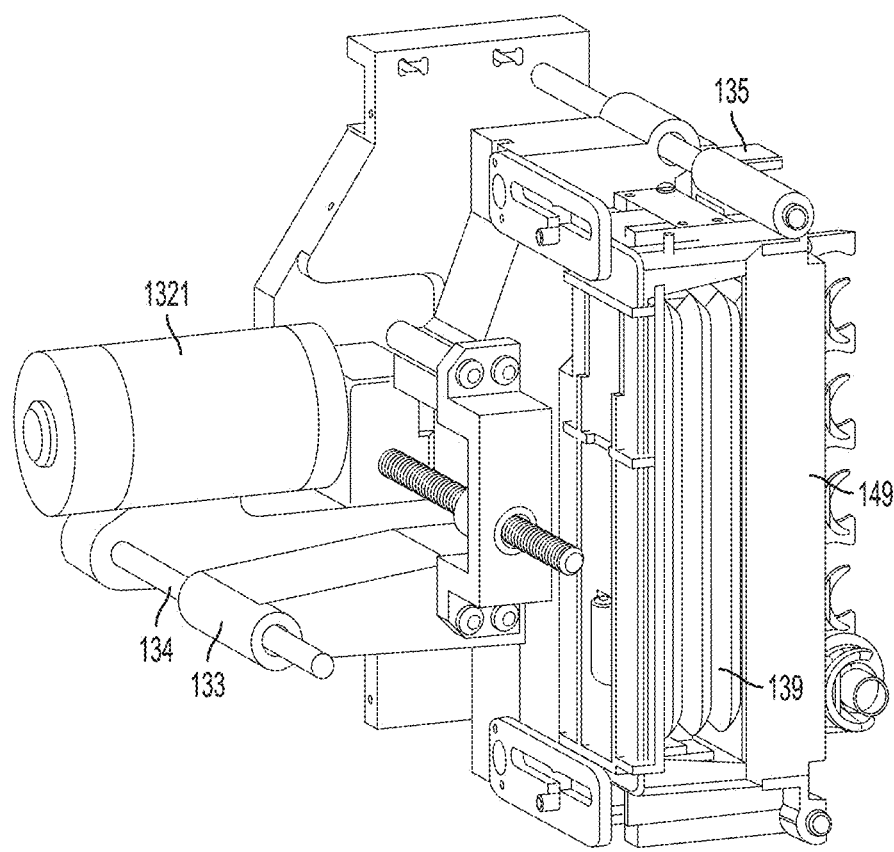
FIG. 62 is another left rear perspective view of the carriage drive assembly and cap stripper of FIG. 61.

FIG. 59 shows a left side perspective view of the carriage drive assembly 132, which more clearly shows how a stripper element of the cap stripper 149 is arranged to move in and out (a direction generally perpendicular to the rods 134) along grooves 149*a* in the housing of the cap stripper 149. Each of the semicircular cut outs of the stripper element may engage a corresponding groove of a cap 31 on a line 30 by extending forwardly when the cap 31 is appropriately positioned in front of the stripper 149 by the drive element 133 and the carriage 146. With the stripper element engaged with the caps 31, the cap stripper 149 may move with the carriage 146 as the drive element 133 moves. FIG. 60 shows a partial rear view of the carriage drive assembly 132. In this embodiment, the drive element 133 is moved toward the cassette 24 mounting location 145 by a first air bladder 137 which expands to force the drive element 133 to move to the right in FIG. 60. The drive element can be moved to the left by a second air bladder 138. Alternatively, drive element 133 can be moved back and forth by means of one or more motors coupled to a linear drive gear assembly, such as a ball screw assembly (in which the carriage drive assembly is attached to a ball nut), or a rack and pinion assembly, for example. The stripper element 1491 of the cap stripper 149 can be moved in and out of the cap stripper housing by a third bladder, or alternatively, by a motor coupled to a linear drive assembly, as described previously.

FIGS. 61-63B show another embodiment of a carriage drive assembly 132 and cap stripper 149. As can be seen in the rear view of the carriage drive assembly 132 in FIG. 61, in this embodiment the drive element 133 is moved right and left by a screw drive mechanism 1321. As can be seen in the right rear perspective view of the carriage drive assembly 132 in FIG. 62, the stripper element is moved outwardly and inwardly by an air bladder 139, although other arrangements are possible as described above.

Figure 63A:
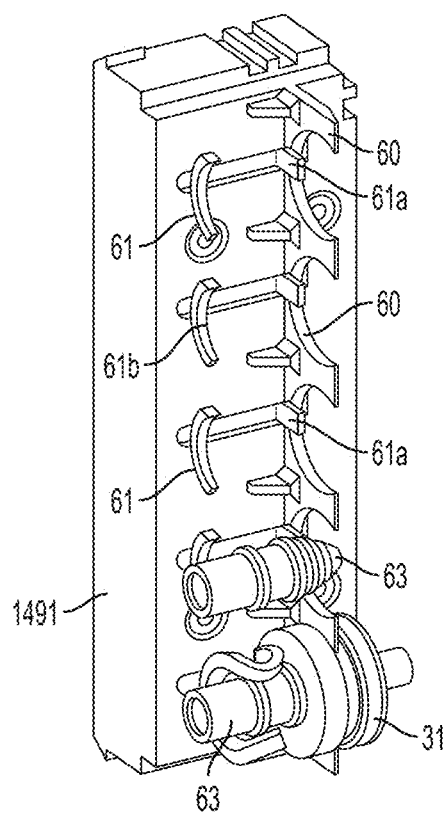
FIG. 63A is a left front perspective view of the cap stripper element of FIG. 62.
Figure 63B:
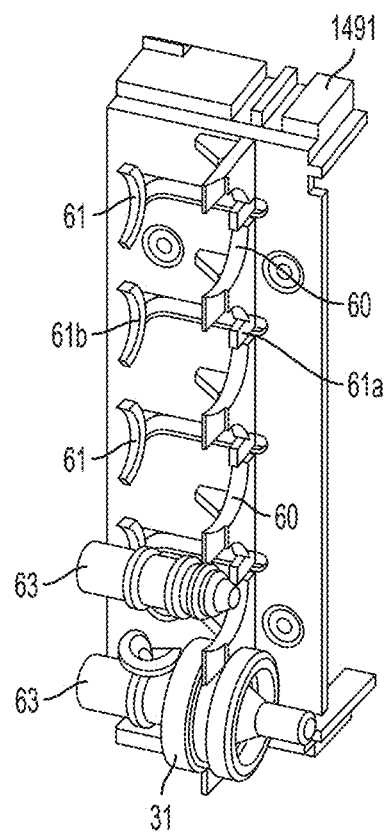
FIG. 63B is a right front perspective view of the cap stripper element of FIG. 62.

FIGS. 63A and 63B show left and right front perspective views of another embodiment for the stripper element 1491 of the cap stripper 149. The stripper element 1491 in the embodiment shown in FIG. 59 included only fork-shaped elements arranged to engage with a cap 31 of a solution line 30. In the FIGS. 63A and 63B embodiment, the stripper element 1491 not only includes the fork-shaped elements 60, but also rocker arms 61 that are pivotally mounted to the stripper element 1491. As will be explained in more detail below, the rocker arms 61 assist in removing spike caps 63 from the cassette 24. Each of the rocker arms 61 includes a solution line cap engagement portion 61*a* and a spike cap engagement portion 61*b*. The rocker arms 61 are normally biased to move so that the spike cap engagement portions 61*b* are positioned near the stripper element 1491, as shown in the rocker arms 61 in FIG. 63B. However, when a cap 31 is received by a corresponding fork-shaped element 60, the solution line cap engagement portion 61*a* contacts the cap 31, which causes the rocker arm 61 to pivot so that the spike cap engagement portion 61*b* moves away from the stripper element 1491, as shown in FIG. 63A. This position enables the spike cap engagement portion 61*b* to contact a spike cap 63, specifically a flange on the spike cap 63.

Figure 64:
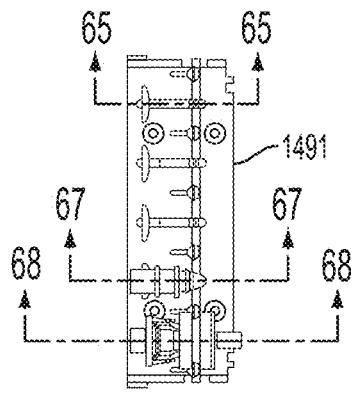
FIG. 64 is a front view of the cap stripper element of FIG. 62.
Figure 65:
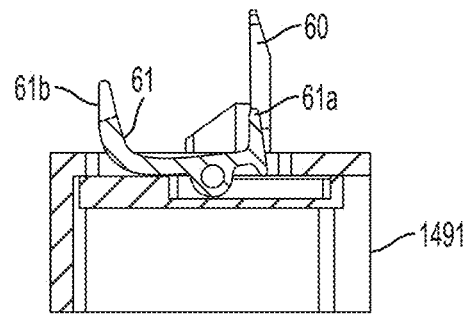
FIG. 65 is a cross sectional view along the line 65-65 in FIG. 64.
Figure 66:
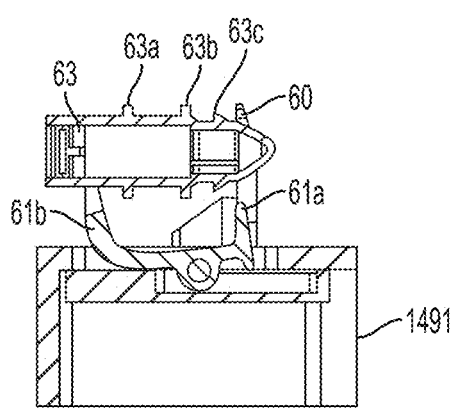
FIG. 66 is a cross sectional view along the line 66-66 in FIG. 64.
Figure 67:
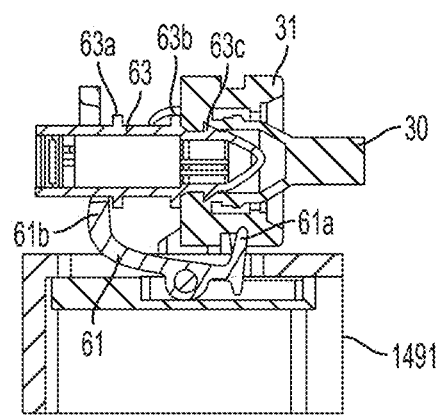
FIG. 67 is a cross sectional view along the line 67-67 in FIG. 64.

FIG. 64 shows a front view of the stripper element 1491 and the location of several cross-sectional views shown in FIGS. 65-67. FIG. 65 shows the rocker arm 61 with no spike cap 63 or solution line cap 31 positioned near the stripper element 1491. The rocker arm 61 is pivotally mounted to the stripper element 1491 at a point approximately midway between the spike cap engagement portion 61*b* and the solution cap engagement portion 61*a*. As mentioned above, the rocker arm 61 is normally biased to rotate in a counterclockwise direction as shown in FIG. 65 so that the spike cap engagement portion 61*b* is positioned near the stripper element 1491. FIG. 66 shows that the rocker arm 61 maintains this position (i.e., with the spike cap engagement portion 61*b* located near the stripper element 1491) even when the stripper element 1491 advances toward a spike cap 63 in the absence of a solution line cap 31 engaging with the fork-shaped element 60. As a result, the rocker arm 61 will not rotate clockwise or engage the spike cap 63 unless a solution line cap 31 is present. Thus, a spike cap 63 that does not engage with a solution line cap 31 will not be removed from the cassette 24.

FIG. 67 shows an example in which a solution line cap 31 is engaged with the fork-shaped element 60 and contacts the solution line cap engagement portion 61a of the rocker arm 61. This causes the rocker arm 61 to rotate in a clockwise direction (as shown in the figure) and the spike cap engagement portion 61b to engage with the spike cap 63. In this embodiment, engagement of the portion 61b includes positioning the portion 61b adjacent a second flange 63a on the spike cap 63 so that when the stripper element 1491 moves to the right (as shown in FIG. 67), the spike cap engagement portion 61b will contact the second flange 63a and help pull the spike cap 63 from the corresponding spike 160. Note that the solution line cap 31 is made of a flexible material, such as silicone rubber, to allow a barb 63c of the spike cap 63 to stretch the hole 31b of cap 31 (see FIG. 71) and be captured by a circumferential inner groove or recess within cap 31. A first flange 63b on the spike cap 63 acts as a stop for the end of solution line cap 31. In another example, the spike cap 63 does not include a first flange 63b. The walls defining the groove or recess in the cap 31 hole 31b may be symmetrical, or preferably asymmetrically arranged to conform to the shape of the barb 63c. (See FIG. 84 for a cross sectional view of the cap 31 and the groove or recess.) The second flange 63a on spike cap 63 acts as a tooth with which the spike cap engagement portion 61b of the rocker arm 61 engages in order to provide an additional pulling force to disengage the spike cap 63 from the spike 160, if necessary.

Figure 68:
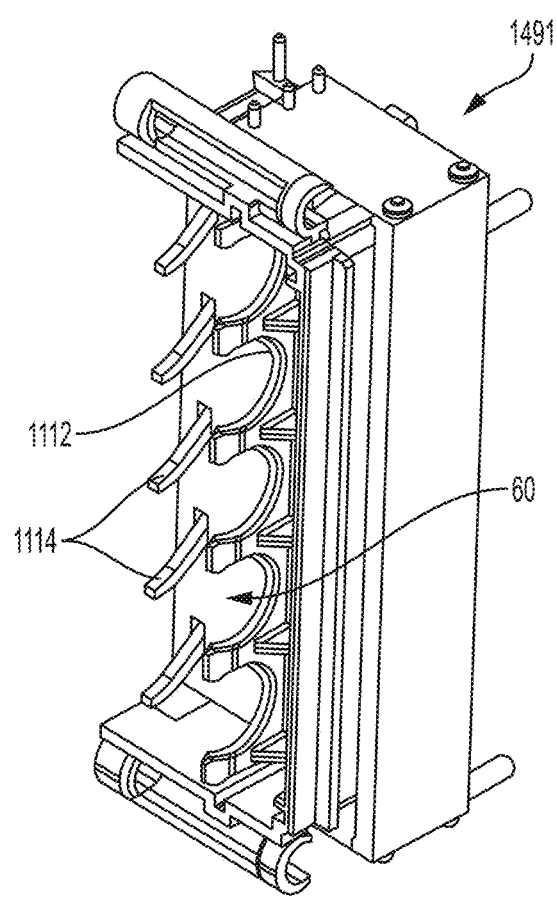
FIG. 68 is a perspective view of an embodiment for a stripper element of a cap stripper.
Figure 69:
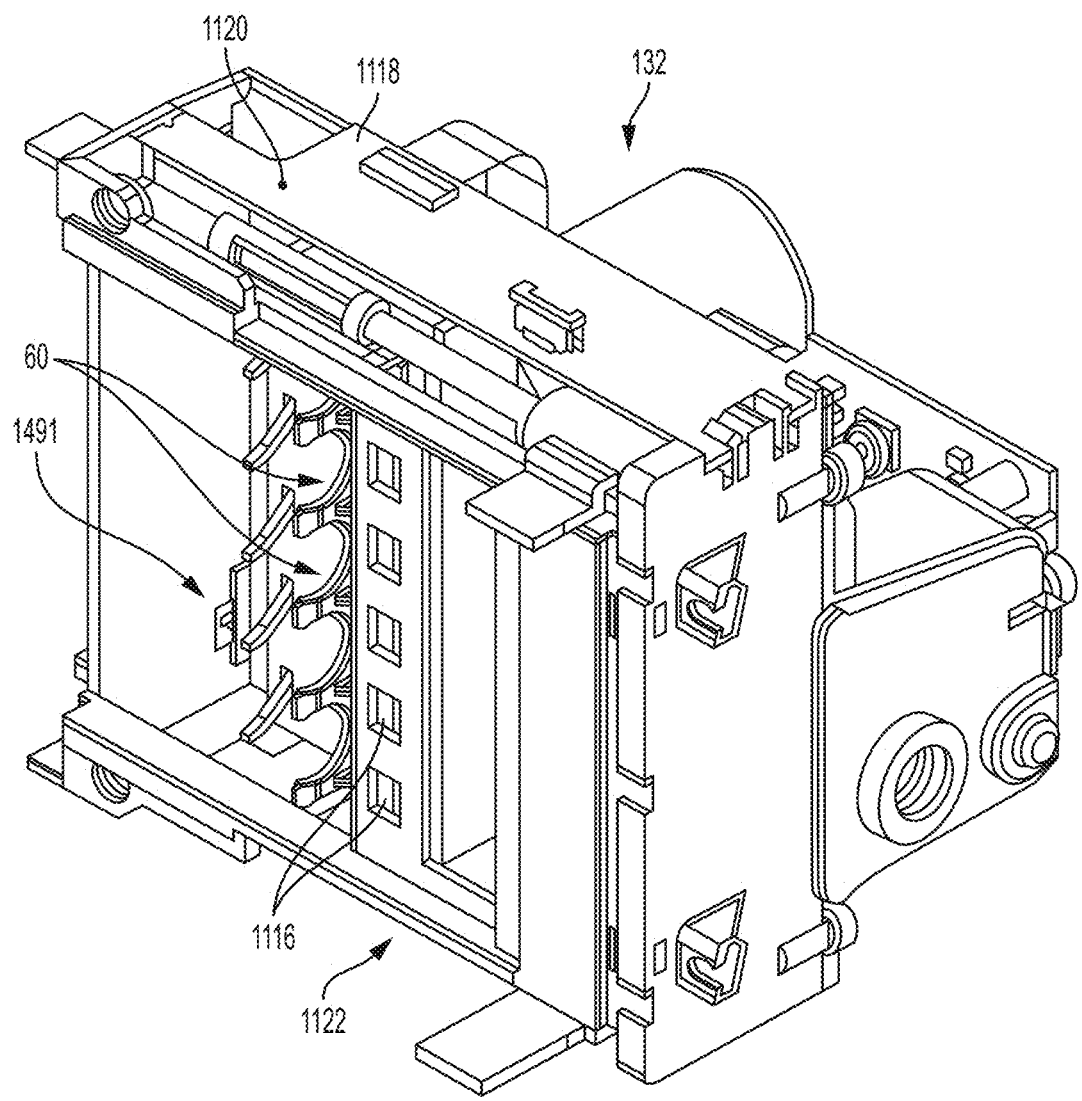
FIG. 69 is a front perspective view of the carriage drive assembly of FIG. 42 showing the position of the stripper element of FIG. 68 within the carriage drive assembly.

FIG. 68 and FIG. 69 show two different perspective views of another embodiment for the stripper element 1491 of the cap stripper 149. The stripper element 1491 in the embodiment shown in FIG. 59 uses fork-shaped elements 60 arranged to engage with a cap 31 of a solution line 30. In the embodiment shown in FIG. 68, the stripper element 1491 not only includes the fork-shaped elements 60, but may also include a plurality of sensing elements 1112, and a plurality of rocker arms 1114. The sensing elements 1112 and rocker arms 1114 may be arranged in two parallel columns that run vertically along the stripper element 1491. In an embodiment, each vertical column may contain five individual sensing elements 1112 and rocker arms 1114, each being positioned to generally align in a row corresponding with each of the fork-shaped elements 60. Each sensing element 1112 may be mechanically connected or linked to one of the corresponding rocker arms 1114. In addition, the assembly comprising each sensing element 1112 and rocker arm 1114 may include a biasing spring (not shown) that keeps each rocker arm 1114 biased toward a non-engagement position and sensing element 1112 in a position to be contacted and moved by the presence of a solution line cap 31 in fork-shaped element 60. Each sensing element 1112 can be displaced and tilted toward the back of the stripper element 1491 by contact with a corresponding solution line cap 31 in forked-shaped element 60. Through the mechanical connection between sensing element 1112 and rocker arm 1114, rocker arm 1114 can pivotally rotate or tilt laterally toward spike cap 63 upon contact between solution line cap 31 and sensing element 1112. As rocker arm 1114 rotates or tilts toward spike cap 63, it can engage second flange 63a on spike cap 63, allowing the stripper assembly to remove spike cap 63 from its corresponding spike.

Figures 70A, 70B, 70C:
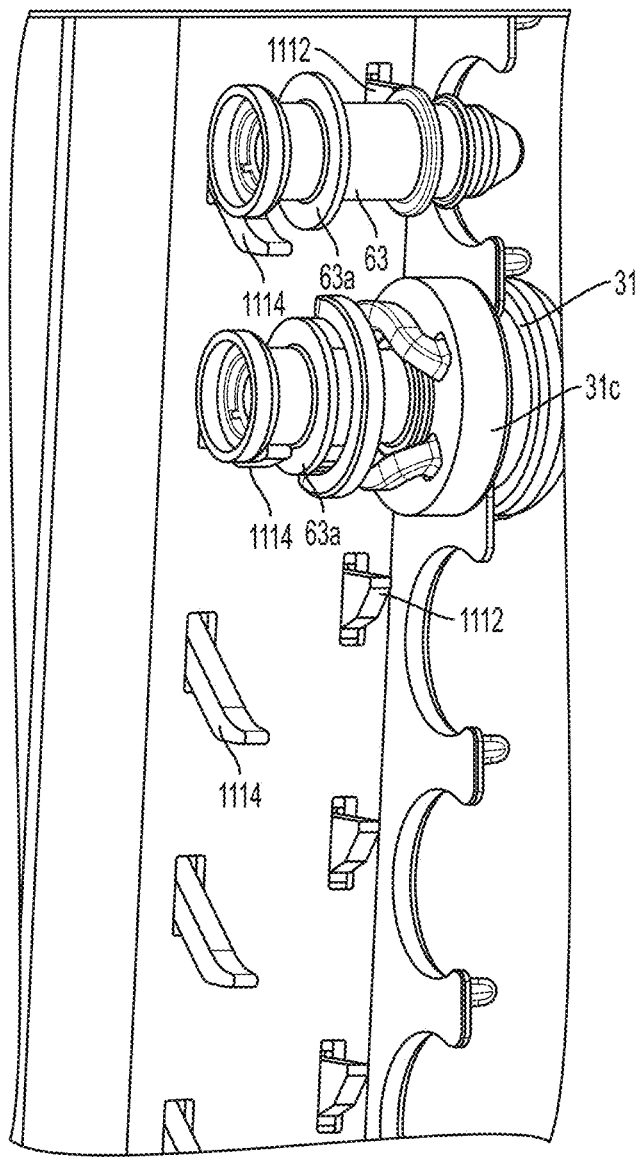
FIG. 70A is a perspective view of a portion of the stripper element of FIG. 68, in which a spike cap is positioned.
FIG. 70B is a perspective view of a portion of the stripper element of FIG. 68, in which a solution line cap is positioned over a spike cap.
FIG. 70C is a perspective view of a portion of the stripper element of FIG. 68, showing a sensor element and rocker arm in the absence of a spike cap.

FIGS. 70A-C illustrate the relationship between sensing element 1112 and a solution line cap 31, and between rocker arm 1114 and spike cap 63. FIG. 70C shows the sensing element 1112 and rocker arm 1114 in the absence of a spike cap 63 and solution line cap 31. As shown in FIG. 70B, an outer flange 31c of solution line cap 31 has a diameter sufficiently large to make contact with sensing element 1112. As shown in FIG. 70A, in the absence of a solution line cap 31, the mere presence of spike cap 63 alone does not contact sensing element 1112 sufficiently enough to displace it and cause it to rotate away from spike cap 63. As shown in FIG. 70B, the displacement of sensing element 1112 causes rotation or tilting of rocker arm 1114 toward spike cap 63, ultimately to the point of being positioned adjacent flange 63a of spike cap 63. As shown in FIG. 70A, when rocker arm 1114 is in a non-deployed position, it can clear the outer circumference of second flange 63a of spike cap 63 by a pre-determined amount (e.g., 0.040 inch). Upon movement of rocker arm 1114 into a deployed position, its range of travel may be configured so as to provide a slight compression force against its corresponding spike cap 63 to ensure a secure engagement.

Once a rocker arm 1114 is positioned adjacent flange 63a of a spike cap 63, movement of stripper element 1491 to the right will engage spike cap 63 via flange 63a and help to pull spike cap 63 from its corresponding spike 160. In the absence of a solution line and its associated solution line cap 31, stripper element 1491 will not remove the corresponding spike cap 63, keeping its associated spike 160 sealed. Thus, fewer than the maximum number of cassette spikes 161 may be accessed when fewer than the maximum number of solution lines need to be used.

Figure 71:
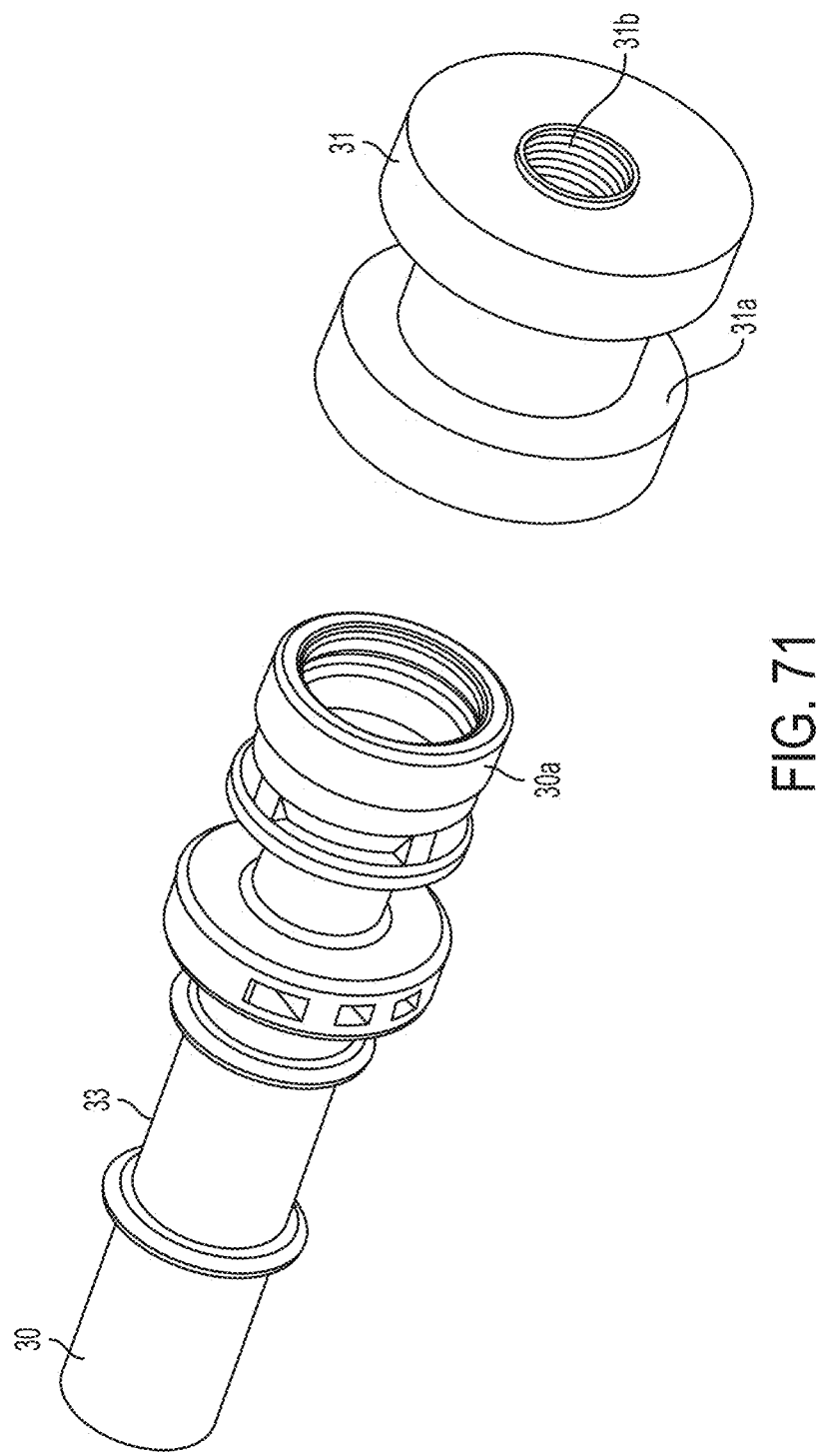
FIG. 71 is a close-up exploded view of the connector end of a solution line in an illustrative embodiment.

FIG. 71 shows a close-up exploded view of the connector end 30a of a solution line 30 with the cap 31 removed. In FIG. 71, the caps 31 are shown without a finger pull ring like that shown in FIG. 72 for clarity. A pull ring need not be present for operation of the cap 31 with the cycler 14. It may be useful, however, in allowing an operator to manually remove the cap 31 from the terminal end of solution line 30, if necessary. In this illustrative embodiment, the indicator at indicator region 33 has an annular shape that is sized and configured to fit within a corresponding slot of the carriage 146 when mounted as shown in FIGS. 37 and 38. Of course, the indicator may take any suitable form. The cap 31 is arranged to fit over the extreme distal end of the connector end 30a, which has an internal bore, seals, and/or other features to enable a leak-free connection with a spike 160 on a cassette 24. The connector end 30a may include a pierceable wall or septum (not shown—see FIG. 84 item 30b) that prevents leakage of solution in the line 30 from the connector end 30a, even if the cap 31 is removed. The wall or septum may be pierced by the spike 160 when the connector end 30a is attached to the cassette 24, allowing flow from the line 30 to the cassette 24. As discussed above, the cap 31 may include a groove 31a that is engaged by a fork-shaped element 60 of the cap stripper 149. The cap 31 may also include a hole 31b that is arranged to receive a spike cap 63. The hole 31b and the cap 31 may be arranged so that, with the cap stripper 149 engaged with the groove 31a and the spike cap 63 of a spike 160 received in the hole 31b, the cap 31 may grip the spike cap 63 suitably so that when the carriage 146/cap stripper 149 pulls the cap 31 away from the cassette 24, the spike cap 63 is removed from the spike 160 and is carried by the cap 31. This removal may be assisted by the rocker arm 61 engaging with the second flange 63a or other feature on the spike cap 63, as described above. Thereafter, the cap 31 and spike cap 63 may be removed from the connector end 30a and the line 30 attached to the spike 160 by the carriage 146.

Solution Line Connector Heater

In one embodiment, a connector heater may be provided near the indicator region 33 of the solution lines 30. The connector heater may control the temperature of the connector end 30a and in particular the pierceable wall or septum 30b in order to limit the carriage force required attach the solution lines to the spikes 160 on the cassette 24. There may be enough variation in ambient (room) temperature to affect the hardness of the pierceable wall or septum 30b of the connector end 30a of the solution line, which may in turn affect the performance of the carriage 146 in joining the spike 160 to the connector end 30a of the solution line 30. For example, at lower ambient temperatures, the increased hardness of the pierceable wall or septum 30b may require a greater force for spike 160 to penetrate it. On the other hand, at higher ambient temperatures, the pierceable wall or septum may be so soft as to deform rather than separate when contacted by the spike 160.

The temperature of the connector ends 30a may be controlled in a number of ways, which may include placing a heating element in an appropriate location (e.g., at or near location 2807 on the door 141), installing a temperature sensor to monitor the temperature of connector ends 30a, and using a controller to receive temperature data and modulate the operation of the heating element. The temperature may be measured by a temperature sensor element mounted on the stripper element 1491 or on the carriage 146. Alternatively, the temperature of the connector end 30a may be determined using an infra-red (IR) sensor tuned to measure surface temperature of the connector end 30a.

The controller may be a software process in the automation computer 300. Alternatively, the controller may be implemented in the hardware interface 310. The controller may modulate the power sent to a resistance heater, for example, in one of a number of ways. For example, the controller may send a PWM signal to a MOSFET that can modulate the flow of electrical power to the resistance heater. The controller may control the measured temperature to the desired temperature through a number of algorithms. One exemplary algorithm includes a proportional-integral (PI) feedback loop on the measured temperature to set the heater power. Alternatively, the heater power can be modulated in an open loop algorithm that sets the heater power based on the measured ambient temperature.

In another embodiment, the temperature of the connector end 30a may be controlled by mounting a radiant heater in the door 141 at location 2807, for example, and aimed at the connector ends. Alternatively, the temperature of the connector ends may be controlled by mounting a thermo-electric element at location 2807, for example, on the door 141. The thermo-electric element may provide either heating or cooling to the area surrounding the connector ends when mounted on the carriage 146. The radiant heater or thermo-electric element may be modulated by a controller to maintain the temperature within a given range. The preferred temperature range for the connector end 30a depends on the material comprising the pierceable wall or septum, and may be determined empirically. In one embodiment, the piercable wall is PVC and the preferred temperature range is set at about 10° C. to 30° C., or more preferably to a temperature range of about 20° C. to 30° C.

In an embodiment, the connector heater near the indicator region 33 may be used after the door is closed and before the solution lines 30 are attached to the cassette 24. The automation computer 300 or a controller enables the connector heater if the measured temperature near the connector 30a is outside a preferred range. The automation computer 300 or a controller may delay the auto-connection process until the measured temperature is within the preferred range. The connector heater may be disabled after the auto-connection process is completed.

Set Loading and Operation

Once treatment is complete, or the line 30 and/or the cassette 24 are ready for removal from cycler 14, the cap 31 and attached spike cap 63 may be re-mounted on the spike 160 and the line 30 before the door 141 is permitted to be opened and the cassette 24 and line 30 removed from the cycler 14. Alternatively, the cassette 24 and solution containers with lines 30 can be removed en bloc from cycler 14 without re-mounting cap 31 and the attached spike cap 63. An advantage of this approach includes a simplified removal process, and avoidance of any possible fluid leaks onto the cycler or surrounding area from improperly re-mounted or inadequately sealing caps.

Figure 72:
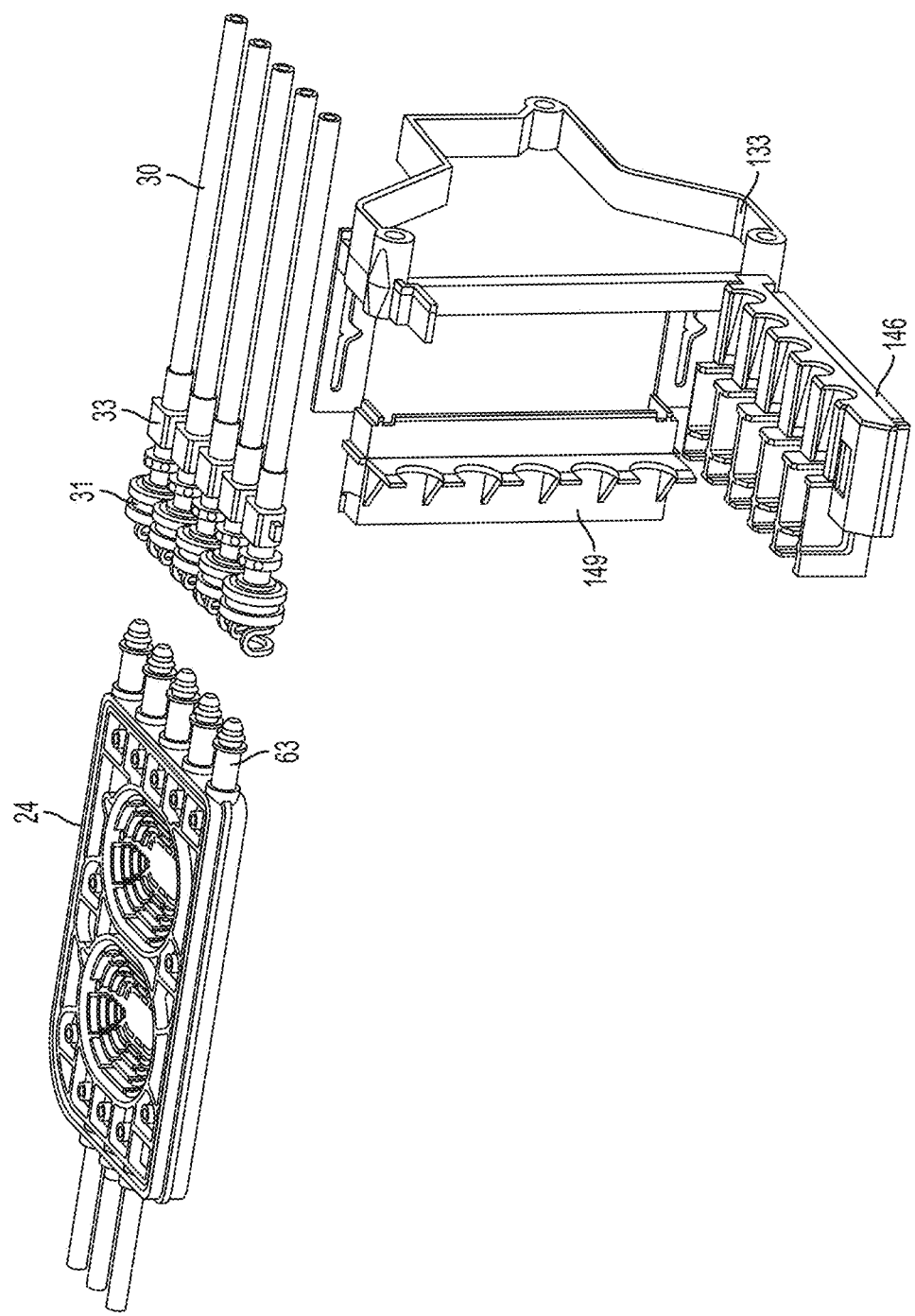
FIG. 72 is a schematic view of a cassette and solution lines being loaded into the cycler of FIG. 37.
Figure 73:
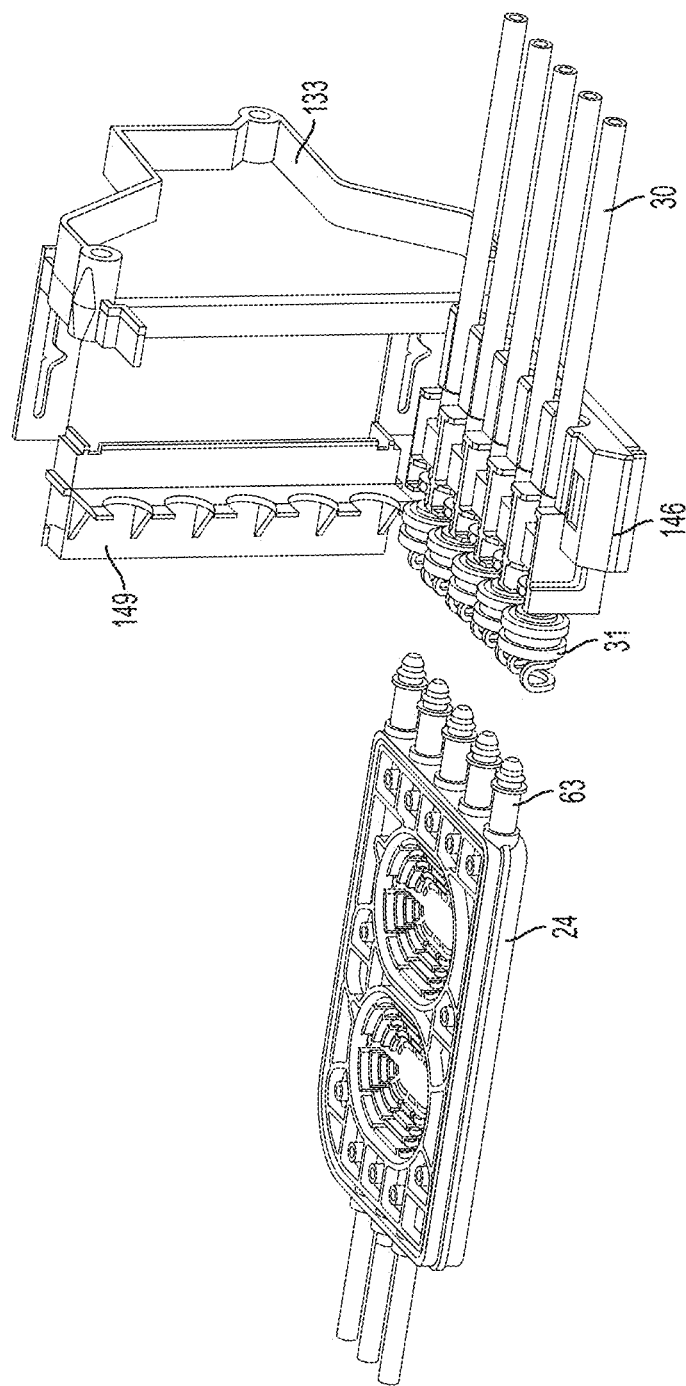
FIG. 73 is a schematic view of the cassette and solution lines after placement in respective locations of the door of the cycler of FIG. 37.
Figure 74:
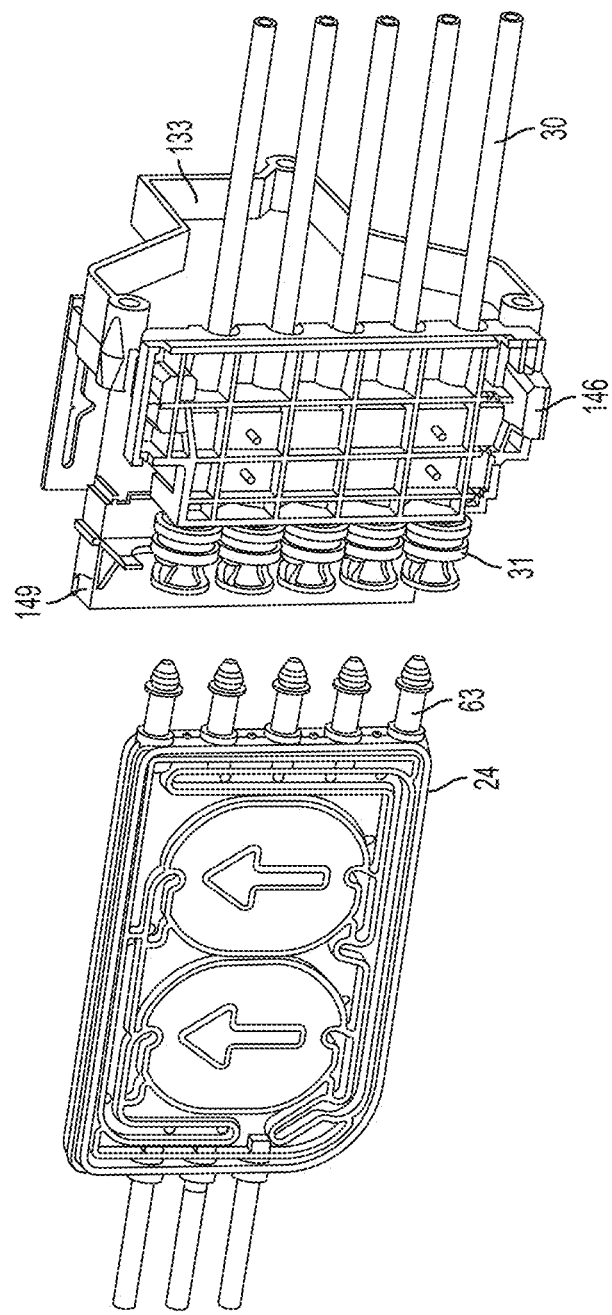
FIG. 74 is a schematic view of the cassette and solution lines after the door of the cycler is closed.
Figure 75:
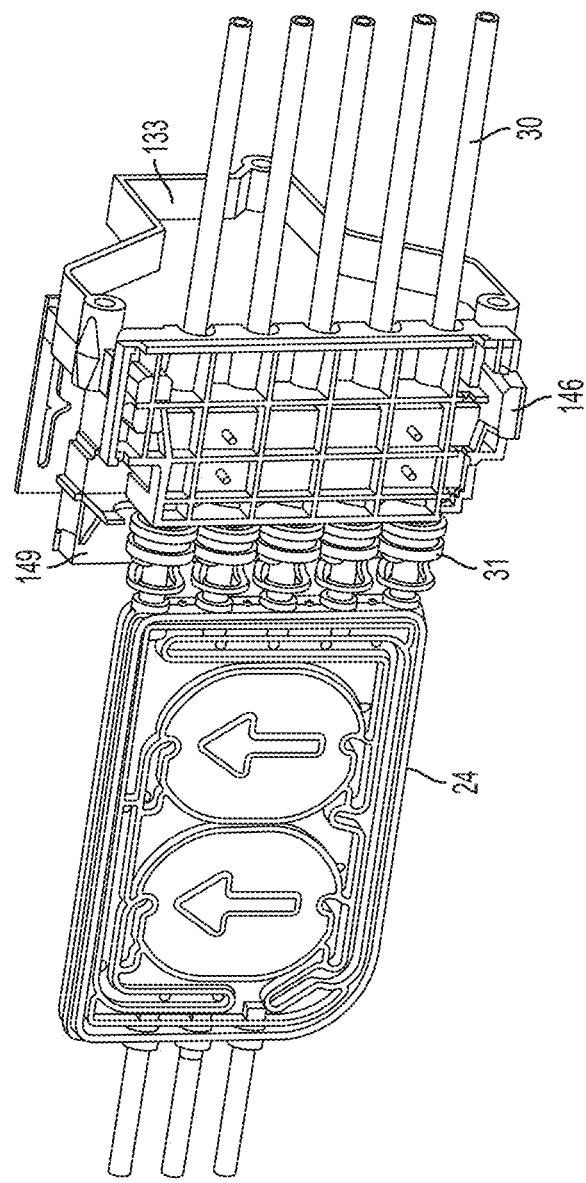
FIG. 75 is a schematic view of the solution lines being engaged with spike caps.
Figure 76:
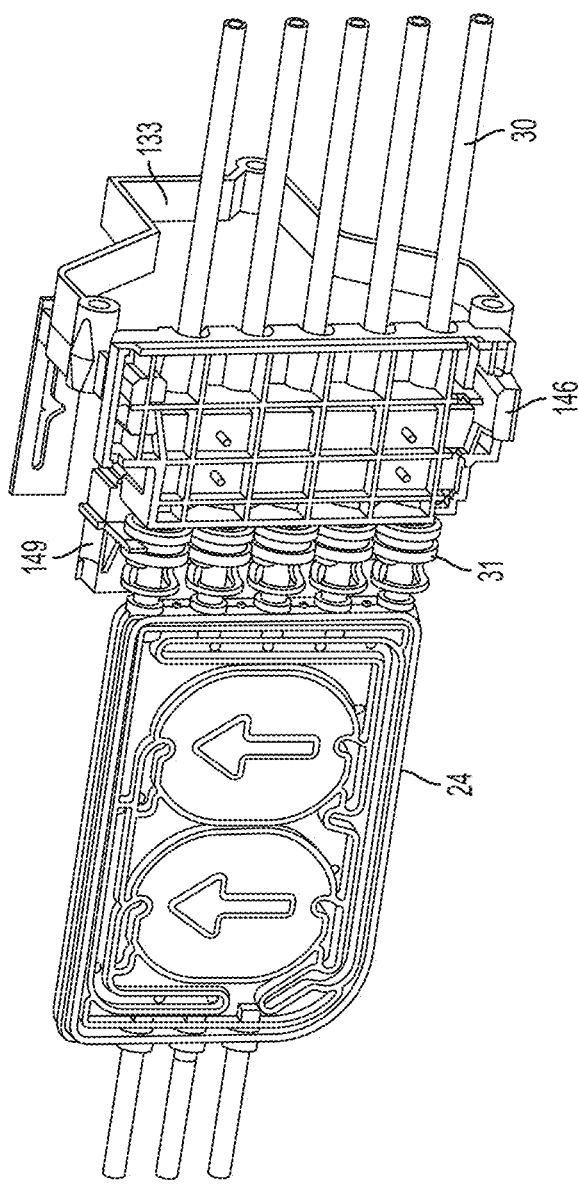
FIG. 76 is a schematic view of the cap stripper engaging with spike caps and solution line caps.
Figure 77:
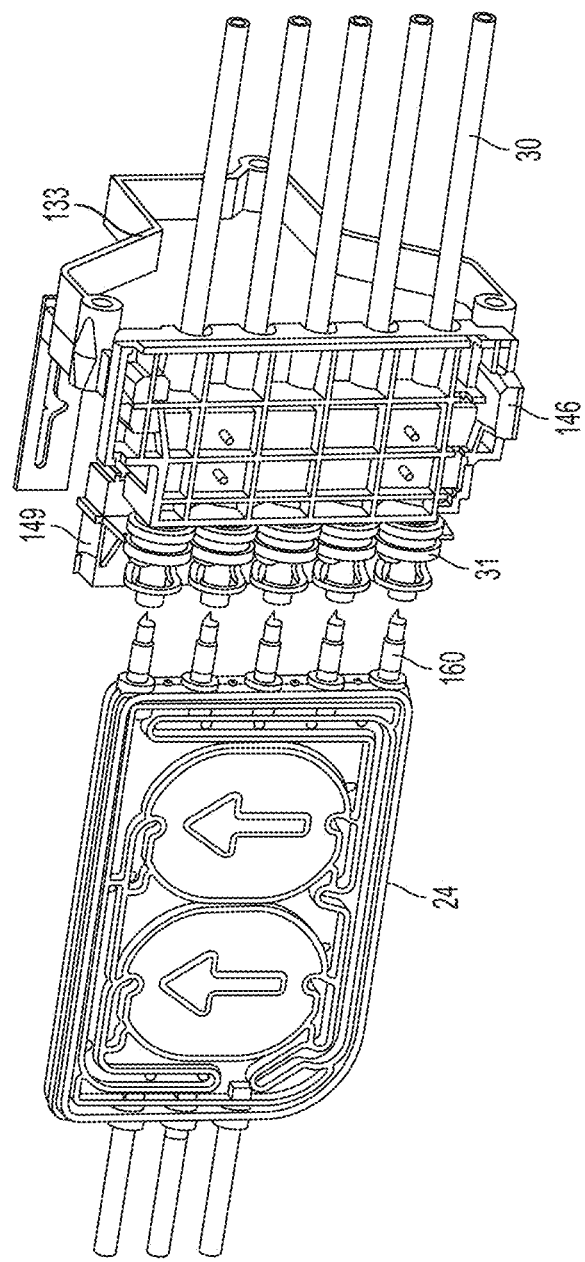
FIG. 77 is a schematic view of the solution lines with attached caps and spike caps after movement away from the cassette.
Figure 78:
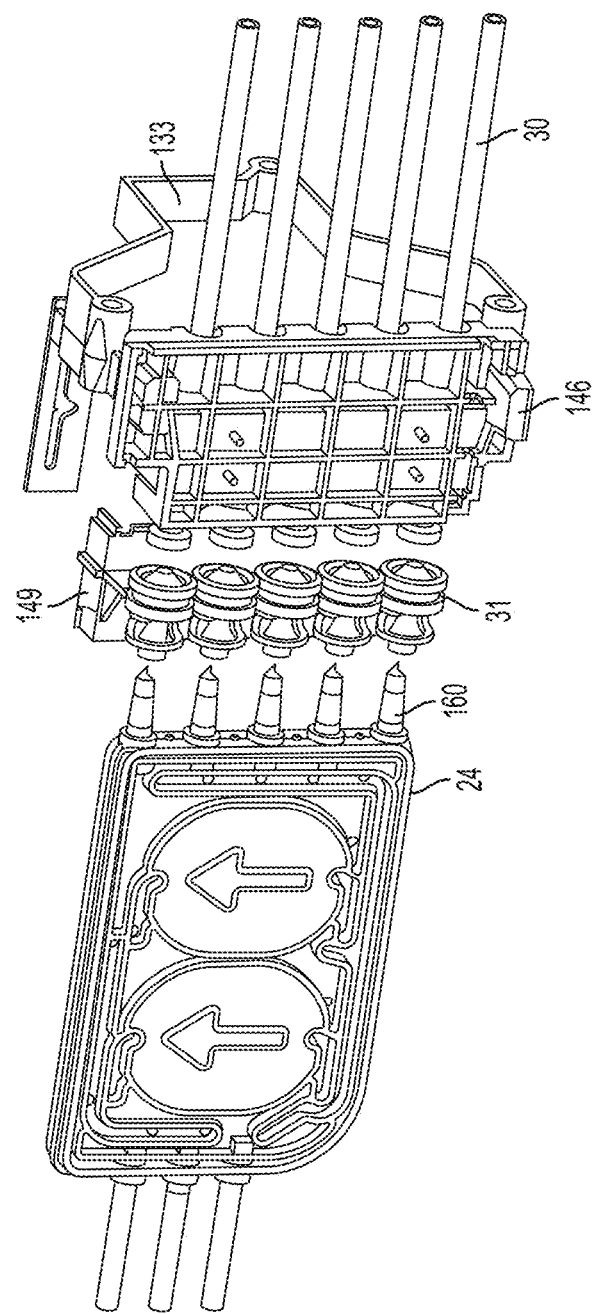
FIG. 78 is a schematic view of the solution lines after movement away from the solution line caps and spike caps.
Figure 79:
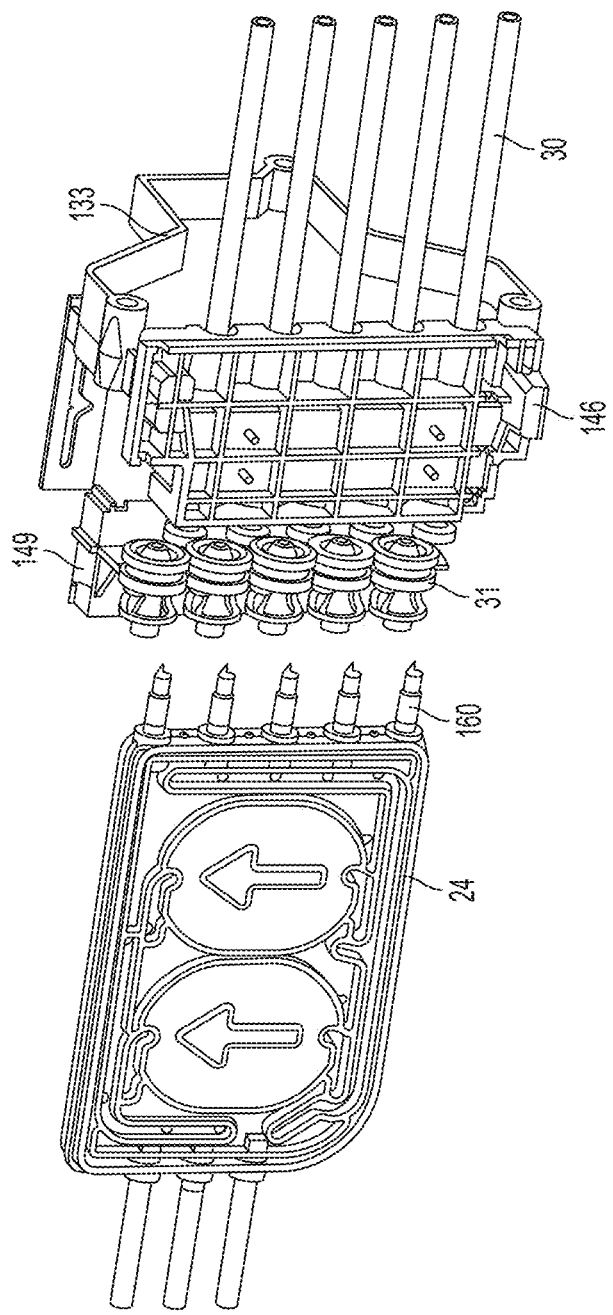
FIG. 79 is a schematic view of the cap stripper retracting with the solution line caps and spike caps.
Figure 80:
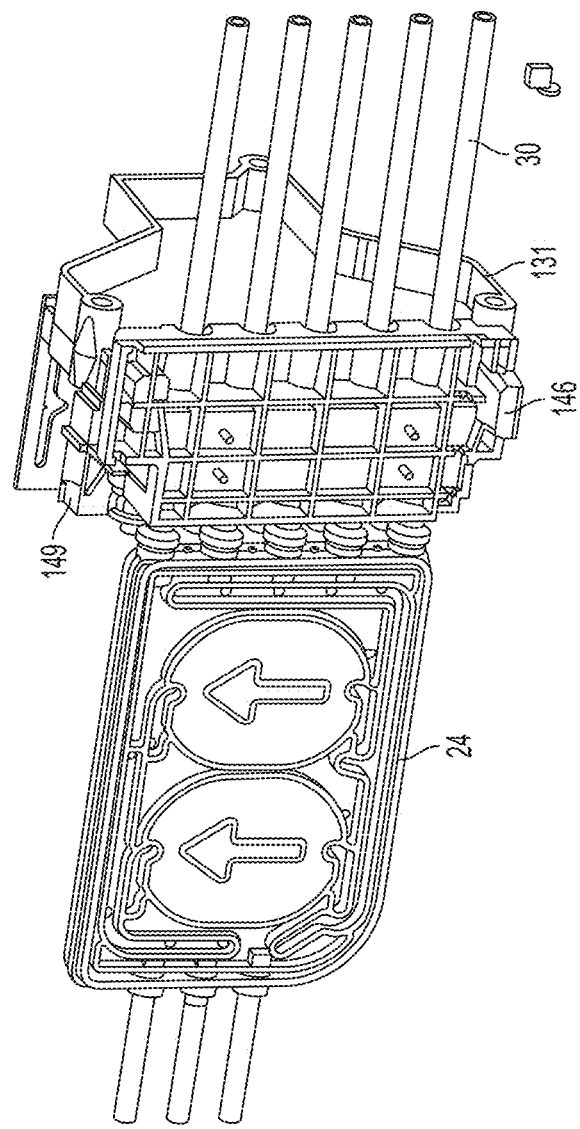
FIG. 80 is a schematic view of the solution lines being engaged with the spikes of the cassette.

FIGS. 72-80 show a perspective view of the carriage 146, cap stripper 149 and cassette 24 during a line mounting and automatic connection operation. The door 141 and other cycler components are not shown for clarity. In FIG. 72, the carriage 146 is shown in a folded down position, as if the door 141 is open in the position shown in FIG. 8. The lines 30 and cassette 24 are positioned to be lowered onto the door 141. In FIG. 73, the lines 30 are loaded into the carriage 146 and the cassette 24 is loaded into the mounting location 145. At this point the door 141 can be closed to ready the cycler for operation. In FIG. 74, the door 141 is closed. Identifiers or indicators located at indicator region 33 on the lines 30 may be read to identify various line characteristics so that the cycler 14 can determine what solutions, how much solution, etc., are loaded. In FIG. 75, the carriage 146 has moved to the left, engaging the caps 31 on the lines 30 with corresponding spike caps 63 on the cassette 24. During the motion, the drive element 133 engages the cap stripper 149 and moves the cap stripper 149 to the left as well. However, the cap stripper 149 remains in a retracted position. In FIG. 76, the cap stripper 149 moves forward to engage the fork-shaped elements 60 with the caps 31, thereby engaging the caps 31 that have been coupled to the spike caps 63. If present, the rocker arms 61 may move to an engagement position with respect to the spike caps 63. Next, as shown in FIG. 77, the carriage 146 and the cap stripper 149 move to the right, away from the cassette 24 so as to pull the caps 31 and spike caps 63 from the corresponding spikes 160 on the cassette 24. It is during this motion that the rocker arms 61, if present, may assist in pulling spike caps 63 from the cassette 24. In FIG. 78, the cap stripper 149 has stopped its movement to the right, while the carriage 146 continues to move away from the cassette 24. This causes the connector ends 30a of the lines 30 to be pulled from the caps 31, leaving the caps 31 and spike caps 63 mounted on the cap stripper 149 by way of the fork-shaped elements 60. In FIG. 79, the cap stripper 149 retracts, clearing a path for the carriage 146 to move again toward the cassette 24. In FIG. 80, the carriage 146 moves toward the cassette 24 to engage the connector ends 30a of the lines 30 with the corresponding spikes 160 of the cassette 24. The carriage 146 may remain in this position during cycler operation. Once treatment is complete, the movements shown in FIGS. 72-80 may be reversed to recap the spikes 160 and the solution lines 30 and remove the cassette 24 and/or lines 30 from the cycler 14.

The cycler can be configured to verify that all caps 31 have been removed from the cap stripper 149 before any attempt is made to start a new therapy using the cycler. In an embodiment, this may be performed before a new cassette and solution line set have been installed in the cycler—either at the end of a therapy or during the startup period preceding a new therapy. Alternatively or additionally, a residual cap detection procedure can be performed after the installation of a new cassette and solution line set, but preferably before any cassette spike caps have been engaged with solution line caps.

The cap detection system comprises a sensor to detect the position of the cap stripper relative to a plane in which an installed cassette and set of one or more solution lines reside when mounted in the cycler. Movement of the cap stripper forward or aft (i.e. toward or away from the plane) can be monitored by a cycler controller using a position sensor (e.g., Hall sensor). If a solution line cap/spike cap has not been removed from the cap stripper by the user, its presence will interfere with movement of the cap stripper toward the plane to a pre-determined position corresponding to full deployment of the cap stripper. The presence of a cap on the cap stripper, interfering with full deployment of the cap stripper toward the plane can cause the controller to issue an alert to the user. If one or more solution lines have been mounted in the cycler, the interference will likely be between the remaining one or more caps on the cap stripper and the one or more caps of the solution lines. If no solution lines have been mounted in the cycler, the controller can command the cap stripper to move laterally in a direction parallel to the plane to a point at which a raised feature of the carriage (e.g., walls 5510*a* or 5510*b*) provided an interference with any remaining cap in the cap stripper during a commanded movement of the cap stripper toward the plane.

In an embodiment, position sensors for the cap stripper 149 are configured to detect the extent of forward deployment of the cap stripper toward the carriage when the door 141 is closed. After the door 141 is closed (FIG. 74) and before any lateral movement of the carriage 146, the cycler controller initiates a forward deployment of the cap stripper 149. The position of the cap stripper 149 may be monitored by one or more displacement sensors or by a camera aimed at the appropriate location. For example, one or more Hall effect sensors can be configured to sense a magnet embedded in or attached to the cap stripper 149. If one or more cap(s) 31 from a previous mounting operation remain in the cap stripper 149, the leftover cap 31 will be pushed against a newly installed solution line and cap 31 on the carriage 146, preventing the cap stripper 149 from displacing to a fully deployed position. If no new cassette or solution line set have been installed, the cycler controller can direct the movement of the carriage 146 laterally to a pre-determined location that causes one or more features of the carriage 146 to act as an interference element against a residual cap 31 on the cap stripper 149, but that allows the cap stripper 149 to fully deploy if it is not holding a residual cap 31. In some embodiments, the cap stripper 149 may be required to move beyond a predetermined threshold location for the auto-connect process to be allowed to continue. The predetermined threshold location may be chosen such that it is sufficiently beyond the point at which deployment of the cap stripper 149 would be impeded if a leftover cap 31 is present.

The Hall effect sensor may be installed in a location that is protected, separate, partitioned from, or fluidically isolated from the cap stripper 149 while still being able to sense a magnet on the cap stripper 149.

If the cap stripper 149 is deployed by means of an inflatable bladder, the bladder can optionally not be inflated to maximum pressure when checking for leftover caps 31. Instead an inflation pressure need only be sufficient to cause to cap stripper 149 to displace toward the carriage 146, but less than a pressure needed to actually engage a solution line cap installed in the carriage. This pressure may, for example, be a predetermined pressure; or it may be variable, reaching a level necessary to move the cap stripper 149. In such embodiments, once the position sensor detects movement the controller may either cease bladder inflation or limit inflation pressure. In some embodiments, the controller may require the cap stripper 149 to deploy by a predetermined amount before the bladder inflation pressure is limited.

In embodiments in which a mechanism other than an inflatable bladder is used to move the cap stripper 149, other devices may be introduced to limit the force applied by the deployment mechanism during this pre-therapy cap detection test. For example, a torque or pressure sensor or strain gauge may be connected to a gear and motor assembly to feed back similar information to the controller to limit the force applied by the assembly.

Other position sensors may be used, including but not limited to, an optical sensor, contact sensor (e.g. microswitch), rangefinding sensor, etc. In other embodiments, the cycler may use sensing elements 1112 (see, for example, FIG. 68) to determine if caps 31 are present in the cap stripper 149. A camera can be used to identify a characteristic of a cap 31 on the cap stripper 149, such as its shape, color, opacity, light absorption or reflection characteristics, etc.

Figure 81:
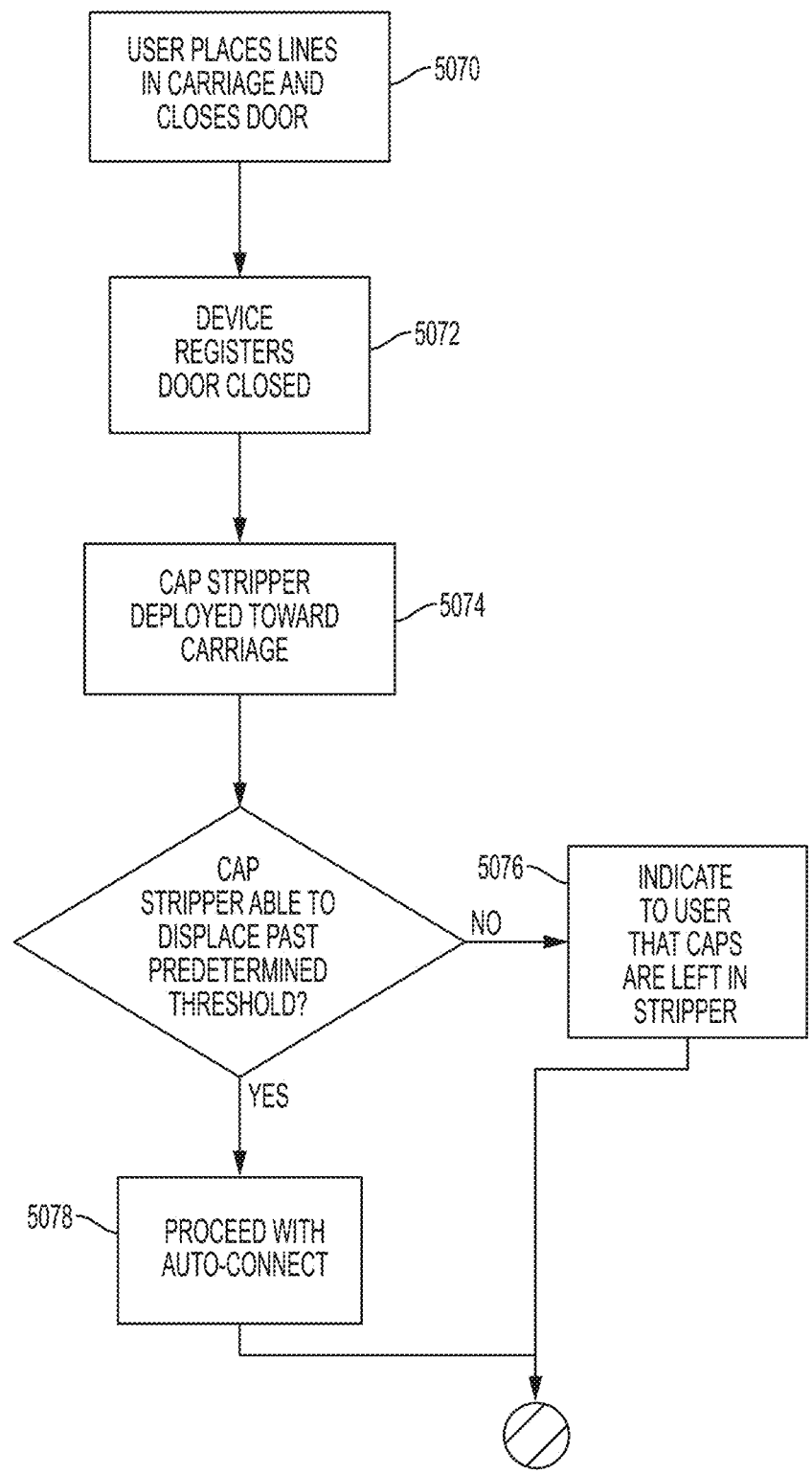
FIG. 81 depicts a flowchart detailing a number of example steps which may be used to detect the presence of leftover caps in a cap stripper.

FIG. 81 depicts a flowchart detailing an example of a number of steps that may be used to detect the presence of leftover caps 31 in a cap stripper 149. The steps shown in FIG. 81 detect the presence of leftover caps 31 by deploying the cap stripper 149 and monitoring its displacement. Additionally, the flowchart shown in FIG. 81 checks for the presences of caps 31 in the cap stripper 149 after a set has been installed in the cycler. The test may be performed before and/or after a cassette and solution lines have been installed.

As shown, in step 5070, a user may place the solution lines in the carriage 146 and close the door of the cycler. In step 5072, the cycler may register that the door of the cycler has been closed. After the cycler registers that the door has been closed, the cycler may deploy the cap stripper 149 toward the carriage 146 in step 5074.

The procedure may be performed before installation of a new cassette and solution line set. In such an embodiment, the steps 5070 and 5072 may not be performed. Instead, a step in which the carriage 149 is moved laterally to a pre-determined position may be performed. The predetermined position may be selected such that the carriage 149 acts as an interference element for the cap-bearing cap stripper 149.

Figure 82:
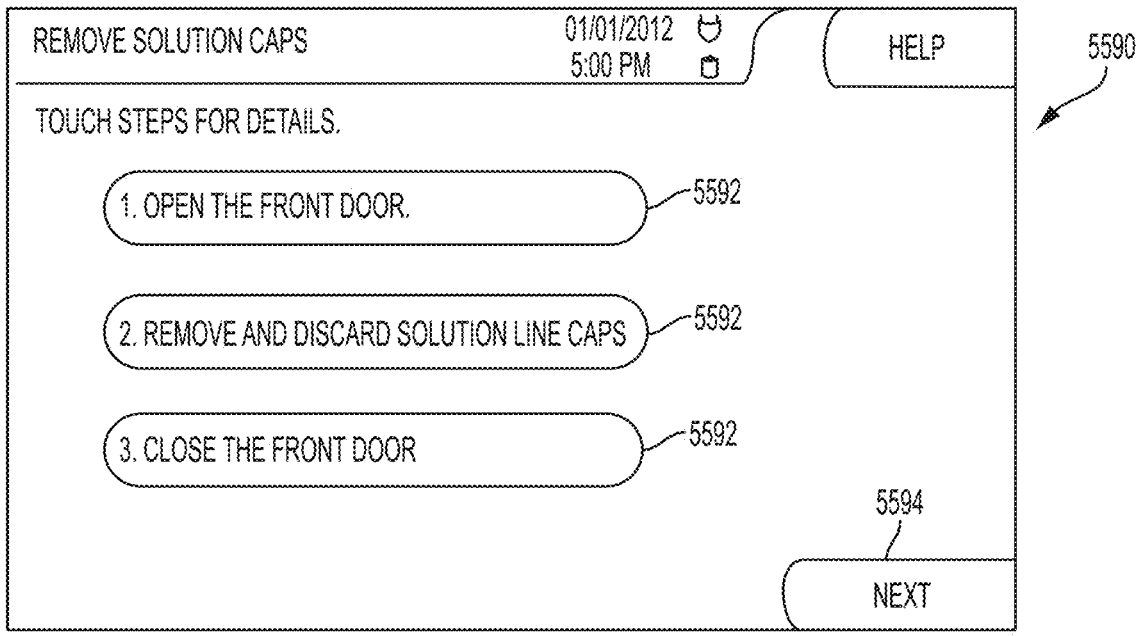
FIG. 82 depicts an example screen which may be generated for display on a user interface of a cycler by a processor of the cycler the displays instructions on how to remove caps from a cap stripper.

The cycler may then check to see if the cap stripper 149 is able to displace past a predetermined threshold location. In the event that the cap stripper 149 is unable to displace beyond the predetermined location, a user may be notified of the presence of caps 31 left in the cap stripper 149 in step 5076. If the cap stripper 149 is able to displace beyond the predetermined threshold, a cycler may proceed with later steps of a solution line connection process in step 5078. In this step, the cycler may, for example, connect the cassette spike caps to the solution line caps installed in the carriage. FIG. 82 depicts an example screen shot 5590 which may be generated for display on a user interface of a cycler by a processor of the cycler. The example screen 5590 shown in FIG. 82 may, for example, be displayed in step 5076 of FIG. 81. As shown, the example screen 5590 informs a user that there are solution line caps present in the cap stripper of the cycler. The screen 5590 also includes instructions on how to remove the solution line caps from the cap stripper. In the example embodiment, the instructions are text instructions, though in other embodiments, the instructions may include any combination of text, graphics, and/or animations.

The instructions are divided into a number of steps which may be associated with user selectable buttons 5592 on the user interface. For example, the user interface of the cycler may be a touch screen. A user may touch, tap, double tap, etc. one of the selectable buttons 5592 on the screen 5590 to get more detailed instructions on how to perform the associated step. For example, when the processor of the cycler detects that a user has interacted with one of the buttons 5592, the processor may generate a message for display on the screen 5590 with additional detail, or may display a new screen with additional information. Alternatively, when the processor of the cycler detects that a user has interacted with one of the buttons 5592, the processor may generate another screen for display that provides additional detail.

The screen 5590 also includes a next button 5594. A user may interact with the next button 5594 to inform the processor of the cycler that the residual caps have been removed from the cap stripper. In some embodiments, the cycler may re-check for caps to verify that they have been removed from the cap stripper. Optionally, the next button may be disabled until the cycler processor detects that the door of the cycler has been opened and closed.

Figure 83:
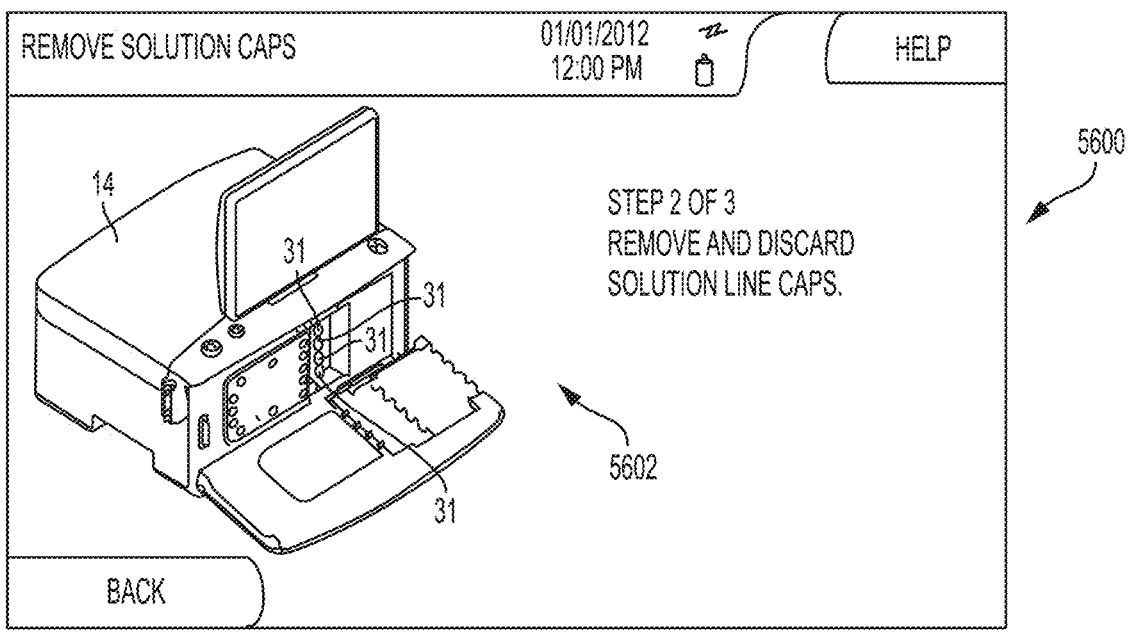
FIG. 83 depicts an example screen which may be generated for display on a user interface of a cycler by a processor of the cycler that displays instructions on how to remove caps from a cap stripper.

FIG. 83 depicts an example screen 5600 which may be generated for display on a user interface of a cycler by a processor of the cycler. The example screen 5600 shown in FIG. 83 may for example, be displayed in response to a user interacting with the button 5592 labeled "Remove and discard solution line caps." in FIG. 82. The example screen 5600 includes text describing how the user may complete the step. Additionally, the example screen 5600 includes a graphic 5602 of a cycler 14. The graphic 5602 may indicate to a user where the solution line cap 31 or caps 31 are located. In some embodiments, the screen 5600 may optionally include an animation which demonstrates to the user how to remove the solution line caps 31.

Figure 84:
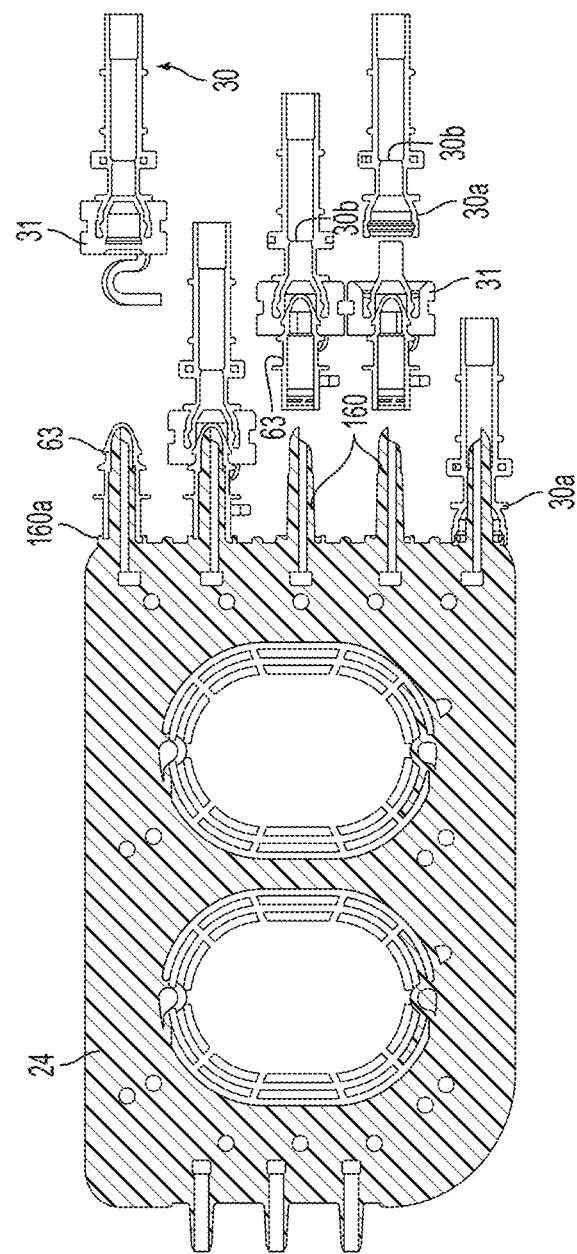
FIG. 84 is a cross sectional view of a cassette with five stages of a solution line connection operation shown with respect to corresponding spikes of the cassette.

To further illustrate the removal of caps 31 and spike caps 63, FIG. 84 shows a cross-sectional view of the cassette 24 at five different stages of line 30 connection. At the top spike 160, the spike cap 63 is still in place on the spike 160 and the solution line 30 is positioned away from the cassette 24, as in FIG. 74. At the second spike 160 down from the top, the solution line 30 and cap 31 are engaged over the spike cap 63, as in FIGS. 75 and 76. At this point, the cap stripper 149 may engage the cap 31 and spike cap 63. At the third spike 160 from the top, the solution line 30, cap 31 and spike cap 63 have moved away from the cassette 24, as in FIG. 77. At this point, the cap stripper 149 may stop movement to the right. At the fourth spike 160 from the top, the solution line 30 continues movement to the right, removing the cap 31 from the line 30, as in FIG. 78. Once the caps 31 and 63 are retracted, the solution line 30 moves to the left to fluidly connect the connector end 30a of the line 30 to the spike 160, as in FIG. 80.

Various sensors can be used to help verify that the carriage 146 and cap stripper 149 move fully to their expected positions. In an embodiment, the carriage drive assembly 132 can be equipped with six Hall effect sensors (not shown): four for the carriage 146 and two for the cap stripper 149. A first cap stripper sensor may be located to detect when the cap stripper 149 is fully retracted. A second cap stripper sensor may be located to detect when the cap stripper 149 is fully extended. A first carriage sensor may be located to detect when the carriage 146 is in the "home" position, i.e. in position to permit loading the cassette 24 and lines 30. A second carriage sensor may be located to detect when the carriage 146 is in position to have engaged the spike caps 63. A third carriage sensor may be located to detect when the carriage 146 has reached a position to have removed the caps 31 from the lines 30. A fourth carriage sensor may be located to detect when the carriage 146 has moved to a position to have engaged the connector ends 30a of the lines 30 with the corresponding spikes 160 of the cassette 24. In other embodiments, a single sensor can be used to detect more than one of the carriage positions described above. The cap stripper and carriage sensors can provide input signals to an electronic control board ("autoconnect board"), which in turn can communicate specific confirmation or error codes to the user via the user interface 144.

FIG. 69 shows a perspective view of an alternative embodiment of the carriage drive assembly 132. The carriage drive assembly 132 in the embodiment shown in FIG. 58 included only the drive element 133, the rods 134, the tabs 135 and the window 136. In the FIG. 69 embodiment, the carriage drive assembly 132 not only includes the drive element 133, the rods 134, the tabs 135, and the window 136, but may also include a vertical column of AutoID view boxes 1116. The view boxes 1116 may be positioned directly adjacent to the window 136. Also, the view boxes 1116 may be positioned and shaped so that the horizontal axis of each of the five slots 1086 located on the carriage 146 run through the center of a corresponding view box 1116, when the carriage 146 moves either right or left along the guides 130. The view boxes 1116 may allow for the AutoID camera 1104, which is attached to the camera board 1106, to detect if the solution line caps 31 are positioned on the lines 30 prior to the engaging of the solution lines with the spike cap 63. Alternatively, in some embodiments, the individual view boxes may not be necessary. Instead, the window 136 may be enlarged so that the caps 31 may be seen through the single window 136. Checking for the solution line 30 caps 31 may allow for confirmation that the user hasn't removed the caps 31 prematurely. Once the presence or absence of the caps 31 is determined, the camera 1104 can provide a corresponding input signal to an electronic control board (referred to as the autoconnect board later in the specification), which in turn can communicate specific confirmation or error codes, relating to the presence of the caps 31 on the lines 30, to the user via the user interface 144.

In accordance with another aspect of the disclosure, the carriage drive assembly 132 may include an autoconnect board 1118. The autoconnect board 1118 may be attached to the top of the carriage drive assembly 132, and may extend the entire length of the assembly 132. In this illustrative embodiment, there may also be an LED 1120 mounted to the autoconnect board 1118. The LED 1120 may be located in a fixed position directly above the fork-shaped elements 60. Also, the LED 1120 may be directed is a fashion so that the light being emitted from the LED 1120 travels downward across the stripper element 1491. In accordance with another aspect of the present disclosure, the carriage drive assembly 132 may also include a fluid board 1122. The fluid board 1122 may be attached to the bottom of the carriage drive assembly 132, and may also extent the length of the assembly 132. In this illustrative embodiment, there may be a receiver 1124 (not pictured) mounted to the fluid board 1122 at a location directly below the LED 1120, which is mounted to the autoconnect board 1118. Therefore, the LED 1120 can emit light across the fork-shaped elements 60, and if the light it detected by the receiver 1124 then there are no solution line caps 31 left in the stripper element 1491, however, if the light is interrupted on its way towards the receiver 1124 then there may be a cap 31 left in the stripper element 1491. This LED 1120 and receiver 1124 combination allows for the detection of caps 31 that may have been inadvertently left in the stripper element 1491 either by the user or by the cycler 14. In accordance with an aspect of the disclosure, the fluid board 1122 may also have the ability to detect humidity, moisture, or any other liquid that may be present inside of the carriage drive assembly 132, which could potentially cause the cycler 14 to fail.

There may be an advantage in adjusting the force with which the carriage 146 engages the spike caps 63, depending on how many lines 30 are being installed. The force required to complete a connection to the cassette 24 increases with the number of caps 31 that must be coupled to spike caps 63. The sensing device for detecting and reading information from the line indicators at indicator regions 33 can also be used to provide the data required to adjust the force applied to drive element 133. The force can be generated by a number of devices, including, for example, the first air bladder 137, or a linear actuator such as a motor/ball screw. An electronic control board (such as, for example, the autoconnect board) can be programmed to receive input from the line detection sensor(s), and send an appropriate control signal either to the motor of a linear actuator, or to the pneumatic valve that controls inflation of air bladder 137. The controller 16 can control the degree or rate of movement of drive element 133, for example by modulating the voltage applied to the motor of a linear actuator, or by modulating the pneumatic valve controlling the inflation of bladder 137.

In accordance with an aspect of the present disclosure, it may be necessary for the carriage drive assembly 132 to be capable of generating a force of at least 550 N (124 lbf) on carriage 146, in order to engage the membrane ports with spikes 160. This force is to be measured in the carriage direction of the membrane port spiking onto the cassette 24. The maximum force required to spike a sterilized PVC membrane port onto the spike 160 may be 110 N. Additionally, the maximum force required to spike a sterilized JPOC membrane port onto the spike 160 may be 110 N. These force requirements ensure carriage drive assembly 132 is able to spike five JPOC ports. In an alternative embodiment, the PVC port force requirement may be lowered further based on current insertion forces.

The aspect of the invention by which caps 31 on lines 30 are removed together with caps 63 on spikes 160 of the cassette 24 may provide other advantages aside from simplicity of operation. For example, since spike caps 63 are removed by way of their engagement with a cap 31 on a line 30, if there is no line 30 mounted at a particular slot on the carriage 146, the spike cap 63 at that position will not be removed. For example, although the cassette 24 includes five spikes 160 and corresponding spike caps 63, the cycler 14 can operate with four or less (even no) lines 30 associated with the cycler 14. For those slots on the carriage 146 where no line 30 is present, there will be no cap 31, and thus no mechanism by which a spike cap 63 at that position can be removed. Thus, if no line 30 will be connected to a particular spike 160, the cap 63 on that spike 160 may remain in place during use of the cassette 24. This may help prevent leakage at the spike 160 and/or contamination at the spike 160.

Figure 85:
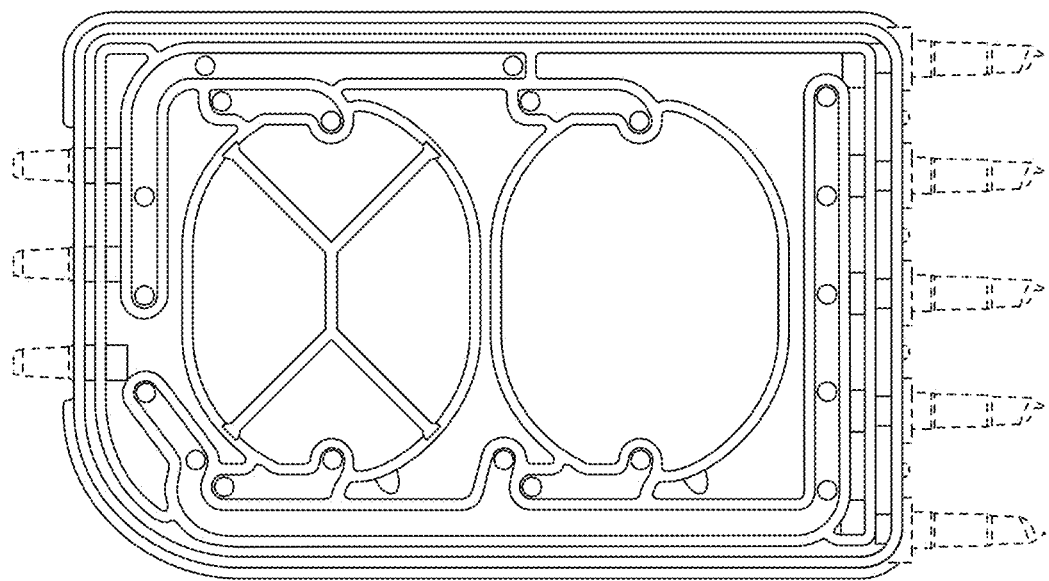
FIG. 85 is a rear view of a cassette in another illustrative embodiment including different arrangements for a rear side of the cassette adjacent the pump chambers.

The cassette 24 in FIG. 84 includes a few features that are different from those shown, for example, in the embodiment shown in FIGS. 3, 4 and 6. In the FIGS. 3, 4 and 6 embodiment, the heater bag port 150, drain line port 152 and patient line port 154 are arranged to have a central tube 156 and a skirt 158. However, as mentioned above and shown in FIG. 84, the ports 150, 152, 154 may include only the central tube 156 and no skirt 158. This is also shown in FIG. 85. The embodiment depicted in FIG. 85 includes raised ribs formed on the outside surface of the left-side pump chamber 181. The raised ribs may also be provided on the right-side pump chamber 181, and may provide additional contact points of the outside walls of pump chambers 181 with the mechanism in the door 141 at the cassette mounting location 145, which presses the cassette 24 against the control surface 148 when the door 141 is closed. The raised ribs are not required, and instead the pump chambers 181 may have no rib or other features, as shown for the right-side pump chamber 181 in FIG. 85. Similarly, the spikes 160 in FIGS. 3, 4 and 6 embodiment include no skirt or similar feature at the base of the spike 160, whereas the embodiment in FIG. 84 includes a skirt 160a. This is also shown in FIG. 85. The skirt 160a may be arranged to receive the end of the spike cap 63 in a recess between the skirt 160a and the spike 160, helping to form a seal between the spike 160 and the spike cap 63.

Figure 86:
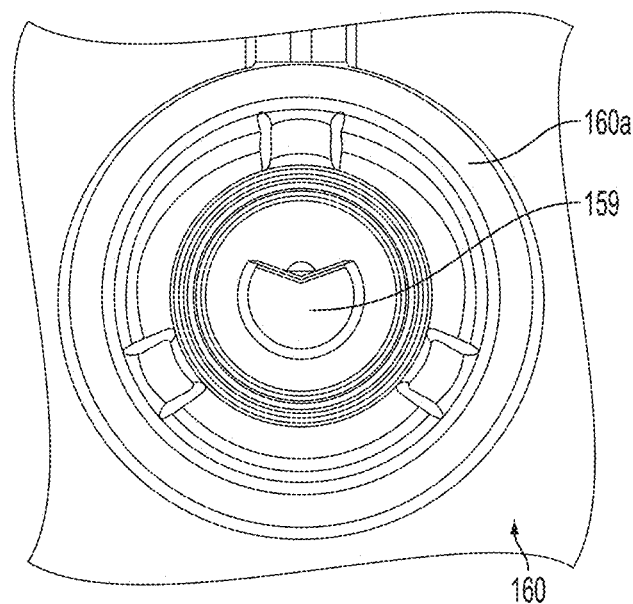
FIG. 86 is an end view of a spike of a cassette in an illustrative embodiment.

Another inventive feature shown in FIG. 84 relates to the arrangement of the distal tip of the spike 163 and the lumen 159 through the spike 160. In this aspect, the distal tip of the spike 160 is positioned at or near the longitudinal axis of the spike 160, which runs generally along the geometric center of the spike 160. Positioning the distal tip of the spike 160 at or near the longitudinal axis may help ease alignment tolerances when engaging the spike 160 with a corresponding solution line 30 and help the spike 160 puncture a septum or membrane 30b in the connector end 30a of the line 30. As a result, the lumen 159 of the spike 160 is located generally off of the longitudinal axis of the spike 160, e.g., near a bottom of the spike 160 as shown in FIG. 84 and as shown in an end view of a spike 160 in FIG. 86. Also, the distal end of the spike 160 has a somewhat reduced diameter as compared to more proximal portions of the spike 160 (in this embodiment, the spike 160 actually has a step change in diameter at about ⅔ of the length of the spike 160 from the body 18). The reduced diameter of the spike 160 at the distal end may provide clearance between the spike 160 and the inner wall of the line 30, thus allowing the septum 30b a space to fold back to be positioned between the spike 160 and the line 30 when pierced by the spike 160. The stepped feature 160b on the spike 160 (shown, e.g., in FIG. 87) may also be arranged to engage the line 30 at the location where the septum 30b is connected to the inner wall of the line 30, thus enhancing a seal formed between the line 30 and the spike 160.

Figure 87:
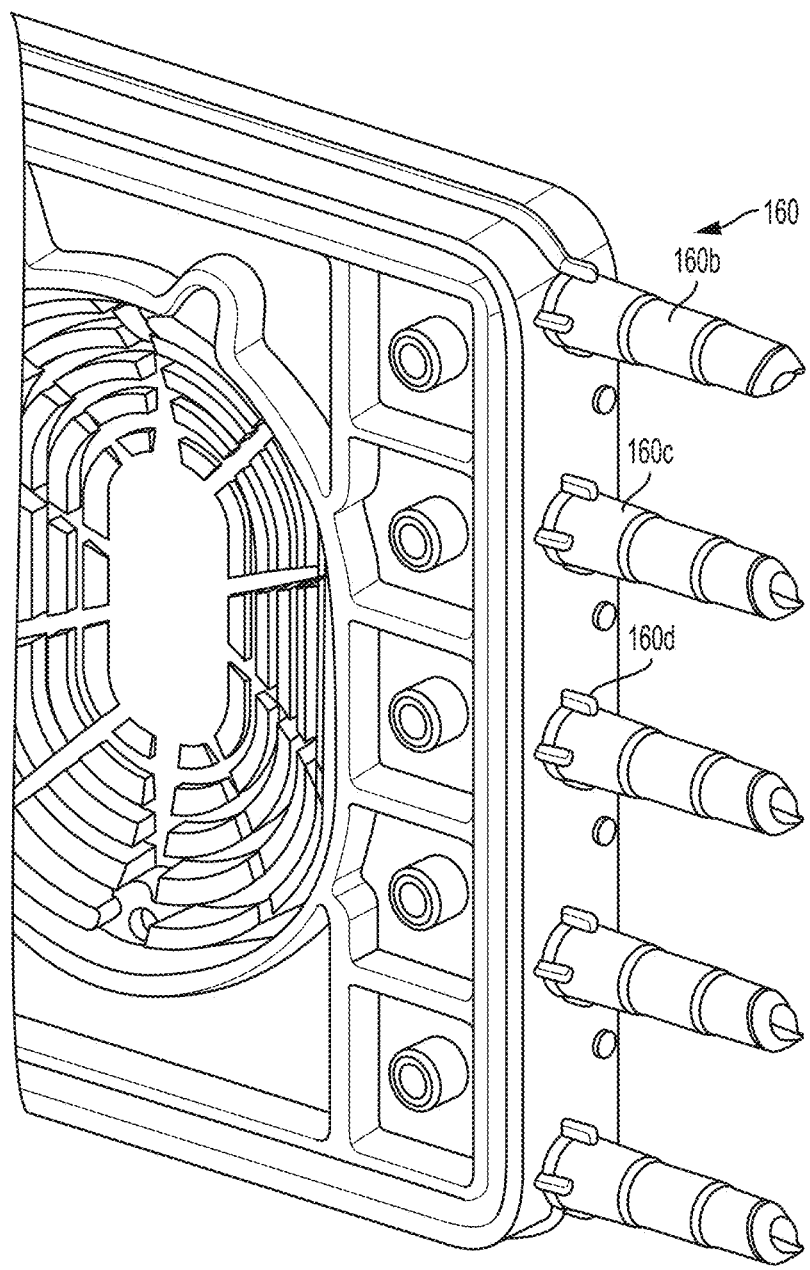
FIG. 87 is a perspective view of an alternative embodiment of the spikes of a cassette.

In another embodiment, as shown in FIG. 87, the length of the base 160c of spike 160 may be shortened to reduce the force required to remove the spike cap 63 from spike 160, or to reduce the force required to spike the connector end 30a of solution line 30. Shortening the base 160c reduces the area of frictional contact between spike 160 and its cap 63, or between spike 160 and the internal surface of connector end 30a. In addition, the skirt 160a at the base of spike 160 may be replaced by individual posts 160d. The posts 160d allow the spike cap 63 to be properly seated onto spike 160 while also allowing for more thorough circulation of sterilization fluid or gas around spike 160 during the sterilization process prior to or after packaging of the dialysate delivery set 12.

Figure 88:
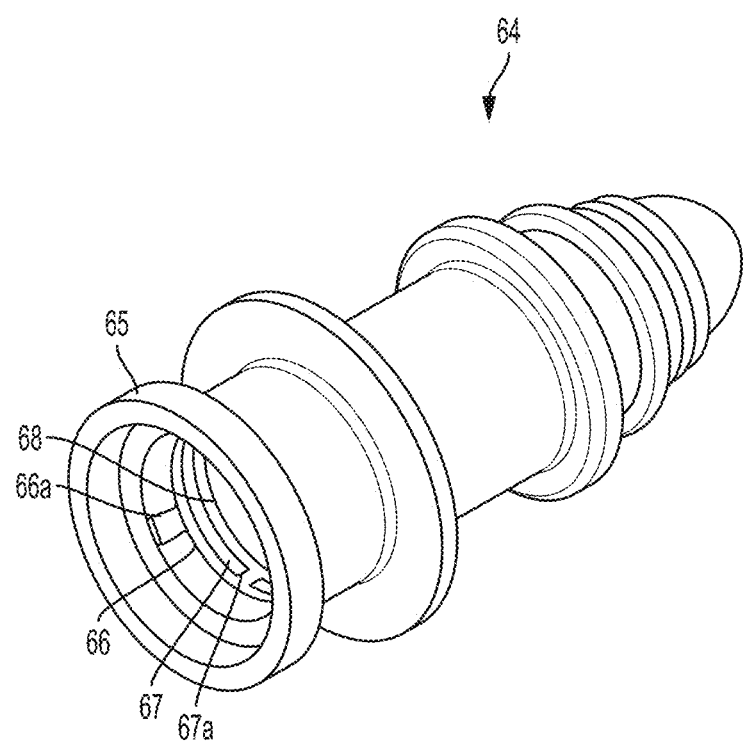
FIG. 88 shows an embodiment of a spike cap configured to fit over the spikes shown in FIG. 87.
Figure 89:
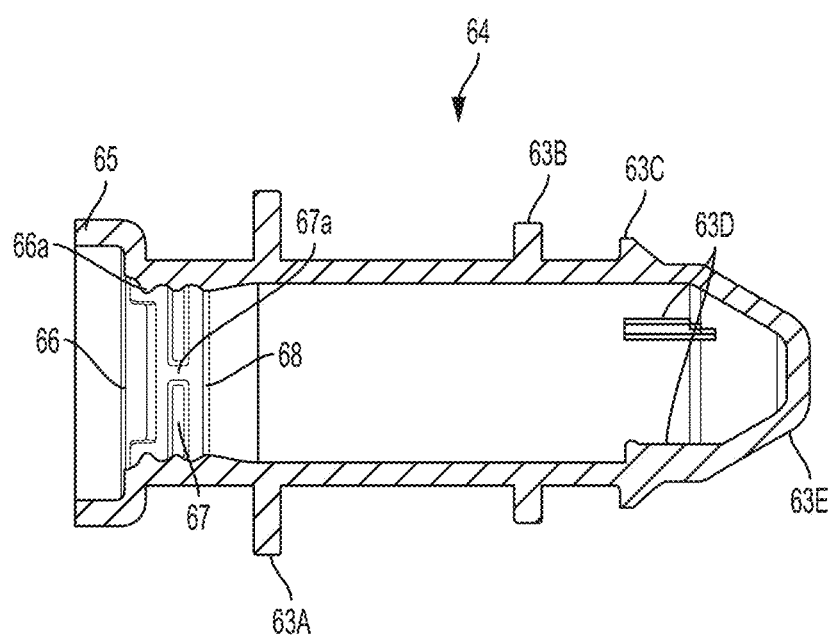
FIG. 89 is a cross-sectional view of a spike cap shown in FIG. 88.

To more fully take advantage of the embodiment shown in FIG. 87, a spike cap 64, as shown in FIG. 88 may be used. A skirt 65 on the base of spike cap 64 is constructed to fit snugly over the posts 160d of the base of spike 160 shown in FIG. 87. In addition, interrupted ribs 66, 67 within the inner circumference of the base of spike 160 may provide a snug fit between spike cap 64 and the base 160c of spike 160, while also permitting sterilizing gas or fluid to penetrate more distally over the base of a capped spike 160. As shown in FIG. 89, in a cross-sectional view of spike cap 64, a set of three inner ribs 66, 67, 68 may be used to provide a snug fit between spike cap 64 and the base 160c of spike 160. In an embodiment, rib 66 and rib 67 have interruptions or gaps 66a and 67a along their circumference to permit gas or fluid external to the cassette to flow over the base 160c of spike 160. A third rib 68 may be circumferentially intact in order to make a sealing engagement between spike cap 64 and the base 160c of spike 160, sealing off the base 160c from rest of the external surface of spike 160. In other embodiments, ribs within spike cap 64 may be oriented longitudinally rather than circumferentially, or in any other orientation to provide a snug fit between spike cap 64 and spike 160, while also permitting an external gas or fluid to make contact with the outside of the base 160c of spike 160. In the embodiment shown, for example, the outer surface of the cassette, spike cap and most of the base 160c of spike 160 can be sterilized by exposing the cassette externally to ethylene oxide gas. Because the diameter of the stepped feature 160b and the distal end of spike 160 are smaller than the inner diameter of the overlying portion of spike cap 64, any gas or fluid entering the spike lumen from within the cassette can reach the outer surface of spike 160 up to the sealing rib 68. Thus any sterilizing gas such as ethylene oxide entering the fluid passages of the cassette 24 may reach the remainder of the external surface of spike 160. In an embodiment, the gas may enter the cassette 24 through a vented cap, for example, on the end of patient line 34 or drain line 28.

Figure 90:
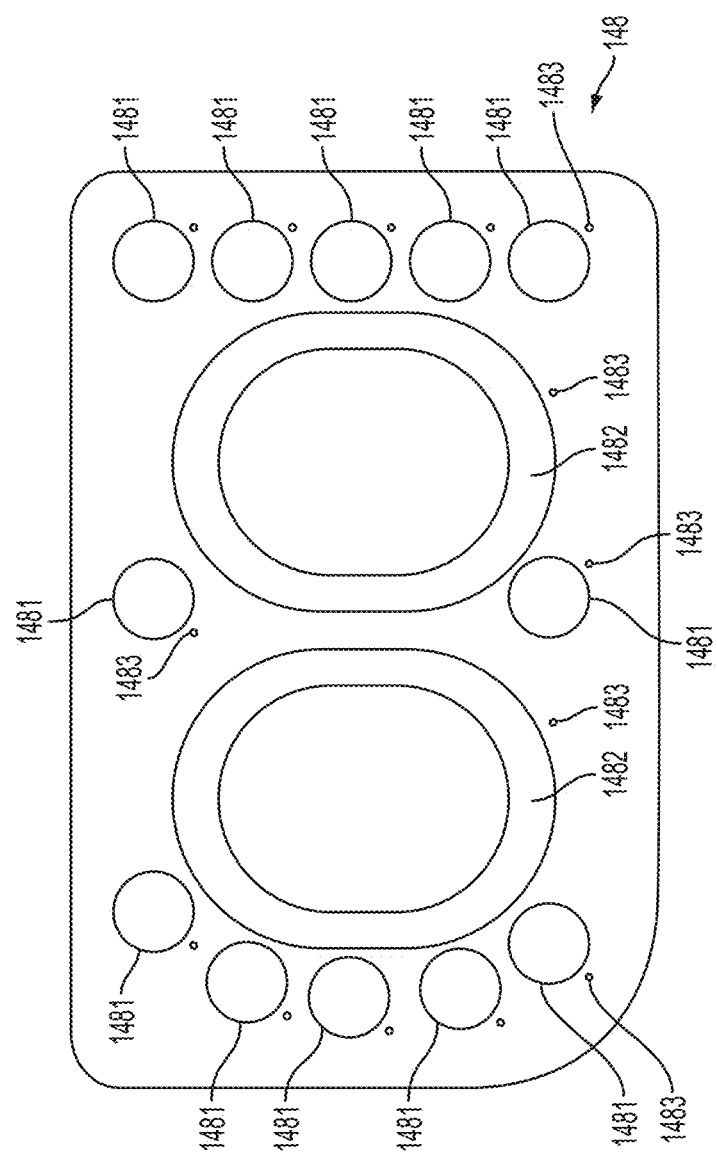
FIG. 90 is a front view of a control surface of the cycler for interaction with a cassette in the FIG. 37 embodiment.

The spike cap 34 may include 3 or more centering ribs 64D that contact the end of the spike 160. The ribs 64D are oriented along the major access of spike cap 34 and located near the closed end of the spike cap 34. Preferably there are at least three ribs 63D to center the closed end of the cap on the spike without over constraining the cap/spike orientation. The spike cap 64 includes a tapered end with a blunt tip to facilitate the penetration of the spike cap 34 into the hole 31b of the solution cap 31. The tapered end will guide the spike cap 34 if it misaligned with the hole 31b. The blunt tip avoids snagging the solution cap 31 unlike a sharp tip that might catch the inside edge of the hole 31b and dig into the solution cap material. In contrast a blunt tip can slide past the edges of the hole 31b. Once the cassette 24 and lines 30 are loaded into the cycler 14, the cycler 14 must control the operation of the cassette 24 to move fluid from the solution lines 30 to the heater bag 22 and to the patient. FIG. 90 shows a plan view of the control surface 148 of the cycler 14 that interacts with the pump chamber side of the cassette 24 (e.g., shown in FIG. 6) to cause fluid pumping and flow path control in the cassette 24. When at rest, the control surface 148, which may be described as a type of gasket, and comprise a sheet of silicone rubber, may be generally flat. Valve control regions 1481 may (or may not) be defined in the control surface 148, e.g., by a scoring, groove, rib or other feature in or on the sheet surface, and be arranged to be movable in a direction generally transverse to the plane of the sheet. By moving inwardly/outwardly, the valve control regions 1481 can move associated portions of the membrane 15 on the cassette 24 so as to open and close respective valve ports 184, 186, 190 and 192 of the cassette 24, and thus control flow in the cassette 24. Two larger regions, pump control regions 1482, may likewise be movable so as to move associated shaped portions 151 of the membrane 15 that cooperate with the pump chambers 181. Like the shaped portions 151 of the membrane 15, the pump control regions 1482 may be shaped in a way to correspond to the shape of the pump chambers 181 when the control regions 1482 are extended into the pump chambers 181. In this way, the portion of the control sheet 148 at the pump control regions 1482 need not necessarily be stretched or otherwise resiliently deformed during pumping operation.

Each of the regions 1481 and 1482 may have an associated vacuum or evacuation port 1483 that may be used to remove all or substantially all of any air or other fluid that may be present between the membrane 15 of cassette 24, and the control surface 148 of cycler 14, e.g., after the cassette 24 is loaded into the cycler 14 and the door 141 closed. This may help ensure close contact of the membrane 15 with the control regions 1481 and 1482, and help control the delivery of desired volumes with pump operation and/or the open/closed state of the various valve ports. Note that the vacuum ports 1482 are formed in locations where the control surface 148 will not be pressed into contact with a wall or other relatively rigid feature of the cassette 24. For example, in accordance with one aspect of the invention, one or both of the pump chambers of the cassette may include a vacuum vent clearance region formed adjacent the pump chamber. In this illustrative embodiment as shown in FIGS. 3 and 6, the base member 18 may include vacuum vent port clearance or extension features 182 (e.g., recessed areas that are fluidly connected to the pump chambers) adjacent and outside the oval-shaped depressions forming the pump chambers 181 to allow the vacuum vent port 1483 for the pump control region 1482 to remove any air or fluid from between membrane 15 and control surface 148 (e.g., due to rupture of the membrane 15) without obstruction. The extension feature may also be located within the perimeter of pump chamber 181. However, locating vent port feature 182 outside the perimeter of pump chamber 181 may preserve more of the pumping chamber volume for pumping liquids, e.g., allows for the full footprint of pump chamber 181 to be used for pumping dialysate. Preferably, extension feature 182 is located in a vertically lower position in relation to pump chamber 181, so that any liquid that leaks between membrane 15 and control surface 148 is drawn out through vacuum port 1483 at the earliest opportunity. Similarly, vacuum ports 1483 associated with valves 1481 are preferably located in a vertically inferior position with respect to valves 1481.

Figure 91:
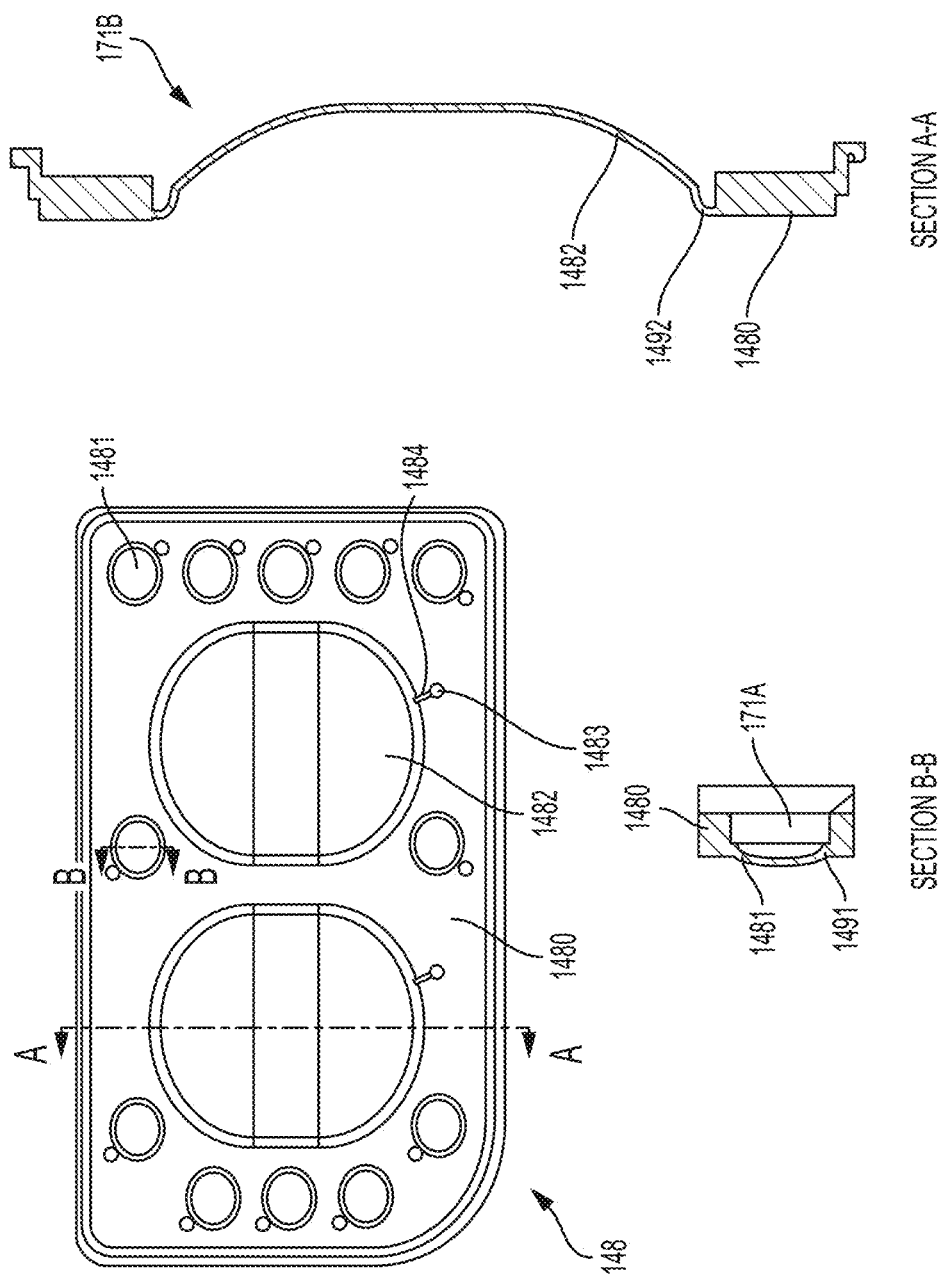
FIG. 91 is a front view and selected cross-sectional views of an embodiment of a control surface of the cycler.

FIG. 91 shows that control surface 148 may be constructed or molded to have a rounded transition between the base element 1480 of control surface 148 and its valve and pump control regions 1481, 1482. The junctions 1491 and 1492 may be molded with a small radius to transition from base element 1480 to valve control region 1481 and pump control region 1482, respectively. A rounded or smooth transition helps to prevent premature fatigue and fracture of the material comprising control surface 148, and may improve its longevity. In this embodiment, channels 1484 leading from vacuum ports 1483 to the pump control regions 1482 and valve control regions 1481 may need to be lengthened somewhat to accommodate the transition feature.

Figure 92:
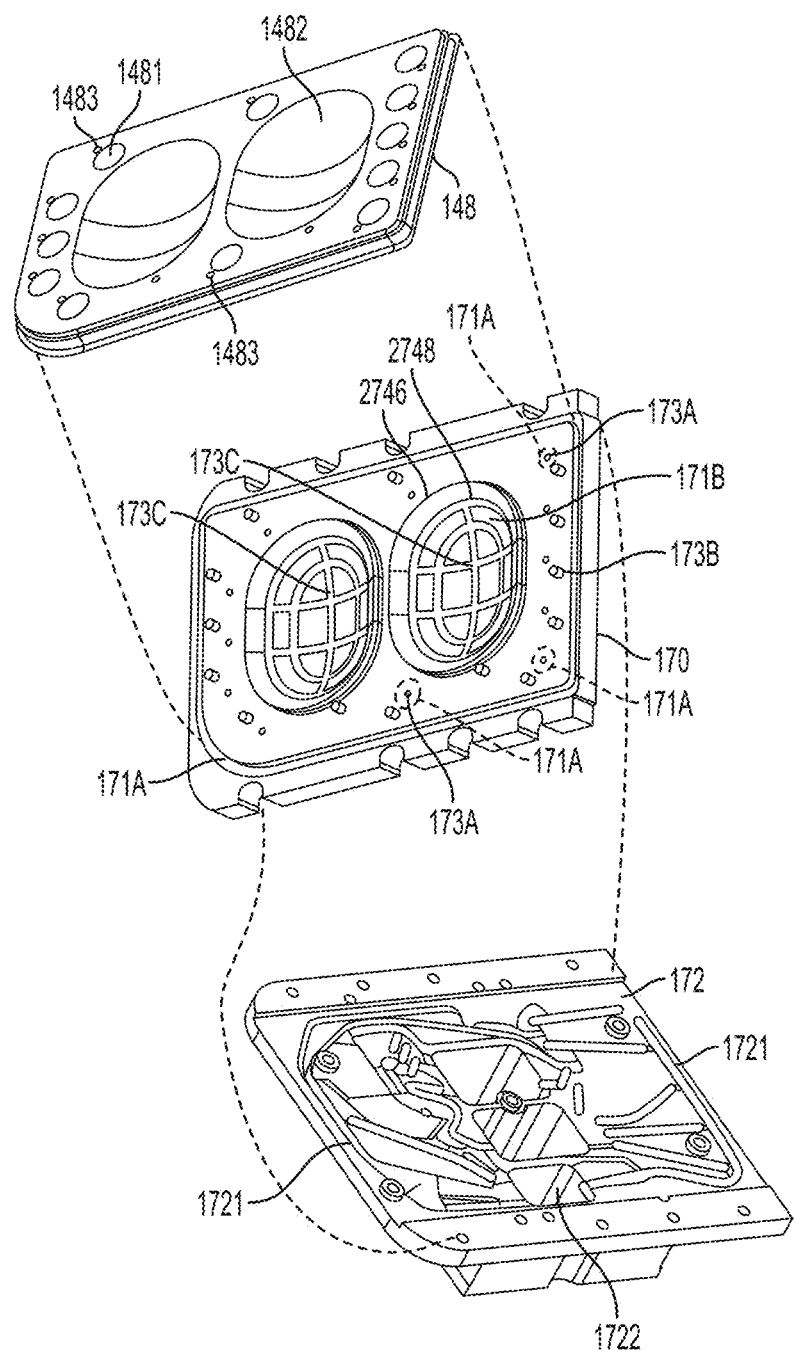
FIG. 92 is an exploded view of an assembly for the interface surface of FIG. 90, with the mating pressure delivery block and pressure distribution module.

The control regions 1481 and 1482 may be moved by controlling a pneumatic pressure and/or volume on a side of the control surface 148 opposite the cassette 24, e.g., on a back side of the rubber sheet that forms the control surface 148. For example, as shown in FIG. 92, the control surface 148 may be backed by a mating or pressure delivery block 170 that includes control chambers or depressions 171A located in association with each control region 1481, and control chambers or depressions 171B, located in association with each control region 1482, and that are isolated from each other (or at least can be controlled independently of each other if desired). The surface of mating or pressure delivery block 170 forms a mating interface with cassette 24 when cassette 24 is pressed into operative association with control surface 148 backed by mating block 170. The control chambers or depressions of mating block 170 are thus coupled to complementary valve or pumping chambers of cassette 24, sandwiching control regions 1481 and 1482 of control surface 148 adjacent to mating block 170, and the associated regions of membrane 15 (such as shaped portion 151) adjacent to cassette 24. Air or other control fluid may be moved into or out of the control chambers or depressions 171A, 171B of mating block 170 for the regions 1481, 1482, thereby moving the control regions 1481, 1482 as desired to open/close valve ports of the cassette 24 and/or effect pumping action at the pump chambers 181. In one illustrative embodiment shown in FIG. 92, the control chambers 171A may be arranged as cylindrically-shaped regions backing each of the valve control regions 1481. The control chambers or depressions 171B may comprise ellipsoid, ovoid or hemi-spheroid voids or depressions backing the pump control regions 1482. Fluid control ports 173A may be provided for each control chamber 171A so that the cycler 14 can control the volume of fluid and/or the pressure of fluid in each of the valve control chambers 1481. Fluid control ports 173C may be provided for each control chamber 171B so that the cycler 14 can control the volume of fluid and/or the pressure of fluid in each of the volume control chambers 1482. For example, the mating block 170 may be mated with a manifold 172 that includes various ports, channels, openings, voids and/or other features that communicate with the control chambers 171 and allow suitable pneumatic pressure/vacuum to be applied to the control chambers 171. Although not shown, control of the pneumatic pressure/vacuum may be performed in any suitable way, such as through the use of controllable valves, pumps, pressure sensors, accumulators, and so on. Of course, it should be understood that the control regions 1481, 1482 may be moved in other ways, such as by gravity-based systems, hydraulic systems, and/or mechanical systems (such as by linear motors, etc.), or by a combination of systems including pneumatic, hydraulic, gravity-based and mechanical systems.

Figure 93:
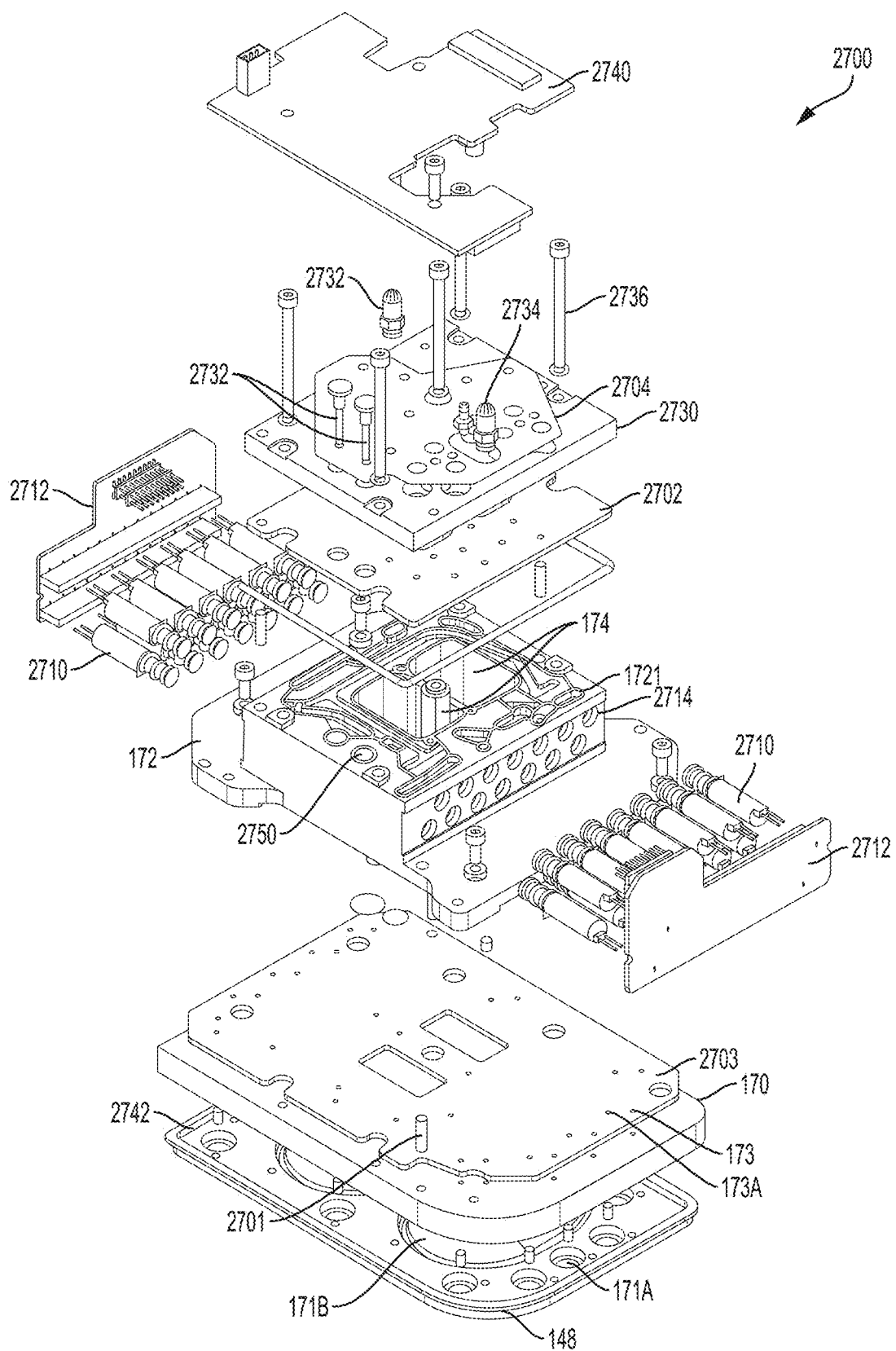
FIG. 93 is an exploded view of the integrated manifold.
Figure 94:
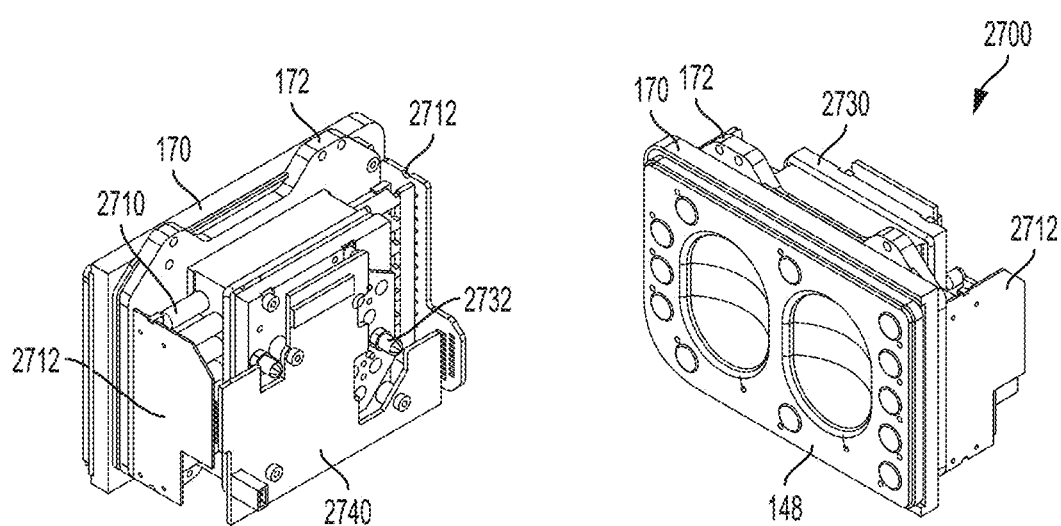
FIG. 94 shows two isometric views of the integrated manifold.

FIG. 93 shows an exploded view of an integrated pressure distribution module or assembly 2700 for use in a fluid flow control apparatus for operating a pumping cassette, and suitable for use as pressure distribution manifold 172 and mating block 170 of cycler 14. FIG. 94 shows a view of an integrated module 2700 comprising a pneumatic manifold or block, ports for supply pressures, pneumatic control valves, pressure sensors, a pressure delivery or mating block and a control surface or actuator that includes regions comprising flexible membranes for actuating pumps and valves on a pumping cassette. The integrated module 2700 may also include reference chambers within the pneumatic manifold for an FMS volume measurement process for determining the volume of fluid present in a pumping chamber of a pumping cassette. The integrated module may also comprise a vacuum port, and a set of pathways or channels from interfaces between the actuator and flexible pump and valve membranes of a pumping cassette to a fluid trap and liquid detection system. In some embodiments, the pneumatic manifold may be formed as a single block. In other embodiments, the pneumatic manifold may be formed from two or more manifold blocks mated together with gaskets positioned between the manifold blocks. The integrated module 2700 occupies a relatively small space in a fluid flow control apparatus, and eliminates the use of tubes or flexible conduits connecting the manifold ports with corresponding ports of a pressure delivery module or block mated to a pumping cassette. Among other possible advantages, the integrated module 2700 reduces the size and assembly cost of the pneumatic actuation assembly of a peritoneal dialysis cycler, which may result in a smaller and less expensive cycler. Additionally, the short distances between pressure or vacuum distribution ports on the pressure distribution manifold block and corresponding pressure or vacuum delivery ports on a mating pressure delivery block, together with the rigidity of the conduits connecting the ports, may improve the responsiveness of an attached pumping cassette and the accuracy of cassette pump volume measurement processes. When used in a peritoneal dialysis cycler 14, in an embodiment, an integrated module comprising a metallic pressure distribution manifold mated directly to a metallic pressure delivery block may also reduce any temperature differences between the control volume 171B and the reference chamber 174 of the cycler 14, which may improve the accuracy of the pump volume measurement process.

An exploded view of the integrated module 2700 is presented in FIG. 93. The actuator surface, mounted on a mating block or pressure delivery block, is analogous or equivalent to the gasket or control surface 148, that includes flexible regions arranged to move back and forth to pump fluid and/or open and close valves by pushing or pulling on a membrane 15 of a pump cassette 24. With respect to cycler 14, the control surface 148 is actuated by the positive and negative pneumatic pressure supplied to the control volumes 171A, 171B behind the control regions 1481, 1482. The control surface 148 attaches to the pressure delivery block or mating block 170 by fitting tightly on a raised surface 2744 on the front surface of the mating block 170 with a lip 2742. The mating block 170 may include one or more surface depressions 2746 to align with and support the oval curved shape of one or more corresponding pump control surfaces 1482, forming a pump control chamber. A similar arrangement, with or without a surface depression, may be included in forming a valve control region 171A to align with a corresponding control surface 1481 for controlling one or more valves of a pumping cassette. The mating block 170 may further include grooves 2748 on the surface of depression 2746 of mating block 170 behind the pump control surface 1482 to facilitate the flow of control fluid or gas from the port 173C to the entire back surface the pump control surface 1482. Alternatively, rather than having grooves 2748, the depression 2746 may be formed with a roughened surface or a tangentially porous surface.

The mating block 170 connects the pressure distribution manifold 172 to the control surface 148, and delivers pressure or vacuum to various control regions on control surface 148. The mating block 170 may also be referred to as a pressure delivery block in that it provides pneumatic conduits to supply pressure and vacuum to the valve control regions 1481 and the pump control regions 1482, vacuum to the vacuum ports 1483 and connections from the pump control volumes 171B to the pressure sensors. The ports 173A connect the valve control volumes 171A to the pressure distribution manifold 172. The ports 173C connect the pump control volume 171B to the pressure distribution manifold 172. The vacuum ports 1483 are connected to the pressure distribution manifold 172 via ports 173B. In one embodiment, the ports 173B extend above the surface of the pressure delivery block 170 to pass through the control surface 148 to provide vacuum at port 1483 without pulling the control surface 148 onto the port 173B and blocking flow.

The pressure delivery block 170 is attached to the front face of the pressure distribution manifold 172. The ports 173A, 173B, 173C line up with pneumatic circuits on the pressure distribution manifold 172 that connect to valve ports 2714. In one example, the pressure delivery block 170 is mated to the pressure distribution manifold 172 with a front flat gasket 2703 clamped between them. The block 170 and manifold 172 are held together mechanically, which in an embodiment is through the use of bolts 2736 or other types of fasteners. In another example, rather than a flat gasket 2703, compliant elements are placed in or molded in either the pressure delivery block 170 or the pressure distribution manifold 172. Alternatively, the pressure delivery block 170 may be bonded to the pressure distribution manifold 172 by an adhesive, double sided tape, friction welding, laser welding, or other bonding method. The block 170 and manifold 172 may be formed of metal or plastic and the bonding methods will vary depending on the material.

The pressure distribution manifold 172 contains ports for the pneumatic valves 2710, reference chambers 174, a fluid trap 1722 and pneumatic circuitry or of the integrated module 2700 connections provides pneumatic connections between the pressure reservoirs, valves, and contains ports 2714 that receive multiple cartridge valves 2710. The cartridge valves 2710 include but are not limited to the binary valves 2660 controlling flow to valve control volumes 171A, the binary valves X1A, X1B, X2, X3 controlling flow to pump control volumes 171B, and the binary valves 2661-2667 controlling flow to the bladders 2630, 2640, 2650 and pressure reservoirs 2610, 2620. The cartridge valves 2710 are pressed into the valve ports 2714 and electrically connected to the hardware interface 310 via circuit board 2712.

The pneumatic circuitry in the pressure distribution manifold 172 may be formed with a combination of grooves or slots 1721 on the front and back faces and approximately perpendicular holes that connect the grooves 1721 on one face to valve ports 2714, the fluid trap 1722 and to grooves and ports on the opposite face. Some grooves 1721 may connect directly to the reference chambers 174. A single perpendicular hole may connect a groove 1721 to multiple valve ports 174 that are closely spaced and staggered. Sealed pneumatic conduits are formed when the grooves 1721 are isolated from one another by, in one example, the front flat gasket 2703 as shown in FIG. 93.

The presence of liquid in the fluid trap 1722 may be detected by a pair of conductivity probes 2732. The conductivity probes 2732 slide through a back gasket 2704, a back plate 2730 and holes 2750 before entering the fluid trap 1722 in the pressure distribution manifold 172.

The back plate 2730 seals the reference volumes 174, the grooves 1721 on the back face of the pressure distribution manifold 172 and provides ports for the pressure sensors 2740 and ports for pressure and vacuum lines 2734 and vents to the atmosphere 2732. In one example, the pressure sensors may be IC chips soldered to a single board 2740 and pressed as a group against the back gasket 2704 on the back plate 2730. In one example, bolts 2736 clamp the back plate 2730, pressure distribution manifold 172 and pressure delivery block 170 together with gaskets 2703, 2702 between them. In another example, the back plate 2730 may be bonded to the pressure delivery manifold 172 as described above. The assembled integrated module 2700 is presented in FIG. 95.

Figure 95:
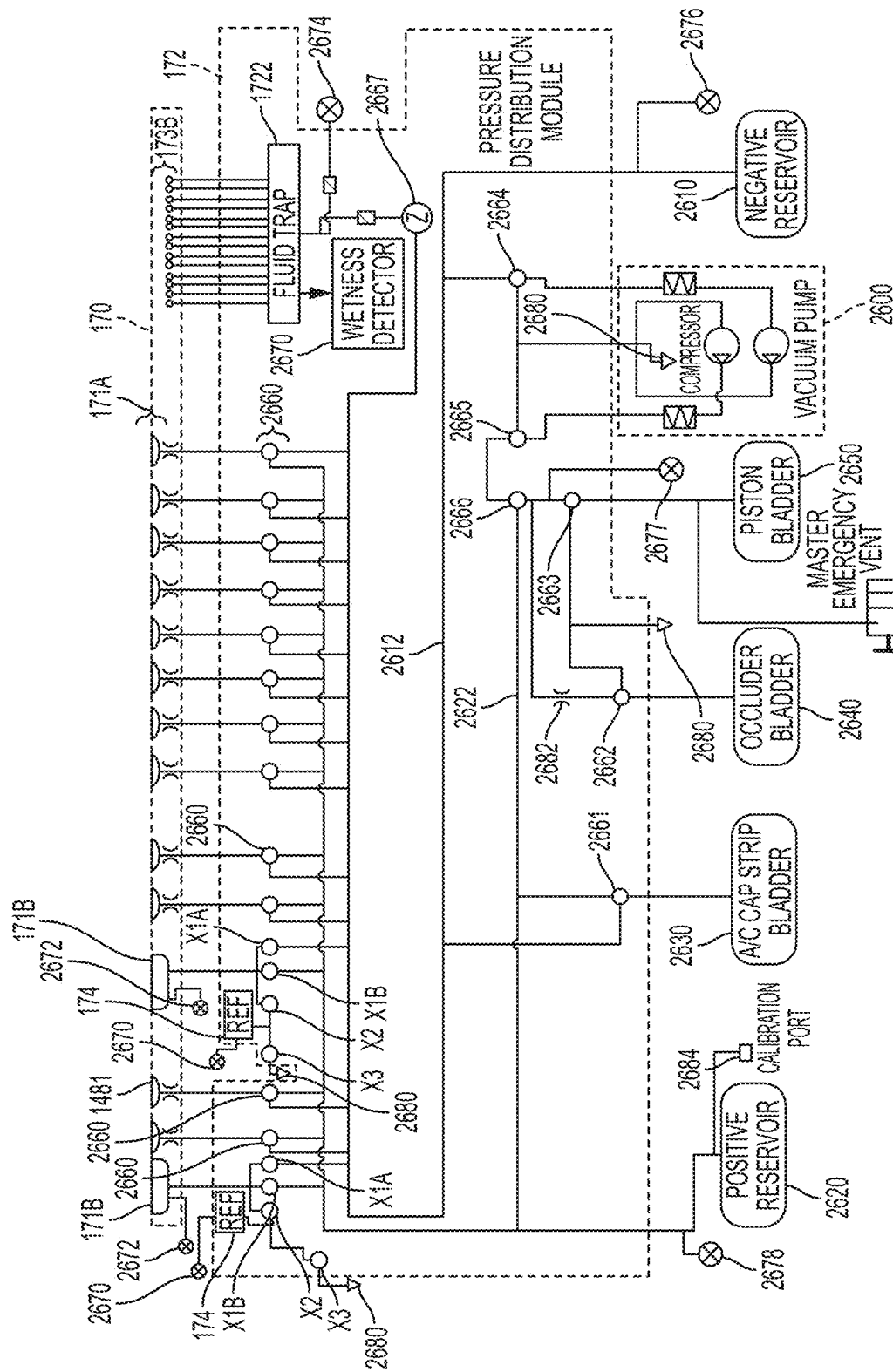
FIG. 95 shows a schematic of the pneumatic system that controls fluid flow through the cycler.

FIG. 95 presents a schematic of the pneumatic circuit in the integrated manifold 2700 and pneumatic elements outside the manifold. The pump 2600 produces vacuum and pressure. The pump 2600 is connected via 3 way valves 2664 and 2665 to a vent 2680 and the negative or vacuum reservoir 2610 and the positive reservoir 2620. The pressure in the positive and negative reservoirs 2620, 2610 are measured respectively by pressure sensors 2678, 2676. The hardware interface 310 controls the speed of the pump 2600 and the position of 3-way valves 2664, 2665, 2666 to control the pressure in each reservoir. The auto-connect stripper element bladder 2630 is connected via 3-way valve 2661 to either the positive pressure line 2622 or the negative or vacuum line 2612. The automation computer 300 commands the position of valve 2661 to control the location of the stripper element 1461. The occluder bladder 2640 and piston bladder 2650 are connected via 3-way valves 2662 and 2663 to either the pressure line 2622 or vent 2680. The automation computer 300 commands valve 2663 to connect the piston bladder 2650 to the pressure line 2622 after the door 141 is closed to securely engage the cassette 24 against the control surface 148. The occluder bladder 2640 is connected to the pressure line 2622 via valve 2662 and restriction 2682. The occluder bladder 2640 is connected to the vent 2680 via valve 2662. The orifice 2682 advantageously slows the filling of the occluder bladder 2640 that retracts the occluder 147 in order to maintain the pressure in the pressure line 2622. The high pressure in the pressure line 2622 keeps the various valve control surfaces 171A and the piston bladder 2650 actuated against the cassette 24, which prevents flow to or from the patient as the occluder 147 opens. Conversely the connection from the occluder bladder 2640 to the vent 2680 is unrestricted, so that occluder 147 can quickly close.

The valve control surfaces 1481 are controlled by the pressure in the valve control volume 171A, which in turn is controlled by the position of the 3-way valves 2660. The valves 2660 can be controlled individually via commands from the automation computer 300 passed to the hardware interface 310. The valves controlling the pumping pressures in the pump control volumes 171B are controlled with 2-way valves X1A, X1B. The valves X1A, X1B in one example may be controlled by the hardware interface 310 to achieve a pressure commanded by the automation computer 300. The pressure in each pump control chamber 171B is measured by sensors 2672. The pressure in the reference chambers is measured by sensors 2670. The 2-way valves X2, X3 respectively connect the reference chamber 174 to the pump control chamber 171B and the vent 2680.

The fluid trap 1722 is to the vacuum line 2612 during operation as explained elsewhere in this application. The fluid trap 1722 is connected by several lines to the ports 173B in the pressure delivery block 170. The pressure in the fluid trap 1722 is monitored by pressure sensor 2674 that is mounted on the back plate 2730.

The vacuum ports 1483 may be employed to separate the membrane 15 from the control surface 148 at the end of therapy before or during the opening the door. The vacuum provided by the negative pressure source to the vacuum ports 1483 sealingly engages the membrane 15 to the control surface 148 during therapy. In some instances a substantial amount of force may be needed to separate the control surface from the cassette membrane 15, preventing the door 141 from freely rotating into the open position, even when the application of vacuum is discontinued. Thus, in an embodiment, the pressure distribution module 2700 is configured to provide a valved channel between the positive pressure source and the vacuum ports 1483. Supplying positive pressure at the vacuum ports 1483 may aid in separating the membrane 15 from the control surface 148, thereby allowing the cassette 24 to separate more easily from the control surface 148 and allow the door 141 to open freely. The pneumatic valves in the cycler may be controlled by the automation computer 300 to provide a positive pressure to the vacuum ports 1483. The manifold 172 may include a separately valved channel dedicated for this purpose, or alternatively it may employ the existing channel configurations and valves, operated in a particular sequence.

In one example the vacuum ports 1483 may be supplied with positive pressure by temporarily connecting the vacuum ports 1483 to the positive pressure reservoir 2620. The vacuum ports 1483 are normally connected to the vacuum reservoir 2610 via a common fluid collection chamber or fluid trap 1722 in the manifold 172 during therapy. In one example, the controller or automation computer may open valve X1B between the positive pressure reservoir and the volume control chamber 171B and the valve X1A between the negative pressure reservoir and the same volume control chamber 171B simultaneously, which will pressurize the air in the fluid trap 1722 and the vacuum ports 1483. The pressurized air will flow through the vacuum ports 1483 and between the membrane 15 and the control surface 148, breaking any vacuum bond between the membrane and control surface. However, in the illustrated manifold, the stripper element 1491 of the cap stripper 149 may extend while the positive pressure is supplied to common fluid collection chamber 1722 fluid, because the stripper bladder 2630 is connected to a the vacuum supply line 2612. In this example, in a subsequent step, the fluid trap 1722 may be valved off from the now-pressurized vacuum line and the two valves X1A, X1B connecting the positive and vacuum reservoirs to the volume control chamber 171B may be closed. The vacuum pump 2600 is then operated to reduce the pressure in the vacuum reservoir 2610 and the vacuum supply line 2612, which in turn allows the stripper element 1491 to be withdrawn. The door 141 may then be opened after detaching the cassette 24 from the control surface 148 and retracting the stripper element 1491.

In accordance with an aspect of the disclosure, the vacuum ports 1483 may be used to detect leaks in the membrane 15, e.g., a liquid sensor in a conduit or chamber connected to a vacuum port 1483 may detect liquid if the membrane 15 is perforated or liquid otherwise is introduced between the membrane 15 and the control surface 148. For example, vacuum ports 1483 may align with and be sealingly associated with complementary vacuum ports 173B in mating block 170, which in turn may be sealingly associated with fluid passages 1721 leading to a common fluid collection chamber 1722 in manifold 172. The fluid collection chamber 1722 may contain an inlet through which vacuum can be applied and distributed to all vacuum ports 1483 of control surface 148. By applying vacuum to the fluid collection chamber 1722, fluid may be drawn from each of the vacuum ports 173B and 1483, thus removing fluid from any space between the membrane 15 and the control surface 148 at the various control regions. However, if there is liquid present at one or more of the regions, the associated vacuum port 1483 may draw the liquid into the vacuum ports 173B and into the lines 1721 leading to the fluid collection chamber 1722. Any such liquid may collect in the fluid collection chamber 1722, and be detected by one or more suitable sensors, e.g., a pair of conductivity sensors that detect a change in conductivity in the chamber 1722 indicating the presence of liquid. In this embodiment, the sensors may be located at a bottom side of the fluid collection chamber 1722, while a vacuum source connects to the chamber 1722 at an upper end of the chamber 1722. Therefore, if liquid is drawn into the fluid collection chamber 1722, the liquid may be detected before the liquid level reaches the vacuum source. Optionally, a hydrophobic filter, valve or other component may be placed at the vacuum source connection point into the chamber 1722 to help further resist the entry of liquid into the vacuum source. In this way, a liquid leak may be detected and acted upon by controller 16 (e.g., generating an alert, closing liquid inlet valves and ceasing pumping operations) before the vacuum source valve is placed at risk of being contaminated by the liquid.

In the example schematic shown in FIG. 95, a calibration port 2684 is depicted. The calibration port 2684 may be used to calibrate the various pressure sensors 2670, 2672, 2674, 2676, 2677, 2678 in the pneumatic system. For example, a pressure reference may be connected to the pneumatic circuit of the cycler via the calibration port 2684. With the pressure reference connected, the valves of the pneumatic system may be actuated so as to connect all of the pressure sensors 2670, 2672, 2674, 2676, 2677, 2678 to the same fluid volume. A known pressure may then be established in the pneumatic system using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly. In some embodiments, selected pressure sensors of the pressure sensors 2672, 2674, 2676, 2677, 2678 may be connected and brought to the pressure of the reference for calibration in groups or individually.

Any fluid handling device (i.e. base unit) that is configured to actuate diaphragm-based pumps and valves on a removable cassette can take advantage of its pneumatic (or hydraulic) cassette interface to receive a calibrating reference pressure via a specialized calibrating cassette (or 'cassette fixture'). A calibrating cassette can have the same overall dimensions as a standard fluid pumping cassette, so that it can provide a sealing interface with the cassette interface or control surface of the base unit. One or more of the pump or valve regions can be allowed to communicate with a corresponding region of the interface to which it mates, so that a reference pneumatic or hydraulic pressure can be introduced through the calibrating cassette and into the pneumatic or hydraulic flow paths of the base unit (e.g. via a pneumatic or hydraulic manifold).

For example, in a pneumatically operated peritoneal dialysis cycler, the pneumatic circuitry of the cycler may be accessed directly through the cassette interface of the cycler. This may for example, be accomplished using a modified cassette or cassette fixture which allows the control surface 148 to create a seal against the cassette fixture. Additionally, the cassette fixture may be constructed to include at least one access port in fluid communication with a vacuum port 173B of the cassette interface. In the absence of a vacuum port (e.g. in embodiments having slits or perforations in the control surface) the access port may instead be placed in communication with the vacuum vent feature of the cassette interface or control surface.

The cassette fixture (or calibrating cassette) may be constructed to have a direct flow path from an external cassette port to the access port facing the device interface, the external cassette port then being available for connection to a pressure reference. As described above, all or some of the pressure sensors 2670, 2672, 2674, 2676, 2677, 2678 may be placed into fluid communication with a common volume, through the appropriate actuation of pneumatic control valves in the pressure distribution manifold. A known pressure may be established in that volume using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly.

In some embodiments of a pressure distribution manifold, it may not be possible for all of the pressure sensors 2670, 2672, 2674, 2676, 2677, 2678 to be connected to a common volume at one time. In that case, the flow paths to the individual pressure sensors 2670, 2672, 2674, 2676, 2677, 2678 may need to be opened in a sequential manner to ensure calibration of all sensors. Additionally, it should be noted that once calibrated, one or more of the pressure sensors 2670, 2672, 2674, 2676, 2677, 2678 may be used to calibrate other pressure sensors 2670, 2672, 2674, 2676, 2677, 2678 in a pressure distribution manifold of a base unit or cycler. The previously calibrated pressure sensor or sensors may be placed into a common volume with the uncalibrated pressure sensor (e.g. via suitable valve actuations). The pressure of the common volume may be known via the calibrated pressure sensor(s). The uncalibrated pressure sensor's reading may be compared to the known pressure of the common volume and then calibrated accordingly.

Figure 96:
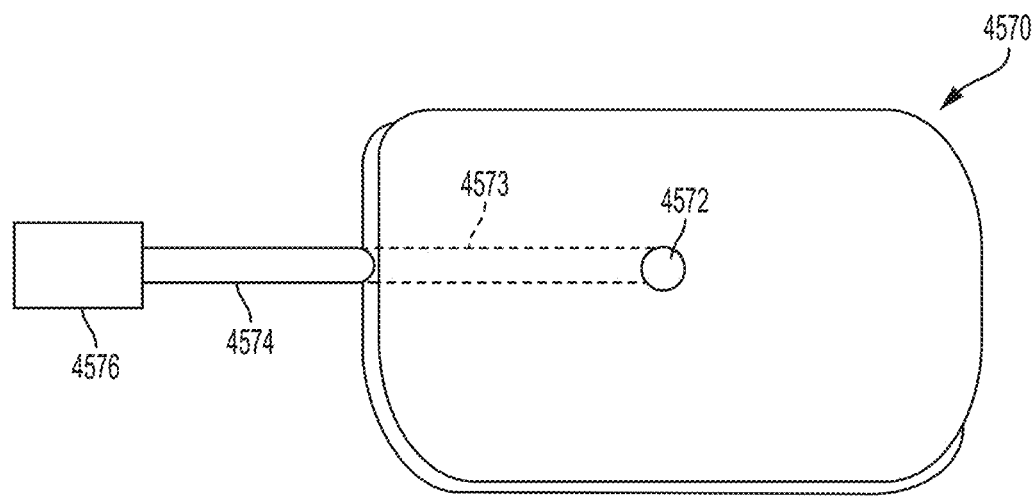
FIG. 96 is a front side view of an embodiment of a cassette fixture.

FIG. 96 depicts a schematized view of an embodiment of a cassette fixture 4570. As shown, the cassette fixture 4570 has the same outline as a standard pump cassette 24 described earlier. The cassette fixture 4570 includes an access port 4572 associated with a specific valve or pump region of a standard cassette to align with its corresponding region on the cassette interface (control surface) of the base unit. The cassette fixture 4570 otherwise can have a flat smooth interface surface to allow the control surface to seal against it when it is mated to the base unit or cycler. Preferably, the cassette fixture 4570 is formed from a metal or other hard, stiff material. A resistance to flexing or deformation under pressure may help to increase reliability and consistency over multiple calibrations of multiple cyclers. As shown, the cassette fixture 4570 includes an access port 4572 which is recessed into the face of the cassette fixture 4570. The access port 4572 communicates with a fluid path 4573 extending to tubing 4574 leading away from the cassette fixture 4570. A cassette port or fitting may be included on the side of the cassette for connection via tubing to a reference pressure source 4576 in the example embodiment.

Figure 97:
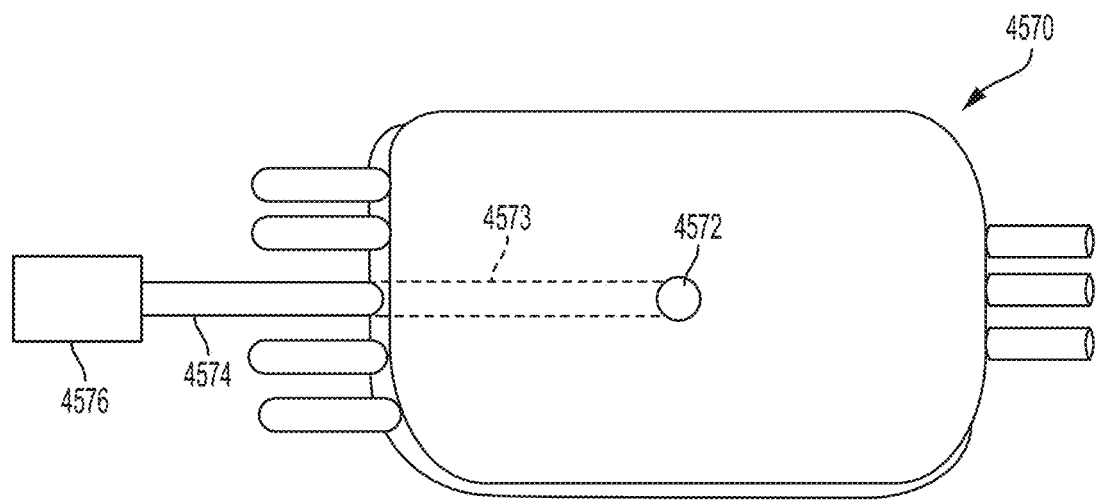
FIG. 97 shows another example of a cassette fixture which is made from a modified cassette such as the cassette shown in FIG. 3.
Figure 98:
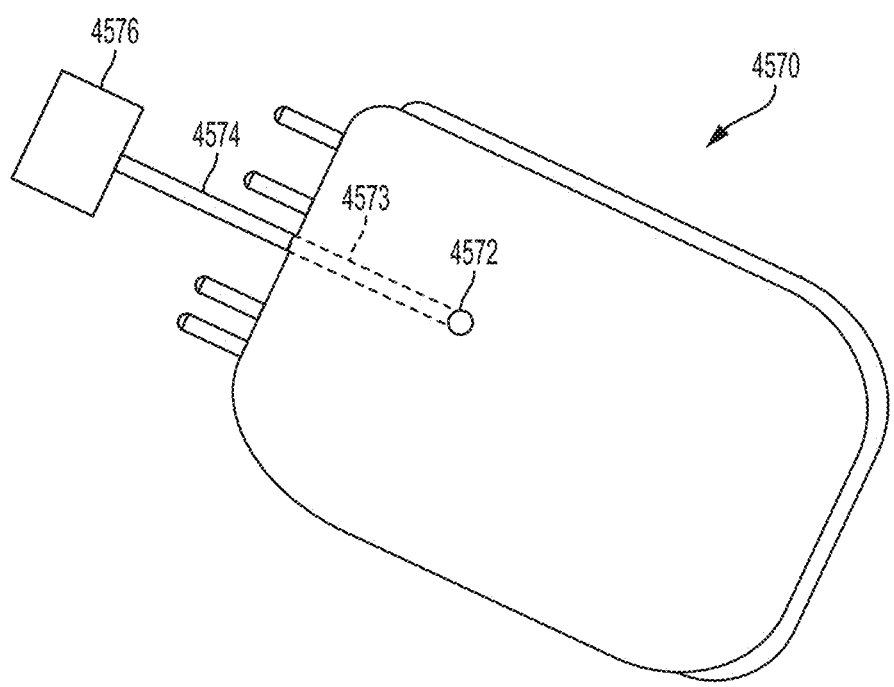
FIG. 98 shows another example of a cassette fixture which is made from a modified cassette.

FIGS. 97 and 98 depict other representations of a cassette fixture 4570 adapted from a modified cassette such as the cassette 24 shown in FIG. 3. In such examples, the cassette fixture 4570 may be made by removing or not including the sheeting or membrane from the control side of the cassette which faces a control surface or cassette interface 148 (see, for example, FIG. 90) of a cycler when installed in the cycler. Referring to FIG. 3, for example, the membrane 15 may not be included on the cassette 24. Thus, the pneumatic circuit of the cycler may be accessed directly through the cassette 24. Alternatively, the membrane or sheeting may be interrupted (e.g. removed, perforated, slit, or the like) on only a portion of the cassette to create the cassette fixture 4570. For example, the membrane may be modified in this manner in the area over which an access port 4572 of the cassette fixture 4570 is located.

Additionally, tubing 4574 may be attached to one or more of the external connection sites of a standard cassette to create the necessary fluid communication path of a cassette fixture 4570. The external connection sites can include any tubing attachment sites on the standard cassette, or may comprise more robust fittings for repeated use in calibration procedures. Referring to FIG. 3, external connection sites may include the cassette spikes 160 and/or the ports 150, 152 and 154. The cassette may then be modified so that all other external connection sites may be blocked, plugged or otherwise sealed.

As above, the tubing 4574 leads from a fluid flowpath 4573 fluidically connected to an access port 4572 in the cassette fixture 4570 to provide a connection path to a pressure reference 4576. The access port 4572 may be a pre-existing opening or valve port in the cassette body. Additionally, the fluid path 4573 may be any pre-existing pathway or combination of pathways in the cassette body which allow fluid communication from the access port 4572 to the tubing 4574 or an associated fitting on the side of the cassette. For example, a fluid path 4573 may include one or more valve port, valve well, pump chamber, and/or channel in the cassette body or any combination thereof.

In one embodiment, the inner wall of the control chambers 171B can include raised elements somewhat analogous to the spacer elements 50 of the pump chamber, e.g., as shown in FIG. 92 for the control chambers 171B associated with the pump control regions 1482. These raised elements can take the form of plateau features, ribs, or other protrusions that keep the control ports recessed away from the fully retracted control regions 1482. This arrangement may allow for a more uniform distribution of pressure or vacuum in the control chamber 171B, and prevent premature blocking of any control port by the control surface 148. A pre-formed control surface 148 (at least in the pump control regions) may not be under a significant stretching force when fully extended against either the inner wall of the pump chamber of the cassette 24 during a delivery stroke, or the inner wall of the control chamber 171 during a fill stroke. It may therefore be possible for the control region 1482 to extend asymmetrically into the control chamber 171B, causing the control region 1482 to prematurely close off one or more ports of the control chamber before the chamber is fully evacuated. Having features on the inner surface of the control chamber 171B that prevent contact between the control region 1482 and the control ports may help to assure that the control region 1482 can make uniform contact with the control chamber inner wall during a fill stroke.

As suggested above, the cycler 14 may include a control system 16 with a data processor in electrical communication with the various valves, pressure sensors, motors, etc., of the system and is preferably configured to control such components according to a desired operating sequence or protocol. The control system 16 may include appropriate circuitry, programming, computer memory, electrical connections, and/or other components to perform a specified task. The system may include pumps, tanks, manifolds, valves or other components to generate desired air or other fluid pressure (whether positive pressure—above atmospheric pressure or some other reference—or negative pressure or vacuum—below atmospheric pressure or some other reference) to control operation of the regions of the control surface 148, and other pneumatically-operated components. Further details regarding the control system 16 (or at least portions of it) are provided below.

In one illustrative embodiment, the pressure in the pump control chambers 171B may be controlled by a binary valve, e.g., which opens to expose the control chamber 171 to a suitable pressure/vacuum and closes to cut off the pressure/ vacuum source. The binary valve may be controlled using a saw tooth-shaped control signal which may be modulated to control pressure in the pump control chamber 171B. For example, during a pump delivery stroke (i.e., in which positive pressure is introduced into the pump control chamber 171B to move the membrane 15/control surface 148 and force liquid out of the pump chamber 181), the binary valve may be driven by the saw tooth signal so as to open and close at a relatively rapid rate to establish a suitable pressure in the control chamber 171B (e.g., a pressure between about 70-90 mmHg). If the pressure in the control chamber 171B rises above about 90 mmHg, the saw tooth signal may be adjusted to close the binary valve for a more extended period. If the pressure drops below about 70 mmHg in the control chamber 171B, the saw tooth control signal may again be applied to the binary valve to raise the pressure in the control chamber 171. Thus, during a typical pump operation, the binary valve will be opened and closed multiple times, and may be closed for one or more extended periods, so that the pressure at which the liquid is forced from the pump chamber 181 is maintained at a desired level or range (e.g., about 70-90 mmHg).

In some embodiments and in accordance with an aspect of the disclosure, it may be useful to detect an "end of stroke" of the membrane 15/pump control region 1482, e.g., when the membrane 15 contacts the spacers 50 in the pump chamber 181 or the pump control region 1482 contacts the wall of the pump control chamber 171B. For example, during a pumping operation, detection of the "end of stroke" may indicate that the membrane 15/pump control region 1482 movement should be reversed to initiate a new pump cycle (to fill the pump chamber 181 or drive fluid from the pump chamber 181). In one illustrative embodiment in which the pressure in the control chamber 171B for a pump is controlled by a binary valve driven by a saw tooth control signal, the pressure in the pump chamber 181 will fluctuate at a relatively high frequency, e.g., a frequency at or near the frequency at which the binary valve is opened and closed. A pressure sensor in the control chamber 171B may detect this fluctuation, which generally has a higher amplitude when the membrane 15/pump control region 1482 are not in contact with the inner wall of the pump chamber 181 or the wall of the pump control chamber 171B. However, once the membrane 15/pump control region 1482 contacts the inner wall of the pump chamber 181 or the wall of the pump control chamber 171B (i.e., the "end of stroke"), the pressure fluctuation is generally damped or otherwise changes in a way that is detectable by the pressure sensor in the pump control chamber 171B. This change in pressure fluctuation can be used to identify the end of stroke, and the pump and other components of the cassette 24 and/or cycler 14 may be controlled accordingly.

Figure 114:
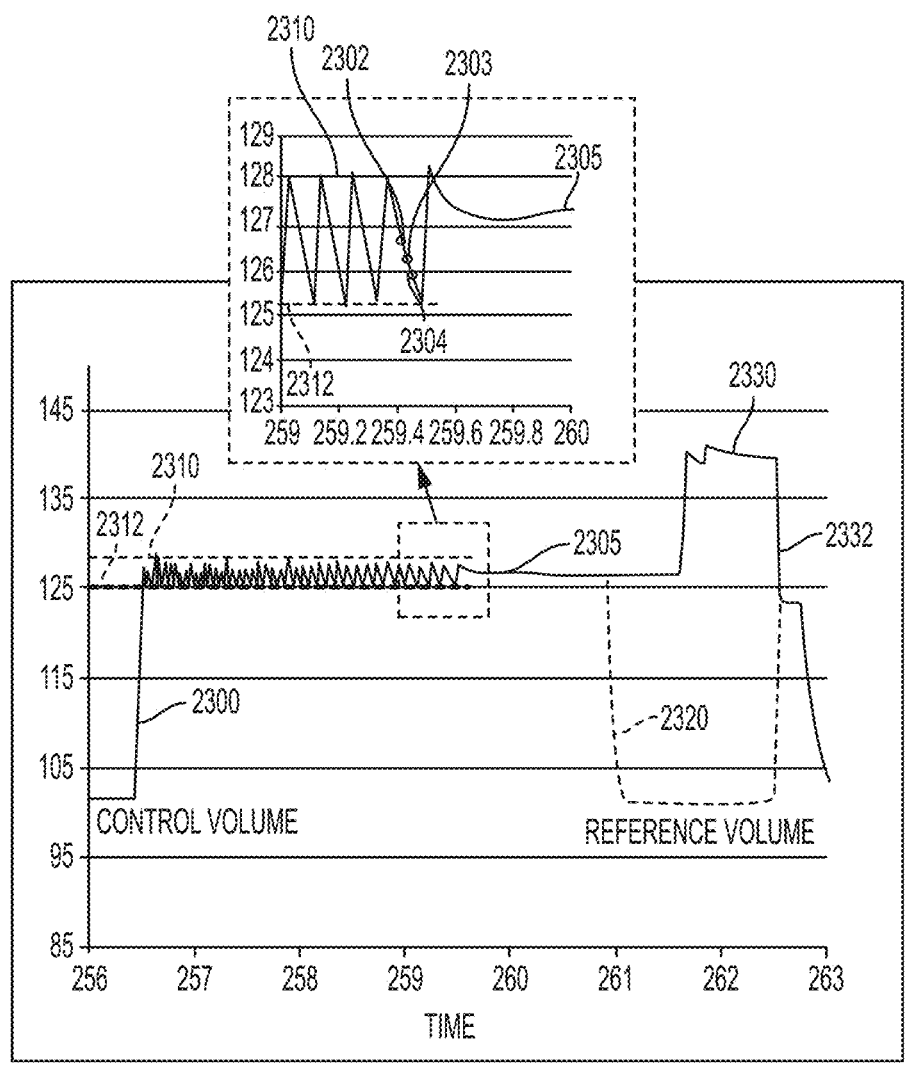

In one embodiment, the pneumatic pressure applied to the control chamber 171B is actively controlled by a processor receiving a signal from a pressure transducer 2672 (FIG. 37C) connected to the control chamber 171B and a fast acting binary valve X1A, X1B between a pressure reservoir 2620, 2610 and the control chamber 171B. The processor may control the pressure with a variety of control algorithms including closed loop proportional or proportional-integrator feedback control that varies the valve duty cycle to achieve the desired pressure in the control volume 171B. In one embodiment, the processor controls the pressure in the control chamber with an on-off controller often called a bang-bang controller. The on-off controller monitors the pressure in the control volume 171B during a deliver stroke and open the binary valve X1B (connecting the control volume 171B to the positive reservoir 2620) when the pressure is less than a lower first limit and closes the binary valve X1B when the pressure is above a higher second limit. During a fill stroke, the on-off controller opens the binary valve X1A (connecting the control volume 171B to the negative reservoir 2610) when the pressure is greater than a third limit and closes the binary valve X1A when the pressure is less than a fourth limit, where the fourth limit is lower than the third limit and both the third and fourth limits are less than the first limit. A plot of the pressure over time as during a deliver stroke and the subsequent FMS measurement is shown in FIG. 114. The control chamber pressure 2300 oscillates between the lower first limit 2312 and the higher second limit 2310 as the membrane 15 moves across the control chamber 171B. The pressure stops oscillating between the limits when the membrane 15 stops moving. The membrane 15 typically stops moving when it contacts either the stadium steps 50 of the cassette or it contacts the control chamber surface 171B. The membrane 15 may also stop moving if the outlet fluid line is occluded.

The automation computer (AC) 300 detects the end of stroke by evaluating the pressure signals. There are many possible algorithms to detect the end of pressure oscillation that indicate the end-of-stroke (EOS). The algorithms and methods to detect EOS in the section labeled "Detailed Description of the system and Method of Measuring Change Fluid Flow Rate" in U.S. Pat. No. 6,520,747 and the section describing the filtering to detect end of stroke in U.S. Pat. No. 8,292,594 are herein incorporated by reference.

One example of an algorithm to detect EOS, the AC 300 evaluates the time between the pressure crossing the first and second limits during a deliver stroke or third and fourth limits during a fill stroke. The on-off controller opens and closes the valves X1A, X1B in response to the pressure oscillating between the two limits as the control chamber volume changes during the fill or deliver stroke. When the membrane 15 stops moving at the end-of-stroke, the pressure changes will significantly diminish so that the pressure no longer exceeds one or both limits. The AC 300 may detect EOS by measuring the time between the pressure exceeding alternating limits. If the time since the pressure crossed the last limit exceeds a predefined threshold, then the AC 300 may declare an EOS. The algorithm may further include an initial period during which the AC 300 does not measure the time between limit crossings.

In another example algorithm, the AC 300 evaluates the derivative of the pressure signal with respect to time. The AC 300 may declare an EOS, if the derivative remains below a minimum threshold for a minimum length of time. In a further example, the minimum threshold is the average of the absolute value of the average pressure derivative during the stroke. The algorithm calculates the slope (derivative with respect to time) of a curve fit to a set of data points, where the data points are taken from a moving window. The absolute value of each slope is then averaged over the stroke to calculate the absolute value of the average pressure derivative. In another example of an EOS algorithm, the AC 300 may not include the pressure data until after an initial delay. The AC 300 ignores the initial pressure data to avoid false EOS detections due to irregular pressure traces that occasionally occur during the early part of the stroke. In another example, the AC 300 declares an EOS only after the second derivative of the pressure in the later part of the stroke has remained below a threshold for a minimum time and a wait period of time has past.

The criteria to declare an EOS may be optimized for different pumping conditions. The optimized EOS detection conditions include the second pressure derivative threshold, the minimum time to remain below the second derivative threshold, the duration of the initial delay and a length of the wait period. These EOS detection criteria may be optimized differently, for example, the fill stroke from the bags 20, 22, the deliver stroke to the patient, the fill stroke from the patient, and the deliver stroke to the bags 20,22. Alternatively each EOS detection criteria may be a function of the pumping pressure in the control chamber 171B.

Occluder

In one aspect of the disclosure, an occluder for opening/closing one or more flexible lines may include a pair of opposed occluding members, which may be configured as resilient elements, such as flat plates made of a spring steel (e.g., leaf springs), having a force actuator configured to apply a force to one or both of the occluding members to operate the occluder. In certain embodiments, the force actuator may comprise an expandable or enlargable member positioned between the resilient elements. With the expandable member in a reduced size condition, the resilient elements may be in a flat or nearly flat condition and urge a pinch head to engage with one or more lines so as to pinch the lines closed. However, when the expandable member urges the resilient elements apart, the resilient elements may bend and withdraw the pinch head, releasing the lines and allowing flow through the lines. In other embodiments, the occluding members could be essentially rigid with respect to the levels of force applied by the force actuator. In certain embodiments, the force actuator may apply a force to one or both opposed occluding members to increase the distance between the occluding members in at least a portion of the region where they are opposed to effect opening or closing of the flexible tubing.

Figure 99:
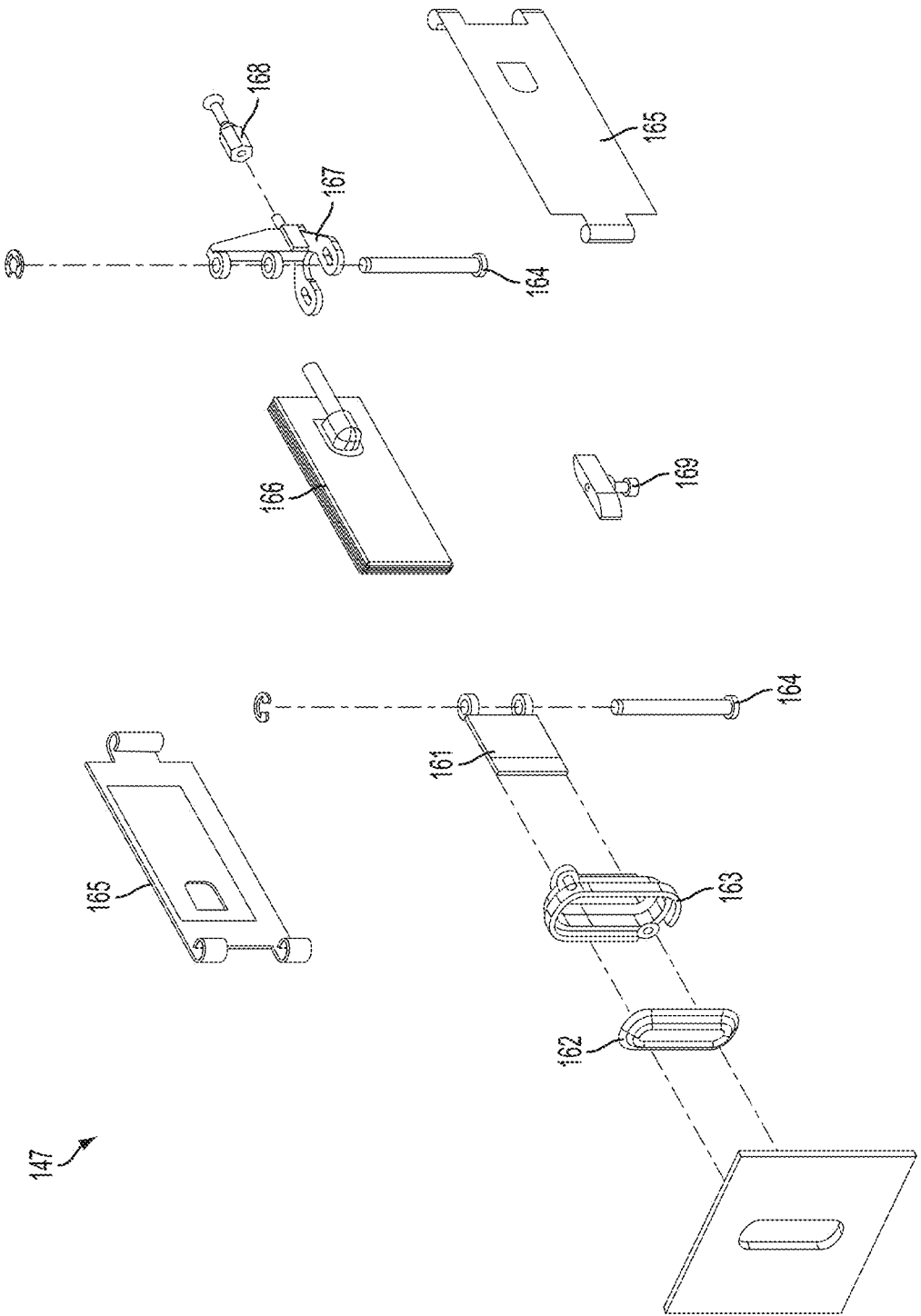
FIG. 99 is an exploded perspective view of an occluder in an illustrative embodiment.
Figure 100:
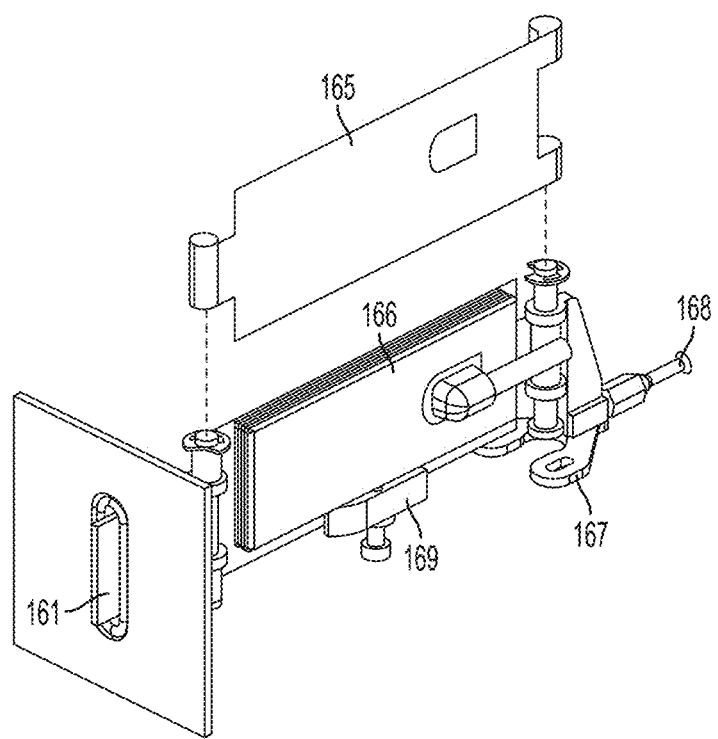
FIG. 100 is a partially exploded perspective view of the occluder of FIG. 99.

FIG. 99 shows an exploded view and FIG. 100 shows a partially assembled view of an illustrative embodiment of an occluder 147 that may be used to close, or occlude, the patient and drain lines 34 and 28, and/or other lines in the cycler 14 or the set 12 (such as, for example, the heater bag line 26). The occluder 147 includes an optional pinch head 161, e.g., a generally flat blade-like element that contacts the tubes to press the tubes against the door 141 and pinch the tubes closed. In other embodiments, the function of the pinch head could be replaced by an extending edge of one or both of occluding members 165. The pinch head 161 includes a gasket 162, such as an O-ring or other member, that cooperates with the pinch head 161 to help resist entry of fluid (air or liquid for example) into the cycler 14 housing, e.g., in case of leakage in one of the occluded lines. The bellows gasket 162 is mounted to, and pinch head 161 passes through, a pinch head guide 163 that is mounted to the front panel of the cycler housing, i.e., the panel exposed by opening the door 141. The pinch head guide 163 allows the pinch head 161 to move in and out of the pinch head guide 163 without binding and/or substantial resistance to sliding motion of the pinch head 161. A pivot shaft 164 attaches a pair of opposed occluder members, comprising in the illustrated embodiment spring plates 165, that each include a hook-shaped pivot shaft bearing, e.g., like that found on standard door hinges, to the pinch head 161. That is, the openings of shaft guides on the pinch head 161, and the openings formed by the hook-shaped bearings on the spring plates 165 are aligned with each other and the pivot shaft 164 is inserted through the openings so the pinch head 161 and the spring plates 165 are pivotally connected together. The spring plates 165 may be made of any suitable material, such as steel, and may be arranged to be generally flat when unstressed. The opposite end of the spring plates 165 includes similar hook-shaped bearings, which are pivotally connected to a linear adjustor 167 by a second pivot shaft 164. In this embodiment, the force actuator comprises a bladder 166 is positioned between the spring plates 165 and arranged so that when fluid (e.g., air under pressure) is introduced into the bladder, the bladder may expand and push the spring plates 165 away from each other in a region between the pivot shafts 164. The bladder 166 may be attached to one or both spring plates 165 by pressure sensitive adhesive (PSA) tape. A linear adjustor 167 is fixed to the cycler housing 82 while the pinch head 161 is allowed to float, although its movement is guided by the pinch head guide 163. The linear adjustor 167 includes slot holes at its lower end, allowing the entire assembly to be adjusted in position and thus permitting the pinch head to be appropriately positioned when the occluder 147 is installed in the cycler 14. A turnbuckle 168 or other arrangement may be used to help adjust the position of the linear adjustor 167 relative to the housing 82. That is, the pinch head 161 generally needs to be properly positioned so that with the spring plates 165 located near each other and the bladder 166 substantially emptied or at ambient pressure, the pinch head 161 suitably presses on the patient and drain lines so as to pinch the tubes closed to flow without cutting, kinking or otherwise damaging the tubes. The slot openings in the linear adjustor 167 allows for this fine positioning and fixing of the occluder 147 in place. An override release device, such as provided by release blade 169 is optionally positioned between the spring plates 165, and as is discussed in more detail below, may be rotated so as to push the spring plates 165 apart, thereby withdrawing the pinch head 161 into the pinch head guide 163. The release blade 169 may be manually operated, e.g., to disable the occluder 147 in case of power loss, bladder 166 failure or other circumstance.

Additional configurations and descriptions of certain components that may be instructive in constructing certain embodiments of the occluder are provided in U.S. Pat. No. 6,302,653. The spring plates 165 may be constructed from any material that is elastically resistant to bending forces and which has sufficient longitudinal stiffness (resistance to bending) to provide sufficient restoring force, in response to a bending displacement, to occlude a desired number of collapsible tubes. In the illustrated embodiment, each spring plate is essentially flat when unstressed and in the shape of a sheet or plate. In alternative embodiments utilizing one or more resilient occluding members (spring members), any occluding member(s) that is elastically resistant to bending forces and which has sufficient longitudinal stiffness (resistance to bending) to provide sufficient restoring force, in response to a bending displacement to occlude a desired number of collapsible tubes may be utilized. Potentially suitable spring members can have a wide variety of shapes as apparent to those of ordinary skill in the art, including, but not limited to cylindrical, prism-shaped, trapezoidal, square, or rectangular bars or beams, I-beams, elliptical beams, bowl-shaped surfaces, and others. Those of ordinary skill in the art can readily select proper materials and dimensions for spring plates 165 based on the present teachings and the requirements of a particular application.

Figure 101:
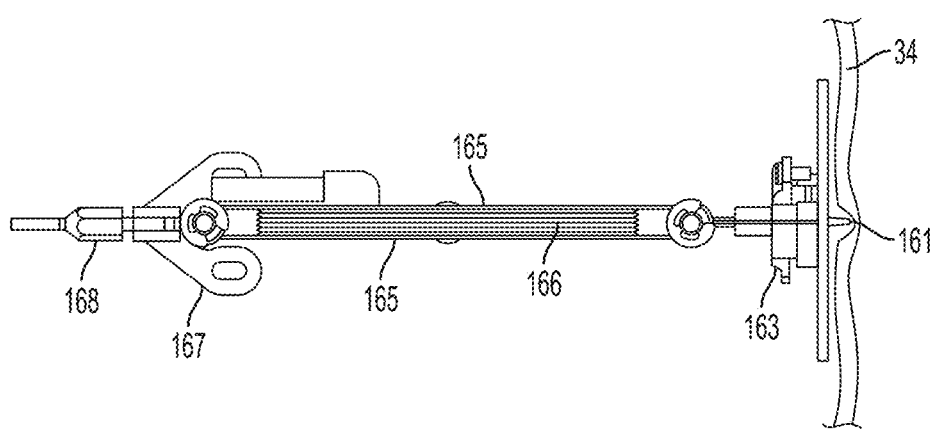
FIG. 101 is a top view of the occluder of FIG. 99 with the bladder in a deflated state.
Figure 102:
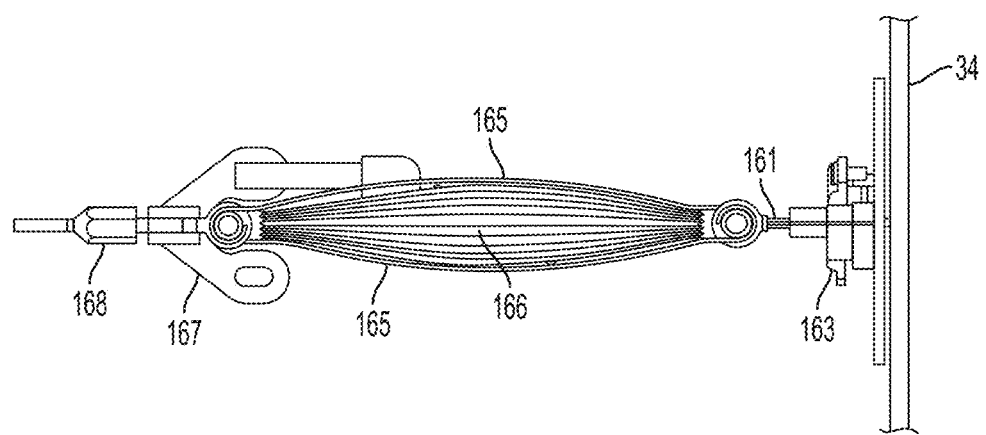
FIG. 102 is a top view of the occluder of FIG. 99 with the bladder in an inflated state.

FIG. 101 shows a top view of the occluder 147 with the bladder 166 deflated and the spring plates 165 located near each other and in a flat or nearly flat condition. In this position, the pinch head 161 is fully extended from the pinch head guide and the front panel of the cycler 14 (i.e., the panel inside of the door 141) and enabled to occlude the patient and drain lines. FIG. 102, on the other hand, shows the bladder 166 in an inflated state in which the spring plates 165 are pushed apart, thereby retracting the pinch head 161 into the pinch head guide 163. Note that the linear adjustor 167 is fixed in place relative to the cycler housing 82 and thus fixed relative to the front panel of the housing 82. As the spring plates 165 are moved apart, the pinch head 161 moves rearward relative to the front panel since the pinch head 161 is arranged to move freely in and out of the pinch head guide 163. This condition prevents the pinch head 161 from occluding the patient and drain lines and is the condition in which the occluder 147 remains during normal operation of the cycler 14. That is, as discussed above, various components of the cycler 14 may operate using air pressure/vacuum, e.g., the control surface 148 may operate under the drive of suitable air pressure/vacuum to cause fluid pumping and valve operation for the cassette 24. Thus, when the cycler 14 is operating normally, the cycler 14 may produce sufficient air pressure to not only control system operation, but also to inflate the bladder 166 to retract the pinch head 161 and prevent occlusion of the patient and drain lines. However, in the case of system shut down, failure, fault or other condition, air pressure to the bladder 166 may be terminated, causing the bladder 166 to deflate and the spring plates 165 to straighten and extend the pinch head 161 to occlude the lines. One possible advantage of the arrangement shown is that the return force of the spring plates 165 is balanced such that the pinch head 161 generally will not bind in the pinch head guide 163 when moving relative to the pinch head guide 163. In addition, the opposing forces of the spring plates 165 will tend to reduce the amount of asymmetrical frictional wear of the pivot shafts and bushings of the assembly. Also, once the spring plates 165 are in an approximately straight position, the spring plates 165 can exert a force in a direction generally along the length of the pinch head 161 that is several times larger than the force exerted by the bladder 166 on the spring plates 165 to separate the spring plates 165 from each other and retract the pinch head 161. Further, with the spring plates 165 in a flat or nearly flat condition, the force needed to be exerted by fluid in the collapsed tubing to overcome the pinching force exerted by the pinch head 161 approaches a relatively high force required, when applied to the spring plates at their ends and essentially parallel to the plane of the flattened spring plates, to buckle the spring plates by breaking the column stability of the flattened spring plates. As a result, the occluder 147 can be very effective in occluding the lines with a reduced chance of failure while also requiring a relatively small force be applied by the bladder 166 to retract the pinch head 161. The dual spring plate arrangement of the illustrative embodiment may have the additional advantage of significantly increasing the pinching force provided by the pinch head, for any given force needed to bend the spring plate, and/or for any given size and thickness of spring plate.

In some circumstances, the force of the occluder 147 on the lines may be relatively large and may cause the door 141 to be difficult to open. That is, the door 141 must oppose the force of the occluder 147 when the pinch head 161 is in contact with and occluding lines, and in some cases this may cause the latch that maintains the door 141 in a closed state to be difficult or impossible to operate by hand. Of course, if the cycler 14 is started and produces air pressure to operate, the occluder bladder 166 can be inflated and the occluder pinch head 161 retracted. However, in some cases, such as with a pump failure in the cycler 14, inflation of the bladder 166 may be impossible or difficult. To allow opening of the door, the occluder 147 may include a manual release. In this illustrative embodiment, the occluder 147 may include a release blade 169 as shown in FIGS. 99 and 100 which includes a pair of wings pivotally mounted for rotary movement between the spring plates 165. When at rest, the release blade wings may be aligned with the springs as shown in FIG. 100, allowing the occluder to operate normally. However, if the spring plates 165 are in a flat condition and the pinch head 161 needs to be retracted manually, the release blade 169 may be rotated, e.g., by engaging a hex key or other tool with the release blade 169 and turning the release blade 169, so that the wings push the spring plates 165 apart. The hex key or other tool may be inserted through an opening in the housing 82 of the cycler 14, e.g., an opening near the left side handle depression in the cycler housing 82, and operated to disengage the occluder 147 and allow the door 141 to be opened.

Pump Volume Delivery Measurement

In another aspect of the invention, the cycler 14 may determine a volume of fluid delivered in various lines of the system 10 without the use of a flowmeter, weight scale or other direct measurement of fluid volume or weight. For example, in one embodiment, a volume of fluid moved by a pump, such as a pump in the cassette 24, may be determined based on pressure measurements of a gas used to drive the pump. In one embodiment, a volume determination can be made by isolating two chambers from each other, measuring the respective pressures in the isolated chambers, allowing the pressures in the chambers to partially or substantially equalize (by fluidly connecting the two chambers) and measuring the pressures. Using the measured pressures, the known volume of one of the chambers, and an assumption that the equalization occurs in an adiabatic way, the volume of the other chamber (e.g., a pump chamber) can be calculated. In one embodiment, the pressures measured after the chambers are fluidly connected may be substantially unequal to each other, i.e., the pressures in the chambers may not have yet completely equalized. However, these substantially unequal pressures may be used to determine a volume of the pump control chamber, as explained below.

Figure 103:
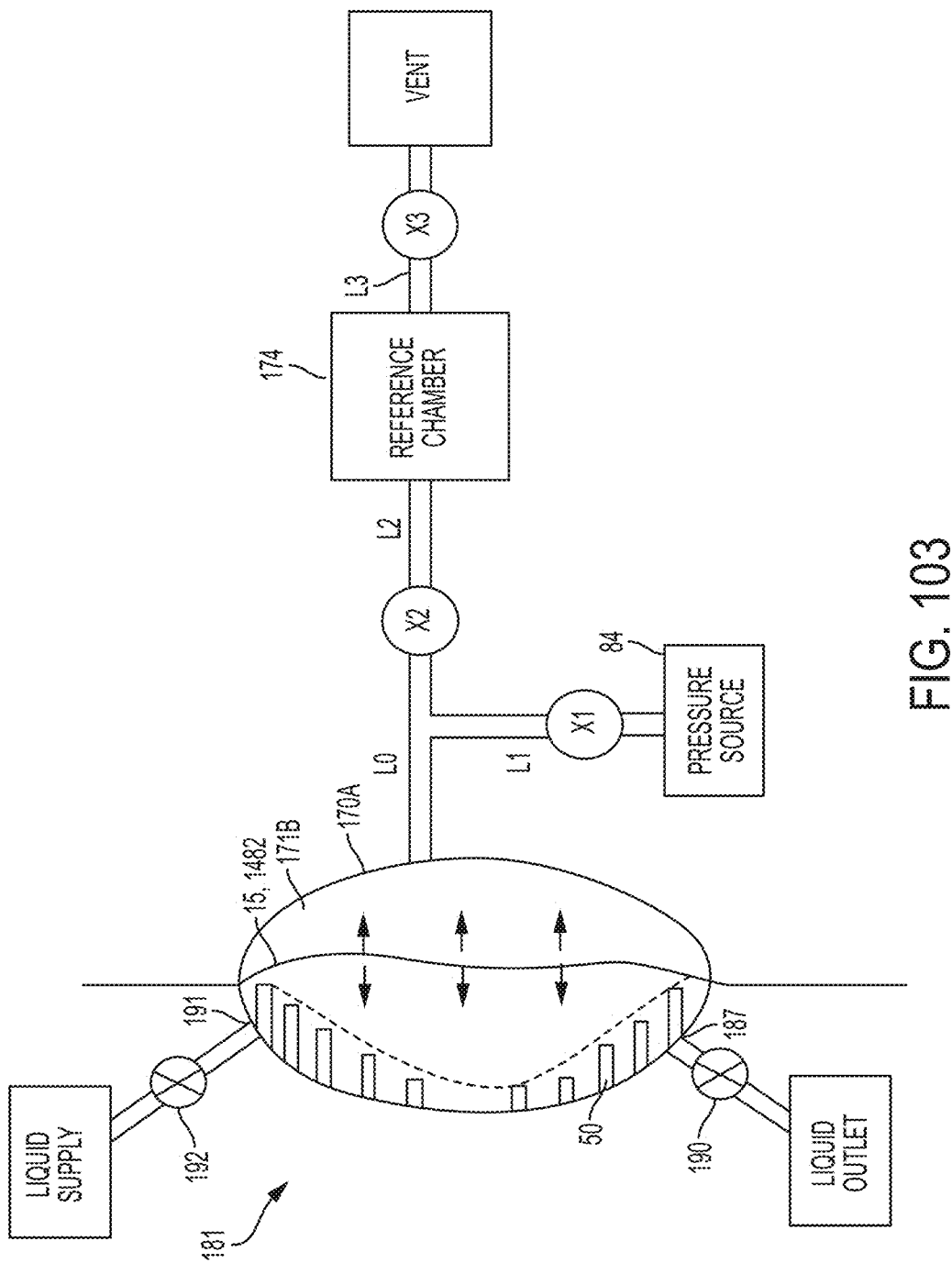
FIG. 103 is a schematic view of a pump chamber of a cassette and associated control components and inflow/outflow paths in an illustrative embodiment.

For example, FIG. 103 shows a schematic view of a pump chamber 181 of the cassette 24 and associated control components and inflow/outflow paths. In this illustrative example, a liquid supply, which may include the heater bag 22, heater bag line 26 and a flow path through the cassette 24, is shown providing a liquid input at the upper opening 191 of the pump chamber. The liquid outlet is shown in this example as receiving liquid from the lower opening 187 of the pump chamber 181, and may include a flow path of the cassette 24 and the patient line 34, for example. The liquid supply may include a valve, e.g., including the valve port 192, that can be opened and closed to permit/impede flow to or from the pump chamber 181. Similarly, the liquid outlet may include a valve, e.g., including the valve port 190, that can be opened and closed to permit/impede flow to or from the pump chamber 181. Of course, the liquid supply could include any suitable arrangement, such as one or more solution containers, the patient line, one or more flow paths in the cassette 24 or other liquid source, and the liquid outlet could likewise include any suitable arrangement, such as the drain line, the heater bag and heater bag line, one or more flow paths in the cassette 24 or other liquid outlet. Generally speaking, the pump chamber 181 (i.e., on the left side of the membrane 14 in FIG. 103) will be filled with an incompressible liquid, such as water or dialysate, during operation. However, air or other gas may be present in the pump chamber 181 in some circumstances, such as during initial operation, priming, or other situations as discussed below. Also, it should be understood that although aspects of the invention relating to volume and/or pressure detection for a pump are described with reference to the pump arrangement of the cassette 24, aspects of the invention may be used with any suitable pump or fluid movement system.

FIG. 103 also shows schematically to the right of the membrane 15 and the control surface 1482 (which are adjacent each other) a control chamber 171B, which may be formed as a void or other space in the mating block 170A associated with the pump control region 1482 of the control surface 1482 for the pump chamber 181, as discussed above. It is in the control chamber 171B that suitable air pressure is introduced to cause the membrane 15/control region 1482 to move and effect pumping of liquid in the pump chamber 181. The control chamber 171B may communicate with a line L0 that branches to another line L1 and a first valve X1 that communicates with a pressure source 84 (e.g., a source of air pressure or vacuum). The pressure source 84 may include a piston pump in which the piston is moved in a chamber to control a pressure delivered to the control chamber 171B, or may include a different type of pressure pump and/or tank(s) to deliver suitable gas pressure to move the membrane 15/control region 1482 and perform pumping action. The line L0 also leads to a second valve X2 that communicates with another line L2 and a reference chamber 174 (e.g., a space suitably configured for performing the measurements described below). The reference chamber 174 also communicates with a line L3 having a valve X3 that leads to a vent or other reference pressure (e.g., a source of atmospheric pressure or other reference pressure). Each of the valves X1, X2 and X3 may be independently controlled. Pressure sensors may be arranged, e.g., one sensor at the control chamber 171B and another sensor at the reference chamber 174, to measure pressure associated with the control chamber and the reference chamber. These pressure sensors may be positioned and may operate to detect pressure in any suitable way. The pressure sensors may communicate with the control system 16 for the cycler 14 or other suitable processor for determining a volume delivered by the pump or other features.

As mentioned above, the valves and other components of the pump system shown in FIG. 103 can be controlled so as to measure pressures in the pump chamber 181, the liquid supply and/or liquid outlet, and/or to measure a volume of fluid delivered from the pump chamber 181 to the liquid supply or liquid outlet. Regarding volume measurement, one technique used to determine a volume of fluid delivered from the pump chamber 181 is to compare the relative pressures at the control chamber 171B to that of the reference chamber 174 in two different pump states. By comparing the relative pressures, a change in volume at the control chamber 171B can be determined, which corresponds to a change in volume in the pump chamber 181 and reflects a volume delivered from/received into the pump chamber 181. For example, after the pressure is reduced in the control chamber 171B during a pump chamber fill cycle (e.g., by applying negative pressure from the pressure source through open valve X1) so as to draw the membrane 15 and pump control region 1482 into contact with at least a portion of the control chamber wall (or to another suitable position for the membrane 15/region 1482), valve X1 may be closed to isolate the control chamber from the pressure source, and valve X2 may be closed, thereby isolating the reference chamber 174 from the control chamber 171B. Valve X3 may be opened to vent the reference chamber to ambient pressure, then closed to isolate the reference chamber. With valve X1 closed and the pressures in the control chamber and reference chamber measured, valve X2 is then opened to allow the pressure in the control chamber and the reference chamber to start to equalize. The initial pressures of the reference chamber and the control chamber, together with the known volume of the reference chamber and pressures measured after equalization has been initiated (but not yet necessarily completed) can be used to determine a volume for the control chamber. This process may be repeated at the end of the pump delivery cycle when the sheet 15/control region 1482 are pushed into contact with the spacer elements 50 of the pump chamber 181. By comparing the control chamber volume at the end of the fill cycle to the volume at the end of the delivery cycle, a volume of liquid delivered from the pump can be determined.

Conceptually, the pressure equalization process (e.g., at opening of the valve X2) is viewed as happening in an adiabatic way, i.e., without heat transfer occurring between air in the control and reference chambers and its environment. The conceptual notion is that there is an imaginary piston located initially at the valve X2 when the valve X2 is closed, and that the imaginary piston moves in the line L0 or L2 when the valve X2 is opened to equalize the pressure in the control and reference chambers. Since (a) the pressure equalization process happens relatively quickly, (b) the air in the control chamber and the reference chamber has approximately the same concentrations of elements, and (c) the temperatures are similar, the assumption that the pressure equalization happens in an adiabatic way may introduce only small error into the volume measurements. Also, in one embodiment, the pressures taken after equalization has been initiated may be measured before substantial equalization has occurred—further reducing the time between measuring the initial pressures and the final pressures used to determine the pump chamber volume. Error can be further reduced, for example, by using low thermal conductivity materials for the membrane 15/control surface 1482, the cassette 24, the control chamber 171B, the lines, the reference chamber 174, etc., so as to reduce heat transfer.

Given the assumption that an adiabatic system exists between the state when the valve X2 is closed until after the valve X2 is opened and the pressures equalize, the following applies:

$$PV^{\gamma} = \text{Constant} \tag{1}$$

where P is pressure, V is volume and γ is equal to a constant (e.g., about 1.4 where the gas is diatomic, such as air). Thus, the following equation can be written to relate the pressures and volumes in the control chamber and the reference chamber before and after the opening of valve X2 and pressure equalization occurs:

$$PrVr^{\gamma} + PdVd^{\gamma} = \text{Constant} = PfVf^{\gamma} \tag{2}$$

where Pr is the pressure in the reference chamber and lines L2 and L3 prior to the valve X2 opening, Vr is the volume of the reference chamber and lines L2 and L3 prior to the valve X2 opening, Pd is the pressure in the control chamber and the lines L0 and L1 prior to the valve X2 opening, Vd is the volume of the control chamber and the lines L0 and L1 prior to the valve X2 opening, Pf is the equalized pressure in the reference chamber and the control chamber after opening of the valve X2, and Vf is the volume of the entire system including the control chamber, the reference chamber and the lines L0, L1, L2, and L3, i.e., Vf=Vd+Vr. Since Pr, Vr, Pd, Pf and γ are known, and Vf=Vr+Vd, this equation can be used to solve for Vd. (Although reference is made herein to use of a "measured pressure" in determining volume values, etc., it should be understood that such a measured pressure value need not necessarily be any particular form, such as in psi units.

Instead, a "measured pressure" or "determined pressure" may include any value that is representative of a pressure, such as a voltage level, a resistance value, a multibit digital number, etc. For example, a pressure transducer used to measure pressure in the pump control chamber may output an analog voltage level, resistance or other indication that is representative of the pressure in the pump control chamber. The raw output from the transducer may be used as a measured pressure, and/or some modified form of the output, such as a digital number generated using an analog output from the transducer, a psi or other value that is generated based on the transducer output, and so on. The same is true of other values, such as a determined volume, which need not necessarily be in a particular form such as cubic centimeters. Instead, a determined volume may include any value that is representative of the volume, e.g., could be used to generate an actual volume in, say, cubic centimeters.

In an embodiment of a fluid management system ("FMS") technique to determine a volume delivered by the pump, it is assumed that pressure equalization upon opening of the valve X2 occurs in an adiabatic system. Thus, Equation 3 below gives the relationship of the volume of the reference chamber system before and after pressure equalization:

$$Vrf=Vri(Pf/Patm)^{-(1/\gamma)} \quad (3)$$

where Vrf is the final (post-equalization) volume of the reference chamber system including the volume of the reference chamber, the volume of the lines L2 and L3 and the volume adjustment resulting from movement of the "piston", which may move to the left or right of the valve X2 after opening, Vri is the initial (pre-equalization) volume of the reference chamber and the lines L2 and L3 with the "piston" located at the valve X2, Pf is the final equalized pressure after the valve X2 is opened, and Patm is the initial pressure of the reference chamber before valve X2 opening (in this example, atmospheric pressure). Similarly, Equation 4 gives the relationship of the volume of the control chamber system before and after pressure equalization:

$$Vdf=Vdi(Pf/Pdi)^{-(1/\gamma)} \quad (4)$$

where Vdf is the final volume of the control chamber system including the volume of the control chamber, the volume of the lines L0 and L1, and the volume adjustment resulting from movement of the "piston", which may move to the left or right of the valve X2 after opening, Vdi is the initial volume of the control chamber and the lines L0 and L1 with the "piston" located at the valve X2, Pf is the final pressure after the valve X2 is opened, and Pdi is the initial pressure of the control chamber before valve X2 opening.

The volumes of the reference chamber system and the control chamber system will change by the same absolute amount after the valve X2 is opened and the pressure equalizes, but will differ in sign (e.g., because the change in volume is caused by movement of the "piston" left or right when the valve X2 opens), as shown in Equation 5:

$$\Delta Vr=(-1)\Delta Vd \quad (5)$$

(Note that this change in volume for the reference chamber and the control chamber is due only to movement of the imaginary piston. The reference chamber and control chamber will not actually change in volume during the equalization process under normal conditions.) Also, using the relationship from Equation 3, the change in volume of the reference chamber system is given by:

$$\Delta Vr=Vrf-Vri=Vri(-1+(Pf/Patm)^{-(1/\gamma)}) \quad (6)$$

Similarly, using Equation 4, the change in volume of the control chamber system is given by:

$$\Delta Vd=Vdf-Vdi=Vdi(-1+(Pf/Pdi)^{-(1/\gamma)}) \quad (7)$$

Because Vri is known, and Pf and Patm are measured or known, $\Delta Vr$ can be calculated, which according to Equation 5 is assumed to be equal to $(-)\Delta Vd$. Therefore, Vdi (the volume of the control chamber system before pressure equalization with the reference chamber) can be calculated using Equation 7. In this embodiment, Vdi represents the volume of the control chamber plus lines L0 and L1, of which L0 and L1 are fixed and known quantities. Subtracting L0 and L1 from Vdi yields the volume of the control chamber alone. By using Equation 7 above, for example, both before (Vdi1) and after (Vdi2) a pump operation (e.g., at the end of a fill cycle and at the end of a discharge cycle), the change in volume of the control chamber can be determined, thus providing a measurement of the volume of fluid delivered by (or taken in by) the pump. For example, if Vdi1 is the volume of the control chamber at the end of a fill stroke, and Vdi2 is the volume of the control chamber at the end of the subsequent delivery stroke, the volume of fluid delivered by the pump may be estimated by subtracting Vdi1 from Vdi2. Since this measurement is made based on pressure, the volume determination can be made for nearly any position of the membrane 15/pump control region 1482 in the pump chamber 181, whether for a full or partial pump stroke. However, measurement made at the ends of fill and delivery strokes can be accomplished with little or no impact on pump operation and/or flow rate.

One aspect of the invention involves a technique for identifying pressure measurement values that are to be used in determining a volume for the control chamber and/or other purposes. For example, although pressure sensors may be used to detect a pressure in the control chamber and a pressure in the reference chamber, the sensed pressure values may vary with opening/closing of valves, introduction of pressure to the control chamber, venting of the reference chamber to atmospheric pressure or other reference pressure, etc. Also, since in one embodiment, an adiabatic system is assumed to exist from a time before pressure equalization between the control chamber and the reference chamber until after equalization, identifying appropriate pressure values that were measured as close together in time may help to reduce error (e.g., because a shorter time elapsed between pressure measurements may reduce the amount of heat that is exchanged in the system). Thus, the measured pressure values may need to be chosen carefully to help ensure appropriate pressures are used for determining a volume delivered by the pump, etc.

As mentioned, L3 of FIG. 103 may have a valve X3 which leads to a vent. In some embodiments, this vent may communicate with the atmosphere or, in other embodiments, another reference pressure. In some embodiments, this vent may be connected via a valve to the control chamber 171B such that the control chamber may be vented (see, e.g., FIG. 95). In prior devices the vent has been used to bring a control chamber 171B from a negative pressure after a fill stroke to ambient pressure before positive pressurization of the control chamber 171B. This brings the control chamber 171B to a higher starting pressure before connection to the pressure source 84 and consequently minimizes the depletion of pressure in a positive pressure source or reservoir 84. As a result a pump supplying a positive pressure reservoir 84 would be required to run less frequently.

On the other hand, it has since been determined that venting a control chamber 171B which is already at a positive pressure to a lower pressure before subsequently positively repressurizing the chamber for an FMS measurement may be advantageous in some scenarios. Though this new step requires additional work (e.g. pump runtime) to keep the pressure source 84 at its pressure set point, it may be done to help mitigate any possible undesirable effects from back pressure (e.g. due to an occluded line leading to or from the associated pumping chamber, or due to a partial occlusion). Additionally, this may help to increase the overall accuracy of volume measurement and fluid accounting. One possible reason for this is that a pump chamber outlet valve 190—in this case a pneumatically operated membrane valve—may not close as efficiently when the control chamber 171B remains positively pressurized.

In some embodiments, a control system 16 of a cycler 14 may vent the control chamber 171B before taking a measurement to determine fluid volume delivered or filled. Additionally, in some embodiments, the control system 16 of a cycler 14 may vent a first control chamber 171B before performing a pumping operation with a second control chamber included in the installed cassette 24.

In the example embodiment shown in FIG. 103, this venting or back pressure relief may be accomplished by opening valves X2 and X3 and closing valve X1. Thus, the control chamber 171B may be placed into communication with the vent via the reference chamber 174. In other embodiments, of course, a control chamber 171B may be placed into more direct communication with a vent. For example, an additional valve associated with a fluid path in direct communication with the vent may be included. Any other suitable configuration may also be used.

In some embodiments, the control chamber 171B may be vented by placing the control chamber 171B into fluid communication with the vent for a suitable or predetermined period of time. In other embodiments, to control venting of a control chamber 171B, the control system 16 of the cycler 14 may use data from a pressure sensor associated with one or both of the control chambers 171B or reference chamber 174 (or in a location fluidly connectable to the control chamber, such as, for example, a pressure distribution module). In such embodiments, data from the pressure sensor(s) may be used to determine whether or not the control chamber 171B has been sufficiently vented. Once a determination is made that the control chamber 171B has been sufficiently vented, the control system 16 of the cycler 14 may close the appropriate valve to isolate the control chamber 171B from the vent. In order for the control system 16 to determine that the control chamber 171B has been sufficiently vented, the control chamber 171B pressure need not necessarily fully equalize with that of the vent.

In some embodiments, in order to relieve back pressure in a control chamber 171B, it may instead be subjected to a negative pressure source for an appropriate or predetermined period of time. In such embodiments, the control chamber 171B may be placed into communication with a pressure source 84. In the example embodiment shown in FIG. 103, this may be accomplished by opening valve X1 and closing at least valve X3. In the case of a positively pressurized control chamber 171B, the pressure source to which the control chamber 171B is connected may be a negative pressure source. In some embodiments, the control system 16 of the cycler 14 may only open a valve to the negative pressure source for a brief period of time. The brief period of time may be of a duration sufficient to bring the pressure in the control chamber 171B to within a pre-determined range of a predetermined value (in an example, this may be approximately atmospheric pressure), before it is allowed to equalize with the pressure source. In other embodiments, the valve X1 may be modulated to produce the same effect. If it is a vari-valve, its orifice opening may be modulated by the controller; whereas if it is a binary valve, the controller may modulate the rate and magnitude of pressure delivery across the valve using, for example, pulse-width-modulation.

Figure 104:
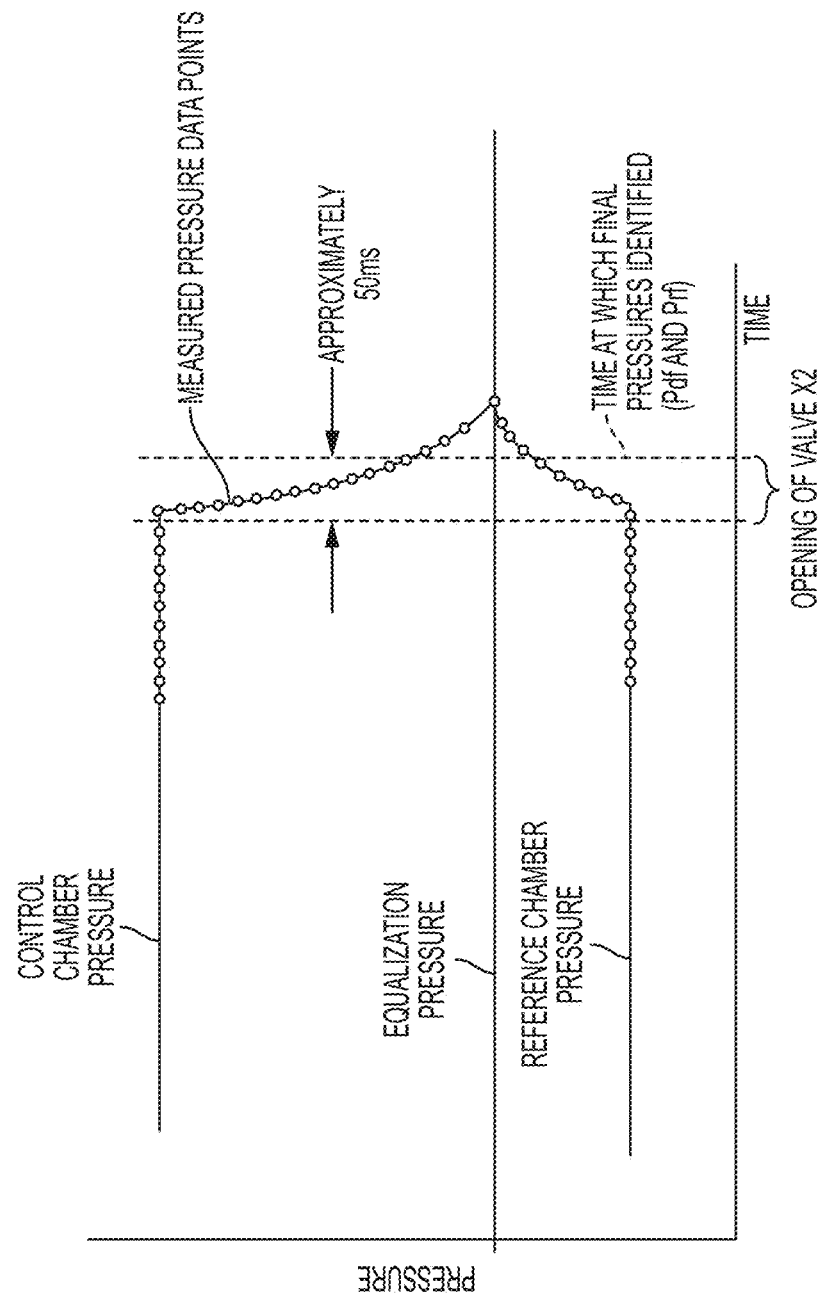
FIG. 104 is a plot of illustrative pressure values for the control chamber and the reference chamber from a point in time before opening of the valve X2 until some time after the valve X2 is opened for the embodiment of FIG. 103.

For purposes of explanation, FIG. 104 shows a plot of illustrative pressure values for the control chamber and the reference chamber from a point in time before opening of the valve X2 until some time after the valve X2 is opened to allow the pressure in the chambers to equalize. In this illustrative embodiment, the pressure in the control chamber is higher than the pressure in the reference chamber before equalization, but it should be understood that the control chamber pressure may be lower than the reference chamber pressure before equalization in some arrangements, such as during and/or at the end of a fill stroke. Also, the plot in FIG. 104 shows a horizontal line marking the equalization pressure, but it should be understood that this line is shown for clarity only. The equalization pressure in general will not be known prior to opening of the valve X2. In this embodiment, the pressure sensors sense pressure at a rate of about 2000 Hz for both the control chamber and the reference chamber, although other suitable sampling rates could be used. Before opening of the valve X2, the pressures in the control chamber and the reference chamber are approximately constant, there being no air or other fluid being introduced into the chambers. Thus, the valves X1 and X3 will generally be closed at a time before opening of the valve X2. Also, valves leading into the pump chamber, such as the valve ports 190 and 192, may be closed to prevent influence of pressure variations in the pump chamber, the liquid supply or liquid outlet.

At first, the measured pressure data is processed to identify the initial pressures for the control chamber and reference chambers, i.e., Pd and Pr. In one illustrative embodiment, the initial pressures are identified based on analysis of a 10-point sliding window used on the measured pressure data. This analysis involves generating a best fit line for the data in each window (or set), e.g., using a least squares technique, and determining a slope for the best fit line. For example, each time a new pressure is measured for the control chamber or the reference chamber, a least squares fit line may be determined for a data set including the latest measurement and the 9 prior pressure measurements. This process may be repeated for several sets of pressure data, and a determination may be made as to when the slope of the least squares fit lines first becomes negative (or otherwise non-zero) and continues to grow more negative for subsequent data sets (or otherwise deviates from a zero slope). The point at which the least squares fit lines begin to have a suitable, and increasing, non-zero slope may be used to identify the initial pressure of the chambers, i.e., at a time before the valve X2 is opened.

In one embodiment, the initial pressure value for the reference chamber and the control chamber may be determined to be in the last of 5 consecutive data sets, where the slope of the best fit line for the data sets increases from the first data set to the fifth data set, and the slope of the best fit line for the first data set first becomes non-zero (i.e., the slope of best fit lines for data sets preceding the first data set is zero or otherwise not sufficiently non-zero). For example, the pressure sensor may take samples every ½ millisecond (or other sampling rate) starting at a time before the valve X2 opens. Every time a pressure measurement is made, the cycler 14 may take the most recent measurement together with the prior 9 measurements, and generate a best fit line to the 10 data points in the set. Upon taking the next pressure measurement (e.g., ½ millisecond later), the cycler 14 may take the measurement together with the 9 prior measurements, and again generate a best fit line to the 10 points in the set. This process may be repeated, and the cycler 14 may determine when the slope of the best fit line for a set of 10 data points first turns non-zero (or otherwise suitably sloped) and, for example, that the slope of the best fit line for 5 subsequent sets of 10 data points increases with each later data set. To identify the specific pressure measurement to use, one technique is to select the third measurement in the $5^{th}$ data set (i.e., the $5^{th}$ data set with which it was found that the best fit line has been consistently increasing in slope and the $1^{st}$ measurement is the pressure measurement that was taken earliest in time) as the measurement to be used as the initial pressure for the control chamber or the reference chamber, i.e., Pd or Pr. This selection was chosen using empirical methods, e.g., plotting the pressure measurement values and then selecting which point best represents the time when the pressure began the equalization process. Of course, other techniques could be used to select the appropriate initial pressure.

In one illustrative embodiment, a check may be made that the times at which the selected Pd and Pr measurements occurred were within a desired time threshold, e.g., within 1-2 milliseconds of each other. For example, if the technique described above is used to analyze the control chamber pressure and the reference chamber pressure and identify a pressure measurement (and thus a point in time) just before pressure equalization began, the times at which the pressures were measured should be relatively close to each other. Otherwise, there may have been an error or other fault condition that invalidates one or both of the pressure measurements. By confirming that the time at which Pd and Pr occurred are suitably close together, the cycler 14 may confirm that the initial pressures were properly identified.

To identify when the pressures in the control chamber and the reference chamber have equalized such that measured pressures for the chamber can be used to reliably determine pump chamber volume, the cycler 14 may analyze data sets including a series of data points from pressure measurements for both the control chamber and the reference chamber, determine a best fit line for each of the data sets (e.g., using a least squares method), and identify when the slopes of the best fit lines for a data set for the control chamber and a data set for the reference chamber are first suitably similar to each other, e.g., the slopes are both close to zero or have values that are within a threshold of each other. When the slopes of the best fit lines are similar or close to zero, the pressure may be determined to be equalized. The first pressure measurement value for either data set may be used as the final equalized pressure, i.e., Pf. In one illustrative embodiment, it was found that pressure equalization occurred generally within about 200-400 milliseconds after valve X2 is opened, with the bulk of equalization occurring within about 50 milliseconds. Accordingly, the pressure in the control and reference chambers may be sampled approximately 400-800 times or more during the entire equalization process from a time before the valve X2 is opened until a time when equalization has been achieved.

In some cases, it may be desirable to increase the accuracy of the control chamber volume measurement using an alternate FMS technique. Substantial differences in temperature between the liquid being pumped, the control chamber gas, and the reference chamber gas may introduce significant errors in calculations based on the assumption that pressure equalization occurs adiabatically. Waiting to make pressure measurements until full equalization of pressure between the control chamber and the reference chamber may allow an excessive amount of heat transfer to occur. In one aspect of the invention, pressure values for the pump chamber and reference chamber that are substantially unequal to each other, i.e., that are measured before complete equalization has occurred, may be used to determine pump chamber volume.

In one embodiment, heat transfer may be minimized, and adiabatic calculation error reduced, by measuring the chamber pressures throughout the equalization period from the opening of valve X2 through full pressure equalization, and selecting a sampling point during the equalization period for the adiabatic calculations. In one embodiment of an APD system, measured chamber pressures that are taken prior to complete pressure equalization between the control chamber and the reference chamber can be used to determine pump chamber volume. In one embodiment, these pressure values may be measured about 50 ms after the chambers are first fluidly connected and equalization is initiated. As mentioned above, in one embodiment, complete equalization may occur about 200-400 ms after the valve X2 is opened. Thus, the measured pressures may be taken at a point in time after the valve X2 is opened (or equalization is initiated) that is about 10% to 50% or less of the total equalization time period. Said another way, the measured pressures may be taken at a point in time at which 50-70% of pressure equalization has occurred (i.e., the reference and pump chamber pressures have changed by about 50-70% of the difference between the initial chamber pressure and the final equalized pressure. Using a computer-enabled controller, a substantial number of pressure measurements in the control and reference chambers can be made, stored and analyzed during the equalization period (for example, 40-100 individual pressure measurements). Among the time points sampled during the first 50 ms of the equalization period, there is a theoretically optimized sampling point for conducting the adiabatic calculations (e.g., see FIG. 104 in which the optimized sampling point occurs at about 50 ms after opening of the valve X2). The optimized sampling point may occur at a time early enough after valve X2 opening to minimize thermal transfer between the gas volumes of the two chambers, but not so early as to introduce significant errors in pressure measurements due to the properties of the pressure sensors and delays in valve actuation. However, as can be seen in FIG. 104, the pressures for the pump chamber and reference chambers may be substantially unequal to each other at this point, and thus equalization may not be complete. (Note that in some cases, it may be technically difficult to take reliable pressure measurements immediately after the opening of valve X2, for example, because of the inherent inaccuracies of the pressure sensors, the time required for valve X2 to fully open, and the rapid initial change in the pressure of either the control chamber or the reference chamber immediately after the opening of valve X2.)

During pressure equalization, when the final pressure for the control chamber and reference chambers are not the same, Equation 2 becomes:

$$PriVri^{\gamma} + PdiVdi^{\gamma} = \text{Constant} = PrfVrf^{\gamma} + PdfVdf^{\gamma} \quad (8)$$

where: Pri=pressure in the reference chamber prior to opening valve X2, Pdi=pressure in the control chamber prior to opening valve X2, Prf=final reference chamber pressure, Pdf=final control chamber pressure.

An optimization algorithm can be used to select a point in time during the pressure equalization period at which the difference between the absolute values of ΔVd and ΔVr is minimized (or below a desired threshold) over the equalization period. (In an adiabatic process, this difference should ideally be zero, as indicated by Equation 5. In FIG. 104 the point in time at which the difference between the absolute values of ΔVd and ΔVr is minimized occurs at the 50 ms line, marked "time at which final pressures identified.") First, pressure data can be collected from the control and reference chambers at multiple points j=1 through n in between the opening of valve X2 and final pressure equalization. Since Vri, the fixed volume of the reference chamber system before pressure equalization, is known, a subsequent value for Vrj (reference chamber system volume at sampling point j after valve X2 has opened) can be calculated using Equation 3 at each sampling point Prj along the equalization curve. For each such value of Vrj, a value for ΔVd can be calculated using Equations 5 and 7, each value of Vrj thus yielding Vdij, a putative value for Vdi, the volume of the control chamber system prior to pressure equalization. Using each value of Vrj and its corresponding value of Vdij, and using Equations 3 and 4, the difference in the absolute values of ΔVd and ΔVr can be calculated at each pressure measurement point along the equalization curve. The sum of these differences squared provides a measure of the error in the calculated value of Vdi during pressure equalization for each value of Vrj and its corresponding Vdij. Denoting the reference chamber pressure that yields the least sum of the squared differences of |ΔVd| and |ΔVr| as Prf, and its associated reference chamber volume as Vrf, the data points Prf and Pdf corresponding to Vrf can then be used to calculate an optimized estimate of Vdi, the initial volume of the control chamber system.

One method for determining where on the equalization curve to capture an optimized value for Pdf and Prf is as follows:

1) Acquire a series of pressure data sets from the control and reference chambers starting just before the opening of valve X2 and ending with Pr and Pd becoming close to equal. If Pri is the first reference chamber pressure captured, then the subsequent sampling points in FIG. 104 will be referred to as Prj=Pr1, Pr2, . . . Prn.

2) Using Equation 6, for each Prj after Pri, calculate the corresponding ΔVrj where j represents the jth pressure data point after Pri.

$$\Delta Vrj = Vrj - Vri = Vri(-1 + (Prj/Pri)^{-(1/\gamma)})$$

3) For each such ΔVrj calculate the corresponding Vdij using Equation 7. For example:

$$\Delta Vr1 = Vri * (-1 + (Pr1/Pri)^{-(1/\gamma)})$$

$$\Delta Vd1 = -\Delta Vr1$$

Therefore, $$Vdi1 = \Delta Vd1 / (-1 + (Pd1/Pdi)^{-(1/\gamma)})$$

$$\vdots$$

$$Vdin = \Delta Vdn / (-1 + (Pdn/Pdi)^{-(1/\gamma)})$$

Having calculated a set of n control chamber system initial volumes (Vdi1 to Vdin) based on the set of reference chamber pressure data points Pr1 to Prn during pressure equalization, it is now possible to select the point in time (f) that yields an optimized measure of the control chamber system initial volume (Vdi) over the entire pressure equalization period.

4) Using Equation 7, for each Vdi1 through Vdin, calculate all ΔVdj,k using control chamber pressure measurements Pd for time points k=1 to n.

For the Vdi corresponding to Pr1:

$$\Delta Vd1,1 = Vdi1 * (-1 + (Pd1/Pdi)^{-(1/\gamma)})$$

$$\Delta Vd1,2 = Vdi1 * (-1 + (Pd2/Pdi)^{-(1/\gamma)})$$

$$\vdots$$

$$\Delta Vd1,n = Vdi1 * (-1 + (Pdn/Pdi)^{-(1/\gamma)})$$

$$\vdots$$

For the Vdi corresponding to Prn:

$$\Delta Vdn,1 = Vdin * (-1 + (Pd1/Pdi)^{-(1/\gamma)})$$

$$\Delta Vdn,2 = Vdin * (-1 + (Pd2/Pdi)^{-(1/\gamma)})$$

$$\vdots$$

$$\Delta Vdn,n = Vdin * (-1 + (Pdn/Pdi)^{-(1/\gamma)})$$

5) Take the sum-square error between the absolute values of the ΔVr's and ΔVdj,k's $$S_1 = \sum_{k=1}^{n} (|\Delta V_{d1,k}| - |\Delta V_{rk}|)^2$$

[S1 represents the sum-square error of |ΔVd| minus |ΔVr| over all data points during the equalization period when using the first data point Pr1 to determine Vdi, the control chamber system initial volume, from Vr1 and ΔVr.]

$$S_2 = \sum_{k=1}^{n} (|\Delta V_{d2,k}| - |\Delta V_{rk}|)^2$$

[S2 represents the sum-square error of |ΔVr| minus |ΔVd| over all data points during the equalization period when using the second data point Pr2 to determine Vdi, the control chamber system initial volume, from Vr2 and ΔVr.]

$$\vdots$$

$$S_n = \sum_{k=1}^{n} (|\Delta V_{dn,k}| - |\Delta V_{rk}|)^2$$

6) The Pr data point between Pr1 and Prn that generates the minimum sum-square error S from step 5 (or a value that is below a desired threshold) then becomes the chosen Prf, from which Pdf and an optimized estimate of Vdi, the control chamber initial volume, can then be determined. In this example, Pdf occurs at, or about, the same time as Prf.

7) The above procedure can be applied any time that an estimate of the control chamber volume is desired, but can preferably be applied at the end of each fill stroke and each delivery stroke. The difference between the optimized Vdi at the end of a fill stroke and the optimized Vdi at the end of a corresponding delivery stroke can be used to estimate the volume of liquid delivered by the pump.

Air Detection

Another aspect of the invention involves the determination of a presence of air in the pump chamber 181, and if present, a volume of air present. Such a determination can be important, e.g., to help ensure that a priming sequence is adequately performed to remove air from the cassette 24 and/or to help ensure that air is not delivered to the patient. In certain embodiments, for example, when delivering fluid to the patient through the lower opening 187 at the bottom of the pump chamber 181, air or other gas that is trapped in the pump chamber may tend to remain in the pump chamber 181 and will be inhibited from being pumped to the patient unless the volume of the gas is larger than the volume of the effective dead space of pump chamber 181. As discussed below, the volume of the air or other gas contained in pump chambers 181 can be determined in accordance with aspects of the present invention and the gas can be purged from pump chamber 181 before the volume of the gas is larger than the volume of the effective dead space of pump chamber 181.

A determination of an amount of air in the pump chamber 181 may be made at the end of a fill stroke, and thus, may be performed without interrupting a pumping process. For example, at the end of a fill stroke during which the membrane 15 and the pump control region 1482 are drawn away from the cassette 24 such that the membrane 15/region 1482 are brought into contact with the wall of the control chamber 171, the valve X2 may be closed, and the reference chamber vented to atmospheric pressure, e.g., by opening the valve X3. Thereafter, the valves X1 and X3 may be closed, fixing the imaginary "piston" at the valve X2. The valve X2 may then be opened, allowing the pressure in the control chamber and the reference chamber to equalize, as was described above when performing pressure measurements to determine a volume for the control chamber.

If there is no air bubble in the pump chamber 181, the change in volume of the reference chamber, i.e., due to the movement of the imaginary "piston," determined using the known initial volume of the reference chamber system and the initial pressure in the reference chamber, will be equal to the change in volume of the control chamber determined using the known initial volume of the control chamber system and the initial pressure in the control chamber. (The initial volume of the control chamber may be known in conditions where the membrane 15/control region 1482 are in contact with the wall of the control chamber or in contact with the spacer elements 50 of the pump chamber 181.) However, if air is present in the pump chamber 181, the change in volume of the control chamber will actually be distributed between the control chamber volume and the air bubble(s) in the pump chamber 181. As a result, the calculated change in volume for the control chamber using the known initial volume of the control chamber system will not be equal to the calculated change in volume for the reference chamber, thus signaling the presence of air in the pump chamber.

If there is air in the pump chamber 181, the initial volume of the control chamber system Vdi is actually equal to the sum of the volume of the control chamber and lines L0 and L1 (referred to as Vdfix) plus the initial volume of the air bubble in the pump chamber 181, (referred to as Vbi), as shown in Equation 9:

$$Vdi = Vbi + Vdfix \qquad (9)$$

With the membrane 15/control region 1482 pressed against the wall of the control chamber at the end of a fill stroke, the volume of any air space in the control chamber, e.g., due to the presence of grooves or other features in the control chamber wall, and the volume of the lines L0 and L1—together Vdfix—can be known quite accurately. (Similarly, with the membrane 15/control region 1482 pressed against the spacer elements 50 of the pump chamber 181, the volume of the control chamber and the lines L0 and L1 can be known accurately.) After a fill stroke, the volume of the control chamber system is tested using a positive control chamber pre-charge. Any discrepancy between this tested volume and the tested volume at the end of the fill stroke may indicate a volume of air present in the pump chamber. Substituting from Equation 9 into Equation 7, the change in volume of the control chamber $\Delta Vd$ is given by:

$$\Delta Vd = (Vbi + Vdfix)(-1 + (Pdf/Pdi)^{-(1/\gamma)}) \qquad (10)$$

Since $\Delta Vr$ can be calculated from Equation 6, and we know from Equation 5 that $\Delta Vr = (-1) \Delta Vd$, Equation 10 can be re-written as:

$$(-1)\Delta Vr = (Vbi + Vdfix)(-1 + (Pdf/Pdi)^{-(1/\gamma)}) \qquad (11)$$

and again as:

$$Vbi = (-1)\Delta Vr/(-1 + (Pdf/Pdi)^{-(1/\gamma)}) - Vdfix \qquad (12)$$

Accordingly, the cycler 14 can determine whether there is air in the pump chamber 181, and the approximate volume of the bubble using Equation 12. This calculation of the air bubble volume may be performed if it is found, for example, that the absolute values of $\Delta Vr$ (as determined from Equation 6) and $\Delta Vd$ (as determined from Equation 7 using Vdi=Vdfix) are not equal to each other. That is, Vdi should be equal to Vdfix if there is no air present in the pump chamber 181, and thus the absolute value for $\Delta Vd$ given by Equation 7 using Vdfix in place of Vdi will be equal to $\Delta Vr$.

After a fill stroke has been completed, and if air is detected according to the methods described above, it may be difficult to determine whether the air is located on the pump chamber side or the control side of the membrane 15. Air bubbles could be present in the liquid being pumped, or there could be residual air on the control (pneumatic) side of the pump membrane 15 because of a condition (such as, for example, an occlusion) during pumping that caused an incomplete pump stroke, and incomplete filling of the pump chamber. At this point, an adiabatic FMS measurement using a negative pump chamber pre-charge can be done. If this FMS volume matches the FMS volume with the positive precharge, then the membrane is free to move in both directions, which implies that the pump chamber is only partially filled (possibly, for example, due to an occlusion). If the value of the negative pump chamber pre-charge FMS volume equals the nominal control chamber air volume when the membrane 15/region 1482 is in contact with the inner wall of the control chamber, then it is possible to conclude that there is an air bubble in the liquid on the pump chamber side of the flexible membrane.

Polytropic FMS for Pump Volume Delivery Measurement

Introduction to FMS

In another aspect of the disclosure, the cycler 14 in FIG. 1 may determine a volume of fluid delivered in various lines of the system 10 without the use of a flowmeter, weight scale or other direct measurement of fluid volume or weight. For example, in one embodiment, a volume of fluid moved by a diaphragm pump, such as a pneumatically driven diaphragm pump including a cassette 24, may be determined based on pressure measurements of a gas used to drive the pump.

In one embodiment, the volume determination is accomplished with a process herein referred to as the two-chamber Fluid Measurement System (2-chamber FMS) process. The volume of fluid pumped by the diaphragm pump may be calculated from the change in the volume of the pneumatic chamber on one side of the diaphragm. The volume of the pneumatic chamber may be measured at the end of each fill and deliver stroke, so that the difference in volume between sequential measurements is the volume of fluid moved by the pump.

The volume of the pneumatic chamber or first chamber is measured with the 2-chamber FMS process that comprises closing the liquid valves into and out of the diaphragm pump, isolating the first chamber from a second chamber of a known volume (reference chamber), pre-charging the first chamber to a first pressure, while pre-charging the second chamber to a second pressure, then fluidically connecting the two chambers, and recording at least the initial and final pressures in each chamber as the pressures equalize. The volume of first chamber may be calculated from at least the initial and final pressures and the known volume of the second chamber.

Figure 105:
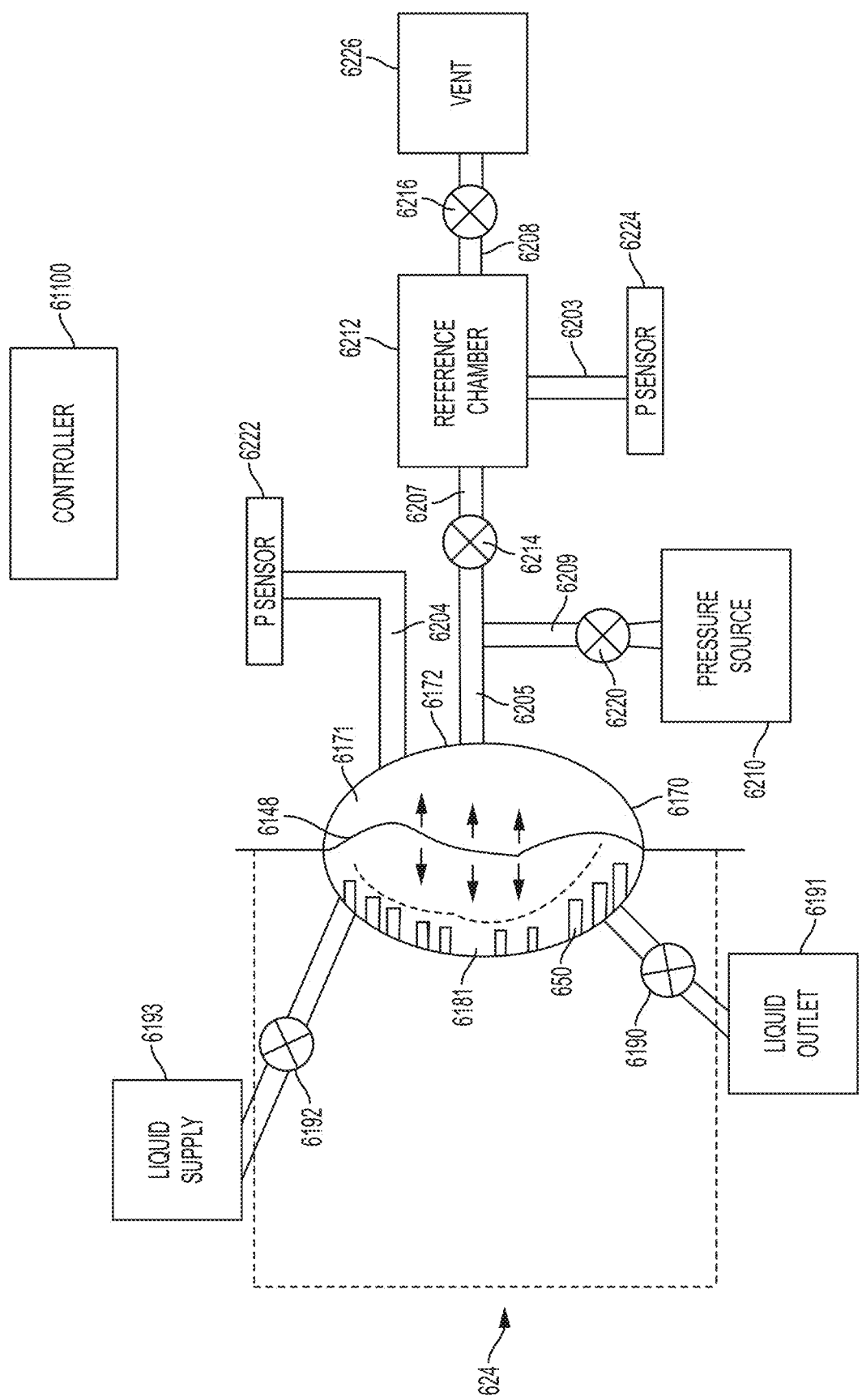
FIG. 105 is a schematic view of a control chamber of a cassette and associated control components including pressure sensors and inflow/outflow paths in an illustrative embodiment.

If the first chamber is precharged to a pressure above the pressure in the second chamber then the 2-chamber FMS process is referred to as positive FMS or +FMS. If the first chamber is precharged to a pressure less than the pressure in the second chamber, then the 2-chamber FMS process is referred to as negative or −FMS. Referring now to FIG. 105, the first chamber is the control chamber 6171 and the second chamber is the reference chamber 6212.

The form of the algorithm to calculate the first chamber volume may depend on the heat transfer characteristics of the first and second chamber and the fluid lines that connect the two chambers. The amount of heat transfer between the structure and the gases during equalization affects the pressures in both the first and second chamber during and after equalization. During equalization, the gas in the chamber with the higher pressure expands toward the other chamber. This expanding gas will cool to a lower temperature and consequently a lower pressure. The cooling of the expanding gas and the loss in pressure may be moderated or reduced by heat transfer from the warmer structure. At the same time, the gas in the chamber initially at a lower pressure is compressed during equalization. The temperature of this compressing gas will rise along with the pressure. The heating of the compressing gas and the rise in pressure may be moderated or reduced by heat transfer from the cooler structure.

The relative importance of heat transfer between the structure (chamber walls, solid material within the chambers) and the gas is a function of the average hydraulic diameter of the chamber, the thermal diffusivity of the gas and the duration of the equalization process. In one example, the two volumes are filled with heat absorbing material such as foam or other matrix that provide enough surface area and thermal mass that the gas temperatures are constant in each chamber during pressure equalization, so that the expansion and compression processes can be modeled as isothermal. In another example, the two chambers are sized and shaped to provide negligible heat transfer, so the expansion and compression processes can be modeled as adiabatic. In another example, the shape and size of the control chamber 6171 changes from measurement to measurement. In measurements after a fill stroke when the control chamber 6171 is small and all the gas is relatively near the chamber wall 6170 or the diaphragm 6148, the heat transfer between the gas and the structure is significant. In measurements after a deliver stroke, the control chamber 6171 is large and open, so that much of the gas is relatively isolated from the chamber walls 6170 or diaphragm 6148 and heat transfer to the gas is negligible. In measurements after a partial stroke the heat transfer between the structure and the gas is significant, but not sufficient to assure constant temperature. In all these measurements, the expansion and compression processes can be modeled as polytropic and the relative importance of heat transfer can be varied from one measurement to the next. A polytropic model can accurately model the equalization process for all geometries and capture the effects of different levels of heat transfer in the first and the second chambers. A more detailed model of the equalization process will more accurately determine the volume of the first chamber from the knowledge of the pressures and the volume of the second chamber.

This section describes an algorithm to calculate the volume of the first chamber 6171 for a polytropic 2-chamber FMS process. The first sub-section describes the two volume FMS or 2-chamber FMS process for an exemplary arrangement of volumes, pressure sources, valves and pressure sensors. The next sub-section conceptually describes the polytropic FMS algorithm for data from a +FMS process and then presents the exact equations to calculate the first volume from the pressure data. The next sub-section presents the concept and equations of the polytropic FMS algorithm for data from a −FMS process. The last sub-section presents the process to calculate the volume of the first chamber 6171 using either set of equations.

The model being described can be applied to any system or apparatus that uses a pneumatically actuated diaphragm pump. The components of the system include a diaphragm pump having at least one pump chamber inlet or outlet with a valved connection to either a fluid source or fluid destination; a pneumatic control chamber separated from the pump chamber by a diaphragm that provides positive or negative pressure to the pump chamber for fluid delivery or filling; the pneumatic control chamber has a valved connection to a reference chamber of known volume and to a positive or negative pressure source; a controller controls the valves of the system and monitors pneumatic pressure in the control chamber and reference chamber. An example of the system is illustrated schematically in FIG. 105, although the specific arrangement of inlets, outlets and fluid and pneumatic conduits and valves can vary to some degree from this illustration. The following description will use a peritoneal dialysis cycler and pump cassette as an example, but the invention is by no means limited to this particular application.

Hardware for 2-Chamber FMS Process

Referring now to FIG. 105, which schematically presents elements of the cycler and the cassette 624 that are involved in the 2-chamber FMS process. The cassette 624 includes two liquid valves 6190, 6192 that are fluidically connected to a liquid supply 6193 and liquid outlet 6191. The cassette 624 includes a diaphragm pump with a variable liquid volume pump chamber 6181 separated by a flexible membrane 6148 from the control chamber 6171. The control chamber 6171 volume is defined by the membrane 6148 and the chamber wall 6170. The control chamber 6171 is the first chamber of unknown volume described above.

A control line 6205 also leads to a connection valve 6214 that communicates with a reference line 6207 and a reference chamber 6212 (e.g., a space suitably configured for performing the measurements described below). The reference chamber 6212 is the second chamber with a known volume described above. The reference chamber 6212 also communicates with an exit line 6208 having a second valve 6216 that leads to a vent 6226 to atmospheric pressure. In another example the vent 6226 may be a reservoir controlled to a desired pressure by one or more pneumatic pumps, a pressure sensor and controller. Each of the valves 6220, 6214 and 6216 may be independently controlled by the controller 61100.

The pressure source 6210 is selectively connected to the control chamber 6171 via lines 6209 and 6205. The pressure source 6210 may include one or more separate reservoirs which are held at specified and different pressures by one or more pneumatic pumps. Each pneumatic pump may be controlled by the controller 61100 to maintain the specified pressure in each reservoir as measured by pressure sensors. A first valve 6220 may control the fluid connection between the pressure source 6210 and the control chamber 6171. The controller 61100 may selectively connect one of the reservoirs in the pressure source 6210 to line 6209 to control the pressure in the control chamber as measured by pressure sensor 6222. In some examples, the controller 1100 may be part of a larger control system in the APD cycler.

The control chamber 6171 is connected to the control pressure sensor 6222 via line 6204. A reference pressure sensor 6224 may be connected to the reference chamber 6212 via line 6203. The pressure sensors 6222, 6224 may be an electromechanical pressure sensor that measures the absolute pressure such as the MPXH6250A by Freescale Semiconductors of Japan. The control pressure sensor 6222 and the reference pressure sensor 6224 are connected to the controller 61100, which records the control and reference pressures for subsequent volume calculations. Alternatively, the pressure sensors 6222, 6224 may be relative pressure sensors that measure the pressure in the control and reference chambers relative to the ambient pressure and the controller 61100 may include an absolute pressure sensor to measure the ambient pressure. The controller 61100 may combine the relative pressure signals from sensors 6222, 6224 and the absolute ambient pressure sensor to calculate the absolute pressures in the control chamber 6171 and reference chamber 6212 respectively.

The valves and other components of the FMS hardware shown in FIG. 105 can be controlled by the controller 61100 to execute the 2-chamber FMS process and measure the resulting pressures in control chamber 6171 and in the reference chamber 6212, then calculate the volume of the control chamber 6171. The controller 61100 may be a single micro-processor or multiple processors. In one example, the pressure signals are received by an A-D board and buffered before being passed to the 61100 controller. In another example, a field-programmable-gate-array (FPGA) may handle all the I/O between the controller 61100 and the valves and sensors. In another example, the FPGA may filter, store and/or process the pressure data to calculate volume of the control chamber.

2-chamber FMS Process in APD Cycler

Figure 106:
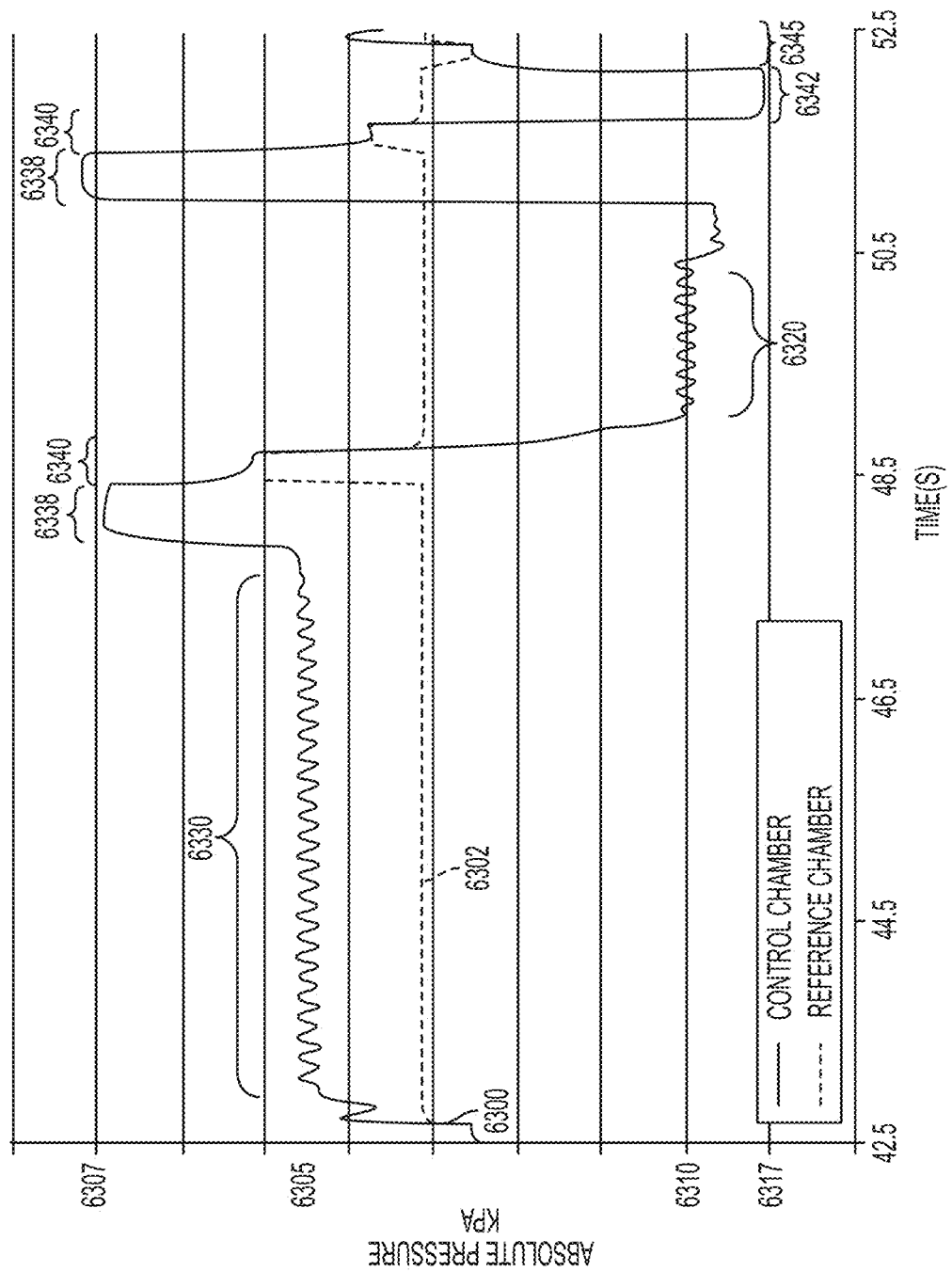
FIG. 106 is a pressure versus time plot for the reference chamber and the control chamber during a pumping and FMS process.

Referring now to pressure vs time plot of FIG. 106 and the elements in FIG. 105. An exemplary pumping and measurement process is described in the plot of the control chamber pressure 6300 and the reference chamber pressure 6302 verses time. As described above, after closing the inlet valve 6192 and opening the outlet valve 6190, the chamber pressure is controlled to a positive value 6305 that pushed fluid out of the pump chamber 6181 during the deliver stroke 6330. At the end of the deliver stroke 6330, the outlet fluid valve is closed and a +FMS process may occur to measure the volume of the control chamber 6171. The FMS process as described elsewhere may consist of bringing the control chamber pressure 6330 to a precharging pressure 6307 and allowing a period of pressure stabilization 6338, followed by a equalization process 6340. In other examples, the control chamber pressure 6330 may be returned to near atmospheric pressure before being increased to the precharge pressure 6307. At the end of equalization process 6340, the reference chamber pressure 6302 and possibly the control chamber pressure 6300 can be returned to near atmospheric values.

The fill stroke 6320 occurs after opening the inlet valve 6192 and brings the control chamber pressure 6300 to a negative pressure 6310, while the reference chamber remains near atmospheric, or at a measured and constant pressure. The negative pressure pulls fluid into the pump chamber 6181. At the end of the fill stroke 6320, the inlet valve 6192 is closed and a +FMS process may occur to determine the volume of the control chamber 6171. In some embodiments, a −FMS process may occur after the +FMS process. The −FMS process may comprise precharging the control chamber to negative pressure 6317, allowing pressure stabilization 6342 and finally an equalization process 6345. The control chamber volume determined from −FMS process may be compared to the control chamber volume determined from the +FMS process to determine whether there is a volume of air or gas in the pump chamber 6181. (For example, if the pump chamber includes an air trap comprising ribs or standoffs on the pump chamber rigid wall, air can accumulate among the standoffs, the diaphragm at its full excursion can be prevented from compressing it by the standoffs, and the air may not be detected by a +FMS process alone). In one example, a −FMS process occurs after the deliver stroke 6330.

Figure 107:
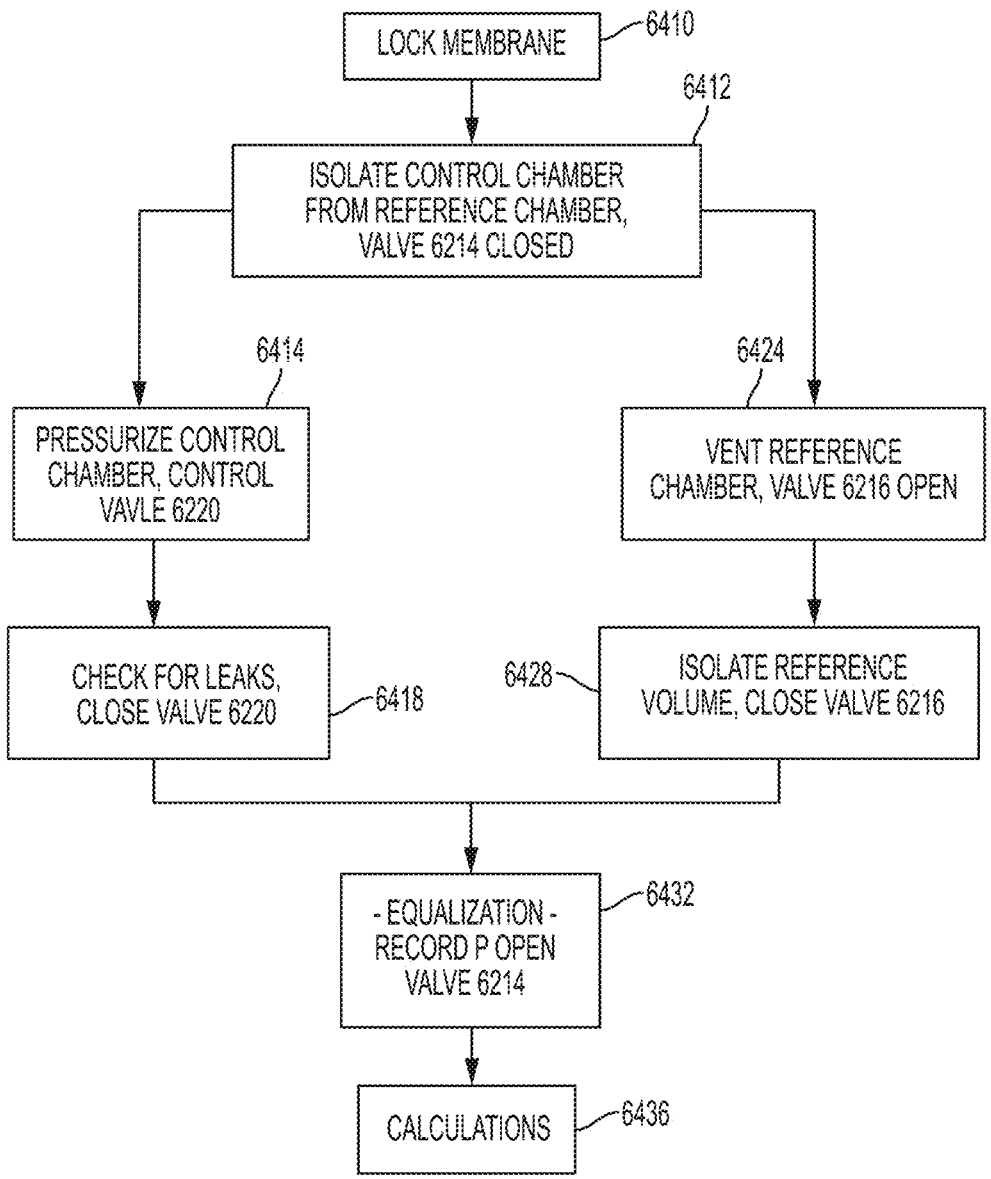
FIG. 107 is a flow chart of pneumatic steps of an FMS process.
Figure 108A:
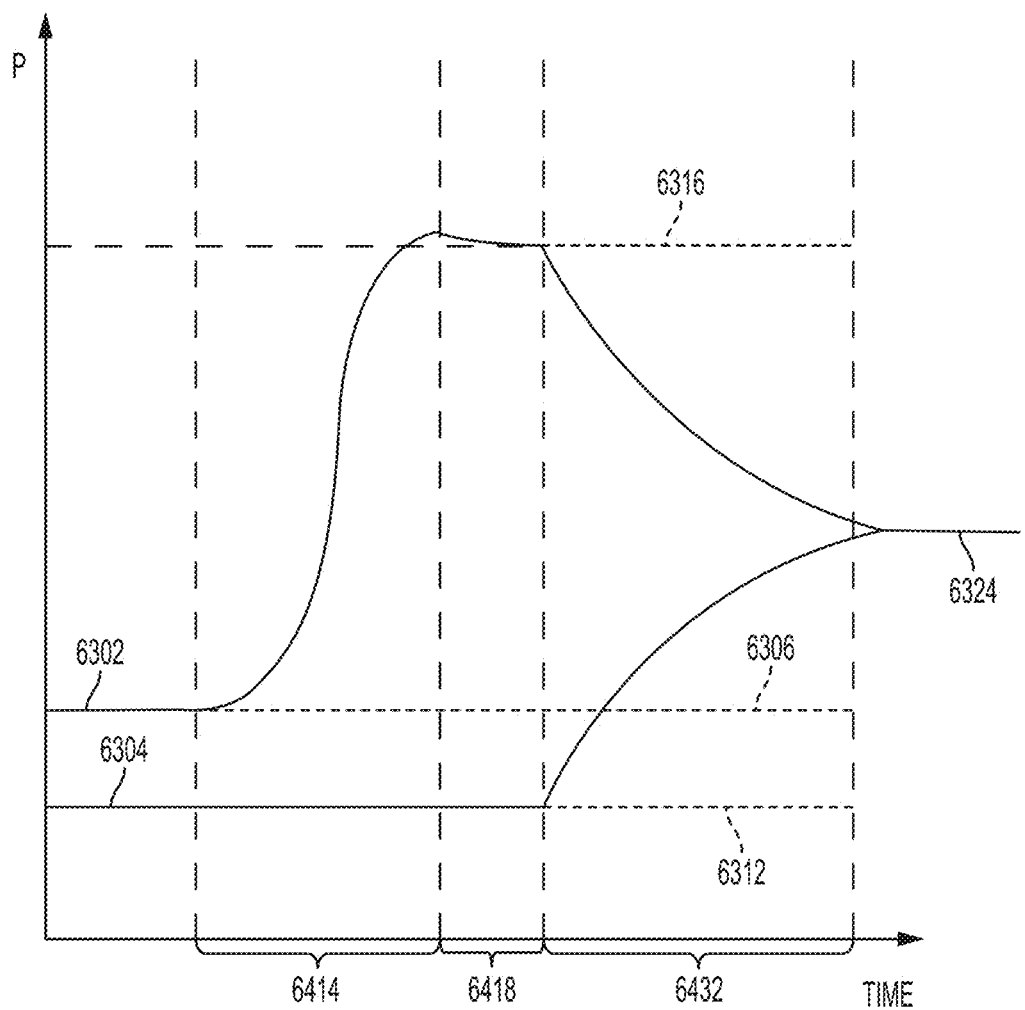
FIG. 108A is a plot of the pumping chamber and reference chamber pressures during the +FMS process.
Figure 108B:
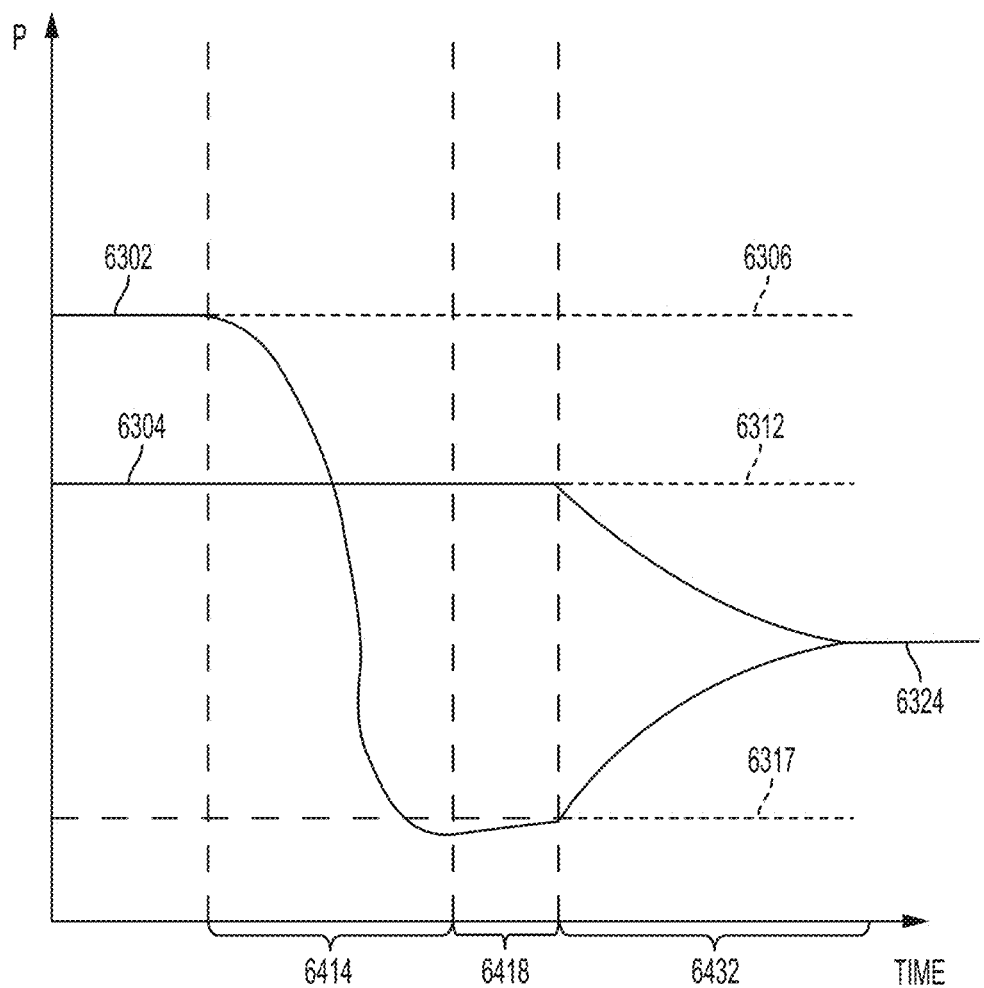
FIG. 108B is a plot of the pumping chamber and reference chamber pressures during the −FMS process.

The +FMS and −FMS processes are described in more detail by referring to the flow chart in FIG. 107, elements in FIG. 105, and the pressure vs. time plots of FIGS. 108A, 108B. The 2-chamber FMS process begins with step 6410 where the position of the membrane 6148 is fixed. The position of the membrane 6148 may be fixed by closing both hydraulic valves 6190, 6192. In some examples, the position of membrane 6148 will vary as the control chamber pressure changes, if gas bubbles are present in the liquid. However the volume of incompressible liquid between the hydraulic valves 6190, 6192 is fixed. The 2-chamber FMS process will generally measure the volume of air or gas on both sides of the membrane 6148, so any bubbles in the pump chamber 6181 on the liquid side of the membrane 6148 are included in the measured volume of the control chamber 6171.

In step 6412, the control chamber 6171 is fluidically isolated from the reference chamber 6212 by closing connection valve 6214. Then the reference chamber 6212 and control chamber 6171 are fluidically isolated from each other in step 6412. In an embodiment, the reference chamber 6212 is connected to the vent 6226 in step 6424 by opening the second valve 6216. The controller 61100 holds the second valve 6216 open, until reference pressure sensor 6224 indicates that the reference pressure has reached ambient pressure. Alternatively, the controller 61100 may control the second valve 6216 to achieve a desired initial reference pressure in the reference chamber 6212 as measured by the reference pressure sensor 6224. Alternatively, the connection valve 6214 may be closed and the second valve 6216 is open before the FMS process begins. In step 6428, once the desired pressure in the reference chamber 6212 is achieved, the second valve 6216 is closed, which fluidically isolates the reference chamber 6212. The reference chamber steps 6424 and 6428 may be programmed to occur concurrently with the control chamber steps 6414 and 6418.

In step 6414, the control chamber 6171 is pressurized to a desired pressure by connecting the control chamber 6171 to the pressure source 6210 by opening the first valve 6220. The controller 61100 monitors the pressure in the control chamber 6171 with pressure sensor 6222 and controls the first valve 6220 to achieve a desired precharge pressure. The desired precharge pressure may be significantly above the initial reference pressure of the reference chamber 6212 or significantly below the initial reference pressure. In one example, the control chamber 6171 is precharged to approximately 40 kPa above the reference pressure for a +FMS process. In another example, the control chamber 6171 is precharged to approximately 40 kPa below the reference pressure for a −FMS process. In other embodiments, the precharge pressures may be any pressure within the range of 10% to 180% of the initial reference pressure.

The controller 61100 closes the first valve 6220 in step 6418 and monitors the pressure in the control chamber 6171 with pressure sensor 6222. The pressure in the control chamber 6171 may move toward ambient pressure during step 6418 due to gas thermally equalizing with the control chamber wall 6170 and membrane 6148. A large change in pressure during step 6418 may indicate a pneumatic or liquid leak that would invalidate a measurement. The 2-chamber FMS process may be aborted or the calculated volume of the control chamber 6171 may be discarded if the rate of pressure change exceeds a pre-determined allowable rate. The rate of pressure change may be examined after a delay from the pressurization step 6414 to allow the gas in the control chamber 6171 to approach thermal equilibrium with the boundaries 6172, 6148 of the control chamber 6171. In one example, the maximum allowed rate of pressure change during step 6418 is 12 kPA/sec. The 2-chamber FMS process may be aborted and restarted if the rate of pressure change exceeds this predetermined value. In another embodiment, the maximum allowable rate of pressure change is a function of—and will vary based on—the calculated control chamber volume. In one example, the maximum allowed pressure change is 3 kPA/sec for a 25 ml volume and 25 kPA/sec for 2 ml volume. In one example, the FMS process may be carried to completion regardless of the leak rate resulting in a calculated volume of the control chamber 6171. The calculated volume may be discarded and the FMS process restarted if the measured rate of pressure change exceeds the allowable limit for the calculated control chamber volume.

The control chamber 6171 and the reference chamber 6212 are fluidically connected in step 6432, when the controller 61100 opens the connection valve 6214 between the two chambers. The controller 61100 monitors the pressures in each chamber with the pressure sensors 6222, 6224 as the pressure in the control chamber 6171 and reference chamber 6212 equalize. The controller 61100 may record the initial pressure pair and at least one pressure pair at the end of equalization in step 6432. A pressure pair refers to a signal from the control pressure sensor 6222 and a signal from the reference pressure sensor 6224 recorded at approximately the same time. Step 6432 extends from a period of time just before the connection valve 6214 is open to a point in time, when the pressure in the control chamber 6171 and reference chamber 6212 are nearly equal.

The 2-chamber FMS process is completed in step 6436, where the recorded pairs of pressures are used to calculate the volume of the control chamber 6171. The calculation of the control chamber 6171 volume is described in detail below.

The +FMS process is sketched as pressure vs. time plot in FIG. 108A. Reference numbers corresponding to those of the steps in FIG. 107 are included to indicate where those steps are depicted in FIG. 108A. The pressure of the control chamber 6171 is plotted as line 6302. The pressure of the reference chamber is plotted as line 6304. The pressure vs. time plot begins after steps 6410, 6412, 6424, 6428 of FIG. 107 have been completed. At this point the pressure in the reference chamber 6212 is at the desired reference pressure 6312. The pressure in the control chamber 6171 begins at an arbitrary pressure 6306 and during step 6414 increases to the precharge pressure 6316. The arbitrary pressure 6306 may be the pressure of the control chamber 6171 at the conclusion of a previous pumping operation. In another embodiment, the arbitrary pressure 6306 may atmospheric pressure. The control chamber pressure 6302 may drop during step 6418. In step 6432, the control chamber pressure 6302 and reference chamber pressure 6304 equalize toward an equilibrium pressure 6324.

The −FMS process is sketched as pressure vs. time plot in FIG. 108B. The pressure of the control chamber 6171 (FIG. 105) is plotted as line 6302. The pressure of the reference chamber 6312 (FIG. 105) is plotted as line 6304. The horizontal time axis is divided in periods that correspond to the process steps identified with the same reference numbers in FIG. 107. The pressure vs. time plot begins when the pressure in the reference chamber 6212 (line 6302) is at the desired reference pressure 6312 and the pressure in the control chamber 6171 (line 6304) is at an arbitrary pressure. During step 6414, the control chamber pressure 6302 decreases to the negative precharge pressure 6317. The control chamber pressure 6302 may rise during step 6418 as the gas cooled by the sudden expansion of step 6414 is heated by the control chamber walls 6172, 6148. In step 6432, the control chamber pressure 6302 and reference chamber pressure 6304 equalize toward an equilibrium pressure 6324.

Polytropic+FMS Algorithm

Referring now to FIG. 105, for illustrative purposes, the equalization process involves the fluid volumes of three distinct structures: control chamber 6171, reference chamber 6212 and the manifold passages 6204, 6205, 6207, 6209 connecting the two chambers 6171, 6212. In one example, each structure has significantly different hydraulic diameters and thus different levels of heat transfer between the structure and the gas. In this example, the reference chamber 6212 has an approximately cubic shape with a hydraulic diameter of approximately 3.3 cm. Heat transfer during the approximately 30 microsecond equalization process is negligibly small and the gas in the reference chamber 6212 volume is likely to be compressed adiabatically, and can be modeled as such. In contrast, in an exemplary construction, the manifold passages 6204, 6205, 6207, 6209, have an approximately 0.2 cm hydraulic diameter, which is about 15 times smaller than the hydraulic diameter of the reference chamber 6212 volume. Heat transfer in the manifold passages 6204, 6205, 6207, 6209 is high and the gas passing through these passages 6204, 6205, 6207, 6209 is more likely to compress or expand isothermally at approximately the temperature of the manifold walls. The hydraulic diameter of the control chamber 6171 in this example has a minimum of value of approximately 0.1 cm when the pumping chamber 6181 is full of liquid at the end of a fill stroke and the control chamber 6171 is at a minimum volume. The hydraulic diameter of the control chamber 6171 in this example has a maximum value of approximately 2.8 cm when the pumping chamber 6181 has delivered the liquid and the control chamber 6171 is at a maximum volume. The expansion of gas in the control chamber 6171 can be more appropriately modeled with a polytropic coefficient that varies with the size of the control chamber 6171. When the control chamber 6171 volume is at a minimum and the expansion process will be nearly isothermal, the polytropic coefficient can be set to approximately 1. When the control chamber 6171 is at a maximum and the expansion process is near adiabatic, the polytropic coefficient may be set to approximately the ratio of specific heats (cp/cv), which equals 1.4 for air. For 2-chamber FMS measurements at partial strokes, the expansion process will occur with significant heat transfer, but not enough to be isothermal. The polytropic coefficient may be set to a value between 1 and 1.4 for measurements at partial strokes. Since the volume of the control chamber 6171 is the unknown quantity of this analysis, the polytropic coefficient for the control chamber 6171 may be based on an estimate of control chamber 6171 volume.

Figure 109A:
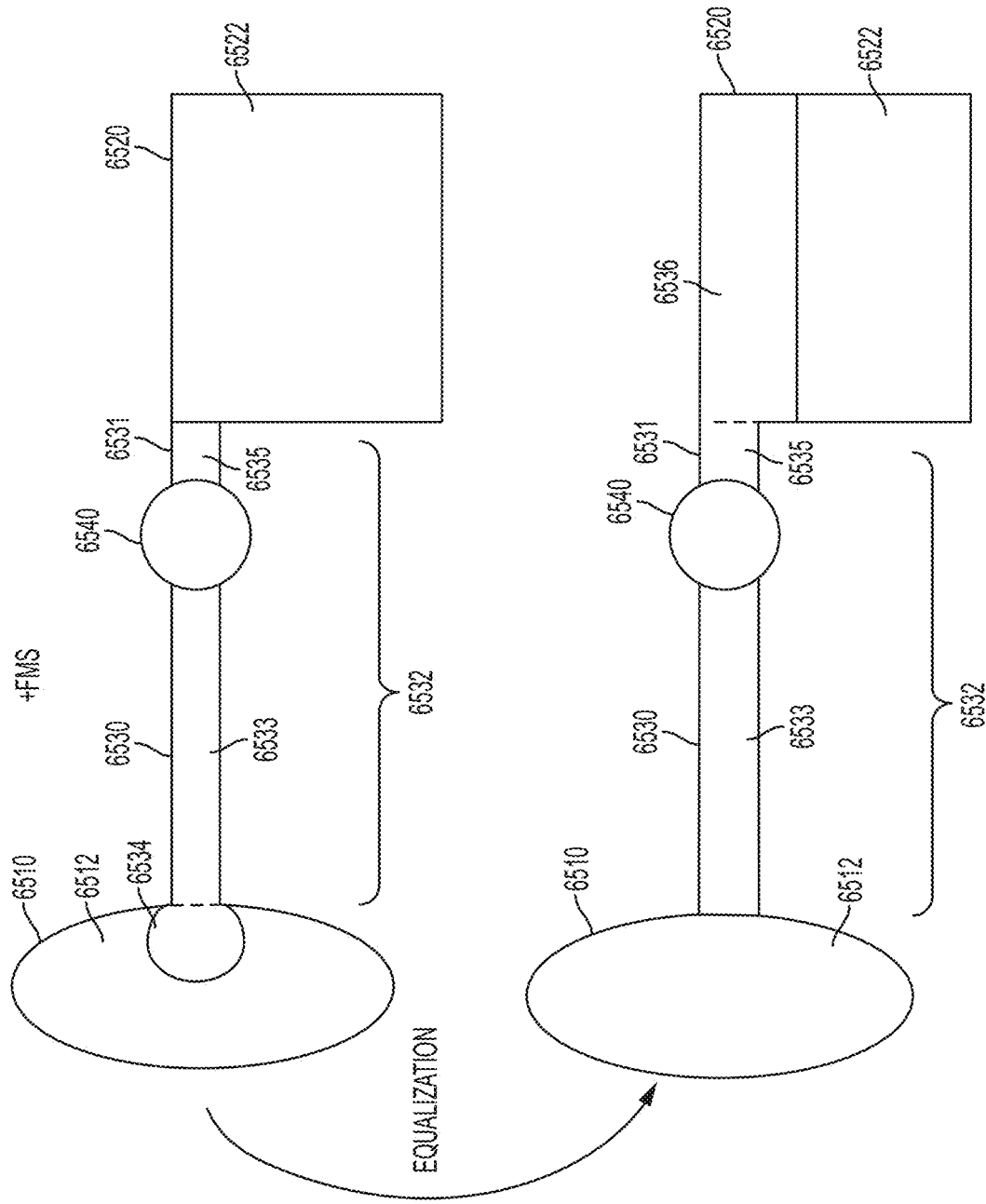
FIG. 109A is an illustration of a polytropic conceptual model of the +FMS process involving three separate closed mass systems.

Referring now to FIG. 109A, the gas in the structures of the control chamber 6510, the reference chamber 6520 and the manifold lines 6530, 6531 can be modeled as three gas masses, 6512, 6532, 6522 that do not mix, but expand, contract, and move through the structures 6510, 6520, 6530, 6531. Conceptually, for modeling purposes, these masses 6512, 6532, 6522 are each a closed-system that may move, change size and exchange energy with the structures, but mass may not enter nor exit the closed-system. The closed-system model is a well understood concept in thermodynamics and fluid dynamics. These masses may also be referred to as a control chamber system 6512, reference chamber system 6522 and a manifold or interconnecting line system 6532.

The volume of the control chamber 6510 can be calculated from the measured control chamber 6510 and reference chamber 6520 pressures based on thermodynamic models of the three masses 6512, 6532, 6522. The control chamber mass or gas 6512 is the gas that occupies the control chamber 6510 at the end of the equalization process. The reference chamber gas 6522 is the gas that occupies the reference chamber 6520 at the beginning of the equalization process. The manifold gas 6532 fills the balance of the structure between the control chamber gas 6512 and the reference chamber gas 6522, including a connecting conduit between the control and reference chambers.

The volume and temperature of the three closed-systems, 6512, 6532, 6522 may then calculated from initial conditions, pressure pairs, heat transfer assumptions and the constraint of a fixed total volume for the three closed-systems. The pressure equalization can be modeled with a different polytropic coefficient for each volume 6510, 6520, 6530, 6531 to capture the relative importance of heat transfer in each. The constant mass, ideal gas and polytropic process equations for the three systems, 6512, 6532, 6522 can be combined and arranged to calculate the volume of the control chamber 6510. The following paragraphs describe the derivation of one or more sets of equations that allow calculation of the control chamber 6510 volume based on pressures measured during the pressure equalization step of the FMS process (see, 6432 of FIGS. 107 and 108A).

Description of Closed Systems for +FMS

The upper image in FIG. 109A presents the position of the three closed-systems 6512, 6532, 6522 at the start of pressure equalization in the +FMS process. The lower image presents the positions of the three closed systems 6512, 6532, 6522 at the end of the pressure equalization. During the equalization process, the locations of the closed systems 6512, 6532, 6522 are between the two extremes presented in FIG. 109A. By way of an example, neither the control chamber system 6512 nor the reference chamber system 6522 fill their respective structures. The following paragraphs present the closed systems 6512, 6532, 6522 in more detail.

The control chamber gas system 6512 is the gas that fills the control chamber 6510 after pressure equalization. Before pressure equalization, the control chamber gas system 6512 is compressed to the precharge pressure that is higher than the final equalization pressure and therefore does not occupy the entire control chamber 6510. The control chamber gas system 6512 may be modeled as expanding in a polytropic process during pressure equalization of the +FMS process, where the pressure and the volume are related by:

$$p_f V_{CC}^{nCC} = \text{constant}$$

where $p_f$ is the equalized pressure, $V_{CC}$ is the volume of the control chamber 6510, and nCC is the polytropic coefficient for the control chamber 6510.

The reference gas system 6522 is the gas that occupies the entire reference volume 6520 before equalization. The reference gas system 6522 is compressed during equalization as the higher pressure gas in the control chamber 6510 expands and pushed the manifold gas system 6532 into the reference chamber 6520. In one example shown in FIG. 93, the reference chambers (depicted as 174 in FIG. 93) are sufficiently open or devoid of interior features/elements that compression or expansion processes during pressure equalization may be modeled as adiabatic. In this case, the polytropic coefficient (n) may be set equal to approximately the specific heat ratio of the gas present in the chamber. The pressure and the volume of the reference chamber gas 6522 are related by:

$$p_{R0} V_{Ref}^{nR} = \text{constant}$$

where $p_{R0}$ is the initial reference pressure, $V_{Ref}$ is the volume of the reference chamber, and nR is the specific heat ratio for the gas in the reference chamber (nR=1.4 air). In another example, where the chamber 6520 is at least partially filled with a heat absorbing material such as open cell foam, wire mesh, particles, etc. that provides for a near-isothermal expansion, the polytropic coefficient for the reference chamber (nR) may have a value of approximately 1.0.

In the +FMS process, the conduit or manifold gas system 6532 occupies all of the volume of the interconnecting volume 6530, 6531 and a fraction 6534 of the control chamber 6510 before equalization. After equalization, the conduit gas system 6532 occupies the interconnecting volume 6530, 6531 and part of the reference volume 6520. The portion of the conduit gas system 6532 that exists in interconnecting volume 6530 on the control chamber side of the valve 6540 is herein labeled as 6533. The portion of the conduit gas system 6532 that exits in the interconnecting volume 6531 on the reference chamber side of the valve 6540 is referred to as 6535. The portion of the conduit gas system 6532 that exist in the control chamber 6510 pre-equalization is herein labeled as 6534. The portion of the conduit gas system 6532 that exists in the reference chamber 6520 after equalization is referred to as 6536.

In one example the interconnecting volumes 6530 and 6531 may be narrow passages that provide high heat transfer and assure the conduit gas system 6532 in volumes 6530 and

6531 is near the temperature of the solid boundaries or walls of the passages. The temperature of the structure surrounding the interconnecting volumes 6530, 6531 or manifold passages is herein referred to as the wall temperature ($T_w$). In another example, the temperature of the conduit gas system 6532 in volumes 6530, 6531 is in part a function of the wall temperature. The portion of the conduit or manifold gas system in the control chamber 6534 may be modeled with the same temperature as control chamber gas system 6512. The control chamber portion of the conduit gas system 6534 experiences the same expansion as the control chamber gas system 6512 and may be conceived of as having the same temperature as the control chamber gas system 6512. The portion of the lines or manifold gas system in the reference chamber 6536 may be modeled with a temperature that is in part a function of the wall temperature. In another example, the reference chamber portion of the conduit gas system 6536 may be modeled as not interacting thermally with the boundaries of the reference chamber 6520, so that the temperature of the conduit gas system portion 6536 is a function of the wall temperature and the reference chamber 6520 pressures.

The equations in this section use the following nomenclature:
variables
γ: specific heat ratio
n: polytropic coefficient
p: pressure
V: volume
T: temperature
superscripts:
n: polytropic coefficient
nCC: polytropic coefficient for the control chamber
nR: polytropic coefficient for the reference chamber
subscripts:
c: control chamber system
CC: physical control chamber
f: value at end of equalization
i: $i^{th}$ value
IC: physical interconnecting volume or manifold passages
IC_R: physical interconnecting volume on the reference chamber side of valve
IC_CC: physical interconnecting volume on the control chamber side of valve
l: lines or interconnecting/manifold system
0: value at start of equalization
pmp: pump
r: reference system
Ref: physical reference chamber
w: wall of interconnecting volume The equations for the control chamber 6510 may derived from the conceptual model of the three separate mass systems in FIG. 109A and the understanding that the total volume of the control chamber mass 6510, reference chamber mass 6520 and interconnecting volumes mass 6530, 6531 is fixed. This relationship can be expressed as the sum of the volume changes of each closed system 6512, 6522, 6532 being zero for each $i^{th}$ set of values from the start to the end of pressure equalization:

$$0 = \text{change in volume of control chamber mass} + \text{change in volume of interconnecting mass} + \text{change in volume of reference chamber mass} \quad (13)$$

$$0 = \Delta V_{ci} + \Delta V_{ri} + \Delta V_{li}$$

where the $i^{th}$ value of $\Delta V_{ci}$, $\Delta V_{ri}$, $\Delta V_{li}$ represents these values at the same point in time. Equations can be developed for the volume change of the control chamber gas system ($\Delta V_{ci}$), the reference gas system ($\Delta V_{ri}$), and the conduit gas system ($\Delta V_{li}$) based on the pressure/volume relationship of a polytropic process and the ideal gas law. The equation for the $i^{th}$ volume change of the control chamber gas system 6512 is equal to the $i^{th}$ volume of the control chamber mass 6512 less the volume of the control chamber mass 6512 at the start of equalization. The volume of the control chamber mass 6512 at time i is calculated from the volume of the control chamber 6510 times the ratio of the final control chamber 6510 pressure over the control chamber 6510 pressure at time i, raised to one over the polytropic coefficient for the control chamber 6510:

$$\text{current change in volume of control chamber mass} = \text{current volume of control chamber mass} - \text{initial volume of control chamber mass} \quad (14)$$

$$\Delta V_{ci} = V_{CC}\left(\frac{P_{CCf}}{P_{CCi}}\right)^{1/nCC} - V_{CC}\left(\frac{P_{CCf}}{P_{CC0}}\right)^{1/nCC}$$

The equation for the reference gas system volume change ($\Delta V_r$) is derived from the pressure/volume relationship for a polytropic process. The equation for the $i^{th}$ volume change of the reference chamber gas system 6522 is equal to the $i^{th}$ volume of the reference chamber mass 6522 less the volume of the reference chamber mass 6522 at the start of equalization. The volume of the reference chamber mass 6522 at time i is calculated from the structural volume of the reference chamber 6520 times the ratio of the initial reference chamber 6520 pressure over the reference chamber 6520 pressure at time i, raised to one over the polytropic coefficient for the reference chamber 6520:

$$\text{current change in volume of reference chamber mass} = \text{current volume of reference chamber mass} - \text{initial volume of reference chamber mass} \quad (15)$$

$$\Delta V_{ri} = V_{Ref}\left(\frac{P_{Ref0}}{P_{Refi}}\right)^{1/nR} - V_{Ref}$$

The equation for the volume change of the interconnecting gas system 6532 ($\Delta V_l$) is derived from the constant mass gas of the system ($V*\rho$=constant). The equation for the $i^{th}$ volume change of the conduit gas system 6532 is equal the current volume of the system less the original volume of the interconnecting gas system 6532. The current volume of the interconnecting or line gas system 6532 is the initial volume times the ratio of initial over current density of the system. The initial volume of the interconnecting gas system 6532 is the sum of the volumes 6534, 6533 and 6535 pictured in the upper image FIG. 109A:

$$\frac{\text{current change in volume}}{\text{of interconnecting mass}} = \quad (16)$$

$$\frac{\text{current volume of}}{\text{interconnecting mass}} + \frac{\text{initial volume of}}{\text{interconnecting mass}}$$

$$\Delta V_{li} = (\Delta V_{cf} + V_{IC}) \frac{\rho_{l0}}{\rho_{li}} - (\Delta V_{cf} + V_{IC}).$$

The density terms $\rho_{l0}$, $\rho_{li}$ are the average density of the gases in the conduit gas system at the start of equalization and at some point, i, during equalization. The conduit gas system 6532 includes gases as different temperatures and pressures. The conduit gas system 6532 includes gas in the volume in the control chamber 6510 in a volume labeled 6534, gas in manifold passages on the control chamber side of the valve 6540 labeled 6533, gas in manifold passages on the reference chamber side of the valve 6540 labeled 6535, and gas in the reference chamber labeled 6536.

These four equations may be combined develop an expression for the volume ($V_{CC}$) of the control chamber 6510 as a function of the measured pressure pairs at the start of pressure equalization ($P_{CC\ 0}$, $P_{Ref\ 0}$), at any point during the equalization ($P_{CC\ i}$, $P_{Ref\ i}$), the Control Chamber 6510 pressure at approximately the end of equalization ($P_{CC\ f}$) and the Fixed Volumes of the reference chamber ($V_{Ref}$) and interconnecting volume ($V_{IC}$):

$$V_{CC} = \frac{V_{Ref}\left[\left(\frac{P_{Ref\ 0}}{P_{Ref\ i}}\right)^{1/nR} - 1\right] + V_{IC}\left(\frac{\rho_{l0}}{\rho_{li}} - 1\right)}{\left[1 - \left(\frac{P_{CCf}}{P_{CCi}}\right)^{1/nCC}\right] + \left[\left(\frac{P_{CCf}}{P_{CC0}}\right)^{1/nCC} - 1\right]\left(\frac{\rho_{l0}}{\rho_{li}}\right)} \quad (17)$$

where the densities of the manifold or line system 6532 ($\rho_{l\ 0}$, $\beta_{l\ i}$) are evaluated with the initial pressure pairs ($P_{CC\ 0}$, $P_{Ref\ 0}$) and any pressure pair ($P_{CC\ i}$, $P_{Ref\ i}$) during equalization along with the associated temperatures as described below.

The densities of the conduit gas system ($\rho_{l\ 0}$, $p_{l\ i}$) in equations (16) may be calculated from the volume-weighted average density for each physical volume (i.e. control chamber 6510, reference chamber 6520, and interconnecting volumes 6530, 6531):

$$\rho_{li} = \frac{\rho_{CCi}(\Delta V_{cf} - \Delta V_{ci}) + \rho_{IC\_CC}V_{IC\_CC} + \rho_{IC\_R}V_{IC\_R} - \rho_{ri}\Delta V_{ri}}{(\Delta V_{cf} - \Delta V_{ci} + V_{IC\_CC} + V_{IC\_R} + \Delta V_{ri})} \quad (18)$$

$$\rho_{CCi} = \frac{P_{CCi}}{R\ T_{CCi}} = \text{density of gas in control chamber}$$

$$\rho_{IC\_CCi} = \frac{P_{CCi}}{R\ T_{IC\_CC}} = \begin{array}{l}\text{density of gas in manifold line}\\ \text{on control chamber side of valve}\end{array}$$

$$\rho_{IC\_Ri} = \frac{P_{Refi}}{R\ T_{IC\_CC}} = \begin{array}{l}\text{density of gas in manifold line}\\ \text{on reference chamber side of valve}\end{array}$$

$$\rho_{ri} = \frac{P_{Refi}}{R\ T_{lr}} = \begin{array}{l}\text{density of gas in}\\ \text{reference chamber}\end{array}$$

where R is the universal gas constant for air, the temperatures, $T_{IC\_CC}$, $T_{IC\_R}$, $T_{lr}$, may be functions in part of the temperature of the interconnecting volume walls. In another example, the temperatures, $T_{IC\_CC}$, $T_{IC\_R}$, $T_{lr}$, may be functions in part of the temperature of the interconnecting volume walls and the gas temperature of the control chamber ($T_{CCi}$) In another example, the temperatures, $T_{IC\_CC}$, $T_{IC\_R}$, $T_{lr}$, may be the interconnecting wall temperature ($T_W$). In another example, the temperatures may be control chamber temperature ($T_{CCi}$) The value of $\Delta V_{ri}$ is calculated from equation (14). The value of $\Delta V_{cf} - \Delta V_{ci}$ is the volume of 6534 and is calculated as $$\Delta V_{cf} - \Delta V_{ci} = V_{CC\ Est}\left[1 - \left(\frac{P_{CCf}}{P_{CCi}}\right)^{1/nCC}\right] \quad (19)$$

The density of the conduit gas system 6532 before pressure equalization may be calculated from an equation similar to (18) that is the volume-weighted average density for each physical volume (i.e. control chamber 6510 and interconnecting volumes 6530, 6531):

$$\rho_{l0} = \frac{\dfrac{P_{CCi}(\Delta V_{cf})}{T_{CC0}} + \dfrac{P_{CC}V_{IC\_CC}}{T_W} + \dfrac{P_{Ref}V_{IC\_R}}{T_W}}{R(\Delta V_{cf} + V_{IC\_CC} + V_{IC\_R})} \quad (20)$$

The change in the control chamber gas system volume ($\Delta V_{cf}$) used in equation (18) is calculated from the physical volume of the control chamber 6510 times the quantity one minus the ratio of the final control chamber pressure over the initial control chamber pressure raised to one over the polytropic coefficient for the control chamber:

$$\Delta V_{cf} = V_{CC\ Est}\left[1 - \left(\frac{P_{CCf}}{P_{CCi}}\right)^{1/nCC}\right]. \quad (21)$$

An estimate of the control chamber 6510 volume can be derived by assuming constant temperature for the conduit gas system 6532, so that the density ratio ($p_{l\ 0}/p_{l\ f}$) is equal to the pressure ratio ($P_{l\ 0}/P_{l\ f}$). To further simplify the estimate, the polytropic coefficient is replaced by the specific heat ratio ($\gamma$). In this simpler equation, the control chamber 6510 volume is a function of the measured pressure pairs at the start of pressure equalization ($P_{CC\ 0}$, $P_{Ref\ 0}$) and at the end of equalization ($P_{CC\ f}$, $P_{Ref\ f}$) and the fixed volumes of the reference chamber ($V_{Ref}$) and interconnecting volume ($V_{IC}$):

$$V_{CC\ Est} = \frac{V_{Ref}\left[\left(\frac{P_{Ref\ 0}}{P_{Ref\ f}}\right)^{\frac{1}{\gamma}} - 1\right] + V_{IC}\left(\frac{P_{CC0}}{P_{CCf}} - 1\right)}{\left[\left(\frac{P_{CC0}}{P_{CCf}}\right)^{\frac{1}{\gamma}} - 1\right]\left(\frac{P_{CC0}}{P_{CCf}}\right)}. \quad (22)$$

The gas in the three closed systems 6512, 6522, 6532 may be modeled as an ideal gas, so the temperature can be determined from the initial conditions and the new pressure or volume:

$$T_i = T_0\left(\frac{p_0}{p_i}\right)^{(n-1)/n} \text{ or } T_i = T_0\left(\frac{V_0}{V_i}\right)^{n-1} \quad (23)$$

The initial temperature of the gas in the control chamber ($T_{CC\ 0}$) may be calculated from the temperature of the interconnecting volume walls, the precharge pressure 6316 (FIG. 108A) and the pressures in the control chamber 6510 just before precharge 6306. The the compression of gas in the control volume to the precharge pressure can be modeled as a polytropic process and using the ideal gas law in equation (23). The control chamber 6510 pressure before precharging 6306 is referred herein as the pumping pressure (Ppmp):

$$T_{CC0} = T_W \left(\frac{P_{pmp}}{P_{CC0}}\right)^{\frac{1}{nCC}-1}. \quad (24)$$

The temperature of the gas in the control chamber 6510 at the $i^{th}$ step ($T_{CC\,i}$) during expansion may be calculated from the initial control chamber 6510 temperature, the precharge pressure 6316 (FIG. 108A) and the $i^{th}$ control chamber 6510 pressure ($P_{CC\,i}$) using equation (23):

$$T_{CCi} = T_{CC0}\left(\frac{P_{CC0}}{P_{CCi}}\right)^{\frac{1}{nCC}-1} \quad (25)$$

The value of the polytropic coefficient for the control chamber gas system (nCC) used in equations 14, 17, 19, 21, 25 may vary with the volume of the control chamber 6510 and range from approximately 1 for small volumes to approximately the specific heat ratio for large volumes. The specific heat ratio for air and other systems of predominantly diatomic molecules is 1.4. In one example the value of nCC (for +FMS) can be expressed as a function of the estimated control chamber volume (eqn 22):

$$nCC=1.4-3.419\times10^{-5}(23.56-V_{CCEst})^{3.074} \quad (26)$$

A method to determine a relationship between the volume of the control chamber ($V_{CC}$) and its polytropic coefficient (nCC) is described in a following section.

Polytropic −FMS Algorithm

A −FMS algorithm similar to the +FMS algorithm, described above, can be developed to calculate the volume of the control chamber 6171 in FIG. 105 from the control chamber 6171 and reference chamber 6212 pressures for a −FMS process. In the −FMS process the first chamber (e.g. 6171) is precharged to a pressure below the known second chamber (e.g. 6212).

Figure 109B:
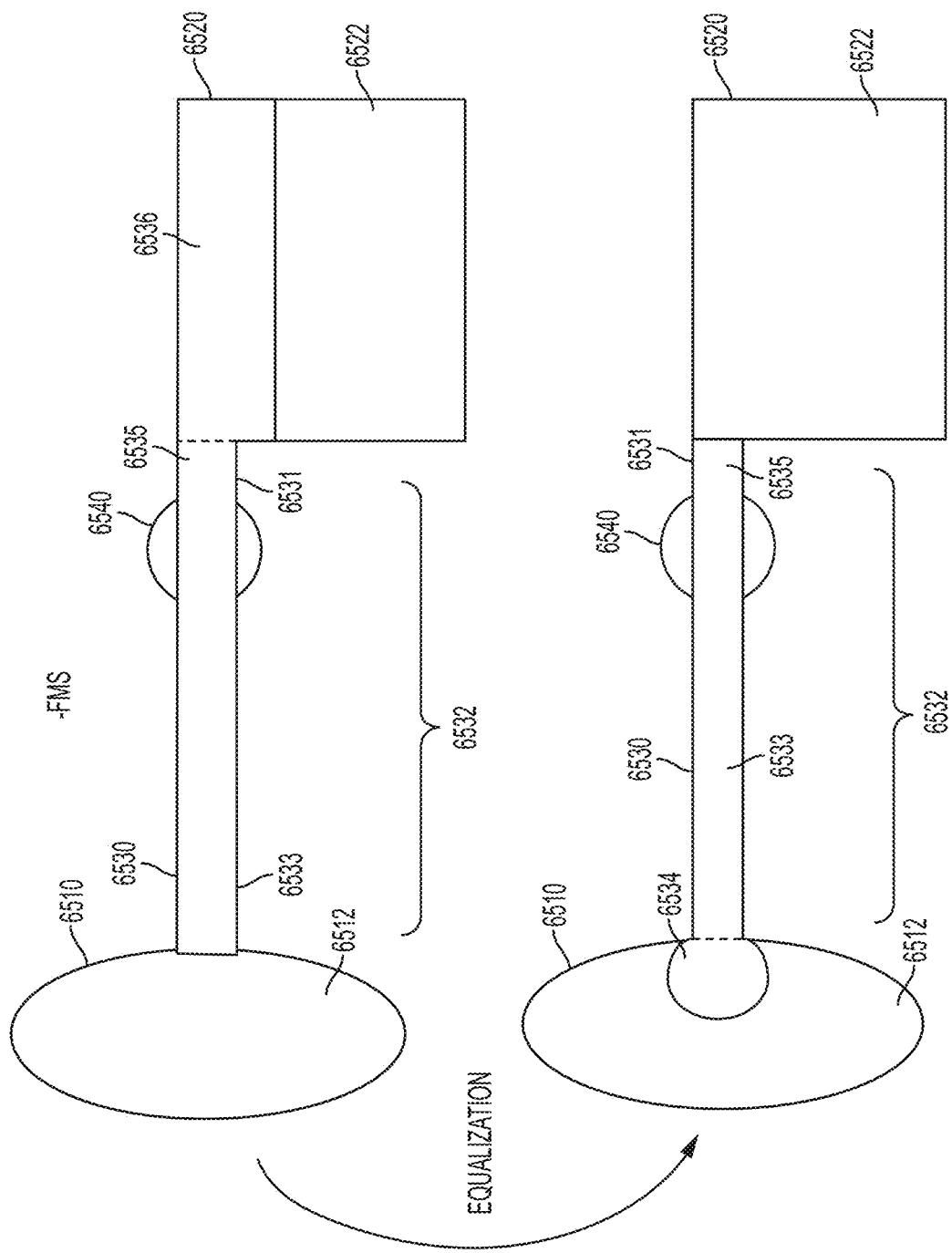
FIG. 109B is a plot of the polytropic expansion constant for +FMS verses control chamber volume.

Referring now to FIG. 109B, the gas in the structures of the control chamber 6510, the reference chamber 6520 and the manifold lines 6530, 6531 can be modeled as three gas masses, 6512, 6532, 6522 that do not mix, but expand, contract, and move through the structures 6510, 6520, 6530, 6531. The volume of the control chamber 6510 can be calculated from the measured control chamber 6510 and reference chamber 6520 pressures based on thermodynamic models of the three masses 6512, 6522, 6532. In the −FMS algorithm, the control chamber mass 6512 is the gas that occupies the control chamber 6510 at the start of the equalization process. The reference chamber mass 6522 is the gas that occupies the reference chamber 6520 at the end of the equalization process. The manifold gas 6532 fills the balance of the structure between the control chamber gas 6512 and the reference chamber gas 6522.

The volume and temperature of the three conceptual closed-systems, 6512, 6532, 6522 may then be calculated from initial conditions, pressure pairs, heat transfer assumptions and the constraint of a fixed total volume for the 3 closed-systems 6512, 6532, 6522. The pressure equalization can be modeled with a different polytropic coefficient for each volume 6510, 6520, 6530, 6531 to capture the relative importance of heat transfer in each. The constant mass, ideal gas and polytropic process equations for the three systems, 6512, 6522, 6532 can be combined and arranged to calculate the volume of the control chamber 6510. The following paragraphs describe the derivation of one or more sets of equations that allow calculation of the control chamber 6510 volume based on pressures measured during the pressure equalization step of the −FMS process.

Description of Closed Systems for −FMS

The upper image in FIG. 109B presents the positions of the three closed-systems 6512, 6522, 6532 at the start of pressure equalization in the −FMS process. The lower image presents the positions of the three closed systems 6512, 6522, 6532 at the end of the pressure equalization. During the equalization process, the locations of the closed systems 6512, 6522, 6532 are between the two extremes presented in FIG. 109B. By way of an example, neither the control chamber system 6512 nor the reference chamber system 6522 fill their respective structures 6510, 6520. The following paragraphs present the closed systems in more detail.

The control chamber gas system 6512 in the −FMS algorithm is the gas that fills the control chamber 6510 before equalization. The control chamber gas system 6512 is compressed during pressure equalization as the initially higher pressure reference chamber gas system 6522 expands and pushes the manifold gas system 6532 into the control chamber 6510. The control chamber gas system 6512 may modeled with a polytropic compression during pressure equalization of the −FMS process, where the pressure and the volume are related by:

$$p_0 V_{CC}^{nCC} = \text{constant}$$

where $p_0$ is the initial pressure in the control chamber 6510, $V_{CC}$ is the volume of the control chamber 6510, and nCC is the polytropic coefficient for the control chamber 6510.

The reference gas system 6522 in the −FMS algorithm is the gas that occupies the entire reference volume 6520 after equalization. The reference gas system 6522 expands during equalization as the higher pressure gas in the reference chamber 6520 pushes the manifold gas system 6532 out of the reference chamber 6520 and toward the control chamber 6510. In one example shown in FIG. 93, the reference chambers (labeled 174 in FIG. 93) are sufficiently open or devoid of interior features/elements that compression or expansion processes during pressure equalization may be modeled as adiabatic, so the polytropic coefficient (nR) may be set equal to approximately the specific heat ratio of the gas present in the chamber. The pressure and the volume of the reference chamber gas 6522 are related by:

$$p_{R0} V_{Ref}^{nR} = \text{constant}$$

where $p_{R0}$ is the initial reference chamber 6520 pressure, $V_{Ref}$ is the volume of the reference chamber 6520, and nR is the specific heat ratio for the reference chamber (nR=1.4 air). In another example, where the reference chamber 6520 is filled with a heat absorbing material such as open cell foam, wire mesh, particles, etc that provides for a near-isothermal expansion, the polytropic coefficient for the reference chamber (nR) may have a value of approximately 1.0.

In the −FMS process, the conduit or manifold gas system 6532 occupies all of the volume of the interconnecting volume 6530, 6531 and a fraction 6536 of the reference chamber 6520 before equalization. After equalization, the conduit gas system 6532 occupies the interconnecting volume 6530, 6531 and a fraction 6534 of the control chamber 6510. The portion of the conduit gas system 6532 that exists in interconnecting volume 6530 on the control chamber side of the valve 6540 is herein labeled as 6533. The portion of the conduit gas system 6532 that exits in the interconnecting volume 6531 on the reference chamber side of the valve 6540 is referred to as 6535. The portion of the conduit gas system 6532 that exists in the control chamber 6510 is herein labeled as 6534. The portion of the conduit gas system 6532 that exists in the reference chamber 6520 is referred to as 6536.

In one example the interconnecting volumes 6530 and 6531 may be narrow passages that provide high heat transfer that assure the conduit gas system 6532 in volumes 6530 and 6531 is near the temperature of the solid boundaries or walls of the passages. The temperature of the structure surrounding the interconnecting volumes 6530, 6531 or manifold passages is herein referred to as the wall temperature ($T_W$). In another example, the temperature of the conduit gas system 6532 in volumes 6530, 6531 is in part a function of the wall temperature. The portion of the conduit gas system in the control chamber 6534 may be modeled with the same temperature as control chamber gas system 6512. The control chamber portion of the conduit gas system 6534 experiences the same expansion as the control chamber gas system 6512 and may be conceived of as having the same temperature as the control chamber gas system 6512. The portion of the lines or manifold gas system in the reference chamber 6536 may be modeled with a temperature that is in part a function of the wall temperature. In another example, the reference chamber portion of the conduit gas system 6536 may be modeled as not interacting thermally with the boundaries of the reference chamber 6520, so that the temperature of the conduit gas system portion in the reference chamber 6536 is a function of the wall temperature and the reference chamber 6520 pressures.

The equations in this section use the following nomenclature:

variables
γ: specific heat ratio
n: polytropic coefficient
p: pressure
V: volume
T: temperature
superscripts:
n: polytropic coefficient
nCC: polytropic coefficient for the control chamber
nR: polytropic coefficient for the reference chamber
subscripts:
c: control chamber system
CC: physical control chamber
f: value at end of equalization
i: $i^{th}$ value
   IC: physical interconnecting volume or manifold passages
IC_R: physical interconnecting volume on the reference chamber side of valve
IC_CC: physical interconnecting volume on the control chamber side of valve
l: lines or manifold/interconnecting system
0: value at start of equalization
pmp: pump
r: reference system
Ref: physical reference chamber
w: wall temperature of interconnecting volume The equations for the control chamber 6510 may derived from the conceptual model of the three separate mass systems in FIG. 109B and the understanding that the total volume of the control chamber mass 6512, reference chamber mass 6522 and interconnecting volumes mass 6532 is fixed. This relationship can be expressed as the sum of the volume changes of each closed system 6512, 6522, 6532 being zero for each $i^{th}$ set of values from the start to the end of pressure equalization:

$$0 = \text{change in volume of control chamber mass} + \text{change in volume of interconnecting mass} + \text{change in volume of reference chamber mass} \quad (13)$$

$$0 = \Delta V_{ci} + \Delta V_{ri} + \Delta V_{li}$$

where the $i^{th}$ value of $\Delta V_{ci}$, $\Delta V_{ri}$, $\Delta V_{li}$ represents these values at the same point in time. Equations can be developed for the volume change of the control chamber gas system ($\Delta V_{ci}$), the reference gas system ($\Delta V_{ri}$), and the conduit gas system ($\Delta V_{li}$) based on the pressure/volume relationship of a polytropic process and the ideal gas law. The equation for the $i^{th}$ volume change of the control chamber gas system 6512 is equal to the $i^{th}$ volume of the control chamber mass 6512 less the volume of the control chamber mass 6512 at the start of equalization. The volume of the control chamber mass 6512 at time i is calculated from the volume of the control chamber 6510 times the ratio of the final control chamber 6510 pressure over the control chamber 6510 pressure at time i, raised to one over the polytropic coefficient for the control chamber 6510:

$$\text{current change in volume of control chamber mass} = \text{current volume of control chamber mass} + \text{initial volume of control chamber mass} \quad (27)$$

$$\Delta V_{ci} = V_{CC}\left(\frac{P_{CC0}}{P_{CCi}}\right)^{1/nCC} - V_{CC}$$

The equation for the reference gas system volume change ($\Delta V_r$) is derived from the pressure/volume relationship for a polytropic process. The equation for the $i^{th}$ volume change of the reference chamber gas system 6522 is equal to the $i^{th}$ volume of the reference chamber mass 6522 less the volume of the reference chamber mass 6522 at the start of equalization. The volume of the reference chamber mass 6522 at time i is calculated from the structural volume of the reference chamber 6520 times the ratio of the initial reference chamber 6520 pressure over the reference chamber 6520 pressure at time i, raised to one over the polytropic coefficient for the reference chamber 6520:

$$\text{current change in volume of reference chamber mass} = \text{current volume of reference chamber mass} + \text{initial volume of reference chamber mass} \quad (28)$$

$$\Delta V_{ri} = V_{Ref}\left(\frac{P_{Reff}}{P_{Refi}}\right)^{1/nR} - V_{Ref}\left(\frac{P_{Reff}}{P_{Ref0}}\right)^{1/nR}$$

The equation for the volume change of the interconnecting gas system 6532 ($\Delta V_l$) is derived from the constant mass gas of the system ($V*\beta$=constant). The equation for the $i^{th}$ volume change of the conduit or manifold gas system 6532 is equal the current volume of the system 6532 less the original volume of the system 6532. The current volume of the interconnection or manifold gas system 6532 is the initial volume times the ratio of initial over current density of the system 6532. The initial volume of the interconnecting gas system 6532 is the sum of the volumes 6534, 6533 and 6535 pictured in FIG. 109B:

$$\begin{aligned}\frac{\text{current change in volume}}{\text{of interconncting mass}} &= \\ &\frac{\text{current volume of}}{\text{interconnecting mass}} + \frac{\text{initial volume of}}{\text{interconnecting mass}} \\ \Delta V_{li} &= (\Delta V_{Rf} + V_{IC})\frac{\rho_{l0}}{\rho_{li}} - (\Delta V_{Rf} + V_{IC}).\end{aligned} \quad (29)$$

The density terms $\rho_{l0}$, $\rho_{li}$ are the average density of the gases in the conduit gas system 6532 at the start of equalization and at some point, i, during equalization. The conduit gas system 6532 includes gases as different temperatures and pressures. The conduit gas system 6532 includes gas in the volume of the control chamber 6510 in a volume labeled 6534, gas in manifold passages on the control chamber side of the valve 6540 labeled 6533, gas in manifold passages on the reference chamber side of the valve 6540 labeled 6535, and gas in the reference chamber labeled 6536.

These four equations may be combined develop an expression for the volume ($V_{CC}$) of the control chamber 6510 as a function of the measured pressure pairs at the start of pressure equalization ($P_{CC\ 0}$, $P_{Ref\ 0}$), at any point during the equalization ($P_{CC\ i}$, $P_{Ref\ i}$), the reference chamber 6520 pressure at approximately the end of equalization ($P_{Ref\!f}$) and the fixed volumes of the reference chamber ($V_{Ref}$) and interconnecting volume ($V_{IC}$):

$$V_{CC} = \frac{V_{Ref}\left[\left(\frac{P_{Ref\!f}}{P_{Ref\ i}}\right)^{1/nR} - \left(\frac{P_{Ref\!f}}{P_{Ref\ 0}}\right)^{1/nR}\right] + (\Delta V_{Rf} + V_{IC})\left(\frac{\rho_{l0}}{\rho_{li}} - 1\right)}{\left[1 - \left(\frac{P_{CC\ 0}}{P_{CC\ i}}\right)^{1/nCC}\right]} \quad (30)$$

where the densities of the line system 6532 ($\rho_{l\ 0}$, $\rho_{l\ i}$) are evaluated with the initial pressure pairs ($P_{CC\ 0}$, $P_{Ref\ 0}$) and any pressure pair ($P_{CC\ i}$, $P_{Ref\ i}$) during equalization along with the associated temperatures as described below.

The densities of the conduit gas system ($\rho_{l\ 0}$, $\rho_{l\ i}$) in equations (29) may be calculated from the volume-weighted average density for each physical volume (i.e. control chamber 6510, reference chamber 6520, and interconnecting volumes 6530, 6531):

$$\rho_{li} = \frac{-\rho_{CCi}(\Delta V_{cf}) + \rho_{IC_{CC}}V_{IC_{CC}} + \rho_{IC_R}V_{IC_R} + \rho_{ri}\Delta V_{ri}}{(\Delta V_{cf} + V_{IC\_CC} + V_{IC\_R} + \Delta V_{ri})} \quad (31)$$

$$\rho_{CCi} = \frac{P_{CCi}}{R\,T_{CCi}} = \text{density of gas in control chamber}$$

$$\rho_{IC\_CCi} = \frac{P_{CCi}}{R\,T_{IC\_CC}} = \begin{matrix}\text{density of gas in manifold line} \\ \text{on control chamber side of valve}\end{matrix}$$

$$\rho_{IC\_Ri} = \frac{P_{Refi}}{R\,T_{IC\_CC}} = \begin{matrix}\text{density of gas in manifold line} \\ \text{on reference chamber side of valve}\end{matrix}$$

$$\rho_{ri} = \frac{P_{Refi}}{R\,T_{lr}} = \begin{matrix}\text{density of gas in} \\ \text{reference chamber}\end{matrix}$$

where R is the universal gas constant for air, the temperatures, $T_{IC\_CC}$, $T_{IC\_R}$, $T_{lc}$, may be functions in part of the temperature of the interconnecting volume walls. In another example, the temperatures, $T_{IC\_CC}$, $T_{IC\_R}$, $T_{lcr}$ may be functions in part of the temperature of the interconnecting volume walls and the gas temperature of the reference chamber ($T_{Ref\ i}$). In another example, the temperatures, $T_{IC\_CC}$, $T_{IC\_R}$, $T_{lc}$, may be the interconnecting wall temperature ($T_W$). In another example, the temperatures may be reference chamber temperature ($T_{Ref\ i}$).

The value of $\Delta V_{cf}$ for equation (31) is calculated from equation (27), where the final control chamber pressure ($P_{CCf}$) is used for $P_{CCi}$ and $V_{CC\_Est}$ is used for $V_{CC}$.

The value of $\Delta V_{ri}$ for equation (31) is calculated from equation (28).

The density of the conduit gas system 6532 before pressure equalization may be calculated from a equation similar to equation (31) that is the volume-weighted average density for each physical volume (i.e. control chamber 6510 and interconnecting volumes 6530, 6531):

$$\rho_{l0} = \frac{\frac{P_{ref0}(\Delta V_{rf})}{T_W} + \frac{P_{CC}V_{IC\_CC}}{T_W} + \frac{P_{Ref}V_{IC\_R}}{T_W}}{R(\Delta V_{rf} + V_{IC\_CC} + V_{IC\_R})} \quad (32)$$

An estimate of the control chamber 6510 volume can be derived by assuming constant temperature for the conduit or manifold gas system 6532, so that the density ratio ($\rho_{i\ 0}/\rho_{i\ f}$) is equal to the pressure ratio ($P_{l\ 0}/P_{l\ f}$). To further simplify the estimate, the polytropic coefficient is replaced by the specific heat ratio ($\gamma$). In this simpler equation, the volume of the control chamber ($V_{CC}$) in the –FMS process can be expressed as a function of three pressures [i.e. the measured pressure pair at the start of pressure equalization ($P_{CC\ 0}$, $P_{Ref\ 0}$), and a single equalization pressure ($P_f$)], as well as the fixed volumes of the reference chamber ($V_{Ref}$) and interconnecting volume ($V_{IC}$), and the polytropic coefficients for the reference chamber (nR) and control chamber (nCC):

$$V_{CC\ Est} = \frac{V_{Ref}\left[1 - \left(\frac{P_f}{P_{Ref\ 0}}\right)^{1/\gamma}\right] + (\Delta V_{Rf} + V_{IC})\left(\frac{P_{CC0}}{P_f} - 1\right)}{\left[1 - \left(\frac{P_{CC0}}{P_f}\right)^{1/\gamma}\right]}. \quad (33)$$

The gas in the three closed systems 6512, 6522, 6532 may be modeled as an ideal gas, so the temperature can be determined from the initial conditions and the new pressure or volume:

$$T_i = T_0\left(\frac{p_0}{p_i}\right)^{(n-1)/n} \text{ or } T_i = T_0\left(\frac{V_0}{V_i}\right)^{n-1} \quad (23)$$

The initial temperature of the gas in the control chamber ($T_{CC\ 0}$) may be calculated from the temperature of the interconnecting volume walls, the precharge pressure 6316 (FIG. 108B) and the pressures in the control chamber 6510 just before precharge 6306 (see FIG. 108B) modeling it as polytropic process and using the ideal gas law in equation (23). The control chamber pressure before precharging 6306 is referred herein as the pumping pressure (Ppmp):

$$T_{CC0} = T_W \left( \frac{P_{pmp}}{P_{CC0}} \right)^{\frac{1}{nCC} - 1} \quad (24)$$

The value of the polytropic coefficient for the control chamber gas system (nCC) may vary with the volume of the control chamber 6510 and range from approximately 1 for small volumes to approximately the specific heat ratio for large volumes. The specific heat ratio for air and other systems of predominantly diatomic molecules is 1.4. In one example the value of nCC for −FMS can be expressed as a function of the estimated control chamber volume (equation 21):

$$nCC = 1.507 - 1.5512 \times 10^{-5} (23.56 - V_{CC\,Est})^{3.4255} \quad (34)$$

A method to determine a relationship between the volume of the control chamber ($V_{CC}$) and its polytropic coefficient (nCC) is described in a following section.

Determining the Polytropic Coefficient $N_{CC}$

The value of polytropic coefficient $n_{CC}$ may be determined experimentally or analytically. In possible understanding, the polytropic coefficient compares the potential temperature change of the gas due to heat transfer with the structure to temperature change caused by pressure changes. The value of the polytropic coefficient may vary with the pressure changes, the rate of pressure changes and the shape and size of the gas volume.

Figure 110A:
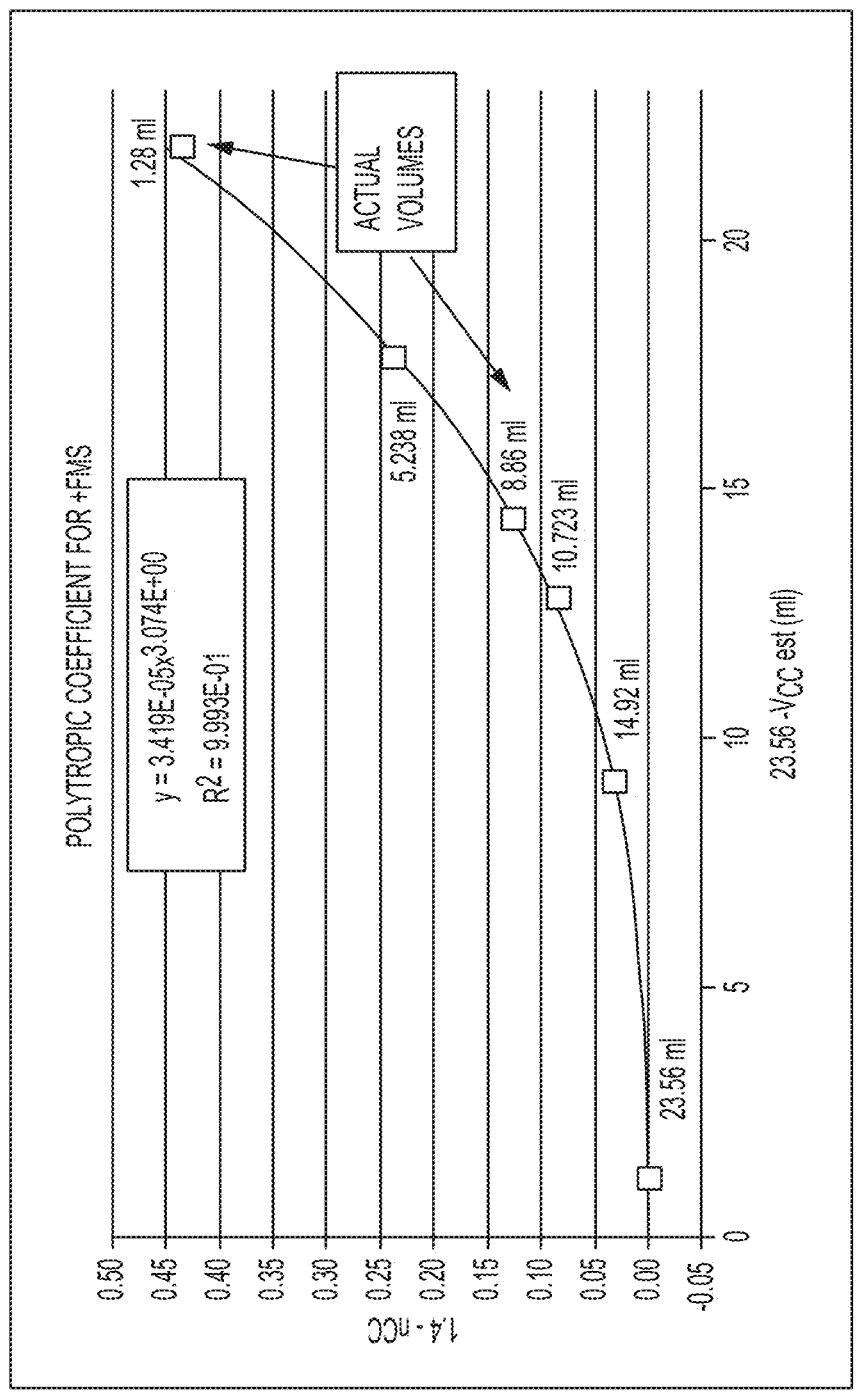
FIG. 110A is an illustration of the polytropic conceptual model of the −FMS process involving three separate closed mass systems.

In one embodiment, the polytropic coefficient $N_{CC}$ is determined experimentally by creating control chamber 6171 (FIG. 105) with a known volume and executing the +FMS process or the −FMS processes and recording the control chamber and reference chamber pressures during equalization. The polytropic +FMS algorithm comprising eqns (17), (18), (20) is applied to the set of pressure measurements and the known control chamber volume ($V_{CC}$) in order to solve for the value of the polytropic coefficient for the control chamber ($n_{CC}$). This process to determine the polytropic coefficient was repeated for several different volumes ranging 1.28 ml, which is the typical of the control chamber 6171 after a fill stroke to 23.56 ml which is typical of the control chamber 6171 after a deliver stroke. The FMS process may be repeated several times for each volume to improve the accuracy of the determination of $n_{CC}$. One example of this experimental determination $n_{CC}$ for +FMS process is shown in FIG. 110A, where the value of $n_{CC}$ is plotted versed the estimated volume of the control chamber ($V_{CC\,Est}$) as calculated by eqn (22) for six different volumes. A power equation was fit to the data to produce eqn (26) which expresses the polytropic coefficient in terms of the estimated volume control chamber. The plot in FIG. 110A plots the value, 1.4-$n_{CC}$, vs. 23.56-$V_{CC\,Est}$ in order to better fit the data with simple equation.

Figure 110B:
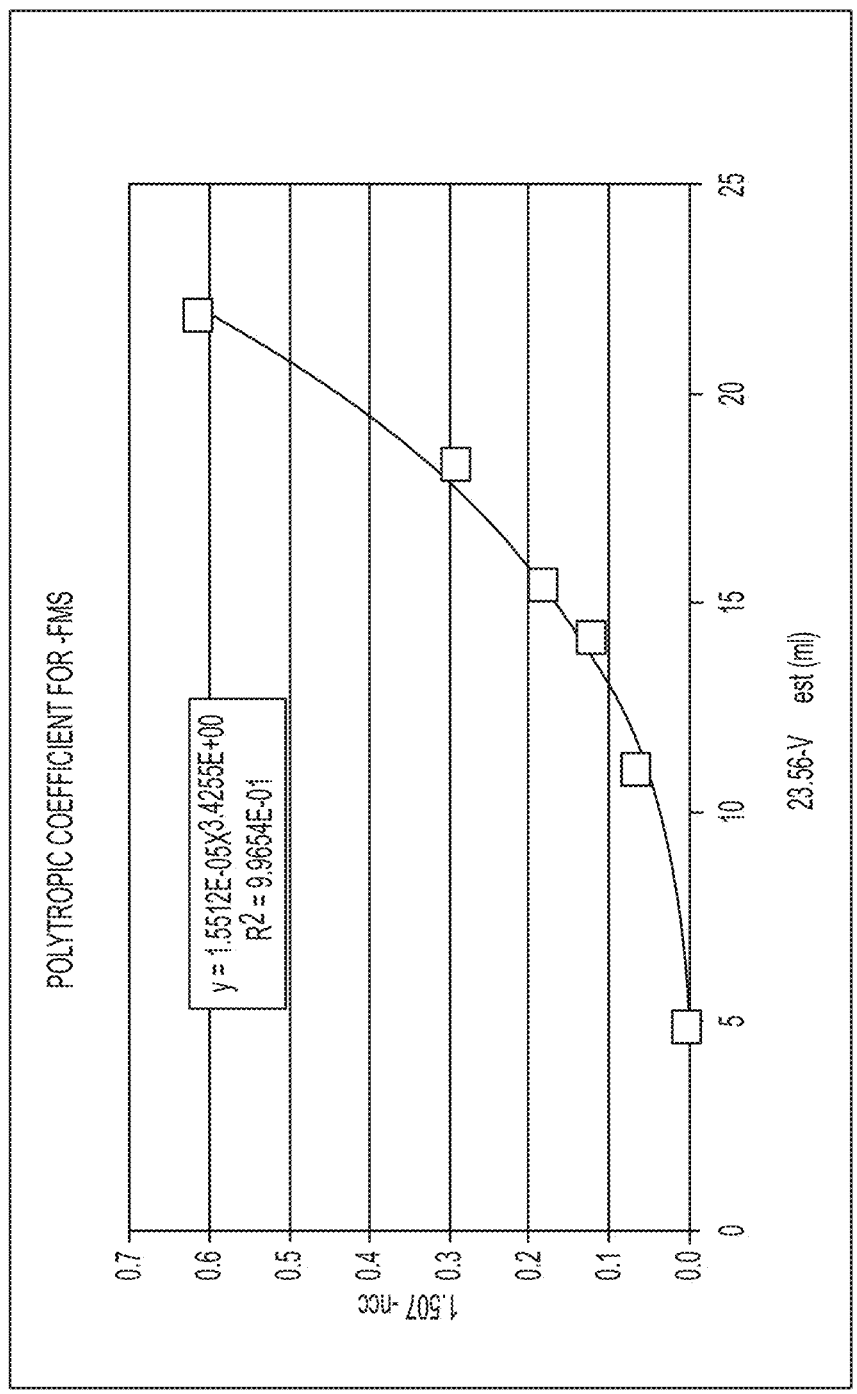
FIG. 110B is a plot of the polytropic expansion constant for −FMS verses control chamber volume.

In a similar fashion, the polytropic coefficient ($n_{CC}$) for −FMS may be determined by applying the −FMS process to a known control chamber volume and recording the control chamber and reference chamber pressures during equalization. The polytropic −FMS algorithm comprising eqns (30), (31), (32) is applied to the set of pressure measurements and the known control chamber volume ($V_{CC}$) in order to solve for the value of the polytropic coefficient for the control chamber ($n_{CC}$). This process to determine the polytropic coefficient was repeated for several different volumes. An example of the resulting values for $n_{CC}$ for the −FMS process is shown in FIG. 110B, where the value of $n_{CC}$ is plotted versed the estimated volume of the control chamber ($V_{CC\,Est}$) as calculated by eqn (33) for six different volumes. A power equation was fit to the data to produce eqn (34) which expresses the polytropic coefficient ($n_{CC}$) in terms of the estimated volume control chamber ($V_{CC\,Est}$). The plot in FIG. 110B plots the value, 1.507-$n_{CC}$, vs. 23.56-$V_{CC\,Est}$ in order to better fit the data with simple equation.

In one embodiment, the fixed known control chamber volume is created by attaching a machined volume to the front of the mounting plate 170 (FIG. 92), so that machined volume is sealed to the mounting plate and covers the ports 173C connecting the control chamber to pressure source and pressure sensor.

Polytropic FMS Calculation Procedure for $V_{CC}$

Figure 111:
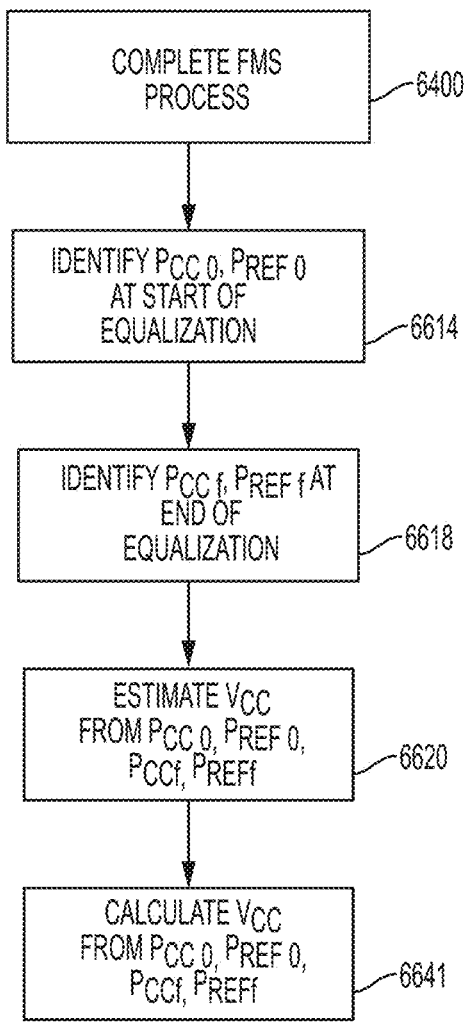
FIG. 111 is a flow chart of basic AIA FMS calculation steps.
Figure 112:
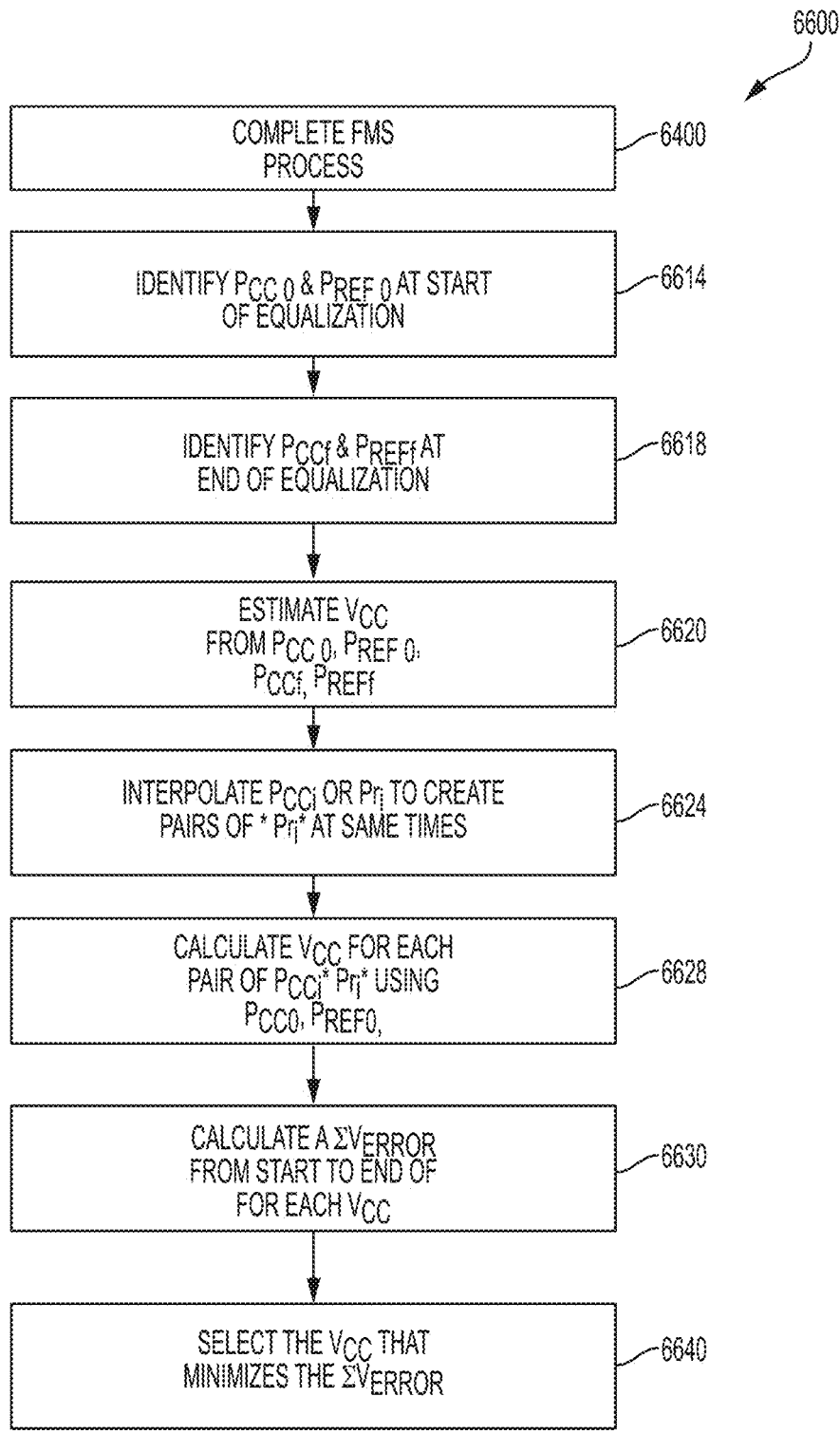
FIG. 112 is a more detailed flow chart of AIA FMS calculation steps.

Referring now for FIGS. 111 and 112 that present flowcharts to calculate the volume of the control chamber from the pressure data recorded during an 2-chamber FMS process and the polytropic FMS algorithm. The flowchart in FIG. 111 presents a relatively simple process that requires a minimum of pressure data to calculate the volume of the control chamber ($V_{CC}$). The flowchart in FIG. 112 describes a more complex calculation to more accurately calculate the volume of the control chamber ($V_{CC}$) that requires multiple pressure pairs during the equalization process.

The simple polytropic FMS calculation procedure presented in FIG. 111 is executed by a processor or controller and starts with step 6400 that comprises completing either the +FMS or −FMS process described above and storing in memory multiple pressure pairs that were recorded during the equalization process. In step 6614, the controller analyzes the multiple pressure pairs to identify the initial control chamber pressure ($P_{CC\,0}$) and the initial reference pressure ($P_{Ref\,0}$) as the control chamber and reference pressures when the equalization process starts. Methods or procedures to identify the start of equalization or the initial pressures are described in a previous section titled Pump Volume Delivery Measurement, where the initial control chamber and reference chamber pressures are referred to as Pd and Pr. In step 6618, the controller analyzes the multiple pressure pairs to identify the final control chamber pressure ($P_{CC\,f}$) and the final reference pressure ($P_{Ref\,f}$) when the control chamber and reference chamber pressures have nearly equalized or are changing at a sufficient low rate. One or more methods to identify when the control chamber and reference chamber pressures have nearly equalized are described in a previous section titled Pump Volume Delivery Measurement.

Alternatively, steps 6614 and 6618 to identify the initial and final pressures for the control chamber and reference chamber may occur during the FMS process 6400. The controller or FPGA processor may identify the initial and final pressures and store only those values. In one example, the initial pressures could be the control chamber and reference pressures, when the connection valve opens, and the final pressures could be the control chamber and reference pressures when the second valve opens to vent the reference and control chambers after equalization.

In step 6620, the volume of the control chamber is estimated from the initial and final pressures using either eqn (22) for a +FMS process or eqn (34) for a −FMS process. In step 6641, for a +FMS process, the resulting estimate of the control chamber volume ($V_{CC\,Est}$) is then used in eqns (26) to calculate the polytropic coefficient for the control chamber ($n_{CC}$). This polytropic value ($n_{CC}$) and the estimated volume ($V_{CC\ Est}$) along with initial and final pressure pairs are supplied to eqns (17), (18), (19) for a +FMS process to calculate the control chamber volume ($V_{CC}$). In step 6641 for a −FMS process, the polytropic coefficient ($n_{CC}$) is calculated with eqn 34 and the control chamber volume ($V_{CC}$) is calculated with eqns. (30), (31), (32).

A processor such as controller 61100 in FIG. 105, may perform steps 6614-6618 (FIG. 111) on the stored pressure pairs. In an alternative embodiment, a processor 61100 may perform steps 6614 and 6618 during the pressure equalization without storing the pressure pair A more complex calculation of the control chamber volume ($V_{CC}$) is described in FIG. 112. The initial steps of completing the FMS 6400, identifying the initial control chamber pressure ($P_{CC\ 0}$) and initial reference chamber pressure ($P_{Ref\ 0}$) 6614, identifying the final control chamber pressure ($P_{CC\ i}$) and final reference chamber pressure ($P_{Ref\ f}$) 6618, and estimating the control chamber volume ($V_{CC\ Est}$) 6620 are the same as described above for FIG. 111.

The steps 6624, 6628, 6630 and 6640 are similar to the calculation steps described above in the section titled Pump Volume Delivery Measurement, except that the calculation of the control chamber volume ($V_{CC}$) is based on eqns. (17), (18), (19) for a +FMS process and eqns. (30), (31), (32) for a −FMS process. In step 6624, the pressure pairs of the control chamber pressure ($P_{CC\ i}$) and reference chamber pressure ($P_{r\ i}$) are corrected by interpolations with previous subsequent pressure pairs to calculate pressures pairs ($P_{CC\ i}^*$, $P_{r\ i}^*$) that occurred at exactly the same time. In other embodiments step 6624 is skipped and subsequent calculations use the uncorrected pressure pair ($P_{CC\ i}$, $P_{r\ i}$). In step 6628, a control chamber volume ($V_{CC}$) is calculated for each pressure pair. In steps 6630, 6640, the optimization algorithm described in the section titled Pump Volume Delivery Measurement is carried to out identify the optimal final pressure pair ($P_{CC\ f}$, $P_{Ref\ f}$) and the resulting control chamber volume ($V_{CC}$).

In an alternative embodiment, the calculations described FIGS. 111, 112 may be carried out in a processor that is separate from the controller 61100 in FIG. 105. The calculations may for example be carried out in the FPGA that also handles the input and output signals to and from the actuators, valves and pressure sensors.

Air Detection with the Polytropic FMS Algorithm

Referring now to FIG. 103, another aspect of the invention involves the determination of a presence of air in the pump chamber 181, and if present, a volume of air present. Such a determination can be important, e.g., to help ensure that a priming sequence is adequately performed to remove air from the cassette 24 and/or to help ensure that air is not delivered to the patient. In certain embodiments, for example, when delivering fluid to the patient through the lower opening 187 at the bottom of the pump chamber 181, air or other gas that is trapped in the pump chamber may tend to remain in the pump chamber 181 and will be inhibited from being pumped to the patient unless the volume of the gas is larger than the volume of the effective dead space of pump chamber 181. As discussed below, the volume of the air or other gas contained in pump chambers 181 can be determined in accordance with aspects of the present invention and the gas can be purged from pump chamber 181 before the volume of the gas is larger than the volume of the effective dead space of pump chamber 181.

A determination of an amount of air in the pump chamber 181 may be made at the end of a fill stroke, and thus, may be performed without interrupting a pumping process. For example, at the end of a fill stroke during which the membrane 15 and the pump control region 1482 are drawn away from the cassette 24 such that the membrane 15/region 1482 are brought into contact with the wall of the control chamber 172. A +FMS procedure as described in FIG. 107 may be carried out to measure the pressure equalization and calculate the apparent volume of the control chamber 171 (FIG. 11) as described above. However, the +FMS procedure after a fill stroke, provided that the membrane is off the spacers 50, will also measure the volume of any gas or air bubbles on the liquid side of the membrane 15.

The volume of the control chamber when the membrane 15 is against the control chamber wall 172 is generally a known value based on the design and manufacturing process. This minimum control chamber volume is $V_{CC\ Fix}$. The control chamber volume measured during a +FMS procedure at the end of a fill command is $V_{CC+}$. If the measured control chamber volume ($V_{CC+}$) is greater than $V_{CC\ Fix}$, then the control system 66 or controller 1100 may command a −FMS procedure that calculates a control chamber volume ($V_{CC-}$). If the −FMS procedure gives substantially the same control chamber volume as the +FMS, then the controller may recognize that the fill line is occluded. Alternatively if the −FMS procedure produces a smaller control chamber volume, then the controller recognizes the difference as the size of the sum of the air bubbles ($V_{AB}$):

$$V_{AB} = V_{CC+} V_{CC-} \tag{30}$$

A similar method may be used at the end of the deliver stroke, when the membrane 15 is against the spacers 50. A +FMS procedure will not measure the volume of air in the liquid, but only the volume of air in the control chamber 171, when the membrane 15 is against the spacers 50. However, a −FMS procedure will pull the membrane away from the spacers 50 and will measure the volume of air on the dry side (i.e. control chamber 171) and the liquid side (pump chamber 181) of the membrane 15. Therefore for the air volume in the liquid ($V_{AB}$) can also be determined at the end of the deliver stroke:

$$V_{AB} = V_{CC-} - V_{CC+} \tag{31}$$

Air Calibration

A further aspect of this disclosure includes a method to calibrate the −FMS process and +FMS process with direct measurements of the control chamber volume 6171 (FIG. 105) using pressure measurements independent of the pressure measurements associated with an FMS process. This method to calibrate the 2-chamber FMS processes is herein referred to as the Air Cal method. The hardware references in this section will be directed to FIG. 105, but apply equally to the equivalent hardware components other pneumatically actuated diaphragm pumps. The Air Cal method provides a number of benefits including but not limited to: improving the accuracy of the 2-chamber FMS method over the full range of control chamber volumes; allowing the use of nominal volumes for the reference chamber ($V_{Ref}$) 6212 and the volume of the interconnecting volumes ($V_{IC}$) 6204, 6205, 6207, 6209. The method also allows for compensation of differences between the actual and nominal volumes of the reference chamber 6212 and the interconnecting volumes 6204, 6205, 6207, 6209. The method also allows for compensation of differences between the actual and the assumed heat transfer in the different volumes of the 2-chamber FMS hardware including the control chamber 6171, reference chamber 6212 and the interconnecting volumes, 6204, 6205, 6207, 6209.

The Air Cal method combines control chamber 6171 pressure measurements with a measurement of displaced fluid to measure the volume of the control chamber 6171 at several membrane 6148 positions between touching the control chamber wall 6172 and contacting the spacers 650 on the cassette 624. These measurements of the control chamber volume (VCIso) are compared to the FMS calculated values for the control chamber volumes (VFMS i) to calculate a calibration coefficient (CCal i) for each calculated FMS volume (VFMS i). A calibration equation can then be fitted to a plot of the CCal i values versus the VFMS i values. The calibration equation may then be used to improve the accuracy of the control chamber volume calculations. The Air Cal method may be applied to both the +FMS and −FMS processes and may result in separate calibration equations for each.

Air Calibration for +FMS

Figure 113A:
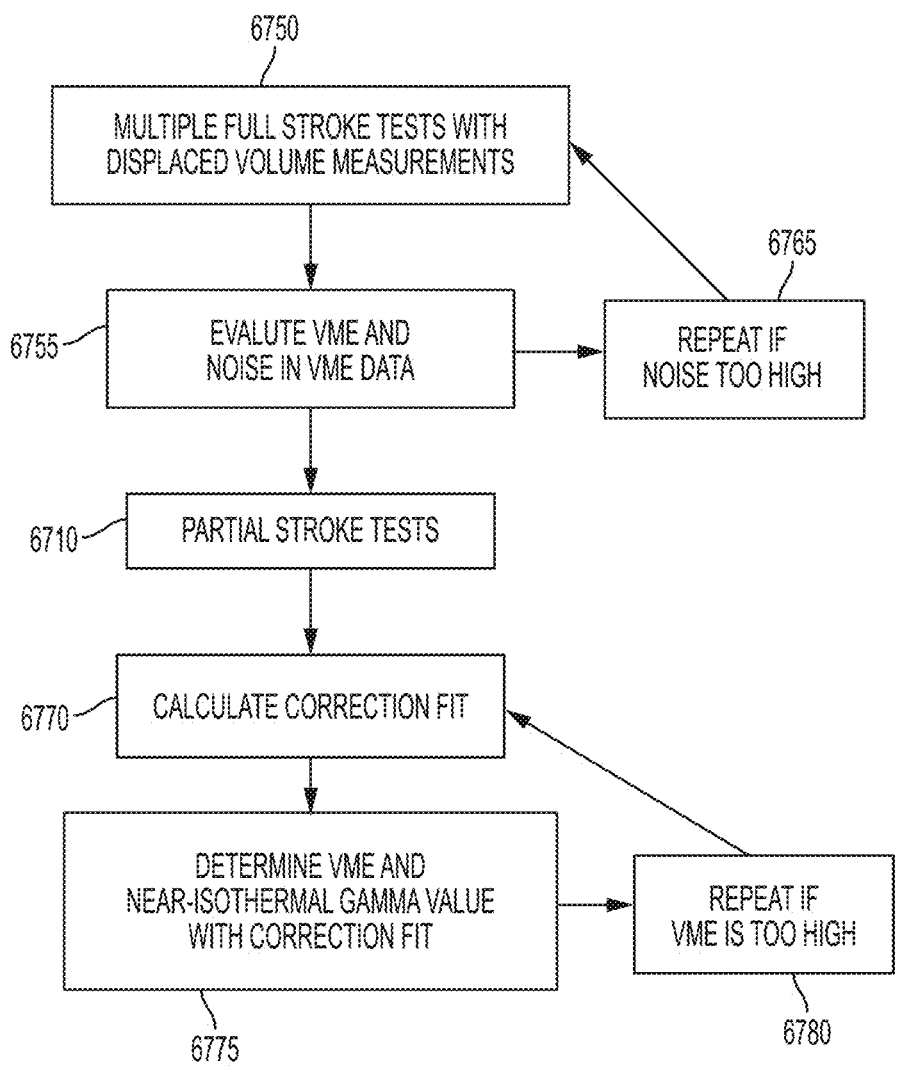
FIG. 113A is a flow chart for an FMS calibration method for a diaphragm pump.
Figure 113B:
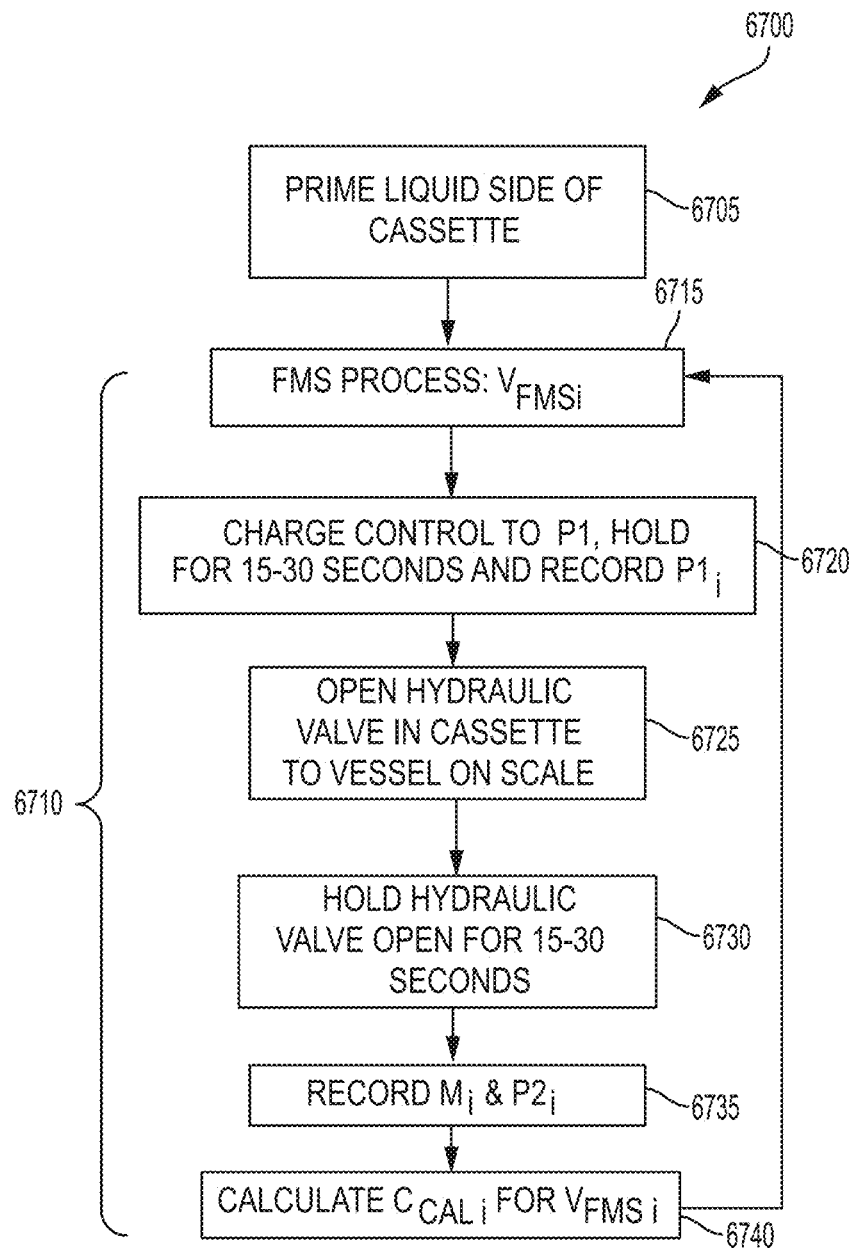
Figure 113D:
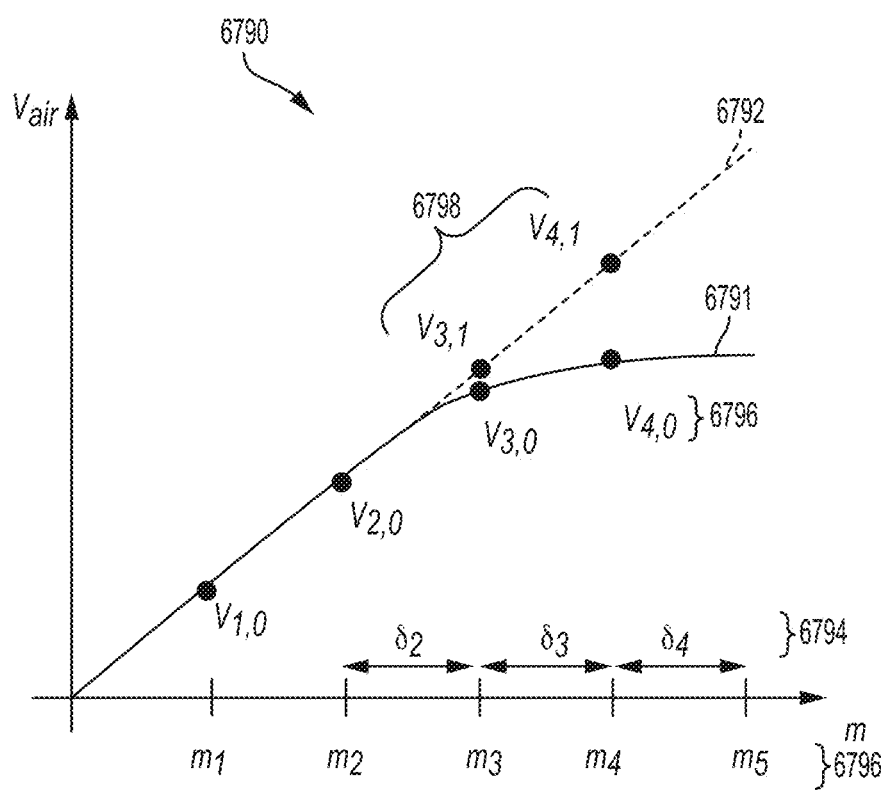

The flow chart 6700 in FIG. 113 describes an example of the Air Cal method. The hardware setup for the Air Cal includes a pneumatically driven pump that is primed with liquid and the outlet plumbed to a mass scale (labeled liquid outlet 6191 in FIG. 105) or graduated cylinder. The hardware setup also includes 2-chamber FMS hardware such as a control volume or chamber 6171, pressure sensors 6222, 6224, a number of valves 6214, 6220 and a reference volume or chamber 6212. A controller 61100 to command the pneumatic valves 6214, 6220, record the pressures from the pressure sensors 6222, 6224 and perform the 2-chamber FMS procedure and calculations is also included.

One example of the hardware setup is the combination of the cassette 24 and the APD cycler 14 in which it is installed shown in FIG. 10. In this example, the output of the cassette 24 would be plumbed to a mass scale, graduated cylinder, or other fluid measuring apparatus.

Referring back to FIG. 113 and the hardware references in FIG. 105, the first step, 6705, primes the pump or cassette 624 and output lines with liquid. The prime also fills the pump chamber 6181 with fluid.

As indicated by the bracket for cycle 6710, the procedure cycles through steps 6715 through 6740 several times during the Air Cal method. The first step of Air Cal cycle 6710 completes a +FMS process 6715 that produces a provisional measurement of the control chamber volume (VFMS i) for i=1. The Air Cal procedure applies equally to other volume measurement techniques which may alternatively be used step 6715. In step 6720, the pressure in the control chamber 6171 is increased to approximately P1 by controlling first valve 6220 and holding the gas for a period of time to allow the gas to come into thermal equilibrium with the chamber walls 6172, and the gasket 6148. In one example, the pressure is held at P1 for 15 to 30 seconds. In another example, the pressure is raised to P1, the pneumatic valve 6220 is closed and the gas in the control chamber 6171 comes to thermal equilibrium with the walls 6172, 6148. The control chamber 6171 is isolated by closing valves 6220 and 6214. The pressure at the end of step 6720 is recorded at P1$i$.

In step 6725, a hydraulic valve 6190 in cassette 624 is released or opened, which allows the pressure in the control chamber 6171 to push fluid through hydraulic valve 6190 and onto the mass scale (labeled liquid outlet 6191 in FIG. 105). In step 6730 the hydraulic valve 6190 is held open long enough for the gas or air in the control chamber 6171 to reach pressure equilibrium with liquid on the pump side 6181 (which happens quickly) and to come to thermal equilibrium with the control chamber walls 6172, 6148 (which may take several seconds). In one example, the hydraulic valve 6190 is held open for 15 to 30 seconds. In step 6735, the pressure in the control chamber 6171 is recorded at P2$i$ and the change in the mass scale is recorded at M$_i$. The hydraulic valve 6190 is then closed.

In step 6740, the calibration coefficient (CCal) is calculated from the first and second pressures (P1$i$, P2$i$) and the displaced liquid mass (M$_i$):

$$C_{Cal\,i} = \frac{V_{CIso\,i}}{V_{FMS\,i}} \tag{35}$$

where $V_{CIso\,i}$ is the isothermal determined volume of the control chamber at the $i^{th}$ position:

$$V_{CIso\,i} = M_i * \rho \frac{P_{2i}/P_{1i}}{1 - P_{2i}/P_{1i}} \tag{36}$$

where $\rho$ is the density of the liquid in the cassette 624 and where $V_{FMS\,i}$ is calculated per eqns (17), (18), (19) for a +FMS process.

Cycle 6710 may be repeated multiple times until the membrane 6148 reaches the far side of the pump volume or chamber 6181 and contacts the spacers 650. In step 6745, an equation for the calibration coefficient as a function of the FMS determined volume CCal(VFMS) is fit to the data. The output of the FMS calculations for the volume of the control chamber 6171 described in the previous sections can now be corrected to obtain a more accurate measure of the control chamber 6171 volume for all possible volumes:

$$V_{CC} = V_{FMS} \cdot C_{cal}(V_{FMS}) \tag{37}$$

Air Calibration for −FMS

A calibration coefficient can also be obtained for the −FMS process by the Air Cal procedure described in FIG. 113. In the −FMS Air Cal method, the pump chamber 6181 and the fluid line to the scale (e.g. liquid outlet 6191) are primed (step 6705) and the container on the scale is partial filled with liquid. A −FMS process is completed in step 6715 resulting in a −FMS measurement of the control chamber 6171 volume (VFMS i) using and eqns (30), (31), (32). In step 6720, the control chamber 6171 pressure is charged to a pressure P1 that is well below the ambient pressure. In step 6725, the low pressure in the control chamber 6171 draws fluid into the pump chamber 6181 and out of the container on the mass scale. Steps 6730 through 6745 are the same as described above for the +FMS Air Cal procedure. The resulting equation for the calibration coefficient as a function of the −FMS calculated volume CCal(VFMS) may be applied to −FMS results.

Improved Air Calibration

The accuracy of the $V_{CISO\,i}$ values may be further increased by considering the $V_{CISO\,i-1}$ and $V_{CISO\,i+i}$ values. The procedure described in FIG. 113, determines the control chamber 6171 volumes sequentially, which may cause their values to be related. Thus value of $V_{CISO\,i}$ may be expected to smoothly change from the ith−1 to the $i^{th}$ to the ith+1 position and so on. This dependence on nearby results is especially useful at the maximum and minimum values, which are harder to accurately measure due to the small volume of liquid moved by the pumps. The value of any control chamber volume (VCIso i) can be expressed by two other independent measurements including the previous control chamber volume ($V_{CIso\,i-1}$) plus the displaced liquid volume, the following control chamber volume ($V_{CIso\,i+1}$) minus the displaced liquid volume:

$$V_{CIso\,i} = V_{CIso\,i-1} + \rho \cdot m_{i-1} = V_{CIso\,i} = V_{CIso\,i+1} - \rho \cdot m_{i+1}$$

Thus the values of VCIso can be improved by averaging them with the adjoining values and the displaced volumes ($\rho \cdot m_{i-1}$):

$$V_{CIso\ i,1} = \tfrac{1}{3}(V_{CIso\ i-1} + \rho \cdot m_{i-1} + V_{CIso\ i} + V_{CIso\ i+1} - \rho \cdot m_{i+1}) \quad (38)$$

The resulting averaged values $V_{CIso\ i,1}$ can be averaged again by feeding $V_{CIso\ i,1}$ into equation (38) on the right side to produce $V_{CIso\ i,2}$. This iterative averaging process can be continued until the values of $V_{CIso\ i}$ stop changing or converge to a value.

The process is a little different for the first and last volume, as there are values on only one side. The equation to average the first $V_{CIso\ 1,1}$ and last $V_{CIso\ N,1}$ volumes are:

$$V_{CIso\ 1,1} = \tfrac{1}{2}(V_{CIso\ 1} + V_{CIso\ 2} - \rho \cdot m_2) \quad (39)$$

$$V_{CIso\ N,1} = \tfrac{1}{2}(V_{CIso\ N} + V_{CIso\ N-1} - \rho \cdot m_{N-1}) \quad (40)$$

Again, the resulting averaged values $V_{CIso\ 1,1}$ and $V_{CIso\ N,1}$ can be fed into the right hand side of equations (39) (40) to calculate $V_{CIso\ 1,2}$ and $V_{CIso\ N,2}$. This iterative averaging process can be continued until the values of $V_{CIso\ 1}$ and $V_{CIso\ N}$ stop changing or converge to a value. In cases, where the initial values of $V_{CIso\ 1}$ and $V_{CIso\ N}$ are questionable or known to be be unreliable, the initial values of $V_{CIso\ 1,2}$ and $V_{CIso\ N,2}$ can be set based on their more reliable neighbor values:

$$V_{CIso\ 1,1} = (V_{CIso\ 2} - \rho \cdot m_2)$$

$$V_{CIso\ N,1} = (V_{CIso\ N-1} - \rho \cdot m_{N-1})$$

Then subsequent averaging for $V_{CIso\ 1,2}$ and $V_{CIso\ N,2}$ can proceed as above.

Substantially Instantaneous or Continuous Flow Rate and Stroke Displacement Estimation In some embodiments, the flow rate to or from a pump chamber of a diaphragm pump, and/or the stroke displacement of a pump chamber (i.e. the extent to which the diaphragm has traversed the pump chamber) may be estimated while a pumping stroke is occurring. This may be accomplished either during a fluid delivery stroke, or a fluid filling stroke of the diaphragm pump. These estimates may be available during the progression of a pump stroke once sufficient data is collected for controller analysis, the controller then being able to act on continuously updated pressure information to calculate a cumulative volume of fluid moved into or out of the pumping chamber. Such real-time information may aid in an early determination of an end of stroke, may reduce the number of partial strokes performed, may permit more accurate delivery of small volumes or increments of fluid, may more efficiently deliver a precise target fluid volume, and may provide for earlier detection of occlusions and other reduced flow conditions, as well aid in priming of a fluid line, etc. This information may also help to increase fluid throughput through a pumping cassette.

Flow rate and stroke displacement or stroke progress estimation during a pump stroke may be accomplished by monitoring pressure decay in a control chamber while a pump stroke is in progress. Data produced from monitoring the rate of pressure decay may be used by a controller to determine fluid flow rate through a pumping chamber. Since pressure decay during a pump stroke is indicative of a change in volume of the control chamber as the pumping chamber fills with or empties of fluid, monitoring this decay over the course of a pump stroke may allow a controller to estimate stroke displacement as it occurs.

In embodiments in which an on/off, binary, or "bang-bang" pressure controller is used, the pressure controller may need to repeatedly actuate a valve to connect and disconnect a control chamber to a pressure reservoir in order to maintain a desired pressure during pumping. For example, as fluid is pumped out of a pumping chamber during a delivery stroke, the volume of the associated control chamber will increase. This will in turn cause a decay in the pressure of the control chamber. The process or algorithm can be used either with the application of negative pressure to fill the pumping chamber or with the application of positive pressure to evacuate fluid from the pumping chamber. The term 'pressure decay' as used herein is meant to refer to a decay in the absolute value of the actual pressure being measured (i.e., a decrease toward ambient pressure in an applied positive pressure, or an increase toward ambient pressure in an applied negative pressure). Once the pressure in the control chamber falls out of an allowed pressure range, the pressure controller may regulate the control chamber pressure by opening a valve to a pressure reservoir. The allowed pressure range may be within a range of a pressure set point. This pressure regulation or maintenance may involve connecting the chamber to a suitable pressure source for a period of time sufficient to bring the control chamber pressure approximately to a desired value and/or back within the allowed range. The pressure will again decay as more fluid is delivered to or from the pumping chamber and re-pressurization will again be needed. This process will continue until the end of the stroke is reached.

The repeated re-pressurization will generate a pressure regulation waveform that appears substantially saw tooth in nature. An example plot showing a pressure regulation waveform as described above is depicted in FIG. 114. As shown, the waveform oscillates between a lower pressure threshold 2312 and an upper pressure threshold 2310. The pressure decays (see data points 2302-2304) as the stroke progresses, fluid moves out of the pumping chamber, and the volume of the control chamber changes. In the example plot in FIG. 114, the control chamber volume is expanding as fluid is pumped out of the pumping chamber of the diaphragm pump to a destination. An end-of-stroke is indicated when the pressure decay levels off 2305, at which point an FMS volume determination can be conducted by fixing the chamber volume (i.e., closing inlet and outlet fluid valves to the pumping chamber), and equalizing 2332 the chamber pressure with the pressure of a known reference volume.

Each pressure decay may be monitored such that the volume of the control chamber can be approximately known during the course of a pump stroke. This information may allow a determination of the amount of pump stroke displacement that has occurred when compared with the initial volume of the chamber. The initial volume of the pumping chamber can be determined, for example, by performing a pre-stroke FMS measurement. This method generally involves determining the volume of a closed chamber by measuring its change in pressure when brought into communication with a reference chamber of known volume and pressure. The determination involves closing fluid inlet an outlet valves of the pumping chamber to ensure a constant volume of the control chamber of the pump, and then connecting the control chamber to a reference chamber. The process may be modeled as isothermal or adiabatic, depending on the heat transfer properties and dynamics of the system. The system may also be modeled as a polytropic process to optimize measurement accuracy. Other methods of determining the initial volume of the control chamber can be used. For example, the controller may be programmed to assume that the initial control chamber volume is substantially the control volume physically measured during manufacture of the chambers of the pumping system. This assumption may be employed, for example, when the controller has computed that a preceding end-of-stroke state was fully reached.

The determination of real-time or continuous volume changes in the control and pumping chambers of a diaphragm pump during a pump stroke is substantially different from previously disclosed pressure-based volume determinations, in that a fluid inlet or outlet valve remains open to allow fluid to continue to flow into or out of the pumping chamber. Additionally a reference chamber of known volume and pressure is unnecessary. To distinguish this process from a control chamber/reference chamber equalization process (a 'two-chamber' FMS), the continuous measurement process here described can more aptly be considered a 'one-chamber' FMS. Although the pumping chamber remains open to an inlet or outlet fluid line, the associated control chamber remains a closed system, which allows for determination of a second volume once an initial volume is known. Pressure data is repeatedly sampled while the control volume is isolated from a gas source or sink (i.e., no change in mass in the control volume). Under these circumstances, controller calculations based on an algorithm using a polytropic process may provide more accurate results. The method is only now feasible, because electronic processors capable of rapid data acquisition and computation are now available. For example, a high speed application specific integrated circuit can be employed, or preferably an FPGA device can now be dedicated to this task, relieving a main system processor from having to share its computing resources and reduce its efficiency. A sufficiently robust FPGA in some embodiments can be reconfigurable or reprogrammable for the blocks of time needed to perform on-the-fly or real time volume measurements during a pump stroke, while maintaining some resources for other tasks. Real time or on-the-fly volume measurements may be accomplished by finding the volume of the control chamber at two points between a closure and an opening of the supply valve used to regulate the control or pumping chamber pressure. The volume difference between the two points in time may allow the controller to estimate a relatively real-time flow rate.

As shown in FIG. 114, a high-speed controller can acquire a series of pressure data points 2302, 2303, 2304, each of which allows the controller to successively compute a chamber volume change associated with each point. Assuming that the controller has determined a starting volume of the control chamber, a change in volume at a subsequent pressure decay point can be computed. An ending volume associated with point 2302, for example, may then be used as a starting volume at point 2303 in order to calculate the ending volume at point 2303, and so on.

Figure 115:
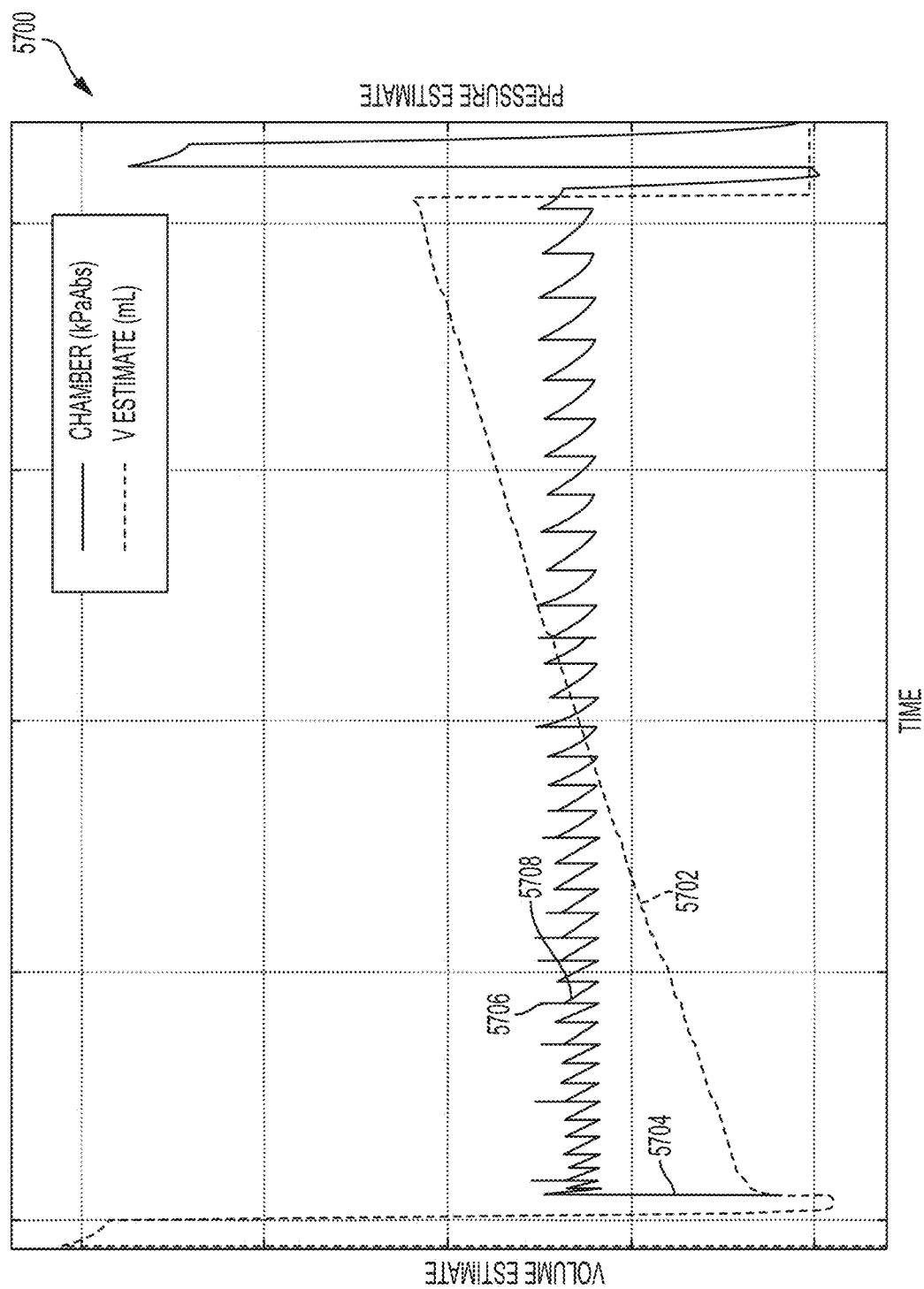

FIG. 115 depicts an example graph 5700 with traces representative of pressure in a control chamber and estimated pumped volume from that chamber. The volume estimate trace 5702 is created by sampling pressure data points on each pressure decay 5708 of the pressure trace 5704. As described above, the controller may use the pressure difference between two pressure data points to determine a volume displaced in an associated pumping chamber. The controller may then calculate a cumulative volume of fluid moved in or out of the pumping chamber. As more and more pressure decay 5708 and re-pressurization events 5706 occur, the cumulative volume indicated by the volume estimate trace 5704 increases. Since the processor is capable or rapidly sampling and analyzing the data points, the volume estimate is able to be updated continuously as shown in the example graph 5700. As a result, the volume delivered to or from the pumping chamber can be accurately estimated while the stroke is in progress. This estimate is generated without halting the pumping of fluid and without the use of a reference chamber.

Any number of suitable mathematical methods may be used to model the pressure decay of the control (or pumping) chamber throughout a pump stroke. But it should be understood that a pressure decay curve at one point in the pump stroke may appear quite similar to a pressure decay curve at another point during the pump stroke, yet represent a different amount of volume change in the pumping chamber. Programming a controller to analyze the pressure decay curves during a pump stroke by using a polytropic model may help to resolve these potential differences in volume change.

One-chamber FMS—computing real-time or continuous volume changes in the control or pumping chamber using a polytropic model—may be feasible in systems using either binary or variable orifice valves connecting the pump control chamber to a pressure reservoir (positive or negative pressure). Pressure data can be acquired and analyzed during the time that either type of valve is closed (although this time period is likely much shorter when a vari-valve is used). In either case, the pressure decay during fluid egress (or pressure rise during fluid ingress) can be sampled, the volume change computed, and the process repeated to provide real-time volume change data. In the following description, a polytropic modeling process is applied to a system using binary valves in regulating the pressure in the control or pump chamber. The description applies to other types of valves and pressure regulation protocols.

In general, a one-chamber FMS protocol can be applied to any gas-driven (e.g., air-driven) diaphragm pump having a fluid pumping chamber separated from a control chamber by a flexible diaphragm. During a pump stroke, as fluid either enters or leaves the pumping chamber, the control chamber will be a closed system for at least part of the time as the the controller regulates the pressure delivered to the control chamber and diaphragm. A valve connecting the control chamber to a pressure source will close once the pressure in the control chamber reaches or exceeds a high threshold value. The valve will open again (either fully or partially) as the pressure decays from fluid movement into or out of the pumping chamber, creating alternating periods during the pump stroke in which the control chamber is closed to air ingress or egress. During these phases in which the control chamber is isolated, a change in pressure reflects a change in the volume of the control chamber—and therefore the pumping chamber. An initial volume at the beginning of the pressure decay period must be known from a prior measurement, or assumed. A terminal volume can then be calculated from a measured pressure change between the initial and terminal volume. The terminal volume can then be used as the initial volume for the next calculation as the pressure decays further during the control chamber isolation phase. In this way, a controller can rapidly acquire pressure readings during the pressure decay phases of the pump stroke to compute in a nearly continuous manner the change in volume of the pumping chamber, and can thus estimate an instantaneous fluid flow rate into or out of the pump. The relationship between pressure and volume of a gas in a closed system is governed by a standard equation describing the behavior of ideal gases, and it may be best to assume a polytropic process in the calculation, in which a polytropic coefficient can vary between 1 and a value representing the heat capacity ratio of the gas used in the pump (adiabatic coefficient for that gas).

A polytropic process is governed by the equation:

$$PV^n = \text{constant}$$

where P=pressure, V=volume, and the polytropic exponent, "n", is a number between 1 and γ (γ being 1.4, the coefficient describing an adiabatic system for most gases including air). Since the right hand side of the equation is a constant, two consecutive points in time can be compared. To compare two consecutive points in time, the following equation may be employed:

$$P_t V_t^n = P_{t-1} V_{t-1}^n$$

where $P_t$ is the pressure at time t, $V_t$ is the volume at time t, $P_{t-1}$ is the pressure at time t−1, and $V_{t-1}$ is the volume at time t−1.

Rearranging the equation to solve for $V_t$ and simplifying yields the following equations:

$$V_t^n = \frac{P_{t-1} V_{t-1}^n}{P_t}$$

$$V_t = \sqrt[n]{\frac{P_{t-1} V_{t-1}^n}{P_t}}$$

$$V_t = \frac{P_{t-1}^{1/n} \times V_{t-1}^{n/n}}{P_{t-1}^{1/n}}$$

$$V_t = V_{t-1} \left(\frac{P_{t-1}}{P_t}\right)^{1/n}$$

As shown in the above equations, the current volume of the chamber, $V_t$, can be determined if the volume at the end of the preceding time interval has been determined. This volume may then be used to determine stroke displacement if desired. Additionally, by tracking the amount of time between $V_t$ and $V_{t-1}$, it is possible to determine a rate of flow over that time span. An average flow rate over a portion of the pump stroke may be determined by averaging multiple flow rate determinations using successively paired pressure data values. Additionally, knowing the starting volume and nominal ending volume of the control chamber may provide an independent determination of the amount of time needed to complete the pump stroke. In an example, a data sample set may be acquired every 10 ms and may include 20 data samples. In such embodiments, the amount of time between $V_t$ and $V_{t-1}$ will be 0.5 ms. The preferred data sampling rate will depend, among other things, on the expected duration of a pump stroke, the rate of pressure decay observed by the controller, the degree of measurement error or noise associated with the pressure signal, and the sampling speed and processing capability of the controller (e.g., whether a dedicated FPGA is being used).

In some embodiments, the controller may compute the volume change at each data point sampled. This has the advantage of minimizing the effects of heat transfer between measurement points. On the other hand, the signal noise during measurement may yield a less accurate computation for the change in actual volume. In another embodiment, the processor may sample a set of pressure data points within a time period in which heat transfer is presumed to be at an acceptable level, and the pressure data set may be filtered or smoothed by the processor before an initial smoothed pressure measurement and a final smoothed pressure measurement is used to compute the final volume at the end of the time period. The effects of signal noise on the accuracy of the measurement can thus be reduced.

There are time periods during a pumping stroke in which pressure data acquisition is either not possible or inadvisable. For example, when the pressure supply valve is open and the pump chamber pressure is spiking, fluid flow into or out of the pumping chamber continues. As a first approximation, it may be assumed that the fluid flow rate during this short period of time remains approximately unchanged from the flow rate measured shortly before the opening of the pressure supply valve. The volume change estimated in this manner may then be added to the volume representing the last measured pressure data point to arrive at the initial volume for the next measured pressure data point. Additionally, there may be prescribed points of time during a stroke at which pressure data points may be ignored. For example, depending on the data sampling rate, pressure information immediately preceding a pressure rise during a pressurization event may be inaccurate. Some aliasing may also be present for data points directly following a pressurization event. In an embodiment, data points collected by the controller within a predetermined period of time before and after a pressurization event may be discarded or ignored to further improve the accuracy of the flow determination process.

In embodiments which use an FPGA for pressure data acquisition and analysis, issues stemming from an inferior sampling rate may present less of a concern. In certain embodiments, an FPGA may also have the resource capacity to control the relevant valves in the pumping system. By controlling the pressure supply valves, the FPGA may be able to schedule the sampling of pressure data more efficiently. Synchronization of events may be improved, and aliasing problems with data sampling may be reduced.

Certain assumptions may also be made at the beginning of a pump stroke. A small amount of fluid movement into or out of the pumping chamber is likely to be present prior to the first pressure decay event. Although inertial forces may limit the initial fluid flow, the controller can be programmed to estimate an initial fluid flow and volume change prior to the first data sampling point during pressure decay. Such an assumption may allow for the estimation of changes in chamber volume while pressure decay information at the beginning of the stroke is not available. The amount of fluid assumed to have been moved at the start of a stroke may depend on the pumping pressure applied to the control and pumping chambers. The controller may be programmed to include a pre-determined volume of fluid movement based on the value of the applied pressure. Alternatively, after number of data points have been sampled to determine an estimated flow rate, the flow rate may be used to extrapolate for the volume moved while the data was unavailable. It may, for example, be assumed that the flow rate over that period of time was substantially equal to the currently estimated flow rate. This assumption that the flow rate is constant may then be used to determine an estimate of the volume moved over the period which data was unavailable.

Figure 116:
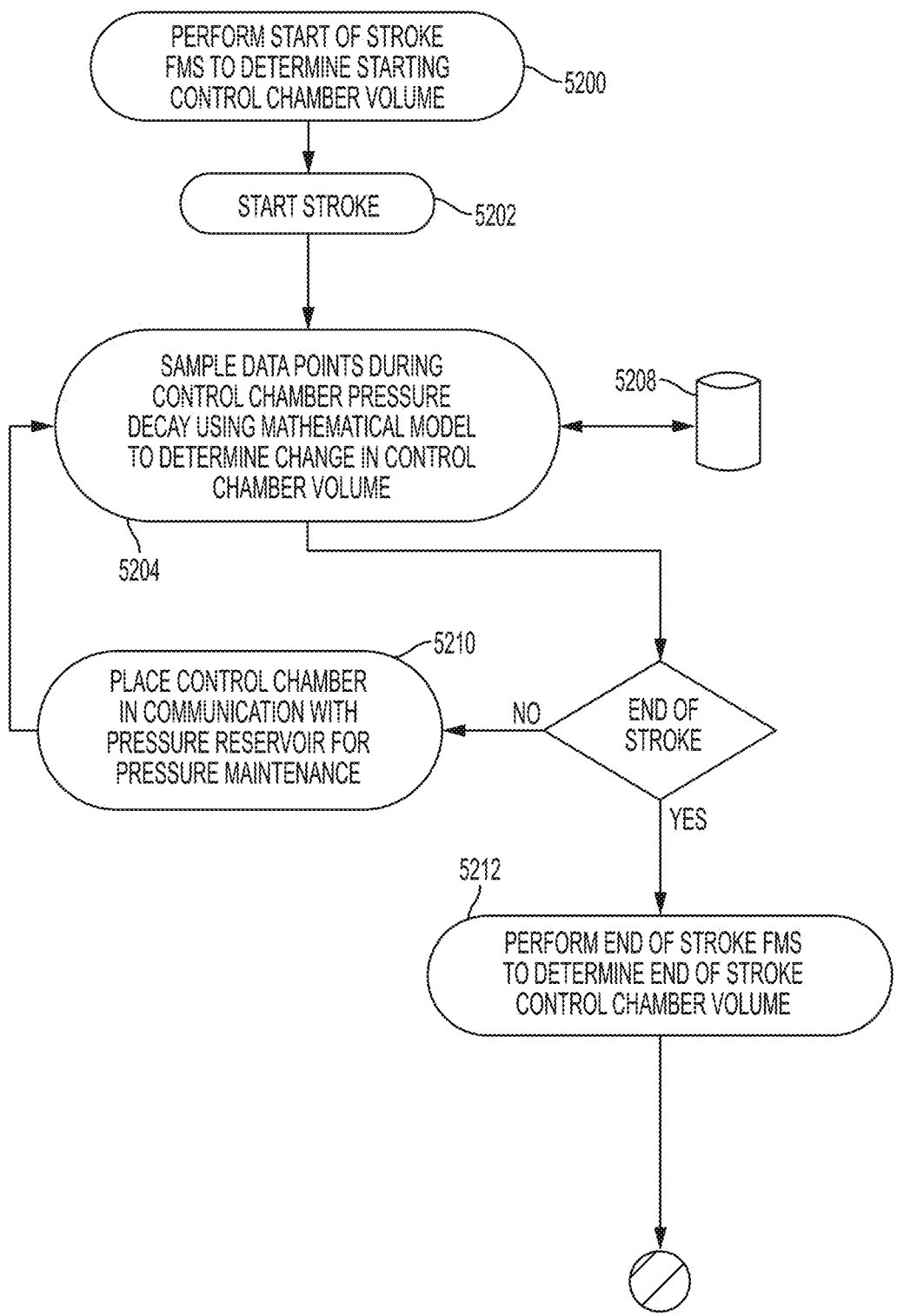

FIG. 116 shows a flowchart detailing an example of a number of steps which may be used to estimate control chamber volume changes during a pump stroke. As shown, the flowchart begins in step 5200, where a pre-stroke FMS measurement is made, which in an embodiment includes freezing the volume of the pumping and control chambers, measuring control chamber pressures and equalizing pressures with a reference volume chamber. This measurement may provide a starting control chamber volume measurement. Alternatively, the starting control chamber volume may be assumed by the controller to be a fixed and known quantity if the controller has calculated that the preceding end-of-stroke of the pumping chamber has been fully completed. A pump stroke may then be started in step 5202. In step 5204, the control chamber pressure decay (or the decay of the absolute value of the pressure) may be monitored as the stroke displaces and causes fluid to move into or out of the pumping chamber. In some specific embodiments, multiple data points may be sampled along each decay curve and the mathematical model described above may be used to determine changes in control chamber volume as the pump stroke proceeds. Data points and volume information may be saved in memory 5208.

Assuming the end of stroke is not detected, once the pressure in the control chamber falls outside of a predetermined range (e.g. falls below a predetermined pressure value), step 5210 may be performed. In step 5210, the pressure controller may perform pressure maintenance on the control chamber (i.e. re-pressurize the control chamber) to bring the control chamber pressure back to approximately a preprogrammed desired value (which may, for example, be at or near a high pressure bound of the range). After completing step 5210, step 5204 may be repeated with the collected data again being saved in memory 5208. This may continue until an end of stroke condition is detected. (End of stroke detection is described elsewhere).

In the event an end of stroke condition is detected, a post-stroke FMS measurement (determining volume by measuring control gas pressure) may be taken in step 5212. This measurement may be compared to the measurement from step 5200 to check and/or more precisely determine the total volume moved during the stroke. Additionally, this post-stroke FMS measurement may serve as the starting control chamber volume measurement for the next stroke performed by that pump chamber.

Other means of determining that the pump has fully completed its pump stroke may be used. If so, the result of that determination may then be used to initialize the controller to the control chamber's starting volume for the next pump stroke. Methods other than volume determination by pressure measurement may be used to assess the final volume of the control and pumping chambers, whether or not a pump stroke has been fully completed. However the final chamber volume is determined, that value may then be used to initialize the controller as the chamber's starting volume for the next pump stroke.

The polytropic coefficient, "n", of the above described mathematical model may be initialized at a specific value. For example, in some embodiments, the coefficient may be set to 1.4 or γ (representing an adiabatic process for air). The initialized value may differ depending on the embodiment, the type of control fluid, or the intended flow rate. For example, embodiments with a relatively fast flow rate may be more appropriately modeled as an adiabatic system while embodiments with a slower flow rate may be more appropriately modeled as an isothermal system.

The coefficient may then be adjusted to a value yielding greater agreement between the computed real-time flow rate and the measured final volume change at end-of-stroke over a plurality of pump strokes. This may be done by using feedback collected over one or more pump strokes using any suitable software algorithm, or using a controller such as a proportional controller or PID controller. Feedback may be in the form of a calculated delivered volume determined by a comparison of the pre-stroke and post-stroke FMS measurement. The final FMS measurement volume and estimated real-time volume change determined using a current value for "n" may be compared. If the volumes differ by more than a predetermined amount the value for "n" may be adjusted. The new coefficient value may then be saved and used as the initial value for the next pump stroke. In an example, the coefficient "n" may be adjusted using data collected over several pump strokes. For example, values for "n" that would have yielded the final (e.g. FMS measured) volume moved for a number of strokes may be averaged together. In the absence of significant changes in ambient conditions (e.g., fluid or environmental temperature changes), an averaging or other numerical filtering procedure may decrease the time needed to produce accurate flow rate and stroke displacement measurements, as it may not be necessary to have the controller perform repeated comparisons of pre-stroke and post-stroke FMS measurements.

Figure 117:
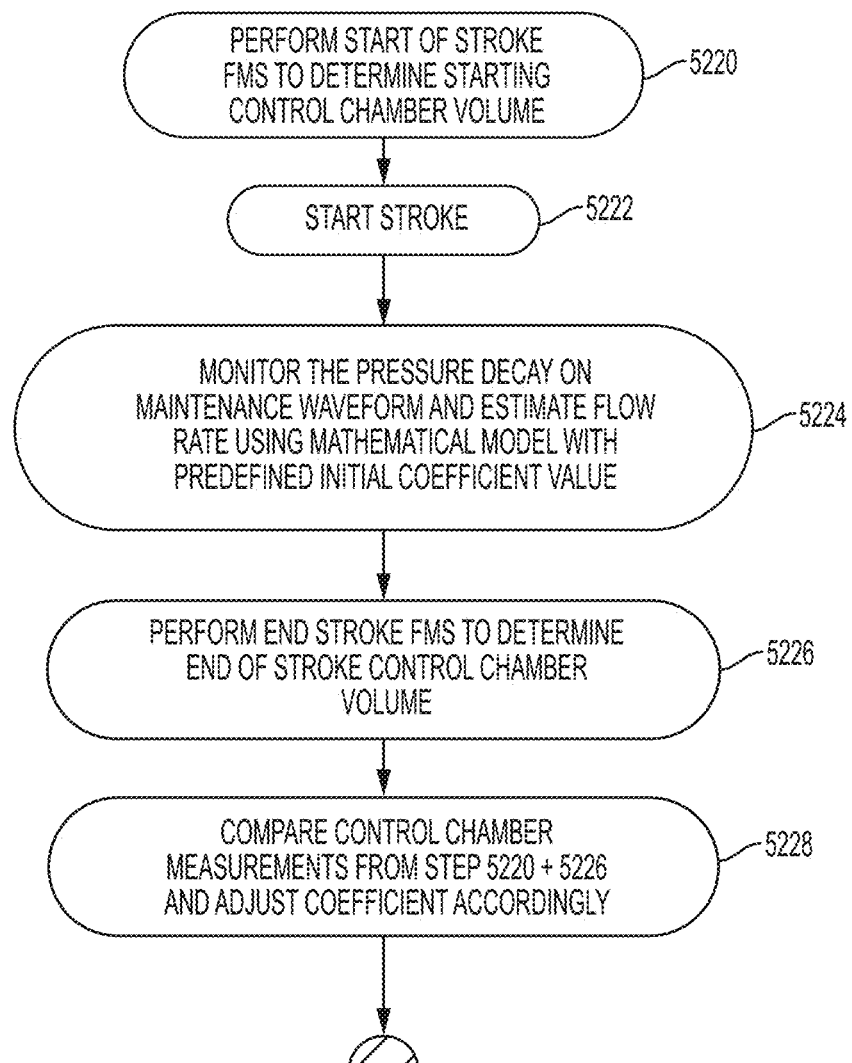

FIG. 117 shows a flowchart outlining an example of a number of steps to adjust the coefficient of the mathematical model as described above. As shown, in step 5220, a pre-stroke FMS measurement may be taken to determine a starting volume for a control chamber. The stroke may then begin in step 5222. In step 5224, the pressure decay on the pressure regulation waveform may be monitored. Volume change of the control chamber may be determined using the example mathematical pressure-volume model with a pre-defined initial exponent coefficient value. Once the stroke has completed, in step 5226, a post-stroke FMS measurement may be made to determine the end of stroke control chamber volume. In step 5228, the volume measurements from step 5220 and 5226 may be compared to determine the total control chamber volume change over the stroke. The coefficient may be adjusted based on this comparison to align the two final values if necessary. For example, the coefficient may be adjusted to the value which would have yielded the volume change found by using the FMS measurements.

As mentioned above, a flow rate estimation as a stroke is progressing may be used for a number of purposes including, but not limited to, detection of occlusions, detection of low flow or no flow conditions, detection of end of stroke, detection of fluid line prime state, etc. The flow rate estimation may be monitored to determine if it is likely that an end of stroke condition is present. For example, if the real-time flow rate drops below a predefined threshold (e.g. 15 mL/min), it may be an indication that a pump stroke has been fully completed (i.e. the maximum volume of fluid has been moved given the physical limitations of the pump). If the flow rate estimate drops below the predefined threshold, an FMS measurement may be performed on the chamber and the volume delivered may be verified. If the FMS measurement determines the end of stroke has been reached, the chamber may move onto the next pumping operation (or pump stroke). If an end of stroke condition has not been reached, the controller may undertake a number of actions, including, for example, attempting to resume the pump stroke. Alternatively, the detection of a reduced flow condition may be indicative of an occlusion of the fluid line, an occlusion alert or alarm may be triggered, or a fluid pushback attempt may be made to determine if an occlusion exists.

In some embodiments, the controller may be programmed with an arming routine (a software trigger) to keep it from declaring an end-of-stroke condition prematurely. This may help to avoid false triggering of an end of stroke determination. For example, a lack of cumulative pressure data at the beginning of a stroke may increase the effect of signal noise in a flow rate determination. In an example, the controller may be programmed with a trigger that is armed only after a pre-determined time period has elapsed after the initiation of the pump stroke. In some embodiments the software trigger may be the attainment of a predetermined flow rate value. Or the trigger may be armed after is the controller estimates that a predetermined volume of fluid has been moved. Requiring that the end of stroke detection trigger be armed before an end of stroke condition is detected may help to reduce the number of partial strokes performed and may help to increase throughput of fluid through a pumping cassette. To help prevent a scenario in which the arming criteria is not reached and the end of stroke is never detected, the trigger may be armed after the stroke has been in progress for a predetermined amount of time. In other embodiments, after a predetermined period of time has elapsed since the beginning of the stroke without the arming criteria being met, and end of stroke may automatically be triggered.

Figure 118:
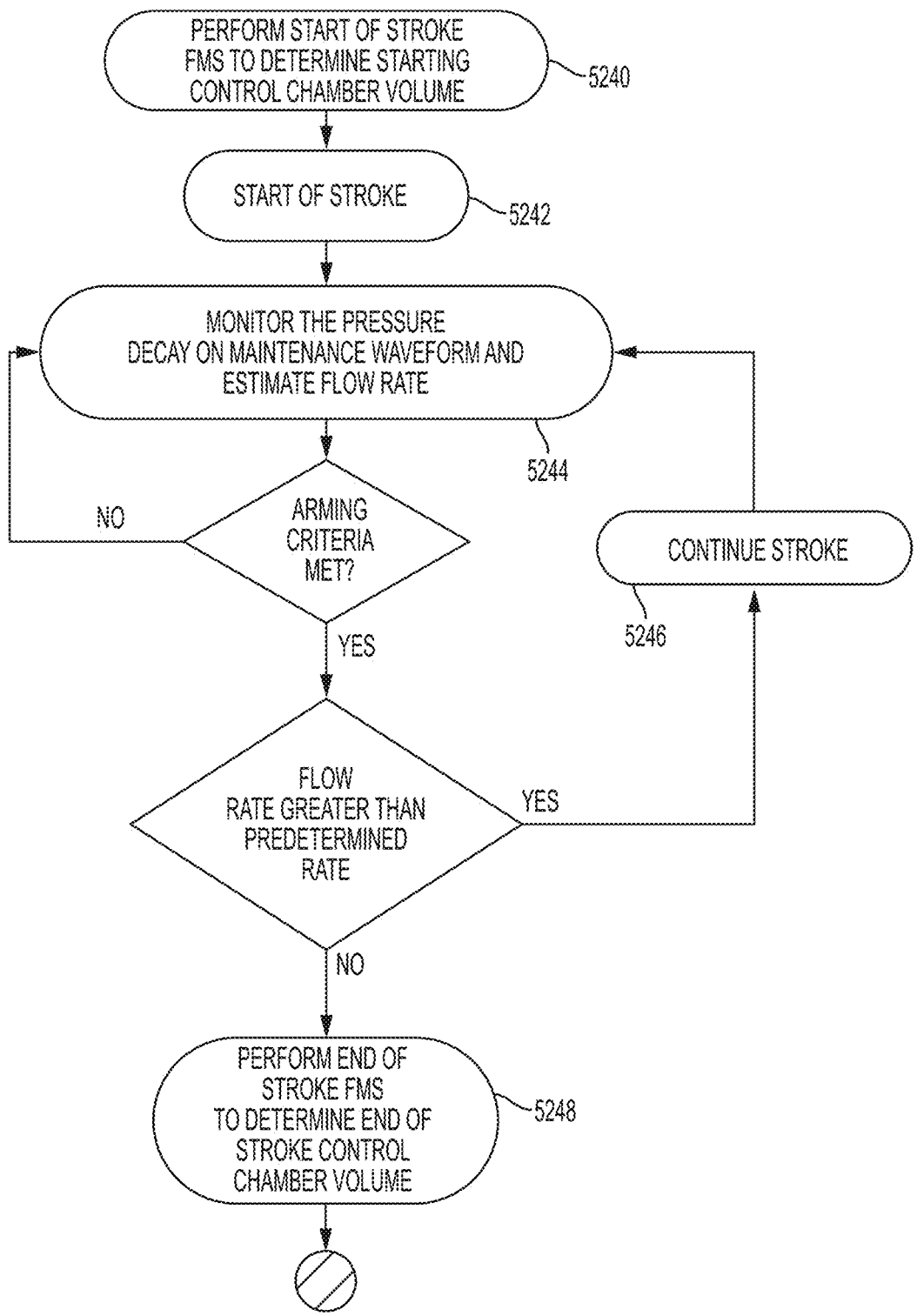

FIG. 118 shows a flowchart outlining a number of example steps to detect end of stroke based on a real-time flow rate estimation. As shown, in step 5240, a pre-stroke measurement may be performed to determine the starting volume of a control chamber. The pump stroke is then started in step 5242. As the stroke progresses, in step 5244, the pressure decay on the control chamber pressure regulation or maintenance waveform is monitored. A flow rate is estimated based on the pressure decay. When the end of stroke arming criteria is met, the controller determines whether the flow rate is above a pre-established or predetermined flow rate. If the flow rate is above the predetermined flow rate, the pump stroke continues in step 5246 and flow rate estimation continues in step 5244. In the event that the flow rate drops below the predetermined flow rate, in step 5248, the stroke may be ended and an end of stroke FMS measurement may be made to determine the control chamber volume.

In some embodiments, estimation of control chamber volume change over the progression of the stroke may be used to predict the amount of time necessary to complete the stroke. Since the starting volume as well as the nominal or projected end volume of the stroke is known and flow rate may be determined using control chamber volume change, the controller may use this information to estimate how long the entire stroke should take. Correspondingly, the controller can calculate an estimate of how much time is needed to complete the remaining portion of the stroke. Once the predicted end time of the stroke is reached, the stroke may be stopped and an FMS measurement may be made. In the event that the FMS measurement indicates the stroke was a partial stroke, a number of actions may be taken. In some embodiments, a cycler may attempt to retry the stroke. Alternatively, controller detection of a reduced flow condition may be an indication for an occlusion alert or alarm, or a pushback attempt may be made to determine if an end-of-line occlusion can be relieved.

Figure 119:
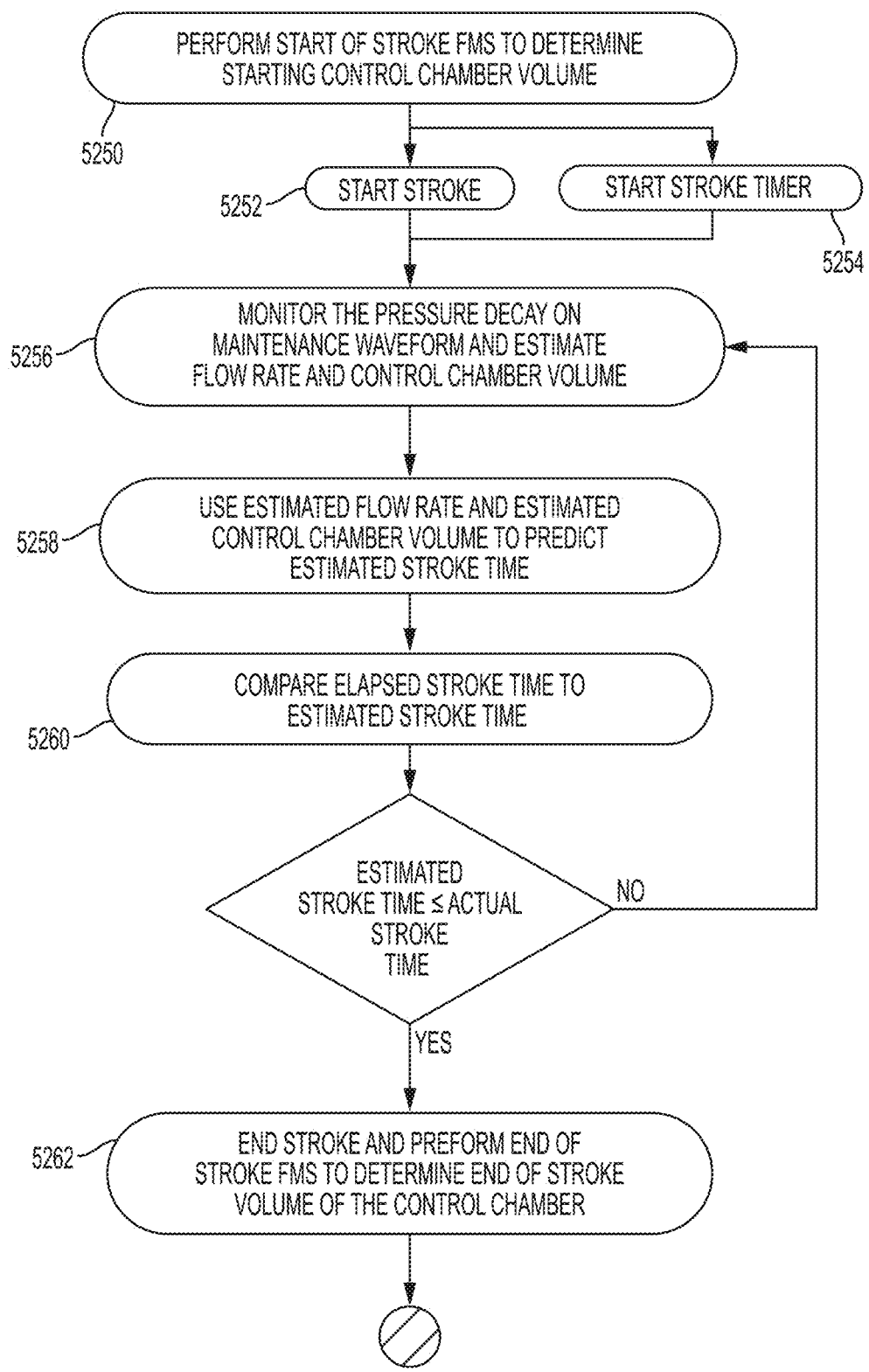

FIG. 119 shows a flowchart outlining a number of example steps which may be used to determine end of stroke by predicting time necessary to complete a stroke. As shown, in step 5250, a pre-stroke FMS measurement may be taken to determine the starting volume of a control chamber. A stroke is started in step 5252. When the stroke begins, a stroke timer can be started in step 5254. As the stroke progresses, in step 5256, the pressure decay on the pressure regulation or maintenance waveform for the control chamber is monitored. This may be used to estimate the control chamber volume and flow rate. These estimates may then be used in step 5258 to project an estimated stroke time. The estimated stroke time may be calculated by finding the difference between a current chamber volume and the projected end of stroke chamber volume. The estimated flow rate may then be used to find the amount of time required to complete the stroke. The estimated end-of-stroke time may then be compared to the elapsed stroke time in step 5260. If the estimated end-of-stroke time is longer than the elapsed stroke time, steps 5256, 5258, and 5260 may be repeated. If the estimated end-of-stroke time is less or equal to than the actual elapsed stroke time, the controller may declare an end of stroke condition. In step 5262, the stroke is ended and an FMS measurement may be taken to determine the post-stroke volume of the control chamber. In some embodiments, remaining stroke time estimations may be made until a predetermined amount of stroke time remains or a predetermined amount of stroke displacement has occurred. The controller continues the stroke until that time expires and step 5262 can then be performed.

The availability of real-time flow rate estimation offered by the exemplary mathematical model described above may allow for earlier detection of reduced flow conditions as well. Instead of having a controller wait for a stroke to finish, performing a volume measurement and comparing it to a previous measurement, the controller can be programmed to respond to a real-time flow rate that is less than an expected flow rate threshold. The controller can be programmed to stop the pump stroke at that point to perform a more precise volume measurement (e.g., via an FMS measurement) to verify the flow rate estimate. Thus, reduced flow conditions may be detected without the need to complete prolonged pumping strokes caused by the reduced flow. This may save time, reduce patient discomfort, and may help to increase overall fluid throughput of a pumping cassette. It may also allow a therapy to transition more quickly from the end of a drain phase to the fill phase of the next cycle. This increased efficiency may allow for more therapy time to be allocated to dwells. In one example, the controller may be programmed to declare a reduced flow condition when the flow rate estimate is below a threshold of 50 mL/min. In some embodiments, before a reduced flow condition is declared, the flow rate may have to remain below the threshold for a predefined period of time (e.g. 30 seconds).

Optionally, there may be a plurality of reduced flow condition classifications defined by different flow thresholds. For example, in addition to a low flow threshold (e.g. <50 mL/min) the controller may be programmed to recognize a 'no flow' threshold which is set lower than the low flow threshold (e.g. <15 mL/min).

Figure 120:
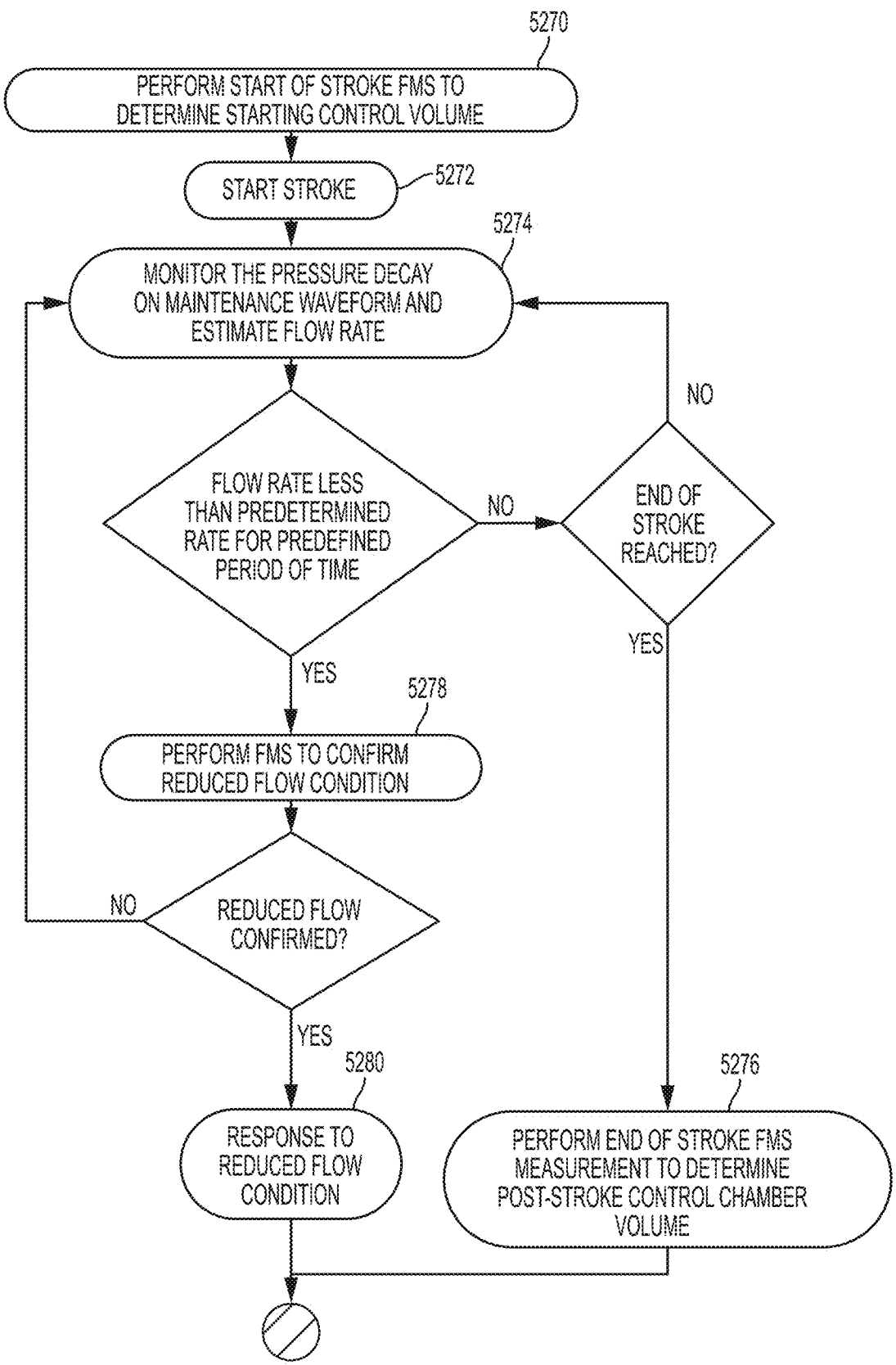

FIG. 120 shows a flowchart outlining a number of example steps which may be used to detect a reduced flow condition during a pump stroke. As shown, in step 5270 a pre-stroke FMS measurement may be taken to determine the starting volume of a control chamber. A stroke is then started in step 5272. In step 5274, the pressure decay on the pressure regulation or maintenance waveform may be monitored such that real-time control chamber volume change and flow rate may be estimated. The controller continues with the pump stroke as long as the flow rate is greater than a predetermined flow rate for a predetermined period of time. The controller continues to monitor the pressure decay waveforms as described in step 5274. If the end of stroke is reached, an end of stroke FMS measurement may be made in step 5276 to determine the end of stroke control chamber volume. If is the controller determines that the flow rate is less than the predetermined flow rate for a predetermined period of time, an FMS measurement may be made in step 5278 to confirm that a reduce flow condition exists. If the reduced flow condition is not confirmed, the stroke may continue, and the controller continues to compute flow rate based on the control chamber pressure regulation or maintenance waveform as described above in step 5274.

If the reduced flow condition is confirmed by the FMS measurement in step 5278, in step 5280 a reduced flow or occlusion notification, alert, or alarm may be sent to the user. This may be done via a user interface and may be accompanied by an audible message or tone, vibratory indication, etc. The response generated by the cycler controller may be dependent on the flow rate detected. Before indicating an occlusion is present, a pushback of fluid into the fluid reservoir (or peritoneal cavity, depending on the fluid line) may be triggered. In the event that the pushback attempt is unsuccessful, the controller may issue an occlusion alert.

In some embodiments, in the event a reduced flow condition is detected, a cycler controller may verify whether or not a target volume for a pumping operation (e.g. a drain phase) has been achieved (e.g., a completed peritoneal drain). If the target volume or more has been moved, the controller may declare that the pumping operation has been completed. In some embodiments, a device controller may require a minimum defined time period to have elapsed to ensure that the fluid reservoir (e.g, solution bag, heater bag, or a patient's peritoneum) is substantially empty.

Real-time measurement of fluid flow during a pump stroke can permit the targeting of specific fluid volume deliveries less than a full pump stroke volume, or an integer multiple of a full pump stroke volume. The controller may be programmed to end a stroke when the chamber volume change estimated through pressure measurement indicates that the target volume has been delivered or withdrawn. Upon this occurrence, the controller may initiate an FMS measurement to confirm that the target volume was actually reached. Real-time fluid flow measurement may avoid the need to perform multiple FMS measurements while repeatedly making small displacement partial strokes to avoid over-shooting the target volume. Such a targeting scheme may be particularly desirable in a pediatric application in which the amount of time spent approaching but not overshooting a target volume would otherwise take a relatively large portion of time in a pumping operation.

Figure 121:
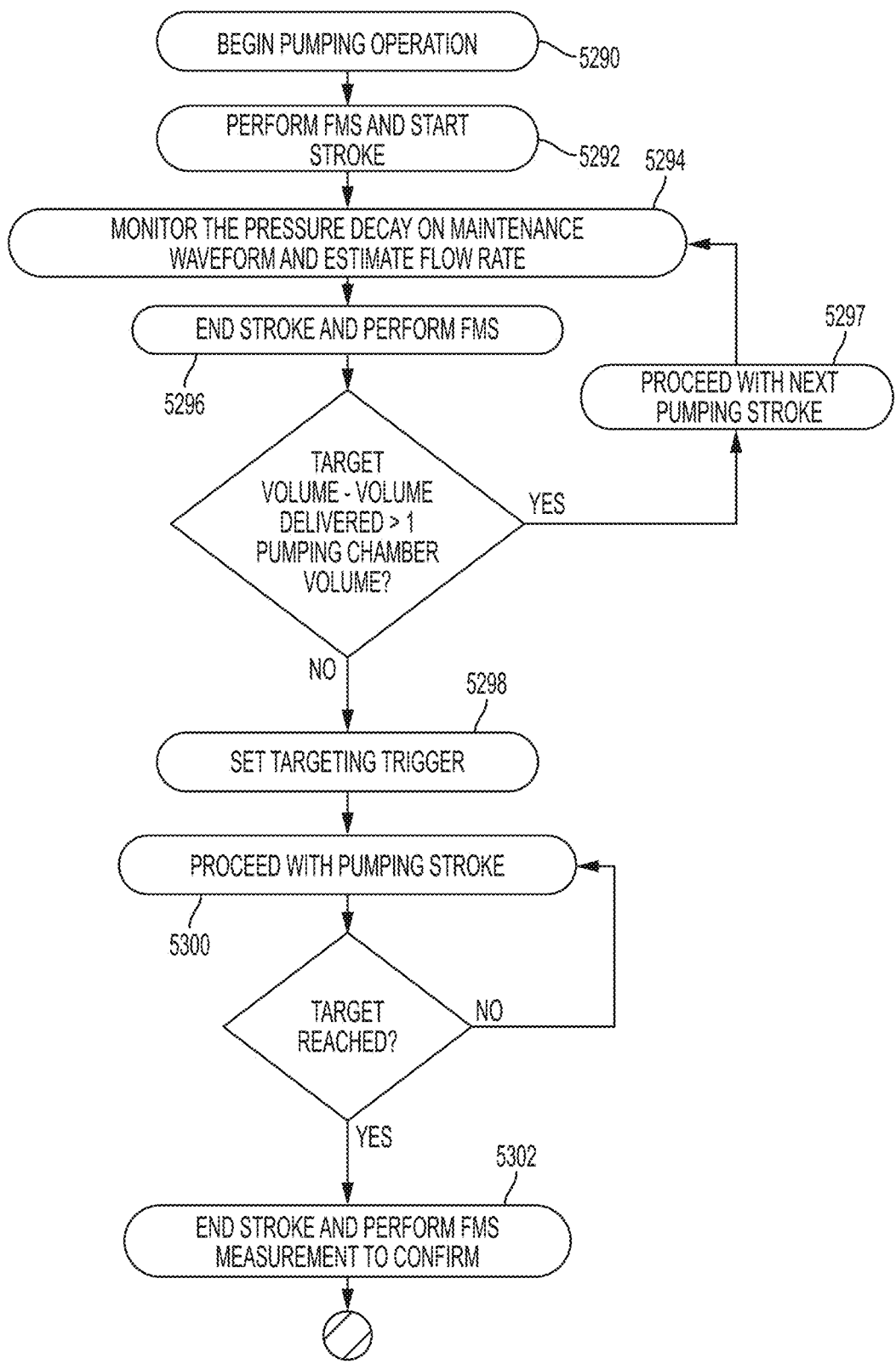

FIG. 121 shows a flowchart outlining a number of example steps that may be used to determine when a target volume of fluid has been moved. As shown, the steps make use of an estimated volume moved based on measurement of pressure decay during a stroke to end the stroke when the target volume is estimated to have been reached. A pumping operation begins at step 5290. This operation may, for example, be a fill phase for a peritoneal dialysis cycle. When the pumping operation begins, an FMS measurement may be made and a pump stroke is started as shown in step 5292. During the stroke, the pressure decay on the pressure regulation or maintenance waveform may be monitored in step 5294. This allows for an estimation of volume displacement and flow rate as the stroke progresses. The stroke may end and a post-stroke FMS measurement may be conducted in step 5296. A cycler controller tracks the computed cumulative volume to see if the difference between the target volume and the total volume of fluid delivered during the pumping operation is greater than a full pump chamber volume. If so, the controller proceeds to command the next pump stroke in step 5297. Steps 5294, 5296, and 5297 may be repeated until the difference between the target volume and total volume pumped is less than the volume of one full pump chamber. At this point, in step 5298, if the delivery of another full chamber volume would cause the target volume to be exceeded, step 5298 is performed.

In step 5298, a targeting trigger may be set as the difference between the total delivered volume for the pumping operation and the target volume for the pumping operation. The pump stroke may then proceed in step S300 until the controller calculates through pressure decay measurements that the target volume has been reached. At this point, step S302 may be performed in which the stroke is ended and an FMS measurement may be made to confirm that the target volume of fluid has been moved.

Computing an estimated flow rate from a pressure decay curve during a pump stroke may also allow the controller to close a valve or valves in a preemptive manner in order to more precisely deliver a pre-determined fluid volume. That is, the valve(s) may be closed before the target volume is delivered to account for a delay between the controller command and the valve's mechanical response. The flow which occurs during the period of time required to physically close the valve (s) may then cause the target volume to be substantially met. Specifically, the controller may estimate the amount of time required to physically to close the valve(s). In some embodiments, this estimation may be a preprogrammed value. For example, for a particular valve arrangement the response delay may be approximately 100 ms. Based on a real time computation of the flow rate, the volume of fluid moved during the valve response delay can be estimated. This amount of fluid may be subtracted from the target volume to yield a valve closure trigger volume. Once the valve closure trigger volume has been met, the cycler controller can command the valves to close.

Fluid Line Prime State Using Estimated Flow Rate and Estimated Stroke Displacement In some embodiments, in-stroke computed flow rate and estimated stroke displacement may be used to determine the prime state of a fluid line. As described above in relation to FIGS. 20-28, a patient line may include a feature (e.g. a restriction such as an orifice) which presents relatively little impedance to the flow of air, but a comparatively high degree of impedance to the flow of a dissimilar fluid, e.g. a liquid such as dialysate. The feature may be located proximal to or at the terminal downstream end of the line. The feature may have a flow path having a smaller cross sectional area than that of the fluid conduit in the main part of the fluid line. When liquid reaches the feature, the flow slows and this will be reflected in the flow rate estimation conducted during the pump stroke (i.e., the pressure decay curve shows a shallower decline). The flow rate may be monitored and when it is determined that the flow rate has decreased to a restricted flow rate or decreased to within a range of the restricted rate, the controller can declare that fluid in the line has reached the restriction. Stroke displacement estimation may also be useful in determining whether change in flow rate is due to an end-of-stroke condition or liquid flow being impeded by the feature. The impedance feature may be placed near the end of the line such that when it is detected that liquid has reached the feature, the line may be determined to be primed.

Detecting an impedance change in a line may have other uses. For example, a A flow restriction can be used to detect when a fluid flowing past the restriction changes in composition, density, viscosity, etc. In such embodiments, impedance restriction may be placed at a location of interest in the conduit. Flow rate through the conduit may be monitored to detect the change in flow when the composition or fluid of differing properties or characteristics reaches the restriction.

Figure 122:
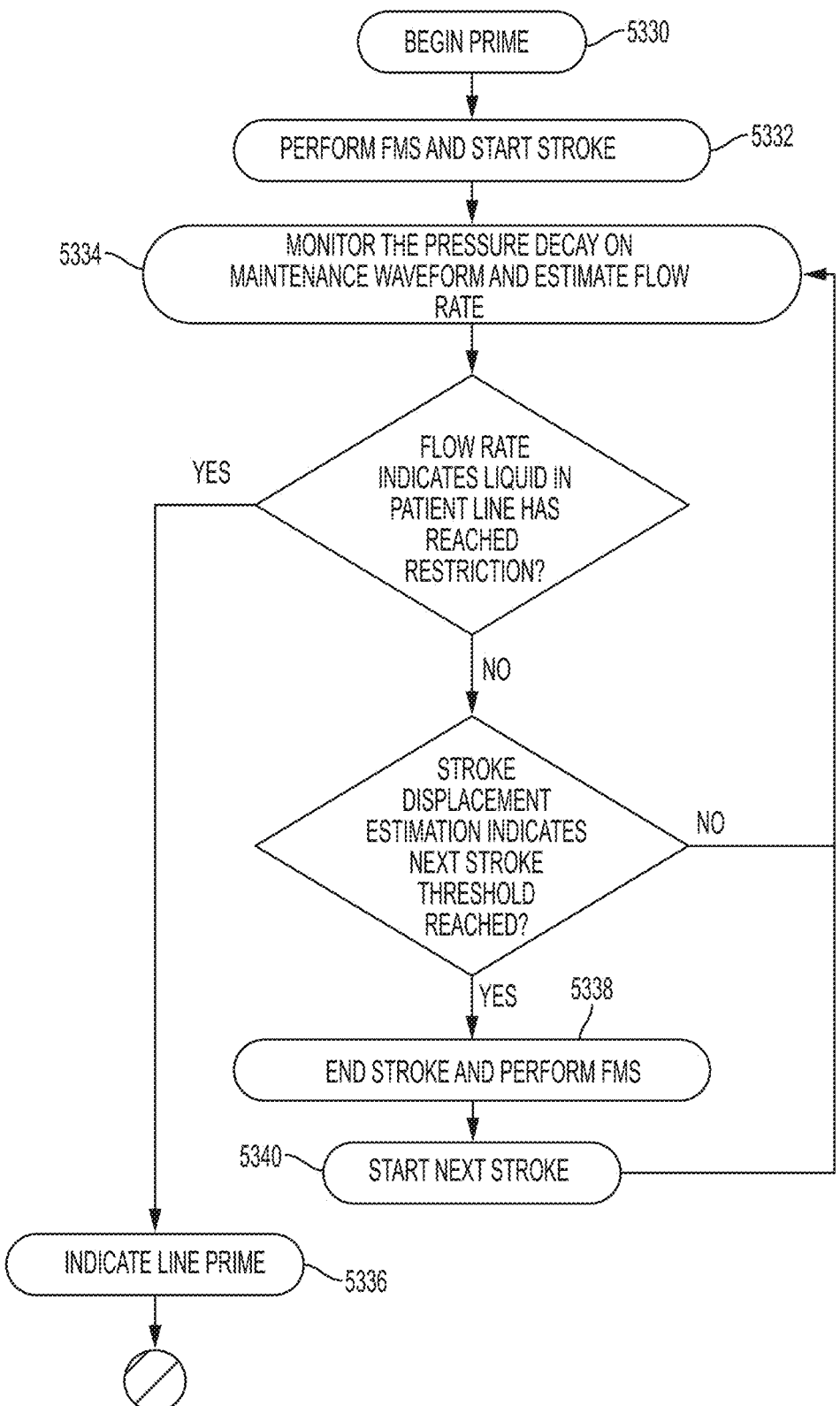

FIG. 122 shows a flowchart outlining a method to detect that a patient line has been primed by monitoring the slope of a pressure decay curve, computing a flow rate, or estimating a stroke displacement. In the example flowchart, for illustrative purposes only, deliver strokes are depicted for the priming of a fluid line. It can be assumed that after a chamber has finished its stroke, that chamber performs a fill stroke and is refilled. The flowchart also begins with each chamber in a filled state.

Priming of the line is begun in step S330. This may include performing a pre-stroke FMS measurement and starting a stroke in step S332. Step S334 may occur as the stroke is in progress. In step S334, the pressure decay on the pressure maintenance waveform may be monitored such that a flow rate and stroke displacement computation or estimation may be made. If the flow rate indicates that liquid in the patient line has reached the restriction, the user may be notified, in step S336, that the line has been primed.

If the flow rate does not indicate that the restriction has been reached, the stroke may continue until a stroke displacement threshold has been reached. Once the stroke displacement estimation indicates that the stroke displacement threshold has been reached, the stroke may be ended and a post stroke FMS measurement may be made in step S338. The stroke displacement threshold may be set so that it is less than the displacement necessary to deliver a full chamber volume. Thus, partial strokes may be purposefully delivered when the patient line is primed. This will ensure that a detected decrease in flow rate is not attributable to an end-of-stroke condition having been reached. Once the post stroke FMS measurement in step S338 has finished, the next pump stroke may begin in step S340. In a single pump system, the controller can command a pump-filling operation to re-fill the pumping chamber with fluid. In a dual pump system, the controller can alternatively command a second pump to begin delivery of fluid from its pump chamber. As shown, after the next stroke begins, the flowchart resets to step S334. Flow rate and stroke displacement are again estimated during the stroke. A cycler may continue making pump strokes until the flow rate indicates that the line has been primed.

FIG. 123 shows a flowchart outlining steps used to detect that a patient line has been primed by computing flow rate. After a chamber has finished its stroke, that chamber performs a fill stroke and is refilled. The steps depicted by the flowchart are assumed to begin with each chamber in a filled state.

In step S354, the pressure decay on the pressure regulation or maintenance waveform may be monitored in order for the controller to compute a flow rate. When the flow rate is determined to have slowed, the current stroke may be ended and a post stroke FMS measurement may be performed in step S356. The next pumping stroke may then begin in step S358. In the example embodiment in FIG. 123, a subsequent pumping stroke at 5358 is delivered from another pumping chamber in a multi-chamber pumping cassette. In step S360, the pressure decay on the pressure maintenance waveform may be monitored so that a controller can compute a flow rate during the stroke. If the flow rate estimation at the start of this stroke indicates a slow or low flow rate condition, the controller can declare that the line is primed. Preferably, this determination is made in a short amount of time so as to minimize the amount of fluid pumped if the line is indeed fully primed. The stroke is ended and an FMS measurement may be made in step S362. A user may then be notified that the line is primed in step S364.

In the event that the flow rate is not slow or low, the controller may conclude that the previous reduction in flow rate was due to an end-of-stroke condition being reached. In this event, the flowchart returns to step S354 where stroke continues and the pressure decay on the pressure maintenance waveform for the control chamber continues to be monitored. Flow rate estimations continue to be made and the steps outlined in the flowchart may repeat as described above until it is determined that the line has been primed.

FIG. 124 shows a flowchart outlining steps to detect that a patient line has been primed by setting a target delivery volume of fluid. This volume may be set to be equal to the nominal interior volume of the patient line included in the set. A pre-stroke FMS measurement may be performed and a stroke may be started in step S372. In step S374, the pressure decay on the pressure maintenance waveform during a pump stroke may be monitored such that a flow rate estimation and stroke displacement estimation may be made. In some embodiments, step S374 may be optional. Once the stroke has been delivered, the stroke may be ended and a post-stroke FMS measurement may be conducted. If the difference between the target volume of fluid and the total volume of fluid delivered is greater than the full volume of a pump chamber, then step S378 may be performed and the next pumping stroke begins. As shown, step S374 may be repeated while the delivery stroke is in progress.

In the event that after a stroke is completed, the difference between the target volume of fluid and the total volume of fluid delivered is less than the volume of a full pumping chamber, the cycler may proceed with the next delivery pumping stroke in step S380. When the estimated flow rate is observed to have slowed, the controller may declare the line to be primed. The stroke may be ended and an FMS measurement may be made in step S384. The user may then be notified in step S386 that the line has been primed.

In some embodiments, the controller may verify that a line has been primed by valving the line to a second pump and commanding the second pump to begin a pump stroke. If the pressure decay during the second pump stroke indicates a reduced flow rate similar to that of the first pump, the controller can declare that the line is indeed primed.

Set Differentiation

In some embodiments, a controller-computed flow rate and estimated stroke displacement may be used to determine which type of fluid line set is installed in a cycler (the types of fluid line sets may differ in total volume due to variations in tubing length, diameter, size and number of drip chambers, Y-connections or branches, etc.). The controller can also use the same procedure to cross-check previously acquired information about the fluid set. This information may be acquired through a user input via the user interface of the cycler. Additionally, in some embodiments, the controller may acquire this information by using an input device or sensor configured to read a bar code, data matrix or other identification marking.

A preset pumping pressure may be used to pump fluid through the line when computing a flow rate for such a determination. A lower flow rate will indicate a smaller diameter line, or one of greater length. In this manner, a controller may be able to determine, for example, whether an adult set or a pediatric set (which will have smaller fluid conduit) is installed in the medical device. This determination may be made when the medical device is priming the patient line of the set. The medical device may differentiate between sets with different length lines, for example, by monitoring the amount of volume pumped in order to prime the line. Longer lines (e.g. sets which include an extension)

will require a larger priming volume than shorter lines. In some embodiments, flow rate data and prime volume data may be analyzed together to differentiate between set types. Flow rate data and prime volume data may be compared to a list of expected values from a number of different sets which may be used in a medical device in order to determine which set is installed in the device.

FIG. 125 shows a flowchart outlining a number of example steps which may be used by a cycler to differentiate which set of one or more different sets has been installed in a medical device (such as a peritoneal dialysis cycler). In the example embodiment shown in FIG. 125 this determination is made during priming of a line (e.g. the patient line) included in the set. As the line is primed in step 5580, the flow rate during the prime and the volume delivered to the line during the prime are monitored in steps 5584 and 5582 respectively. As described above, a pre-determined pumping pressure may be used to help ensure variations in flow rate between different sets are attributable to the type of installed set.

The medical device may detect the prime status of the line with a prime sensor such as any of those described herein. When the prime is finished, the controller may, in step 5586 compare the flow rate and volume primed to a stored list of expected values for different sets that are available to be installed in the medical device. In some embodiments, these expected values may be determined empirically at the time of manufacture. Optionally, a range of values may be listed for each of the sets. The set type is identified in step 5588. This may be done by determining which set type in the list is closest to the observed flow rate and prime volume values during the prime. If the set type identified in step 5588 does not match previously collected data about the set, the controller may notify the user. This notification may include a visual notification on a user interface and may also be accompanied by an audio tone or alert.

Additionally, if other data has been collected about the set (e.g. from a marking or indicia on the set or from a therapy program) it may be used to verify set type identified in step 5588 is an expected set type. In the event that the set type identified in step 5588 is inconsistent with other previously collect set related data, step 5589 may be performed and the controller may generate a notification for the user.

Head Height Detection

In some circumstances, it may be useful to determine the heightwise location of the patient relative to the cassette 24 or other portion of the system. For example, dialysis patients in some circumstances can sense a "tugging" or other motion due to fluid flowing into or out of the patient's peritoneal cavity during a fill or drain operation. To reduce this sensation, the cycler 14 may reduce the pressure applied to the patient line 34 during fill and/or drain operations. However, to suitably set the pressure for the patient line 34, the cycler 14 may determine the height of the patient relative to the cycler 14, the heater bag 22, drain or other portion of the system. For example, when performing a fill operation, if the patient's peritoneal cavity is located 5 feet above the heater bag 22 or the cassette 24, the cycler 14 may need to use a higher pressure in the patient line 34 to deliver dialysate than if the patient's peritoneal cavity is located 5 ft below the cycler 14. The pressure may be adjusted, for example, by alternately opening and closing a binary pneumatic source valve for variable time intervals to achieve the desired target pump chamber pressure. An average desired target pressure can be maintained, for example, by adjusting the time intervals to keep the valve open when the pump chamber pressure is below the target pressure by a specified amount, and to keep the valve closed when the pump chamber pressure is above the target pressure by a specified amount. Any adjustments to maintain the delivery of a complete stroke volume can be made by adjusting the fill and/or delivery times of the pump chamber. If a variable orifice source valve is used, the target pump chamber pressure can be reached by varying the orifice of the source valve in addition to timing the intervals during which the valve is opened and closed. To adjust for patient position, the cycler 14 may momentarily stop pumping of fluid, leaving the patient line 34 in open fluid communication with one or more pump chambers 181 in the cassette (e.g., by opening suitable valve ports in the cassette 24). However, other fluid lines may be closed, such as the upper valve ports 192 for the pump chambers 181. In this condition, the pressure in the control chamber for one of the pumps may be measured. As is well known in the art, this pressure correlates with the "head" height of the patient, and can be used by the cycler 14 to control the delivery pressure of fluid to the patient. A similar approach can be used to determine the "head" height of the heater bag 22 (which will generally be known), and/or the solution containers 20, as the head height of these components may have an effect on pressure needed for pumping fluid in a suitable way.

Noise Reduction Features of the Cycler

In accordance with aspects of the invention, the cycler 14 may include one or more features to reduce noise generated by the cycler 14 during operation and/or when idle. In one aspect of the invention, the cycler 14 may include a single pump that generates both pressure and vacuum that are used to control the various pneumatic systems of the cycler 14. In one embodiment, the pump can simultaneously generate both pressure and vacuum, thereby reducing overall run time, and allowing the pump to run more slowly (and thus more quietly). In another embodiment, the air pump start and/or stop may be ramped, e.g., slowly increases pump speed or power output at starting and/or slowly decreases pump speed or power output at shut down. This arrangement may help reduce "on/off" noise associated with start and stop of the air pump so pump noise is less noticeable. In another embodiment, the air pump may be operated at a lower duty cycle when nearing a target output pressure or volume flow rate so that the air pump can continue operating as opposed to shutting off, only to be turned on after a short time. As a result, disruption caused by repeated on and off cycles of the air pump may be avoided.

FIG. 126 shows a perspective view of an interior section of the cycler 14 with the upper portion of the housing 82 removed. In this illustrative embodiment, the cycler 14 includes a single air pump 83, which includes the actual pump and motor drive contained within a sound barrier enclosure. The sound barrier enclosure includes an outer shield, such as a metal or plastic frame, and a sound insulation material within the outer shield and at least partially surrounding the motor and pump. This air pump 83 may simultaneously provide air pressure and vacuum, e.g., to a pair of accumulator tanks 84. One of the tanks 84 may store positive pressure air, while the other stores vacuum. A suitable manifold and valve arrangement may be coupled to the tanks 84 so as to provide and control air pressure/vacuum supplied to the components of the cycler 14.

In accordance with another aspect of the invention, components that require a relatively constant pressure or vacuum supply during cycler operation, such as an occluder, may be isolated from the source of air pressure/vacuum at least for relatively long periods of time. For example, the occluder 147 in the cycler 14 generally requires a constant air pressure in the occluder bladder 166 so that the patient and drain lines remain open for flow. If the cycler 14 continues to operate properly without power failure, etc., the bladder 166 may be inflated once at the beginning of system operation and remain inflated until shut down. The inventors have recognized that in some circumstances air powered devices that are relatively static, such as the bladder 166, may "creak" or otherwise make noise in response to slight variations in supplied air pressure. Such variations may cause the bladder 166 to change size slightly, which causes associated mechanical parts to move and potentially make noise. In accordance with an aspect of the bladder 166 and other components having similar pneumatic power requirements, may be isolated from the air pump 83 and/or the tanks 84, e.g., by the closing of a valve, so as to reduce variations of pressure in the bladder or other pneumatic component, thus reducing noise that may be generated as a result of pressure variations. Another component that may be isolated from the pneumatic supply is the bladder in the door 141 at the cassette mounting location 145 which inflates to press the cassette 24 against the control surface 148 when the door 141 is closed. Other suitable components may be isolated as desired.

In accordance with another aspect of the invention, the speed and/or force at which pneumatic components are actuated may be controlled to as to reduce noise generated by component operation. For example, movement of the valve control regions 1481 to move a corresponding portion of the cassette membrane 15 so as to open or close a valve port on the cassette 24 may cause a "popping" noise as the membrane 15 slaps against and/or pull away from the cassette 24. Such noise may be reduced by controlling the rate of operation of the valve control regions 1481, e.g., by restricting the flow rate of air used to move the control regions 1481. Air flow may be restricted by, for example, providing a suitably small sized orifice in the line leading to the associated control chamber, or in other ways.

A controller may also be programmed to apply pulse width modulation ("PWM") to the activation of one or more pneumatic source valves at a manifold of cycler 14. The pneumatic pressure delivered to various valves and pumps of cassette 24 can be controlled by causing the associated manifold source valves to open and close repeatedly during the period of actuation of a valve or pump in cassette 24. The rate of rise or fall of pressure against membrane 15/control surface 148 can then be controlled by modulating the duration of the "on" portion of the particular manifold valve during the actuation period. An additional advantage of applying PWM to the manifold source valves is that variable pneumatic pressure can be delivered to the cassette 24 components using only a binary (on-off) source valve, rather than a more expensive and potentially less reliable variable-orifice source valve.

In accordance with another aspect of the invention, the movement of one or more valve elements may be suitably damped so as to reduce noise generated by valve cycling. For example, a fluid (such as a ferro fluid) may be provided with the valve element of high frequency solenoid valves to damp the movement of the element and/or reduce noise generated by movement of the valve element between open and closed positions.

In accordance with another embodiment, pneumatic control line vents may be connected together and/or routed into a common, sound-insulated space so that noise associated with air pressure or vacuum release may be reduced. For example, when the occluder bladder 166 is vented to allow the spring plates 165 (see, for example, FIG. 99) to move toward each other and occlude one or more lines, the air pressure released may be released into a sound insulated enclosure, as opposed to being released into a space where noise associated with the release may be heard more easily. In another embodiment, lines that are arranged to release air pressure may be connected together with lines that are arranged to release an air vacuum. With this connection (which may include a vent to atmosphere, an accumulator or other), noise generated by pressure/vacuum release may be further reduced.

Control System

The control system 16 described in connection with FIG. 1 has a number of functions, such as controlling dialysis therapy and communicating information related to the dialysis therapy. While these functions may be handled by a single computer or processor, it may be desirable to use different computers for different functions so that the implementations of those functions are kept physically and conceptually separate. For example, it may be desirable to use one computer to control the dialysis machinery and another computer to control the user interface.

FIG. 127 shows a block diagram illustrating an exemplary implementation of control system 16, wherein the control system comprises a computer that controls the dialysis machinery (an "automation computer" 300) and a separate computer that controls the user interface (a "user interface computer" 302). As will be described, safety-critical system functions may be run solely on the automation computer 300, such that the user interface computer 302 is isolated from executing safety-critical functions.

The automation computer 300 controls the hardware, such as the valves, heaters, and pumps that implement the dialysis therapy. In addition, the automation computer 300 sequences the therapy and maintains a "model" of the user interface, as further described herein. As shown, the automation computer 300 comprises a computer processing unit (CPU)/memory 304, a flash disk file system 306, a network interface 308, and a hardware interface 310. The hardware interface 310 is coupled to sensors/actuators 312. This coupling allows the automation computer 300 to read the sensors and control the hardware actuators of the APD system to monitor and perform therapy operations. The network interface 308 provides an interface to couple the automation computer 300 to the user interface computer 302.

The user interface computer 302 controls the components that enable data exchange with the outside world, including the user and external devices and entities. The user interface computer 302 comprises a computer processing unit (CPU)/memory 314, a flash disk file system 316, and a network interface 318, each of which may be the same as or similar to their counterparts on the automation computer 300. The Linux operating system may run on each of the automation computer 300 and the user interface computer 302. An exemplary processor that may be suitable for use as the CPU of the automation computer 300 and/or for use as the CPU of the user interface computer 302 is Freescale's Power PC 5200B®.

Via the network interface 318, the user interface computer 302 may be connected to the automation computer 300. Both the automation computer 300 and the user interface computer 302 may be included within the same chassis of the APD system. Alternatively, one or both computers or a portion of said computers (e.g., display 324) may be located outside of the chassis. The automation computer 300 and the user interface computer 302 may be coupled by a wide area network, a local area network, a bus structure, a wireless connection, and/or some other data transfer medium.

The network interface 318 may also be used to couple the user interface computer 302 to the Internet 320 and/or other networks. Such a network connection may be used, for example, to initiate connections to a clinic or clinician, upload therapy data to a remote database server, obtain new prescriptions from a clinician, upgrade application software, obtain service support, request supplies, and/or export data for maintenance use. According to one example, call center technicians may access alarm logs and machine configuration information remotely over the Internet 320 through the network interface 318. If desired, the user interface computer 302 may be configured such that connections may only be initiated by the user or otherwise locally by the system, and not by remote initiators.

The user interface computer 302 also comprises a graphics interface 322 that is coupled to a user interface, such as the user interface 144 described in connection with FIG. 37. According to one exemplary implementation, the user interface comprises a display 324 that includes a liquid crystal display (LCD) and is associated with a touch screen. For example, a touch screen may be overlaid on the LCD so that the user can provide inputs to the user interface computer 302 by touching the display with a finger, stylus or the like. The display may also be associated with an audio system capable of playing, among other things, audio prompts and recorded speech. The user may adjust the brightness of the display 324 based on their environment and preference. Optionally, the APD system may include a light sensor, and the brightness of the display may be adjusted automatically in response to the amount of ambient light detected by the light sensor.

The brightness of the display may be set by the users for two different conditions: high ambient light and low ambient light. The light sensor will detect the ambient light level and the control system 16 will set the display brightness to the preselected levels for either high or low ambient light based on the measured ambient light. The user may select the brightness level for high and low ambient light by selection a value from 1 to 5 for each condition. The user interface may be a slider bar for each condition. In another example the user may select a number. The control system may set the button light levels to match the display light levels.

The LCD display and/or the touch screen of the display 324 may develop faults, where they do not display and/or respond correctly. One theory, but not the only theory, of the cause is an electro-static discharge from a user to the screen that changes the values in the memories of the drivers for the LCD display and touch screen. The software processes UIC executive 354 or the AC executive 354 may include a low priority sub-process or thread that checks the constant memory registers of the drivers for the touch screen and LCD display. If thread finds that any of the constant values in the memory registers are different from those stored elsewhere in the User Interface computer 302 or automation computer 300, then the thread calls for another software process to reinitialize the drivers for LCD display and/or the touch screen. In one embodiment, the LCD display is driven by a Seiko Epson S1d13513 chip and the touch screen is driven by Wolfson Microelectronics WM97156 chip. Examples of the constant register values include but are not limited to the number of pixels display on the screen, the number colors displayed.

In addition, the user interface computer 302 comprises a USB interface 326. A data storage device 328, such as a USB flash drive, may be selectively coupled to the user interface computer 302 via the USB interface 326. The data storage device 328 may comprise a "patient data key" used to store patient-specific data. Data from dialysis therapies and/or survey questions (e.g., weight, blood pressure) may be logged to the patient data key. In this way, patient data may be accessible to the user interface computer 302 when coupled to the USB interface 326 and portable when removed from the interface. The patient data key may be used for transferring data from one system or cycler to another during a cycler swap, transferring new therapy and cycler configuration data from clinical software to the system, and transferring treatment history and device history information from the system to clinical software. An exemplary patient data key 325 is shown in FIG. 128.

As shown, the patient data key 325 comprises a connector 327 and a housing 329 coupled to the connector. The patient data key 325 may be optionally be associated with a dedicated USB port 331. The port 331 comprises a recess 333 (e.g., in the chassis of the APD system) and a connector 335 disposed within the recess. The recess may be defined, at least in part, by a housing 337 associated with the port 331. The patient data key connector 327 and the port connector 335 are adapted to be selectively electrically and mechanically coupled to each other. As may be appreciated from FIG. 128, when the patient data key connector 327 and the port connector 335 are coupled, the housing 329 of the patient data storage device 325 is received at least partially within the recess 333.

The housing 329 of the patient data key 325 may include visual cues indicative of the port with which it is associated and/or be shaped to prevent incorrect insertion. For example, the recess 333 and/or housing 337 of the port 331 may have a shape corresponding to the shape of the housing 329 of the patient data key 325. For example, each may have a non-rectangular or otherwise irregular shape, such as an oblong shape with an upper indentation as shown in FIG. 128. The recess 333 and/or housing 337 of the port 331 and the housing 329 of the patient data key 325 may include additional visual cues to indicate their association. For example, each may be formed of the same material and/or have the same or a similar color and/or pattern.

In a further embodiment, as shown in FIG. 129, the housing 329 of the patient data key 325 may constructed to be sloped away from connector 327 to carry any liquids that may splash onto the key 325 away from connector 327 and toward the opposite end of the housing 329, where a hole 339 in the housing 329 may help drain the liquid off and away from the patient data key 325 and its coupling with the port connector 335.

In one embodiment, the port 331 and recess 333 are located on the front panel 1084 of cycler 14 as shown in FIG. 35. The patient data key 325 is inserted in the port 331 before the door 141 is closed and therapy is started. The door 141 includes a second recess 2802 to accommodate the patient data key 325, when the door 141 is closed. Locating the patient data key 325 behind the door 141 assures that all the therapy data may be recorded on to the PDK. This location prevents a user from removing the key mid-therapy.

Alternatively or additionally, the patient data key 325 may comprise a verification code that is readable by the APD system to verify that the patient data key is of an expected type and/or origin. Such a verification code may be stored in a memory of the patient data key 325, and be read from the patient data key and processed by a processor of the APD system. Alternatively or additionally, such a verification code may be included on an exterior of the patient data key 325, e.g., as a barcode or numeric code. In this case, the code may be read by a camera and associated processor, a barcode scanner, or another code reading device.

If the patient data key is not inserted when the system is powered on, an alert may be generated requesting that the key be inserted. However, the system may be able to run without the patient data key as long as it has been previously configured. Thus, a patient who has lost their patient data key may receive therapy until a replacement key can be obtained. Data may be stored directly to the patient data key or transferred to the patient data key after storage on the user interface computer 302. Data may also be transferred from the patient data key to the user interface computer 302.

In addition, a USB Bluetooth® adapter 330 may be coupled to the user interface computer 302 via the USB interface 326 to allow, for example, data to be exchanged with nearby Bluetooth®-enabled devices. For example, a Bluetooth®-enabled scale in the vicinity of the APD system may wirelessly transfer information concerning a patient's weight to the system via the USB interface 326 using the USB Bluetooth® adapter 330. Similarly, a Bluetooth®-enabled blood pressure cuff may wirelessly transfer information concerning a patient's blood pressure to the system using the USB Bluetooth® adapter 330. The Bluetooth® adapter may be built-in to the user interface computer 302 or may be external (e.g., a Bluetooth® dongle).

The USB interface 326 may comprise several ports, and these ports may have different physical locations and be used for different USB device. For example, it may be desirable to make the USB port for the patient data key accessible from the front of the machine, while another USB port may be provided at and accessible from the back of the machine. A USB port for the Bluetooth® connection may be included on the outside of the chassis, or instead be located internal to the machine or inside the battery door, for example.

As noted above, functions that could have safety-critical implications may be isolated on the automation computer. Safety-critical information relates to operations of the APD system. For example, safety-critical information may comprise a state of a APD procedure and/or the algorithms for implementing or monitoring therapies. Non safety-critical information may comprise information that relates to the visual presentation of the screen display that is not material to the operations of the APD system.

By isolating functions that could have safety-critical implications on the automation computer 300, the user interface computer 302 may be relieved of handling safety-critical operations. Thus, problems with or changes to the software that executes on the user interface computer 302 will not affect the delivery of therapy to the patient. Consider the example of graphical libraries (e.g., Trolltech's Qt® toolkit), which may be used by the user interface computer 302 to reduce the amount of time needed to develop the user interface view. Because these libraries are handled by a process and processor separate from those of the automation computer 300, the automation computer is protected from any potential flaws in the libraries that might affect the rest of the system (including safety-critical functions) were they handled by the same processor or process.

Of course, while the user interface computer 302 is responsible for the presentation of the interface to the user, data may also be input by the user using the user interface computer 302, e.g., via the display 324. To maintain the isolation between the functions of the automation computer 300 and the user interface computer 302, data received via the display 324 may be sent to the automation computer for interpretation and returned to the user interface computer for display.

Although FIG. 127 shows two separate computers, separation of the storage and/or execution of safety-critical functions from the storage and/or execution of non safety-critical functions may be provided by having a single computer including separate processors, such as CPU/memory components 304 and 314. Thus, it should be appreciated that providing separate processors or "computers" is not necessary. Further, a single processor may alternatively be used to perform the functions described above. In this case, it may be desirable to functionally isolate the execution and/or storage of the software components that control the dialysis machinery from those that control the user interface, although the invention is not limited in this respect.

Other aspects of the system architecture may also be designed to address safety concerns. For example, the automation computer 300 and user interface computer 302 may include a "safe line" that can be enabled or disabled by the CPU on each computer. The safe line may be coupled to a voltage supply that generates a voltage (e.g., 12 V) sufficient to enable at least some of the sensors/actuators 312 of the APD system. When both the CPU of the automation computer 300 and the CPU of the user interface computer 302 send an enable signal to the safe line, the voltage generated by the voltage supply may be transmitted to the sensors/actuators to activate and disable certain components. The voltage may, for example, activate the pneumatic valves and pump, disable the occluder, and activate the heater. When either CPU stops sending the enable signal to the safe line, the voltage pathway may be interrupted (e.g., by a mechanical relay) to deactivate the pneumatic valves and pump, enable the occluder, and deactivate the heater. In this way, when either the automation computer 300 or the user interface computer 302 deems it necessary, the patient may be rapidly isolated from the fluid path, and other activities such as heating and pumping may be stopped. Each CPU can disable the safe line at any time, such as when a safety-critical error is detected or a software watchdog detects an error. The system may be configured such that, once disabled, the safe line may not be re-enabled until both the automation computer 300 and user interface computer 302 have completed self-tests.

FIG. 130 shows a block diagram of the software subsystems of the user interface computer 302 and the automation computer 300. In this example, a "subsystem" is a collection of software, and perhaps hardware, assigned to a specific set of related system functionality. A "process" may be an independent executable which runs in its own virtual address space, and which passes data to other processes using inter-process communication facilities.

The executive subsystem 332 includes the software and scripts used to inventory, verify, start and monitor the execution of the software running on the CPU of the automation computer 300 and the CPU of the user interface computer 302. A custom executive process is run on each of the foregoing CPUs. Each executive process loads and monitors the software on its own processor and monitors the executive on the other processor.

The user interface (UI) subsystem 334, handles system interactions with the user and the clinic. The UI subsystem 334 is implemented according to a "model-view-controller" design pattern, separating the display of the data ("view") from the data itself ("model"). In particular, system state and data modification functions ("model") and cycler control functions ("controller") are handled by the UI model and cycler controller 336 on the automation computer 300, while the "view" portion of the subsystem is handled by the UI screen view 338 on the UI computer 302. Data display and export functionality, such as log viewing or remote access, may be handled entirely by the UI screen view 338. The UI screen view 338 monitors and controls additional applications, such as those that provide log viewing and a clinician interface. These applications are spawned in a window controlled by the UI screen view 338 so that control can be returned to the UI screen view 338 in the case of an alert, an alarm or an error.

The therapy subsystem 340 directs and times the delivery of the dialysis treatment. It may also be responsible for verifying a prescription, calculating the number and duration of therapy cycles based upon the prescription, time and available fluids, controlling the therapy cycles, tracking fluid in the supply bags, tracking fluid in the heater bag, tracking the amount of fluid in the patient, tracking the amount of ultra-filtrate removed from patient, and detecting alert or alarm conditions.

The machine control subsystem 342 controls the machinery used to implement the dialysis therapy, orchestrating the high level pumping and control functionality when called upon by the therapy subsystem 340. In particular, the following control functions may be performed by the machine control subsystem 342: air compressor control; heater control; fluid delivery control (pumping); and fluid volume measurement. The machine control subsystem 342 also signals the reading of sensors by the I/O subsystem 344, described below.

The I/O subsystem 344 on the automation computer 300 controls access to the sensors and actuators used to control the therapy. In this implementation, the I/O subsystem 344 is the only application process with direct access to the hardware. Thus, the I/O subsystem 344 publishes an interface to allow other processes to obtain the state of the hardware inputs and set the state of the hardware outputs.

FPGA

In some embodiments, the Hardware Interface 310 in FIG. 132 may be a separate processor from the automation computer 300 and the User Interface 302 that may perform a defined set of machine control functions and provide an additional layer of safety to the cycler controller 16. A second processor, such as a field programmable gate array (FPGA) may increase the responsiveness and speed of the cycler 14 by moving some computing tasks from the automation computer 300 to the hardware interface 310 (e.g., an FPGA), so that the automation computer 300 can devote more resources to fluid management and therapy control, as these comprise resource-intensive calculations. The hardware interface 310 may control the pneumatic valves and record and temporarily store data from the various sensors. The real time control of the valves, pressure levels and data recording by the hardware interface 310 allows the automation computer 300 to send commands and receive data, when the software processes or functions running on the automation computer 300 are ready for them.

A hardware interface processor 310 may advantageously be implemented on any medical fluid delivery apparatus, including (but not limited to) a peritoneal dialysis cycler 14, in which fluid is pumped by one or more pumps and an arrangement of one or more valves from one or more source containers of fluid (e.g., dialysate solution bags, or a heater bag containing fluid to be infused) to a patient or user. It may also be implemented on a fluid delivery apparatus that is configured to pump fluid from a patient or user (e.g., peritoneal dialysis cycler) to a receptacle (e.g., drain bag). A main processor may be dedicated to controlling the proper sequence and timing of pumps and valves to perform specific functions (e.g., pumping from a solution bag to a heater bag, pumping from a heater bag to a user, or pumping from a user to a drain receptacle), and to monitor the volumes of fluid pumped from one location to the next. A secondary (hardware interface) processor (e.g. an FPGA) may correspondingly be dedicated to collect and store data received from various sensors (e.g., pressure sensors associated with the pumps, or temperature sensors associated with a heating system) at an uninterrupted fixed rate (e.g., about 100 Hz or 2000 Hz), and to store the data until it is requested by the main processor. It may also control the pumping pressures of the pumps at a rate or on a schedule that is independent from any processes occurring in the main processor. In addition to other functions (see below) it may also open or close individual valves on command from the main processor.

In one example the Hardware Interface 310 may be a processor that performs a number of functions including but not limited to:

- Acquiring pneumatic pressure sensor data on a predictable and fine resolution time base;
- Storing the pressure data with a timestamp until requested by automation computer 300;
- Validating the messages received from that automation computer 300;
- Providing automated control of one or more pneumatic valves 2660-2667;
- Controlling some valves with a variable pulse width modulation (PWM) duty cycle to provide Pick & Hold functionality and/or control some valves with current feedback;
- Provide automated and redundant safety checking of valve combinations, maximum pressures and temperatures and ability.
- Independent of the other computers 300, 302 putting the cycler 14 into a failsafe mode as needed.
- Monitoring status of buttons on the cycler 14 and controlling the level of button illumination;
- Controlling the Auto Connect screw-drive mechanism 1321 and monitoring the Auto-Connect position sensing;
- Detecting the presence of solution caps 31 and/or spike caps 63;
- Control of the pneumatic pump;
- Control of the prime sensor LED and detector;
- Detecting over-voltages and testing hardware to detect over-voltages;
- Controlling and monitoring one or more fluid detectors;
- Monitoring the latch 1080 and proximity sensor 1076 on the door 141;
- Monitoring critical voltages at the system level.

The Hardware Interface 310 may comprise a processor separate from the processors in the automation computer 300 and user interface 302, A to D converters and one or more IO boards. In another embodiment, the hardware interface is comprised of a FPGA (Field Programmable Gate Array). In one embodiment the FPGA is a SPARTAN® 3A in the 400K gate and 256 ball package made by Xilinx Inc. of California. The Hardware Interface 310 is an intelligent entity that is employed to operate as an independent safety monitor for many of the Control CPU functions. There are several safety critical operations where either the Hardware Interface or the Control CPU serves as a primary controller and the other serves as a monitor.

The hardware interface 310 serves to monitor the following automation computer 300 functions including but not limited to:

Monitoring the integrity of system control data being received from the automation computer 300;

Evaluating the commanded valve configurations for combination that could create a patient hazard during therapy;

Monitoring the fluid and pan temperature for excessive high or low temperatures;

Monitoring and testing the overvoltage monitor; and

Provide a means for the automation computer 300 to validate critical data returned from the hardware interface.

FIG. 131 is a schematic representation of one arrangement of the automation computer 300, the UI computer 302 and the hardware interface processor 310. The hardware interface 310 is connected via a communication line to the automation computer 300 and connects to the sensors and actuators 312 in the cycler 14. A voltage supply 2500 provides power for the safety critical actuators that can be enabled or disabled by any of the computers 300, 302, 310. The safety critical actuators include but are not limited to the pneumatic valves, the pneumatic pump and a safety relay on the heater circuit. The pneumatic system is configured to safe condition when unpowered. The pneumatic safe condition may include occluding the lines 28,34 to the patient, isolating the control chambers 171 and/or closing all the valves 184, 186, 190, 192, on the cassette 24. The safety relay 2030 in the heater circuit 2212 is open, preventing electrical heating, when the relay is unpowered. Each computer 300, 302, 310 controls a separate electrical switch 2510 that can each interrupt power to the valves, pump and safety relay. If any of the three computers detects a fault condition, it can put the cycler 14 in a failsafe condition by opening one of the three switches 2510. The electrical switches 2510 are controlled by the safety executive process 352, 354 in the UI computer 302, and automation computer 300 respectively.

FIG. 132 is a schematic illustration of the connections between the Hardware Interface 310, the various sensors, the pneumatic valves, the bag heater and the automation computer 300. The Hardware Interface 300 controls each of the pneumatic valves 2660-2667 and the pneumatic pump or compressor 2600 via pulse-width-modulated DC voltages. FIG. 132 presents an alternative embodiment of the safe line 2632 supplying power to the pneumatic valves 2660-2667, pump 2600 and heater safety relay 2030, in which a single switch 2510 is driven by an AND gate 2532 connected to the three computers 300, 302, 310. The prime sensor is controlled and monitored by the Hardware Interface 310. The brightness of the button LEDs is controlled by the Hardware Interface 310 via a PWM'd voltage.

The data signals from the buttons, pressure sensors, temperature sensors and other elements listed in FIG. 132 are monitored by the Hardware Interface 310, and the data is stored in a buffer memory until called for by the automation computer 300. The digital inputs are connected directly to the Hardware Interface 310. The analog signals from pressure, temperature, current sensors and others are connected to Analog-to-Digital-Converter (ADC) boards that convert the analog signals to digital values and may a scale and/or offset the digital values. The outputs of the ADCs are communicated over SPI buses to the Hardware Interface 310. The data is recorded and stored in the buffer at a fixed rate. Some of the data signals may be recorded at a relatively slow rate, including the pressure data on the pressure reservoirs and the fluid trap, temperatures, and current measurements. The low speed data may be recorded at 100 Hz. The adiabatic FMS volume measurement algorithm can be improved with high speed pressure data that is recorded at regular intervals. In a preferred embodiment, the pressure data from the sensors on the control volume 171 and the reference chamber 174 are recorded at 2000 Hz. The data may be stored in random-access-memory (RAM) along with a time stamp. The rate of data collection may preferably proceed independently of the automation computer 300 and of processes or subroutines on the hardware interface. The data is reported to the automation computer 300, when a process calls for that value.

The transfer of data between the hardware interface 310 to the automation computer 300 may occur in a two step process where a data packet transferred and stored in a buffer before being validated and then accepted for use by the receiving computer. In one example, the sending computer transmits a first data packet, followed by a second transmission of the cyclic redundancy check (CRC) value for the first data packet. The receiving computer stores the first data packet in a memory buffer and calculates a new CRC value first data packet. The receiving computer then compares the newly calculated CRC value to the CRC value received and accepts the first data packet if the two CRC values match. The cyclic redundancy check (CRC) is an error-detecting code commonly used in digital networks and storage devices to detect accidental changes to raw data. Blocks of data entering these systems get a short check value attached, based on the remainder of a polynomial division of their contents; on retrieval the calculation is repeated, and corrective action can be taken against presumed data corruption if the check values do not match. The data is not transferred between the automation computer and hardware interface if CRC values do not match. If multiple consecutive data packets fail the CRC test, the receiving computer may signal an alarm and put the machine in a fail-safe condition by de-energizing the safe line 2632. In one example, the alarm condition occurs on the third consecutive failed CRC check.

The automation computer 300 passes commands to open selected valves and set specified pressures in specified volumes to the hardware interface 300. The hardware interface 310 in turn controls the valve position by providing a PWM'd voltage to each valve. The hardware interface 310 opens valves as requested with a pick-and-hold algorithm, where the valve is initially actuated with a high voltage or current, and then held in place with a lower voltage or current. Pick-and-hold operation of valves may advantageously reduce the power draw and the level of heat dissipation inside the cycler 14.

The hardware interface 310 controls the pressure in the specified volume by opening and closing the valves between the specified volume and the appropriate pressure reservoir based on the measured pressure in the specified volume. The hardware interface 310 may also control the pressure in the pressure reservoirs by opening and closing the valves between a pneumatic pump and one of the pressure reservoirs based on the measured pressure in the reservoir. The specified volumes may include each of the control chambers 171, the reference volumes 174, the fluid trap and the positive and negative reservoirs. The hardware interface 310 may control the pressure in each of these specified volumes via a number of control schemes, including but not limited to on-off control, or proportional control of the valve with a PWM signal. In one example, as described above, the hardware interface 310 implements an on-off controller, sometimes referred to as a bang-bang controller, which sets a first and second limit and closes the valve when the pressure exceeds the upper second limit and opens the valve when the pressure is less than the first lower limit. In another example, the hardware interface 310 may operate valves between the specified volume and both pressure reservoirs to achieve a desired pressure. In other examples the automation computer 300 may specify one or more valves and command a specific valve to control the pressure as measured by a specified sensor.

The hardware interface 310 controls the position and operation of the Auto-Connect carriage. The movement and positioning of the Auto-Connect carriage 146 is controlled in real time by the hardware interface based on the measured position of the carriage 146. The automation computer 300 may command a particular function or position for the carriage. The hardware interface 310 carries out the commanded function without burdening memory or processing of the automation computer 300. The positioning of the carriage 146 is controlled with a feedback loop from a position sensor. In addition, the FPGA detects the presence of solution caps 31 and/or spike caps 63 with sensing elements 1112 as described above. Alternatively, the presence of the caps 31 and/or spike caps 63 can be detected by a range of sensing technologies, including but not limited to vision systems, optical sensors that can be blocked by a solution cap 31 and/or spike cap 63, or, for example, a micro-switch on the stripper element 1491.

The hardware interface 310 may implement safety functions independently of the automation computer 300 or the user interface computer 302. The independent action of the hardware interface 310 to disable the safety line 2632 and/or signal an alarm to the safety executives 352, 354 further reduces the possibility of an unsafe condition occurring. The hardware interface 310 may send an alarm and/or de-energize the safe line 2632 for defined valve combinations at any time. Shutting the cycler down based on disallowed valve positions protects the patient and preserves the ability to complete the therapy (after a reset if needed). The hardware interface 310 may also alarm and de-energize the safe line at unsafe conditions including excessive temperature on the heater pan and/or bag button, excessive pressure in control chamber or reservoir. The hardware interface may alarm and de-energize the safe line when water or other liquid is detected in the fluid trap.

Heater Control System

The following descriptions of a heater control system, including (but not limited to) a dual-voltage heater control system and a heater current leakage optimization and safety system may be applied to any device that operates a heater at high (e.g., line) voltages. For example, these heater control systems may be incorporated into the presently disclosed peritoneal dialysis cycler. In addition, they may be incorporated into peritoneal dialysis systems disclosed in U.S. Pat. Nos. 5,350,357, 5,431,626, 5,438,510, 5,474,683 and 5,628,908, or any hemodialysis system, such as a hemodialysis system disclosed in U.S. Pat. Nos. 8,246,826, 8,357,298, 8,409,441 and 8,393,690.

The control systems described above may be used to ensure that the solution delivered to a patient is maintained within a pre-determined range of temperatures. During the therapy process, the cycler 14 fills the heater bag 22 with solution from the connected solution containers 20, via a heater bag line 26. The heater bag 22 rests on the heater pan 142 which may include electrical resistance heaters. The heater bag 22 may be covered with an insulated cover 143. A heater controller may function so as to control the thermal energy delivered to the heater pan 142 in order to control the temperature of the solution to a desired set point prior to delivering the solution to the patient. The solution temperature should be within a safe range prior to being delivered to the patient's abdominal cavity in order to avoid injuring or causing discomfort to the patient, or causing hypothermia or hyperthermia. The heater controller may also limit the temperature of the heater pan to touch-safe temperatures. The heater controller is constructed to heat and maintain the solution within a range of acceptable temperatures in a timely manner in order to ensure the most effective therapy.

FIG. 133 is a schematic view of an exemplary embodiment of a solution heater system 500. In this example, the solution heater system 500 is located within the housing 82 of the cycler 14. The housing includes an insulated lid 143 that may be affixed to the top of the housing 82. The housing 82 and the heater lid 143 may therefore define a region that serves to house the components of the solution heater system 500. The solution heater system may include the following elements: housing 82, heater lid 143, heater pan 22, heater elements 508, heater pan temperature sensors 504, button temperature sensor 506, insulating ring 507 and heater control electronics 50. The heater pan 142 is positioned inside the housing 82, and may accommodate a heater bag 22 when positioned on top of the heater tray 142. Preferably, the heater pan 142 is inclined to place the inlet and/or outlet of the heater bag in a dependent position, to help ensure that fluid in the bag is always in contact with the inlet/outlet regardless of the amount of fluid in the bag. In an embodiment, there can be up to six or more heater pan temperature sensors 504 (only one exemplary heater pan temperature sensor 504 is shown in FIG. 133) positioned along the floor of the heater pan 142. Additionally, there may be a button temperature sensor 506 positioned within the heater pan 142. The button sensor 506 is positioned to make good thermal contact with the heater bag, while being thermally isolated from the heater pan 142 by an insulating ring 507, in order to provide an approximation of the temperature of the fluid or dialysate in the bag. In another embodiment, the button sensor 506 may comprise a pair of thermistors mounted on an aluminum button. The aluminum button is thermally isolated by an insulating ring made of, for example, LEXAN® 3412R plastic or another low thermal conductivity material. The button temperature sensor 506 may be located near the end of the tray where the fluid lines connect to the heater bag 22 in order to better measure the temperature of the fluid within the heater bag when the heater bag is less than approximately one-third full. The button sensor 506 may also be referred to as the fluid or dialysate temperature sensor. There may also be a plurality of heater elements 508 positioned under the heater pan 142, more toward the superior end of the pan, with the bag sensor located more toward the dependent portion of the pan, in order for the sensor to provide a more accurate reading of the fluid temperature within the bag, and to be relatively unaffected by the heater elements 508. The thermal output of the heater elements 508 may be controlled by the heater control electronics 505 to achieve the desired fluid temperature in the heater bag. The heater control electronics 505 may include but not be limited to a heater control module 509 that produces a Pulse Width Modulation (PWM) signal (PWM signal 511, represented in FIG. 134). Electrical hardware in the input-output (IO) subsystem 344 connects electrical power to the heater elements 508 based on the PWM signal 511, and hardware on the IO subsystem 344 reads the output of heater pan temperature sensors 504 and button temperature sensor 506. The PWM signal 511 may control the power supplied to each of the heater elements 508, and consequently the solution heater system 500 may then heat the heater bag 22 to a user-settable comfort temperature, which may be controlled within a preferred safe temperature range.

The solution heater system 500 may also limit the surface temperature of the heater pan 142 to a safe-to-touch temperature. The hardware components of the heater control circuitry 505 may be part of controller 16. There may also be insulation 510 positioned below the heater element 508 which functions to thermally isolate the heater pan 142 and heater bag 22 from the electronic and pneumatic components of the cycler 12. Additionally, the heater lid 143 may insulate the heater bag 22 from the surrounding environment. The solution heater system 500 may thus be constructed to bring the solution temperature inside the heater bag 22, as measured by the button temperature sensor 506, to the desired fluid set point temperature 550 (see FIG. 135) as quickly as possible, and maintaining that desired fluid set point temperature 550 through the rest of the therapy cycle. In some embodiments, the temperature sensors connect to the hardware interface 310. The same hardware interface 310 may control a safety relay that disables the heater.

In some embodiments, the heater elements may include thermal switches that open when the temperature of the switch exceeds a first pre-determined value. The switch will close again once the temperature of the switch drops below the second lower pre-determined value. The thermal switch may be incorporated directly into the heater elements or may be mounted on the outside of the heater element or on the heater pan. The thermal switches provide an additional layer of protection against unsafe pan temperatures.

In another example, the thermal switch may be a thermal fuse with a one-time fusible link. A service call will be required to replace the blown thermal fuse, which may advantageously provide an opportunity to inspect and/or test cycler 14 before restarting therapy. FIG. 134 shows a schematic block diagram of the software context of the heater control subsystem. In an embodiment, the logic of the heater control circuitry 505 may be implemented as a heater control module 509 in the machine control subsystem 342 in the APD System software architecture. The heater controller software may be implemented in the controller 16 (FIG. 127) as described below. Additionally, the therapy subsystem 340 may supply information to the machine control subsystem 342 such as the heater bag volume and the set point for the button temperature sensor 506. The heater elements 508 may be enabled by the therapy subsystem 340. The machine control subsystem 342 may also read temperature values from the I/O subsystem 344, which is located below the machine control subsystem 342. Furthermore, the heater controller 509 may output a PWM signal 511 which may then control the power supplied to the heater elements 508.

In an embodiment, the machine control subsystem 342 may be called periodically (e.g., approximately every 10 milliseconds) to service the I/O subsystem 344, update variables, and detect conditions. The machine control subsystem 342 may also send updated signals to the heater control module 509 periodically (e.g., approximately every 10 ms.). The updated signals may include the heater bag volume, heater pan temperatures 515, the button temperature 517, the set point temperature 550 and the heater enable function. The heater control module may average some or all of these signals continuously, but only calculate and update its output 511 at a lower frequency (e.g, every 2 seconds).

In another aspect, the solution heater system 500 may be able to control the solution temperature in the heater bag 22 within a given range of a desired fluid set point temperature 550 (see FIG. 134 and FIG. 139-141). Furthermore, the solution heater system 500 has been designed to function within pre-defined specifications under a variety of different operating conditions, such as a relatively wide range of ambient temperatures (e.g., approximately 5° C. to approximately 37° C.), bag fill volumes (e.g., approximately 0 mL to approximately 3200 mL), and solution container 20 temperatures (e.g., between approximately 5° C. and approximately 37° C.). In addition, the solution heater system 500 is capable of functioning within specifications even if the solution in the heater bag 22 and the solution introduced during the replenish cycle may be at different temperatures. The solution heater system 500 has also been designed to function within specifications with heater supply voltages varying as much as +10% of nominal voltage.

The solution heater system 500 may be considered to be an asymmetrical system, in which the solution heater system 500 can increase the solution temperature with the heater elements 508, but relies on natural convection to lower the solution temperature in the heater bag 22. The heat loss may be further limited by the insulation 510 and the insulated cover 143. One possible consequence is that in the event of a temperature overshoot, the APD system 10 may delay a patient fill while the heater bag slowly cools. A possible consequence of placing the heater elements on the heater pan 142 is that the heater pan 142 may be at a substantially higher temperature than that of the heater bag 22 during the heating process. A simple feedback control on the heater bag temperature as recorded by the button temperature sensor 506, may not turn the heater off soon enough to avoid the thermal energy at a higher temperature in the heater pan from causing the heater bag 22 to overshoot the desired set point temperature 550. Alternatively controlling the heaters 508 to achieve a heater pan temperature 504 that would not cause the heater bag temperature to overshoot may result in a slow heater system and thus delay therapy.

In order to minimize the time for the solution in the heater bag to achieve the set point temperature 550 without overshoot, the heater control module may implement a control loop that varies the electrical power of the heater elements 508 to achieve a desired fluid temperature in the heater bag, in part by controlling the equilibrium temperature of the heater pan 142, the heater bag 22 and the fluid within the heater bag 22. In one embodiment, a Proportional-Integral (PI) controller controls an equilibrium temperature 532 that is a function of the temperatures of the heater bag 22 and the heater pan 142 and the volume of solution in the heater bag. The equilibrium temperature may be understood to be the temperature that the solution in the heater bag 22 and the heater pan 142 would reach if the heater were turned off and the two components allowed to reach equilibrium. The equilibrium temperature may also be understood as the weighted average of the target temperature for the heater pan 142 and the measured temperature of the solution-filled heater bag, weighted by the thermal capacitance of each. The equilibrium temperature may also be calculated as the weighted average of the measured heater pan temperature and the solution temperature, in which the temperatures are weighted by their respective thermal capacitances. In an embodiment, the weighted average temperature of the heater pan and fluid in the heater bag may be calculated as the sum of the target heater pan temperature times the thermal capacitance of the heater pan plus the fluid temperature times the thermal capacitance of the fluid in the heater bag, where the sum is divided by the sum of the thermal capacitance of the heater pan plus the thermal capacitance of the fluid in the heater bag. The weighted averages of the heater pan and fluid may be alternatively weighted by the mass of the heater pan and fluid in the bag or the volume of the heater pan and fluid in the bag.

The control of the equilibrium temperature may be implemented using a number of control schemes, such as, for example, single feedback loops using proportional, integral and or derivative controllers and nested loops. One embodiment of a control scheme using cascaded nested control loops is shown in FIG. 135. The outer loop controller 514 may control the heater bag temperature as measured by the button temperature sensor 506 to the fluid set point temperature 550 by varying the heater pan set point temperature 527 supplied to the inner loop controller 512. Alternatively, the outer loop controller 514 may control the equilibrium temperature of the heater bag 22, fluid and heater pan 142 to the fluid set point temperature 550 by varying the heater pan set point temperature 527. The temperature of the heater bag 22 and fluid may be measured by the button temperature sensor 506 and the heater pan temperature may be measured by one or more of the heater pan temperature sensors 504. The outer loop controller may include one or more of the following elements: proportional controller, integral controller, derivative controller, saturation limits, anti-windup logic and zero-order hold logic elements.

The inner loop controller 512 may control the heater pan temperature to the heater pan set point temperature 527 by varying the thermal output of the heater elements 508. The temperature of the pan may be measured by one or more of the heater pan temperature sensors 504. The inner loop controller may include one or more of the following elements: proportional controller, integral controller, derivative controller, saturation limits, anti-windup logic and zero-order hold logic elements.

An exemplary implementation of the heater control module 509 utilizes a PI regulator cascade-coupled with a Proportional-Integral-Derivative (PID) controller. In the FIG. 135 embodiment, a PID inner loop controller 512 may control the temperature of the heater pan 142, and a PI outer loop controller 514 may control the equilibrium temperature of the heater bag, the fluid in the heater bag and the heater pan as measured by the heater pan temperature sensors 504 and button temperature sensor 506. The loop controller 514 differs from a standard PI regulator in that any overshoot of the desired fluid set point 550 by the solution heater system 500 may be minimized by a logic controllable integrator as described below. In an embodiment, the heater pan temperature signal 515 and the button temperature sensor (heater bag) signal 517 are low-pass filtered through a pair of control filters 519 at a relatively high frame rate (e.g., a full 100 Hz frame rate), while the heater control module 509 may change the output of the heaters at a lower rate (e.g., rate of ½ Hz).

FIG. 136 shows a schematic diagram of one embodiment of the inner loop controller 512 (heater pan controller). In this embodiment, the inner loop controller 512 uses a standard PID regulator including but not limited to a differencing element 519 to produce a temperature error and a proportional gain element 522 to create an PWM signal 511. The inner loop controller 512 may further include a discrete-time integrator 516 to reduce the offset error. The inner loop controller 512 may also include an anti-windup logic element 518 to minimize overshoot due a temperature error existing for a long period of time when the output of the inner loop controller 512 is saturated. The inner loop controller 512 may further include a discrete derivative term 520 that acts on the heater pan actual temperature 515 to improve heater responsiveness. The inner loop controller 512 may further include a saturation limit element 521 that sets a maximum and/or minimum allowed heater command or PWM signal 511. The inner loop controller 512 may further include zero-order hold logic 523 to hold the PWM signal 511 constant between controller calculations that occur approximately every 2 seconds.

FIG. 137 shows a schematic diagram of the outer loop controller 514 (button temperature sensor controller). In this example, the outer loop controller 514 utilizes a modified PI-type regulator, which may include differencing elements 531, an integrator 534 and a proportional gain element 526. The outer loop controller 514 may further include an integrator switching logic 522 and corresponding switch 529, to allow the integrator to be switched on or off by logic in the heater control module 509. The outer loop controller 514 may further include a command feed forward 524 to improve the responsiveness of the outer loop controller 514. The outer loop controller 514 may further include a proportional feedback term 526 to act on a weighted combination of the button temperature sensor target temperature 517 and the heater pan target temperature 527. The resulting measurement is an equilibrium temperature 532 as described above. The outer loop controller 514 may further include a saturation limit element 521 and/or a low pass filter 542. The saturation limit element 521 in the outer loop sets a maximum allowed target pan temperature 527. The low pass filter 542 may be designed to filter out transient control signals at frequencies outside the bandwidth of the solution heater system 500.

The integral elements 534 in the outer loop controller 514 may be turned on by a switch 529 when some or all of the following conditions are present: the rate of change of the button temperature 517 is below a pre-determined threshold, the button temperature 517 is within a pre-determined number of degrees of the fluid set point temperature 550, or the bag volume is greater than a pre-determined minimum and neither of the controllers 512, 514 are saturated. An equilibrium temperature feedback loop may control the transient behavior of the solution heater system 500, and may be dominant when the surrounding ambient temperature is in a normal to elevated range. The action of the integrator 516 may only be significant in colder environments, which may result in a substantial temperature difference between the button sensor actual temperature 517 and the heater pan actual temperature 515 at equilibrium. The feed-forward term 524 may pass the fluid set point temperature 550 through to the heater pan target temperature 527. This action will start the heater pan target temperature 527 at the fluid set point temperature 550, instead of zero, which thereby improves the transient response of the solution heater system 500.

The heater module 509 may also include a check that turns off the PWM signal 511 if the heater pan actual temperature 515 crosses a pre-determined threshold (this threshold may be set to be slightly higher than the maximum allowed heater pan target temperature 527). This check may not be triggered under normal operation, but may be triggered if the heater bag 22 is removed while the temperature of the heater pan 142 is at a pre-determined maximum value.

The PI controller 514 may include a proportional term that acts on the equilibrium temperature 532. The equilibrium temperature is the heater bag temperature measured by the button sensor 506 that would result if the heater 508 was turned off and the heater pan 142 and the solution-filled heater bag 22 were allowed to come to equilibrium. The equilibrium temperature can be better understood by referring to FIG. 138, which shows a schematic block diagram of the heater pan 142 and heater bag 22 in a control volume analysis 546. The control volume analysis 546 depicts a model environment in which the equilibrium temperature

532 may be determined. In this illustrative embodiment, the solution heater system 500 may be modeled in as control volume 548, which may comprise at least two thermal masses: the heater pan 142 and the heater bag 22. The boundary of the control volume 548 may be assumed to function as a perfect insulator, in which the only heat transfer is between the heater pan 142 and the heater bag 22. In this model, thermal energy 549 may be added to the system via the heater elements 508, but thermal energy may not be removed from the heater pan 142 and heater bag 22. In this model, as in the solution heater system 500, it is desirable to heat the heater pan 142 just enough that the heater bag 22 reaches its target temperature as the heater pan 142 and heater bag 22 come to equilibrium. Therefore, the equilibrium temperature 532 may be calculated as a function of the initial temperature of the heater bag 22 and the initial temperature of the heater pan 142:

$$E = M_P C_p T_p + V_b \rho_b C_b T_b = (M_P C_p + V_b \rho_b C_b) T_e$$

where $M_P$, $c_p$ are the mass and specific heat of the heater pan 142, $V_P$, $\rho_b$, $c_b$ are the volume, density and specific heat of the solution in the bag, $T_p$ and $T_b$ are the temperatures of the heater pan 515 and the button 517 respectively. Solving for the equilibrium temperature yields a linear combination of pan and button temperatures:

$$T_e = cT_b + (1-c)T_p$$

where $$C = \frac{V_b}{k + V_b} \text{ and } k = \frac{M_P C_p}{\rho_b C_b}$$

The constant c is an equilibrium constant, k is the thermal capacitance ratio of the heater pan over the solution. The subscript b denotes the solution in the heater bag 22, while p denotes the heater pan 142.

In this model, allowing the heater module 509 to control the equilibrium temperature 532 during the initial transient may allow for rapid heating of the heater bag 22 while also reducing the heater pan actual temperature 515 sufficiently early to prevent thermal overshoot. The c parameter may be determined empirically. The heater module 509 may set c to a value larger than the measured value to underestimate the total energy required to reach the desired set point 550, further limiting the thermal overshoot of the solution heater system 500.

FIG. 139 shows graphically the performance of solution heater system 500 of the disclosed embodiment operating under normal conditions. The measured temperatures of the heater pan sensors 504, the button temperature sensor 506 and an additional temperature probe are plotted against time. The fluid temperature probe was part of the experimental setup up to verify the control scheme. The fluid probe temperature is shown as line 552. The button temperature is shown as line 517 and the heat pan temperatures are shown as line 515. Line 550 is the target temperature for the button temperature sensor 506. At the start of this trial, the heater bag is substantially empty, the heater is off and fluid is not moving, so that all the temperatures are at a nominal value. At a time T=1, the fluid at 25 C starts to flow into the heater bag 22 bringing down the probe and button temperatures 552, 517, while the heater turns on and increases the heater pan temperature 515. Under normal operation, proportional control of the equilibrium temperature 532 may be sufficient to heat the solution within the heater bag 22 to a temperature close to the desired fluid set point temperature 550. Therefore, in FIG. 139, the solution heater system 500 functions effectively, and the heater pan actual temperature 515, the button sensor actual temperature 517, and a probe temperature 552 all converge to the fluid set point temperature 550 within approximately 50 minutes.

FIG. 140 shows graphically the performance of the solution heater system 500 operated in a high temperature environment in which the ambient temperature is 35 C. As described above, the trial begins with the heater bag being substantially empty. Once the fluid starts to flow and the heater turns on, the probe and button temperatures 552, 517 decrease and the heater pan temperature 515 increases. In a high temperature environment, the solution heater system 500 functions in a manner substantially similar to normal conditions. Thus, proportional control of the equilibrium temperature 532 may again be sufficient to heat the solution within the heater bag 22 to a temperature close to the desired fluid set point temperature 550. In FIG. 139, the solution heater system 500 functions effectively and within desired specifications, and the heater pan actual temperature 515, the button sensor actual temperature 517, and a probe temperature 552 all converge to the desired set point temperature 550 within approximately 30 minutes.

FIG. 141 shows graphically the performance of the solution heater system 500 operated in a cold environment where the ambient temperature is 10 degrees C. and the source fluid is 5 degrees C. As described above, the trial begins with the heater bag being substantially empty. Once the fluid starts to flow and the heater turns on, the probe and button temperatures 552, 517 decrease and the heater pan temperature 515 increases. In a cold environment, setting the desired fluid set point temperature 550 equal to the equilibrium temperature 532 may lead to a steady-state error in the temperature of the button sensor 506. The heat loss in cold environments may necessitate a large temperature difference between the heater pan 142 and the button sensor 506 during thermal equilibrium. Since the equilibrium temperature 532 is a weighted sum of the heater pan 142 and the button sensor 506, the temperature of the button sensor 506 may be below the fluid set point temperature 550 if the temperature of the heater pan 142 is above the desired fluid set point temperature 550 at equilibrium. This may occur even if the equilibrium temperature 532 is equal to the fluid set point temperature 550. To compensate for this steady-state-error an integral term may be added to outer PI controller 514 that acts on the temperature error of the button sensor 506. The integrator 538 may be turned on when one or more of the following conditions are met: a first derivative of the temperature of the button sensor 506 is low; the button sensor 506 is close to the fluid set point temperature 550, the volume of the heater bag 22 exceeds a minimum threshold; and neither inner PID loop 512 or outer PI controller 514 are saturated. In this illustrative embodiment, the switching of the integral term may minimize the effect of the integrator 538 during normal operation and may also minimize the overshoot caused by integration during temperature transients. Therefore, in FIG. 141, the solution heater system 500 functions effectively and within desired specifications, and the heater pan actual temperature 515, the button sensor actual temperature 517, and a probe temperature 552 all converge to the fluid set point temperature 550 within approximately 30 minutes.

In summary, the disclosed temperature controller can achieve good thermal control of a two component system, in which the mass of the first component varies over time, and in which the second component includes a heater or cooler, and both components are in an insulated volume. This thermal control can be achieved by controlling the equilibrium temperature. The temperature controller determines the temperature of both components as well as the mass of the variable component. The temperature controller varies the heating or cooling of the second component to bring the equilibrium temperature to the desired set point temperature. The equilibrium temperature is the thermal capacitance weighted average temperature of the two components. The controller may use a proportional feedback loop to control the equilibrium temperature.

The temperature controller may also include an integral term that responds to the difference between the set point temperature and the temperature of the first component. The integral term optionally may be turned on when some or all of the following conditions are met:
- the rate of temperature change of the first component is low;
- the temperature of the first part is near the set point temperature;
- the volume of the first part exceeds some minimum level;
- the control output signal is not saturated.

The temperature controller may also include a feed-forward term that adds the set point temperature to the output of the proportional and integral terms.

Further, the temperature controller may be the outer loop controller of a cascade temperature controller in which the outer loop controller includes at least a proportional control term on the equilibrium temperature and outputs a set point temperature for the inner controller. The inner controller controls the temperature of the first component with the heater or cooler elements to the set point temperature produced by the outer controller.

Universal Power Supply

In accordance with an aspect of the disclosure, the APD system 10 may include a universal power supply that converts line voltage to one or more levels of DC voltage for some or all of the electro-mechanical elements and electronics in the cycler 14, and provides AC power to the electric heater for the heater pan 142. The electro-mechanical elements in the cycler 14 may include pneumatic valves, electric motors, and pneumatic pumps. The electronics in the cycler 14 may include the control system 16, display 324, and sensors. AC power is supplied to a heater controller to control the temperature of the solution in the heater bag 22 on the heater tray 142 to a desired set point prior to delivering the solution to the user/patient. The universal power supply changes the configuration of two (or more) heater elements to accommodate two ranges of AC line voltages: e.g., a first range of 110±10 volts rms; and a second range of 220±20 volts rms. This arrangement is intended to accommodate using the APD system 10 in a number of different countries. During the start of a therapy session, the APD cycler 14 fills the heater bag 22 with solution from the connected solution containers 20, via a heater bag line 26. In an alternative embodiment, a pre-filled bag of solution may be placed on a heater pan 142 at the start of a therapy.

PWM Heater Circuit

The heater controller in the APD cycler modulates the electrical power delivered to the heater elements attached to the heater pan 142. The APD cycler may be used in various locations around the world and may be plugged into AC mains that supply power from 100 to 230 volts rms. The heater controller and circuits may adapt to the variety of AC voltages while continuing to supply sufficient heater power and not blowing fuses or damaging heater elements in a number of ways.

One embodiment of a heater circuit is presented in FIG. 142, where a pulse width modulator (PWM) based circuit 2005 controls the temperature of the heater pan 142 with a pulse-width-modulated (PWM) element 2010 connected between one lead of the AC mains 2040 and the heater element 2000. The controller 2035 is operably connected to the relay 2030 and the PWM element 2010. The controller 2035 monitors the operation of the heater by interrogating the voltage detect 2020 and temperature sensor 2007. The controller 2035 may modulate the amount of power delivered to the heater 2000 via a signal to the PWM element 2010. The PWM or pulse-width-modulated element is closed for some fraction of a fixed period between 0 and 100%. When the PWM element 2010 is closed 0% of the time, no electrical energy flows to the heater 2000. The heater is continuously connected to the AC mains 2040 when the PWM element is closed 100%. The controller 2035 can modulate the amount of power dissipated by the heater 2000 by setting the PWM element 2010 to a range of values between 0 and 100%, inclusive.

The PWM elements 2010 switch large current flows on and off multiple times a second. PWM elements 2010 are typically some kind of solid state relay (SSR). SSRs for AC voltage typically include a triggering circuit that controls the power switch. The triggering circuit may be, for example, a reed relay, a transformer or an optical coupler. The power switch may be a silicon control rectifier (SCR) or a TRIAC. The SCR or TRIAC are also referred to as thyristors. One example of a SSR is the MCX240D5® by Crydom Inc.

In one example, the controller 2035 may modulate the PWM element value in order to control the temperature of the heater pan 142 as measured by temperature sensor 2007. In another example, the controller 2035 may modulate the PWM element value to control the temperature of the fluid in the heater bag 22. In another example the controller 2935 may control the PWM element 2010 to provide a fixed schedule of heater power. The controller 2035 may command a safety relay 2030 that opens the heater circuit and stops the flow of electrical power to the heater 2000. The safety relay 2030 may be controlled by a separate controller (not shown) in order to provide a safety circuit independent of the controller 2035.

The PWM based circuit 2005 may include a voltage detect element 2020 that provides a signal to the controller 2035 indicative of the voltage on the AC mains 2040. In one example, the voltage detect element 2020 may measure the AC potential across the AC mains 2040. In another example the voltage detect element 2020 may measure the current flow through the heater 2000. The controller 2035 may calculate the voltage across the AC mains from a known resistance of the heater element 2000, the PWM element 2010 signal and the measured current.

The PWM based circuit 2005 may vary the maximum allowed duty cycle of PWM element 2010 to accommodate different AC Mains voltage. The heater element 2000 may be designed to provide the maximum required power with the lowest possible AC voltage. The controller may vary the duty cycle of the PWM element 2010 to provide a constant maximum heater power for a range of voltages at the AC mains. For example, the voltage supplied to the heater 2000 from a 110 volt AC line may be supplied at a 100% duty cycle, and the same amount of electrical power may be delivered to the heater 2000 from a 220 volt AC line if the PWM element 2010 is set to 25%. The duty cycle of the PWM element 2010 may be further reduced below the maximum value to control the temperature of the heater pan 142.

The temperature of the heater element 2000 and the heater pan 142 may be controlled by the average heater power over a time constant that is a function of the thermal mass of the element and heater pan. The average heater power may be calculated from the heater resistance, which is relatively constant, and the rms voltage across the heater element 2000. In a practical sized heater, the PWM frequency is much faster than the time constant of the heater system, so the effective voltage across the heater element is simply the PWM duty cycle multiplied by the rms voltage.

One method to control the heater pan temperature of the circuit in FIG. 142 may direct the controller 2035 to set a maximum PWM duty cycle based on the measured voltage at 2020. The maximum duty cycle may be calculated from the desired maximum heater power, known resistance of the heater element 2000 and the measured voltage. One possible example of the calculation is:

$$PWM_{MAX} = (P_{MAX} * R_{HEATER})^{0.5} / V_{rms}$$

where $PWM_{MAX}$ is the maximum allowed PWM duty cycle, $P_{MAX}$ is the maximum heater power, $R_{HEATER}$ is the nominal resistance of the heater element 2000, and $V_{rms}$ is the supplied voltage as measured by the Voltage Detect 2020. Another example of the calculation is:

$$PWM_{MAX} = P_{MAX} / (I^2 * R_{HEATER})$$

where I is the current flow through heater when the voltage is applied. The controller 2035, after setting the maximum PWM duty cycle, then varies the PWM duty cycle of the PWM element 2010 to control the temperature of the heater pan 142 as measured by a temperature sensor 2007. The controller may control the PWM element to achieve a desired temperature in a number of ways, including, for example, a PID feedback loop, or a PI feedback system.

In an alternative method and configuration, the PWM circuit 2005 does not include the voltage detect 2020. In this alternative method the controller 2035 varies the PWM duty cycle of the PWM element 2010 to achieve the desired heater pan temperature as measured by temperature sensor 2007. The controller 2035 begins the heating cycle at a minimum PWM duty cycle and increases the PWM duty cycle until the temperature sensor reports the desired temperature to the controller 2035. The rate of increase of the PWM rate may be limited or controlled to avoid excessive currents that could trip and blow the fuses 2050. The controller 2035 may alternatively use small gains in a feedback calculation to limit rate of PWM duty cycle increase. Alternatively the controller may use a feed forward control to limit the rate of PWM duty cycle increase.

Dual-Voltage Heater Circuit

An example of a dual-voltage heater circuit 2012 that changes the resistance of the heater is shown as a schematic block diagram in FIG. 143. The block diagram in FIG. 143 presents one example of a dual-voltage heater circuit 2012 to provide approximately constant heater power for the two standard AC voltages of 110 and 220 volts rms. Dual-voltage heater circuit 2012 limits the maximum current flow by reconfiguring the heater and thus is less sensitive to software errors setting the duty cycle of the PWM element as in circuit 2005. Circuit 2012 lowers the maximum current flows through the PWM element 2010 which allows for smaller and less expensive SSRs. The selection of the heater configuration in circuit 2012 is separated from the heater modulation to improve control and reliability. The PWM elements 2010A, 2010B that modulate the heater power are typically SSR, which typically fail closed, thus providing maximum power. The heater select relay 2014 may be an electromechanical relay, which while less than ideal for high cycle applications, may typically be preferred for safety critical circuits, due in part to the tendency of electromechanical relays to fail open. The selection of the heater configuration by the processor allows more control of heater configuration.

In the event of the AC Mains voltage fluctuating, perhaps due to a brown-out, the controller preferably holds the heater configuration constant. In contrast, a circuit that automatically changes the heater configuration based on the instantaneous voltage could fluctuate between heater configurations. This may result in high current flows if the circuit does not respond fast enough to line voltage that returns to its original level from a temporarily lower level. This is more likely to be a problem when only a hardware-enabled circuit is used to respond to voltage fluctuations. A more efficient and reliable solution may be obtained if a programmable controller is used to either analyze the likely cause of the input voltage fluctuation, or to respond only to the measured current flow through the heater averaged over a period of time. In an embodiment, the processor receives input from the user or patient in selecting the heater configuration (parallel or series), and the dual-voltage heater circuit 2012 does not automatically switch between configurations in response to fluctuating line voltage. In another embodiment, the processor measures the current flow in the series configuration (i.e. the higher resistance configuration) at full power, selects a heater configuration appropriate to the AC mains voltage at the start of therapy, and does not change configuration for the duration of therapy.

The dual-voltage heater circuit 2012 may comprise two heater elements 2001, 2002 that can be connected in parallel or in series with one another to provide the same heater power for two different voltages at the AC mains 2040. Each heater element 2001, 2002 may comprise one or more heater sub-elements. The electrical resistance of heater elements 2001, 2002 is preferably approximately equal. The controller 2035 may receive a signal from the current sense 2022 and control the heater select relay 2014 to connect the heater elements 2001, 2002 in either series or parallel. The controller 2035 may change the electrical arrangement of the two heater elements to limit the current flow resulting from different AC mains voltages. One example of a current sense 2022 is a current sense transformer AC-1005 made by Acme Electric.

The power in the heater elements 2001, 2002 may be further modulated by the PWM elements 2010A, 2010B controlled by the controller 2035 to achieve a desired temperature as measured by temperature sensor 2007, or to achieve other control goals as described above. The PWM elements 2010A, 2010B may be a solid state relays such as MCX240D5® by Crydom Inc. The safety relay 2030 may be configured to disconnect the heater elements 2001, 2002 from the AC mains 2040. The safety relay 2030 may be controlled by the controller 2035 or another processor or safety circuit (not shown).

The safety relay 2030 and heater select relay 2014 may be solid state or electro-mechanical relays. In a preferred embodiment, the safety relay 2030 and/or heater select relay 2014 are electro-mechanical relays. One example of an electro-mechanical relay is a G2AL-24-DC12 relay made by OMRON ELECTRONIC COMPONENTS and other manufacturers. Electro-mechanical relays are often preferred for safety critical circuits as they are considered to be more robust and more reliable than solid state relays, and have a tendency to fail open. They may also be less susceptible to various failures in the controller software.

In one example, the heater select relay 2014 comprises a double-pole double-throw relay, in which the outputs connect to the heater elements 2001, 2002. The heater select relay 2014, in the non-energized state, connects the heater elements 2001, 2002 in series such that the current flows through one element and then the other. The series configuration may be achieved, in one example circuit, by the following: connect the first end of the heater element 2001 to L1 circuit 2041 via PWM element 2010A; connect the joined ends of heater elements 2001, 2002 to an open circuit via the first pole 2014A; connect second end of heater element 2002 to the L2 circuit 2042 via the second pole 2014B. In an energized state, the heater select relay 2014 connects the heater elements in parallel such that approximately half the current flows through each PWM and heater element. The parallel configuration may be achieved in the same example circuit by the following: connect the first end of the heater element 2001 to L1 circuit 2041 via PWM element 2010A; connect the second end of heater element 2002 to the L1 circuit 2041 via PWM element 2010B; connect the joined ends of heater elements 2001, 2002 to L2 circuit 2042 via the first pole 2014A. The preferred circuit connects the heater elements 2001, 2002 in series in the unpowered condition as it is a safer configuration because the resulting higher resistance will limit current flows and avoid overloading the fuses 2050, or overheating the heating elements 2001, 2002 if connected to a higher voltage AC main.

Another example of a heater circuit 2112 that changes the effective resistance of the heater by changing the heater configuration is shown in FIG. 144 as a schematic block diagram. The heater circuit 2112 is similar to heater circuit 2012 (shown in FIG. 143) except that heater circuit 2112 provides better leakage current protection in the event that the L1 and L2 power circuits are reversed at the wall socket. The reversal of the L1 and L2 power circuits is possible if the power was incorrectly wired in the building that supplies power to the heater circuit. Wiring in a residential building may not be as reliable as a hospital, where all the electrical system is installed and maintained by qualified personnel.

The electrical components and connections between the PWM elements 2010A, 2010B, the nominal L1 circuit 2041, heater elements 2001, 2002, heater select relay 2014 and the nominal L2 circuit 2042 in heater circuit 2112 are arranged to minimize leakage current regardless of wall socket polarity. In the non-energized state as shown in FIG. 144, the heater select relay 2014 connects the heater elements 2001, 2002 in series with the PWM element 2010A. One possible circuit that connects the heater elements in series includes: the first end of heater element 2001 connected to the L1 circuit 2041 via PWM element 2010A; the second end of heater element 2001 connected to the first end of heater element 2002 via the first pole 2014A, a L1 2014C and the second pole 2014B; and the second end of heater element 2002 connected to the L2 circuit 2042 via PWM element 2010B. In the energized state, the heater elements 2001, 2002 and PWM elements 2010A, 2010B are connected in parallel. In an energized state, the heater select relay 2014 connects the heater elements in circuit 2122 in parallel such that approximately half the current flows through each PWM and heater element. One possible circuit to connect the two heater and PWM elements in parallel includes: the first end of heater element 2001 connected to the L1 circuit 2041 via PWM element 2010A; the second end of heater element 2001 connected via the first pole 2014A to the L2 circuit; the first end of heater element 2002 is connected to the L1 circuit 2041 via the second pole 2014B; the second end of heater element 2002 is connected to the L2 circuit 2042 via the PWM element 2010B. The safety relay 2030 is located on the L2 circuit 2042 and creates a fail-safe condition of no current flow by opening if a fault occurs. The control of the safety relay is described below. The controller 2035 controls the heater configuration to limit the current flow as measured by the current sense 2022 to levels below the current rating for the fuses 2050, heater elements 20001, 2002, the PWM elements 2010A, 2010B and limits total heater power. The controller 2035 varies the duty cycle of the PWM elements 2010A, 2010B to control the heater pan 142 temperature as measured by the sensor 2007.

Dual-Voltage Heater Circuit Implementation

A circuit diagram 2212 of one embodiment of the present invention is shown in FIG. 145, which is equivalent to heater circuit 2012 in FIG. 143. In the circuit 2212, the heater elements 2001, 2002 are connected in series by the heater select relay 2014 when the relay coil 2014D is not energized. The controller (not shown) connects the heater elements 2001, 2002 and PWM elements 2010A, 2010B in parallel by supplying a signal at node 2224, which closes transistor switch 2224A, and energizing the relay coil using the Vs DC power 2214, The controller modulates the heater power by varying the duty cycle of the PWM elements 2010A, 2010B through a signal at node 2220 and powered with Vsupply 2210. The current flow is measured with the current sense 2022. The safety relay 2030 is normally open. The safety relay 2030 may be controlled by an FPGA board that is separate from the controller. The FPGA board monitors the operation of the APD cycler, including the heater pan temperature and the current sense and several other parameters. The FPGA board may open the relay by removing the signal at node 2228. The safety relay coil 2030D is powered by the Vsafety 2218.

In one example, the voltage supplying Vsupply 2210, Vs 2214, Vsafety 2218 may be the same voltage source. In another example each voltage source be controllable to provide additional operation control of the heater circuit for added safety. In one example the Vsafety 2218 may be controlled by multiple processors in the APD cycler 14. If any of the processors detects an error and fails, then the Vsafety circuit is opened, the Safety Relay 2030 is opened and heater power is turned off.

Dual-Voltage Heater Circuit Operation

In a typical dual-voltage scenario, a user may wish to use the peritoneal dialysis cycler in either a 110 volt environment or a 220 volt environment (i.e. in most cases a 100% difference in voltage to which the device may be exposed). More generally, however, the dual-voltage heater circuit can be configured for any scenario in which a first voltage and a second higher voltage may be used. The circuit switching system would only be limited by the ability of the controller to discriminate between the current flows resulting from a first voltage or a second voltage being applied to the heater. The elements of the system can include a heater comprising a first heater element connected to a second heater element by a heater select relay, the heater select relay being configured to connect the first heater element either in series or in parallel with the second heater element. A current sense element is configured to measure current flow through the heater. A controller can then be configured to receive the current flow information from the current sense element, and command the heater select relay to switch to either a parallel or series configuration to more closely approximate a current flow that has been pre-determined to provide an optimal degree of heater function and responsiveness. In most cases, it may be safer to have the cycler power up for initial use in a default mode with the heater select relay in a series configuration.

The heater circuit is operated to provide adequate heater power without allowing damaging currents to flow through the heater elements 2001, 2002 or the fuses 2050. The heater circuit 2212 may be configured before the therapies are run on the APD cycler 14 and not changed during operation regardless of the voltage changes in the AC mains. The control system 16 (in FIG. 127) starts up the heater control circuit 2212 with the heater select relay 2014 un-energized, so the heater elements are connected in series to minimize the current. As one part of the startup processes, software in the automation computer 300 may run a current flow test of the heaters by commanding the PWM elements 2010A, 2010B to 100% duty cycle and the resulting test current is measured by the current sense 2022 and communicated to the automation computer 300. The duty cycle of the PWM elements 2010 may be reset to zero after current flow test.

In one example method, the automation computer 300 evaluates the measured test current against a predetermined value. If the measured test current is above a given value, the automation computer 300 will proceed with the ADP cycler startup procedure. If the measured test current value is below that same given value, then the automation computer 300 will energize the heater select relay to reconfigure the heater elements 2001, 2002 in parallel. The current flow test is repeated and if the new measured test current is above the predetermined value the automation computer 300 will proceed with the ADP cycler startup procedure. If the measure test current from the current flow test with parallel heater elements, is below above the predetermined value, the automation computer 300 will signal an error to the user interface computer 302.

Alternatively, the automation computer 300 may calculate a test voltage based on the measured test current and heater element configuration. If the test voltage is in the range of 180 to 250 volts rms, then the automation computer 300 will proceed with the ADP cycler startup procedure. If the test voltage is in the range of 90 to 130 V rms, then the automation computer 300 will energize the heater select relay to reconfigure the heater elements 2001, 2002 in parallel, repeat the current flow test, and recalculate the test voltage. If the test voltage is in the range of 90 to 130 V rms, the automation computer 300 will proceed with the ADP cycler startup procedure, if not automation computer 300 will signal an error to the user interface computer 302.

In another example method, the automation computer 300 compares the measured test current with the heater elements configured in series to a series-low-range and series-high-range of current values. The series-low-range is consistent with a low AC voltage flowing through the heater elements arranged in series. The series-high-range is consistent with a high AC voltage flowing through the heater elements arranged in series. In an exemplary embodiment, the low AC voltage includes rms values from 100 to 130 volts, while the high AC voltage includes rms values from 200 to 250 volts.

If the measured test current is outside of low-range and the high-range, then the automation computer 300 may determine that the heater circuit is broken and signal an error to the user interface computer 302. If the measured test current is within the high-range, the heater configuration is left unchanged and the startup of the APD cycler 14 may continue. If the measured test current is within the low-range and the heater elements are arranged in series, then the automation computer 300 may reconfigure the heater elements 2001, 2002 to a parallel arrangement by energizing the heater select relay 2014 through a signal at node 2224. The automation computer 300 may control the heater select relay 2014 via a command sent to the hardware interface 310 that in turn provides the signal to actuate the heater select relay 2014.

The automation computer 300 may repeat the current flow test after reconfiguring the heater elements into a parallel arrangement by again commanding the PWM elements 2010A, 2010B to 100% duty cycle and measuring the current flow with the current sense 2022. The measured test current may be evaluated against the parallel-low-range of current values. If the measured test current is within the parallel-low-range values proceed with the ADP cycler startup procedure. If the newly measured test current is outside the parallel-low-range values, then automation computer 300 will signal an error to the user interface computer 302.

The FPGA controller implemented in the hardware interface 310 may be programmed to command the safety relay 2030 to open through a signal at node 2228 while the heater select relay 2014 is switched. The safety relay 2030 may be opened each time the heater select relay 2014 is opened or closed to prevent a short circuit from one pole to the other within the heater select relay 2014.

Dual-Voltage Heater Circuit Operation with User Input

In an alternative embodiment, the automation computer 300 may require user intervention before reconfiguring the heater elements 2001, 2002. Requiring user input provides a valuable safety feature of one embodiment of the present invention. FIG. 146 shows a logic flow chart illustrating a method 2240 to include the user in configuring the heater elements appropriately for the available AC voltage. In step 2241, the control system 16 (in FIG. 127) starts up the heater control circuit 2212 (FIG. 145) with the heater select relay 2014 un-energized, so the heater elements are connected in series to minimize the current. In setup 2242, the automation computer 300 commands the PWM elements 2010A, 2010B to 100% duty cycle and the current is measured by the current sense 2022 and the measure test current is communicated to the processor. The duty cycle of the PWM elements 2010 may be reset to zero after the test current is measured. In step 2244, the automation computer 300 compares the measured test current to a first range. In step 2245, if the measured test current is within the first range, then the heater configuration is correct and the APD operation proceeds in step 2254. In an alternative embodiment, method 2240 includes step 2245A where the user interface computer 302 ask the user to confirm the AC mains voltage that the automation computer 300 determined from measured test current and the heater configuration before proceeding from step 2245. If the user does not confirm the AC voltage level, method 2240 will proceed to step 2252 and displays an error.

In step 2246, if the measured current is outside the second range, then method 2240 displays an error in step 2252, otherwise the method 2240 proceeds to step 2247. In step 2247, if the user confirms low AC voltage then the heater configuration will be changed in step 2248, otherwise the method 2240 displays an error in step 2252. In step 2248, the automation computer 300 reconfigures the heater elements 2001, 2002 to a parallel arrangement by energizing the heater select relay 2014 through a signal at node 2224. After reconfiguring the heater elements in step 2248, the method 2240 retests the heater in step 2242 and continues through the logic flow chart of method 2240.

An alternative embodiment, a user or patient may store the AC voltage as high or low in the memory of the control system 16 so that the automation computer 300 need not query the user or patient at each treatment to confirm the AC voltage. FIG. 147 shows a logic flow chart illustrating a method 2260 where the AC voltage value is stored in the memory of the control system 16. The steps 2241 through 2246 are the same as method 2240 described above. In step 2249, the memory is queried for the stored AC voltage value. If the stored AC voltage value is low, then the method 2260 proceeds to step 2248 and reconfigures the heater elements into a parallel arrangement. If the stored AC voltage is high nor zero, then the user interface computer 302 may query the user to confirm a low AC mains voltage. If a user confirms the low AC voltage, then the method 2260 proceeds to step 2248 and reconfigures the heater elements into a parallel arrangement. Step 2248 may also include the setting the stored AC voltage to low. After reconfiguring the heater elements in step 2248, the method 2260 retests the heater in step 2242 and continues through the logic flow chart of method 2260.

In one example, method 2260 may include a step 2245A which reads from memory or calculates the test voltage from the measured test current and heater configuration and then has the user interface computer 302 asks the user to confirm the test voltage. The method may include a step between 2245 and 2246, where if the heater has been reconfigured to a parallel arrangement and the current is not within the high range, then the method proceeds to step 2252 and shuts down the APD cycler 14.

The methods 2240 and 2260 may evaluate the measured test current by a number of different methods. A preferred method was described above and alternative examples are as are described below. The first range in step 2245 may be a range of current levels that would provide the desired amount of maximum heater power for the current heater element configuration. Alternatively step 2245 may calculate a test voltage from the measured test current and heater element configuration and evaluate if the test voltage is correct for the heater configuration: approximately 110 V rms for parallel configuration and approximately 220 V rms for series configuration. Alternatively step 2245 may test if the measured test current is above a given predetermined value. The second range in step 2246 may be a range of current values corresponding to approximately 110 V rms in a series configuration. Alternatively step 2246 may calculate a test voltage from the measured test current and heater element configuration and evaluate if the test voltage approximately 110 V rms for a series configuration. Alternatively, step 2246 may evaluate if the measure test current is below a given predetermined value.

In another embodiment, the selected AC voltage value in method 2260 may be preloaded in the factory or distribution center based on the expected location of usage. For example, the AC voltage value may be selected for low if the APD cycler will be used in the US, Canada or Japan. For another example, the AC voltage value may be selected for high if the APD cycler will be used in Europe, or Asia.

For machines expected to operate in a given region, this database may be as simple as a regional voltage being loaded on the machine at the factory, or loaded by a technician during initial set-up at a place of operation. These regional AC voltage value prescriptions may be entered manually, using a memory stick or similar device, using a personal data key (PDK), a compact disc, bar code reader over the world wide web using an Ethernet or wireless connection or by any other data transfer mechanism obvious to one skilled in the art. In other embodiments, sets of regional voltages may be accessible to control system 16 and may be used to inform a user of the typical operating voltage in his or her area. In one embodiment, prior to accepting a user input in step 2247 to change voltage from a previous setting, a user would be informed of the typical voltage of a region; thus a user unfamiliar with the value of regional voltages would only be required to know his or her current location to provide a safeguard against voltage incompatibility.

In another embodiment, APD cycler 14 would be equipped with a mechanism to determine its current location, for example a GPS tracker, an Ethernet connection and a mechanism to determine the location of the connection, or a mode where user interface 302 can be used to enter the present location, such as country or continent. In an embodiment, after starting up in a series heater configuration and running a current flow test, a user may simply be queried as to his or her present location; if the response to that query matches both the voltage associated with the measured test current and heater configuration and the typical voltage for that region, then treatment is allowed to proceed.

In one embodiment of the present invention a manual switch (not shown), or alternately a logic switch, is used to set the APD machine to the appropriate, safe voltage for use. The instantaneous voltage is measured and this measurement, either as the specific value or as a categorical descriptor, is displayed to the user. The user must respond that the measured voltage is within the safe operating range for the machine as currently configured, or alternately must respond by altering the configuration of the machine, before power is allowed to flow to the heating element. The configuration could be altered electronically, for example via the user interface computer 302, or could be performed manually by flipping a switch.

In another embodiment of the present invention, a rectifier converts any incoming alternating current (AC) into a single direct current (DC). The heater circuit would resemble heater circuit 2005 in FIG. 140 except the voltage detect 2020 element is replaced with a universal DC supply that rectifies the AC voltage into a selected DC voltage. The electrical power supplied to the heater elements 2001, 2002 may be modulated by a PWM element in the rectifier or by a separate PWM element 2030. The heater circuit may include a safety relay 2010. The single voltage DC power source allows the use of one heater configuration. The PWM element 2030 in this embodiment may comprise one or more IGBT or an MOSFET switches and related electrical hardware. In a preferred embodiment, the incoming alternating current would be converted to direct current in the range of 12V to 48V.

In another embodiment, the heater element 2000 may comprise a Positive Temperature Coefficient (PTC) element that self limits the power dissipated. The internal electrical resistance of a PTC element increases with temperature, so the power level is self limiting. PTC heater elements are commercially available from companies such as STEGO that are rated to run on voltages from 110 to 220 V rms. A heater circuit employing a PTC heating element would resemble heater circuit 2005 with the voltage detect element 2020 removed. The heater power would be controlled with the PWM element 2010 using a Triac.

Additional Heater Circuit Embodiments

In another embodiment of the dual voltage heater circuit, the heater elements are separated from both lines of the AC mains by modulating switches. This embodiment may also comprise AND circuitry that closes the modulating switches only when both a first controller and a second controller enable the modulating switch. The first controller may send PWM signals to the modulating switches in order to control the electrical power delivered to the heater elements. The second controller may enable the modulating switches if the PD system is operating in an acceptable manner. The second controller may disable the modulating switches if an alert or an alarm or an unsafe condition exits. The AND circuitry that allows control of the modulating switches removes the need for separate safety relays. This embodiment may include a voltage selector switched that may be controlled with a signal from the controller, or a external switch controlled by the user, or a jumper wire for manual switching.

FIG. 148 depicts an example heater circuit 2930 which may be included in any fluid handling device, such as an automated peritoneal dialysis machine. The example heater circuit 2930 depicted in FIG. 148 includes an adaptive or reconfigurable heater element 2917 which may be configured to operate at a plurality of voltages while still producing approximately the same heat output. Additionally, the heater circuit 2930 provides enhanced leakage protection even in the event that the line and neutral wires are reversed at a wall socket.

As shown, the heater circuit 2930 in FIG. 148 includes a controller 2904. The controller 2904 may control various components of the heater circuit 2930. In some embodiments, the controller 2904 may include one or more processors. For example, the controller 2904 may include a control processor and a safety processor which is independent of the control processor. The controller 2904 may control the temperature of a heater pan 2914 by selectively connecting a line end of the AC mains 2900 to a heater element 2917 and enabling current flow through the heater element 2917. In the example embodiment, the heater element 2917 includes a set of two resistive elements 2918A, 2918B. In other embodiments, the heater element 2917 may include more than two resistive elements, or additional sets of resistive elements. Additionally, each resistive element, may in some embodiments include one or a number of sub elements.

As shown, the configuration of the resistive elements 2918A, 2918B of the heater element 2917 is alterable by means of a heater select relay 2920. The heater select relay 2920 may be controlled by means of a signal from the controller 2904. In the example embodiment in FIG. 148, the heater select relay 2920 is depicted as a double-pole double-throw relay. The heater select relay 2920 may be an electromechanical relay or a solid state relay. Since the heater select relay 2920 will be switched relatively infrequently (e.g., only at startup), it may be desirable to use an electromechanical relay.

In a non-energized state (shown in FIG. 148) the heater select relay 2920 may configure the heater element 2917 such that its resistive elements 2918A, 2918B are in series with one another. This configuration, being a higher resistance configuration, may be used when the AC mains 2900 is supplying power to the device at a higher voltage (e.g. 230V). In other embodiments, this may be a default configuration for safety reasons at start-up of the device. Preferably, the non-energized state of the heater select relay 2920 is configured to have the resistive elements 2918A, 2918B in series. This series configuration is most limiting of current flow through the resistive element 2918A, 2918B, since upon start-up, the incoming AC mains 2900 voltage may not be known, or measured, or pre-set. If the controller 2904 of the heater circuit 2930 is configured to determine the proper configuration of the heater element 2917 after the device has been turned on (either through measurement of the source, or through querying of the user, or through detection of the shape or configuration of electrical plug in use), then the set of resistive elements 2918A, 2918B preferably is configured in series when the device is turned on.

As shown, the heater circuit 2930 includes a current sense element 2906. Such an element may be used to determine the amount of current flow through the heater element 2917. A signal from the current sense element 2906 may be provided to the controller 2904. In some embodiments, the signal from the current sense element 2906 may be routed through various types of circuitry for amplification or filtering purposes.

Depending on the amount of current flow through the heater element 2917, the configuration of the heater select relay 2920 may be changed. In some embodiments, if the current sense element 2906 detects a current flow below a predetermined threshold, the heater select relay 2920 may alter the configuration of the heater element 2917. If the current sense element 2906 detects a current flow above the predetermined threshold, the heater select relay 2920 may keep the heater element 2917 in its current configuration.

In some embodiments, additional thresholds may be employed. There may, for example, be a no current flow threshold, or parallel configuration fault threshold. Such a series fault or no current threshold may be used to detect a fault condition when, for example, the heater element 2917 is commanded to be on. For example, in a scenario in which a thermal fuse has blown, an open circuit may be present and no current may flow through the heater element 2917. In the event that current flow is determined to be below the no current flow threshold, the heater select relay 2920 may be kept in its current configuration and the controller 2904 may disable the heater element 2917. Additionally, in such a scenario, the device may notify a user that a fault condition exists. A parallel configuration fault threshold may be set to detect a scenario in which the heater element 2917 is configured in parallel and one of the resistive elements 2918A, 2918B is non-functional (e.g. its thermal fuse has blown). In the event that the current sense element 2906 detects a current indicative of such a situation, the device may notify a user that a fault condition exists. In some embodiments, the therapy may optionally be allowed to continue. In this case, the notification may indicate to the user that the therapy may include fewer cycles as it will take longer for fluid in a heater bag to be heated by only a single resistive element 2918A, 2918B.

In alternate embodiments, other logic, such as any of the logic described above, may be employed by the controller 2904 to determine when and if the heater select relay 2920 should alter the heater element 2917 configuration.

Preferably, the heater element may be reconfigured by the controller only once each time the device is turned on. Additionally, the controller 2904 may preferably disable the heater element 2917 when switching the heater select relay 2920 In the example embodiment shown in FIG. 148, this may, for example, be accomplished by switching both pulse width modulated elements 2908, 2910 off.

A current sense element 2906 may also be used advantageously for other applications. The current sense element 2906 may be used upon startup or during pre-therapy to assess whether a heater element 2917/heater circuit 2930 is functioning properly. For example, to ensure that an enable signal for the heater element 2917 is not stuck on, the controller may set the enable signal to off while commanding the heater element 2917 to operate at 100% duty cycle. In embodiments where an enable signal is used, when the enable signal set to off, the heater element 2917 should not be powered regardless of the commanded duty cycle. Instead of monitoring temperature sensor data from one or more temperature sensor associated with the heater pan 2914 to determine if heating is occurring, the current sense element 2906 may be monitored. In the event that current is flowing through the heater element 2917, it may be determined that a fault condition exists. This may allow for a reliable determination of whether or not such a fault exists to be made quickly. When relying on the temperature sensors, time must be allotted during the test for the heater pan 2914 to warm up. Such a warm up time is not necessary if a current sense element 2906 is monitored instead. It should be noted that the current sense element 2906 may, for example, also be used during startup to determine that the heater element 2917 draws current when the controller 2904 commands the heater element 2917 to be powered. In the event that the heater element 2917 does not draw current when the heater element 2917 is commanded to be powered, a fault condition may be signaled. Upon determination of the above faults, the user may be notified that the fault condition exists.

In embodiments in which a heater element 2917 may not be reconfigured, or may only be reconfigured manually (e.g. by means of a jumper on a circuit board), including a current sense element 2906 in a heater circuit 2930 may also be advantageous. For example, the current sense element 2906 may be monitored to ensure that the AC mains 2900 is supplying the intended voltage for the configuration. In the event that the current sense element 2906 indicates that the AC mains 2900 is not at the intended voltage, the device may be configured to notify a user and may cut power to the heater element 2917 depending on the AC mains 2900 voltage. For example, if the heater element 2917 is configured for 120V operation, the current sense element 2906 may be monitored to determine that the current flow is not indicative that the AC mains 2900 is supplying 230V. In the event that the current sense element 2906 detects that a heater element 2917 configured for 120V is receiving power from a 230V AC mains 2900, the heater element 2917 may be disabled by a controller 2904. Additionally, the device may notify the user (e.g. via the user interface) that the device is connected to the incorrect mains voltage. If the heater element 2917 is configured for 230V operation, the current sense element 2906 may be monitored to determine that the current flow is not indicative that the AC mains 2900 is supplying 120V. In the event that the current sense element 2906 detects that a heater element 2917 configured for 230V is receiving power from a 120V AC mains 2900, the device may notify the user (e.g. via the user interface) that the device is connected to the incorrect mains voltage. In this scenario, the user may be allowed to continue with the therapy, however, the notification provided to the user may inform the user that the therapy is likely to include fewer cycles because the heater element 2917 may be unable to heat fluid in a heater bag as quickly as if the heater element 2917 was its intended AC mains 2900 voltage.

As mentioned above, the controller 2904 may control the temperature of the heater pan 2914 by selectively connecting the AC mains 2900 to a heater element 2917 and enabling current flow through the heater element 2917. In the example embodiment, this selective connection may be established by means of a pulse width modulated element (eg, solid state relay) 2908, 2910. The pulse width modulated element 2908, 2910 may be any suitable type of switch capable of switching large current flows off/on multiple times a second. In a preferred embodiment, the pulse width modulated element 2908, 2910 is a solid state relay. In such embodiments, the pulse width modulated element 2908, 2910 may specifically be a TRIAC or a suitable arrangement of silicon control rectifiers. Preferably, the degree of coupling between the triggering circuit and the pulse width modulated element 2908, 2910 should be minimized. In some embodiments, an optical coupler may be used. In such embodiments each of the pulse width modulated elements 2908, 2910 may include a photo sensitive diode, and may be controlled by modulation circuitry that lights an LED.

The signal applied to the pulse width modulated element 2908, 2910 by the controller 2904 may control the duty cycle of the pulse width modulated element 2908, 2910. By varying the duty cycle of the pulse width modulated element 2908, 2910 the controller 2904 may define the amount of time that the heater element 2917 is on and heating the heater pan 2914. The controller 2904 may modulate a pulse width modulated element 2908, 2910 based on feedback from a number of sensors 2916A, 2916B, associated with the heater pan 2914. Though two sensors 2916A, 2916B are shown in the example embodiment, various embodiments may include a larger or smaller number of sensors. Additionally or alternatively, the controller 2904 may control the duty cycle of the pulse width modulated element 2908, 2910 using information from the current sense element 2906. In various embodiments, the controller 2904 may employ any of the logic described herein to control the heater pan 2914 temperature or duty cycle of the pulse width modulated element 2908, 2910.

The number of sensors 2916A, 2916B may include a temperature sensor such as a thermocouple or thermistor or other suitable temperature sensor. In such embodiments, the number of sensors 2916A, 2916B may provide information related to the temperature of the heater pan 2914. In some embodiments, such sensors 2916A, 2916B may be positioned so as to measure the temperature of an object (e.g. a dialysate bag or reservoir) which is resting on the heater pan 2914. In such embodiments, the sensors may be substantially thermally isolated from the heater pan 2914. In some embodiments, one or more of the sensors 2916A, 2916B may be positioned so as to measure the temperature of an object on the heater pan 2914 and one or more of the sensors 2916A, 2916B may be arranged to measure the temperature of the heater pan 2914 itself. In some specific embodiments, five sensors may measure the temperature of the heater pan 2914, and two sensors may be used to measure the temperature of an object on the heater pan 2914. In such embodiments, the temperature data from the sensors measuring the temperature of the object on heater pan 2914 may be fed into a control loop controlling the temperature of the heater pan 2914. In some embodiments, the control loop may be used to set a target temperature for the heater pan 2914.

The number of sensors 2916A, 2916B may include a pressure sensor in some embodiments. In such embodiments, one or more pressure sensor (s) may provide information related to the weight of an object (e.g. dialysate bag or reservoir) which is resting on the heater pan 2914. In some embodiments, the number of sensors 2916A, 2916B may include a sensor or sensors configured to monitor fluid flow into and/or out of an object (e.g. dialysate bag or reservoir) resting on the heater pan 2914.

In an example embodiment, the controller 2904 may modulate a pulse width modulated element 2908, 2910 to heat dialysate in a dialysate reservoir resting on the heater pan 2914. The controller 2904 may employ logic to heat the dialysate to within a predetermined temperature range. The controller 2904 may use feedback from the number of sensors 2916A, 2916B to control heating of the dialysate to within the predetermined temperature range, preferably selected to avoid significantly raising or lowering a recipient's body temperature. Selection of the appropriate range may depend on the mass or volume of fluid to be heated and infused, either or both of which can be measured and included in a calculation to determine the appropriate temperature range. For example, the mass of fluid may be calculated from a pressure sensor monitoring the weight of a dialysate reservoir, and the volume of fluid infused may be determined from FMS measurements of pressure-volume relationships in the membrane-based pumps.

The heater circuit 2930 shown in FIG. 148 may also include a number of safety relays 2912A, 2912B and one or more fuses (or circuit breakers) 2902. The safety relays 2912A, 2912B may be controlled by the controller 2904 as shown, or may be controlled by a separate controller which is independent of the controller 2904. The safety relays 2912A, 2912B may be switched to open circuit in the event that a failure condition is detected. The safety relays 2912A, 2912B may be any suitable variety of relays, for example, solid state relays or electromechanical relays. In some embodiments, the pulse width modulated elements 2908, 2910 may also perform the role of the safety relays 2912A, 2912B. That is, the pulse width modulated elements 2908, 2910 and safety relays 2912A, 2912B need not be separate components. The one or more fuses 2902 may additionally serve to protect the heater circuit 2930 in the event that a failure condition occurs. If the fuse 2902 is subjected to an excessive amount of current flow, the fuse 2902 may trip or blow protecting the heater circuit 2930 from the high current. In some embodiments each of the nominally hot and nominally neutral lines may include a separate fuse 2902.

The heater circuit 2930 in FIG. 148 is also arranged such that it minimizes touch or leakage current. The heater circuit 2930 is arranged such that the circuit protects against touch or leakage current even in the event that the line and neutral wires are reversed at a wall socket. As shown, in the example embodiment there may be a capacitive coupling between the heater element 2917 and the heater pan 2914. In the example embodiment shown in FIG. 148, this capacitive coupling is illustrated by capacitor 2926. This capacitive coupling allows a certain amount of touch or leakage current to exist. To limit leakage current, suitable insulation or layers of insulation (not shown) may be provided between the heating element 2917 and the heater pan 2914. The insulation may be selected from any number of suitable insulating materials with a low dielectric constant and high dielectric strength. It should also be noted that the materials selection for the enclosure and any coatings may be chosen to aid in minimizing leakage current.

Additionally, the arrangement and subsequent control of the safety relays 2912A, 2912B and the pulse width modulated elements 2908, 2910 may be configured to aid in the reduction of touch or leakage current. Leakage current between the heater element 2917 and the heater pan 2914 will be higher when the heater element 2917 is at a higher voltage. Thus it may be desirable to protect against a situation in which the heater element 2917 rests at the full voltage of the AC mains 2900. Such a scenario may occur in the event that the heater element 2917 is connected to the AC mains 2900 when the heater element 2917 is not on. (i.e. not passing current). A pair of safety relays may be effective in preventing AC mains voltage from reaching the heater element when the heater is not in use. But during operation of the heater using a PWM signal, the heater element could be exposed to AC mains voltage during the 'off' phases of the PWM signal, depending on the polarity of the AC mains connection. By connecting a solid state relay (or PWM element) to both the first pole and second pole of AC mains (e.g., in a 220 volt system), or to both the line wire and neutral wire of AC mains (e.g., in a 110 volt system), commanding the same PWM signal to both solid state relays effectively ensures that the 'off' phases of the PWM signal will reliably isolate the heater element from AC mains voltage regardless of the polarity of the AC mains connection. A dual solid state relay arrangement can be used to reduce touch or leakage current more generally with any device (e.g., a heater or a motor) having a load that is powered by high voltage and controlled by a series of on-off (such as PWM) signals. A solid state relay connected to each pole of the high voltage source and receiving the same control signal can effectively reduce the touch or leakage current of the device powered by the high voltage source.

Situations in which this may occur in a typical 110 volt system include when the nominally neutral line provides a closed return path for electricity provided by the AC mains 2900. This can happen when the nominally neutral line does not include a pulse width modulated element 2908, 2910. This can also happen when a pulse width modulated element 2908, 2910 on the nominally neutral line is modulated to a 100% duty cycle. In these scenarios, in the event that the polarity of the line and neutral wires are reversed at the wall outlet, the heater element 2917 will rest at the full voltage of the AC mains 2900 when the heater element 2917 is off.

By placing a pulse width modulated element 2908, 2910 on both line and neutral legs of the heater circuit 2930 (or, for example on both the first and second poles of the AC mains source), such a scenario can be prevented, thus minimizing leakage current due to the capacitive coupling of the heater element 2917 and the heater pan 2914. As shown, the controller 2904 may be configured to send the same control signal to each of the pulse width modulated elements 2908, 2910. Thus, the pulse width modulated elements 2908, 2910 may be operated in tandem with one another at the same duty cycle. In this manner, the heater element 2917 can be prevented from resting at the full AC mains 2900 voltage even if the polarity of the line and neutral wires are reversed. Controlling the pulse width modulated elements 2908, 2910 in this manner prevents a scenario in which one of the pulse width modulated elements 2908, 2910 is in an active state while the other is not. Thus a heater circuit 2930 which minimizes leakage current by preventing a heater element 2917 from resting at the full AC mains 2900 voltage may include a controller 2904, heater element 2917, pulse width modulated elements 2908, 2910 and the AC mains 2900. Heater circuit 2930 may also have other functionalities and may include other optional and additional components as shown in FIG. 148.

As shown in FIG. 148, the safety relays 2912A and 2912B may be operated in tandem by the controller 2904 (or an additional but not shown controller independent of controller 2904). This may help to backstop a situation, for example, in which a pulse width modulated element 2908, 2910 fails in the closed position.

FIG. 149 shows an example graph 2950 depicting leakage current to a heater pan from a heater element over time. As shown, heating begins at about 50 seconds. This graph 2950 plots leakage current over time in a situation in which the nominally neutral wire provides a closed return path for power from the AC mains and the polarity of the circuit is reversed. That is, the nominally neutral wire is actually a line wire or hot wire. As shown, leakage current starts at approximately 68 microamps and rises to 73 microamp at approximately 65 seconds, next the controller begins to PWM the heater circuit which results in a fluctuating leakage current between a low value of approximately 70 microamps when the heater is on and approximately 90-100 microamps when the heater is off. This is because the heater is allowed to rest at a relatively high AC mains voltage (e.g. 230V). When the heater is turned on, the voltage drop across the resistive elements of the heater element decreases the amount of current passing through the capacitive coupling between the heater element and the heater pan, thus causing the leakage current to drop. As shown, in the example graph 2950 in FIG. 149 leakage current is between about 100 and 90 μA when the heater is off and between about 70 and 65 μA when the heater is on.

FIG. 150 shows another example graph 2960 depicting leakage current to a heater pan from a heater element over time. Again, heating begins at about 50 seconds. This graph 2960 plots leakage current over time in a situation in which both the nominally hot and nominally neutral wires are modulated in tandem as described above in relation to FIG. 148. As shown, leakage current in graph 2960 starts at approximately 65 microamps and increases to approximately 70 microamps at approximately 65 seconds, when the controller begins to PWM the heater. The leakage current then drops to about 44 μA, while the heater is off and returns to approximately 65 to 70 microamps when the heater is turned on. When the heater is turned on, leakage current is about the same as in graph 2950 (FIG. 149). In FIG. 150, when the heater is turned off, however, leakage current is about 44 μA, significantly lower than that of graph 2950.

FIG. 151 depicts an example of a heater circuit 2932 wherein a PWM element or solid state relay 2908, 2910 is placed on each line from the AC mains to better isolate the heater element while the heater power is off and reduce leakage current to the heater tray 2914 that may experience capacitive coupling to the heater elements. The PWM elements 2908, 2910 are controlled by both the controller 2904 and a safety controller 2934. Each PWM element 2908, 2910 receives a control signal from an AND circuit (not shown in FIG. 151) that in turn receives control signals from the controller 2904 and from the safety controller 2934. The AND circuit outputs an enable or 'on' signal to the PWM elements 2908, 2910 only when it receives an enable command from both the controller 2904 and the safety controller 2934. Not all components depicted in FIG. 151 are necessary for implementation of the above safety system. The components of heater circuit 2932 including the fuse 2902, PWM elements 2908, 2910, current sense 2906, heater select relay 2920, heater 2917, heater elements 2918A, 2918B, temperature sensors 2819A, 2916B and heater tray 2914 are described in greater detail above.

FIG. 151A depicts another example of a heater circuit 2932A. The heater circuit 2932A shown is similar to that depicted in FIG. 151. The heater circuit 2932A includes a first controller 2931 and second controller 2933. The PWM elements 2908, 2910 are controlled by both the first controller 2931 and a second controller 2933. Each PWM element 2908, 2910 receives a control signal from a gating circuit (not shown in FIG. 151A) that in turn receives control signals from the first controller 2931 and from the second controller 2933. The gating circuit outputs an enable or 'on' signal to the PWM elements 2908, 2910 only when it receives an enable command from both the first controller 2931 and the second controller 2933.

Also shown in FIG. 151A is a safety voltage source 2937. In an embodiment, voltage from the safety voltage source 2937 may be required for the PWM elements 2908, 2910 to enable current flow to the heater 2917. In some embodiments, a gating circuit may also require voltage from a safety voltage source 2937 in order for the PWM elements 2908, 2910 to enable current flow to the heater 2917. The safety voltage source 2937 may be controlled by either the first processor 2931 or second processor 2933 as in the example embodiment. Optionally, the safety voltage source 2937 may instead or additionally be controlled by a dedicated hardware component 2939. This component 2939 may, for example, monitor for over-voltage conditions. The dedicated hardware component 2939 may control the safety voltage source 2937 to prevent the PWM elements 2908, 2910 from allowing current flow to the heater 2917. For example, if an over-voltage condition is detected by the dedicated hardware component 2939, the safety voltage source 2937 may be controlled to prevent the PWM elements 2908, 2910 from allowing current flow to the heater 2917.

FIGS. 152 to 157 depict a specific example of the circuit 2930 shown in FIG. 148. Such a circuit may switch the configuration of a heater element based on a sensed current flow through the heater element. The specific example circuit may also be arranged to minimize leakage current by providing a pulse width modulated element on the nominally hot side of the heater element as well as the nominally neutral side of the heater element and controlling each in tandem with one another. Note that when the AC mains deliver a nominal 220-230 VAC, the "neutral line" is a second hot line that provides an alternating voltage that is out of phase with the alternating voltage supplied by the nominally "hot wire". Herein, the neutral wire or the neutral side of the heater refers to the wire or heater connected to the neutral side of 120 VAC mains or to the out-of-phase side of 220-230 VAC mains.

FIG. 152 depicts an AC mains input 2990 for the example circuit. Traces 3000 and 3002 represent the line and neutral wires, here denoted as L1 and L2, of the circuit. In the example embodiment, the convention of L1 and L2 instead of Line/Hot and Return/Neutral is used to emphasize that the leakage current characteristics of the circuit are independent of the polarity of L1 and L2. Referring now also to FIG. 153, as shown, the AC mains input 2990 is connected to the AC switch 2292 of the circuit. In the example embodiment this connection is made by AC L1 switch pole in 3008 and AC L2 switch pole in 3010. AC L2 switch out 3012 connects the power switch 2992 to one end of the heater circuitry 2994 (see FIG. 154) of the example circuit. AC L1 switch out 3014 connects the power switch 2992 to the other end of the heater circuitry 2994 of the example circuit.

As shown in FIG. 154, both AC L1 switch out 3014 and AC L2 switch out 3012 are respectively connected to pulse width modulated elements 3013 and 3015. In the example embodiment, the pulse width modulated elements 3013 and 3015 are solid state relays. In some embodiments, the pulse width modulated elements 3013 and 3015 may be solid state relays with a zero crossover switching characteristic. Specifically, in the example embodiment, the pulse width modulated elements are silicon control rectifiers. In other embodiments other types of relays may be used. For example, in some embodiments, the pulse width modulated elements 3013 and 3015 may be TRIACs.

In the example embodiment, a safety voltage from 3071 is shown connected to the pulse width modulated elements (solid state relays) 3013 and 3015. As mentioned above in relation to FIG. 151A, the safety voltage may be provided from a safety voltage source 2939 (see FIG. 151A). The presence of the safety voltage may be necessary for the pulse width modulated elements (solid state relays) 3013 and 3015 to enable current flow to the heater element 3019. In a failsafe condition, a processor of the heater system (e.g. processor 2933 of FIG. 151A) or a dedicated hardware component (see 2939 of FIG. 151A) may prevent the safety voltage from reaching the pulse width modulated elements 3013 and 3015.

The pulse width modulated element (solid state relay) 3015 is connected to a heating element 3019 via heater AC L1 3016. Heater AC L1 3016 may pass through a current sensing element 3017 on its way to the heating element 3019. The current sensing element 3017 may be configured to sense current flow through the heating element 3019. In some embodiments the current sensing element 3017 may be a current sense transformer. The current sensing element 3017 and related components will be further described later in the specification. Pulse width modulated element 3015 may be modulated between an active (on) and inactive (off) state by a signal sent through heater control A 3050. This signal will also be further described later in the specification.

Pulse width modulated element 3015 is also connected to a heater configuration relay 3026 via heater AC L1 3016. In the example embodiment, the heater element 3019 is a heater element consisting of at least one set of resistive elements that may be arranged either in series or parallel. In the example embodiment, the heater configuration relay 3026 is an electromechanical relay. In other embodiments, the heater configuration relay 3026 may be any other suitable type of relay. As shown, the heater element 3019 is configured for series operation. In series configuration, heater AC L1 3016 does not connect to the heater element 3019 through configuration switch 3028B of the heater configuration relay 3026, but is directly connected to one end of the heater element 3019 as shown. In parallel configuration, both configuration switches 3028A, and 3028B of the heater configuration relay 2026 would be in the opposite position. In this position, heater AC L1 3016 would be directly connected to one end of the heater element 3019 and connected to another end of the heating element 3019 through heater configuration relay 3026 and heater AC L1/L2 3024.

In the example embodiment, as shown in series configuration, the pulse width modulated element 3013 is connected to the heater element 3019 through: AC L2 switch 3032, the heater configuration relay 3026 (via configuration switch 3028B), and heater AC L1/L2 3024. When the heater element 3019 is configured for parallel, the pulse width modulated element 3013 is connected to the heating element 3019 through: AC L2 switch 3032, the heater configuration relay 3026 (via configuration switch 3028A), and heater AC L2 3020. Pulse width modulated element 3013 may be modulated between an active (on) and inactive (off) state by a signal sent through heater control B 3058. This signal will be described later in the specification. In the example embodiment the position of configuration switches 3028A, and 3028B of the heater configuration relay 2026 may be controlled via a signal sent through configuration select 3078. Alternatively, in some embodiments, the configuration may be manually set through manual configuration select 3080. For example, a jumper box may be manually placed over a number of pins in order to select the configuration. Depending on the selected configuration, the heater configuration relay's 2026 configuration switches 3028A, and 3028B may be appropriately positioned by energizing or not energizing coil 3082 of the heater configuration relay 3026. The configuration signals sent through configuration select 3078 and manual configuration select 3080 will be further described later in the specification.

FIG. 155 depicts an example of modulation circuitry or gating circuitry, or an 'AND' circuit which may be used in the circuit shown from FIG. 152 to FIG. 157. As shown, the example modulation circuitry shown in FIG. 155 includes a number of switches which may be current controlled switches. The AND circuit is configured to provide a path to ground for voltage from 3071 through 3050 when a positive voltage is applied at 3040 and at 3042, which are connected to the controller and safety processor respectively. The AND circuit serves to pass the PWM signal from the supplying controller (e.g. controller 2904 or safety controller 2934 of FIG. 151) to the PWM element 3015 (FIG. 154) only if the other of the controlling processors is supplying an enable signal. In an example, the AND circuit serves to pass the PWM signal from the supplying controller (e.g. controller 2904 or safety controller 2934 of FIG. 151) to the PWM element 3015 (FIG. 154) only if the safety processor 2934 (FIG. 151) is outputting an enable signal. As shown, the switches comprise three transistors 3044, 3046, and 3048, which may for example be MOSFETs. Accompanying pull-up and pull down resistors are also included. In the example embodiment, transistors 3046 and 3044 are respectively controlled by signals from a control processor and a safety processor (neither shown). Thus, in order for the heater element 3019 (see FIG. 154) to be switched on via heater control A 3050 (see also FIG. 154) through transistor 3048, both the control and safety processors must cooperate and command that the heater element 3019 should be powered. The signal from the control processor may travel into the modulation circuitry through control processor heater signal line 3040. The signal from the safety processor may travel into the modulation circuitry through safety processor signal line 3042.

The signals from the control processor and safety processor may be based on logic that incorporates sensor data. For example, the control processor and safety processor may use data from a sensor or sensors, such as a temperature sensor(s) associated with the heater element, to determine when the heater element should be on or off. Various types of control logic that may be used for control of a heater element are described elsewhere herein.

In some embodiments, the control and safety processors may send the same signal to their respective transistors 3046, and 3044. In some embodiments, the control and safety processors may send different signals to their respective transistors 3046, and 3044. In a specific embodiment, the control processor (or alternatively the safety processor) may send an enable signal to transistor 3046. The other processor may send a pulse width modulated signal to transistor 3044. Transistor 3048 will allow the heater element 3019 (see FIG. 154) to be switched on when both the enable signal and pulse width modulated signal command that the heater element 3019 should be powered. The pulse width modulated (PWM) element 3015 (see FIG. 154), in this example, would effectively be modulated with the pulse width modulated signal applied to transistor 3044 by the PWM'ing processor. This configuration also ensures that in an event in which the processors issue conflicting commands, i.e. a fault condition, the pulse width modulated element 3015 (see FIG. 154) does not allow current flow through the heater element 3019.

FIG. 156 depicts modulation circuitry or gating circuitry or an 'AND' circuit that may be used in the example circuit shown from FIG. 152 to FIG. 157. As shown, the example modulation circuitry shown in FIG. 156 is similar to that shown in FIG. 155. The AND circuit is configured to provide a path to ground for voltage from 3071 through 3058 to the PWM element 3013 (FIG. 154) when a positive voltage is applied at 3040 and at 3042, which are connected to the controller and safety processor respectively. The AND circuit serves to pass the PWM signal from the supplying controller (e.g. controller 2904 or safety controller 2934 of FIG. 151) to the PWM element 3013 (FIG. 154) only if the other of the controlling processors is supplying an enable signal. In an example, the AND circuit serves to pass the PWM signal from the supplying controller (e.g. controller 2904 or safety controller 2934 of FIG. 151) to the PWM element 3013 (FIG. 154) only if the safety processor 2934 (FIG. 151) is outputting an enable signal. The modulation circuitry includes three transistors 3052, 3054, and 3056, which may, for example, be MOSFETs. Accompanying pull-up and pull down resistors are also included. In the example embodiment, transistors 3054, and 3052 are respectively controlled by signals from a control processor and a safety processor (neither shown). Thus, in order for the heater element 3019 (see FIG. 154) to be switched on via heater control B 3058 (see also FIG. 154) through transistor 3056, both the control and safety processors must cooperate and command that the heater element 3019 should be powered. The signal from the control processor may travel into the modulation circuitry through control processor heater signal line 3040. The signal from the safety processor may travel into the modulation circuitry through safety processor signal line 3042.

In the example embodiment, the signals applied to control processor heater signal line 3040 and safety processor signal line 3042 in FIG. 156 may be identical to the signals applied to control processor heater signal line 3040 and safety processor signal line 3042 in FIG. 155. That is, both pulse width modulated elements 3013 and 3015 (see FIG. 154) may be pulse width modulated in tandem at the same duty cycle in some embodiments. Consequently, regardless of the polarity of L1 and L2 in the circuit shown in FIG. 152, there will not be a condition in which the heater element 3019 is held at mains voltage. When the heater element 3019 is not in the "on" state, the heater element 3019 will not be connected to the mains voltage source. It should be noted that this is also true regardless of the configuration of the heater element 3019; whether the heater element 3019 is configured in series or parallel, it will not be allowed to rest at the mains voltage.

In some embodiments, there may only be a single modulation circuit. In such embodiments, the third transistor of the modulation circuit (either 3048 or 3056) may control the state of both pulse-width-modulated elements 3013 and 3015 (see FIG. 154). Additionally, the modulation circuits shown in FIG. 155 and FIG. 156 may be used to control the pulse-width-modulated elements 3013 and 3015 such that they function as safety relays when necessary. For example, in the event that a failure condition is detected, the control signals sent by one or both the processors may command the pulse-width-modulated elements 3013 and 3015 to turn off or into an inactive state.

In both FIG. 155 and FIG. 156, a safety voltage from 3045 is shown connected to the gating circuitry. As mentioned above in relation to FIG. 151A, the safety voltage may be provided from a safety voltage source 2939 (see FIG. 151A). In an embodiment, the presence of the safety voltage may be necessary for the gating circuitry to enable the pulse width modulated elements (solid state relays) 3013 and 3015 (see FIG. 154) to enable current flow to the heater element 3019. In a failsafe condition, a processor of the heater system (e.g. processor 2933 of FIG. 151A) or a dedicated hardware component (see 2939 of FIG. 151A) may prevent the safety voltage from reaching the gating circuitry.

FIG. 157 depicts example circuitry which may be included in embodiments of a heater circuit that include a current sense element 3017 (see FIG. 154). The example circuitry depicted in FIG. 157 may be used to process and filter the signal from the current sense element 3017. As shown, the signal from a current sense element 3017 may be carried by trace 3070 and 3074. This signal may be subjected to rectification via a suitable rectifier 3073. The example rectifier 3073 in FIG. 157 is depicted as a quadruple Schottky barrier diode. A voltage limiting element 3072 is also included. In the example embodiment, the voltage limiting element 3072 is depicted as a Zener diode. In the example embodiment, the signal is then passed through a unity gain amplifier 3075. The signal may also be subjected to a low pass filter 3077, which may serve to smooth out the rectified AC signal. In some embodiments the signal may be passed through an operational amplifier 3079 for amplification. In one example, the gain of the operational amplifier 3079 can be set at approximately 4.4. As shown, in the example embodiment, the signal then may pass through an additional low pass filter 3081. The signal may then be fed to a controller (not shown) via trace 3076.

In various embodiments, the signal may be subject to different degrees of amplification and filtering. For example, in some embodiments, the signal may be subjected to additional filtering. In some embodiments, additional filtering, amplification, etc. may be performed on the signal on a separate circuit board (e.g. the board on which the controller resides). Preferably, the components are selected to keep the signal from becoming saturated. In particular, the components are preferably chosen so that the signal will not become saturated at the highest anticipated current the circuit may encounter.

The controller (not shown) can use the signal from trace 3076 to make a determination about how a heater element 3019 should be configured. The controller can then send a command signal to the heater configuration relay 3026 (see FIG. 154) based upon this determination. As mentioned above, this signal may be sent through the configuration select 3078 trace.

Database and User Interface systems

Referring to FIG. 130, the database subsystem 346, also on the user interface computer 302, stores all data to and retrieves all data from the databases used for the onboard storage of machine, patient, prescription, user-entry and treatment history information. This provides a common access point when such information is needed by the system. The interface provided by the database subsystem 346 is used by several processes for their data storage needs. The database subsystem 346 also manages database file maintenance and back-up.

The UI screen view 338 may invoke a therapy log query application to browse the therapy history database. Using this application, which may alternatively be implemented as multiple applications, the user can graphically review their treatment history, their prescription and/or historical machine status information. The application transmits database queries to the database subsystem 346. The application can be run while the patient is dialyzing without impeding the safe operation of the machine.

The remote access application, which may be implemented as a single application or multiple applications, provides the functionality to export therapy and machine diagnostic data for analysis and/or display on remote systems. The therapy log query application may be used to retrieve information requested, and the data may be reformatted into a machine neutral format, such as XML, for transport. The formatted data may be transported off-board by a memory storage device, direct network connection or other external interface 348. Network connections may be initiated by the APD system, as requested by the user.

The service interface 356 may be selected by the user when a therapy is not in progress. The service interface 356 may comprise one or more specialized applications that log test results and optionally generate a test report which can be uploaded, for example, to a diagnostic center. The media player 358 may, for example, play audio and/or video to be presented to a user.

According to one exemplary implementation, the databases described above are implemented using SQLite®, a software library that implements a self-contained, serverless, zero-configuration, transactional SQL database engine.

The executive subsystem 332 implements two executive modules, the user interface computer (UIC) executive 352 on the user interface computer 302 and the automation computer (AC) executive 354 on the automation computer 300. Each executive is started by the startup scripts that run after the operating system is booted and includes a list of processes it starts. As the executives go through their respective process lists, each process image is checked to ensure its integrity in the file system before the process is launched. The executives monitor each child process to ensure that each starts as expected and continue monitoring the child processes while they run, e.g., using Linux parent-child process notifications. When a child process terminates or fails, the executive either restarts it (as in the case of the UI view) or places the system in fail safe mode to ensure that the machine behaves in a safe manner. The executive processes are also responsible for cleanly shutting down the operating system when the machine is powering off.

The executive processes communicate with each other allowing them to coordinate the startup and shutdown of the various application components. Status information is shared periodically between the two executives to support a watchdog function between the processors. The executive subsystem 332 is responsible for enabling or disabling the safe line. When both the UIC executive 352 and the AC executive 354 have enabled the safe line, the pump, the heater, and the valves can operate. Before enabling the lines, the executives test each line independently to ensure proper operation. In addition, each executive monitors the state of the other's safe line.

The UIC executive 352 and the AC executive 354 work together to synchronize the time between the user interface computer 302 and the automation computer 300. The time basis is configured via a battery backed real-time clock on the user interface computer 302 that is accessed upon startup. The user interface computer 302 initializes the CPU of the automation computer 300 to the real-time clock. After that, the operating system on each computer maintains its own internal time. The executives work together to ensure sufficiently timekeeping by periodically performing power on self tests. An alert may be generated if a discrepancy between the automation computer time and the user interface computer time exceeds a given threshold.

FIG. 158 shows the flow of information between various subsystems and processes of the APD system. As discussed previously, the UI model 360 and cycler controller 362 run on the automation computer. The user interface design separates the screen display, which is controlled by the UI view 338, from the screen-to-screen flow, which is controlled by the cycler controller 362, and the displayable data items, which are controlled by the UI model 360. This allows the visual representation of the screen display to be changed without affecting the underlying therapy software. All therapy values and context are stored in the UI model 360, isolating the UI view 338 from the safety-critical therapy functionality.

The UI model 360 aggregates the information describing the current state of the system and patient, and maintains the information that can be displayed via the user interface. The UI model 360 may update a state that is not currently visible or otherwise discernable to the operator. When the user navigates to a new screen, the UI model 360 provides the information relating to the new screen and its contents to the UI view 338. The UI model 360 exposes an interface allowing the UI view 338 or some other process to query for current user interface screen and contents to display. The UI model 360 thus provides a common point where interfaces such as the remote user interface and online assistance can obtain the current operational state of the system.

The cycler controller 362 handles changes to the state of the system based on operator input, time and therapy layer state. Acceptable changes are reflected in the UI model 360. The cycler controller 362 is implemented as a hierarchical state machine that coordinates therapy layer commands, therapy status, user requests and timed events, and provides view screen control via UI model 360 updates. The cycler controller 362 also validates user inputs. If the user inputs are allowed, new values relating to the user inputs are reflected back to the UI view 338 via the UI model 360. The therapy process 368 acts as a server to the cycler controller 362. Therapy commands from the cycler controller 362 are received by the therapy process 368.

The UI view 338, which runs on the UI computer 302, controls the user interface screen display and responds to user input from the touch screen. The UI view 338 keeps track of local screen state, but does not maintain machine state information. Machine state and displayed data values, unless they are in the midst of being changed by the user, are sourced from the UI model 360. If the UI view 338 terminates and is restarted, it displays the base screen for the current state with current data. The UI view 338 determines which class of screens to display from the UI model 360, which leaves the presentation of the screen to the UI view. All safety-critical aspects of the user interface are handled by the UI model 360 and cycler controller 362.

The UI view 338 may load and execute other applications 364 on the user interface computer 302. These applications may perform non-therapy controlling tasks. Exemplary applications include the log viewer, the service interface, and the remote access applications. The UI view 338 places these applications within a window controlled by the UI view, which allows the UI view to display status, error, and alert screens as appropriate. Certain applications may be run during active therapy. For example, the log viewer may be run during active therapy, while the service interface and the remote access application generally may not. When an application subservient to the UI view 338 is running and the user's attention is required by the ongoing therapy, the UI view 338 may suspend the application and regain control of the screen and input functions. The suspended application can be resumed or aborted by the UI view 338.

FIG. 159 illustrates the operation of the therapy subsystem 340 described in connection with FIG. 130. The therapy subsystem 340 functionality is divided across three processes: therapy control; therapy calculation; and solution management. This allows for functional decomposition, ease of testing, and ease of updates.

The therapy control module 370 uses the services of the therapy calculation module 372, solution management module 374 and machine control subsystem 342 (FIG. 130) to accomplish its tasks. Responsibilities of the therapy control module 370 include tracking fluid volume in the heater bag, tracking fluid volume in the patient, tracking patient drain volumes and ultra filtrate, tracking and logging cycle volumes, tracking and logging therapy volumes, orchestrating the execution of the dialysis therapy (drain-fill-dwell), and controlling therapy setup operations. The therapy control module 370 performs each phase of the therapy as directed by the therapy calculation module 370.

The therapy calculation module 370 tracks and recalculates the drain-fill-dwell cycles that comprise a peritoneal dialysis therapy. Using the patient's prescription, the therapy calculation module 372 calculates the number of cycles, the dwell time, and the amount of solution needed (total therapy volume). As the therapy proceeds, a subset of these values is recalculated, accounting for the actual elapsed time. The therapy calculation module 372 tracks the therapy sequence, passing the therapy phases and parameters to the therapy control module 370 when requested.

The solution management module 374 maps the placement of solution supply bags, tracks the volume in each supply bag, commands the mixing of solutions based upon recipes in the solution database, commands the transfer of the requested volume of mixed or unmixed solution into the heater bag, and tracks the volume of mixed solutions available using the solution recipe and available bag volume.

FIG. 160 shows a sequence diagram depicting exemplary interactions of the therapy module processes described above during the initial 'replenish' and 'dialyze' portions of the therapy. During the exemplary initial replenish process 376, the therapy control module 370 fetches the solution ID and volume for the first fill from the therapy calculation module 372. The solution ID is passed to the solution management module 374 with a request to fill the heater bag with solution, in preparation for priming the patient line and the first patient fill. The solution management module 374 passes the request to the machine control subsystem 342 to begin pumping the solution to the heater bag.

During the exemplary dialyze process 378, the therapy control module 370 executes one cycle (initial drain, fill, dwell-replenish, and drain) at a time, sequencing these cycles under the control of the therapy calculation module 372. During the therapy, the therapy calculation module 372 is updated with the actual cycle timing, so that it can recalculate the remainder of the therapy if needed.

In this example, the therapy calculation module 372 specifies the phase as "initial drain," and the therapy control module makes the request to the machine control subsystem 342. The next phase specified by the therapy calculation module 372 is "fill." The instruction is sent to the machine control subsystem 342. The therapy calculation module 372 is called again by the therapy control module 370, which requests that fluid be replenished to the heater bag during the "dwell" phase. The solution management module 374 is called by the therapy control module 370 to replenish fluid in the heater bag by calling the machine control subsystem 342. Processing continues with therapy control module 370 calling the therapy calculation module 372 to get the next phase. This is repeated until there are no more phases, and the therapy is complete.

Pump Monitor/Math Repeater

The Pump Monitor/Math Repeater process is a software process or function that runs on the automation computer 300 separate from the safety executive 354. The Pump Monitor/Math Repeater process is implemented in as two separate threads or sub-functions that run independently. The math repeater thread, herein referred to as the MR thread, confirms the FMS calculation result. The Pump Monitor thread, referred to as the PM thread, monitors the net fluid and air flow across relevant endpoints from information provided in the routine status messages from the Machine process 342. The relevant endpoints may include but not be limited to 5 potential bag spikes, the heater bag, patient port and drain port. The PM thread will also monitor the heater pan temperature via information from the IO Server process. The PM thread will signal an alarm to the safety executive 354, if predefined limits for fluid flow, air flow or temperature are exceeded.

The MR thread accepts the high speed pressure data and repeats the FMS calculation described above to recalculate the fluid volume displaced. The MR thread compares its recalculated fluid volume to the volume calculated by the Machine process 342 and sends a message to the safety executive. In another example, the MR thread declares and error condition if the two fluid volume values do not match.

The PM thread monitors several aspects of the pumping process as a safety check on the functioning of the cycler 14. The PM thread will declare an invalid pump operation error condition if the Hardware Interface 310 reports valves open that do not correspond to the commanded pump action by the Machine subsystem 342. An example of an invalid valve condition would be if any port valve 186, 184 (FIG. 6) are open, while the pump was in an idle mode. The state of valves in the cassette is mapped to the state of the corresponding pneumatic valves 2710, which are energized by the hardware interface 310. Another example of an invalid valve condition would be a port valve 184, 186 that is open that does not correspond to the specified source or sink of fluid.

The PM thread will declare an error condition if excess fluid is pumped to the patient while the heater button temperature sensor 506 reports less than a given temperature. In a preferred embodiment, the PM thread will declare an error condition more than 50 ml of fluid is pumped to the patient while the button temperature is less than 32° C.

The PM thread will maintain a numerical accumulator on the amount of fluid pumped to the patient. If total volume of fluid pumped to the patient exceeds a specified amount, the PM thread will declare an error. The specified amount may be defined in the prescription information and may include an additional volume equal to one chamber volume or approximately 23 ml.

The PM thread will maintain a numerical accumulator on the amount of air measured in the pumping chamber by the FMS method for air taken from each bag. If the total amount of air from any bag exceeds the maximum allowed volume of air for that bag, then the PM thread will declare an error. In a preferred embodiment, the maximum allowed air volume for the heater bag is 350 ml and the maximum allowed air volume for a supply bag is 200 ml. A large air volume from a bag indicates that it may have a leak to the atmosphere. The maximum allowed air volume for the heater bag may be larger to account for out-gassing when the fluid is heated.

Alert/Alarm Functions

Conditions or events in the APD system may trigger alerts and/or alarms that are logged, displayed to a user, or both. These alerts and alarms are a user interface construct that reside in the user interface subsystem, and may be triggered by conditions that occur in any part of the system. These conditions may be grouped into three categories: (1) system error conditions, (2) therapy conditions, and (3) system operation conditions.

"System error conditions" relate to errors detected in software, memory, or other aspects of the processors of the APD system. These errors call the reliability of the system into question, and may be considered "unrecoverable." System error conditions cause an alarm that is displayed or otherwise made known to the user. The alarm may also be logged. Since system integrity cannot be guaranteed in the instance of a system error condition, the system may enter a fail safe mode in which the safe line described herein is disabled.

Each subsystem described in connection with FIG. 130 is responsible for detecting its own set of system errors. System errors between subsystems are monitored by the user interface computer executive 352 and automation computer executives 354. When a system error originates from a process running on the user interface computer 302, the process reporting the system error terminates. If the UI screen view subsystem 338 is terminated, the user interface computer executive 352 attempts to restart it, e.g., up to a maximum of three times. If it fails to restart the UI screen view 338 and a therapy is in progress, the user interface computer executive 352 transitions the machine to a fail safe mode.

When a system error originates from a process running on the automation computer 300, the process terminates. The automation computer executive 354 detects that the process has terminated and transitions to a safe state if a therapy is in progress.

When a system error is reported, an attempt is made to inform the user, e.g., with visual and/or audio feedback, as well as to log the error to a database. System error handling is encapsulated in the executive subsystem 332 to assure uniform handling of unrecoverable events. The executive processes of the UIC executive 352 and AC executive 354 monitor each other such that if one executive process fails during therapy, the other executive transitions the machine to a safe state.

"Therapy conditions" are caused by a status or variable associated with the therapy going outside of allowable bounds. For example, a therapy condition may be caused by an out-of-bounds sensor reading. These conditions may be associated with an alert or an alarm, and then logged. Alarms are critical events, generally requiring immediate action. Alarms may be prioritized, for example as low, medium or high, based on the severity of the condition. Alerts are less critical than alarms, and generally do not have any associated risk other than loss of therapy or discomfort. Alerts may fall into one of three categories: message alerts, escalating alerts, and user alerts.

The responsibility for detecting therapy conditions that may cause an alarm or alert condition is shared between the UI model and therapy subsystems. The UI model subsystem 360 (FIG. 158) is responsible for detecting alarm and alert conditions pre-therapy and post-therapy. The therapy subsystem 340 (FIG. 130) is responsible for detecting alarm and alert conditions during therapy.

The responsibility for handling alerts or alarms associated with therapy conditions is also shared between the UI model and therapy subsystems. Pre-therapy and post-therapy, the UI model subsystem 360 is responsible for handling the alarm or alert condition. During a therapy session, the therapy subsystem 340 is responsible for handling the alarm or alert condition and notifying the UI Model Subsystem an alarm or alert condition exists. The UI model subsystem 360 is responsible for escalating alerts, and for coordinating with the UI view subsystem 338 to provide the user with visual and/or audio feedback when an alarm or alert condition is detected.

"System operation conditions" do not have an alert or alarm associated with them. These conditions are simply logged to provide a record of system operations. Auditory or visual feedback need not be provided.

Actions that may be taken in response to the system error conditions, therapy conditions, or system operation conditions described above are implemented by the subsystem (or layer) that detected the condition, which sends the status up to the higher subsystems. The subsystem that detected the condition may log the condition and take care of any safety considerations associated with the condition. These safety considerations may comprise any one or combination of the following: pausing the therapy and engaging the occluder; clearing states and timers as needed; disabling the heater; ending the therapy entirely; deactivating the safe line to close the occluder, shut off the heater, and removing power from the valves; and preventing the cycler from running therapies even after a power cycle to require the system to be sent back to service. The UI subsystem 334 may be responsible for conditions that can be cleared automatically (i.e., non-latching conditions) and for user recoverable conditions that are latched and can only be cleared by user interaction.

Each condition may be defined such that it contains certain information to allow the software to act according to the severity of the condition. This information may comprise a numeric identifier, which may be used in combination with a lookup table to define priority; a descriptive name of the error (i.e., a condition name); the subsystem that detected the condition; a description of what status or error triggers the condition; and flags for whether the condition implements one or more actions defined above.

Conditions may be ranked in priority such that when multiple conditions occur, the higher priority condition may be handled first. This priority ranking may be based on whether the condition stops the administration of therapy. When a condition occurs that stops therapy, this condition takes precedence when relaying status to the next higher subsystem. As discussed above, the subsystem that detects a condition handles the condition and sends status information up to the subsystem above. Based on the received status information, the upper subsystem may trigger a different condition that may have different actions and a different alert/alarm associated with it. Each subsystem implements any additional actions associated with the new condition and passes status information up to the subsystem above. According to one exemplary implementation, the UI subsystem only displays one alert/alarm at a given time. In this case, the UI model sorts all active events by their priority and displays the alert/alarm that is associated with the highest priority event.

A priority may be assigned to an alarm based on the severity the potential harm and the onset of that harm. Table 1, below, shows an example of how priorities may be assigned in this manner.

TABLE 1

| CONDITION | ONSET OF POTENTIAL HARM — POTENTIAL RESULT OF FAILURE TO RESPOND TO THE CAUSE OF ALARM | | |
|---|---|---|---|
| | IMMEDIATE | PROMPT | DELAYED |
| death or irreversible injury | high priority | high priority | medium priority |
| reversible injury | high priority | medium priority | low priority |
| minor discomfort or injury | medium priority | low priority | low priority or no alarm signal |

In the context of Table 1, the onset of potential harm refers to when an injury occurs and not to when it is manifested. A potential harm having an onset designated as "immediate" denotes a harm having the potential to develop within a period of time not usually sufficient for manual corrective action. A potential harm having an onset designated as "prompt" denotes a harm having the potential to develop within a period of time usually sufficient for manual corrective action. A potential harm having an onset designated as "delayed" denotes a harm having the potential to develop within an unspecified time greater than that given under "prompt."

Figure 161:
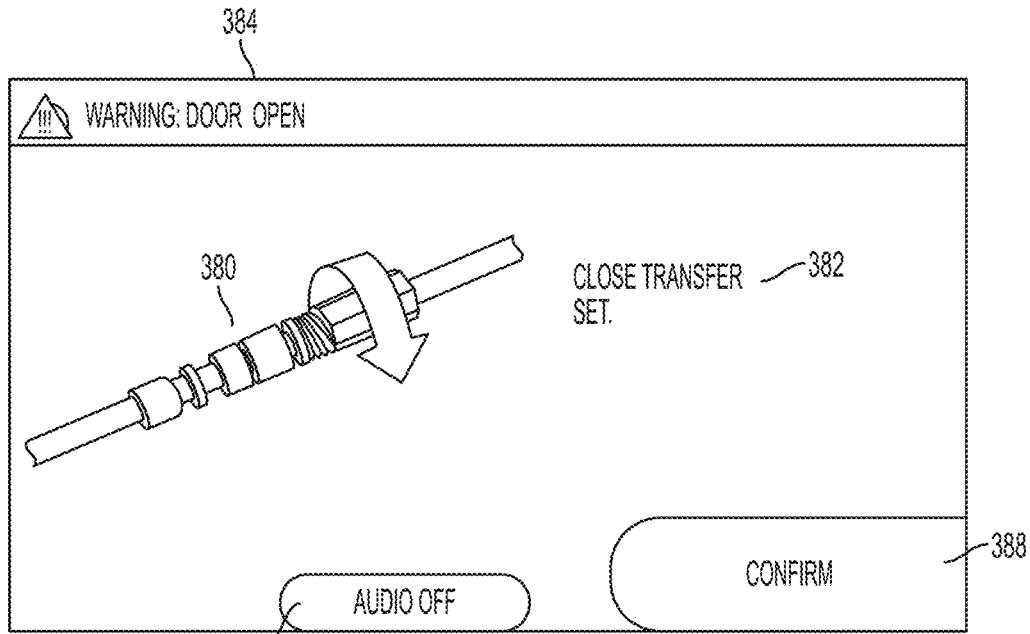
Figure 162:
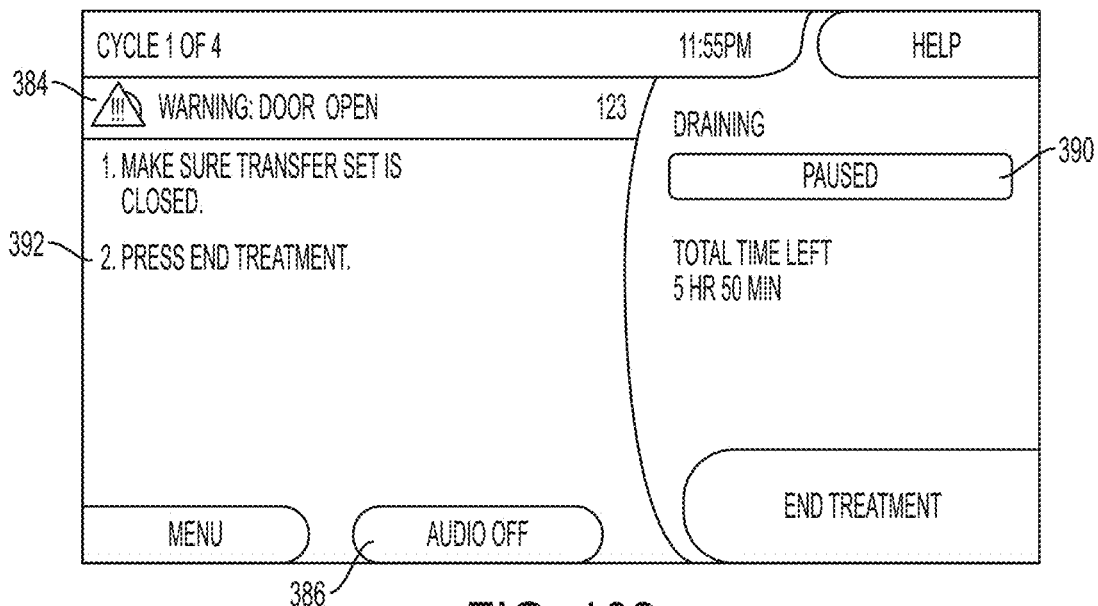

FIGS. 161-166 show exemplary screen views relating to alerts and alarms that may be displayed on a touch screen user interface. FIG. 161 shows the first screen of an alarm, which includes a diagram 380 and text 382 instructing a user to close their transfer set. The screen includes a visual warning 384, and is also associated with an audio warning. The audio warning may be turned off my selecting the "audio off" option 386 on the touch screen. When the user has closed the transfer set, the user selects the "confirm" option 388 on the touch screen. FIG. 162 shows a similar alarm screen instructing a user to close their transfer set. In this case, an indication that draining is paused 390 and an instruction to select "end treatment" are provided 392.

As previously discussed, alerts generally do not have associated risk other than loss of therapy or discomfort. Thus, an alert may or may not cause the therapy to pause. Alerts can be either "auto recoverable," such that if the event clears the alert automatically clears, or "user recoverable," such that user interaction with the user interface is needed to clear the alert. An audible alert prompt, which may have a volume that may be varied within certain limits, may be used to bring an alert to the attention of a user. In addition, information or an instruction may be displayed to the user. So that such information or instruction may be viewed by the user, an auto-dim feature of the user interface may be disabled during alerts.

In order to reduce the amount of disturbance to the user, alerts may be categorized into different types based on how important an alert is and how quick a user response is required. Three exemplary types of alerts are a "message alert," an "escalating alert," and a "user alert." These alerts have different characteristics based on how information is visually presented to the user and how the audible prompt is used.

Figure 163:
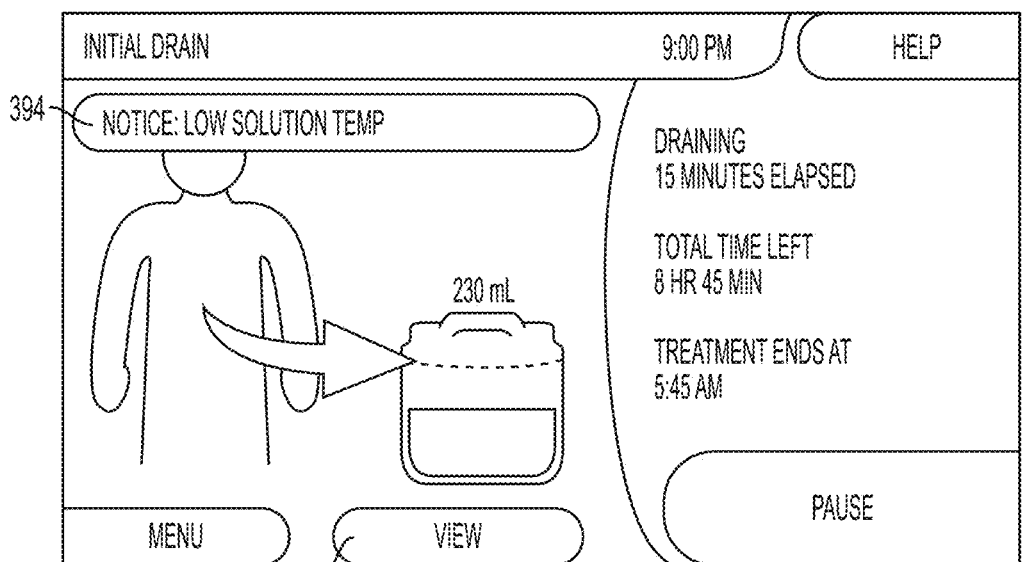
Figure 164:
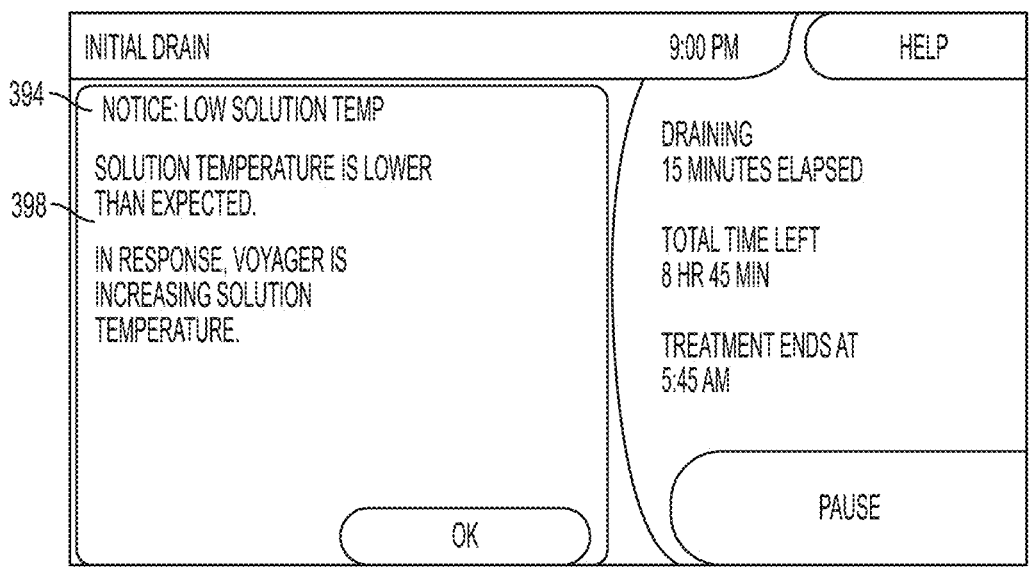

A "message alert" may appear at the top of a status screen and is used for informational purposes when a user interaction is not required. Because no action needs to be taken to clear the alert, an audible prompt is generally not used to avoid disturbing, and possibly waking, the patient. However, an audible alert may be optionally presented. FIG. 163 shows an exemplary message alert. In particular, FIG. 163 shows an under-temperature message alert 394 that may be used to inform a user when the dialysate is below a desired temperature or range. In this case, a user does not need to take any action, but is informed that therapy will be delayed while the dialysate is heated. If the patient desires more information, the "view" option 396 may be selected on the touch screen. This causes additional information 398 concerning the alert to appear on the screen, as shown in FIG. 164. A message alert may also be used when there is a low flow event that the user is trying to correct. In this case, a message alert may be displayed until the low flow event is cleared to provide feedback to the user on whether the user fixed the problem.

Figure 165:
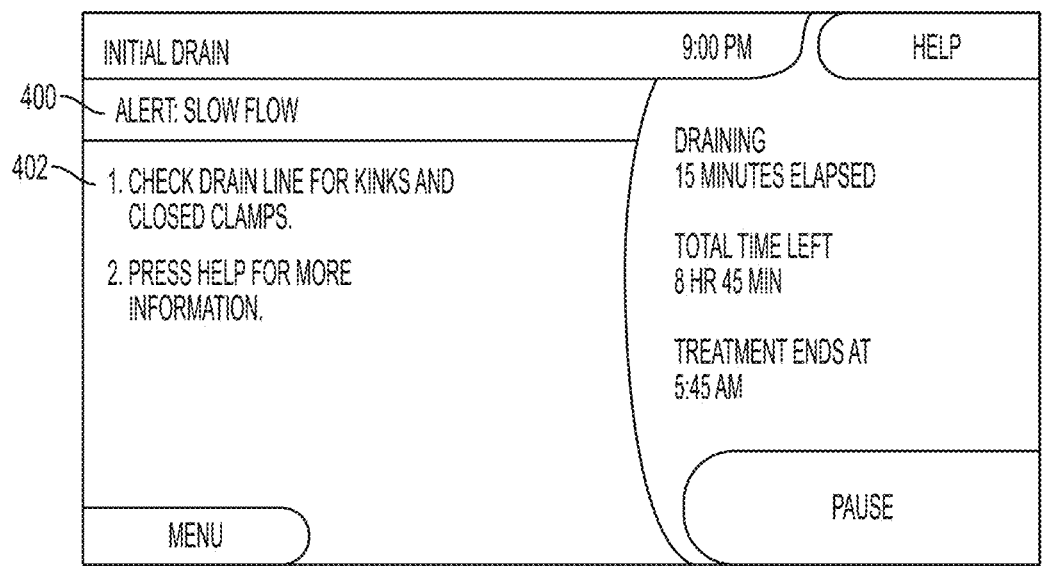
Figure 166:
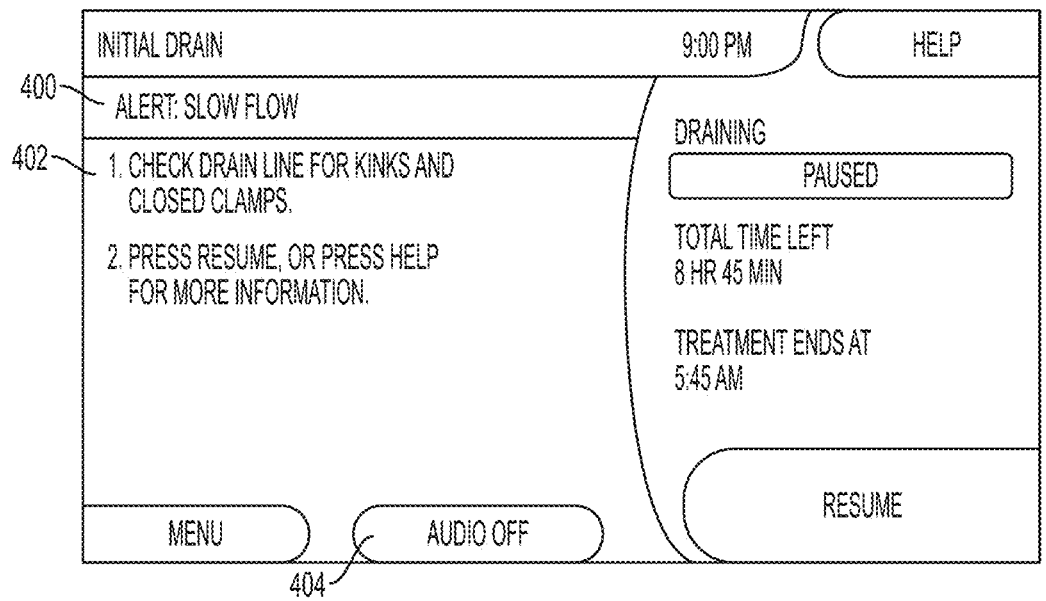

An "escalating alert" is intended to prompt the user to take action in a non-jarring manner. During an escalating alert, a visual prompt may displayed on the touch screen and an audible prompt may be presented (e.g., once). After a given period of time, if the event that caused the alert is not cleared, a more emphatic audible prompt may be presented. If the event causing the alert is not cleared after an additional period of time, the alert is escalated to a "user alert." According to one exemplary implementation of a user alert, a visual prompt is displayed until the alert is cleared and an audible prompt, which can be silenced, is presented. The UI subsystem does not handle the transition to from escalating alert to user alert. Rather, the subsystem that triggered the original event will trigger a new event associated with the user alert. FIG. 165 shows a screen view displaying information concerning an escalating alert. This exemplary alert includes an on-screen alert message 400 and a prompt 402 instructing the user to check the drain line for kinks and closed clamps, as well as and an audible prompt. The audible prompt may be continuous until it is silenced by the user. FIG. 166 shows a screen view including an "audio off" option 404 that may be selected to silence the audible prompt. This alert can be used directly, or as part of the escalating alert scheme.

Each alert/alarm is specified by: an alert/alarm code, which is a unique identifier for the alert/alarm; an alert/alarm name, which is a descriptive name of the alert/alarm; an alert/alarm type, which comprises the type of alert or level of alarm; an indication of whether an audible prompt is associated with the alert/alarm; an indication of whether the alert and associated event can be bypassed (or ignored) by the user; and the event code of the event or events that trigger the alert/alarm.

During alarms, escalating alerts and user alerts, the event code (which may be different from the alert or alarm code, as described above) may be displayed on the screen so that the user can read the code to service personnel if needed. Alternatively or additionally, a voice guidance system may be used so that, once connected to a remote call center, the system can vocalize pertinent information about the system configuration, state, and error code. The system may be connected to the remote call center via a network, telephonic connection, or some other means.

An example of a condition detected by the therapy subsystem is described below in connection with FIG. 167. The condition results when the APD system is not positioned on a level surface, which is important for air management. More particularly, the condition results when a tilt sensor detects that APD system is tilted beyond a predetermined threshold, such as 35°, with respect to a horizontal plane. As described below, a recoverable user alert may be generated by the therapy subsystem if the tilt sensor senses an angle with an absolute value greater than the predetermined threshold. To avoid nuisance alarms, the user may be directed to level the APD system before therapy begins. The tilt threshold may be lower during this pre-therapy period (e.g., 35°). The user may also be given feedback concerning whether the problem is corrected.

When the tilt sensor detects an angle of tilt exceeding a threshold value during therapy, the machine subsystem 342 responds by stopping the pump in a manner similar to detecting air in the pump chamber. The therapy subsystem 340 asks for status and determines that the machine layer 342 has paused pumping due to tilt. It also receives status information concerning the angle of the machine. At this point, the therapy subsystem 340 generates a tilt condition, pauses therapy, and sends a command to the machine subsystem 342 to pause pumping. This command triggers clean-up, such as taking fluid measurement system (FMS) measurements and closing the patient valve. The therapy subsystem 340 also starts a timer and sends an auto recoverable tilt condition up to the UI model 360, which sends the condition to the UI view 338. The UI view 338 maps the condition to an escalating alert. The therapy subsystem 340 continues to monitor the tilt sensor reading and, if it drops below the threshold, clears the condition and restarts therapy. If the condition does not clear before the timer expires, the therapy subsystem 340 triggers a user recoverable "tilt timeout" condition that supersedes the auto-recoverable tilt condition. It sends this condition to the UI model 360, which sends the condition to the UI view 338. The UI view 338 maps the condition to a user alert. This condition cannot be cleared until a restart therapy command is received from the UI subsystem (e.g., the user pressing the resume button). If the tilt sensor reading is below the threshold, the therapy resumes. If it is not below the threshold, the therapy layer triggers an auto recoverable tilt condition and starts the timer.

Prioritized Audible Signals

The cycler may provide audible signals and voice guidance to the user to communicate a range of information including but not limited to number selection, sound effects (button selection, action selection), machine condition, operational directions, alerts, and alarms. The cycler controller 16 may cause a speaker to annunciate audible signals and vocalizations from stored sound files stored in memory on one or both of the computers 300, 302 in the control system 16. Alternatively, vocalizations may be stored and produced by a specialized voice chip.

In some instances, the cycler may have multiple audible signals to annunciate at the same time or sequentially in a very short time. The annunciation of several signals in a short period of time may overwhelm the user resulting in annoyance or the loss of critical safety information. The cycler controller 16 may assign priorities to each audible signal and suppress the lower priority signals to allow the clear communication of higher priority audible signals. In one instance, the audible signals are prioritized from the highest priority alarm signals to the lowest priority annunciation of a sequence of numbers:

1. Alarms
2. Alerts
3. Sound Effects
4. Voice Guidance
5. Annunciation for a sequence of numbers.

Alarms and alerts are described above. Sound effects may confirm sounds to indicate that a button, or choice has been selected. Sound effects may also announce or confirm a particular action is being taken by the cycler. Voice guidance may include voiced instructions to execute a particular procedure, access help, contact a call center and other directing instructions. Annunciation for a sequence of numbers may include reading back to the user or the call center the number that the user had just keyed in or it may read the user allowable values for requested input.

Audible Sleep Aid

The cycler 14 may include an option to play soothing sounds at night to aid sleeping. The playing of sounds such as rain, ocean waves, etc. are referred to as sound therapy. Sound therapy for sleep can provide some users with a higher tolerance for nighttime noises and the masking or replacing of nighttime noise with more rhythmic, soothing sounds that minimize sleep disturbance. Sound therapy may help individuals suffering from hearing conditions such as hyperacusis and tinnitus. The user interface 324 may provide the user with a menu to select types of sound, volume levels and duration so that the sound therapy can play before and/or during the initial period of sleep. The sound files may be stored in the memories of the computers 300, 302 and played by the speaker in the cycler 14. In another example, the cycler may include an output jack to drive external speakers. In another example, the sound files and/or the speaker driver electronics may be separate from either the automation computer 300 or the user interface computer 302. The sound files may include but not be limited to rain sounds, thunder storms, ocean waves, thunder, forest sounds, crickets, white noise, and pink noise (varying amplitude and more bass).

Battery Operation

The cycler may include a rechargeable lithium ion battery for use as a backup power source. At a minimum this battery helps to ensure that the cycler does not turn off without alerting the user and saving the current state of the treatment. A power management system may be implemented by the cycler when on battery power that is contingent on the amount of charge remaining in the battery. If the battery is sufficiently charged, the cycler can prevent brownouts or short power outages from interfering with the completion of a therapy. The cycler control circuitry can measure the state of charge of the battery, and can correlate the battery charge level with operable states. This information may be obtained empirically through testing, and the correlations between battery charge level and the ability to operate the various subsystems may be stored in memory. The following functions may be associated with the battery charge level:

Level 4: Enough power to perform one cycle of therapy. Implemented if, for example, the charge level of the battery is equal to or greater than approximately 1100 milliamp-hours.

Level 3: Enough power to perform a user drain. Implemented if, for example, the charge level of the battery is equal to or greater than approximately 500 milliamp-hours.

Level 2: Enough power to end therapy, display alert, and guide user through post-therapy breakdown. Implemented if, for example, the charge level of the battery is equal to or greater than approximately 300 milliamp-hours.

Level 1: Enough power to end therapy and display an alert. Implemented if, for example, the charge level of the battery is equal to or greater than approximately 200 milliamp-hours.

Level 0: Not enough power to operate.

If there is enough charge in the battery (Level 4), the cycler will continue with the therapy until the current cycle is finished. This may not include replenishing the heater bag or heating the solution. Therefore, if already in a fill phase, the cycler may continue the therapy if the solution in the heater bag is in the proper temperature range and there is enough solution in the heater bag. If the battery only has enough capacity to perform a 20 minute drain (Level 3), the cycler will alert the user, and give the user the option to either drain or end treatment without draining. If the battery only has enough power to alert the user (Level 2) it will not give the user the option to drain and the user will be guided through the post-therapy breakdown. If there is not enough power to guide the user through breakdown (Level 1), the user will be prompted to disconnect and then the cycler will power down. At this battery level the cycler may not have enough power to release the door, so the user may not be able to breakdown the therapy. During start up, the cycler can assess the state of the batter, and alert the user if the battery has a fault or if the battery does not have a sufficient charge to at least alert the patient if main power is lost. The cycler may be programmed to not allow the user to start a treatment without the battery having enough capacity to provide and alert and guide the user through post-therapy breakdown (Battery Level 2).

Another example of battery charge levels and available therapy choices or machine actions sets 4 battery charge levels and the available therapy choices or machine actions:

Level 4:

If the fill process has not started, then suspend operation until the AC power is restored. The suspend is limited to 30 mins.

If the fill process has started, then complete cycle including the fill, dwell and drain processes.

The heater bag will not be refilled as there is no heating during battery operation.

End therapy, and guide user through post-therapy breakdown including removal of the of the dialysate delivery set 12a from the cycler 14.

Level 3:

If in the fill or drain process, then suspend operation until the AC power is restored. The suspend is limited to 30 mins.

If the drain process has started, then complete the cycle.

The heater bag will not be refilled as there is no heating during battery operation.

End therapy, and guide user through post-therapy breakdown including removal of the of the dialysate delivery set 12a from the cycler 14.

Level 2:

End therapy, and guide user through post-therapy breakdown including removal of the of the dialysate delivery set 12a from the cycler 14.

Level 1:

End therapy.

Level 0:

Not enough power to operate.

An alert will be displayed to the user or patient at levels 1-4. The control system 16 may extend the cycler operation on battery power by dimming the display screen 324 after a given time period from the last screen touch. In another example the display screen 324 may dim after a given period from the appearance of the most recent message, alert or warning. In one example, the display screen 324 will dim 2 minutes after the more recent screen touch or last. The display screen 324 may include a message or symbol indicating operation on battery power.

The electrical circuitry connecting the battery to the pneumatic valves may include a regulated voltage boost converter that steps-up the supplied variable battery voltage to a consistent voltage. The supplied battery voltage may drop as the battery is discharged, in one example, a Li-Ion battery at full charge may supply 12.3 volts. The supplied voltage may drop as the battery is depleted to as low as 9 volts when the battery is fully discharged. The pneumatic valves may require a minimum voltage to reliably open fully. In one example, the minimum voltage to reliably open the valve may be 12 volts.

A regulated voltage boost converter may be placed between the supply battery and the valves to assure sufficient voltage to reliably open the valves as battery discharges. The regulated voltage boost converter will output a regulated voltage at a higher value than the variable battery voltage input. In one example, the regulated voltage boost converter may be an integrated chip such as the TPS61175 made by Texas Instruments. A regulated voltage buck/boost converter may also be used between the battery and the valves. The buck/boost converter is able to supply a regulated voltage output from supplied voltages that are higher, equal to, or lower than the input voltage.

In one embodiment, the PWM duty cycle of the valve drivers may vary with the measured battery voltage. The valves may be operated in a pick-and-hold manner, where an initially higher voltage is applied to open the valve and then a lower voltage is applied to hold the valve in desired condition. The PWM duty cycle for the hold function may be scaled inversely with the measure battery voltage to provide a consistent averaged voltage or current to the valves. The PWM duty cycle may be scaled inversely with measured battery voltage for the higher voltage open or pick operation.

Screen Display

As discussed previously, the UI view subsystem 338 (FIG. 158) is responsible for the presentation of the interface to the user. The UI view subsystem is a client of and interfaces with the UI model subsystem 360 (FIG. 158) running on the automation computer. For example, the UI view subsystem communicates with the UI model subsystem to determine which screen should be displayed to the user at a given time. The UI view may include templates for the screen views, and may handle locale-specific settings such as display language, skin, audio language, and culturally sensitive animations.

There are three basic types of events that occur in the UI view subsystem. These are local screen events that are handled by the individual screens, model events in which a screen event must propagate down to the UI model subsystem, and polling events that occur on a timer and query the UI model subsystem for status. A local screen event only affects the UI view level. These events can be local screen transitions (e.g., in the case of multiple screens for a single model state), updates to view settings (e.g., locality and language options), and requests to play media clips from a given screen (e.g., instructional animations or voice prompts). Model events occur when the UI view subsystem must consult with the UI model subsystem to determine how to handle the event. Examples that fall into this category are the confirmation of therapy parameters or the pressing of the "start therapy" button. These events are initiated by the UI view subsystem, but are handled in the UI model subsystem. The UI model subsystem processes the event and returns a result to the UI view subsystem. This result drives the internal state of the UI view subsystem. Polling events occur when a timer generates a timing signal and the UI model subsystem is polled. In the case of a polling event, the current state of the UI view subsystem is sent to the UI model subsystem for evaluation. The UI model subsystem evaluates the state information and replies with the desired state of the UI view subsystem. This may constitute: (1) a state change, e.g., if the major states of the UI model subsystem and the UI view subsystem are different, (2) a screen update, e.g., if values from the UI model subsystem change values displayed on-screen, or (3) no change in state, e.g., if the state of the UI model subsystem and the UI view subsystem are identical. FIG. 168 shows the exemplary modules of the UI view subsystem 338 that perform the functions described above.

As shown in FIG. 168, the UI model client module 406 is used to communicate events to the UI model. This module 406 is also used to poll the UI model for the current status. Within a responsive status message, the UI model subsystem may embed a time to be used to synchronize the clocks of the automation computer and the user interface computer.

The global slots module 408 provides a mechanism by which multiple callback routines (slots) can subscribe to be notified when given events (signals) occur. This is a "many-to-many" relationship, as a slot can be bound to many signals, and likewise a signal can be bound to many slots to be called upon its activation. The global slots module 408 handles non-screen specific slots, such as application level timers for UI model polling or button presses that occur outside of the screen (e.g., the voice prompt button).

The screen list class 410 contains a listing of all screens in the form of templates and data tables. A screen is made up of a template and an associated data table that will be used to populate that screen. The template is a window with widgets laid out on it in a generic manner and with no content assigned to the widgets. The data table includes records that describe the content used to populate the widgets and the state of the widgets. A widget state can be checked or unchecked (in the case of a checkbox style widget), visible or hidden, or enabled or disabled. The data table can also describe the action that occurs as a result of a button press. For example, a button on window 'A' derived from template '1' could send an event down to the UI model, whereas that same button on window 'B' also derived from template '1' could simply cause a local screen transition without propagating the event down to the UI model. The data tables may also contain an index into the context-sensitive help system.

The screen list class 410 forwards data from the UI model to the intended screen, selects the proper screen-based data from the UI model, and displays the screen. The screen list class 410 selects which screen to display based on two factors: the state reported by the UI model and the internal state of the UI view. In some cases, the UI model may only inform the UI view that it is allowed to display any screen within a category. For example, the model may report that the machine is idle (e.g., no therapy has been started or the setup phase has not yet occurred). In this case, it is not necessary to confer with the UI model when the user progresses from a menu into its sub-menu. To track the change, the UI view will store the current screen locally. This local sequencing of screens is handled by the table entries described above. The table entry lists the actions that respective buttons will initiate when pressed.

The language manager class 412 is responsible for performing inventory on and managing translations. A checksum may be performed on the list of installed languages to alert the UI view if any of the translations are corrupted and or missing. Any class that wants a string translated asks the language manager class 412 to perform it. Translations may be handled by a library (e.g., Qt®). Preferably, translations are requested as close as possible to the time of rendering. To this end, most screen template member access methods request a translation right before handing it to the widget for rendering.

A skin comprises a style-sheet and images that determine the "look and feel" of the user interface. The style-sheet controls things such as fonts, colors, and which images a widget will use to display its various states (normal, pressed, disabled, etc.). Any displayed widget can have its appearance altered by a skin change. The skin manager module 414 is responsible for informing the screen list and, by extension, the screen widgets, which style-sheet and skin graphics should be displayed. The skin manager module 414 also includes any animated files the application may want to display. On a skin change event, the skin manager will update the images and style-sheet in the working set directory with the proper set, which is retrieved from an archive.

The video manager module 416 is responsible for playing locale-appropriate video given a request to display a particular video. On a locale change event, the video manager will update the videos and animations in the working set directory with the proper set from an archive. The video manager will also play videos that have accompanying audio in the audio manager module 418. Upon playback of these videos, the video manager module 416 will make the appropriate request to the audio manager module 418 to play the recording that belongs to the originally requested video clip.

Similarly, the audio manager module 418 is responsible for playing locale-appropriate audio given a request to play a particular audio clip. On a locale change event, the audio manager will update the audio clips in the working set directory with the proper set from an archive. The audio manager module 418 handles all audio initiated by the UI view. This includes dubbing for animations and sound clips for voice prompts.

The database client module 420 is used to communicate with the database manager process, which handles the interface between the UI view subsystem and the database server 366 (FIG. 158). The UI view uses this interface to store and retrieve settings, and to supplement therapy logs with user-provided answers to questions about variables (e.g., weight and blood pressure).

The help manager module 422 is used to manage the context-sensitive help system. Each page in a screen list that presents a help button may include an index into the context-sensitive help system. This index is used so that the help manager can display the help screen associated with a page. The help screen may include text, pictures, audio, and video.

The auto ID manager 424 is called upon during pre-therapy setup. This module is responsible for capturing an image (e.g., a photographic image) of a solution bag code (e.g., a datamatrix code). The data extracted from the image is then sent to the machine control subsystem to be used by the therapy subsystem to identify the contents of a solution bag, along with any other information (e.g., origin) included in the code.

Using the modules described above, the UI view subsystem 338 renders the screen views that are displayed to the user via the user interface (e.g., display 324 of FIG. 127). FIGS. 169-175 show exemplary screen views that may be rendered by the UI view subsystem. These screen views illustrate, for example, exemplary input mechanisms, display formats, screen transitions, icons and layouts. Although the screens shown are generally displayed during or before therapy, aspects of the screen views may be used for different input and output functions than those shown.

The screen shown in FIG. 169 is an initial screen that provides the user the option of selecting between "start therapy" 426 to initiate the specified therapy 428 or "settings" 430 to change settings. Icons 432 and 434 are respectively provided to adjust brightness and audio levels, and an information icon 436 is provided to allow the user to solicit more information. These icons may appear on other screens in a similar manner.

FIG. 170 shows a status screen that provides information the status of the therapy. In particular, the screen indicates the type of therapy being performed 438, the estimated completion time 440, and the current fill cycle number and total number of fill cycles 442. The completion percentage of the current fill cycle 444 and the completion percentage of the total therapy 446 are both numerically and graphically displayed. The user may select a "pause" option 448 to pause therapy.

FIG. 171 shows a menu screen with various comfort settings. The menu includes brightness arrows 450, volume arrows 452 and temperature arrows 454. By selecting either the up or down arrow in each respective pair, a user can increase or decrease screen brightness, audio volume, and fluid temperature. The current brightness percentage, volume percentage and temperature are also displayed. When the settings are as desired, a user may select the "OK" button 456.

FIG. 172 shows a help menu, which may be reached, for example, by pressing a help or information button on a prior screen. The help menu may include text 458 and/or an illustration 460 to assist the user. The text and/or illustration may be "context sensitive," or based on the context of the prior screen. If the information provided to the user cannot conveniently be provided in one screen, for example in the case of a multi-step process, arrows 462 may be provided to allow the user to navigate backward and forward between a series of screens. When the user has obtained the desired information, he or she may select the "back" button 464. If additional assistance is required, a user may select the "call service center" option 466 to have the system contact the call service center.

FIG. 173 illustrates a screen that allows a user to set a set of parameters. For example, the screen displays the current therapy mode 468 and minimum drain volume 470, and allows a user to select these parameters to be changed. Parameters may be changed in a number of ways, such as by selecting a desired option from a round robin style menu on the current screen. Alternatively, when the user selects a parameter to be changed, a new screen may appear, such as that shown in FIG. 174. The screen of FIG. 174 allows a user to adjust the minimum drain volume by inputting a numeric value 472 using a keypad 474. Once entered, the user may confirm or cancel the value using buttons 476 and 478. Referring again to FIG. 173, a user may then use the "back" and "next" arrows 480, 482 to navigate through a series of parameters screens, each including a different set of parameters.

Once all desired parameters have been set or changed (e.g., when the user has navigated through the series of parameters screens), a screen such as that shown in FIG. 175 may be presented to allow a user to review and confirm the settings. Parameters that have changed may optionally be highlighted in some fashion to draw the attention of the user. When the settings are as desired, a user may select the "confirm" button 486.

Automated Peritoneal Dialysis Therapy Control

Continuous ambulatory peritoneal dialysis ("CAPD") is traditionally performed manually, with a patient or user transferring dialysis solution from a bag into his or her peritoneal cavity, having the fluid dwell in the abdomen for three to six hours, and then allowing the fluid to empty into a collection or drain bag. This is typically done three or four times a day. Automated peritoneal dialysis ("APD") differs from CAPD in that APD is achieved with the aid of a peritoneal dialysis machine ("cycler") that performs a series of fill-dwell-drain cycles during a period of several hours (e.g. when asleep or at night). In APD, the fluid introduced during a fill phase of a cycle, plus any ultrafiltration fluid, may not drain completely during the following drain phase of the cycle. This may be a result of the user's position in bed, leading to sequestration of fluid, for example, in a recess in the peritoneal cavity, and preventing an indwelling catheter from accessing all of the fluid present. In continuous cycling peritoneal dialysis ("CCPD"), the cycler attempts to perform a full drain after a fill and dwell phase in order to prevent accumulation of retained fluid (a residual intraperitoneal volume) with each succeeding cycle. APD generally comprises a plurality of short nighttime exchanges of dialysate while the user is connected to the cycler and asleep. At the end of a nighttime therapy, a volume of dialysis fluid—possibly of different composition—may be left in the peritoneal cavity during the day for continued exchange of solutes, transfer of waste compounds, and ultrafiltration. In intermittent peritoneal dialysis ("IPD"), multiple exchanges of dialysate are performed over a period of time (e.g., at night), without having a prolonged residual (or daytime) dwell cycle.

Therapy with a cycler generally begins with an initial drain phase to attempt to ensure that the peritoneal cavity is empty of fluid. The characteristics of the dialysate solution usually cause some transfer of fluid from the patient's tissues to the intraperitoneal space—ultrafiltration. As therapy proceeds through a series of cycles, fluid may accumulate in the intraperitoneal cavity if the drain phase does not yield the volume of fluid infused during the fill phase, plus the volume of ultrafiltered fluid produced during the time that dialysate solution is in the peritoneal cavity. In some modes, the cycler may be programmed to issue an alarm to the user when the drain volume has not matched the volume of fluid infused plus the expected ultrafiltration ("UF") volume. The expected UF volume is a function of—among other things—the individual patient's physiology, the chemical composition of the dialysate solution, and the time during which the dialysate solution is expected to be present in the peritoneal cavity.

In other modes, the cycler may proceed to the next fill-dwell-drain cycle if a pre-determined amount of drain time has passed and a pre-determined minimum percentage (e.g. 85%) of the preceding fill volume has been drained. In this case, the cycler may be programmed to alarm if the drain flow decreases below a pre-determined rate after the minimum drain time and before the minimum drain percentage has been reached. The cycler may be programmed to alert the user after several minutes (e.g., two minutes) of attempting but failing to maintain a pre-determined flow rate when pumping fluid from the peritoneal cavity. A low-flow condition may be detectable by the cycler because of the increased amount of time required to fill a pump chamber before end-of-stroke is detected by the controller. A zero-flow or no-flow condition may be detectable by the cycler because of the detection by the controller of a premature end-of-stroke state. The duration of the time delay before alerting the user or initiating a new fill-dwell-drain cycle may be programmed to be a few minutes in a low-flow condition (e.g., 2 minutes), and may be shorter (e.g., 30 seconds) in a no-flow condition. A shorter wait-time during a no-flow condition may be preferable, for example, because it may be associated with a greater degree of patient discomfort, or may be the result of a quickly correctable problem, such as a bend in the patient line or catheter. This time delay may be programmed at the cycler manufacturing stage or may be selectable by a clinician as a prescription parameter. The extent of the delay may be governed, among other things, by the countervailing desire of the user or clinician to stay within the targeted total therapy time (keeping in mind that little dialysis is likely to occur when the intraperitoneal volume ("IPV") is low or close to zero). If a full drain is not achieved, the cycler may also track the amount of fluid estimated to be accumulating with each cycle, and issue a warning or alarm if the cumulative IPV exceeds a pre-determined amount. This maximum IPV may be a parameter of the therapy prescription programmed into the cycler by the clinician, taking account of the particular physiological characteristics of the individual patient/user.

One method of dealing with the cumulative retention of fluid during a series of CCPD cycles is to convert the CCPD therapy to a tidal peritoneal dialysis ("TPD") therapy. TPD generally comprises a fill-dwell-drain cycle in which a drain volume is intentionally made a prescribed fraction of the initial fill volume (which may also be initially be entered by the clinician as a prescription parameter). A pre-determined percentage of the infused fluid, or a pre-determined amount of fluid is arranged to remain in the peritoneal cavity during the subsequent fill-dwell-drain cycles during a therapy. Preferably, the subsequent fill volumes are also reduced to match the drain volume (minus the expected UF) in order to maintain a relatively constant residual intraperitoneal volume. For example, an initial fill volume of 3000 ml may be introduced at the beginning of therapy, followed by subsequent drain and fill plus expected UF volumes amounting to only 1500 ml, i.e. 50% of the initial fill volume. The reserve or residual fluid in the peritoneal cavity is then drained completely at the end of therapy. In an alternative mode, a complete drain may be attempted after a pre-determined or prescribed number of fill-dwell-drain cycles (e.g., a complete drain may be attempted after three cycles of tidal therapy, this grouping comprising a therapy "cluster"). TPD may be beneficial in that users may experience less discomfort associated with repeated large fill volumes or repeated attempts to fully empty the peritoneal cavity. Low-flow conditions associated with small intraperitoneal fluid volumes may also be reduced, thus helping to avoid extending the total therapy time. To reduce the discomfort associated with attempting to drain small residual volumes, for example, the tidal drain volume may be set at 75% of the initial fill volume (plus-or-minus expected UF volume), for example, leaving approximately 25% as a reserve or residual volume in the peritoneal cavity for the duration of therapy, or for the duration of a cluster of cycles.

A cycler may also be programmed to convert a CCPD mode of therapy to a TPD mode of therapy during the course of therapy if the user chooses to keep a residual volume of fluid in the peritoneal cavity at the end of the subsequent drain phases (e.g., for comfort reasons). In this case, the cycler is programmed to calculate a choice of residual volumes (or volumes as a percent of initial fill volume) based on the number of extra cycles to be added to the therapy and the volume of remaining dialysate to be infused. For example, the cycler controller can calculate the remaining fill volumes based on the remaining cycles that include an additional one, two or more cycles. Having determined the fill volumes for each of these possibilities, the cycler controller can calculate how much residual volume can be left at the end of each remaining drain phase while ensuring that the IPV remains under a maximum prescribed IPV (Max IPV). The cycler may then present the user with a range of possible residual volumes (as a percentage of the initial fill volume or in volumetric terms) available for each remaining cycle in a therapy extended by one, two or more cycles. The user may make the selection based on the number of extra cycles chosen and the desired amount of post-drain residual volume. Switching to tidal therapy may help to reduce the number of low-drain-flow alerts to the user, which can be particularly advantageous during nighttime therapy.

In switching to tidal mode, the cycler may be programmed to select a reserve or residual volume percentage (volume remaining in the peritoneal cavity as a percent of the fill volume plus expected UF). Alternatively, the reserve volume may be user-selectable or clinician-selectable from a range of values, optionally with the clinician having the ability to select a wider range of possible values than the user. In an embodiment, the cycler may calculate the effects of adding one, two or three additional cycles on the remaining fill volumes and the expected residual IP volume percentage, and give the user or clinician the option of selecting among those calculated values. Optionally, the cycler may be constrained to keep the residual IP volume percentage below a pre-determined maximum value (e.g., a percentage of the initial fill volume plus expected UF, or a percentage of the maximum permissible IPV).

If CCPD is converted to TPD, one or more therapy cycles (fill-dwell-drain cycles) may need to be added to a therapy to use all of the prescribed volume of dialysate for the therapy session. The remaining volume to be infused going forward would then be divided by the remaining number of cycles. Furthermore, the cycler may be programmed to allow the clinician or user to select between extending the targeted total therapy time to accommodate the additional cycles (cycle-based therapy), or to attempt to maintain the targeted therapy time by adjusting the dwell times (i.e., shortening them) if necessary to reduce the fill-dwell-drain cycle durations going forward (time-based therapy).

In an alternative embodiment, the cycler may allow the residual IP volume to fluctuate (optionally within pre-determined limits) from one cycle to the next, depending on how much fluid can be drained within a specified drain time interval. The time available for the drain phase may be limited if the cycler has been programmed to complete the therapy within the previously scheduled time, or the drain phase may be terminated to prevent the cycler from attempting to pull fluid at a slow rate for a prolonged period of time. In switching from CCPD to TPD, if the cycler adds one or more additional cycles to perform a complete therapy with the available dialysate solution, then meeting the scheduled therapy end-time may require shortening the dwell times, or reducing each drain phase, which could cause the residual volume for the tidal mode to vary, depending on the drain flow conditions. As the cycler estimates and tracks the amount of residual volume, it may be programmed to calculate whether the subsequent fill volume plus expected UF volume will reach or exceed a prescribed maximum IPV. If so, the cycler can alert and provide the user with two or more options: the user may terminate treatment, repeat or extend a drain phase in an attempt to lower the residual intraperitoneal volume, or add a cycle to reduce the subsequent fill volumes. After calculating the effect on treatment time of adding an additional one or more cycles (increased number of cycles vs. reduced fill and drain times at lower volumes) the cycler may optionally reduce subsequent dwell times by an amount of time necessary to offset the additional therapy time generated by an additional one or more cycles.

The cycler may be programmed to deliver an optional last-fill phase that delivers fresh dialysate of the same or a different composition to the user's peritoneal cavity for an extended dwell time while not connected to the cycler (e.g., a prolonged dwell phase for a "day therapy," i.e., during the day following a nighttime therapy). At the user's option, the last fill volume may be selected to be less than the fill volumes used during nighttime therapy. The cycler may also optionally prompt the user to select an optional extra last drain to give the user the chance to completely empty the peritoneal cavity prior to the infusion of a last fill volume (which may be carried by the user for a relatively prolonged period of time after the end of nighttime therapy). If this function is enabled, the cycler may prompt the user to sit up or stand, or otherwise move about to mobilize any trapped fluid in the peritoneal cavity during this last drain phase.

The cycler may also be programmed to account for an expected amount of ultrafiltration ("UF") fluid produced during a dwell phase on or off the machine, and to alert the user if a minimum drain volume that includes the volume infused plus this expected UF is not drained either initially at the beginning of therapy, or during a fill-dwell-drain cycle during therapy. In an embodiment, the cycler may be programmed for a minimum initial drain volume and a minimum initial drain time, and to pause or terminate the drain phase if the measured drain flow rate has decreased below a pre-determined threshold value for a pre-determined number of minutes. The minimum initial drain volume may comprise the volume of the last fill phase in the preceding nighttime therapy, plus an expected UF volume from the day therapy dwell phase. If the minimum (or more) initial drain volume is achieved, the minimum initial drain time is reached, and/or the drain flow rate has decreased, the IPV tracked by the cycler controller may be set to zero at the end of the initial drain phase. If not, the cycler may alert the user. The cycler may allow the user to bypass the minimum initial drain volume requirement. For example, the user may have manually drained at some time before initiating APD. If the user elects to forego adherence to the minimum initial drain volume, the cycler may be programmed to perform a full drain at the end of the first cycle regardless of the type of therapy selected by the user. If enabled, this feature helps to ensure that the second fill-dwell-drain cycle begins at an IPV that is as close to zero as possible, helping to ensure that a prescribed maximum IPV should not be exceeded during subsequent cycles of the therapy.

The cycler may also be programmed to allow the user to pause therapy. During a pause, the user may have the option to alter the therapy by reducing the fill volume, reducing therapy time, terminating a planned "day therapy," or ending therapy altogether. In addition, the user may have the option to perform an immediate drain at any time during therapy. The volume of an unscheduled drain may be selected by the user, whereupon the cycler may resume the cycle at the stage at which it was interrupted.

The cycler may be programmed to have a prescriber or "clinician" mode. A software application may be enabled to allow a clinician to create or modify a set of parameters forming the therapy prescription for a particular patient or user, as well as setting the limits within which a user may adjust user-accessible parameters. The clinician mode may also allow a clinician to fix one or more treatment parameters that would otherwise be accessible to a user, as well as lock a parameter to prevent a user from changing it. A clinician mode may be password-protected to prevent unauthorized access. The clinician mode application may be constructed to interface with a database to read and write the parameters comprising a prescription. Preferably, a "user mode" permits a user to access and adjust user-accessible parameters during a pre-therapy startup phase of a therapy.

In addition, an "active therapy mode" may optionally be available to a user during therapy, but with access to only a subset of the parameters or parameter ranges available in the user mode. In an embodiment, the cycler controller may be programmed to allow parameter changes during active therapy mode to affect only the current therapy, the parameter settings being reset to previously prescribed values before subsequent therapies. Certain parameters preferably are not user-adjustable at all, user-adjustable with concurrence of a clinician through a prescription setting, or user-adjustable only within a range of values set by a clinician in programming a prescription. Examples of parameters that may not be adjustable solely by the user include, for example, the minimum initial drain volume or time, maximum initial fill volume, and maximum IPV. User-adjustable parameters may include, for example, the tidal drain frequency in a cluster (e.g., adjustable between 1 and 5 cycles), and the percentage of a tidal therapy fill volume to be drained (e.g., adjustable up or down by a pre-determined amount from a default value of, for example, 85%). In an alternative embodiment, the clinician mode may allow a clinician to prevent a user from programming a maximum IPV to be greater than a pre-determined multiple (e.g., 200%) of the initial fill volume assigned to a nighttime fill-dwell-drain cycle.

The cycler may also be programmed to routinely alert the user and to request confirmation when a user-adjustable parameter is entered that is outside of pre-determined ranges. For example, if the maximum IPV has been made user-adjustable in the clinician mode, the cycler may alert the user if he or she attempts to select a Max IPV value outside of a fractional range (e.g., 130-160%) of the programmed fill volume for nighttime therapy.

The cycler may also be programmed to alert the user (and possibly seek confirmation) if the initial drain volume has been made user-adjustable in the clinician mode, and the user selects an initial drain volume below a pre-determined percentage of the fill volume of the last therapy (e.g., if it is adjusted to be less than 70% of the last fill volume). In another example, the cycler may be programmed to alert the user (and possibly seek confirmation) if the total expected UF volume has been made user-adjustable by the clinician mode, and the user selects a total expected UF volume to be below a certain percentage of the total volume processed for a nighttime therapy (e.g., if the total expected UF volume is set at less than 7% of the total nighttime therapy volume). Generally the expected UF volume may be determined empirically by a clinician based on a user's prior experience with peritoneal dialysis. In a further embodiment, the cycler may be programmed to adjust the expected UF volume value according to the actual UF volume in one or more preceding cycles of a therapy. This volume may be calculated in a CCPD mode by calculating the difference between a measured full drain volume and the measured fill volume that preceded it. In some cases, it may be difficult to determine when the peritoneal cavity is fully drained of fluid, and it may be preferable to take an average value of the difference between a full drain volume and a preceding fill volume over a number of cycles.

Some of the programmable treatment settings may include:
  the number of daytime exchanges using the cycler;
  the volume of solution to be used for each daytime exchange;
  the total time for a nighttime therapy;

the total volume of dialysis solution to be used for nighttime therapy (not including a last fill volume if a daytime dwell phase is used);

the volume of dialysis solution to be infused per cycle;

in a Tidal therapy, the volume of fluid to be drained and refilled during each cycle (a percentage of the initial fill volume in a nighttime therapy);

the estimated ultrafiltration volume to be produced during a nighttime therapy;

the volume of solution to be delivered at the end of a therapy and to be left in the peritoneal cavity for an extended period (e.g, daytime dwell);

the minimum initial drain volume required to proceed with a therapy;

the maximum intraperitoneal volume known or estimated to be present that the cycler will allow to reside in the patient's peritoneal cavity (which may be based on the measured volumes introduced into the peritoneal cavity, the measured volume removed from the peritoneal cavity, and the estimated volume of ultrafiltration produced during therapy).

Some of the more advanced programmable treatment settings for the cycler may include:

the frequency of full drains to be conducted during tidal peritoneal dialysis;

the minimum percentage of the volume delivered to the peritoneum during a day therapy that must be drained before a subsequent fill is allowed;

prompting the user to perform an extra drain phase at the end of therapy if a pre-determined percentage of the estimated total UF is not collected;

a minimum length of time required to perform an initial drain before therapy begins;

a minimum length of time required to perform subsequent drains, either in day-therapy mode or night-therapy mode;

variable dwell times, adjusted by the cycler controller to maintain a fixed total therapy time when either the fill times or drain times have been changed (thus helping to avoid disruptions of the user's schedule;

The cycler can provide the user with alerts or warnings about parameters that have been entered outside a recommended range of values. For example, a warning may be issued if:

the minimum initial drain volume before a therapy is less than a pre-determined percentage of the currently prescribed last-fill volume at the end of the previous therapy (e.g., <70%);

the maximum IPV is outside a pre-determined percentage range of the fill volume per cycle (e.g., <130% or >160%);

the UF volume threshold to trigger an alert to perform an extra drain at the end of therapy is less than a pre-determined percentage of the estimated UF volume per therapy (e.g. <60%);

the calculated or entered dwell time is less than a pre-determined number of minutes (e.g., <30 minutes);

the estimated UF volume per therapy is more than a pre-determined percentage of the total dialysis solution volume per therapy (e.g., >25%);

the sum of all the solution bag volumes for a therapy should be somewhat greater than the volume of solution used during a CCPD therapy session, in order to account for priming of fluid lines and for loss of fluid to drain during air mitigation procedures.

In the clinician mode, in addition to having a selectable maximum IPV, the cycler may be programmed to accept separate minimum drain times for initial drains, day-therapy drains, and night-therapy drains. In the user mode or in the active-therapy mode, the cycler may be programmed to prevent a user from skipping or shortening the initial drain phase at the start of a therapy. In addition, the cycler may permit early termination of the initial drain phase only after a series of escalating low-drain-flow alerts have been issued. (An initial alert may instruct the user to change positions or re-position the peritoneal dialysis catheter, which may then be followed by additional alternative instructions if low flow conditions persist, up to a maximum number of alerts). The cycler may also require the user to confirm any change the user makes to the planned therapy, including bypassing a phase. The clinician may specify in a prescription setting to prevent the user from bypassing a drain phase during nighttime therapy. During therapy, the cycler controller may be programmed to not reset the IPV to zero unless the drain volume exceeds the preceding fill volume (to account for the additional IPV produced by ultrafiltration). The cycler may also be programmed to display to the user the estimated IPV during fills, and may notify the user if any drain volume exceeds the fill volume by a pre-determined amount (e.g. drain volume greater than fill volume plus expected UF volume). The cycler may also be programmed to identify errors in user input and to notify the user of apparent input errors. For example, the number of cycles during a therapy calculated by the cycler, based on the prescription parameters entered by the clinician or user, should be within a pre-determined range (e.g. 1-10). Similarly, the dwell time calculated by the cycler should be greater than zero. In addition, the maximum IPV entered by the user or clinician should be greater than or equal to the fill volume per cycle, plus the expected UF volume. Furthermore, the cycler may be programmed to reject an entered value for maximum IPV that is greater than a pre-determined amount over the fill volume per cycle (e.g., maximum IPV ≤200% of initial fill volume). In some cases, it may be desirable for the cycler to be programmed to set the maximum IPV to no greater than the last fill volume if the solution is to remain in the peritoneal cavity for a prolonged period of time, such as during a daytime therapy. In this case, the cycler may be programmed to alert the user if the cycler controller calculates that the last drain volume amounts to less than a complete drain, whereupon the cycler may provide the user with a choice to terminate therapy or undertake another drain phase.

Managing Increasing IPV while Minimizing Alarms

In an embodiment, the cycler may be programmed to track and manage an increasing IPV during a therapy without converting the therapy from continuous cycling peritoneal dialysis ("CCPD") therapy to a standard tidal peritoneal dialysis ("TPD") therapy, which would fix the residual volume to a percentage of the initial fill volume. Rather, an adaptive tidal therapy mode may be initiated, in which the residual volume is allowed to fluctuate or 'float' in response to any slow-drain conditions that may be encountered during any drain phase. The cycler may be programmed to permit this mode to operate as long as any subsequent fill volume plus expected UF does not exceed a prescribed maximum IPV ("Max IPV"). Thus the dwell-phase IPV may be permitted to increase or decrease during a therapy up to a maximum IPV, preferably set by a clinician in the clinician mode. In this adaptive tidal therapy mode, at each drain phase during a therapy, the cycler continues to attempt a complete drain within the allotted time, or as long as a low-flow or no-flow condition has not been detected for a prescribed or pre-set number of minutes. The residual volume at the end of the drain phase is allowed to vary or 'float' as long as it does not exceed an amount that would lead to exceeding the maximum IPV in the next fill phase or during the next dwell phase. In a preferred embodiment, the cycler may be programmed to not issue an alert or alarm to the user as long as it calculates that the subsequent fill phase or dwell phase will not reach or exceed maximum IPV.

The cycler may be programmed to deliver full fill volumes during each cycle of a therapy until the cycler controller calculates that the next fill volume will likely cause the IPV to exceed the maximum IPV. At a convenient time (such as, e.g., the end of a drain phase), the cycler controller may be programmed to calculate a maximum residual IP volume, which represents the maximum permissible residual IP volume at the end of a drain to allow the next cycle to proceed with the previously programmed fill volume. Partial drains will be permitted by the cycler without alarming or issuing an alert as long as the amount of fluid drained brings the residual IPV below the maximum residual IPV. If the estimated or predicted IPV at the end of a drain phase is less than the maximum residual IPV, the cycler can proceed with a full fill phase in the next cycle without risking exceeding the Max IPV. If the estimated IPV at the end of a drain is greater than the maximum residual IPV, the cycler controller may trigger an alert to the user that the subsequent fill plus UF may exceed the maximum IPV. In an embodiment, the cycler may display several options for the user to respond to this alert: it may allow the user to terminate therapy, to attempt another drain phase, or to proceed to enter a revised-cycle therapy mode, in which each subsequent fill volume is reduced and one or more cycles are added to the therapy (thereby ensuring that the remaining volume of fresh dialysate is used during that therapy). In an embodiment, a clinician or user may enable the cycler at the beginning of therapy to automatically enter this revised-cycle therapy mode without having to alert the user during therapy.

In some circumstances, the number of additional cycles may be limited by the planned total therapy time. For example, the duration of night time therapy may be limited by the time at which the user is scheduled to wake up or to get up to go to work. For nighttime therapy, the cycler controller may be programmed, for example, to prioritize the use of all dialysate solution that was planned for therapy in favor of ending therapy at the scheduled time. If the clinician or user has selected the dwell time to be adjustable, then the cycler controller will (1) add one or more cycles to ensure that the fill volume plus expected UF does not exceed maximum IPV; (2) ensure that all of the dialysis solution is used for therapy; and (3) attempt to reach the targeted end-of-therapy time by shortening the dwell times of the remaining cycles. An alternative option available to the user is to extend the end-of-therapy time. In a preferred embodiment, the cycler is programmed to add one or two additional cycles to the therapy to permit a reduced fill volume in order to prevent exceeding the maximum IPV. The cycler controller is programmed to recalculate the maximum residual IPV using the reduced fill volume occasioned by the increased number of cycles. Thus, if a low flow condition during drain occurs at the same IPV, the new higher maximum residual IPV may permit dialysis to proceed without exceeding maximum IPV.

If the fill volume cannot be reduced enough by adding a maximum allowable number of extra cycles (e.g., 2 cycles in an exemplary night time therapy scenario), then the cycler may present the user with two options: re-attempt a drain phase, or end therapy. The cycler may be programmed to reset the fill volume again after an adjustment of the fill volume, possibly adding an additional cycle, if a low flow condition at the end of drain is again encountered at an IPV above the newly recalculated and reset maximum residual IPV. Thus the cycler may be programmed to repeatedly adjust the subsequent fill volumes to prevent exceeding maximum IPV if a premature low flow condition is repeatedly encountered.

Replenishment Limitation on Dwell Time Reductions

In an embodiment, if the cycler reduces fill volumes by adding one or more cycles, then it may also reduce the dwell time in order to attempt to keep the therapy session within the total scheduled therapy time. This mode may be useful for nighttime therapy, so that the patient may be reasonably assured that therapy will have ended before a planned time of awakening in the morning. However, the cycler will continue to replenish the heater bag as needed during therapy, the replenishment generally occurring during dwell phases (when the PD cassette is not otherwise pumping to or from the patient). Therefore, in some circumstances, total therapy time may need to be extended when the required reduction in remaining dwell times leads to a total remaining dwell time that is less than the total estimated time needed to replenish the heater bag with the remaining fresh dialysate. The cycler controller may therefore calculate a maximum dwell time reduction available for the remaining therapy cycles, and extend total therapy time to ensure that the remaining fresh dialysate is properly heated. Because the cycler controller keeps track of the volume of dialysate in the heater bag, the temperature of the dialysate in the heater bag, and the volume of remaining fresh dialysate that is scheduled to be infused, it can calculate an estimate of the amount of time needed to replenish the heater bag to a pre-determined volume (given its intrinsic pumping capacity), and the time needed to bring the dialysate in the heater bag up to the prescribed temperature before it is infused into the user. In an alternative embodiment, the cycler controller may interrupt pumping operations to or from the user at any time in order to engage the pumps for replenishment of the heater bag. The cycler controller may be programmed, for example, to prevent the volume of fluid in the heater bag from dropping below a pre-determined volume at any time during therapy, other than during the last cycle. In an embodiment, the cycler may be programmed to deliver fluid to the heater bag at a greater flow rate than when it is transferring fluid to or from the user. If binary valves are used to regulate the flow of control fluid or gas between the positive/negative pressure reservoirs and the control or actuation chambers of the cassette pumps, the controller may issue on-off commands to the valves at different pressure levels measured in the control or actuation chambers of the pumps. Thus the pressure threshold in the pump control or actuation chamber at which the controller triggers an 'off' command to the binary valve may have an absolute value that is greater during delivery to or from the heater bag than the corresponding pressure threshold when the cycler is delivering or pulling fluid to or from the user's peritoneal cavity. A higher average pressure applied to the pump membrane may be expected to result in a greater flow rate of the liquid being pumped. A similar approach may be used if variable orifice valves are used to regulate the flow of control fluid or gas between the pressure reservoirs and the control or actuation chambers of the cassette pumps. In this case, the controller may modulate the flow resistance offered by the variable orifice valves to maintain a desired pressure in the pump control chamber within pre-determined limits as the pump membrane is moving through its stroke.

Exemplary Modes of Therapy FIG. 176 is a graphical illustration (not to scale in either volumes or time) of an adaptive tidal mode of the cycler when in a CCPD mode. The initial drain at the beginning of therapy is omitted for clarity. The maximum IPV (Max IPV) 700 is a prescription parameter preferably set by the clinician. The initial fill volume 702 is also preferably set by the clinician as a prescription parameter. The expected UF volume is represented by the additional IPV increase 704 during the dwell phase 706. The expected UF volume for an entire therapy may be entered by a clinician into the prescription, and the cycler may then calculate the dwell time per cycle based on the number of cycles during the therapy, and thus the expected UF volume per cycle. It should be noted that ultrafiltration is expected to occur throughout the fill-dwell-drain cycle, and the expected UF volume may include the volume of fluid ultrafiltered throughout the cycle period. In most cases, the dwell time is much larger than the fill or drain times, rendering the ultrafiltration volumes during fill or drain relatively insignificant. The fill and drain times may be adjustable by altering the pressure set points used by the controller to regulate the control valves between the pressure reservoirs and the pumps. However, the adjustability of liquid delivery flow rates and pressures to the user is preferably limited in order to ensure user comfort. Thus the expected UF volume per cycle 704 may be reasonably representative of ultrafiltration during the cycle. The drain phase 708 of the cycle in this example is a full drain, as would occur in a CCPD mode of therapy.

The maximum residual volume 710 can be calculated by the cycler controller once the Max IPV 700, the initial fill volume 702, and the expected UF volume are entered by the clinician. The maximum residual volume 710 is an indication of the 'headroom' 712 available in the peritoneal cavity to accommodate more fluid before reaching Max IPV 700. In an adaptive tidal mode within a CCPD mode of therapy, as long as a drain volume 714, 716 leaves an estimated residual volume 718, 720 less than the maximum residual volume 710, the subsequent fill volume 722, 724 can remain unchanged, because Max IPV 700 is not expected to be breached. As shown in FIG. 176, the occurrence of a low-flow condition at the residual volumes 718 and 720 triggers the cycler to initiate the next fill phase 722 and 724. During this form of therapy, the cycler will continue to attempt to perform a full drain 726 within an allotted time assuming a low-flow or no-flow condition is not encountered before the estimated zero IPV is reached. Thus, even if a full drain is not performed (because of a low-flow or no-flow condition), in this case, full fill volumes will continue to be infused, the residual IPV will be allowed to float within a pre-determined range, and the user preferably will not be disturbed by any alarms or alert notifications.

FIG. 177 is a graphical illustration of how the cycler may handle incomplete drains that fail to reach the maximum residual IPV 710. In this case, the drain phase 730 of the third cycle encounters a low-flow or no-flow condition that prevents the cycler from draining the peritoneal cavity below the maximum residual IPV 710. Given the estimated residual volume 732 (the estimated residual volume after a pre-determined duration of a low-flow condition), the cycler calculates that a subsequent fill phase volume 734 will likely cause the prescribed Max IPV 700 to be reached or exceeded 736. Therefore, at the end of drain phase 730, the cycler may alert the user to this issue. The user may then have the option to terminate therapy, instruct the cycler to re-attempt a drain phase (after possibly changing positions or repositioning the PD catheter), or instruct the cycler to enter into a revised-cycle therapy mode in which the subsequent fill volumes are reduced and one or more cycles added to complete the therapy with the planned total volume of dialysate. To keep within the allotted or prescribed total therapy time, the cycler can calculate the duration of the modified cycles by reducing the fill and drain times to account for the reduced fill and drain volumes, and then determining whether and how much the dwell times need to be reduced to meet the designated ending time of the therapy session.

A user may optionally enable a revised-cycle mode of CCPD at the beginning of a therapy, so that the occurrence of a low-flow condition during therapy can trigger the revised-cycle mode without disturbing the user with an alert or alarm. Otherwise, the user may select the revised-cycle mode upon the occurrence of a low-flow condition above the maximum residual IPV. If the user elects to enter a revised-cycle mode, the cycler controller may calculate the required fill volumes for each of an additional one, two or more cycles (remaining fill volume divided by the remaining planned cycles plus the additional one or more cycles). If one additional cycle yields a fill volume (plus expected UF) low enough to avoid reaching or exceeding Max IPV, the cycler (either automatically or at the user's option) will resume CCPD at that new fill volume 738. Otherwise, the cycler controller will calculate a new fill volume based on an additional two cycles of therapy. (Rarely, more than two additional cycles may be required to ensure that Max IPV is not breached during the remaining therapy. If the additional cycles require a substantial reduction in the remaining dwell times, the cycler may alert the user, particularly if a minimum dwell time has been prescribed, or heater bag replenishment limitations will require a lengthening of the total therapy time). The now-reduced fill volume 738 allows the cycler controller to re-calculate a revised maximum residual IPV 740, which is a function of the sum of the new fill volume plus the expected UF volume per cycle. Any subsequent drain phases that leave an estimated residual IP volume less than the revised maximum residual volume 740 will preferably not trigger any further alerts or alarms to the user, allowing for the adaptive mode of tidal therapy to remain enabled. In an embodiment, the cycler may re-calculate the expected UF volume if it has reduced the duration of the remaining dwell phases in order to stay within the planned total therapy time. Any re-calculated reduction in the expected UF volume may further increase the revised maximum residual IPV. In the example shown in FIG. 177, the cycler continues to perform CCPD mode therapy, and happens to be able to drain fully in the remaining cycles. In order not to further inconvenience the user, the cycler may optionally refrain from making any further adjustments to the therapy (particularly if the total volume of dialysate and the total therapy time have been kept within the prescribed parameters).

FIG. 178 illustrates that a planned standard tidal peritoneal dialysis (TPD) therapy may also be subject to a revised-cycle mode of TPD therapy if the cycler controller calculates that the user's Max IPV 700 is likely to be reached or exceeded during therapy. In this example, a user or clinician has selected a standard tidal therapy, in which a planned residual IP volume 742 (in actual volumetric terms or as a percentage of the initial fill volume) has been selected. As an optional feature of the cycler, the user or clinician has also chosen to perform a complete drain 744 after every three tidal fill-dwell-drain cycles, comprising a cycle cluster during a therapy session. In this example, a low-flow condition preventing draining below the maximum residual volume 710 occurs at the end of the third cycle 746. At the option of the user or clinician, the cycler either alerts the user to choose to end therapy, repeat a drain phase, or initiate a revised-cycle TPD therapy, or the cycler is allowed to automatically initiate a revised-cycle TPD therapy. In this case, the addition of a sixth cycle with a consequent reduction of the fill volume to a revised fill volume 748, is sufficient to avoid exceeding the Max IPV 700, which otherwise would have occurred 750. In this example, the cycler proceeds to perform a complete drain 744 at the end of a cluster, but resumes a standard TPD therapy thereafter. If the planned residual volume has been specified to be a percentage of the initial fill volume of the cluster, then that percentage may be applied to a revised residual IPV 752. The cycler may then calculate the subsequent drain volumes 754 by calculating the appropriate fraction of the revised fill volume 748 plus expected UF volume in order to drain to the revised residual IPV 752. Any subsequent fill volumes 758 may remain similar to the revised fill volume 748, as long as the cycler calculates that the Max IPV 700 will not be breached. Alternatively, the subsequent fill volumes may be reduced in a manner designed to maintain a relatively constant revised dwell-phase IPV 756. In this case, the cycler controller may be programmed to make the additional calculations necessary to ensure that the entire remaining dialysate solution will be properly divided among a revised fill volume 748 and later fill volumes reduced to maintain a revised dwell-phase IPV 756. In an alternative embodiment, the clinician or user may select the prescribed residual IP volume 742 to be relatively fixed volumetrically throughout therapy. In this case, the cycler controller may convert the percentage value of the residual IP volume 742 into a volumetric value (e.g. in milliliters), and continue to use that targeted residual volume after the revised-cycle mode has been instituted. In any event, the cycler controller may continue to apply the Max IPV 700 limitation in calculating any revised fill volumes.

FIG. 179 illustrates how an adaptive tidal therapy mode may be employed during a standard tidal therapy. In this example, a slow-drain condition 760 is encountered below the maximum residual volume 710. As an optional feature of the cycler, the user or clinician has also chosen in this example to perform a complete drain 764 after every four tidal fill-dwell-drain cycles, comprising a cycle cluster during a therapy session. In this case, the cycler calculates that the Max IPV 700 will not be reached if the tidal fill volume 762 is maintained. The cycler may be programmed to continue the tidal therapy at a revised residual IP volume 760 in order to avoid another slow-drain condition. Alternatively, the cycler may be programmed to attempt to drain back to the previously prescribed residual IP volume 742. Since tidal therapy can continue without risk of breaching Max IPV 700, the user need not be alerted to the institution of a revised or floating residual volume of the adaptive tidal therapy mode. A full drain 764 is initiated as prescribed, and if successful, the cycler controller may re-institute the originally prescribed tidal therapy parameters. In an embodiment, the cycler may be programmed to alert the user if a full drain cannot be achieved at the end of a tidal therapy cluster.

Adaptive Filling

In some scenarios, variations or alterations from a programmed therapy may cause a cycler to be unable to complete the therapy as prescribed. For example, if more solution volume is used than anticipated during a therapy and the number cycles programmed for the therapy, "n", is maintained, the last fill of the therapy may not be completed as prescribed, because there is not enough solution available to complete at least one fill in the therapy. (Generally, a fill volume must be sufficient to result in a minimum volume of intra-peritoneal fluid during a dwell phase). In one example, the cycler may be programmed to adjust each fill cycle volume to ensure that a minimum amount of fluid volume resides in the peritoneal cavity during each dwell phase. A fill volume may need to be greater than anticipated, for example, if a prior fluid drain volume exceeds the expected amount (for example, through the action of the user during therapy), or if the controller exceeds the anticipated drain volume during a previous cycle to avoid exceeding the pre-programmed Max IPV or a newly adjusted Max IPV. In this case, a subsequent fill volume may be greater than anticipated to maintain the pre-determined dwell volume for that cycle. This may potentially reduce the amount of solution available for the last cycle to a fill volume that will fail to provide the required intraperitoneal dwell volume during the last cycle.

To avoid these scenarios, during a therapy, the cycler controller may command that at least one cycle be dropped from the number of cycles programmed for the therapy. Thus, the number of cycles that will occur over the therapy will then be one or more less than "n". A cycle may be dropped, for example, if a fractional or non-integer number of cycles are calculated for a therapy, either at the beginning of therapy or at any time during the therapy. Additionally, it may occur if a user performs a drain during a tidal therapy that deviates from the programmed tidal percentage and/or modulus for the therapy. For example, a user may elect to perform a full drain during a tidal therapy. The controller may then drop a cycle because there may no longer be enough remaining dialysate in the solution bags to complete every programmed cycle of the therapy.

In the event that a cycle is dropped from therapy, the expected times for remaining phases of the therapy may be adjusted, for example, to increase the expected dwell times. This increase in expected dwell times may allow for a larger volume of UF to accumulate in the peritoneal cavity. Ultrafiltration may increase due to the infusion of fresh solution into the peritoneal cavity, when, for example, a user performs a full drain during a tidal therapy, and the peritoneal cavity is subsequently refilled to the initial fill volume with fresh solution. The concentration gradient for certain solutes will be greater and may result in more ultrafiltration during the dwell phase. Additionally, if the controller calculates expected UF per cycle based upon a preprogrammed expected total UF over the therapy, dropping a cycle may cause the controller to recalculate and expect a greater UF volume per cycle. In an embodiment, the controller may recalculate expected ultrafiltrate volume values for the remaining cycle(s) after a cycle is dropped from the therapy, accounting for any reduction in total therapy time, and optionally accounting for increased ultrafiltration from the use of a fresher solution earlier in the therapy.

In some scenarios, this increase may be sufficient to cause an anatomical reservoir volume, or in the specific example, an intraperitoneal volume (IPV) of the patient to exceed a preprogrammed maximum volume during a cycle. This is more likely to occur if the Max IPV volume is set unusually low. Though some embodiments may avoid such a scenario by calculating per cycle UF once at the beginning of therapy, it may be preferable to use an adaptive fill volume which is responsive to such therapy changes. In some embodiments, the number of cycles in the therapy may be kept at the programmed number, "n". The fill volume for the remaining cycles would then be altered from the programmed fill volume for the therapy to ensure that the Max IPV threshold is not exceeded.

FIG. 180 depicts an example plot 5390 which shows the peritoneal reservoir volume over time for a tidal therapy.

The plot is depicted for illustrative purposes and is not to scale. The example tidal therapy is programmed to have a total therapy volume of 2000 mL, an initial fill volume of 1000 mL, and a tidal percentage of 50%. The total expected UF for the therapy is set at 750 mL. The maximum IPV volume 5392 is set at 1400 mL. The therapy is programmed or calculated to have a total of three cycles. In FIG. 180, the therapy proceeds as programmed without a cycle being dropped.

An initial drain 5394 is performed and brings the patient IPV down to 0 mL. The initial fill 5396 of 1000 mL is then delivered to the peritoneal cavity. As shown, the IPV rises after the fill is complete due to the UF volume 5398 accumulating in the peritoneal cavity of the patient. In the example embodiment, 250 mL of UF accumulates per cycle. Though the example plot 5390 appears to depict the UF as accumulating during dwell phase, this is for illustrative purposes only. In reality, this UF would accumulate continuously over the fill, dwell, and drain.

When the first dwell 5400 is completed, 50% of the initial fill volume and the expected UF is drained from the patient in the drain 5402 of the first cycle. This brings the patient IPV to 500 mL. A fill 5404 of 500 mL is then pumped to the patient to bring the patient up to a 1000 mL IPV for the dwell 5406 of the next cycle. When the dwell 5406 completes, this drain and fill process is repeated with drain 5408 and fill 5410. After the dwell 5412 of the last cycle, the patient is fully drained to empty in drain 5414. The total volume delivered over the therapy is 2000 mL as programmed. The maximum IPV threshold 5392 is also not breached at any time during the therapy.

FIG. 181 depicts an example plot 5420 which shows the peritoneal reservoir volume over time for a tidal therapy. This therapy is programmed to have the same parameters as that shown in FIG. 180. The plot 5420 is shown with solid and dashed lines. The solid lines indicate portions of the plot 5420 where the therapy is the same as in FIG. 180. The dashed lines indicate where the plot 5420 departs from the plot 5390 shown in FIG. 180.

To start, an initial drain 5422 drains the patient to empty and then an initial fill 5424 delivers 1000 mL to the patient as in FIG. 180. This leaves 1000 mL of the total therapy volume remaining for the rest of the therapy. While the first dwell 5426 is occurring the 250 mL of UF accumulates. This leaves an expected UF volume for the remaining portion of the therapy of 500 mL.

During the therapy in FIG. 181, a user elects to perform a full drain 5428 after the first dwell 5426. At the end of the full drain 5428, the patient is left in an empty state. The cycler then fills the patient in the second fill 5430 of the therapy. This fill 5430 delivers 1000 mL of solution to the patient in order to keep the dwell volume at the programmed amount. After the second fill 5430, the programmed 2000 mL therapy volume has been used and there may be no more solution remaining to deliver to the patient. As a result, in the example embodiment, this causes a cycle to be dropped from the therapy, shortening the therapy to two cycles. In turn, the remaining expected UF volume of 500 mL is then preferably redistributed to the remaining fill-dwell phase of the second cycle. As shown, this causes the Max IPV threshold 5392, which in this example is set at 1400 mL, to be crossed (fill volume+UF=1500 mL).

In some embodiments, the cycler controller may be configured to recognize and adapt to such a scenario before it occurs. This may be accomplished by having the controller compute before dropping a cycle and performing a fill that the current patient volume plus the next fill volume and the expected UF per cycle does not exceed the Max IPV threshold 5392. If the calculation indicates that the max IPV threshold 5392 will be exceeded, the controller may alter the fill volume so that a breach of the Max IPV threshold 5392 is avoided. This may result in maintaining the "n" number of fills programmed for the therapy (in this example, 3 fills).

The fill volume may be adapted or changed from the originally programmed volume such that the remaining therapy volume is spread out over the remaining cycles. This may ensure that the fill volume and the expected UF accumulated during a cycle does not exceed the Max IPV threshold 5392. It may also ensure that the full therapy volume of dialysate solution is used. By using the full therapy volume, waste of solution staged for use during the therapy is minimized. The user may be prompted to acknowledge or confirm acceptance of the newly calculated adapted fill volume. In other embodiments, a user may be presented with one or more options to change the therapy, each of which will avoid exceeding the max IPV threshold 5392. The user may select a desired option. The options need not be limited to those described herein.

The following equation may be used to determine an adapted fill volume for a cycle:

$$V_T = (V_{NEW} * \text{Full Fills Remaining}) + ((\text{Tidal \%} * V_{NEW}) * \text{Tidal Fills Remaining})$$

Where $V_T$ is equal to the Therapy Volume Remaining and $V_{NEW}$ is equal to the new fill volume or adapted fill volume for the cycle.

The equation may be rearranged to solve for $V_{NEW}$ to determine the adapted fill volume. Using the example therapy in FIG. 181, when it is detected that a non-adapted fill volume will cause the Max IPV threshold 5392 to be exceeded, $V_{NEW}$ may be determined as follows:

$$1000 \text{ mL} = (V_{NEW} * 1) + ((0.5 * V_{NEW}) * 1)$$

Which simplifies to:

$$1000 \text{ mL} = 1.5 \, V_{NEW}$$

Which may be rearranged to solve for $V_{NEW}$:

$$V_{NEW} = 1000 \text{ mL} / 1.5 = 666.6 \text{ mL}$$

The above equation assumes that the tidal percentage is maintained in the remaining cycles of the therapy volume. Optionally, the equation may allow for the tidal percentage to be changed in the remaining cycles of the therapy.

FIG. 182 depicts an example plot 5350 showing the intraperitoneal volume over time for a tidal therapy. The therapy parameters are the same as those programmed in FIGS. 180 and 181. As shown, the fill volume is adapted after a user initiated full drain 5452. The adapted fill volume ensures that the max IPV threshold 5392 is not exceeded during the therapy and that the entirety of the programmed therapy volume is consumed. A cycle is not dropped, as dropping the cycle would not allow the full therapy volume to be used without exceeding the max IPV threshold 5392. Additionally, the tidal percentage is kept at the programmed value in the example plot 5350 shown in FIG. 182.

In some embodiments, a cycle may be dropped and a calculation may then be made to determine if the max IPV threshold 5392 will be breached. The dropped cycle may then be brought back so that the programmed number of cycles for the therapy is maintained. Alternatively, the calculation may be made preemptively before dropping the cycle to determine if dropping the cycle will cause the max IPV threshold 5392 to be exceeded.

Referring back to FIG. 182, calculated above as $V_{NEW}$, the second fill 5454 is 666 mL (rounded for convenience). The 250 mL of UF 5398 accumulated during the cycle does not then cause the max IPV threshold 5392 to be exceeded. During the second drain 5456 the tidal percentage is kept at 50% and the patient is drained to 333 mL. The fill 5458 of the last cycle of 333 mL brings the patient's IPV back to the calculated new fill volume, $V_{NEW}$. Again, the UF 5398 for the last cycle is able to accumulate without the max IPV threshold 5392 being exceeded. The patient is then drained to empty in the drain 5460 of the last cycle to conclude the therapy.

In some embodiments, the controller may adjust the tidal percentage may to keep the IPV of the patient closer to the initial fill volume. Alternatively, in some embodiments the tidal therapy may be converted to a non-tidal therapy after the first adapted fill volume is delivered to the patient. For example, the first adapted fill may be delivered and the dwell may be allowed to elapse. In the following drain, a cycler may only drain the expected UF for the cycle and the therapy may enter a UF maintenance mode. In some embodiments, the expected UF plus an optional extra margin of fluid may be drained. This may allow the next fill to bring the IPV of the patient back to approximately the initial fill volume. Again this should allow for the full therapy volume to be used without the max IPV threshold 5392 for the therapy being exceeded. In another embodiment, the tidal therapy may be converted to a CCPD therapy with the remaining solution volume split between a number of cycles.

In some embodiments, the fill volume may be adapted while still dropping a cycle from the therapy. In such scenarios, the fill volume may be lowered such that the expected UF per cycle after a cycle is dropped does not cause the max IPV threshold 5392 to be exceeded. In some embodiments, the fill volume may be recalculated as:

$$V_{NEW} = \text{Max IPV} - (\text{Expected UF} + \text{Optional Margin})$$

Using this equation and referring to the example therapy described in FIG. 181, after the user elects to perform a full drain, the fill volume may be recalculated based on the new expected UF after the last cycle is dropped. The fill volume may be changed to 825 mL (15% margin on expected UF). Thus the therapy may be completed without the max IPV threshold 5392 being breached. In such embodiments, some solution will be unused at the end of the therapy.

In addition to implementing an adaptive fill volume, the controller can optionally be programmed to perform a fill volume less than the previously programmed fill volume (a 'shorted fill'). This can be useful, for example, if the number of calculated cycles is a non-integer number, which can occur if a programmed therapy volume does not divide evenly into a number of defined cycles. The therapy may perform a shorted fill on the last cycle if a predetermined percentage (e.g. 85%) of the programmed fill volume is available. If the predetermined percentage is not available, the controller can drop the cycle and leave the extra solution unused.

In some cases, if more solution than expected is used during a portion of the therapy, then the remaining solution volume for the last cycle may fall below a predetermined percentage threshold. This can occur in response to a number of factors, such as tolerances in volume targeting (e.g. a small over-delivery may be allowed). Consequently, the controller may drop the last programmed cycle in response, and may reconfigure the remaining dwell phases to increase the expected UF per cycle. this could cause the Max IPV threshold 5392 to be exceeded.

In some embodiments, this situation may be avoided by preventing the cycler controller from dropping the last cycle of the therapy. The remaining volume in the attached bags may be delivered to the patient for the last fill regardless of what percentage of the programmed fill volume is remaining. Alternatively, if the therapy is a CCPD therapy, the therapy may be converted to a tidal therapy. The tidal percentage may be selected so that the programmed fill volume is maintained without dropping a cycle.

In some embodiments, such a scenario can be avoided by performing the shorted fill at the beginning of therapy (e.g. during the first fill). This may ensure that the remaining therapy volume may be divided between the remaining cycles so that substantially the full programmed fill volume may be delivered to the patient during each cycle. Thus the last fill volume will be expected to be all or nearly all of the programmed fill volume instead of a volume closer to the predetermined percentage threshold. This effectively creates a buffer volume. Whether the last fill cycle is still performed may still be subject to the predetermined percentage of the programmed fill volume threshold. But the likelihood of the threshold not being met may be reduced, owing to the implementation of the buffer fill volume.

The controller can optionally be programmed to assign a range to the threshold fill volume, as a percentage of a programmed fill volume. This range may be viewed as a hysteresis band placed around the predetermined percentage of programmed fill volume threshold. This hysteresis band can be useful in accommodating small differences between expected volume used and actual volume used during a therapy. The controller may be programmed to apply a hysteresis band as a range of percentage values on either or both sides of the predetermined percent threshold. In some embodiments, this hysteresis band may be clinician or user programmable.

Pump Operation Synchronization

In various embodiments, during pumping, pump chambers of a cassette may be synchronized. The following description of pump operations may apply to any device that operates a pump cassette having two or more pumps. In an embodiment, such a device may be, for example a peritoneal dialysis cycler. In other embodiments, it may be an intravenous infusion pump system or an extracorporeal circulation pumping system using a pump cassette (such as, e.g., a hemodialysis or cardiopulmonary bypass system), or another type of pumping system using a pump cassette. Exemplary systems in which the following pump synchronizing operations may be implemented include for example, the peritoneal dialysis systems disclosed in U.S. Pat. Nos. 5,350,357, 5,431,626, 5,438,510, 5,474,683 and 5,628,908. They may also include, for example, the hemodialysis system disclosed in U.S. Pat. Nos. 8,246,826, 8,357,298, 8,409,441 and 8,393,690. They may also include, for example, the cardiopulmonary bypass systems disclosed in U.S. Pat. No. 8,105,265. In the following description, the term cycler is intended to encompass other pumping devices (such as those noted above) that may incorporate the use of a pump cassette.

A number different synchronization schemes may be used. Such synchronization schemes may serve to temporally dictate when various steps of a pumping operation occur (i.e. the filling and delivery of a cassette pumping chamber and any associated volume measurements, venting, etc.). Additionally, such synchronization schemes may serve to temporally structure pumping operations occurring across multiple pumping chambers of a cassette.

In some embodiments, pumping operations may use different synchronization schemes when different tasks are being performed. For example, a first type of chamber synchronization scheme may be used when draining fluid from a patient, while a second type of chamber synchronization scheme may be used when emptying a remaining dialysate volume from a heater bag (or other reservoir) after a therapy has concluded. The synchronization scheme selected may be optimized for handling relatively large throughputs of fluid volume. The synchronization scheme may also be optimized to minimize patient discomfort. Depending on the task being performed, one or more of a number of synchronization schemes may be assigned to each different pumping operation as appropriate.

FIG. 183 depicts a flowchart detailing a number of example steps which may be used to synchronize pumping operations in a two-chamber pump cassette. As shown in the example embodiment, the flowchart depicts a synchronization scheme for a two-chamber cassette, although the procedure may readily be generalized for a multi-chamber cassette. For example, a similar scheme may be used for a cassette with additional pump chambers (e.g. sets of chambers ganged together such that they operate in parallel). As shown, at step 4000, the controller may cause Chamber A to execute a fill step. A fill step entails subjecting the target chamber of the cassette to a negative pressure while that chamber is in fluidic communication with a desired source reservoir. In some embodiments, the negative pressure may be applied for a predetermined time period sufficient to substantially fill the target chamber. If only a partial fill volume is desired, then the cycler controller may estimate any desired pump fill volume by calculating a relationship between the fill volume and the time taken to reach that fill volume through a series of volume measurements at periodic intervals during a fill cycle.

In step 4002, the device or cycler (via a device controller) may then make a measurement of the volume which was filled in Chamber A. Any type of volume measurement means may be used to perform this step, including, for example, pressure measurements in relation to a reference chamber (FMS), acoustic volume sensing, pump membrane position sensing, etc. As shown in FIG. 183, an FMS-type measurement may be used, including any of the FMS methods described herein. The measurement of the current volume in the chamber may be compared to a previous measurement (e.g. the volume measurement taken after a preceding delivery) to determine the volume with which the chamber was filled. Additionally, in some embodiments, this measurement may be an indirect measurement from which the current volume may be inferred, such as, for example: the time spent in the fill mode before measurement as a percentage of a reference time representing complete filling; optical, ultrasonic or electrical capacitive detection or estimation of the relative position of the pump membrane in the pumping chamber, as an indication of the percentage of a full liquid volume when the membrane is fully retracted; or a variation in the pressure waveform detected as the pump membrane travels through its excursion, modeled against an empirically determined reference variation during testing. At about this time, the cycler may also begin step 4004, the filling of Chamber B.

The cycler may deliver the volume contained in Chamber A to a desired destination in step 4006. A deliver step may entail subjecting the designated chamber of the cassette to a positive pressure while that chamber is in fluidic communication with a desired destination reservoir. In some embodiments, the positive pressure may be applied for a predetermined time period sufficient to substantially deliver most or all of the volume of the designated chamber. After delivering Chamber A, in step 4008, the cycler may then make a measurement of the volume which was delivered by Chamber A during step 4006. In some embodiments, measurement of the current volume in the chamber may be compared to a previous measurement (e.g. the volume measurement taken in step 4002) to determine the volume delivered from Chamber A. Chamber B may continue to fill as steps 4002, 4006, and 4008 are completed.

As shown, after step 4008 is completed, the cycler may wait for a predetermined time period to elapse before Chamber A is refilled. This period of time may be selected so that it is about equal to the amount of time which will be needed to complete step 4004, which can be determined empirically, for example, through a series of pumping steps at the beginning of a therapy.

After filling of Chamber B is complete, in step 4010, the cycler may then make a measurement of the volume which was filled in Chamber B during step 4004. In some embodiments, this may take place while Chamber A is waiting for the predetermined time period to elapse, or alternatively at the end of the time period. Thus, while the measurement is being taking in step 4010, Chamber A may return to step 4000 and begin refilling.

The cycler may then deliver the volume in Chamber B in step 4012. Step 4012 may occur while Chamber A is refilling. After delivering from Chamber B, in step 4014 the cycler may then make a measurement of the volume which was delivered from Chamber B during step 4012. Again, this may occur as Chamber A is refilling.

As shown, after step 4014 is completed, the device may wait for a predetermined time period to elapse before Chamber B is refilled. This period of time may be selected so that it is about equal to the amount of time which will be needed to complete step 4000. After Chamber A has finished refilling, the device may, as described above, take a measurement of the volume refilled in step 4002. At this point, the device may return to step 4004 and being refilling of Chamber B. The example steps in the flowchart may repeat as necessary until a desired task is complete (e.g. patient is drained to empty).

FIG. 184 depicts another embodiment for synchronizing pumping operations in a two-chamber cassette. As shown in the example embodiment, the flowchart depicts a synchronization scheme for a two-chamber pump cassette, although the procedure can readily be generalized for use on a cassette with additional chambers (e.g. sets of chambers ganged together such that they operate in parallel). As shown, at step 4020, the device may cause Chamber A to execute a fill step. In step 4022, the device may then make a measurement of the volume which was filled in Chamber A during step 4020. As before, any type of suitable sensor or suitable measurement means may be used to perform this step. As shown in FIG. 184, an FMS-type measurement, such as any of those described herein may be used. In other embodiments, and as previously noted, acoustic volume sensing or any of other suitable measurement means may be used.

The cycler may then deliver the volume contained in Chamber A to its destination in step 4024. At this time, the cycler may also begin step 4028, the filling of Chamber B. After delivering Chamber A, in step 4026, the cycler may make a measurement of the volume which was delivered from Chamber A during step 4024. Chamber B may continue to fill as steps 4024 and 4026 are completed.

As shown, after step 4026 is completed, the cycler may check to see that the volume in Chamber A was appropriately delivered. This may, for example involve comparing the measurements from steps 4022 and 4026. The cycler may use this comparison to determine whether a predetermined amount or proportion of the fill volume was delivered. When the predetermined amount or proportion of the fill volume is delivered, the cycler may consider the chamber fully delivered. In the event that the cycler determines that the Chamber A volume was not fully delivered, the cycler may perform steps 4024 and 4026 again. These steps may be repeated until the cumulative volume from each attempt falls within the predetermined amount or proportion of the measurement from step 4022. In some embodiments, there may be a limit to the number of times these steps may be repeated before the cycler proceeds to the next step and attempts to deliver Chamber B. In some embodiments, once this limit is reached, and if a predetermined amount of fluid has not been delivered, an occlusion alarm or the like may be triggered by the cycler controller.

After it has been determined that Chamber A has been fully delivered, step 4030 may be performed. In step 4030, the cycler may make a measurement of the volume which was filled into Chamber B during step 4028. Additionally, after it is determined that the full volume of Chamber A has been fully delivered (or a retry limit has been reached) the cycler may check to see if a predetermined period of time has elapsed. In the event that the predetermined period of time has not elapsed, the cycler may wait for the remainder of the predetermined time period to elapse before Chamber A is refilled. This period of time may be selected such that it is about equal to the amount of time which will be needed to complete step 4028. Step 4032 may also be performed after the predetermined period of time has elapsed. It may be desirable that step 4032 begin after Chamber A has begun being refilled.

After delivering Chamber B, in step 4034, the cycler may then make a measurement of the volume which was delivered from Chamber B during step 4032. Chamber A may continue to fill as steps 4032 and 4034 are completed.

As shown, after step 4034 is completed, the cycler may check to see that the volume in Chamber B was fully delivered. This may, for example involve comparing the measurements from steps 4030 and 4034. The cycler may use this comparison to determine whether a predetermined amount or proportion of the fill volume was delivered. In the event that the cycler determines that the Chamber B volume was not fully delivered, the cycler may perform steps 4032 and 4034 again. These steps may be repeated until the cumulative volume from each attempt falls with the predetermined amount or proportion of the measurement from step 4030. In some embodiments, there may be a limit to the number of times these steps are repeated before the device proceeds to a next step and attempts to deliver Chamber A. If a limit exists, once it is reached, an occlusion alarm or the like may be triggered by the system controller. In other embodiments, once this limit is reached, the cycler may enter a troubleshooting mode to test for various conditions (e.g. an occlusion) and issue an alert or alarm if necessary. After it has been determined that Chamber B has been fully delivered, step 4022 may be performed. In step 4022, the cycler may make a measurement of the volume which was filled into Chamber A during step 4020. Additionally, after it is determined that the full volume of Chamber B has been fully delivered (or a limit of attempts has been reached) the cycler may check to see if a predetermined period of time has elapsed. In the event that the predetermined period of time has not elapsed, the cycler may wait for the remainder of the predetermined time period to elapse before Chamber B is refilled. This period of time may be selected such that it is about equal to the amount of time that will be needed to complete step 4020. Step 4024 may also be performed after the predetermined period of time has elapsed. Step 4024 preferably may begin after the refilling of Chamber B has begun. The example steps in the flowchart may be repeated as necessary until a desired task is complete (e.g. patient is drained to empty). FIG. 185 depicts a flowchart detailing another embodiment for synchronizing pumping operations in a two-chamber cassette. Specifically, the flowchart shown in FIG. 185 depicts a number of example steps that may be followed to synchronize delivery of fluid from a two-chamber pump cassette, although the scheme may readily be generalized for use in a cassette with additional chambers (e.g. sets of chambers ganged together such that they operate in parallel). The flowchart depicted in FIG. 185 begins after each of Chamber A and Chamber B has been filled and an initial measurement of the fill volumes has been taken.

As shown, in the example delivery synchronization scheme, the chambers deliver their volumes one after the other in sequential fashion. Starting at step 4040, Chamber A may deliver its volume to the desired destination. The cycler may then conduct a measurement of the volume delivered in step 4042. This measurement may be compared to the initial fill volume measurement to determine how much of or if the entire volume was delivered.

In the example flowchart, steps 4044, 4046, 4048, 4050 are shown in dashed outline form. These steps are optional and may not be included in all embodiments. In some embodiments, the cycler may not deliver the volume in a chamber all at once. Instead, in some embodiments, multiple delivery and measurement steps may occur before the entire volume is delivered from the chamber. In this case, steps 4044, 4046, 4048, 4050 provide additional delivery and measurement steps sufficient to deliver the entire chamber volume. In some embodiments, a greater or lesser number of delivery and measurement steps may be used.

Additionally, in some embodiments, the cycler may attempt to deliver a chamber volume multiple times in the event that the measurement taken in 4042 is lower than desired or indicates that the chamber was not fully delivered. In this case, steps 4044, 4046, 4048, 4050 may be performed as needed until the entire chamber volume has been delivered. In some embodiments, additional steps may be added to allow the cycler to deliver the entire chamber volume. In some embodiments, there may be a limit to the number of delivery and measurement steps that may be performed before the cycler stops trying to deliver and proceeds to act on the next chamber. In the example embodiment, after completing delivery from Chamber A, the cycler may proceed to step 4052. In step 4052, the cycler may begin delivery from Chamber B. After completing step 4052, the cycler may take a measurement of the volume which was delivered in step 4054. This measurement may be compared to the initial fill volume measurement to determine how much of or if the entire volume was delivered.

In the example flowchart, steps 4056, 4058, 4060, and 4062 are shown in dashed outline form. These steps are optional and may not be included in all embodiments. In some embodiments, the cycler may not deliver the volume in a chamber all at once. Instead, in some embodiments, multiple delivery and measurement steps may occur before the entire volume is delivered from the chamber. Additionally, in some embodiments, the cycler may attempt to deliver a chamber volume multiple times in the event that the measurement taken in 4052 is lower than desired. In such embodiments, the cycler may operate similarly to the steps described above in reference to steps 4044, 4046, 4048, 4050.

After each of Chamber A and Chamber B has been emptied, the cycler may refill each of the chambers. The cycler may then take measurements of the volume of fluid that occupies each chamber. After taking these measurements, the cycler may again deliver Chamber A and Chamber B as described above. This process may be repeated as necessary until a desired task is complete (e.g. patient is drained to empty).

It may be advantageous to release or reduce the magnitude of any existing pressure in a pumping chamber of a pump cassette before a volume measurement of the pumping chamber is attempted. In an embodiment, the pump control chamber may be vented to atmosphere before an FMS chamber volume measurement is made. In other embodiments, the magnitude of the existing pressure in the pumping chamber may be reduced without necessarily allowing it to reach atmospheric pressure, as long as a predetermined or prescribed level of accuracy of the FMS measurement can be obtained. The following description involves venting procedures for a two-pump cassette, but the venting procedure may be applied equally to a pump cassette having a single pumping chamber, or one having a plurality of pumping chambers. Exemplary systems in which the following pump venting operations may be implemented include for example, the peritoneal dialysis systems disclosed in U.S. Pat. Nos. 5,350,357, 5,431,626, 5,438,510, 5,474,683 and 5,628,908, the contents of which are all incorporated herein in their entireties. They may also include, for example, the hemodialysis system disclosed in U.S. Pat. Nos. 8,246,826, 8,357,298, 8,409,441 and 8,393,690, the contents of which are also all incorporated herein in their entireties. They may also include, for example, the cardiopulmonary bypass systems disclosed in U.S. Pat. No. 8,105,265, the contents of which are also incorporated herein in its entirety.

FIG. 186 depicts a flowchart detailing another embodiment for synchronizing pumping operations in a two-chamber cassette. Specifically, the flowchart shown in FIG. 186 depicts a number of example steps that may be followed to synchronize delivery of fluid from a two-chamber pump cassette, although the scheme may readily be generalized for use in a cassette with additional chambers (e.g. sets of chambers ganged together such that they operate in parallel). The flowchart depicted in FIG. 186 begins after each of Chamber A and Chamber B has been filled and a measurement of the fill volumes has been taken.

As shown, the example flowchart is similar to that depicted in FIG. 186. All of the steps from FIG. 185 are included, except that an additional step 4064 has been added. In this added step, the pressure in the chamber is altered to relieve the chamber of any back-pressure that may have developed due to, for example an occluded or partially occluded fluid line in communication with the chamber. In an embodiment, the chamber is vented. In some embodiments, the chamber may be vented to the atmosphere. In other embodiments, the chamber may be vented to a pressure source which is at a pressure lower than the pressure existing in the camber during or after a delivery stroke. In alternate embodiments, the chamber may not be vented in step 4064, but rather subjected to a negative pressure. Any other approaches to venting the pumping chamber known in the art can also be used. This may help to increase the overall accuracy of volume measurement and fluid accounting. Additionally, this venting may help to mitigate any possible effects from back pressure (e.g. due to an occluded or partially occluded line). Vent steps may also be referred to herein as back pressure relief steps.

As shown in FIG. 186, the vent step 4064 occurs after Chamber A has finished delivering its volume and before Chamber B begins delivering its volume. In alternate embodiments, there may be additional vent steps (not shown in FIG. 186), or the vent step 4064 may occur at a different time. For example, in some embodiments, the vent step 4064 may be performed prior to each post-delivery volume measurement taken on either of the chambers. Alternatively, vent step 4064 may be performed prior to both post-fill and post-delivery volume measurements taken on either of the chambers. Additionally, it should be noted that vent steps may be added to any other synchronization scheme, including but not limited to those described herein. For example, one or more vent or back pressure relief steps may be added to the synchronization scheme depicted in FIG. 184. In a specific example, a back pressure relief or venting step may be added between each delivery and post-delivery measurement in FIG. 184.

FIG. 187A depicts a flowchart detailing another embodiment for synchronizing pumping operations in a two-chamber pump cassette. Specifically, the flowchart shown in FIG. 187A depicts a number of example steps that can be used to synchronize delivery of fluid from a two-chamber pump cassette, although the scheme may readily be generalized for use in a cassette with additional chambers (e.g. sets of chambers ganged together such that they operating in parallel). The flowchart depicted in FIG. 187A begins after each of Chamber A and Chamber B has been filled and a measurement of the fill volumes has been taken.

As shown, the cycler begins by delivering the volume from Chamber A in step 4070. The cycler then vents Chamber A in step 4072. After venting Chamber A, the cycler takes a measurement in step 4074 of the volume delivered from Chamber A during step 4070. The cycler can use the measurement from step 4074 to check that the volume in Chamber A was fully delivered. This may, for example involve comparing the initial fill measurement with the measurement from step 4074. The cycler can use this comparison to determine whether a predetermined amount or proportion of the fill volume was delivered. In the event that the cycler determines that the Chamber A volume was not fully delivered, the cycler can perform steps 4070, 4072, and 4074 again. These steps may be repeated until the cumulative volume from each attempt falls within a predetermined amount or proportion of the initial measurement of the volume filled into Chamber A. As in other embodiments, the cycler (i.e. its controller) may be programmed to limit the number of retries the cycler is allowed to perform. If the limit is reached, the cycler controller can trigger a user alert or alarm.

After the volume in Chamber A has been delivered to the desired destination, the cycler can begin filling of Chamber A in step 4076. After Chamber A has begun filling or after Chamber A has filled, the cycler begins to deliver Chamber B in step 4078. After Chamber B has been delivered, Chamber B can be vented in step 4080. After venting, in step 4082, the cycler takes a measurement of the volume delivered from Chamber B during step 4078. The cycler uses the measurement from step 4082 to check that the volume in Chamber B was fully delivered. This may, for example involve comparing the initial fill measurement with the measurement from step 4082. The cycler uses this comparison to determine whether a predetermined amount or proportion of the fill volume was delivered. In the event that the cycler determines that the Chamber B volume was not fully delivered, the cycler may perform steps 4078, 4080, and 4082 again. These steps can be repeated until the cumulative volume from each attempt falls within a predetermined amount or proportion of the initial measurement of the volume filled into Chamber B. As in the other embodiments described, the cycler (i.e. its controller) may be programmed to limit the number of retries the cycler is allowed to perform. If the limit is reached, the cycler controller can trigger a user alert or alarm.

After the volume in Chamber B has been delivered to the desired destination, the cycler begins filling of Chamber B in step 4084. After Chamber B has begun filling or after Chamber B has filled, the cycler begins to deliver Chamber A in step 4070. The example steps in the flowchart may repeat as necessary until a desired task is complete (e.g. patient is drained to empty).

A number of flowcharts demonstrating pumping operation processes which include one or more vent or back pressure relief steps are depicted in FIGS. 186, 187A, and 189. An example graph depicting pressurizing in a pump chamber during a pumping operation with a back pressure relief step is depicted in FIG. 187B.

FIG. 187B depicts an example graph 4071 which plots pressure in a control chamber over a deliver stroke, back pressure relief step, and volume measurement step. Though the graph 4071 is exemplary of any pump chamber performing such steps in any synchronization scheme, the reference numerals for chamber A in FIG. 187A are included on the graph 4071 to indicate an example deliver stroke 4070, back pressure relief step 4072, and volume measurement step 4074.

As shown, the delivery stroke 4070 is conducted at a positive pressure. As fluid is delivered the volume of the control chamber increases and controller commands the chamber to be repressurized so that its pressure remains within a desired or predetermined range. At the end of the deliver stroke 4070, a back pressure relief step 4072 is commanded by the cycler controller. In the example back pressure relief step 4072, the control chamber is vented toward ambient pressure. This may, for example, be done by actuating any suitable valve or combination of valves in a pneumatic circuit in order to place the chamber in fluid communication with the atmosphere. As described elsewhere herein, in other embodiments, a back pressure relief step may involve connecting the chamber to a venting reservoir other than the atmosphere (e.g. a reservoir which is at a pressure below that of the deliver pressure or delivery pressure range).

After the back pressure relief step 4072 is completed, the chamber may be repressurized such that a volume measurement 4074 (e.g., via an FMS procedure) may be made. In the example graph 4071, this volume measurement is made by pressurizing the chamber to a known positive pressure and then allowing it to equalize with a reference chamber having a known volume at a known or measured pressure. The post equalization pressure is read to determine the volume of the chamber, as described elsewhere.

FIG. 188 depicts a flowchart detailing another embodiment for synchronizing pumping operations in a two-chamber cassette. Specifically, the flowchart shown in FIG. 188 depicts a number of example steps that may be followed to synchronize delivery of fluid from a two-chamber pump cassette, although the scheme may readily be generalized for use in a cassette with additional chambers (e.g. sets of chambers ganged together such that they operating in parallel). The flowchart depicted in FIG. 188 begins after each of Chamber A and Chamber B has been filled and a measurement of the fill volumes has been taken.

FIG. 188 depicts a synchronization scheme in which delivery from Chamber A and Chamber B can be interleaved or interlaced with one another. As shown, one chamber may be delivering fluid while the other chamber may be taking a volume measurement. In some embodiments, such a synchronization scheme is used if a chamber or chambers do not fully empty during a delivery step. In other embodiments, the cycler may not be programmed to deliver the full chamber volume in one step. Such a synchronization scheme may be used, for example, in such embodiments.

In step 4090, the cycler delivers from Chamber A. After delivering from Chamber A, in step 4092, the cycler takes a measurement of the volume delivered from Chamber A during step 4090. As shown, at about the same time the cycler begins to deliver from Chamber B in step 4102. Thus the cycler can interleave or interlace delivery and volume measurements. As shown, steps 4094, 4096, 4098, and 4100 for Chamber A and steps 4104, 4106, 4108, 4110, and 4112 may be similarly interleaved or interlaced with each other. In some embodiments or in some instances a greater or lesser number of steps may be included. For example, the cycler may perform additional interleaved steps until the full volume from the chambers has been delivered to the desired destination.

FIG. 189 depicts a flowchart detailing another embodiment for synchronizing pumping operations in a two-chamber pump cassette. Specifically, the flowchart shown in FIG. 189 depicts a number of example steps that may be used to synchronize delivery of fluid from a two-chamber cassette, although the scheme may readily be generalized for use in a cassette with additional chambers (e.g. sets of chambers ganged together such that they operating in parallel). The flowchart depicted in FIG. 189 begins after each of Chamber A and Chamber B has been filled and a measurement of the fill volumes has been taken.

As shown, the example flowchart in FIG. 189 is similar to that depicted in FIG. 188. All of the steps from FIG. 189 are included, except that additional steps 4120, 4122, 4124, 4126, 4128, and 4130 have been added. In these added steps, the pressure in the chambers may be altered to relieve the chambers of any back-pressure (positive or negative) that may have developed due to, for example an occluded or partially occluded fluid line in communication with the chamber. In an embodiment, the chambers are vented. In some embodiments in which a chamber is vented, the chamber may, for example, be vented to the atmosphere, or to a source of positive or negative pressure above or below atmospheric pressure. Venting may occur for a predetermined period of time. In various embodiments, the predetermined period of time may not necessarily be of sufficient duration to allow the chamber to substantially equalize with the venting source, be it the atmosphere, or a positive or negative pressure reservoir. In other embodiments, the chambers may be vented to a pressure source which is at a pressure lower than the delivery pressure. In alternate embodiments, the chamber may not be vented, but rather subjected to a negative pressure. Any other suitable means of venting the pumping chamber may also be used. This venting may help to mitigate any possible effects from back pressure (e.g. due to an occluded or partial occlusion). Additionally, this may help to increase the overall accuracy of volume measurement and fluid accounting.

As shown, the back pressure relief steps 4120, 4122, 4124, 4126, 4128, and 4130 occur before post-delivery volume measurements in the example embodiment. These steps are not interleaved or interlaced as are the delivery steps and volume measurement steps. Instead, the timing of these steps may occur independently, in order to optimize back pressure relief. Additionally, in some embodiments, venting steps may be included prior to all volume measurements taken by a cycler. For example, some embodiments can include a venting step prior to volume measurements taken to determine a volume filled during a fill step. Such additional venting steps may, for instance, be added into any of the above described synchronization schemes. As with post-delivery venting steps, post-fill venting steps may occur independently and not be interleaved or interlaced with other steps.

In some embodiments, synchronization of pumping operations may be accomplished by using a shared resource system and running each pump chamber of a cassette as an independent state machine. For an independent state machine to perform an operation, it may be required to be in possession of an exclusive access token or resource. That is, if one independent state machine (i.e. pump chamber) is in possession of a token, the other chamber will be unable to also possess that token. As soon as a chamber is finished with an operation (e.g. FMS, filling, or delivering), the chamber may release the associated token. This will make the token or resource available for another chamber's possession. The released token may then be possessed by another chamber as soon as another chamber is ready to acquire it.

Using the specific example of a fill operation, a chamber independent state machine may be required to have possession of a fill bus resource or token. Likewise, delivery operations may require an independent state machine to have possession of a delivery resource or token. Each of the fill and delivery buses may be treated as exclusive access resources.

Such a scheme may eliminate the need for a separate software layer which governs pumping operation and pump synchronization. Instead, the function of this layer would be realized as an emergent behavior of the synchronization scheme. Furthermore, such a scheme may help to increase throughput of fluid through a pumping cassette when compared with other synchronization schemes such as that shown in FIG. 184. This increase in throughput may shorten the time required for a cycler to complete a prescribed fill or drain of a connected patient. As a result, the greater throughput may help to increase the proportion of a therapy spent in the dwell phase of each cycle.

In embodiments in which a pumping cassette includes multiple pump chambers configured to be operated in parallel, the pump chambers that operate in parallel with one another may be assigned to a single independent state machine. Additionally, in some embodiments, a non-pump chamber independent state machine may also be included. This independent state machine may have the capability to take possession of one or more resources to control pumping operations.

In the above, description, the tokens are described as mutual exclusion or mutex tokens. It should, however, be appreciated that any suitable variety of synchronizing tokens may also be used. For example, in some embodiments, semaphore tokens may be used. In such embodiments, the semaphore tokens may be binary semaphore tokens.

FIG. 190 shows a flowchart outlining a synchronization scheme in which pump chambers are treated as independent state machines which acquire exclusive access tokens. In the example embodiment, only two pump chambers are included, though as would be appreciated by one skilled in the art, such a scheme could be generalized for a pump cassette with any number of pump chambers. In the example flowchart, the pump chambers are synchronizing a pumping operation generically referred to as operation "X" since any pumping operation may be synchronized in such a manner. To perform operation "X", a pump chamber must have possession of the bus for that operation. This possession is controlled by token "X".

The example flowchart starts with chamber A of the pumping cassette ready to perform operation "X" and chamber B not yet ready to perform operation "X". As shown, in step 5090 chamber A acquires token "X". Chamber A then begins performing operation "X" in step 5092. While Chamber A is performing operation "X", chamber B becomes ready to perform operation "X". Since chamber B is ready to perform operation "X", chamber B performs step 5094 and checks for the availability of token "X". Since the token is currently in held by chamber A and the token is treated as an exclusive access resource, chamber B will be unable to take possession of the token in order to perform the pumping operation. Chamber B may then repeatedly check for the availability of the token. Alternatively, chamber B may reserve token "X" for usage as soon as token "X" becomes available. When chamber A finishes performing operation "X", chamber A will release possession of token "X" in step 5096. This will allow chamber B to acquire and hold the token. As shown, in step 5098 chamber B acquires token "X". Chamber B then begins performing operation "X" in step 5100. In some embodiments, additional logic may be employed before a pump chamber releases a resource or token. For example, in some embodiments, the controller may check whether the pump chamber transferred more than a predetermined amount of fluid. This may help to prevent a pump chamber from releasing a token if only a partial stroke has been completed. Checking for partial strokes may help to increase throughput of fluid through a pumping cassette. Additionally, checking for partial strokes may aid in air management depending on the embodiment.

FIG. 191 depicts an example flowchart in which the amount of fluid moved during a pumping stroke is checked before that chamber releases possession of a token. The flowchart depicted in FIG. 191 begins after the chamber has become ready to perform a specific pumping operation, operation "X", and after the chamber has checked for the availability of the token for that operation. As shown, in step 5110, the chamber acquires token "X". With token "X" in the chamber's possession, no other chamber will be able to perform operation "X". The chamber may then perform operation "X" in step 5112.

A controller may then determine whether or not the pump chamber has only performed a partial stroke. This may for example be done after a controller detects the end of stroke for the pumping operation performed in step 5112. A controller may determine if a partial stroke has occurred by, for example, estimating the volume delivered by the chamber during the pump stroke. In some embodiments, this may be done by monitoring instantaneous flow rate information as the pump stroke occurs. Such monitoring of instantaneous flow rate information is described elsewhere in the specification. Alternatively or additionally, the controller may estimate the amount of stroke displacement that has occurred to see if a partial stroke has occurred. Such monitoring of stroke displacement is also described elsewhere in the specification.

In the event that the estimate indicates that the stroke was not a partial stroke, the chamber may release the token it is in possession of in step 5114. After releasing the token, the chamber may perform a post stroke FMS reading in step 5116. This reading may then be compared to the pre-stroke FMS reading to relatively precisely determine the total volume delivered during the stroke.

In the event that the volume estimate does indicate that a partial stroke occurred, the token may be held by the chamber in step 5118 and the controller can conduct an FMS measurement on that chamber in step 5120. This FMS reading may be compared to a pre-stroke FMS reading to determine if a partial stroke did in fact occur. In the event that the FMS measurement from step 5120 shows that the stroke was not a partial stroke, the chamber may release the token in step 5122. In the event that the FMS reading from step 5120 shows that a partial stroke did occur, the chamber may return to step 5112 and perform the pumping operation again. Since the token for that operation was held, it will not be necessary to wait for another chamber to finish the operation and release the token.

The cycler may repeat a pumping operation until a predetermined amount of fluid is moved or a reduced flow alert is triggered. The predetermined amount of fluid may, for example, be the amount of fluid expected to be moved by a 90% stroke displacement. Alternatively, there may be a limit on the number of retries allowed for a pumping operation. In the event that this limit is exceeded, an alert or alarm (e.g. low flow, no flow, occlusion, etc.) may be triggered. In some embodiments, if the limit is exceeded, the token may be released by the chamber. Another chamber may then acquire the token and attempt to perform the pumping operation. If that operation also exceeds the number of allowed retries, an alert or alarm such as those described above may be triggered.

Synchronizing Pump Operations with Measurements

In some embodiments, it may be desirable to synchronize pumping operation of a multi-chamber cassette such that pressure changes on one chamber do not occur or are limited while another chamber is performing an FMS measurement or a specific portion of an FMS measurement (the measurement being based on an accurate determination of pressure in the control chamber of a pump). This may be desirable in embodiments in which there may be some transmission of pressurization activities between pumping chambers of the pumping cassette, causing perturbations experienced by a pressure sensor during a volume or FMS measurement when another pumping chamber is experiencing a large pressure swing. By ensuring pressure swings or changes on other chambers do not occur while a chamber is undergoing an FMS measurement, any effect or disturbance on the FMS measurement caused by the pressure swing may be avoided. For example, while the FMS measurement or portion of the FMS measurement is occurring in a pumping chamber/control chamber combination, the controller may prohibit the other pumping chamber from performing an operation that would entail a large pressure change (e.g. a pressure change greater than about 7-8 kPa). For example, a pumping chamber may be prevented from starting a pump stroke, venting, performing an FMS pre-charge, etc. while an FMS measurement is being made on another pumping chamber of the cassette.

In some embodiments, this may be accomplished by creating one or more token(s) which function similarly to the token described above in relation to FIGS. 190 and 191. In general, a token can be viewed as an authorization tag granted by a controller to a pump control portion of the controller or to a separate pump controller to perform an action using the designated pump. The authorization tag or token may be relinquished by the pump controller once the action is completed, the authorization tag then being made available to the pump control portion of the controller or to a separate pump controller for assignment to another pump. As above, the pump (i.e. comprising a pumping chamber and associated control chamber) may be treated as an independent state machine. These tokens may be exclusive access tokens which need to be 'possessed' by a pump/pump chamber in order for the pump/pump chamber to perform specific operations. In one embodiment, there may be an FMS token which, when acquired by a pump state machine, allows its pump and associated control chamber to conduct an FMS measurement. Additionally, an FMS token may effectively prevent other pumps/pumping chambers from acquiring a fill or deliver resource or token when a pump chamber possesses the FMS token. (Possession by a pump/pump chamber of a resource token is meant to refer to possession of an authorization tag or token by a controller of that pump). Alternatively, when a pump chamber state machine possesses the FMS token, other pumping chambers may still be allowed to acquire a fill or deliver token, but may not be allowed to start its stroke right away. An FMS token may optionally be configured prevent other chambers from venting as well.

In other embodiments, additional tokens may be created. This may help to increase pumping cassette fluid throughput while maintaining measurement accuracy of the individual pumps. There may be a critical time during a measurement (e.g., pressure measurement) of the control chamber of a diaphragm pump during which pumping operations in other diaphragm pumps on the pump cassette should be suspended. A measurement token can be assigned to or acquired by a pump in need of a measurement, and an operations initiation token can be assigned to or acquired by any other pump ready to perform a pumping operation (e.g., fill, deliver, vent, etc.). If there is a period of time during the measurement when another pump's operation may disturb the measurement, the operations initiation token can be temporarily preferentially assigned to or acquired by the pump possessing the measurement token during the critical time. In an embodiment, the pump undergoing measurement can acquire the operations initiation token at a time sufficiently ahead of the critical measurement time to ensure that no other pump may initiate operations if the pressure changes during the operation are likely to encroach the critical time period of the pump under measurement.

For example, in some embodiments, there may be an FMS (i.e. measurement) token and a start stroke (i.e. operations initiation) token (sometimes referred to herein as "SS token"). In such embodiments, when the FMS token is possessed by a pump chamber (i.e. the controller has assigned the FMS token to the pump chamber or the state machine for the pump chamber has acquired the token), it may prevent other chambers from performing an FMS measurement. When the start stroke token is possessed by a chamber, it may prevent other chambers from acquiring a fill or deliver resource or token or prevent a stroke from starting after a token is acquired. This may effectively stop other chambers from starting a stroke and experiencing the accompanying pressure change. Optionally, a start stroke token may also prevent venting of other chambers as well.

FIG. 192 shows a flowchart outlining a number of steps which may be used when a pump chamber is performing an FMS measurement. In the example flowchart, a FMS token and a SS token are used to aid in synchronization of FMS measurements. As shown, in step 5130, the pump chamber finishes performing a pumping stroke. Once the stroke has finished, the pump chamber which finished the stroke may check to see if the FMS token is available in step 5132.

In the event that the FMS token is not available, the pump chamber may proceed to step S134. This may, for example, occur if another chamber is performing an FMS measurement and is therefore in possession of the FMS token. In step 5134, the pump chamber will wait for the FMS token to become available. If the FMS token is available or when the FMS token becomes available, the pump chamber will acquire and hold the FMS token in step 5136. Once the chamber is in possession of the FMS token, the chamber will begin performing an FMS measurement in step 5138. Since the chamber is in possession of the FMS token, no other chamber may begin an FMS measurement at this time. Other chambers may, however, still start a stroke since the start stroke token is still free.

Once the chamber reaches a predetermined point in the FMS measurement process, the chamber may proceed to step 5140 and acquire and hold a SS token. This predetermined point may for example be reached a predetermined period of time after the FMS measurement process begins, or a predetermined amount of time before a critical measurement period is reached. For example, this predetermined point may be set such that it is a predetermined amount of time before reference and control chamber equalization occurs. With the SS token held, other chambers may be prohibited from starting a stroke (or, optionally, venting their control chambers). As mentioned above, this may be accomplished in a variety of ways. In some embodiments, other chambers may be prohibited from acquiring a new resource or token. Alternatively, chambers may be able to acquire a new token or resource, but may not be allowed to begin a stroke.

In step 5142, the FMS measurement finishes. After the FMS measurement has finished, the chamber may release the SS token and FMS token in steps 5144 and 5146 respectively. The chamber may then, in step 5147, perform a start stroke check (sometimes referred to herein as SSC) to determine if the start stroke token is available. The start stroke check may, for example, be conducted by acquiring and quickly or immediately releasing the start stroke token. The chamber may also check to see if a resource (e.g. the fill bus) is available at this point. In the event that the SS token is not available, the pump chamber will wait in step 5148 for the SS token to become available. Additionally, the chamber may also have to wait for the desired resource or token to become available. If the SS token is available or when the SS token becomes available, the pump chamber may proceed to step 5150 and begin a stroke (assuming it has acquired the required token).

FIG. 193 depicts an example embodiment in which FMS measurements are synchronized using only an FMS token. As shown, the flowchart begins with a pumping chamber finishing a stroke in step 5160. Once the stroke finishes, the pumping chamber may check to see if the FMS token is available 5162. If the FMS token is not available, the chamber may wait in step 5163 until the FMS token becomes available. If the FMS token is available, or when the FMS token becomes available, the chamber may take the FMS token in step 5164. With the FMS token held, other chambers may be prohibited from beginning an FMS measurement. Additionally, other chambers may be prevented from starting a stroke. Once the FMS token is acquired by the chamber, the chamber may perform an FMS measurement in step 5166. Once the FMS measurement is completed, the FMS token may be released in step 5168.

In step 5170 the controller may then perform an FMS check on the chamber to determine if an FMS measurement is currently in progress. The controller may also check to see if a resource (e.g. the fill bus) is available for the chamber at this point. In the event that the FMS token is not available, the pump chamber will wait in step 5172 for the FMS token to become available. Additionally, the chamber may also have to wait for the desired resource to become available. If the FMS token is available or when the FMS token becomes available, the pump chamber may proceed to step 5174 and begin a stroke (assuming it has acquired the required token).

Referring now to FIGS. 194-199, a number of example graphs show one or more relationships between token possession and control chamber pressures of two pumping chambers over time. The bottom half of the graphs in FIGS. 194-197 and in FIG. 199 depicts a chamber A pressure trace 5133 and a chamber B pressure trace 5135. The top portion of each of these graphs depicts token and/or resource possession by the two chambers. Specifically, these example graphs depict a fill bus field 5180, deliver bus field 5182, FMS token field 5184, and SS token field 5186 which indicates when each of these resources or tokens are possessed by specific chambers. These graphs also have a start stroke check (SSC) field 5188 which indicates when each pumping chamber makes a start stroke check. For exemplary purposes, the graphs shown in FIGS. 194-199 are for a pumping cassette with two pumping chambers (chamber A and chamber B). The processes shown can be generalized as well to a cassette with a plurality of diaphragm pumps. To differentiate between the two chambers, chamber A is assigned a light grey color and chamber B is assigned a dark grey color in the example graphs.

Referring now primarily to FIG. 194, an example graph 5131 is depicted which graphically illustrates pumping synchronization using a start stroke token and a volume measurement token. The ownership status of these tokens is shown respectively in the SS token field 5186 and the start stroke check field 5188. The synchronization scheme depicted in the example graph 5131 employs a volume measurement token and start stroke token to prevent large pressure swings in other chambers (e.g. chamber B) during a critical period of a volume measurement in the chamber being measured (e.g. chamber A). The synchronization scheme is similar to that shown and described in relation to FIG. 192. As mentioned above, this arrangement may help to reduce any influence of a large pressure change in another chamber on a volume measurement in the chamber undergoing measurement.

As shown, the graph 5131 begins with chamber A performing a fill stroke. During a fill stroke a control chamber (e.g. chamber A) will be at negative pressure to draw fluid into the associated pump chamber. This negative pressure is shown in the pressure trace of chamber A 5133. As shown in the fill bus field 5180, chamber A retains control 5137 of the fill bus token for the duration of the fill stroke. This prevents chamber B from beginning a fill stroke. When chamber A has completed the fill stroke 5139, the chamber may acquire the FMS or volume measurement token 5141, if it is available, in order to measure the amount of volume drawn into the pumping chamber. Chamber A may also optionally release the fill bus token at this point. As shown in the fill bus field 5180 of the example graph 5131, chamber A retains the fill bus token for a period of time 5143 after completing the fill stroke 5139. As shown by the pressure trace for chamber A 5133, the example period of time 5143 is sufficient for the pressure of chamber A to rise from the negative fill pressure to near ambient pressure.

When chamber A releases the fill token 5145, chamber B performs a start stroke check 5149. Since the start stroke token is not possessed by another pump chamber (see the start stroke field 5186) chamber B acquires the fill bus token 5151. Once the fill bus token has been acquired by chamber B, the chamber begins filling 5158 as indicated by the chamber B pressure trace 5135. Chamber B continues to fill, retains the fill bus token, and is at negative pressure for the rest of the example graph 5131.

During the volume measurement on chamber A, the chamber is brought to a known positive pressure 5152. This may, for example, allow the chamber, once isolated, to be equalized with a reference chamber of known volume which is at a known pressure to determine the chamber's volume. A pressure trace for the reference chamber is not included on the example graph 5131 and volume measurement is described in further detail elsewhere in the specification. During the volume measurement process of chamber A, the chamber acquires the start stroke token 5153 as shown in the start stroke token field 5186.

As mentioned above, a start stroke token may be acquired by a chamber performing a volume measurement such that large pressure changes in other chambers are prevented during a critical time during the volume measurement. In the example embodiment, the start stroke token may be acquired and held over the critical period plus a predetermined preceding margin period.

In some embodiments, the start stroke token may be acquired and held for close to a latter half of the predicted time required for the volume measurement process. In other embodiments, the start stroke token may be acquired and held for a period of time equal to the sum of the time required for a chamber to equalize with the reference chamber 5154, an optional predetermined preceding period of time 5155, and the longest expected time 5156 required for a chamber to travel from an initial pressure to its regulation range 5157 for a stroke. The time period over which the start stroke token may be held by a chamber can be less than the time period over which the FMS or volume measurement token is held, because not all of the FMS measurement process is necessarily susceptible to pressurization effects of nearby or adjacent chambers. This may allow for increased fluid throughput as other chambers may not have to wait for long periods of time during volume measurements. Instead, chambers may be able to begin a stroke during a large portion of the volume measurement process for another chamber.

The equalization period 5154 may be dependent on the type of volume measurement operation being conducted. The equalization period 5154 may, in some embodiments, be empirically determined and preset for specific volume measurement operations. In some embodiments, the equalization period 5154 may be considered to be the critical period.

The preceding period 5155 may be a preset period of time just prior to the equalization period 5154. In some embodiments, data collected in the preceding period 5155 may be used in post processing to gather additional information about the volume measurement. For example, in some embodiments, the pressure data from the preceding period of time 5155 may be post-processed to determine if the data is indicative of a leak in the system. In such embodiments, the preceding period 5155 and the equalization period may collectively make up the critical period. In other embodiments, the preceding period 5155 may be optional (e.g. in embodiments where a leak test is not performed) and is not included as part of the critical period.

The longest expected time period 5156 may also be a preset period which has been empirically determined. The period 5156 may be the longest expected period of time required for a chamber's pressure to change from an initial pressure (e.g. a vented or ambient/atmospheric pressure) to a pressure regulation range 5157 for a pumping operation. A pressure regulation range 5157 may be a pressure range in which the controller attempts to maintain a chamber at a set point during a pumping operation to help ensure uniform pumping flow. The pressure regulation range 5157 shown in the example graph in FIG. 194 is the pressure range in which the controller attempts to maintain a chamber at during a fill stroke. At least a part of the longest expected time period 5156 may serve as an added margin to the critical period.

Once the volume measurement on chamber A has completed 5159, the chamber releases the start stroke token 5161. At this point chamber A is full of fluid and ready to perform a deliver stroke. Chamber A performs a start stroke check 5165 and since the start stroke token is not owned by another chamber (see start stroke token field 5186), chamber A acquires the delivery bus token 5167 and begins a deliver stroke 5169. When a chamber is performing a deliver stroke, the control chamber may be subjected to a positive pressure to force fluid out of the associated pumping chamber. This is illustrated in the pressure trace for chamber A 5133 during the period (starting at about 4.3 seconds) over which the chamber is in possession of the delivery bus token (see delivery bus token field 5182).

Referring now primarily to FIG. 195, an example graph 5171 is depicted which graphically illustrates pumping synchronization using a start stroke token and a volume measurement token. The ownership status of these tokens is shown respectively in the SS token field 5186 and the start stroke check field 5188. The synchronization scheme depicted in the example graph 5171 employs a volume measurement token and start stroke token to prevent large pressure swings in other chambers during a critical period of another volume measurement. Additionally, the example synchronization scheme illustrated in the graph 5171 uses a fill bus token whose ownership is identified in a fill bus field 5180. The example graph 5171 depicts how such a synchronization scheme may operate when both chambers begin empty. Strokes starting from chambers in this condition may be referred to as initiating strokes. This scenario may occur, for example, when a new cassette is present in a cycler or after a previous pumping procedure finished with all of the chambers fully delivered.

As shown, the example graph 5171 begins with chamber A performing a volume measurement 5173. Before the volume measurement, chamber A acquires FMS token 5175 and holds the FMS or volume measurement token. Since chamber A is in possession of the volume measurement token, chamber B must wait until the volume measurement of chamber A has been completed. At a point during the volume measurement of chamber A, the chamber acquires start stroke token 5176 and holds the start stroke token. This is similar to the description above in relation to FIG. 192 and FIG. 194.

When the volume measurement of chamber A is finished 5177, the chamber releases the FMS or volume measurement token 5179 and releases the start stroke token 5181. Chamber B then acquires the FMS or volume measurement token 5183 and performs a volume measurement 5185. The volume measurement of chamber B may be conducted in the same manner as chamber A.

In the example embodiment, after a volume measurement of chamber A has been made, the chamber is optionally vented 5187 toward ambient pressure or in the example embodiment to within a range of atmospheric or ambient pressure. A chamber may be vented in order to reduce the load on the pneumatic pump by leveraging atmospheric pressure to do some of the work required to bring the chamber pressure down toward ambient before a negative pressure stroke. As mentioned elsewhere, venting may be also be performed after a positive pressure stroke and before an FMS measurement pre-charge in order to mitigate effects of back pressure on fluid in the chamber or on outlet valve closure, and to help increase accuracy of a subsequent volume measurement.

Once the chamber A has been optionally vented, the chamber may perform a start stroke check 5189. Although chamber B is in the process of performing a volume measurement, chamber B has not yet acquired the start stroke token (see the start stroke token field 5186). As a result the start stroke check 5189 performed by chamber A succeeds. Chamber A acquires the fill bus 5191 and begins a fill stroke. This is indicated by the negative pressure of the chamber A pressure trace 5133 while the fill bus token is retained by chamber A.

Once chamber B has finished its volume measurement 5193, the chamber may optionally be vented 5195 similarly to chamber A. Since the fill bus token (see fill bus token field 5180) is in possession of chamber A after chamber B has completed venting, chamber B is unable to acquire the fill bus token. As a result, chamber B must wait 5197 for the fill bus token to be released by chamber A. As indicated by the chamber B pressure trace 5135 the pressure remains constant while the chamber waits for the fill bus token to become available. As soon as chamber A finishes it fill stroke and releases the fill bus token, chamber B will acquire the fill bus token and begin a fill stroke.

Referring now primarily to FIG. 196, an example graph 5199 is depicted which graphically illustrates pumping synchronization using a start stroke token and a volume measurement token. The ownership status of these tokens is shown respectively in the SS token field 5186 and the start stroke check field 5188. The synchronization scheme depicted in the example graph 5199 employs a volume measurement token and start stroke token to prevent large pressure swings in other chambers during a critical period of another volume measurement of the pump chamber of interest. Additionally, the example synchronization scheme illustrated in the graph 5198 uses a fill bus token and deliver bus token whose ownership is identified respectively in a fill bus field 5180 and deliver bus field 5182. The example graph 5198 depicts how such a synchronization scheme may operate when one chamber finishes a fill and another chamber is ready to transition to fill. This scenario may occur several times throughout a pumping procedure. Similar transitions between chambers performing delivery strokes may also occur. For purposes of example, the graph 5198 begins with chamber A performing a fill stroke (as indicated by the chamber A pressure trace 5133) and chamber B empty and waiting to perform a fill stroke (as indicated for the chamber B pressure trace 5135).

As shown, when chamber A completes a fill stroke 5201 it may acquire the FMS or volume measurement token 5203. In the example embodiment, chamber A acquires the FMS or volume measurement token 5203 prior to performing an optional vent 5205 which brings the chamber pressure to within a range of ambient pressure. As mentioned above, a vent may optionally be performed, for instance, to minimize pump run time. As shown in the fill bus field 5180 of the example graph 5198, chamber A retains the fill bus token for a period of time 5207 after completing the fill stroke 5201. As shown by the pressure trace for chamber A 5133, the example period of time 5207 is sufficient for the pressure of chamber A to be vented to near or within a range of ambient pressure. Once chamber A has been sufficiently vented, chamber A may release the fill bus token 5209. The volume measurement of chamber A is similar to that described above in relation to FIG. 192 and FIG. 194

With the fill bus token released 5209 by chamber A, chamber B may then immediately perform a start stroke check 5211 and acquire the fill bus token 5213. As indicated by the chamber B pressure trace 5135, chamber B begins filling 5215 as soon as it has acquired the fill bus token. Chamber B retains the fill bus token and continues performing a fill stroke for the remainder of the example graph 5198. Thus, in the example synchronization scheme, the fill bus may transition from one chamber to another chamber as soon as it becomes available. This rapid transition may allow for increased fluid throughput as the amount of time when the bus is not in use by a chamber is minimized. Transitions for a deliver bus token may occur similarly. As would be appreciated by one skilled in the art, such a synchronization scheme would similarly minimize the amount of time a delivery bus token is not in possession of a pump chamber. This may also help to increase fluid throughput.

Once the volume measurement on chamber A has completed 5217, the chamber releases the start stroke token 5219. At this point chamber A is full of fluid and ready to perform a deliver stroke. Chamber A performs a start stroke check 5221 and since the start stroke token is not owned by another chamber (see start stroke token field 5186), chamber A acquires the delivery bus token 5223 and begins a deliver stroke 5225. This is illustrated by the positive pressure of the chamber A pressure trace 5133 while the chamber is in possession of the delivery bus token. Chamber A retains the deliver bus token 5223 and continues performing a delivery stroke for the remainder of the example graph 5199.

Referring now primarily to FIG. 197, an example graph 5227 is depicted which graphically illustrates pumping synchronization using a start stroke token and a volume measurement token. The ownership status of these tokens is shown respectively in the SS token field 5186 and the start stroke check field 5188. The synchronization scheme depicted in the example graph 5227 employs a volume measurement token and start stroke token to prevent large pressure swings in chambers during a critical period of another volume measurement. Additionally, the example synchronization scheme illustrated in the graph 5227 uses a fill bus token and deliver bus token whose ownership is identified respectively in a fill bus field 5180 and deliver bus field 5182. The example graph 5227 depicts how such a synchronization scheme may operate when a pumping procedure is completed and pumping is stopped. The final strokes before pumping is stopped may be referred to as terminating strokes. Such a scenario may, for example, occur when a target volume has been delivered to a pumping destination. For purposes of example, the graph 5227 begins with chamber A performing a deliver stroke (as indicated by the chamber A pressure trace 5133) and chamber B performing a fill stroke (as indicated for the chamber B pressure trace 5135). In the example graph 5227, the controller has recognized that the target volume will be reached during the current deliver stroke from chamber A.

As shown, when chamber B completes a fill stroke 5229 it may acquire the FMS or volume measurement token 5231. In the example embodiment, chamber B acquires the FMS or volume measurement token 5231 prior to performing an optional vent 5233 which brings the chamber pressure to within a range of ambient pressure. As shown in the fill bus field 5180 of the example graph 5227, chamber B retains the fill bus token for a period of time 5235 after completing the fill stroke 5229. As shown by the pressure trace for chamber B 5133, the example period of time 5235 is sufficient for the pressure of chamber B to be vented to near or within a range of ambient pressure. Once chamber B has been sufficiently vented, chamber B may release the fill bus token 5237. The volume measurement of chamber B may be similar to volume measurements described above in relation to FIG. 192 and FIG. 194. Once chamber B has finished its volume measurement 5239 the chamber may halt pumping operations, release any tokens it possesses and wait for a controller to command pumping to resume.

Chamber A continues its delivery stroke and retains the deliver bus token (see delivery bus token field 5180) until the target volume has been delivered to the pumping destination. In the example graph 5227, a controller may command the delivery stroke to stop 5241 based on a delivered volume estimate maintained during the delivery stroke indicating the target volume has been reached. Such volume estimates are described elsewhere herein (see. e.g. FIG. 114-121). In other embodiments, the controller may simply allow the stroke to finish.

When the delivery volume estimate indicates the target delivery volume has been reached the delivery stroke from a chamber may end 5243. At this point, the chamber may acquire the FMS token 5245 and measure the amount of volume drawn into the pumping chamber. Chamber A may also release the deliver bus token at this point in some embodiments. As shown in the delivery bus field 5182 of the example graph 5227, chamber A retains the delivery bus token for a period of time 5247 after completing the delivery stroke 5243. As shown by the pressure trace for chamber A 5133, the example period of time 5247 is sufficient for the pressure of chamber A to fall to near ambient pressure. Optionally, the chamber may be vented during the period of time 5247 toward ambient pressure before being re-pressurized for a volume measurement. Although this venting procedure may increase the work of the positive pressure reservoir pump, it does so for the benefit of releasing any backpressure that may exist in the pumping chamber and its outlet valve. A volume measurement 5249 may then be made on chamber A and when this measurement is completed the chamber may halt pumping operations, release any tokens it possesses and wait for a controller to command pumping to resume.

Referring now primarily to FIG. 198 and FIG. 199 two example graphs 5178 (FIG. 198) and 5251 (FIG. 199) are depicted. Example graph 5178 details the pressures (in kPa) of pumping chambers as well as the ownership status of a number of resources and tokens over a number of pump strokes. The number of pumping strokes include: initiating strokes (described in relation to FIG. 195) which are performed on empty pumping chambers, delivery and fill transitions (fill transitions described in relation to FIG. 196), and terminating strokes which are performed when a target volume is delivered (described in relation to FIG. 197).

Specifically, the example graph 5178 depicts a fill bus field 5180, deliver bus field 5182, FMS token field 5184, and SS token field 5186 which indicates when each of these resources or tokens are possessed by specific chambers. The graph 5178 also has a start stroke check field 5188 which indicates when each pumping chamber makes a start stroke check. For exemplary purposes, the graph 5178 shown in FIG. 199 is for a pumping cassette with two pumping chambers; the process can be generalized as well to a cassette with a plurality of diaphragm pumps. The pressure of pumping chamber A is shown by line 5190 in the top portion of the graph 5178. The pressure of pumping chamber B is shown by line 5192 in the bottom portion of the graph 5178. In the example graph 5178, the pumping chambers are plotted pumping fluid from a heater bag to a patient. To allow for discernment between pumping chambers, elements of the graph indicating token possession by pump chamber B are shown in a heavier weight than those associated with pump chamber A.

The graph 5251 shown in FIG. 199 is the same as that shown in FIG. 198 except the pressure traces (lines 5190 and 5192) are overlaid on top of one another. The following description directly references graph 5178 (FIG. 198), though the description applies to both graphs 5178 (FIG. 198) and 5251 (FIG. 199). The reference signals used in graph 5251 (FIG. 199) are the same as those used and described in relation to FIG. 198.

The graph or plot 5178 begins with both pump chambers empty before an initial FMS measurement has been taken on either. This portion of the plot 5178 is indicated by the dashed box labeled "Start Pumping". An example graph detailing a number of initiating strokes is described in detail in relation to FIG. 195. As shown, pump chamber A begins by performing an FMS measurement. As shown, the chamber takes control of the FMS token while performing the FMS measurement. Since chamber A has possession of the FMS token, chamber B must wait to perform an FMS measurement. As shown, chamber A takes possession of the SS token for a portion of the FMS measurement. In the example plot 5178, this portion includes the equilibration period of the FMS measurement. When done, chamber A releases the FMS token which is then possessed or acquired by chamber B which performs its own FMS measurement.

While chamber B is performing FMS, but before chamber B takes possession of the SS token, chamber A performs a start stroke check as shown in the SSC field 5188. Since the start stroke token is available, chamber A begins a fill stroke. This fill stroke is allowed to continue after the start stroke token is retained by chamber B. As shown in the fill bus field 5180, chamber A takes possession of the fill resource or token and retains possession of the fill bus until it finishes it fill stroke.

Once chamber B completes its FMS measurement, chamber B is ready to begin a fill stroke. Chamber B, however, is unable to begin a fill stroke because the fill token is unavailable. Chamber B must wait until the fill resource is released by Chamber A to start a fill stroke as is shown in the dashed box labeled "Fill Transition". An example fill transition is described in detail above in relation to FIG. 196. As soon as the fill bus becomes available, chamber B performs a start stroke check, takes possession of the fill token, and begins its fill stroke. Chamber A performs an FMS measurement while this fill stroke is occurring. After completing the FMS measurement, the chamber is ready to deliver the filled chamber volume in a delivery stroke. While chamber B is still performing its fill stroke, chamber A does a start stroke check, takes possession of the deliver token as shown in the deliver bus field 5182, and begins a delivery stroke.

After chamber B finishes its fill stroke and performs an FMS measure to determine the volume filled, the chamber is ready to begin a deliver stroke. Chamber B, however, is unable to begin a deliver stroke because the deliver token is unavailable. Chamber B must wait until the deliver token is released by Chamber A to start a deliver stroke. As soon as the deliver token becomes available, chamber B performs a start stroke check, takes possession of the deliver token, and begins its delivery stroke. This process of alternating pumping may continue as long as necessary to move a desired volume of fluid. In some embodiments, a user may stop or pause this process as well via interaction with the cycler (e.g. through a user interface).

As shown, the pumping synchronization scheme depicted in FIG. 198 is efficient as it helps to reduce the amount of time during which no fluid pumping is occurring. As shown in the deliver bus field 5182, after the first delivery stroke begins, there is relatively little time in which the delivery bus is not occupied delivering fluid from a pump to its destination. Additionally, this is accomplished while at the same time avoiding a large pressure swing during a prescribed portion of each FMS measurement.

As mentioned above, once the desired volume of fluid has been moved or when a user pauses or stops pumping, pumping operations may cease. In the example plot 5178, this is shown in the dashed box labeled "Stop Pumping". An example graph detailing terminating strokes of a pumping procedure is described in detail in relation to FIG. 197. Once the chambers finish their current pumping stroke, they perform an FMS measurement and do not attempt to acquire a token for the next stroke. In some embodiments, the chambers may stop pumping before their current stroke has completed. For example, the chambers may instantaneously estimate volume delivered over the progression of a stroke. Once the desired amount of volume or the target volume has been moved, FMS may be performed and pumping operation may be stopped.

Alternatively, once the volume of fluid moved is close to the desired volume, a chamber may perform partial strokes after which FMS readings are taken. For example, the chamber may be connected to a pressure source or maintained at pumping pressure for a brief period of time before flow is stopped by the cycler. An FMS measurement may then be performed. The brief period of time may be a fraction of the time which would be required to realize substantially full stroke displacement. Thus multiple partial strokes followed by FMS measurements may be made until a target volume is reached.

Built-in Positive and Negative Pressure Reservoirs

FIG. 200 depicts an example bottom, front, left perspective view of a portion of a housing or enclosure 4200 for a device. In this embodiment, the housing portion comprises the bottom of the housing of the device. The device may be a peritoneal dialysis cycler or other dialysis machine in some embodiments. The device may be a hemodialysis machine, a cardiopulmonary bypass machine or any fluid delivery machine in which a positive or negative pressure reservoir is required for various operations of the machine or device. The pressure reservoir can be molded as a part of the housing of the device, providing for potential savings in space and allowing the device to occupy a smaller footprint, which is particularly advantageous for a portable device. As shown, the housing portion 4200 is formed as a multipurpose component. That is, the housing portion 4200 may not only serve as a structure to enclose components of the device, but may be structured to include components or parts of components of the device. These components or portions of components may be built-in, integral parts of the housing portion 4200 structure. For example, a housing portion 4200 may be formed such that it includes or includes a portion of: pressure tanks, reservoirs or vessels, hand holds or gripping structures, various bays, compartments and/or component retaining features, etc.

A housing portion 4200 may be formed in any suitable manner. In specific embodiments, a housing portion 4200 may be injection molded. In such embodiments, the mold (not shown) for the housing portion 4200 may be shaped to form each desired component or portion of each desired component included as a part of the housing portion 4200. A housing portion 4200 may also be RIM molded, compression molded, 3D printed, made with a material additive process, machined from solid stock, vacuum or pressure formed, etc. Additionally, in some embodiments, a housing portion 4200 may be constructed from structural foam such as Noryl.

As shown in the example embodiment depicted in FIG. 200, the housing portion 4200 includes a portion of a pressure reservoir 4201. When completely assembled, a sealing member or sealing assembly 4203 (see FIG. 201) may cover the portion of the pressure reservoir 4201 to complete the pressure reservoir 4201. In the example embodiment, the housing portion 4200 includes a portion of a single pressure reservoir 4201. In other embodiments, a housing portion 4200 may be configured to allow for any suitable number or pressure reservoirs. In various embodiments, a housing portion 4200 may be formed such that pressure reservoirs 4201 may be disposed in any suitable location on a housing portion 4202. It may be desirable to dispose pressure reservoir 4201 in a location which accommodates any space requirements or demands related to other components which will be housed in the enclosure once the device is completely assembled.

As shown, the portion of the pressure reservoir 4201 is recessed into the bottom face of the example housing portion 4200. In other embodiments, a portion of a pressure reservoir 4201 may, for example, be partially or entirely proud of a face of a housing portion 4200. Additionally, a portion of a pressure reservoir 4200 formed as part of a housing portion 4200 may be shaped or dimensioned so as to be space-efficient. In the example embodiment, the pressure reservoir 4201 has a roughly rectangular dimension. In various embodiments, the pressure reservoir may be rounded or include more dramatically rounded edges to increase the robustness of the pressure reservoir 4201 structure. This may, for example, be desirable if the pressure reservoir 4201 is intended to contain relatively high or low pressures, or if the pressure reservoir 4201 may be subject to physical stresses, impact, or the like. Additionally, in some embodiments, the pressure reservoir 4201 structure may be formed such that it includes one or more support members such as, though not limited to a: strut, vault, buttress, counterfort, rib, or the like.

The example pressure reservoir 4201 shown in FIG. 200 includes a port 4205. The port 4205 may be a void which extends all the way through the wall of the housing portion 4200. The port 4205 may allow fluid communication out of the pressure reservoir 4201. In various embodiments, tubing (not shown) may be sealed (permanently or by a coupling) to the port 4205 on the top side of the housing portion 4200. Thus, the pressure reservoir 4201 may be used as a pressure source for a hydraulic or pneumatic system. Additionally, fluid may be pumped into or out of the pressure reservoir 4201 to adjust the pressure of the pressure reservoir 4201. In some embodiments, the port 4205 may be used to both adjust the pressure of the pressure reservoir 4201 (e.g. using a pump) and to provide fluid at a desired pressure to components of a pneumatic or hydraulic system. In some embodiments, a pressure reservoir may include two ports 4205. One port 4205 may be used for pressure adjustment/maintenance while the other may be used to provide fluid at a desired pressure to components of a pneumatic system. The port(s) 4205 may be located so as to minimize the amount of tubing and/or routing of tubing necessary to put a pressure reservoir 4201 in communication with the desired components of a pneumatic system. For example, in some embodiments, port(s) 4205 may be disposed such that they are spatially close to or contiguous with a hydraulic or pneumatic manifold when the device is fully assembled.

Referring now also to FIG. 201, another bottom, front, left perspective of the example housing portion 4200 shown in FIG. 200 is depicted. As shown, the housing portion 4200 is in an assembled state and a sealing member 4203 is attached to the housing portion 4200 such that it completes the pressure reservoir 4201. As shown, the sealing member 4203 is depicted as a cover plate in the example embodiment. The sealing member 4203 may differ in other embodiments.

The sealing member 4203 may be attached to the housing portion 4200 in any number of suitable ways. In some embodiments, the sealing member 4203 may be removably attached to the housing portion 4200 or may be permanently attached to the housing portion 4200. In some embodiments, the sealing member 4203 may be attached using one or more suitable fasteners. In such embodiments, a gasket (not shown) may be placed between the sealing member and the housing portion 4200. In such embodiments, the gasket may be any of a variety of suitable gaskets. For example, the gasket may be a planar gasket, form-in-place gasket, or skeletal gasket designed to follow the contact surfaces between the housing portion and the sealing member. The gasket may comprise an elastomeric material or other compressible material suitable for forming a fluidic seal between walls of the housing portion and the sealing member. In embodiments in which a gasket is included, the sealing member 4203 may include one or more rib features which serve to retain and compress the gasket and aid in forming a seal.

Additionally, a cooperating feature such as a recess or channel may be included in the housing portion 4200 which may cooperate with the one or more ribs on the sealing member 4203. Alternatively, in some embodiments, ribs may be included on the housing portion 4200. In such embodiments, a cooperating feature such as a groove or channel may be included on the sealing member. In various embodiments, o-rings may be used instead of a gasket. Making the sealing member 4203 removable may be desirable because it may increase modularity of the device. That is, if a sealing member 4203 becomes compromised, the sealing member 4203 may be removed and replaced. Thus, the entire housing portion 4200 does not need to be discarded. In some embodiments, the sealing member 4203 may be attached to the housing portion 4200 via adhesive or glue. In some embodiments, solvent bonding may be used. In some embodiments, the sealing member 4203 may be attached to the housing portion 4200 via ultrasonic welding. In such embodiments, it may be desirable that one or both the materials used for the housing portion 4200 and sealing member 4203 be easily ultrasonically welded. In some embodiments the sealing member 4203 may be attached to the housing portion 4200 using vibration welding, hot plate welding, or laser welding. In laser welded embodiments, the sealing member 4203 is preferably optically clear at the wavelength of the laser to be used. The housing portion 4200 is preferably absorbent of the wavelength of the laser. Alternatively, a material which is absorbent to the laser wavelength may be placed between the sealing member 4203 and the housing portion 4200 before laser welding. This material may then serve to weld the sealing member 4203 and housing portion 4200 together when melted by the laser. In some embodiments, the sealing member 4203 may be overmolded to the housing portion 4200. In some embodiments, the sealing member 4203 may be snap or press fit into place on the housing portion 4200. In such embodiments, a gasket may be used.

In some embodiments, a sealing member 4203 may be made of a material which is stiff or has a high modulus of elasticity. Alternatively or additionally, the sealing member 4203 may be suitably thick so as not to deform significantly when the pressure reservoir 4201 is at its maximum or minimum pressure. The sealing member 2403 may be constructed of aluminum, or a reinforced plastic material. In some embodiments, the sealing member 4203 may include a clear window portion overmolded onto an opaque portion. Alternatively, an entire sealing member 4203 may be made of a clear material.

FIG. 202 depicts another bottom, front, left side perspective view of a specific example of a housing portion 4200. As shown, the housing portion 4200 includes portions of a number of pressure reservoir sections 4202a, 4202b. (The pressure reservoir sections 4202a and 4202b may alternatively be denoted simply as two separate pressure reservoirs 4204a and 4204b in a dual pressure reservoir embodiment). In this example, a dual pressure reservoir is formed as an integral component of the housing portion 4200, the dual pressure reservoir comprising a first section for storing positively pressurized air, and a second section for storing negatively pressurized air, the two sections isolated from each other by a dividing wall 4204. In other embodiments, the pressure reservoir sections may be configured to store air at two different positive pressures, or air at two different negative pressures. In other embodiments, there may be more than two sections, each configured to store air or another gas at different pressures, positive or negative. In the example embodiment, the pressure reservoir sections 4202a, 4202b are separated or segregated from one another by a baffle or divider 4204. In the example embodiment, the divider 4204 is formed as an integral part of the housing portion 4200. The divider 4204 in this example is disposed such that the pressure reservoir sections 4202a, 4202b are of substantially equal volume and have substantially the same overall shape, although they may be of different sizes or shapes depending on the operational requirements of the device for each pressure reservoir.

The divider 4204 may help in increase the strength of the walls of the pressure reservoir sections 4202a, 4202b. In the example embodiment, the divider 4204 is a roughly planar projection which extends in a direction generally perpendicular to the bottom face of the housing portion 2400. In other embodiments, a divider 4204 may include a curve or bend to help increase the rigidity or robustness of the pressure reservoirs. In other embodiments, a divider 4204 may help to define a greater number of pressure reservoirs. For example, in some embodiments, a divider 4204 may take the shape of an "X" or "Y".

As shown, the example embodiment in FIG. 202 additionally includes a number of support members or stiffeners 4206. The support members or stiffeners 4206 may be formed as an integral part of the housing portion 4200. In other embodiments, a different number of support members 4206 may be included. In the example embodiment, the support members 4206 are depicted as ribs. As mentioned above, other varieties of support members 4206 may be used. As shown, the support members 4206 may span from the side or perimeter walls of the pressure reservoirs 4202a, 4202b to the divider 4204. In other embodiments, especially those which include support members 4206 which are not ribs, support members 4206 may not extend the entire distance between the side walls of the pressure reservoirs 4202*a*, 4202*b* and the divider 4204. The support members 4206 may be substantially planar and may extend in a direction generally perpendicular to the bottom face of the housing portion 4200. A support member 4206 may serve a number of functions, including, but not limited to: increasing the rigidity of a pressure reservoir, increasing the rigidity of a divider 2404, constraining a wall or a perimeter wall of a pressure reservoir from bowing under pressure, and constraining a gasket from displacement when a pressure reservoir is under pressure. A stiffener need not be planar in shape; for example, it could be bar-shaped, extending from a side or perimeter wall of a reservoir section to the opposing dividing wall.

In the example embodiment, the support members 4206 are structured such that they allow fluid communication between the volumes on opposing sides or each support member 4206. In the example embodiment, the support members 4206 do not extend all the way to the bottom of the divider 4204. This may be done to ensure that the volume on each side of each support member 4206 is in fluid communication with the volume on the opposing side of the support member 4206. In some embodiments, a portion of the support members 4206 may extend to and be substantially level with the bottom face of the divider 2404. In other embodiments, the support members 4206 may include cutouts or pass-throughs which allow fluid communication between volumes on opposing sides of the support members 4206. A lip or ledge 4208 is also shown as part of the housing portion 4200 in the example embodiment. The ledge 4208 surrounds the portions of pressure reservoirs 4202*a*, 4202*b* in the example embodiment. The ledge 4208 may serve as an attachment surface for a sealing member. In the example embodiment a number of threaded holes are included in the ledge 4208. When assembled, fasteners may be threaded into such holes to couple a sealing member to the housing portion 4200. Also a divider 4204 may include one or more threaded hole for the same purpose. In such embodiments, and as shown, a divider 4204 may be thickened in the vicinity of such a threaded hole.

A ridge 4209 may be included along the outer perimeter of the ledge 4208. The ridge projects from the housing portion 4200 in a direction that is substantially perpendicular to the bottom face of the housing portion 4200. The ridge 4209 may serve to help locate a sealing member during assembly. In embodiments where a sealing member is not removable, the sealing member may be glued, bonded, welded, etc. to a surface of the ridge 4209. It may be desirable that a ridge 4209 have a height which is substantially the same as or greater than the thickness of a sealing member.

FIG. 203 depicts an assembled, bottom, front, left perspective view of the example housing portion 4200 shown in FIG. 202. As shown, a sealing member 4207 has been coupled onto the housing portion 4200 via a number of fasteners. In the example embodiment, the sealing member 4207 is a cover plate. As mentioned above, in some embodiments, a gasket, o-ring, or the like may be captured between the sealing member and the housing portion 4200 to help create a seal around the pressure reservoirs.

Referring now to both FIG. 202 and FIG. 204, each pressure reservoir 4202*a*, 4202*b* may include one or more ports 4210*a*, 4210*b*. The ports 4210*a*, 4210*b* in the example embodiment are voids which extend through the entire thickness of the housing portion 4200. The ports 4210*a*, 4210*b* may allow for fluid communication into and out of the pressure reservoirs 4202*a*, 4202*b*. In various embodiments, tubing (not shown) may be permanently sealed or reversibly coupled to the port 4205 on the top side of the housing portion 4200. A top side view of the housing portion 4200 shown in FIGS. 202 and 203 is depicted in FIG. 205. As shown, attachment features 4211 (e.g. nipples) may be included to facilitate attachment of such tubing. Such features may also be formed integral with the housing portion 4200. In the example embodiment, the attachment features 4211 are roughly cylindrical or frusto-conical. In other embodiments, the attachment features 4211 may be barbed hollow projections. As also shown in FIG. 205, each port 4210*a*, 4210*b* may be associated with indicia indicating the chamber or reservoir 4202*a*, 4202*b* to which it is connected. In the example embodiment a "+" and "−" are included to indicate positive vs. Negative pressure reservoirs. In some embodiments, the indicia could indicate "High" and "Low," to indicate a connection to a high pressure chamber or reservoir vs. a low pressure reservoir.

With tubing attached to the attachment features 4211, the pressure reservoirs 4202*a*, 4202*b* may be used as pressure sources for a pneumatic or hydraulic system. Additionally, fluid may be pumped in or out of the pressure reservoirs 4202*a*, 4202*b* to adjust the pressure of the pressure reservoirs 4202*a*, 4202*b*. In some embodiments, the same ports 4210*a*, 4210*b* may be used to both adjust the pressure of each pressure reservoir 4202*a*, 4202*b* (e.g. using a pump) and to provide fluid at a desired pressure to components of a pneumatic or hydraulic system. In some embodiments, a pressure reservoir may include two ports. One port may be used for pressure adjustment/maintenance while the other may be used to provide fluid at a desired pressure to components of a pneumatic or hydraulic system. The ports 4210*a*, 4210*b* may be located so as to minimize the amount of tubing and/or routing of tubing necessary to put a pressure reservoir 4202*a*, 4202*b* in communication with the desired components of a pneumatic system. For example, in some embodiments, ports 4210*a*, 4210*b* may be disposed such that they are spatially proximal to or contiguous with a pneumatic or hydraulic manifold.

In some embodiments, other components of a device may be formed integral to a housing or housing portion 4200. As shown, in the example embodiment in FIG. 202, hand grips 4214*a*, 4214*b* are included as an integral part of the housing portion 4200. The hand holds 4214*a*, 4214*b* are recessed into the bottom face of the housing portion 4200. The hand holds 4214*a*, 4214*b* may aid in carrying the device. Additionally, one or more storage compartments 4212 may be formed as an integral part of a housing portion 4200. Such a storage compartment 4212 may, for example be used to house an on-board power source (e.g. a battery) which may be used to power the device. Referring now also to FIG. 203, a cover 4213 may be coupled into place over the storage compartment 4212 to retain anything stored in the storage compartment. In some embodiments, a storage compartment 4212 may have a void 4215 (see FIG. 204) or the like which allows access to the interior of the device once assembled.

In reference to the top, front, right perspective view of the housing portion 4200 shown in FIG. 205, a number of additional features formed integral with the housing portion 4200 are shown. For example, a pump retaining feature 4220 is shown as an integral formed part of the housing portion 4200. The pump retaining feature 4220 in the example embodiment is a four-walled, roughly rectangular structure which extends from the top face of housing portion 4200 at an angle substantially perpendicular to the top face of the housing portion 4200. The pump retaining feature 4220 may be dimensioned such that a pump component of the device may be stored within the retaining feature 4220. In some embodiments, the pump retaining feature 4220 may be lined with foam, elastomeric material and/or a sound damping material. This may help to reduce noise generated when running a pump component.

A manifold retaining feature 4222 is also shown in the example embodiment in FIG. 205. As shown, the manifold retaining feature 4222 is an integrally formed part of the housing portion 4200. The manifold retaining feature 4222 is a four walled, roughly rectangular structure which extends from the top face of housing portion 4200 at an angle substantially perpendicular to the top face of the housing portion 4200. The manifold retaining feature 4222 may be dimensioned such that a manifold for the device may be placed within the walls of the manifold retaining feature 4222. Also as shown, the manifold retaining feature 4222 many include a number of organizer features 4224. These organizer features 4224 may serve to help organize and hold in place tubing to and from the manifold. In the example embodiment, the organizer features 4224 are recessed into the top edge of the manifold retaining feature 4222.

FIG. 206 depicts a bottom perspective view of a sealing member, cover plate or lid 4230 which may be attached to a housing portion to seal the volume of a pressure reservoir. As shown, the sealing member, cover plate or lid 4230 may include one or more support member(s) or stiffeners 4232. In the specific example embodiment in FIG. 84, there are six support members or stiffeners 4232. In the example embodiment, the support members 4232 are depicted as ribs. As shown, there is a gap between support members along a medial or central plane of the sealing member 4230. This gap may be sized such that a divider such as divider 4204 of FIG. 202 may fit between the support members 4232. In embodiments in which the cover plate is for a single pressure reservoir, such a gap need not be included. The support members 4232 may help to provide strength or rigidity to the sealing member 4230. Additionally, the support members 4232 may constrain walls of a pressure reservoir from deforming when under pressure. For example, the support members 4232 may prevent a side wall of a pressure reservoir from bowing in when the pressure reservoir is under negative pressure. In some embodiments, a support member 4232 may include at least one dovetail feature. Such a feature may for example be located along the side edge of the support member 4232 and may insert into a cooperating dovetail feature included as a part of the pressure reservoir. Thus, the dovetail feature may, for example, serve to prevent a side wall of a pressure reservoir from bowing outward when the pressure reservoir is under positive pressure. In some embodiments, the support members 4232 may be attached to the walls of a pressure reservoir and/or divider via solvent bonding, ultrasonic, chemical or laser welds, or any other suitable means. As shown, the support members 4232 do not extend all the way to the edges of the sealing member 4230. This may allow the sealing member 4230 to seat on a ledge of a housing portion such as the ledge 4208 shown in FIG. 202.

Additionally, in some embodiments, support members may be included as a stand-alone component which may be placed into a pressure reservoir during assembly. In such embodiments, the support members may be attached to a surface of the pressure reservoir during assembly.

In some embodiments, it may be desirable to dispose pressure reservoirs such that the pressure reservoirs are concentric. One, surrounded pressure reservoir may be within the footprint of another, surrounding pressure reservoir. In various embodiments, a pressure reservoir may be within the footprint of another, but not necessarily concentric. The pressure reservoirs may or may not be of substantially equal volumes. Additionally, in some embodiments, the pressure reservoirs may be dimensioned differently. For example, one pressure reservoir may be relatively shallow and wide, while the other may be relatively thin and deep, yet both reservoirs may have substantially equal volumes.

Such pressure reservoirs may be separated by a divider which fluidically isolates the reservoirs from one another when fully assembled. The divider may take the form of any variety of closed shape. A sealing member, and in some embodiments a gasket and/or o-ring, may also be used to seal the volumes of the pressure reservoirs. A sealing member may also define one or more walls of the pressure reservoirs.

Such pressure reservoirs may be pressurized to different pressures (e.g. a positive pressure and a negative pressure). The surrounding pressure reservoir may be kept at a negative pressure while the surrounded pressure reservoir may be kept at a positive pressure. Additionally, the surface area of portion of the sealing member which is over the surrounding pressure reservoir may be greater than that of the surrounded pressure reservoir. Thus the negative pressure in the surrounding pressure reservoir may serve to suction the sealing member into sealing relationship with the pressure reservoirs.

FIG. 207 depicts a bottom perspective view of an example embodiment of a housing structure 4240 including portions of a number of concentric pressure reservoirs 4242, 4244. The example structure 4240 may be formed in any suitable manner known in the art. In specific embodiments, such a structure 4240 may be injection molded, be RIM molded, compression molded, 3D printed, made with a material additive process, machined from solid stock, vacuum or pressure formed, etc. Additionally, in some embodiments, the structure 4240 may be constructed from structural foam such as Noryl. As described above, in some embodiments, the structure may be included as an integrally formed part of an enclosure or portion of an enclosure. When completely assembled, a sealing member or sealing assembly such as a cover plate may cover the open portions of the pressure reservoirs 4242, 4244 to completely enclose the pressure reservoirs 4242, 4244. Such a sealing member may be attached similarly to as described above.

In the example embodiment, the pressure reservoirs 4242, 4244 are concentrically disposed. One pressure reservoir 4244 is disposed inside the footprint of the other of the pressure reservoir 4242. The pressure reservoirs 4242, 4244, have a roughly rectangular footprint in the example embodiment. In other embodiments, the pressure reservoirs 4242, 4244 may take any other suitable shape. In some embodiments, the pressure reservoirs 4242, 4244 may be rounded, hemispherical, etc. to add to the robustness of the structure 4240. A plurality of pressure reservoirs may be concentrically disposed one within the other, and each inner reservoir having a dividing wall separating it from its adjacent outer reservoir. Also in various embodiments, the pressure reservoirs may include support members to add to the robustness of the structure 4240. In embodiments including support members, the support members may be any suitable variety or varieties of support member(s) such as, but not limited to those described herein.

A divider 4246 is included between the two pressure reservoirs 4242, 4244. The divider 4246 serves to fluidically isolate the two pressure reservoirs 4242, 4244 when the sealing member or cover plate is in place. As shown, the divider 4246 may be a wall-like projection which extends in a direction substantially perpendicular to the bottom face of the structure 4240. In the example embodiment, the divider 4246 is stadium-shaped. In other embodiments, the divider 4246 may be any other closed shape including, but not limited to ovoid, circular, polygonal, etc. In some embodiments, a groove 4248 may be recessed into the bottom face of the divider 4246. As shown in the example embodiment, the groove 4248 is disposed at approximately the center of the bottom face of the divider 4246. Such a groove 4248 may be sized so as to accommodate an o-ring (not shown). The o-ring may help to create a fluidic seal between the pressure reservoirs 4242, 4244 when the sealing member is in place.

In other embodiments, a suitable gasket may, for example, be used in place of an o-ring. In still other embodiments, a sealing member may be directly attached to the structure (e.g. via welding, adhesive, solvent bonding, etc.). In such instances, a groove 4248 may not be needed.

As shown, the area of the footprint of the outer pressure reservoir 4242 may be greater than the area of the inner pressure reservoir 4244. The depth of each pressure reservoir 4242, 4244 may be selected so as to ensure that each pressure reservoir 4242, 4244 is of approximately equal volume. In the example embodiment, since the area of the footprint of the inner pressure reservoir 4244 is relatively small, the inner pressure reservoir 4244 has a greater depth than pressure reservoir 4242. This allows each of the pressure reservoirs 4242, 4244 to have relatively equal volumes. This arrangement may change depending on the different operational requirements the device may have for each pressure reservoir volume.

In some embodiments, one of the pressure reservoirs 4242, 4244 may be configured to hold positive pressure while the other is configured to hold negative pressure. In such embodiments, it may be desirable that the outer pressure reservoir 4242 be at the negative pressure and have a larger area footprint than the inner pressure reservoir 4244. This may effectively provide a suction force to a sealing member that acts to suction the sealing member onto the structure 4240 when the device is fully assembled and pressurized. This may also serve to increase the robustness of the seals created when a sealing member is attached to the structure 4240. In an embodiment, the surface area of the outer reservoir at the cover plate is greater than the surface area of the inner reservoir at the cover plate. Charging the outer reservoir with negative pressure would therefore seal the cover plate against the two reservoirs more effectively, and can provide a sealing suction uniformly against the entire outer region of the cover plate, from the perimeter of the cover plate (at the perimeter wall of the outer reservoir) to the dividing wall separating the outer reservoir from the inner reservoir. If there is a desire to keep the volumes of the two reservoirs roughly equal, the inner reservoir can be constructed to be deeper than the outer reservoir to make up for the difference in surface areas at the cover plate.

As shown, in the example embodiment in FIG. 207 a projection 4250 extends into the interior volume of the inner pressure reservoir 4244. The projection 4250 in the example embodiment is substantially cylindrical and extends in a direction which is substantially perpendicular to the bottom face of the structure 4240. As shown, in some embodiments, the projection 4250 may include a threaded hole. A fastener may thread into this hole to couple a sealing member to the structure 4240. In some embodiments, the projection 4250 may include a groove 4251 recessed into the bottom face of the projection 4250. Such a groove 4248 may be sized so as to accommodate an o-ring (not shown). The o-ring may help to create a fluidic seal around the around the fastener when the sealing member is in place A lip or ledge 4252 is also shown as part of the structure 4240 in the example embodiment. The ledge 4252 surrounds the portions of pressure reservoirs 4242, 4244 in the example embodiment. The ledge 4252 may serve as an attachment surface for a sealing member. In the example embodiment a number of threaded holes are included in the ledge 4252. When assembled, fasteners may be threaded into such holes to couple a sealing member to the structure 4240. In some embodiments, a divider 4246 may include one or more threaded holes for the same purpose. In such embodiments, a divider 4246 may thicken in the vicinity of such a threaded hole.

As shown, the ledge 4252 may also include a groove 4254. The groove 4254 may be recessed into the ledge 4252 at any suitable location. In the example embodiment, the groove 4254 is recessed into the ledge 4252 proximal to the perimeter of the outer pressure reservoir 4242. Such a groove 4248 may be sized so as to accommodate an o-ring (not shown). The o-ring may help to create a fluid seal around the outer pressure reservoir 4242 when the sealing member is in place.

Around the perimeter of the bottom of the structure 4240 may be a raised ridge 4256. In the example embodiment, the raised ridge 4256 extends in a direction substantially perpendicular to the bottom face of the structure 4240. The ridge 4256 may serve to help locate a sealing member during assembly. In embodiments in which a sealing member is not removable, the sealing member may be glued, bonded, welded, etc. to a surface of the ridge 4256. It may be desirable that a ridge 4256 have a height which is substantially the same as or greater than the thickness of a sealing member in some embodiments Referring now also to FIG. 208, one or more ports 4258a, 4258b may be included for each of the pressure reservoirs 4242, 4244. The ports 4258a, 4258b may be voids which extend through the entire thickness of the structure 4240. Tubing (not shown) may, for example, be sealed or coupled to the ports 4258a, 4258b as previously described. With the tubing attached, the pressure reservoirs 4242, 4244 may be used as pressure sources for a pneumatic or hydraulic system. Additionally, fluid may be pumped into or out of the pressure reservoirs 4242, 4244 to adjust the pressure of the pressure reservoirs 4242, 4244. In some embodiments, the same ports 4258a, 4258b may be used to both adjust the pressure of each pressure reservoir 4242, 4244 (e.g. using a pump) and to provide fluid at a desired pressure to components of a pneumatic or hydraulic system. In some embodiments, a pressure reservoir may include two ports. One port may be used for pressure adjustment/maintenance while the other may be used to provide fluid at a desired pressure to components of a pneumatic or hydraulic system.

FIG. 209 depicts a top perspective view of the example structure shown in FIGS. 207 and 208. As shown, the depth of the inner pressure reservoir 4244 is greater than that of the outer pressure reservoir 4242. Additionally, the ports 4258a, 4258b are visible in FIG. 209. As shown, attachment features 4260 may be included to facilitate attachment of tubing. Such features may be formed integral to the structure 4240. In the example embodiment, the attachment features 4260 are roughly cylindrical or frusto-conical. In other embodiments, the attachment features 4260 may be barbed projections. As also shown in FIG. 209, each port 4258a, 4258b may be associated with indicia indicating the type of pressure associated with the pressure reservoirs 4242, 4244 with which the port 4258*a*, 4258*b* provides fluidic communication. In the example embodiment a "+" and "−" are included to indicate positive and negative pressure reservoirs. In some embodiments, the indicia may indicate reservoirs having different pressurizations. FIG. 210 depicts a cross-sectional view of the example structure 4240 taken at line 209-209 of FIG. 209. As shown, both pressure reservoirs 4242, 4244 are shown in FIG. 210. The divider 4246, and the groove 4248 in the bottom face of the divider 4246 are also shown, as well as the ledge 4252, the raised ridge 4256, and the groove 4254 in the ledge 4252.

Heater Bag Replenish

The heating of fluids to be delivered to a patient consumes a substantial amount of energy. Any medical apparatus configured to infuse a fluid into a patient's body cavity, or intravenously, can be equipped with a controller that improves the efficiency of a heating device acting on a heater bag containing the fluid to be delivered. Although the following description uses a peritoneal dialysis cycler to illustrate the system, it may be applied in a similar manner to any medical infusion apparatus that controls the replenishment of fluid into a heater bag, the delivery of heated fluid to a patient, the time during which the fluid remains in the patient, and the withdrawal and draining of the fluid from the patient. Regarding the infusion of dialysate solution, it may also be advantageous in some cases to limit the amount of time the solution is kept at an elevated temperature (e.g., body temperature) while awaiting infusion into the patient.

There are many different types of dialysate solution which may be used with a dialysis machine. These solutions may for example have varying concentrations of osmotic agent, varying types of osmotic agents, different electrolytic components, different pH buffering components, various additives, etc. These differences between solutions may cause the solutions to act differently under various conditions. For this reason, the cycler behavior preferably accommodates the needs of any solution which may be used with the machine. Alternatively, a cycler controller can be programmed to have differing behaviors depending upon the type of solution being used. For example, certain solution types may have a limited useable life once brought to a high temperature to prevent precipitation of solutes in the dialysate. The cycler behavior may be designed to accommodate such a dialysate characteristic As mentioned above, various embodiments of a cycler may include a heater assembly which heats dialysate solution in a heater bag resting on the assembly prior to delivering it to the patient. The heater assembly may comprise a heater pan or trough, sized to accept a solution bag or heater bag that has a volume which is greater than the amount of solution that would be delivered to a normal patient in any one fill operation. In standard practice, the heater bag is typically kept substantially full and the solution contained within the bag is kept within a defined temperature range.

In some embodiments, instead of filling substantially the entire heater bag volume with dialysate and maintaining it at or near that full state, the heater bag may only be partially filled with dialysate. This avoids having a large volume of dialysate remaining heated for several fill, dwell, and drain operations. Thus, the amount of time the dialysate is kept at elevated temperature before delivery to the patient can be minimized.

For example, an amount of solution less than the volume of two programmed fills may be pumped to the heater bag. This amount may be referred to as a next cycle fill volume (e.g., volume of fill phase 758, FIG. 178). The next cycle fill volume can comprise an amount of solution needed to complete the next fill of the patient's peritoneal cavity. In some embodiments, a margin or marginal volume of solution may also be added to the next cycle fill volume. Thus the heater bag will be replenished to a volume slightly greater than the solution volume needed to complete the next patient fill. This additional solution may help ensure that the flow rate from the heater bag during a fill of the patient remains relatively high throughout the operation and may serve as a margin in case more solution than anticipated. The marginal volume, may for example, be a preprogrammed, fixed volume or specified as a percentage of the fill volume (or another programmed therapy volume parameter). By replenishing the heater bag in this manner, the amount of time the solution is held at a high temperature before being delivered to a patient may be minimized. In an exemplary embodiment, the replenish volume may be determined as follows:

$$V_R = V_F + \text{Optional Margin} - V_H$$

Where $V_R$ is the determined replenish volume to be transferred to the heater bag, $V_F$ is the programmed next fill volume, and $V_H$ is the volume of the heater bag at the beginning of the replenish operation.

The time at which the heater bag is replenished may also be scheduled in a manner which minimizes the amount of time that its contents are kept at an elevated temperature. This may be done by replenishing the heater bag shortly before the next fill operation is scheduled. For example, the heater bag may be refilled near the end of the dwell phase (e.g. dwell phase 756, FIG. 178) of a cycle. In some embodiments, the cycler may determine or estimate an amount of time which will be needed to replenish the heater bag and heat the solution for the next fill.

Heating of the transferred replenish solution can begin as soon as the heater bag replenish operation begins. The controller can be programmed to calculate an estimated heating time required to raise the temperature of the replenished solution in the heater bag. In some embodiments, that calculation can be based on the temperature drop of the heater bag as the transfer begins, and/or the volume of replenish solution to be transferred to the heater bag. The computation may, for example, include variables such as the initial volume in the heater bag, its temperature, and the degree of temperature drop as a pre-determined volume of replenish fluid is transferred into the bag. Regardless of how the heating time is computed, if it is estimated by the controller to exceed the replenish volume transfer time, the controller may command the pump to begin the replenish operation before the remaining dwell time becomes less than the estimated time needed to bring the replenish volume to the pre-determined temperature.

Optionally, the cycler may estimate the amount of time which will be needed for the subsequent drain operation after the current dwell. This time estimate may then be added to a transfer time estimate, plus possibly an added time margin in determining how much time is available to heat the fluid in the heater bag. The estimate may be taken into account when the cycler is scheduling a replenish. For example, in some embodiments, the replenish may begin when it is determined that a calculated amount of time before the start of the current cycle's drain remains. This amount of time may be calculated as follows:

Time Before Drain (replenish start time)=Optional Margin+Replenish Volume Transfer Time+(if greater than zero (Replenish Volume Heating Time−Drain Time))

Optionally, the controller may compute the contribution that the subsequent drain phase will provide to raise the heater bag fluid to its target temperature (e.g., drain phase 754, FIG. 178). This will allow the controller to initiate heater bag filling later during the dwell phase (e.g., dwell phase 756) by the amount of time available to continue to heat the fluid during the drain phase (e.g. drain phase 754). In some embodiments, at least one estimated amount of time (e.g the replenish/fluid transfer time or heating time) may be inclusive of an added time margin to help ensure that the solution is not less than the programmed temperature by the start of the next cycle. This may help to ensure that a drain is not postponed due to volume transfer in a replenish taking longer than anticipated.

Alternatively, the total volume of the heater bag may be relatively small (e.g. no larger than the volume of about one and a half fills). This may help to ensure that solution in the heater bag is not maintained at high temperature for excessively long periods of time. Instead, the solution in the heater bag will be used over a small number of cycles (e.g. two cycles). In such embodiments, there may be multiple sets available to a user, each of which having differing heater bag sizes. This may allow for a user to perform a therapy with a heater bag which is appropriate for their prescribed fill. In some embodiments, sets with heater bags made of varying materials may also be made available. For example, there may be sets with heater bags which are substantially impermeable to gases such as carbon dioxide.

FIG. 211 shows a flowchart outlining number of example steps which may be used to replenish a heater bag with dialysate solution. The steps shown in FIG. 211 help to minimize the amount of time which the solution is heated in the heater bag before delivery to the patient. The flowchart begins after the heater bag has been initially filled and heated at the start of the therapy. As shown, in step 4900 the cycler fills a patient's peritoneal cavity with solution from the heater bag. This may substantially deplete the heater bag to near empty. The dwell phase of the cycle may then begin. The cycler controller monitors the remaining dwell time to ensure that the remaining dwell time is greater than or equal to the time needed to replenish the heater bag and heat solution for the next fill. When the remaining dwell time no longer exceeds the time needed to replenish the heater bag and heat solution for the next fill, step 4904 may be performed. Alternatively, the cycler may schedule the replenish such that there will be enough time to replenish the heater bag and heat the solution. The cycler controller then waits until the scheduled time and proceeds to step 4904.

In step 4904, the cycler replenishes the heater bag with the volume needed for the next fill operation. As mentioned above, the cycler may fill the heater bag to a volume that is greater than is required for the next fill. For example, the heater bag may be filled to the volume needed for the next fill plus an additional marginal volume of 10-25% of the fill volume. The cycler may also begin to heat the solution pumped to the heater bag in the replenish period to within a pre-determined range of a pre-determined temperature set point. This temperature set point may be fixed or programmable by a user, or by a clinician authorized to alter the prescription parameters and settings of the peritoneal dialysis cycler.

After the time allotted for the dwell phase elapses, the cycler proceeds to step 4906 and begins to drain the patient. Optionally, heating of the solution up to within the range of the temperature set point may continue as step 4906 is performed. After the drain operation completes, the cycler returns to step 4900 and refill the patient with solution from the heater bag. If the solution is not within the range of the temperature set point, the cycler may instead continue to heat the solution in step 4908 until the solution is within a range of the desired temperature set point. This will help to ensure that solution significantly above or below the desired temperature is not delivered to a patient.

Solution Expiration Timers

In some embodiments, a cycler may be programmed to determine a solution set up or staged for use in a dialysis therapy has expired. Additionally, a cycler may be programmed to notify a user when a solution has expired. The cycler controller may disallow use of the expired solution and in some embodiments, may require the user to terminate or abort a therapy such that a new therapy with fresh solution may be set up. This may for example be desirable in cyclers in which very long therapies (e.g. up to 48 hours) may be programmed, or in cyclers which allow a user to pause a therapy for long periods of time.

In some embodiments, a cycler may have one or more solution expiration timers that start or may be triggered to start at a predefined point in the therapy. Each of the solution expiration timers may be used for a different solution reservoir. For example, a first solution expiration timer may be used for a first solution reservoir and a second solution expiration timer may be used for a second solution reservoir. The first solution expiration timer may be triggered to start at a first predefined point and the second solution expiration timer may be triggered to start at a second predefined point. A single solution expiration timer may also be used for a number solution reservoirs containing the same type of dialysate solution. A solution expiration timer may allot a predetermined period of time for the therapy to make use of the solution. The predetermined amount of time may vary depending on the type of solution being used. If there are multiple solution expiration timers, the predetermined amount of time may differ for each timer. If the therapy does not use the solution before the time elapses, the solution may be deemed expired by the cycler and treated accordingly. If there are multiple solution expiration timers with different allotted periods of time, one solution expiration timer expiring may cause one or more other solution expiration timer to also expire.

In some embodiments, the amount of time allotted for a solution expiration timer may vary by temperature of the solution. Solution stored in a staged solution bag may be subject to a first solution expiration timer and may then be subject to a different solution expiration timer after being transferred into a heater bag. In embodiments in which a cycler heats the solution to a temperature set point defined by the user or a prescriber, the system controller may compute an expiration time for that solution expiration timer based on the value of the temperature set point.

In some embodiments, two solution expiration timers may be used. One solution expiration timer may be for a set of staged solution bags and another solution expiration timer may be for the heater bag. The solution bag expiration timer may be programmed to begin when the cycler controller determines that the solution bags have been connected to the set. The heater bag expiration timer may begin each time the heater bag is depleted to a residual volume before it is refilled with fresh solution. For example, in embodiments which schedule replenishes as described above in relation to FIG. 211, the timer may restart at every replenish of the heater bag.

In various embodiments, one or more solution expiration times may be established for each type of dialysate compatible for use with the cycler. The cycler controller may determine which type of solution is programmed for use with the therapy. Information about the solution used for the therapy may also be read from a barcode or the like on a solution line or may be input by the user via a user interface of the cycler. The predetermined period of time allotted for the solution expiration timer may be chosen to match a dialysate solution to be used in the therapy. For example, the cycler controller may match the determined solution type to a predetermined period of time programmed for that solution in a look-up table. If more than one type of solution is to be used for the therapy, the solution with the shortest expiration time may be used to set the predetermined period of time allotted for the solution expiration timer. Multiple solution expiration timers may also be set up so that there is one timer for each of the different solution types used during the therapy.

Alternatively, the one or more solution expiration timer may not be solution specific. In such embodiments, this solution expiration timer may be set such that it would be appropriate for the solution which has the shortest expiration time. The solution expiration times for various solutions may be determined based upon manufacturer recommended values.

If a solution bag expires, the cycler may, for example, no longer draw fluid from that solution bag. The therapy may be allowed to continue if other solution bags connected to the set have not yet expired. Additionally, in some embodiments, the user interface of the cycler may notify a user of the solution bag's expiration. In such embodiments, the user may have the option of replacing the solution bag.

Alternatively, there may only be a single solution bag expiration timer for all of the solution bags attached to the set. In the event that the timer expires, the user may be required to abort the current therapy and begin a new therapy with fresh supplies. If the solution bag expiration timer expires, it may also cause the heater bag expiration timer to expire.

If the heater bag expires, the cycler controller may be programmed to not deliver the solution in the heater bag to the user. The cycler may, for example, pump all of the solution in the heater bag to the drain line to discard the solution. The heater bag may then be refilled and the heater bag expiration timer may be restarted. The user may be notified of the heater bag's expiration. Alternatively, if there is not enough solution to refill the heater bag, the user may be required to abort the current therapy and begin a new therapy with fresh supplies. In some embodiments, any remaining solution may be delivered to the heater bag and heated. This solution may then be delivered to the patient so that it may dwell in the patient while new supplies are gathered. This may help to minimize loss of therapy.

FIG. 212 shows a flowchart outlining a number of example steps which may be employed by a cycler using solution expiration timers. In the example flowchart, the cycler has a solution bag expiration timer and a heater bag expiration timer. As shown, in step 4920 the cycler determines that solution bags have been connected to the set. The cycler may then, in step 4922, begin a solution bag expiration timer. The cycler may then fill the heater bag in step 4924. After the heater bag has been filled, the cycler may start the heater bag expiration timer in step 4926.

In step 4928, the therapy is performed. If during the therapy, the heater bag is emptied and replenished, the heater bag expiration timer may be reset in step 4930. Otherwise, if the therapy concludes before any expiration timers elapse, the therapy may be completed normally. If an expiration timer elapses before the therapy concludes, the cycler may indicate that the solution has expired in step 4932. If it is the heater bag expiration timer that has expired and there is sufficient solution in the solution bags, the cycler may discard the solution in the heater bag and replenish it with solution from the solution bags in step 4934. If there is not enough solution to replenish the heater bag, the cycler may proceed to step 4936 and instruct the user to abort the therapy and start a new therapy with fresh supplies. The cycler may also proceed to step 4936 if it is the solution bag expiration timer that has expired.

FIG. 213 depicts an example screen 5610 which may be generated by a processor for display on a user interface of a cycler. The example screen 5610 indicates to the user that a solution expiration timer has expired. Such a screen may for example be displayed in step 4932 of FIG. 212. In the example embodiment, the solution expiration timer which has expired is the heater bag solution timer.

As shown, the example screen 5610 includes an alert 5612 which declares that solution has expired and provides an error code. The screen 5610 also includes text which informs the user how to resolve the problem. In the example screen 5610, the text instructs the user to postpone a fill phase so that the heater bag solution may be discarded and replaced. A user may be required to navigate to another screen on which they confirm or elect to replace the solution in the heater bag. In the example embodiment, such a screen may be navigated to by interacting with a treatment options button 5614 on the screen 5610. In some embodiments, a resume button 5516 on the screen 5610 may be disabled until a user has replaced the solution.

Also shown on the example screen 5610 is a time notification 5518. The time notification 5518 may inform the user when a solution timer is going to expire. The time notification 5518 may be triggered for display when a predetermined amount of time before a solution expiration timer expires is remaining. In some embodiments, for example, in embodiments where a user may disconnect from a cycler during a therapy, the time notification 5518 may inform a user when they must reconnect and continue the therapy to avoid a solution timer from expiring. In the example embodiment, the time notification 5518 is a reconnect by time which informs the user that they had to reconnect by 7:55 PM to avoid the heater bag expiration timer from expiring. As shown by the clock 5620, the reconnect by time passed 3 minutes ago.

Flow Check

When draining solution from the peritoneal cavity of a patient it is not unusual for a patient to perceive an uncomfortable tugging sensation. Additionally, this tugging sensation may be more prone to occur when the peritoneal cavity is empty or nearly empty. For this reason, it may be desirable for a cycler to perform a flow check to ensure that the patient is carrying fluid that needs to be removed. Such a flow check may for example be performed before all drains or may be performed prior to certain types of drains. For example, since discomfort is more often reported during initial drains, flow checks may be made before an initial drain is performed by the cycler. The flow check may gently attempt to remove fluid from a patient until the controller determines whether or not there is any fluid volume in the patient's peritoneal cavity that requires draining. The cycler may, for example, check to see if a flow rate above a predetermined threshold value can be reached, as this would suggest there is indeed fluid in the patient that should be removed. This may help to minimize or prevent a perceived tugging sensation when there is relatively little fluid, or an insufficient amount of fluid to be drained. The cycler controller may set the pumping pressure for the drain based on the flow rate determined during the flow check. A flow rate above a preset threshold may allow the drain to proceed using a greater force (greater negative pressure).

In prior devices, instead of performing a flow check, the cycler controller would attempt to pull fluid from the peritoneal cavity at a standard or nominal preset pressure. The cycler would be programmed to continue the drain phase until a minimum elapsed drain time or a minimum drain volume was reached. If the resulting flow rate were below a given threshold (e.g. 15 ml/min. over a 45 second period), the cycler would attempt to push fluid back to verify that there was no line occlusion. If no line occlusion was detected, pumping could resume at a lower pressure. If flow remained below a threshold value for another period of time (e.g. 300 seconds), the cycler would either alert the user or allow the user to bypass the remainder of the drain phase. This procedure in some cases could result in episodes of patient discomfort, which now can be mitigated by the flow check procedure.

In some embodiments, a cycler may perform a flow check by attempting to pull fluid from a patient at a flow check pressure. The flow check pressure may be selected so that it is more positive (i.e. closer to atmospheric) than that used during a normal drain operation. For example, the difference between the flow check pressure and the normal drain pressure may be between approximately 2 kPa and 6 kPa. In one example, a flow check pressure may be set at about −6.5 kPa while normal drain pressure may be set at about −9.5 kPa. Other pressure values may be used. The selected pressures may be nominal values that can deviate by a pre-determined margin from the selected pressure while a pumping operation at that pressure is being performed. Additionally, in some embodiments, different flow check pressures may be used for different drains. For example, the flow check pressure used during an initial drain may be weaker (i.e., less negative pressure) than that used during a mid-therapy drain. Selecting the flow check pressure so that it creates a weaker vacuum than the normal draining pressure may feel gentler to the patient. In some embodiments, a user or a clinician may be have the option of setting the flow check pressure.

FIGS. 214A and 214B show a flowchart of a cycler performing an initial drain that starts with a flow check. As mentioned above, flow checks may be performed on other drains during a therapy as well. As shown, the drain starts in step 5530. As shown in step 5532, the drain begins with a flow check at a first pressure which is a flow check pressure. In the example embodiment, the drain begins with a drain pressure of −6.5 kPa.

In the event that the flow rate during the flow check is determined to be greater than a flow rate threshold, the cycler may check to see that a flow rate above the threshold is maintained for a predetermined period of time (e.g. 30 seconds). The flow rate threshold may, for example, be a value between approximately 35 ml/min and 75 ml/min. In an embodiment, the flow rate threshold may be approximately 50 ml/min.

If the flow rate is maintained above the threshold, the cycler controller may set the drain pressure to a second pressure considered to be a normal drain pressure in step 5544. This pressure is generally greater (i.e. more negative) than the flow check pressure. In the example embodiment, the normal drain pressure is shown as −9.5 kPa. The flow rate during the drain may continue to be monitored to determine if the flow rate decreases below the flow rate threshold.

In the event that flow rate during the flow check or a drain at normal pressure is determined to be less than or equal to the flow rate threshold, the pressure for the drain operation may be set to a reduced flow pressure in step 5534. In the example embodiment, the reduced flow pressure is the same as the flow check pressure, though this need not always be the case. If the reduced flow condition persists for a predetermined period of time (e.g. 30 seconds), a reduced flow alert may be signaled to a user in step 5536. In some embodiments, this alert may be a silent alert and be displayed as a text notification on the user interface of the cycler.

In the event that the flow rate is less than the no flow rate, in some embodiments a push back attempt may be performed in step 5538. In a push back attempt, a cycler may attempt to pump a small volume of fluid into the patient's peritoneal cavity. This may allow the cycler controller to determine if the line is occluded, as the cycler will be unable to deliver the fluid if an occlusion is present. If a low flow condition is related to a peritoneal catheter tip being lodged against a surface or in a tissue recess, the push-back of a small amount of fluid may be sufficient to disengage the catheter tip. The low flow condition may thus be relieved without the cycler controller necessarily having to notify the user. The controller in this case may re-attempt a flow check procedure. In some embodiments, step 5538 may only be performed if the flow rate has been below the low flow rate for a defined period of time (e.g. 30 seconds). In the event that the pushback attempt in step 5538 fails, the cycler may notify the user that an occlusion exists in step 5540. The drain may then be paused in step 5542 and a user may have the option of continuing or bypassing the drain. If a user elects to continue the drain, another flow check may be performed in step 5532 and the flowchart may start over.

If a pushback attempt is successful, or a pushback attempt is unnecessary because the flow rate is greater than the no flow threshold, the cycler may check to see if a minimum drain time has expired or elapsed. This time may, for example, be a clinician programmable parameter. If the minimum drain time has not elapsed, the cycler may continue to monitor the flow rate returning to step 5534 or step 5544 to set the drain pressure accordingly.

If the minimum drain time has expired, the cycler may check to determine if the flow rate has been below or equal to the flow rate threshold for greater than a predetermined period of time. This period of time may also be modifiable by a user such as a clinician. In the example embodiment, the period of time is shown as 150 seconds.

In the event that the flow rate has been at or below the flow rate threshold for more than the predetermined period of time, a reduced flow alert may be signaled to the user in step 5546. This alert may include a text notification displayed on the user interface of a cycler and may be accompanied by an audible noise or tone. If the flow rate persists at or below the flow rate threshold, another reduced flow alert may be signaled to the user in step 5548. This alert may be a higher level alert than that signaled in step 5546. The drain may then be paused in step 5542 and the user may elect to bypass or continue the drain as described above.

In the event that the flow rate is above or rises above the flow rate threshold either before or after step 5546 is to be performed, a cycler controller may check to determine if a minimum pre-determined drain volume has been drained from the patient. If the minimum drain volume has not been met, the cycler may continue to monitor the flow rate returning to step 5534 or step 5544 to set the drain pressure accordingly. If the minimum drain volume has been met the cycler may check to determine if the flow rate is above the no flow rate. If the flow rate is above the no flow rate, the cycler may end the drain and proceed to the next phase of a cycle in step 5550. Since the example flowchart shown in FIGS. 214A and 214B applies to an initial drain, the intra-peritoneal volume of the patient may be set to zero in step 5550 as well. In embodiments in which similar logic is used in other therapy drains, the patient volume may not be reset to zero after the drain. In alternative embodiments, if the minimum drain volume has been drained from the patient, the cycler may proceed directly to step 5550.

If the flow rate is determined to be below the no flow rate after the minimum drain volume has been drained from the patient, a cycler controller may command the cycler to perform a pushback in step 5552. In some embodiments, this pushback back may not necessarily be performed. For example, in some embodiments, if a pushback was performed in step 5544, a pushback may not be performed in step 5552. If the pushback is successful, the cycler may end the drain and proceed to the next phase of a cycle in step 5550. If the pushback attempt is unsuccessful, an occlusion alert may be signaled to a user in step 5554. The drain may then be paused in step 5542. A user may then elect to bypass the drain, attempt to resolve the problem and continue with the drain as described above.

In some embodiments, a cycler may be configured to perform either normal drains or soft drains. This may be selectable by a user or caregiver via the user interface of the cycler. A processor or controller of the cycler may generate a screen for display on the user interface which allows the user to alter the pumping pressure from a first pumping pressure (e.g. normal pumping pressure) to a second pumping pressure (e.g. soft pumping pressure or weaker pumping pressure). This screen preferably is presented to the user during a drain. The pumping pressure optionally may only be altered for the pumping chamber fill stroke. In response to the user changing the pumping pressure via the user interface, the processor may control the pneumatic circuit of the cycler to apply a different pumping pressure to the pumping chambers of an installed cassette.

In some embodiments, this feature may be enabled or disabled by a clinician. For example, a clinician may enable such an option for a patient who reports tugging or discomfort during drains. In various embodiments, this option may only be enabled for certain types of drains. For example, a clinician may have the ability to allow the user to perform soft drains during initial drain.

Such an option may allow the user to switch to a gentler drain in the event that a drain at normal drain pressure is causing discomfort. If an option to select a soft drain or normal drain is available, the cycler should preferably default to performing a normal drain as soft drains may shorten the dwell times for a therapy. The option may, for example, only be made available after a reduced flow condition is detected by the cycler controller. In other embodiments, the user may have an option of selecting between normal drains and soft drains when starting the therapy. In some embodiments, the user may be able to specify specific drains as soft drains and other drains as normal drains.

A soft drain may be at a weaker pressure than that of the normal drain, and may be pre-set or may be user-definable via the user interface. The soft drain may, in some embodiments, use a pumping pressure similar to the pumping pressure used during a flow check or may use the pressure set point defined for the flow check. The soft drain pumping pressure may for example, be weaker than the normal drain pumping pressure by between about 2 and 6 kPa. In some embodiments, a user such as a clinician may define the pressure set points for the normal drain and soft drain. Alternatively, the reduced pumping pressure may be selected from a range of pumping pressures. Optionally, a clinician may be allowed to create another drain profile. For example, a clinician may define a normal drain, softer drain, and softest drain pressure. The user may have the ability to select any of these pre-defined drain types if desired. If a user has set a maximum therapy time for a course of therapy, the controller may not modify the drain pressure unless a reduced flow condition has been detected.

FIG. 215 depicts an example user interface screen which may be displayed on the user interface of a cycler during a drain. Specifically, the screen shown in FIG. 215 is an initial drain screen 5000. As shown, the initial drain screen 5000 includes a variety of information about the drain and the therapy. As shown, the screen also includes a switch to soft drain option 5002. The switch to soft drain option 5002 may, in some embodiments, be selected at any time during the drain. In other embodiments, the switch to soft drain option 5002 may not be enabled or may be grayed out until after a user presses a pause button 5004 to pause the drain. This may help to avoid an accidental button press of the switch to soft drain option 5002 which would slow down the drain operation for no need. In other embodiments, the switch to soft drain option 5002 may not be present on all drain screens. Instead, a user may need to navigate to a switch to soft drain option 5002 by selecting a menu option 5006 on the user interface. When the soft drain option 5002 is selected and the drain pressure is dropped to the soft drain pressure, the user interface may similarly be used to return to a normal drain if desired. As would be appreciated by one skilled in the art, other embodiments may have options for multiple different types of drains such as, e.g., a normal drain, softer drain, and softest drain. In some embodiments, instead of providing a button, the switch to soft drain option 5002 may be implemented in the form of a slider bar. One end of the bar may be the weakest pressure which may be defined for use during a drain. The other end of the bar may be the normal drain pressure. The user may select a desired pressure from anywhere in the range of pressures between each end of the bar. Optionally, the controller may compute the effect on therapy time, pumping time or another measure of the lengthening or shortening the time needed to drain a volume of fluid in response to a change in the pumping pressure, and display information on this effect on the user interface. In an embodiment, the user may be required to confirm on the user interface that a change in pumping pressure is still desired.

The triggering flow rate or the time duration at that lower flow rate may vary, depending on patient-related or clinician-related factors. Additionally, the amount of time which the cycler continues pumping at lower pressure may vary. In some embodiments, pumping pressure may be adjusted based upon flow rate at any point in a therapy. For example, in the event that a reduced flow rate is determined to exist, the pumping pressure may be lowered to minimize patient discomfort. Such a reduced flow rate condition may, for example, be a low flow condition of, e.g. 50 mL/min. There may be multiple pumping pressures assigned to a variety of flow conditions. For example, there may be a "normal" pumping pressure which is used in normal flow conditions (e.g. flow greater than 50 mL/min). There may be a low flow pressure for flow conditions which are less than the normal flow condition flow rate. There may also be a no flow pumping pressure which may be used in the event that the flow rate is very low (e.g. less than or equal to 15 mL/min).

Pumping pressure need not be assigned based on discretely defined flow conditions (e.g. normal flow, low flow, no flow). Instead, in such embodiments, pumping pressure may be adjusted on a gradient. That is, the pumping pressure may increase or decrease in magnitude in a relatively continuous manner relative to flow rate. The gradient may be linear or non-linear. For example, the magnitude of the increase in pressure may be proportional to the magnitude of the increase in flow rate and the magnitude of the decrease in pressure may be proportional to the magnitude of the decrease in flow rate. The pumping pressure may be adjusted in a substantially continuous fashion as flow rate data becomes available. This continuous adjustment may occur after each stroke or may occur as each stroke progresses if flow rate is estimated during the progression of the stroke. The controller may be programmed to limit the pump pressure variation to within a pre-determined range of pressures. In embodiments in which the pumping pressure used increases or decreases in magnitude relative to the flow rate, a drain operation may still begin with a flow check. That is, the drain operation may start with the negative pressure for the drain phase being set at an initial flow check pressure for a predetermined period of time. This pressure may be selected so that it would be appropriate for a reduced flow condition (e.g. −6.5 kPa) in order to minimize any tugging sensation experienced by the user at the start of the drain operation. If the flow rate falls below a predefined threshold for more than a predetermined period of time, the cycler controller may stop adjustment of the pumping pressure. If the total volume drained during the drain operation is less than the target volume for the drain, a pushback may be performed to check for an occlusion. If the total volume drained has at least reached the target volume for the drain operation then the cycler controller may determine that the drain operation has completed and move onto the next phase of the therapy.

In some embodiments there may be a plurality of different pressures for each defined flow condition. These different pressures may be assigned based upon the source and the destination for the fluid being moved during the pumping stroke. For example, a first pumping pressure may be used when fluid is being filled into a patient's peritoneal cavity at a defined flow rate or flow rate range. A second pressure may be used when fluid is being drained from the patient at a defined flow rate or flow rate range. A third pressure (e.g., closer to the maximal available pressure from the pressure reservoirs) may be selected if no fluid is being pumped to or from a patient (e.g. chamber to drain, chamber to heater bag, heater bag to chamber, etc.), in which case there may be no need to alter the pressure based upon flow rate.

Automated Effluent Sampling

In some embodiments, when programming a therapy, a user may be able to enable/disable or turn on/off an automated sampling parameter. The automated sampling parameter causes a cycler to automatically fill an effluent sampling bag with spent dialysate from a patient during the therapy. The user may be able to define a number of additional parameters which may be used to specify various aspects of the automated sample taken. For example, these additional parameters may be used to define a sample volume to be taken, and when in the therapy a sample is to be taken. They may also be used to define how many samples are to be taken or how many sample bags are to be filled. In some embodiments, these additional parameters may only be enabled or unlocked for editing if the automating sampling parameter has been enabled. In some embodiments, there may be a variety of pre-set sampling regimens with definable parameters from which a user may choose. For example, a sampling regimen may include parameters appropriate for a peritonitis test. A sampling regimen may also include parameters which would be appropriate for a peritoneal equilibration test or peritoneal membrane transport function test.

In one embodiment, an effluent sampling reservoir may be placed into fluid communication with a set installed in the cycler. The cycler may pump spent fluid from the connected patient into the effluent sampling reservoir as prescribed by the therapy program. In various embodiments, the user may be asked to identify a fluid port of the dialysis set to which the effluent sampling reservoir has been connected or may be directed to attach the reservoir to a specific port. Alternatively, a set intended to be used in therapies with automated effluent sampling may be provided. In such embodiments, the effluent sampling reservoir may be attached to a specific port on the dialysis set and the cycler controller may command pumping to that port when performing an automated sampling operation. In some embodiments a set may include a connector for an automated sampling reservoir which is unique to the automated sampling reservoir and may only couple to a corresponding unique mating connector on an automated sampling reservoir.

In other embodiments, a feature of a set or fluid line installed in a cycler may be used to determine that the cycler is to take an automated effluent sample. In such embodiments, the feature may, for example be a specific geometry which is sensed by one or more sensors in a cycler. When a cycler controller receives data from a sensor indicating that the specific geometry is present, the controller may command the cycler to pump fluid to an effluent sampling reservoir during the therapy. In some embodiments, there may be multiple different geometries which may be detectable by the sensor(s). Each geometry may correspond to effluent sample programs with different sampling parameters. The sensor(s) may be any suitable sensor or combination of sensors, such as, but not limited to a contact sensor (e.g. microswitch).

Alternatively, the feature of the set or fluid line may be a magnet or magnetic feature included as part of the cassette or fluid line. When installed in the cycler, a hall effect sensor in the cycler may detect the presence of the magnet or magnetic feature. When a cycler controller receives data from the hall effect sensor indicating the magnet or magnetic feature is present, the controller may command the cycler to pump fluid to an effluent reservoir during the therapy.

In another embodiment, a cycler may use an optical sensor to read or decode an identifying mark on a set or a fluid line installed in a cycler. The identifying mark may include a code interpretable by the controller that an automated effluent sample is to be taken during a therapy. Additionally, the identifying mark may further be coded to specify various parameters relating to the effluent sample to be taken during the therapy. Such an identifying mark may comprise indicia such as, but not limited to 2-D indicia (e.g. a barcode, data matrix, etc.), or any other suitable indicia. In some embodiments, the indicia may be included on an identification tag 1100 (see FIG. 41) that may snap onto a portion of the set or fluid line.

FIG. 216 shows a flowchart outlining steps which may be used to program and collected an automated effluent sample using a cycler. As shown, in step 5720, the user begins programming a therapy. This may involve specifying various therapy parameters such as any of those commonly defined in the art on a user interface of the cycler. In step

5722 a user enables an automated sampling option or parameter. This may be done using a user interface of the cycler. In some embodiments, the user may then choose between a customized or user specified sampling program or a preset sampling program. This may in some embodiments be accomplished by user interaction with a prompt displayed on the user interface of the cycler.

If a user chooses to use a preset sampling program or regimen, the cycler displays a list of one or more preset regimens on the user interface of the device in step 5724. These preset regimens may for example include a peritonitis test, peritoneal equalization test, single sample, etc. In some embodiments, these presets may be tied to other parameters programmed during the therapy. For example, when a preset is selected the amount of fluid to be pumped into the sampling reservoir may be dependent upon the patient fill volume. Additionally, in some instances a user may have to enter one or more additional parameter once a preset has been selected. For example, if a user selects that a single sample is to be collected, the user may be required to define when in the therapy this is to occur. A user may select the desired sampling regimen or program from the list in step 5726. This may be done via any suitable type of interaction with the user interface of the cycler. The user may then finish programming the therapy in step 5728.

If a user chooses to define a user specified or custom sampling regimen, the cycler may display one or more parameters related to the automated sampling on the user interface of the cycler in step 5730. The user may then define one or more parameter related to the automated sampling to be performed by the cycler in step 5732. This may be done via any suitable type of interaction with the user interface of the cycler. The parameters defined may be, but are not limited to any of those mentioned above. The user may then finish programming the therapy in step 5734.

The therapy is started in step 5736. The therapy continues as programmed in step 5738 until it is time for an automated sample to be taken by the cycler. Once it is time for the sample to be taken, the cycler takes the sample as specified by the therapy program in step 5740. If there are additional samples to be taken during the therapy, the cycler proceeds back to step 5738 and continues the therapy until it is time to take another sample. If there are no additional samples to be taken in the therapy, the cycler completes the therapy in step 5742.

FIG. 217 depicts a flowchart detailing a number of example steps which may be used to program and collected an automated effluent sample using a cycler. In the example embodiment, the cycler includes a sensor which is configured to read an indicia on a set. The indicia on the set may include information about the set or the therapy to be performed. The indicia may also specify whether or not and the manner in which an automated effluent sample is to be taken by the cycler.

As shown, in step 5750, the user installs the set in the cycler. The cycler may then read the indicia on the set 5752. The therapy is started in step 5754. In the event that the indicia indicates that an automated sample is not to be taken during the therapy, the cycler performs and completes the therapy in step 5760.

If the indicia specifies an automated sampling regimen or program, the therapy continues as programmed in step 5756 until it is time for an automated sample to be taken by the cycler. Once it is time for the sample to be taken, the cycler takes the sample as specified by indicia in step 5758. In alternate embodiments, the indicia may specify whether the sample is to be taken and the cycler performs a preprogrammed sampling procedure. If there are additional samples to be taken during the therapy, the cycler proceeds back to step 5756 and continues the therapy until it is time to take another sample. If there are no additional samples to be taken in the therapy, the cycler completes the therapy in step 5760.

While aspects of the invention have been described in conjunction with specific embodiments thereof, it is evident that many alternatives, modifications, and variations will be apparent to those skilled in the art. Accordingly, embodiments of the invention as set forth herein are intended to be illustrative, not limiting. Various changes may be made without departing from the spirit and scope of the invention.

The invention claimed is:

1. A system to withdraw fluid from a cavity of a patient, the system comprising:
a pump configured to provide at least a first negative pressure and at least a first positive pressure to a patient line fluidly connected to the cavity;
a controller configured to measure and control the first negative pressure and the first positive pressure provided by the pump;
the controller also configured to measure at least a first fluid flow rate through from the patient line;
wherein the controller is arranged to control the pump to provide the first negative pressure to the patient line, measure the first fluid flow rate through the patient line, and control the pump to provide the first positive pressure to the patient line if the first fluid flow rate is less than a pre-determined value;
and wherein the controller is arranged to control the pump to provide a second negative pressure to the patient line if a second fluid flow rate through the patient line measured upon application of the first positive pressure is greater than a pre-determined amount.

2. The system of claim 1, wherein the controller is configured to control the pump to apply the first negative pressure for a predetermined period of time.

3. The system of claim 2, wherein the first negative pressure is set to a minimum negative pressure of the at least the first negative pressure.

4. The system of claim 1, wherein the controller is configured to stop adjustment of a pumping pressure provided to the patient line if a flow rate through the patient line is less than a pre-determined threshold flow rate for more than a pre-determined period of time.

5. The system of claim 1, wherein the controller is configured to control the pump to terminate a drain cycle if a cumulative volume of the fluid withdrawn is equal to or greater than a target volume.

6. The system of claim 1, wherein the pump is a pneumatically actuated diaphragm pump comprising a pumping chamber fluidly connected to the patient line, an actuation chamber connected to a pressure distribution manifold and a flexible diaphragm between the actuation chamber and the pumping chamber;
wherein the controller measures an actuation chamber pressure from a pressure sensor in communication with the actuation chamber of the pump, and a reference chamber pressure from a pressure sensor in communication with a reference chamber in valved communication with the actuation chamber of the pump; the controller configured to control a valve in the pressure distribution manifold to deliver the at least the first negative pressure to the actuation chamber; the controller also configured to determine the measured first fluid flow rate based on the actuation chamber pressure and the reference chamber pressure.

7. The system of claim 1, wherein the pre-determined value is in a range of approximately 35 to 75 ml/min.

8. The system of claim 1, wherein the controller is arranged to control the pump to provide the first negative pressure at −6.5 kPa.

9. The system of claim 1, further comprising a user interface and wherein the controller signals an alert if the measured first fluid flow rate is less than the pre-determined value.

10. The system of claim 1, further comprising a user interface and wherein the controller signals an occlusion alert if the measured second fluid flow rate upon application of the first positive pressure is less than the pre-determined amount.

11. The system of claim 1, wherein the controller is arranged to measure a third fluid flow rate after a first period of time after the first fluid flow rate is measured and signals an alert if the third fluid flow rate has been less than the pre-determined value for a second period of time.

12. The system of claim 1, wherein the second negative pressure is equal to the first negative pressure.

13. The system of claim 1, wherein the pump is a pneumatically actuated diaphragm pump comprising a pumping chamber fluidly connected to the patient line, an actuation chamber connected to a pressure distribution manifold and a flexible diaphragm between the actuation chamber and the pumping chamber;

wherein the controller measures an actuation chamber pressure from a pressure sensor in communication with the actuation chamber of the pump; the controller configured to control a valve in the pressure distribution manifold to provide the first negative pressure including a time-varying negative pressure to the actuation chamber; the controller also configured to determine the measured first fluid flow rate based on the time-varying actuation chamber pressure.

14. A system to withdraw fluid from a cavity of a patient, the system comprising:
a pump configured to provide at least a first negative pressure and at least a first positive pressure to a patient line fluidly connected to the cavity;
a controller configured to measure and control the first negative pressure and the first positive pressure provided by the pump;
the controller also configured to measure a first fluid flow rate through the patient line;
wherein the controller is configured to control the pump to provide the first negative pressure to the patient line, measure the first fluid flow rate, and control the pump to provide a second negative pressure to the patient line when the measured first fluid flow rate is greater than a pre-determined value.

15. The system of claim 14, further comprising a user interface, wherein the controller signals an alert when the measured first fluid flow rate is less than the pre-determined value.

16. The system of claim 14, wherein the controller controls is configured to control the pump to provide the second negative pressure to the patient line when the measured first fluid flow rate is greater than the pre-determined value for a first pre-determined period of time.

17. The system of claim 14, further comprising a user interface, wherein the controller signals an alert when the measured first fluid flow rate is less than the pre-determined value for a first pre-determined period of time.

* * * * *

UNITED STATES PATENT AND TRADEMARK OFFICE
CERTIFICATE OF CORRECTION

Page 1 of 1

PATENT NO. : 11,752,248 B2
APPLICATION NO. : 16/247204
DATED : September 12, 2023
INVENTOR(S) : David A. Beavers et al.

It is certified that error appears in the above-identified patent and that said Letters Patent is hereby corrected as shown below:

In the Claims

In Claim 1, Column 266, Line 25, "fluid flow rate through from the patient line;" should be replaced with: --fluid flow rate through the patient line;--

In Claim 16, Column 268, Lines 25-26, "The system of claim 14, wherein the controller controls is configured to control the pump to provide the second" should be replaced with: --The system of claim 14, wherein the controller is configured to control the pump to provide the second--

Signed and Sealed this
Fifth Day of December, 2023

Katherine Kelly Vidal
*Director of the United States Patent and Trademark Office*